(12) United States Patent
Cheng et al.

(10) Patent No.: US 12,110,347 B2
(45) Date of Patent: Oct. 8, 2024

(54) ENZYMATIC SYNTHESIS OF SOLUBLE GLUCAN FIBER

(71) Applicant: NUTRITION & BIOSCIENCES USA 4, INC., Rochester, NY (US)

(72) Inventors: Qiong Cheng, Wilmington, DE (US); Robert DiCosimo, Chadds Ford, PA (US); Arthur Ouwehand, Inga (FI); Zheng You, Wilmington, DE (US); Mark S. Payne, Wilmington, DE (US); Jian Ping Lai, Wallingford, PA (US); Kristin Ruebling-Jass, Wilmington, DE (US); Steven Cary Rothman, Princeton, NJ (US)

(73) Assignee: NUTRITION & BIOSCIENCES USA 4, INC., Rochester, NY (US)

( * ) Notice: Subject to any disclaimer, the term of this patent is extended or adjusted under 35 U.S.C. 154(b) by 102 days.

(21) Appl. No.: 17/680,581

(22) Filed: Feb. 25, 2022

(65) Prior Publication Data
US 2022/0275112 A1   Sep. 1, 2022

Related U.S. Application Data

(63) Continuation of application No. 16/451,501, filed on Jun. 25, 2019, now Pat. No. 11,261,264, which is a continuation of application No. 15/313,347, filed as application No. PCT/US2015/032106 on May 22, 2015, now Pat. No. 10,351,633.

(60) Provisional application No. 62/004,305, filed on May 29, 2014.

(51) Int. Cl.
| | |
|---|---|
| C08B 37/00 | (2006.01) |
| A21D 13/45 | (2017.01) |
| A21D 13/80 | (2017.01) |
| A23C 9/13 | (2006.01) |
| A23G 3/36 | (2006.01) |
| A23G 9/32 | (2006.01) |
| A23L 2/52 | (2006.01) |
| A23L 7/126 | (2016.01) |
| A23L 7/135 | (2016.01) |
| A23L 21/10 | (2016.01) |
| A23L 29/30 | (2016.01) |
| A23L 33/21 | (2016.01) |
| A61K 31/716 | (2006.01) |
| C08L 5/00 | (2006.01) |
| C12N 9/10 | (2006.01) |
| C12N 9/44 | (2006.01) |
| C12P 19/04 | (2006.01) |
| C12P 19/08 | (2006.01) |
| C12P 19/18 | (2006.01) |

(52) U.S. Cl.
CPC ......... *C08B 37/0009* (2013.01); *A21D 13/45* (2017.01); *A21D 13/80* (2017.01); *A23C 9/13* (2013.01); *A23G 3/36* (2013.01); *A23G 9/32* (2013.01); *A23L 2/52* (2013.01); *A23L 7/126* (2016.08); *A23L 7/135* (2016.08); *A23L 21/10* (2016.08); *A23L 29/37* (2016.08); *A23L 33/21* (2016.08); *A61K 31/716* (2013.01); *C08L 5/00* (2013.01); *C12N 9/1051* (2013.01); *C12N 9/246* (2013.01); *C12P 19/04* (2013.01); *C12P 19/08* (2013.01); *C12P 19/18* (2013.01); *C12Y 204/00* (2013.01); *C12Y 204/01002* (2013.01); *C12Y 204/01005* (2013.01); *C12Y 302/01* (2013.01); *C12Y 302/01068* (2013.01); *A23V 2002/00* (2013.01); *C08L 2203/02* (2013.01); *C08L 2203/12* (2013.01); *C08L 2205/16* (2013.01)

(58) Field of Classification Search
CPC ...... C08B 37/0009; A23L 7/135; A23L 7/126; A23L 33/21; A23L 29/37; A23L 21/10; A23L 2/52; A21D 13/45; A21D 13/80; A23C 9/13; A23G 3/36; A23G 9/32; A61K 31/716; C08L 5/00; C08L 2203/02; C08L 2203/12; C08L 2205/16; C12N 9/1051; C12N 9/246; C12P 19/04; C12P 19/08; C12P 19/18; C12Y 204/00; C12Y 204/01002; C12Y 204/01005; C12Y 302/01; C12Y 302/01068; A23V 2002/00
USPC .......................................................... 514/54
See application file for complete search history.

(56) References Cited

U.S. PATENT DOCUMENTS

| | | | |
|---|---|---|---|
| 10,351,633 B2* | 7/2019 | Cheng | A23C 9/13 |
| 2010/0284972 A1* | 11/2010 | Naeye | A61K 45/06 |
| | | | 514/59 |
| 2014/0087431 A1* | 3/2014 | Payne | C12P 19/04 |
| | | | 435/97 |

* cited by examiner

Primary Examiner — Yih-Horng Shiao

(57) ABSTRACT

An enzymatically produced soluble α-glucan fiber composition is provided suitable for use as a digestion resistant fiber in food and feed applications. The soluble α-glucan fiber composition can be blended with one or more additional food ingredients to produce fiber-containing compositions. Methods for the production and use of compositions comprising the soluble α-glucan fiber are also provided.

20 Claims, No Drawings
Specification includes a Sequence Listing.

ENZYMATIC SYNTHESIS OF SOLUBLE GLUCAN FIBER

CROSS-REFERENCE TO RELATED APPLICATIONS

This application is a continuation of U.S. application Ser. No. 16/451,501 (filed Jun. 25, 2019; now U.S. patent Ser. No. 11/261,264), which is a continuation of U.S. application Ser. No. 15/313,347 (filed Nov. 22, 2016; now U.S. patent Ser. No. 10/351,633), which is the National Stage application of International Application No. PCT/US15/32106 (filed May 22, 2015), which claims priority to U.S. Provisional Application No. 62/004,305 (filed May 29, 2014), all of which prior applications are incorporated by reference herein in their entirety.

INCORPORATION BY REFERENCE OF THE SEQUENCE LISTING

The sequence listing provided in the file named "20150515_CL6036WOPCT_SequenceListing_ST25.txt" with a size of 636,928 bytes which was created on May 13, 2015 and which is filed herewith, is incorporated by reference herein in its entirety.

FIELD OF THE INVENTION

This disclosure relates to a soluble α-glucan fiber, compositions comprising the soluble fiber, and methods of making and using the soluble α-glucan fiber. The soluble α-glucan fiber is highly resistant to digestion in the upper gastrointestinal tract, exhibits an acceptable rate of gas production in the lower gastrointestinal tract, is well tolerated as a dietary fiber, and has one or more beneficial properties typically associated with a soluble dietary fiber.

BACKGROUND OF THE INVENTION

Dietary fiber (both soluble and insoluble) is a nutrient important for health, digestion, and preventing conditions such as heart disease, diabetes, obesity, diverticulitis, and constipation. However, most humans do not consume the daily recommended intake of dietary fiber. The 2010 Dietary Fiber Guidelines for Americans (U.S. Department of Agriculture and U.S. Department of Health and Human Services. *Dietary Guidelines for Americans,* 2010. 7th Edition, Washington, DC: U.S. Government Printing Office, December 2010) reports that the insufficiency of dietary fiber intake is a public health concern for both adults and children. As such, there remains a need to increase the amount of daily dietary fiber intake, especially soluble dietary fiber suitable for use in a variety of food applications.

Historically, dietary fiber was defined as the non-digestible carbohydrates and lignin that are intrinsic and intact in plants. This definition has been expanded to include carbohydrate polymers that are not significantly hydrolyzed by the endogenous enzymes in the upper gastrointestinal tract of humans, and additionally are not significantly fermented by the microbiota present in the lower gastrointestinal tract. Soluble oligosaccharide fiber products (such as oligomers of fructans, glucans, etc.) are currently used in a variety of food applications. However, many of the commercially available soluble fibers have undesirable properties such as low tolerance (causing undesirable effects such as abdominal bloating or gas, diarrhea, etc.), lack of digestion resistance, high cost or a production process that requires at least one acid-catalyzed heat treatment step to randomly rearrange the more-digestible glycosidic bonds (for example, α-(1,4) linkages in glucans) into more highly-branched compounds with linkages that are more digestion-resistant. A process that uses only naturally occurring enzymes to synthesize suitable glucan fibers from a safe and readily-available substrate, such as sucrose, may be more attractive to consumers.

Various bacterial species have the ability to synthesize dextran oligomers from sucrose. Jeanes et al. (*JACS* (1954) 76:5041-5052) describe dextrans produced from 96 strains of bacteria. The dextrans were reported to contain a significant percentage (50-97%) of α-(1,6) glycosidic linkages with varying amounts of α-(1,3) and α-(1,4) glycosidic linkages. The enzymes present (both number and type) within the individual strains were not reported, and the dextran profiles in certain strains exhibited variability, where the dextrans produced by each bacterial species may be the product of more than one enzyme produced by each bacterial species.

Glucosyltransferases (glucansucrases; GTFs) belonging to glucoside hydrolase family 70 are able to polymerize the D-glucosyl units of sucrose to form homooligosaccharides or homopolysaccharides. Glucansucrases are further classified by the type of saccharide oligomer formed. For example, dextransucrases are those that produce saccharide oligomers with predominantly α-(1,6) glycosidic linkages ("dextrans"), and mutansucrases are those that tend to produce insoluble saccharide oligomers with a backbone rich in α-(1,3) glycosidic linkages. Mutansucrases are characterized by common amino acids. For example, A. Shimamura et al. (*J. Bacteriology*, (1994) 176:4845-4850) investigated the structure-function relationship of GTFs from *Streptococcus mutans* GS5, and identified several amino acid positions which influence the nature of the glucan product synthesized by GTFs where changes in the relative amounts of α-(1,3)- and α-(1,6)-anomeric linkages were produced. Reuteransucrases tend to produce saccharide oligomers rich in α-(1,4), α-(1,6), and α-(1,4,6) glycosidic linkages, and alternansucrases are those that tend to produce saccharide oligomers with a linear backbone comprised of alternating α-(1,3) and α-(1,6) glycosidic linkages. Some of these enzymes are capable of introducing other glycosidic linkages, often as branch points, to varying degrees. V. Monchois et al. (*FEMS Microbiol Rev.*, (1999) 23:131-151) discusses the proposed mechanism of action and structure-function relationships for several glucansucrases. H. Leemhuis et al. (*J. Biotechnol.*, (2013) 163:250-272) describe characteristic three-dimensional structures, reactions, mechanisms, and α-glucan analyses of glucansucrases.

A non-limiting list of patents and published patent applications describing the use of glucansucrases (wild type, truncated or variants thereof) to produce saccharide oligomers has been reported for dextran (U.S. Pat. Nos. 4,649,058 and 7,897,373; and U.S. Patent Appl. Pub. No. 2011-0178289A1), reuteran (U.S. Patent Application Publication No. 2009-0297663A1 and U.S. Pat. No. 6,867,026), alternan and/or maltoalternan oligomers ("MAOs") (U.S. Pat. Nos. 7,402,420 and 7,524,645; U.S. Patent Appl. Pub. No. 2010-0122378A1; and European Patent EP1151085B1), α-(1,2) branched dextrans (U.S. Pat. No. 7,439,049), and a mixed-linkage saccharide oligomer (lacking an alternan-like backbone) comprising a mix of α-(1,3), α-(1,6), and α-(1,3,6) linkages (U.S. Patent Appl. Pub. No. 2005-0059633A1). U.S. Patent Appl. Pub. No. 2009-0300798A1 to Kol-Jakon et al. discloses genetically modified plant cells expressing a mutansucrase to produce modified starch.

Enzymatic production of isomaltose, isomaltooligosaccharides, and dextran using a combination of a glucosyltransferase and an α-glucanohydrolase has been reported. U.S. Pat. No. 2,776,925 describes a method for enzymatic production of dextran of intermediate molecular weight comprising the concomitant action of dextransucrase and dextranase. U.S. Pat. No. 4,861,381A describes a method to enzymatically produce a composition comprising 39-80% isomaltose using a combination of a dextransucrase and a dextranase. Goulas et al. (*Enz. Microb. Tech* (2004) 35:327-338 describes batch synthesis of isomaltooligosaccharides (IMOs) from sucrose using a dextransucrase and a dextranase. U.S. Pat. No. 8,192,956 discloses a method to enzymatically produce isomaltooligosaccharides (IMOs) and low molecular weight dextran for clinical use using a recombinantly expressed hybrid gene comprising a gene encoding an α-glucanase and a gene encoding dextransucrase fused together; wherein the glucanase gene is a gene from *Arthrobacter* sp., wherein the dextransucrase gene is a gene from *Leuconostoc* sp.

Hayacibara et al. (*Carb. Res.* (2004) 339:2127-2137) describes the influence of mutanase and dextranase on the production and structure of glucans formed by glucosyltransferases from sucrose within dental plaque. The reported purpose of the study was to evaluate the production and the structure of glucans synthesized by GTFs in the presence of mutanase and dextranase, alone or in combination, in an attempt to elucidate some of the interactions that may occur during the formation of dental plaque.

Mutanases (glucan endo-1,3-α-glucanohydrolases) are produced by some fungi, including *Trichoderma, Aspergillus, Penicillium*, and *Cladosporium*, and by some bacteria, including *Streptomyces, Flavobacterium, Bacteroides, Bacillus*, and *Paenibacillus*. W. Suyotha et al., (*Biosci, Biotechnol. Biochem.*, (2013) 77:639-647) describe the domain structure and impact of domain deletions on the activity of an α-1,3-glucanohydrolases from *Bacillus circulans* KA-304. Y. Hakamada et al. (*Biochimie*, (2008) 90:525-533) describe the domain structure analysis of several mutanases, and a phylogenetic tree for mutanases is presented. I. Shimotsuura et al, (*Appl. Environ. Microbiol.*, (2008) 74:2759-2765) report the biochemical and molecular characterization of mutanase from *Paenibacillus* sp. Strain RM1, where the N-terminal domain had strong mutan-binding activity but no mutanase activity, whereas the C-terminal domain was responsible for mutanase activity but had mutan-binding activity significantly lower than that of the intact protein. C. C. Fuglsang et al. (*J. Biol. Chem.*, (2000) 275:2009-2018) describe the biochemical analysis of recombinant fungal mutanases (endoglucanases), where the fungal mutanases are comprised of a $NH_2$-terminal catalytic domain and a putative COOH-terminal polysaccharide binding domain.

Glucans comprising α-(1,6) glycosidic linkages can be enzymatically produced from maltodextrin. The enzyme dextrin dextranase ("DDase"; E.C. 2.4.1.2; sometimes referred to in the alternative as "dextran dextrinase") from *Gluconobacter oxydans* has been reported to synthesize dextrans from maltodextrin substrates. DDase catalyzes the transfer of the non-reducing terminal glucosyl residue of an α-(1,4) linked donor substrate (i.e., maltodextrin) to the non-reducing terminal of a growing α-(1,6) acceptor molecule. Naessans et al. (*J. Ind. Microbiol. Biotechnol.* (2005) 32:323-334) reviews a dextrin dextranase and dextran from *Gluconobacter oxydans*.

Others have studied the properties of dextrin dextranases. Kimura et al. (JP2007181452(A)) and Tsusaki et al. (WO2006/054474) both disclose a dextrin dextransase. Mao et al. (*Appl. Biochem. Biotechnol.* (2012) 168:1256-1264) discloses a dextrin dextranase from *Gluconobacter oxydans* DSM-2003. Mountzouris et al. (*J. Appl. Microbiol.* (1999) 87:546-556) discloses a study of dextran production from maltodextrin by cell suspensions of *Gluconobacter oxydans* NCIB 4943.

JP4473402B2 and JP2001258589 to Okada et al. disclose a method to produce dextran using a dextrin dextranase from *G. oxydans* in combination with an α-glucosidase. The selected α-glucosidase was used hydrolyze maltose, which was reported to be inhibitory towards dextran synthesis.

An "GtfB-type" α-glucosyltransferase that uses α-(1,4) linked glucooligosaccharides substrates instead of sucrose to produce glucooligosaccharides having α-(1,6) glycosidic linkages has also been described. U.S. Patent App. Pub. No. 2012-0165290 to Dijkhuizen et al. describes an GtfB α-glucosyltransferase from *Lactobacillus reuteri* and its use in a method for producing a mixture of glucooligosaccharides having one or more α-(1,6) glycosidic linkages and one or more consecutive α-(1,4) glycosidic linkages by contacting a poly- and/or oligosaccharide substrate comprising at least two α-(1,4) linked D-glucose units with the GtfB under suitable reaction conditions.

The enzymatic addition of α-(1,2) branching to dextrans has been reported. A glucosyltransferase (DsrE) from *Leuconostoc mesenteroides* NRRL B-1299 has a $2^{nd}$ catalytic domain ("CD2") capable of adding α-(1,2) branching to dextrans (U.S. Pat. Nos. 7,439,049 and 5,141,858; Published U.S. Patent Appl. Pub. No. 2009-0123448; and Bozonette et al., *J. Bacteriol.* (2002) 184(20):5723-573). U.S. Patent Appl. Pub. No. 2010-0284972 describes methods and compositions for improving the health of a subject by administering compositions comprising α-(1,2) branched α-(1,6) dextrans. Sarbini et al. (*Appl. Envion. Microbiol.* (2011) 77(15):5307-5315) describes in vitro fermentation of dextran and α-(1,2) branched dextrans by the human fecal microbiota. Brison et al. (*J. Biol. Chem.*, (2012) 287(11): 7915-7924) describes a truncated form of the DsrE glucosyltransferase from *Leuconostoc mesenteroides* NRRL B-1299 (a glucan binding domain (GBD) coupled to the second catalytic domain, CD2 (i.e., GBD-CD2)) that is capable of adding α-(1,2) branching to dextrans.

Various saccharide oligomer compositions have been reported in the art. For example, U.S. Pat. No. 6,486,314 discloses an α-glucan comprising at least 20, up to about 100,000 α-anhydroglucose units, 38-48% of which are 4-linked anhydroglucose units, 17-28% are 6-linked anhydroglucose units, and 7-20% are 4,6-linked anhydroglucose units and/or gluco-oligosaccharides containing at least two 4-linked anhydroglucose units, at least one 6-linked anhydroglucose unit and at least one 4,6-linked anhydroglucose unit. U.S. Patent Appl. Pub. No. 2010-0284972A1 discloses a composition for improving the health of a subject comprising an α-(1,2)-branched α-(1,6) oligodextran. U.S. Patent Appl. Pub. No. 2011-0020496A1 discloses a branched dextrin having a structure wherein glucose or isomaltooligosaccharide is linked to a non-reducing terminal of a dextrin through an α-(1,6) glycosidic bond and having a DE of 10 to 52. U.S. Pat. No. 6,630,586 discloses a branched maltodextrin composition comprising 22-35% (1,6) glycosidic linkages; a reducing sugars content of <20%; a polymolecularity index (Mp/Mn) of <5; and number average molecular weight (Mn) of 4500 g/mol or less. U.S. Pat. No. 7,612,198 discloses soluble, highly branched glucose polymers, having a reducing sugar content of less than 1%, a level of α-(1,6) glycosidic bonds of between 13 and 17% and a molecular weight having a value of between $0.9 \times 10^5$ and $1.5 \times 10^5$ daltons, wherein the soluble highly branched glucose polymers have a branched chain length distribution profile of 70 to 85% of a degree of polymerization (DP) of less than 15, of 10 to 14% of DP of between 15 and 25 and of 8 to 13% of DP greater than 25.

Saccharide oligomers and/or carbohydrate compositions comprising the oligomers have been described as suitable for use as a source of soluble fiber in food applications (U.S. Pat. No. 8,057,840 and U.S. Patent Appl. Pub. Nos. 2010-0047432A1 and 2011-0081474A1). U.S. Patent Appl. Pub. No. 2012-0034366A1 discloses low sugar, fiber-containing carbohydrate compositions which are reported to be suitable for use as substitutes for traditional corn syrups, high fructose corn syrups, and other sweeteners in food products.

There remains a need to develop new soluble α-glucan fiber compositions that are digestion resistant, fermentation resistant by microbiota in the lower gastrointestinal tract, have low viscosity, and are suitable for use in foods and other applications. Preferably the α-glucan fiber compositions can be enzymatically produced from sucrose using enzymes already associated with safe use in humans.

SUMMARY OF THE INVENTION

An α-glucan soluble fiber composition comprising α-(1,2) branching is provided that is suitable for use in a variety of applications including, but not limited to, food applications, compositions to improve gastrointestinal health, and personal care compositions. The soluble fiber composition may be directly used as an ingredient in food or may be incorporated into carbohydrate compositions suitable for use in food applications.

A process for producing the soluble glucan fiber composition is also provided.

Methods of using the soluble fiber composition or carbohydrate compositions comprising the soluble fiber composition in food applications are also provided. In certain aspects, methods are provided for improving the health of a subject comprising administering the present soluble fiber composition to a subject in an amount effective to exert at least one health benefit typically associated with soluble dietary fiber such as altering the caloric content of food, decreasing the glycemic index of food, altering fecal weight, altering cholesterol metabolism, and possibly providing prebiotic effects.

A soluble fiber composition is provided comprising on a dry solids basis the following:
a. a range of:
  i. 0% to 50% of α-(1,3) glycosidic linkages; or
  ii. 0% to 40% α-(1,4) glycosidic linkages; or
  iii. any combination of i) and ii);
b. 1 to 50% of a combination of α-(1,2) and α-(1,2,6) glycosidic linkages;
c. 0-25% α-(1,3,6) glycosidic linkages;
d. less than 99% α-(1,6) glycosidic linkages;
e. a weight average molecular weight of less than 300 kDa;
f. a viscosity of less than 0.25 Pascal second (Pa·s) at 12 wt % in water at 20° C.;
g. a digestibility of less than 20% as measured by the Association of Analytical Communities (AOAC) method 2009.01;
h. a solubility of at least 20% (w/w) in pH 7 water at 25° C.; and
i. a polydispersity index of less than 26.

In one embodiment, the soluble α-glucan fiber composition comprises less than 10% reducing sugars.

In a further embodiment, the sum of the α-(1,3) and α-(1,3,6) glycosidic linkages in the soluble α-glucan fiber composition as described above ranges from 3 to 50%.

In a further embodiment, the soluble α-glucan fiber composition as described above comprises 15-35% α-(1,4) glycosidic linkages. In a further embodiment, a carbohydrate composition comprising:
0.01 to 99 wt % (dry solids basis) of the soluble α-glucan fiber composition as described above is provided.

In another embodiment, a food product, a personal care product or a pharmaceutical product is provided comprising the soluble α-glucan fiber composition or the carbohydrate composition as described above.

In another embodiment, a method to produce an α-glucan fiber composition is provided comprising:
a. providing a set of reaction components comprising:
  i. sucrose;
  ii. an α-glucan substrate having a weight average molecular weight of at least 0.5 kDa, said α-glucan substrate comprising at least 50% α-(1,6) glycosidic linkages;
  iii. a polypeptide comprising an amino acid sequence having at least 90% identity to SEQ ID NO: 6; said polypeptide capable of catalyzing the synthesis of α-(1,2) glycosidic linkages on the α-glucan substrate; and
  iv. optionally one or more acceptors;
b. combining the set of reaction components under suitable aqueous reaction conditions whereby the polypeptide catalyzes the synthesis of an α-glucan fiber composition comprising 1 to 50% α-(1,2) glycosidic linkages; and
c. optionally isolating the α-glucan fiber composition.

In a further embodiment, the above method further comprises a step (d): concentrating the α-glucan fiber composition.

In another embodiment, a method to produce an α-glucan fiber composition is provided comprising:
a. contacting sucrose with at least one glucosyltransferase or a combination of at least one glucosyltransferase and at least one α-glucanohydrolase under suitable aqueous reaction conditions whereby an α-glucan substrate is produced having a weight average molecular weight of at least 0.5 kDa, said α-glucan substrate comprising at least 50% α-(1,6) glycosidic linkages; wherein said α-glucan substrate comprises less than 1% α-(1,2) glycosidic linkages;
b. contacting the α-glucan substrate produced in (a) with a set of reaction components comprising
  i. a polypeptide comprising an amino acid sequence having at least 90% identity to SEQ ID NO: 6; said polypeptide capable of catalyzing the synthesis of α-(1,2) glycosidic linkages on the α-glucan substrate;
  ii. sucrose; and
  iii. optionally one or more acceptors;
c. combining the set of reaction components under suitable aqueous reaction conditions whereby the polypeptide catalyzes the synthesis of an α-glucan fiber composition comprising 1 to 50% α-(1,2) glycosidic linkages; and
d. optionally isolating the α-glucan fiber composition of step (c).

In another embodiment, a method to produce an α-glucan fiber composition is provided comprising:

a. contacting a maltodextrin substrate with
   i. a dextrin dextranase or
   ii. a combination of a dextrin dextranase and at least one α-glucanohydrolase under suitable aqueous reaction conditions; whereby an α-glucan substrate backbone is produced having a weight average molecular weight of at least 0.5 kDa, said α-glucan substrate comprising at least 50% α-(1,6) glycosidic linkages; wherein said α-glucan substrate comprises less than 1% α-(1,2) glycosidic linkages;
b. contacting the α-glucan substrate backbone produced in (a) with a set of reaction components comprising
   i. a polypeptide comprising an amino acid sequence having at least 90% identity to SEQ ID NO: 6; said polypeptide capable of catalyzing the synthesis of α-(1,2) glycosidic linkages on the α-glucan substrate;
   ii. sucrose; and
   iii. optionally one or more acceptors;
c. combining the set of reaction components of (b) under suitable aqueous reaction conditions whereby the polypeptide catalyzes the synthesis of an α-glucan fiber composition comprising 1 to 50% α-(1,2) glycosidic linkages; and
d. optionally isolating the α-glucan fiber composition of step (c).

In another embodiment, a method to produce an α-glucan fiber composition is provided comprising:
a. providing a set of reaction components comprising
   i. a maltodextrin substrate;
   ii. a dextrin dextrinase;
   iii. a polypeptide comprising an amino acid sequence having at least 90% identity to SEQ ID NO: 6; said polypeptide capable of catalyzing the synthesis of α-(1,2) glycosidic linkages on an α-glucan substrate;
   iv. sucrose; and
   v. optionally one or more acceptors;
b. combining the set of reaction components under suitable aqueous reaction conditions whereby an α-glucan fiber composition comprising 1 to 50% α-(1,2) glycosidic linkages is formed; and
c. optionally isolating the α-glucan fiber composition of step (b).

In another embodiment, a method to make a blended carbohydrate composition is provided comprising combining the soluble α-glucan fiber composition as described above with: a monosaccharide, a disaccharide, glucose, sucrose, fructose, leucrose, corn syrup, high fructose corn syrup, isomerized sugar, maltose, trehalose, panose, raffinose, cellobiose, isomaltose, honey, maple sugar, a fruit-derived sweetener, sorbitol, maltitol, isomaltitol, lactose, nigerose, kojibiose, xylitol, erythritol, dihydrochalcone, stevioside, α-glycosyl stevioside, acesulfame potassium, alitame, neotame, glycyrrhizin, thaumantin, sucralose, L-aspartyl-L-phenylalanine methyl ester, saccharine, maltodextrin, starch, potato starch, tapioca starch, dextran, soluble corn fiber, a resistant maltodextrin, a branched maltodextrin, inulin, polydextrose, a fructooligosaccharide, a galactooligosaccharide, a xylooligosaccharide, an arabinoxylooligosaccharide, a nigerooligosaccharide, a gentiooligosaccharide, hemicellulose, fructose oligomer syrup, an isomaltooligosaccharide, a filler, an excipient, a binder, or any combination thereof.

In another embodiment, a method to reduce the glycemic index of a food or beverage is provided comprising incorporating into the food or beverage the present soluble α-glucan fiber composition.

In another embodiment, a method of inhibiting the elevation of blood-sugar level in a mammal is provided comprising administering the present soluble α-glucan fiber composition to the mammal.

In another embodiment, a method of lowering lipids in the living body of a mammal is provided comprising administering the present soluble α-glucan fiber composition to the mammal.

In another embodiment, a method of treating constipation in a mammal is provided comprising administering the present soluble α-glucan fiber composition to the mammal.

In another embodiment, a method to alter fatty acid production in the colon of a mammal is provided comprising a step of administering the present soluble α-glucan fiber composition to the mammal; preferably wherein the short chain fatty acid production is increased and/or the branched chain fatty acid production is decreased.

In another embodiment, a low cariogenicity composition is provided comprising the present soluble α-glucan fiber composition and at least one polyol.

In another embodiment, the use of the present soluble α-glucan fiber composition in a food composition suitable for consumption by animals, including humans is also provided.

BRIEF DESCRIPTION OF THE BIOLOGICAL SEQUENCES

The following sequences comply with 37 C.F.R. §§ 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the European Patent Convention (EPC) and the Patent Cooperation Treaty (PCT) Rules 5.2 and 49.5 (α-bis), and Section 208 and Annex C of the Administrative Instructions. The symbols and format used for nucleotide and amino acid sequence data comply with the rules set forth in 37 C.F.R. § 1.822.

SEQ ID NO: 1 is the amino acid sequence of the GtfJ18 glucosyltransferase from *Leuconostoc mesenteroides* subsp. *mesenteroides* J18 as reported in GENBANK® gi:356644413 having 2771 amino acids.

SEQ ID NO: 2 is the amino acid sequence of the DsrE protein from *Leuconostoc mesenteroides* NRRL 1299 as reported in GENBANK® gi:23320943 (Bozonnet et al., *J. Bacteriol.* 184:5763 (2002)).

SEQ ID NO: 3 is the polynucleotide sequence encoding the mature *Leuconostoc mesenteroides* subsp. *mesenteroides* J18 GtfJ18 protein without the native signal sequence for expression in *E. coli* BL21 DE3 (wherein the resulting strain recombinantly producing the protein is referred to as "EC0059").

SEQ ID NO: 4 is the amino acid sequence of the mature *Leuconostoc mesenteroides* subsp. *mesenteroides* J18 GtfJ18 protein referred to herein as "mature GtfJ18" or "EC0059" (from the respective *E. coli* strain producing the protein).

SEQ ID NO: 5 is the polynucleotide sequence encoding a truncated version of the GtfJ18 protein from *Leuconostoc mesenteroides* subsp. *mesenteroides* J18 comprising part of a glucan binding domain (GBD) and the CD2 catalytic domain having α-(1,2) branching activity (amino acid residues 1664-2771 of SEQ ID NO: 7) as expressed in *E. coli* BL21 DE3 strain referred to herein as "EC0059T1".

SEQ ID NO: 6 is the amino acid sequence of the truncated GtfJ18 protein having α-(1,2) branching activity referred to herein as "gtfJ18T1" or "EC0059T1" (the respective *E. coli* strain producing the truncated protein).

SEQ ID NO: 7 is the amino acid sequence of a *Streptococcus criceti* HS-6 GtfS glucosyltransferase as found in GENBANK® gi: 357235604 (precursor with the native signal sequence) also referred to herein as "GTF5604". The same amino acid sequence is reported under GENBANK® gi:4691428 for a glucosyltransferase from *Streptococcus criceti*. As such, this particular amino acid sequence is also referred to herein as "GTF1428". Alternatively, the enzyme may also be referred to herein as SG1018 (from the respective *Bacillus subtilis* strain used to express GTF5604).

SEQ ID NO: 8 is the polynucleotide sequence encoding the full length wild type sequence (including the native signal sequence) of the *Streptococcus criceti* HS-6 GtfS glucosyltransferase GTF5604 that was cloned and expressed in *Bacillus* expression vector pHYT.

SEQ ID NO: 9 is the amino acid sequence of a *Streptococcus downei* GtfS glucosyltransferase as found in GENBANK® gi: 121729 (precursor with the native signal sequence) also referred to herein as "GTF1729" or "SG1006" (the respective *Bacillus subtilis* strain expressing GTF1729).

SEQ ID NO: 10 is the amino acid sequence of a *Streptococcus salivarius* M18 glucosyltransferase derived from GENBANK® gi: 345526831 (also referred to herein as "GTF6831") where the native signal sequence was substituted with the AprE signal sequence for expression in *Bacillus subtilis*. The enzyme may also be referred to herein as "SG1031" (referring to the respective *Bacillus subtilis* strain expressing GTF6831.

SEQ ID NO: 11 is the amino acid sequence of a *Streptococcus sobrinus* glucosyltransferase derived from GENBANK® gi: 22138845 (also referred to herein as "GTF8845") where the native signal sequence was substituted with the AprE signal sequence (SEQ ID NO: 34) for expression in *Bacillus subtilis*. The enzyme may also be referred to herein as "SG1051" (referring to the respective *Bacillus subtilis* strain expressing GTF8845.

SEQ ID NO: 12 is the amino acid sequence encoding the truncated *Streptococcus mutans* glucosyltransferase referred to herein as "GTF0088" or "SG1066" (referring to the respective *Bacillus subtilis* strain expressing GTF0088.)

SEQ ID NO: 13 is the amino acid sequence of a *Lactobacillus animalis* KCTC 3501 glucosyltransferase derived from GENBANK® gi: 335358117 (also referred to herein as "GTF8117") where the native signal sequence was substituted with the AprE signal sequence for expression in *Bacillus subtilis*. The enzyme may also be referred to herein as "SG1115" (referring to the respective *Bacillus subtilis* strain expressing GTF8117).

SEQ ID NO: 14 is the amino acid sequence of the *Streptococcus mutans* NN2025 Gtf-B glucosyltransferase as found in GENBANK® gi: 290580544.

SEQ ID NO: 15 is the nucleic acid sequence encoding a truncated *Streptococcus mutans* NN2025 Gtf-B (GENBANK® gi: 290580544) glucosyltransferase.

SEQ ID NO: 16 is the amino acid sequence of the truncated *Streptococcus mutans* NN2025 Gtf-B glucosyltransferase (also referred to herein as the "0544 glucosyltransferase" or "GTF0544").

SEQ ID NO: 17 is the amino acid sequence of the *Streptococcus salivarius* Gtf-J glucosyltransferase as found in GENBANK® gi: 47527.

SEQ ID NO: 18 is the polynucleotide sequence encoding the *Streptococcus salivarius* mature Gtf-J glucosyltransferase.

SEQ ID NO: 19 is the amino acid sequence of *Streptococcus salivarius* Gtf-J mature glucosyltransferase (referred to herein as the "7527" glucosyltransferase" or "GTF7527")).

SEQ ID NO: 20 is the nucleic acid sequence encoding the *Paenibacillus humicus* mutanase (GENBANK® gi: 257153265 where GENBANK® gi: 257153264 is the corresponding polynucleotide sequence) expressed in *E. coli* BL21(DE3).

SEQ ID NO: 21 is the amino acid sequence of the mature *Paenibacillus humicus* mutanase (GENBANK® gi: 257153264; referred to herein as the "3264 mutanase" or "MUT3264") expressed in *E. coli* BL21(DE3).

SEQ ID NO: 22 is the nucleic acid sequence encoding the *Penicillium mameffei* ATCC® 18224™ mutanase.

SEQ ID NO: 23 is the amino acid sequence of the *Penicillium mameffei* ATCC® 18224™ mutanase (GENBANK® gi: 212533325; also referred to herein as the "3325 mutanase" or "MUT3325").

SEQ ID NO: 24 is the polynucleotide sequence of plasmid pTrex.

SEQ ID NO: 25 is the polynucleotide sequence encoding the dextrin dextranase from *Gluconobacter oxydans*.

SEQ ID NO: 26 is the amino acid sequence of the dextrin dextranase (EC 2.4.1.2) expressed by a strain *Gluconobacter oxydans* referred to herein as "DDase" (see JP2007181452 (A)).

SEQ ID NO: 27 is the polynucleotide sequence of *E. coli* malQ.

SEQ ID NO: 28 is the polynucleotide sequence of *E. coli* malS.

SEQ ID NO: 29 is the polynucleotide sequence of *E. coli* malP.

SEQ ID NO: 30 is the polynucleotide sequence of *E. coli* malZ.

SEQ ID NO: 31 is the polynucleotide sequence of *E. coli* amyA.

SEQ ID NO: 32 is a polynucleotide sequence of a terminator sequence.

SEQ ID NO: 33 is a polynucleotide sequence of a linker sequence.

SEQ ID NO: 34 is the amino acid sequence of the *B. subtilis* AprE signal peptide used in the expression vector that was coupled to various enzymes for expression in *B. subtilis*.

SEQ ID NOs 35-43 and 52-67 are nucleic acid sequences or amino acid sequences of various glucosyltransferases.

SEQ ID NOs: 44-51 are nucleic acid sequence or amino acid sequences of various mutanases.

SEQ ID NO: 35 is the amino acid sequence of *Streptococcus salivarius* Gtf-L glucosyltransferase as found in GENBANK® gi: 662379.

SEQ ID NO: 36 is the nucleic acid sequence encoding a truncated *Streptococcus salivarius* Gtf-L (GENBANK® gi: 662379) glucosyltransferase.

SEQ ID NO: 37 is the amino acid sequence of the truncated *Streptococcus salivarius* Gtf-L glucosyltransferase (also referred to herein as the "2379 glucosyltransferase" or "GTF2379").

SEQ ID NO: 38 is the amino acid sequence of the *Streptococcus sobrinus* Gtf-I glucosyltransferase as found in GENBANK® gi: 450874.

SEQ ID NO: 39 is the nucleic acid sequence encoding a truncated *Streptococcus sobrinus* Gtf-I (GENBANK® gi: 450874) glucosyltransferase.

SEQ ID NO: 40 is the amino acid sequence of the truncated *Streptococcus sobrinus* Gtf-I glucosyltransferase (also referred to herein as the "0874 glucosyltransferase" or "GTF0874").

SEQ ID NO: 41 is the amino acid sequence of the *Streptococcus* sp. C150 Gtf-S glucosyltransferase as found in GENBANK® gi: 495810459 (previously known as GENBANK® gi: 322373279)

SEQ ID NO: 42 is the nucleic acid sequence encoding a truncated *Streptococcus* sp. C150 gtf-S (GENBANK® gi: 495810459) glucosyltransferase.

SEQ ID NO: 43 is the amino acid sequence of the truncated *Streptococcus* sp. C150 Gtf-S glucosyltransferase (also referred to herein as the "0459 glucosyltransferase", "GTF0459", "3279 glucosyltransferase" or "GTF3279").

SEQ ID NO: 44 is the nucleic acid sequence encoding the *Aspergillus nidulans* FGSC A4 mutanase.

SEQ ID NO: 45 is the amino acid sequence of the *Aspergillus nidulans* FGSC A4 mutanase (GENBANK® gi: 259486505; also referred to herein as the "6505 mutanase" or "MUT6505").

SEQ ID NO: 46 is the nucleic acid sequence encoding a Hypocrea tawa mutanase.

SEQ ID NO: 47 is the amino acid sequence of the Hypocrea tawa mutanase as disclosed in U.S. Patent Appl. Pub. No. 2011-0223117A1 (also referred to herein as the "*H. tawa* mutanase").

SEQ ID NO: 48 is the nucleic acid sequence encoding the *Trichoderma konilangbra* mutanase.

SEQ ID NO: 49 is the amino acid sequence of the *Trichoderma konilangbra* mutanase as disclosed in U.S. Patent Appl. Pub. No. 2011-0223117A1 (also referred to herein as the "*T. konilangbra* mutanase").

SEQ ID NO: 50 is the nucleic acid sequence encoding the *Trichoderma reesei* RL-P37 mutanase.

SEQ ID NO: 51 is the amino acid sequence of the *Trichoderma reesei* RL-P37 mutanase as disclosed in U.S. Patent Appl. Pub. No. 2011-0223117A1 (also referred to herein as the "*T. reesei* 592 mutanase").

SEQ ID NO: 52 is the nucleic acid sequence encoding a truncated *Streptococcus oralis* glucosyltransferase (GENBANK® gi:7684297).

SEQ ID NO: 53 is the amino acid sequence encoding the truncated *Streptococcus oralis* glucosyltransferase referred to herein as "GTF4297".

SEQ ID NO: 54 is the nucleic acid sequence encoding a truncated version of the *Streptococcus mutans* glucosyltransferase (GENBANK® gi:24379358).

SEQ ID NO: 55 is the amino acid sequence encoding the truncated *Streptococcus mutans* glucosyltransferase referred to herein as "GTF9358".

SEQ ID NO: 56 is the nucleic acid sequence encoding a truncated version of the *Streptococcus gallolyticus* glucosyltransferase (GENBANK® gi:32597842).

SEQ ID NO: 57 is the amino acid sequence encoding the truncated *Streptococcus gallolyticus* glucosyltransferase referred to herein as "GTF7842".

SEQ ID NO: 58 is the amino acid sequence of the *Lactobacillus reuteri* glucosyltransferase as found in GENBANK® gi:51574154.

SEQ ID NO: 59 is the nucleic acid sequence encoding a truncated version of the *Lactobacillus reuteri* glucosyltransferase (GENBANK® gi:51574154).

SEQ ID NO: 60 is the amino acid sequence encoding the truncated *Lactobacillus reuteri* glucosyltransferase referred to herein as "GTF4154".

SEQ ID NO: 61 is the amino acid sequence of a *Streptococcus gordonii* glucosyltransferase derived from GENBANK® gi: 1054877 (also referred to herein as "GTF4877") where the native signal sequence was substituted with the AprE signal sequence for expression in *Bacillus subtilis*.

SEQ ID NO: 62 is the amino acid sequence of the *Streptococcus downei* glucosyltransferase as found in GENBANK® gi: 121724.

SEQ ID NO: 63 is the nucleic acid sequence encoding a truncated *Streptococcus downei* (GENBANK® gi: 121724) glucosyltransferase.

SEQ ID NO: 64 is the amino acid sequence of the truncated *Streptococcus downei* glucosyltransferase (also referred to herein as the "1724 glucosyltransferase" or "GTF1724").

SEQ ID NO: 65 is the amino acid sequence of the *Streptococcus dentirousetti* glucosyltransferase as found in GENBANK® gi: 167735926.

SEQ ID NO: 66 is the nucleic acid sequence encoding a truncated *Streptococcus dentirousetti* (GENBANK® gi: 167735926) glucosyltransferase.

SEQ ID NO: 67 is the amino acid sequence of the truncated *Streptococcus dentirousetti* glucosyltransferase (also referred to herein as the "5926 glucosyltransferase" or "GTF5926").

SEQ ID NO: 68 is the amino acid sequence of a "GTFB-type" glucosyltransferase from *Lactobacillus reuteri* GENBANK® gi: 189485784 (also referred to as a "4,6-α-glucanotransferase") structurally related to members of the family 70 glycoside hydrolase glucansucrase enzymes (GH70) capable of synthesizing linear isomalto/maltooligosaccharides from maltooligosaccharides.

SEQ ID NO: 69 is the amino acid sequence of a 4,6-α-glucanotransferase from *Lactobacillus reuteri* ML1 GENBANK® gi: 357208772 structurally related to members of the family 70 glycoside hydrolase glucansucrase enzymes (GH70) capable of synthesizing linear isomalto/maltooligosaccharides from maltooligosaccharides.

SEQ ID NO: 70 is the amino acid sequence of a 4,6-α-glucanotransferase from *Lactobacillus reuteri* JCM 1112 GENBANK® gi: 189485784 structurally related to members of the family 70 glycoside hydrolase glucansucrase enzymes (GH70) capable of synthesizing linear isomalto/maltooligosaccharides from maltooligosaccharides.

SEQ ID ON: 71 is the amino acid sequence of a *Neisseria polysaccharea* amylosucrase (E.C. 2.4.1.4) (GENBANK® gi: 4107260) capable of synthesizing maltooligosaccharides from sucrose and an 1,4-alpha-D-glucosyl substrate using the following reaction:

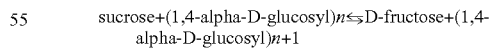

DETAILED DESCRIPTION OF THE INVENTION

In this disclosure, a number of terms and abbreviations are used. The following definitions apply unless specifically stated otherwise.

As used herein, the articles "a", "an", and "the" preceding an element or component of the invention are intended to be nonrestrictive regarding the number of instances (i.e., occurrences) of the element or component. Therefore "a", "an", and "the" should be read to include one or at least one, and the singular word form of the element or component also includes the plural unless the number is obviously meant to be singular.

As used herein, the term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein, the term "obtainable from" shall mean that the source material (for example, sucrose) is capable of being obtained from a specified source, but is not necessarily limited to that specified source.

As used herein, the term "effective amount" will refer to the amount of the substance used or administered that is suitable to achieve the desired effect. The effective amount of material may vary depending upon the application. One of skill in the art will typically be able to determine an effective amount for a particular application or subject without undo experimentation.

As used herein, the term "isolated" means a substance in a form or environment that does not occur in nature. Non-limiting examples of isolated substances include (1) any non-naturally occurring substance, (2) any substance including, but not limited to, any host cell, enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated.

As used herein, the terms "very slow to no digestibility", "little or no digestibility", and "low to no digestibility" will refer to the relative level of digestibility of the soluble glucan fiber as measured by the Association of Official Analytical Chemists International (AOAC) method 2009.01 ("AOAC 2009.01"; McCleary et al. (2010) *J. AOAC Int.*, 93(1), 221-233); where little or no digestibility will mean less than 12% of the soluble glucan fiber composition is digestible, preferably less than 5% digestible, more preferably less than 1% digestible on a dry solids basis (d.s.b.). In another aspect, the relative level of digestibility may be alternatively be determined using AOAC 2011.25 (Integrated Total Dietary Fiber Assay) (McCleary et al., (2012) *J. AOAC Int.*, 95 (3), 824-844.

As used herein, term "water soluble" will refer to the present glucan fiber composition comprised of fibers that are soluble at 20 wt % or higher in pH 7 water at 25° C.

As used herein, the terms "soluble fiber", "soluble glucan fiber", "α-glucan fiber", "cane sugar fiber", "glucose fiber", "soluble dietary fiber", and "soluble glucan fiber composition" refer to the present fiber composition comprised of water soluble glucose oligomers having a glucose polymerization degree of 3 or more that is digestion resistant (i.e., exhibits very slow to no digestibility) with little or no absorption in the human small intestine and is at least partially fermentable in the lower gasterointestinal tract. Digestibility of the soluble glucan fiber composition is measured using AOAC method 2009.01. The present soluble fiber is obtained by the addition of α-(1,2) glycosidic linkages to an α-glucan substrate ("backbone") comprising an effective amount of α-(1,6) glycosidic linkages in the backbone. In one embodiment, the effective amount of α-(1,6) linkages in the α-(1,6) glucan substrate is at least 50%, 60%, 70%, 80%, 90%, 95% or 98% or all α-glycosidic linkages in the molecule. In one embodiment, the present soluble glucan fiber composition is enzymatically synthesized from sucrose (α-D-Glucopyranosyl β-D-fructofuranoside; CAS #57-50-1) obtainable from, for example, sugarcane and/or sugar beets. In another embodiment, the α-glucan substrate ("backbone") having an effective amount of α-(1,6) glycosidic linkages is synthesized from maltodextrins obtainable from processed starch using an enzyme such as a dextrin dextranase where α-(1,2) glycosidic linkages are added using a source of sucrose and a polypeptide having α-(1,2) branching activity. In one embodiment, the α-glucan substrate is first synthesized and then contacted with the polypeptide having α-(1,2) branching activity (sequential reaction design). In another embodiment, the enzyme(s) responsible for synthesizing the α-glucan substrate backbone and the polypeptide having α-(1,2) branching activity are present in the same reaction mixture using an effective amount of sucrose (i.e., a concomitant reaction). In one embodiment, the concomitant reaction comprises a suitable maltodextrins capable of being used as a substrate for a dextrin dextranase, a dextrin dextranase capable of synthesizing an α-glucan comprising an effective amount of α-(1,6) glycosidic linkages, a polypeptide having α-(1,2) branching activity, and an effective amount of sucrose for the additional of α-(1,2) branching. In another embodiment, the sequential or concomitant reactions described above may further comprise an α-glucosidase having endohydrolysis (e.g., a mutanase or dextrinase having endohydrolysis activity). In a preferred embodiment, enzyme(s) used to synthesize the α-glucan substrate "backbone" are selected to produce an α-glucan substrate comprising 1 to 50% α-(1,3) glycosidic linkages, more than 10% but less than 40% α-(1,4) glycosidic linkages, or any combination thereof so long as the polypeptide having α-(1,2) branching activity can introduce α-(1,2) glycosidic linkage to the α-glucan substrate.

As used herein, "weight average molecular weight" or "$M_w$" is calculated as $M_w = \Sigma N_i M_i^2 / \Sigma N_i M_i$; where $M_i$ is the molecular weight of a chain and $N_i$ is the number of chains of that molecular weight. The weight average molecular weight can be determined by technics such as static light scattering, small angle neutron scattering, X-ray scattering, and sedimentation velocity.

As used herein, "number average molecular weight" or "$M_n$" refers to the statistical average molecular weight of all the polymer chains in a sample. The number average molecular weight is calculated as $M_n = \Sigma N_i M_i / \Sigma N_i$ where $M_i$ is the molecular weight of a chain and $N_i$ is the number of chains of that molecular weight. The number average molecular weight of a polymer can be determined by technics such as gel permeation chromatography, viscometry via the (Mark-Houwink equation), and colligative methods such as vapor pressure osmometry, end-group determination or proton NMR.

As used herein, "polydispersity index", "PDI", "heterogeneity index", and "dispersity" refer to a measure of the distribution of molecular mass in a given polymer (such as a glucose oligomer) sample and can be calculated by dividing the weight average molecular weight by the number average molecular weight ($PDI = M_w/M_n$).

It shall be noted that the terms "glucose" and "glucopyranose" as used herein are considered as synonyms and used interchangeably. Similarly the terms "glucosyl" and "glucopyranosyl" units are used herein are considered as synonyms and used interchangeably.

As used herein, "glycosidic linkages" or "glycosidic bonds" will refer to the covalent the bonds connecting the sugar monomers within a saccharide oligomer (oligosaccharides and/or polysaccharides). Example of glycosidic linkage may include α-linked glucose oligomers with 1,6-α-D-glycosidic linkages (herein also referred to as α-D-(1,6) linkages or simply "α-(1,6)" linkages); 1,3-α-D-glycosidic linkages (herein also referred to as α-D-(1,3) linkages or simply "α-(1,3)" linkages; 1,4-α-D-glycosidic linkages (herein also referred to as α-D-(1,4) linkages or simply "α-(1,4)" linkages; 1,2-α-D-glycosidic linkages (herein also referred to as α-D-(1,2) linkages or simply "α-(1,2)" linkages; and combinations of such linkages typically associated with branched saccharide oligomers.

As used herein, "α-glucan substrate backbone", "glucan backbone", "glucan substrate backbone", "substrate backbone" or simply "backbone" will refer to the α-glucan substrate which is acted upon by a polypeptide having α-(1,2) branching activity in the presence of sucrose under suitable aqueous reaction conditions, wherein the net result of the reaction is the addition of at least one α-(1,2) linked glucan to the substrate backbone. Typically the glucan substrate backbone is comprised predominantly of α-1(,6) glycosidic linkages prior to initiating the branching reaction. In one embodiment, the glucan substrate backbone is substantially linear with predominantly α-1(,6) glycosidic linkages and will generally have less than 1% α-(1,2) linkages prior to initiating the branching reaction; especially when the branching reaction is conducted after the glucan substrate backbone has been synthesized. Once the branching reaction is initiated, the polypeptide having α-(1,2) branching activity adds α-(1,2) linked glucose residues to the glucan backbone. As multiple α-(1,2) linked glucose residues may be added during the reaction, the glucan substrate backbone will have an increasing amount (as a percentage of total linkages) of α-(1,2) linked glucan residues. As such, a suitable α-glucan substrate backbone may have more than 1% α-(1,2) linkages so long as the polypeptide having α-(1,2) branching activity is capable of adding additional α-(1,2) linked glucans to the substrate backbone. By proviso, the polypeptide having α-(1,2) branching activity will not include a catalytically active domain capable of adding glycosidic linkages other than α-(1,2) glycosidic linkages. The α-glucan substrate backbone will have a DP of at least 3 and will have at least 50%, preferably at least 60, 70, 80, 90, 95, 96, 97, 98, 99 or 100% α-(1,6) linkages prior to initiating the enzymatic α-(1,2) branching reaction. In one embodiment, the As used herein, the terms "glucansucrase", "glucosyltransferase", "glucoside hydrolase type 70", "GTF", and "GS" will refer to transglucosidases classified into family 70 of the glycoside-hydrolases typically found in lactic acid bacteria such as Streptococcus, Leuconostoc, Weisella or Lactobacillus genera (see Carbohydrate Active Enzymes database; "CAZy"; Cantarel et al., (2009) Nucleic Acids Res 37:D233-238). The GTF enzymes are able to polymerize the D-glucosyl units of sucrose to form homooligosaccharides or homopolysaccharides. Glucosyltransferases can be identified by characteristic structural features such as those described in Leemhuis et al. (J. Biotechnology (2013) 162: 250-272) and Monchois et al. (FEMS Micro. Revs. (1999) 23:131-151). Depending upon the specificity of the GTF enzyme, linear and/or branched glucans comprising various glycosidic linkages may be formed such as α-(1,2), α-(1,3), α-(1,4) and α-(1,6). Some glucosyltransferases may also transfer the D-glucosyl units onto hydroxyl acceptor groups. A non-limiting list of acceptors may include carbohydrates, alcohols, polyols or flavonoids. Specific acceptors may also include maltose, isomaltose, isomaltotriose, and methyl-α-D-glucan, to name a few. The structure of the resultant glucosylated product is dependent upon the enzyme specificity. Examples of glucosyltransferases are provided as amino acid SEQ ID NOs: 1, 2, 4, 6, 7, 9, 10, 11, 12, 13, 14, 16, 17, 19, 35, 37, 38, 40, 41, 43, 53, 55, 57, 58, 60, 61, 62, 64, and 67. In another embodiment, the glucosyltransferase comprises an amino acid sequence selected from the group consisting of 7, 9, 10, 11, 12, 13, 14, 16, and any combination thereof; wherein SEQ ID NO: 6 is a truncated version of a glucosyltransferase capable of adding α-(1,2) branching to a suitable α-glucan substrate backbone. In a further embodiment, a combination of at least one glucosyltransferase and at least one α-glucanohydrolase (such as mutanases and dextrinases described herein) having endohydrolysis activity is used to synthesize the α-glucan substrate "backbone" which can be modified using at least one polypeptide having α-(1,2) branching activity (i.e., SEQ ID NO: 6).

As used herein, the term "Gtf-B type" glucansucrase will refer to polypeptide having 4-6-α-glucosyltransferase activity, such as the GtfB-type glucosyltransferases, typically from strains of Lactobacillus reuteri. Examples include, but are not limited to, SEQ ID NOs 68, 69, and 70. It should be noted that the Gtf-B glucosyltransferase from Streptococcus mutans (SEQ ID NO: 14, 16) was originally annotated as Gtf-B, but it is not considered what is referred to herein as a "Gtf-B type" glucosyltransferase as it does not have 4,6-α-glucosyltransferase activity.

As used herein, the term "amylosucrase" will refer to an enzyme (E.C. 2.4.1.4) structurally related to GH70 glucosyltransferases that is capable of synthesizing maltooligosaccharides from sucrose and an 1,4-alpha-D-glucosyl substrate using the following reaction:

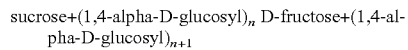

sucrose+(1,4-alpha-D-glucosyl)$_n$ D-fructose+(1,4-alpha-D-glucosyl)$_{n+1}$

An example of an amylosucrase is the Neisseria polysaccharea amylosucrase (GENBANK® gi: 4107260; provided herein as SEQ ID NO: 71).

As used herein, the term "polypeptide having α-(1,2) branching activity" or "enzyme catalyst having α-(1,2) branching activity" will refer to catalytically active glucosyltransferase (or fragment thereof) capable of introducing α-(1,2) glycosidic linkages (using sucrose as a substrate) to an α-glucan substrate "backbone" having an effective amount of α-(1,6) glycosidic linkages. In one embodiment, the polypeptide having α-(1,2) branching activity is a truncated glucosyltransferase comprising a catalytic domain capable of adding α-(1,2) branching to an α-glucan substrate backbone. In one embodiment, the catalytic domain capable of adding α-(1,2) branching further comprises at least one glucan binding domain. Preferably, the polypeptide having α-(1,2) branching activity is a truncated glucosyltransferase wherein the domain capable of synthesizing linkages other than α-(1,2) glycosidic linkage is not present (i.e., the backbone synthesizing domain or "CD1" domain found in enzymes such as the GtfJ18 glucosyltransferase from *Leuconostoc mesenteroides* subsp. *mesenteroides* J18, see GENBANK® gi:356644413 (SEQ ID NO: 1) and the DsrE glucosyltransferase from *Leuconostoc mesenteroides* NRRL-1299 as reported in GENBANK® gi:23320943; SEQ ID NO: 2). In a preferred embodiment, the polypeptide having α-(1,2) branching activity comprises an amino acid sequence having at least 80%, 85%, 90%, 91%, 92%, 93%, 94%, 95%, 96%, 97%, 98%, 99% or 100% amino acid identity to SEQ ID NO: 6. In a further preferred aspect, the polypeptide having α-(1,2) branching activity consists essentially of an amino acid sequence having at least 80%, 85%, 90%, 91%, 92%, 93%, 94%, 95%, 96%, 97%, 98%, 99% or 100% amino acid identity to SEQ ID NO: 6.

As used herein, the term "isomaltooligosaccharide" or "IMO" refers to a glucose oligomers comprised essentially of α-D-(1,6) glycosidic linkage typically having an average size of DP 2 to 20. Isomaltooligosaccharides can be produced commercially from an enzymatic reaction of α-amylase, pullulanase, β-amylase, and α-glucosidase upon corn starch or starch derivative products. Commercially available products comprise a mixture of isomaltooligosaccharides (DP ranging from 3 to 8, e.g., isomaltotriose, isomaltotetraose, isomaltopentaose, isomaltohexaose, isomaltoheptaose, isomaltooctaose) and may also include panose.

As used herein, the term "dextran" refers to water soluble α-glucans comprising at least 95% α-D-(1,6) glycosidic linkages (typically with up to 5% α-D-(1,3) glycosidic linkages at branching points) that are more than 10% digestible as measured by the Association of Official Analytical Chemists International (AOAC) method 2009.01 ("AOAC 2009.01"). Dextrans often have an average molecular weight above 1000 kDa. As used herein, enzymes capable of synthesizing dextran from sucrose may be described as "dextransucrases" (EC 2.4.1.5).

As used herein, the term "mutan" refers to water insoluble α-glucans comprised primarily (50% or more of the glycosidic linkages present) of 1,3-α-D glycosidic linkages and typically have a degree of polymerization (DP) that is often greater than 9. Enzymes capable of synthesizing mutan or α-glucan oligomers comprising greater than 50% 1,3-α-D glycosidic linkages from sucrose may be described as "mutansucrases" (EC 2.4.1.-) with the proviso that the enzyme does not produce alternan.

As used herein, the term "alternan" refers to α-glucans having alternating 1,3-α-D glycosidic linkages and 1,6-α-D glycosidic linkages over at least 50% of the linear oligosaccharide backbone. Enzymes capable of synthesizing alternan from sucrose may be described as "alternansucrases" (EC 2.4.1.140).

As used herein, the term "reuteran" refers to soluble α-glucan comprised 1,4-α-D-glycosidic linkages (typically >50%); 1,6-α-D-glycosidic linkages; and 4,6-disubstituted α-glucosyl units at the branching points. Enzymes capable of synthesizing reuteran from sucrose may be described as "reuteransucrases" (EC 2.4.1.-).

As used herein, the terms "α-glucanohydrolase" and "glucanohydrolase" will refer to an enzyme capable of hydrolyzing an α-glucan oligomer. As used herein, the glucanohydrolase may be defined by the endohydrolysis activity towards certain α-D-glycosidic linkages. Examples may include, but are not limited to, dextranases (EC 3.2.1.1; capable of endohydrolyzing α-(1,6)-linked glycosidic bonds), mutanases (EC 3.2.1.59; capable of endohydrolyzing α-(1,3)-linked glycosidic bonds), and alternanases (EC 3.2.1.-; capable of endohydrolytically cleaving alternan). Various factors including, but not limited to, level of branching, the type of branching, and the relative branch length within certain α-glucans may adversely impact the ability of an α-glucanohydrolase to endohydrolyze some glycosidic linkages.

As used herein, the term "dextranase" (α-1,6-glucan-6-glucanohydrolase; EC 3.2.1.11) refers to an enzyme capable of endohydrolysis of 1,6-α-D-glycosidic linkages (the linkage predominantly found in dextran). Dextranases are known to be useful for a number of applications including the use as ingredient in dentifrice for prevent dental caries, plaque and/or tartar and for hydrolysis of raw sugar juice or syrup of sugar canes and sugar beets. Several microorganisms are known to be capable of producing dextranases, among them fungi of the genera *Penicillium, Paecilomyces, Aspergillus, Fusarium, Spicaria, Verticillium, Helminthosporium* and *Chaetomium*; bacteria of the genera *Lactobacillus, Streptococcus, Cellvibrio, Cytophaga, Brevibacterium, Pseudomonas, Corynebacterium, Arthrobacter* and *Flavobacterium*, and yeasts such as Lipomyces starkeyi. Food grade dextranases are commercially available. An example of a food grade dextrinase is DEXTRANASE® Plus L, an enzyme from *Chaetomium erraticum* sold by Novozymes NS, Bagsvaerd, Denmark.

As used herein, the term "mutanase" (glucan endo-1,3-α-glucosidase; EC 3.2.1.59) refers to an enzyme which hydrolytically cleaves 1,3-α-D-glycosidic linkages (the linkage predominantly found in mutan). Mutanases are available from a variety of bacterial and fungal sources. Examples of mutanases are provided as SEQ ID NOs: 21, 23, 45, 47, 49, 51, and any combination thereof; wherein SEQ ID NOs: 21, 23 and combinations thereof is preferred.

As used herein, the term "alternanase" (EC 3.2.1.-) refers to an enzyme which endo-hydrolytically cleaves alternan (U.S. Pat. No. 5,786,196 to Cote et al.).

As used herein, the term "wild type enzyme" will refer to an enzyme (full length and active truncated forms thereof) comprising the amino acid sequence as found in the organism from which was obtained and/or annotated. The enzyme (full length or catalytically active truncation thereof) may be recombinantly produced in a microbial host cell. Depending upon the microbial host, minor modifications (typically the N- or C-terminus) may be introduced to facilitate expression of the desired enzyme in an active form. The enzyme is typically purified prior to being used as a processing aid in the production of the present soluble α-glucan fiber composition. In one aspect, a combination of at least two wild type enzymes concomitantly present in the reaction system is used in order to obtain the present soluble glucan fiber composition As used herein, the terms "substrate" and "suitable substrate" will refer an α-glucan substrate backbone capable of being modified (i.e., the addition of at least one α-(1,2) glycosidic linkage) under aqueous reaction conditions by the polypeptide having α-(1,2) branching activity in the presence of sucrose. The α-glucan substrate backbone can be synthesized (and optionally isolated) prior to the step of enzymatically introducing α-(1,2) branching or may be concomitantly synthesized in the presence of the α-(1,2) branching enzymes (i.e., glucan substrate backbone synthesis is conducted in the same reaction mixture with the polypeptide having α-(1,2) branching activity in the presence of an effective amount of sucrose. The α-glucan substrate may be produced in a variety of ways including, but not limited to, (1) synthesis from at least one glucosyltransferase (using a polypeptide that is different from the polypeptide having α-(1,2) branching activity) in the presence of sucrose, (2) synthesis from maltodextrin obtainable from starch or sucrose (e.g., maltodextrin substrate synthesized from sucrose using an amylosucrase) using a polypeptide having dextrin dextranase activity, a "Gtf-B type" GH70 glucosyltransferase, or a combination thereof, (3) synthesis using method (1) and/or (2) in the presence of at least one α-glucanohydrolase (i.e., dextranase, mutanase, or a combination thereof), and (4) and any combination of (1), (2) or (3) so long as the α-glucan substrate backbone is capable of being acted upon by the polypeptide having α-(1,2) branching activity. In a further embodiment, the α-glucan substrate maybe synthesized prior to the α-(1,2) branching step or may be synthesized concomitant with the α-(1,2) branching (i.e., the polypeptide having α-(1,2) branching activity and an effective amount of sucrose is present in the aqueous reaction mixture). In the context of synthesizing the α-glucan backbone using any of the above embodiments, the "substrate" may be sucrose, maltodextrin, or a combination thereof; optionally in the presence of one or more additional acceptors. In another embodiment, the substrate composition may further comprise one or more acceptors, such as maltose, isomaltose, isomaltotriose, and methyl-α-D-glucan, to name a few. In one preferred aspect, the α-glucan substrate backbone comprises at least 50% α-(1,6) glycosidic linkages. In a further preferred embodiment, the α-glucan substrate backbone comprises 1 to 50% α-(1,3) glycosidic linkages.

In one embodiment, the α-glucan substrate backbone is synthesized using a combination of at least one glucosyltransferase capable for forming glucose oligomers with at least one α-glucanohydrolase in the same reaction mixture (i.e., they are concomitantly present and active in the reaction mixture). As such the "substrate" for the α-glucanohydrolase is the glucose oligomers concomitantly being synthesized in the reaction system by the glucosyltransferase from sucrose. In one aspect, a two-enzyme method (i.e., at least one glucosyltransferase (GTF) and at least one α-glucanohydrolase) where the enzymes are not used concomitantly in the reaction mixture is excluded, by proviso, form the present methods.

As used herein, the terms "suitable enzymatic reaction mixture", "suitable reaction components", "suitable aqueous reaction mixture", and "reaction mixture", refer to the materials (suitable substrate(s)) and water in which the reactants come into contact with the enzyme(s). The suitable reaction components may be comprised of a plurality of enzymes. In one aspect, the suitable reaction components comprises at least one polypeptide having α-(1,2) branching activity, sucrose, and at least one α-glucan substrate having an effective amount of α-(1,6) glycosidic linkages. The α-glucan substrate having an effective amount of α-(1,6) glycosidic linkages in the "backbone" may be synthesized from (1) sucrose using at least one glucansucrase enzyme, (2) maltodextrins obtainable from processed starch or sucrose that have been contacted with at least one dextrin dextranase, at least one "Gtf-B type" glucosyltransferase, and combinations thereof or (3) any combination thereof. The α-glucan substrate "backbone" having an effective amount of α-(1,6) glycosidic linkages may be synthesized prior to enzymatically adding the α-(1,2) branching or may be synthesized concomitantly in the same reaction mixture comprising at least one polypeptide having α-(1,2) branching activity with the proviso that the polypeptide having α-(1,2) branching activity is not the same as the enzyme(s) used to synthesize the α-glucan substrate "backbone" having an effective amount of α-(1,6) glycosidic linkages. In a further aspect, the α-glucan substrate "backbone" to which α-(1,2) branching is added is produced using a single glucansucrase, a combination of glucansucrases, a combination of at least glucansucrase and at least one α-glucanohydrolase, a dextrin dextranase, a "GtfB type" glucosyltransferase (i.e., a 4,6-α-glucanotransferase; Kralj et al., *Appl. Env. Microbiol.* (2011) 77(22): 8154-8163), a combination of a dextrin dextranase and at least one α-glucanohydrolase, a combination of a "GtfB-type" glucosyltransferase and at least one α-glucanohydrolase, and any combination thereof.

As used herein, "one unit of glucansucrase activity" or "one unit of glucosyltransferase activity" is defined as the amount of enzyme required to convert 1 µmol of sucrose per minute when incubated with 200 g/L sucrose at pH 5.5 and 37° C. The sucrose concentration was determined using HPLC.

As used herein, "one unit of dextranase activity" is defined as the amount of enzyme that forms 1 µmol reducing sugar per minute when incubated with 0.5 mg/mL dextran substrate at pH 5.5 and 37° C. The reducing sugars were determined using the PAHBAH assay (Lever M., 1972, A New Reaction for Colorimetric Determination of Carbohydrates, *Anal. Biochem.* 47, 273-279).

As used herein, "one unit of mutanase activity" is defined as the amount of enzyme that forms 1 µmol reducing sugar per minute when incubated with 0.5 mg/mL mutan substrate at pH 5.5 and 37° C. The reducing sugars were determined using the PAHBAH assay (Lever M., supra).

As used herein, "one unit of dextrin dextranase activity" is defined as the amount of enzyme required to deplete 1 umol of amyloglucosidase-susceptible glucose equivalents when incubated with 25 g/L maltodextrin (DE 13-17) at pH 4.65 and 30° C. Amyloglucosidase-susceptible glucose equivalents are measured by 30 minute treatment at pH 4.65 and 60° C. with *Aspergillus niger* amyloglucosidase (Catalog #A7095, Sigma, 0.6 unit/mL), followed by HPLC quantitation of glucose formed upon amyloglucosidase treatment.

As used herein, the term "enzyme catalyst" refers to a catalyst comprising an enzyme or combination of enzymes having the necessary activity to obtain the desired soluble glucan fiber composition. In one embodiment the enzyme maybe alternatively referred to as a "polypeptide having" a specified activity. In certain embodiments, a combination of enzyme catalysts may be required to obtain the desired soluble glucan fiber composition. The enzyme catalyst(s) may be in the form of a whole microbial cell, permeabilized microbial cell(s), one or more cell components of a microbial cell extract(s), partially purified enzyme(s) or purified enzyme(s). The enzyme catalyst may be a truncated version of a wild type enzyme, so long as the desired activity is retained. In certain embodiments the enzyme catalyst(s) may also be chemically modified (such as by pegylation or by reaction with cross-linking reagents). The enzyme catalyst(s) may also be immobilized on a soluble or insoluble support using methods well-known to those skilled in the art; see for example, *Immobilization of Enzymes and Cells*; Gordon F. Bickerstaff, Editor; Humana Press, Totowa, NJ, USA; 1997.

As used herein, "pharmaceutically-acceptable" means that the compounds or compositions in question are suitable for use in contact with the tissues of humans and other animals without undue toxicity, incompatibility, instability, irritation, allergic response, and the like, commensurate with a reasonable benefit/risk ratio.

As used herein, the term "oligosaccharide" refers to homopolymers containing between 3 and about 30 monosaccharide units linked by α-glycosidic bonds.

As used herein the term "polysaccharide" refers to homopolymers containing greater than 30 monosaccharide units linked by α-glycosidic bonds.

As used herein, the term "food" is used in a broad sense herein to include a variety of substances that can be ingested by humans including, but not limited to, beverages, dairy products, baked goods, energy bars, jellies, jams, cereals, dietary supplements, and medicinal capsules or tablets.

As used herein, the term "pet food" or "animal feed" is used in a broad sense herein to include a variety of substances that can be ingested by nonhuman animals and may include, for example, dog food, cat food, and feed for livestock.

As used herein, "personal care products" means products used in the cosmetic treatment hair, skin, scalp, and teeth, including, but not limited to shampoos, body lotions, shower gels, topical moisturizers, toothpaste, tooth gels, mouthwashes, mouthrinses, anti-plaque rinses, and/or other topical treatments. In some particularly preferred embodiments, these products are utilized on humans, while in other embodiments, these products find cosmetic use with non-human animals (e.g., in certain veterinary applications).

As used herein, the terms "isolated nucleic acid molecule", "isolated polynucleotide", and "isolated nucleic acid fragment" will be used interchangeably and refer to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid or as defined herein | Xaa | X |

It would be recognized by one of ordinary skill in the art that modifications of amino acid sequences disclosed herein can be made while retaining the function associated with the disclosed amino acid sequences. For example, it is well known in the art that alterations in a gene which result in the production of a chemically equivalent amino acid at a given site, but do not affect the functional properties of the encoded protein are common. For example, any particular amino acid in an amino acid sequence disclosed herein may be substituted for another functionally equivalent amino acid. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, and Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products.

As used herein, the term "codon optimized", as it refers to genes or coding regions of nucleic acid molecules for transformation of various hosts, refers to the alteration of codons in the gene or coding regions of the nucleic acid molecules to reflect the typical codon usage of the host organism without altering the polypeptide for which the DNA codes.

As used herein, "synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as pertaining to a DNA sequence, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequences to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, "gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different from that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding sites, and stem-loop structures.

As used herein, the term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., the coding sequence is under the transcriptional control of the promoter. Coding sequences can be operably linked to regulatory sequences in sense or antisense orientation.

As used herein, the term "expression" refers to the transcription and stable accumulation of sense (mRNA) or antisense RNA derived from the nucleic acid molecule of the invention. Expression may also refer to translation of mRNA into a polypeptide.

As used herein, "transformation" refers to the transfer of a nucleic acid molecule into the genome of a host organism, resulting in genetically stable inheritance. In the present invention, the host cell's genome includes chromosomal and extrachromosomal (e.g., plasmid) genes. Host organisms containing the transformed nucleic acid molecules are referred to as "transgenic", "recombinant" or "transformed" organisms.

As used herein, the term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Accelrys Software Corp., San Diego, CA), BLASTP, BLASTN, BLASTX (Altschul et al., *J. Mol. Biol.* 215:403-410 (1990)), and DNASTAR (DNASTAR, Inc. 1228 S. Park St. Madison, WI 53715 USA), CLUSTALW (for example, version 1.83; Thompson et al., *Nucleic Acids Research,* 22(22):4673-4680 (1994)), and the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, NY), Vector NTI (Informax, Bethesda, MD) and Sequencher v. 4.05. Within the context of this application it will be understood that where sequence analysis software is used for analysis, that the results of the analysis will be based on the "default values" of the program referenced, unless otherwise specified. As used herein "default values" will mean any set of values or parameters set by the software manufacturer that originally load with the software when first initialized.

Structural and Functional Properties of the Present Soluble α-Glucan Fiber Composition Human gastrointestinal enzymes readily recognize and digest linear α-glucan oligomers having a substantial amount of α-(1,4) glycosidic bonds. Replacing these linkages with alternative linkages such as α-(1,2), α-(1,3), and α-(1,6) typically reduces the digestibility of the α-glucan oligomers. Increasing the degree of branching (using the alternative linkages) may also reduce the relative level of digestibility.

The present soluble α-glucan fiber composition (comprising α-(1,2) branching) was prepared using cane sugar (sucrose) and a suitable α-glucan substrate backbone using one or more enzymatic processing aids that have essentially the same amino acid sequences as found in nature (or active truncations thereof) from microorganisms which having a long history of exposure to humans (microorganisms naturally found in the oral cavity or found in foods such a beer, fermented soybeans, etc.) and/or those that are generally recognized as safe (GRAS). The soluble fibers have slow to no digestibility, exhibit high tolerance (i.e., as measured by an acceptable amount of gas formation), low viscosity (enabling use in a broad range of food applications), and are at least partially fermentable by gut microflora, providing possible prebiotic effects (for example, increasing the number and/or activity of bifidobacteria and lactic acid bacteria reported to be associated with providing potential prebiotic effects).

The α-glucan substrate backbone suitable for use with the present polypeptides having α-(1,2) branching activity can be synthesized from sucrose, maltodextrin, or a combination thereof depending upon the enzymes selected. The enzymes used to prepare the α-glucan substrate backbone suitable for the α-(1,2) branching reaction may include glucosyltransferases (using sucrose), 4,6-α-glucanohydrolases (using maltodextrin/maltooligosaccharides), dextrin dextranases (using maltodextrin/maltooligosaccharides), each of which may be used alone or in combination with one or more α-glucanohydrolases (e.g., dextranases, mutanases, etc.). The maltodextrin/maltooligosaccharides may be prepared from processed starched or may be synthesized from sucrose using an amylosucrase.

The present soluble α-glucan fiber composition is characterized by the following combination of parameters:
a. a range of:
  a) 0% to 50% of α-(1,3) glycosidic linkages; or
  b) 0% to 40% α-(1,4) glycosidic linkages; or
  c) any combination of a) and b);
b. 1 to 50% of a combination of α-(1,2) and α-(1,2,6) glycosidic linkages;
c. 0-25% α-(1,3,6) glycosidic linkages;
d. less than 99% α-(1,6) glycosidic linkages;

e. a weight average molecular weight of less than 300 kDa;
f. a viscosity of less than 0.25 Pascal second (Pa·s) at 12 wt % in water at 20° C.;
g. a digestibility of less than 20% as measured by the Association of Analytical Communities (AOAC) method 2009.01;
h. a solubility of at least 20% (w/w) in pH 7 water at 25° C.; and
i. a polydispersity index of less than 26, preferably less than 5.

In one embodiment, the soluble α-glucan fiber composition as described above, wherein the sum of the α-(1,3) and α-(1,3,6) glycosidic linkages content ranges from 3% to 50%, preferably 3% to 25%.

In another embodiment, the soluble α-glucan fiber composition as described above comprises 15-35%; preferably 20-30% α-(1,4) glycosidic linkages.

In another embodiment, the soluble α-glucan fiber composition comprises 1% to 40%, preferably 2% to 30% of a combination of α-(1,2) and α-(1,2,6) glycosidic linkages.

In another embodiment, in addition to the above mentioned glycosidic linkage content embodiments, the present α-glucan fiber composition comprises a weight average molecular weight ($M_w$) of less than 300000 Daltons (Da), preferably 1500 to 300000 Da, more preferably 1500 to 90,000 Da, more preferably 1500 to 20,000 Da, and even more preferably 1500 to 16,000 Da.

In one preferred embodiment, the above soluble α-glucan fiber composition comprises 95 to 98% α-(1,6) glycosidic linkages, 2 to 5% of a combination of α-(1,2) and α-(1,2,6) glycosidic linkages, and comprises a weight average molecular weight greater than 10,000 Da; preferably greater than 10,000 Da but less than 20,000 Da.

In another embodiment, in addition to any of the above features, the present α-glucan fiber composition comprises a viscosity of less than 250 centipoise (cP) (0.25 Pascal second (Pa·s)), preferably less than 10 centipoise (cP) (0.01 Pascal second (Pa·s)), preferably less than 7 cP (0.007 Pa·s), more preferably less than 5 cP (0.005 Pa·s), more preferably less than 4 cP (0.004 Pa·s), and most preferably less than 3 cP (0.003 Pa·s) at 12 wt % in water at 20° C.

The present soluble α-glucan composition has a digestibility of less than 20%, preferably less than 15%, 10%, 9%, 8%, 7%, 6%, 5%, 4%, 3%, 2% or 1% digestible as measured by the Association of Analytical Communities (AOAC) method 2009.01.

In addition to any of the above embodiments, the present soluble α-glucan fiber composition has a solubility of at least 20% (w/w), preferably at least 30%, 40%, 50%, 60%, or 70% in pH 7 water at 25° C.

In one embodiment, the present soluble α-glucan fiber composition comprises a reducing sugar content of less than 10 wt %, preferably less than 5 wt %, and most preferably 1 wt % or less.

In another embodiment, the present soluble α-glucan fiber composition comprises a number average molecular weight (Mn) between 1500 and 90,000 g/mol, preferably 1500 to 30,000 g/mol, more preferably 1500 to 20,000, and more preferably 3000 to 16000 g/mol. In one embodiment, the number average molecular weight (Mn) is between 13000 and 16000.

In one embodiment, the present soluble α-glucan fiber composition comprises a caloric content of less than 4 kcal/g, preferably less than 3 kcal/g, more preferably less than 2.5 kcal/g, and most preferably about 2 kcal/g or less.
Compositions Comprising Glucan Fibers Depending upon the desired application, the present glucan fibers/fiber composition may be formulated (e.g., blended, mixed, incorporated into, etc.) with one or more other materials suitable for use in foods, personal care products and/or pharmaceuticals. As such, the present invention includes compositions comprising the present glucan fiber composition. The term "compositions comprising the present glucan fiber composition" in this context may include, for example, a nutritional or food composition, such as food products, food supplements, or functional foods. In a further embodiment, "compositions comprising the present glucan fiber composition" may also include personal care products, cosmetics, and pharmaceuticals.

The present glucan fibers/fiber composition may be directed as an ingredient in a desired product (e.g., foods, personal care products, etc.) or may be blended with one or more additional food grade materials to form a carbohydrate composition that is used in the desired product (e.g., foods, personal care products, etc.). The amount of the α-glucan fiber composition incorporated into the carbohydrate composition may vary according to the application. As such, the present invention comprises a carbohydrate composition comprising the present soluble α-glucan fiber composition. In one embodiment, the carbohydrate composition comprises 0.01 to 99 wt % (dry solids basis), preferably 0.1 to 90 wt %, more preferably 1 to 90%, and most preferably 5 to 80 wt % of the soluble glucan fiber composition described above.

The term "food" as used herein is intended to encompass food for human consumption as well as for animal consumption. By "functional food" it is meant any fresh or processed food claimed to have a health-promoting and/or disease-preventing and/or disease-reducing property beyond the basic nutritional function of supplying nutrients. Functional food may include, for example, processed food or foods fortified with health-promoting additives. Examples of functional food are foods fortified with vitamins, or fermented foods with live cultures.

The carbohydrate composition comprising the present soluble α-glucan fiber composition may contain other materials known in the art for inclusion in nutritional compositions, such as water or other aqueous solutions, fats, sugars, starch, binders, thickeners, colorants, flavorants, odorants, acidulants (such as lactic acid or malic acid, among others), stabilizers, or high intensity sweeteners, or minerals, among others. Examples of suitable food products include bread, breakfast cereals, biscuits, cakes, cookies, crackers, yogurt, kefir, miso, natto, tempeh, kimchee, sauerkraut, water, milk, fruit juice, vegetable juice, carbonated soft drinks, non-carbonated soft drinks, coffee, tea, beer, wine, liquor, alcoholic drink, snacks, soups, frozen desserts, fried foods, pizza, pasta products, potato products, rice products, corn products, wheat products, dairy products, hard candies, nutritional bars, cereals, dough, processed meats and cheeses, yoghurts, ice cream confections, milk-based drinks, salad dressings, sauces, toppings, desserts, confectionery products, cereal-based snack bars, prepared dishes, and the like. The carbohydrate composition comprising the present α-glucan fiber may be in the form of a liquid, a syrup, a powder, granules, shaped spheres, shaped sticks, shaped plates, shaped cubes, tablets, capsules, sachets, or any combination thereof.

In one embodiment, the carbohydrate composition according to the invention may comprise at least two fiber sources (i.e., at least one additional fiber source beyond the present α-glucan fiber composition). In another embodiment, one fiber source is the present glucan fiber and the second fiber source is an oligo- or polysaccharide, selected from the group consisting of resistant/branched maltodextrins/fiber dextrins (such as NUTRIOSE® from Roquette Freres, Lestrem, France; FIBERSOL-2® from ADM-Matsutani LLC, Decatur, Illinois), polydextrose (LITESSE® from Danisco—DuPont Nutrition & Health, Wilmington, DE), soluble corn fiber (for example, PROMITOR® from Tate & Lyle, London, UK), isomaltooligosaccharides (IMOs), alternan and/or maltoalternan oligosaccharides (MAOs) (for example, FIBERMALT™ from Aevotis GmbH, Potsdam, Germany; SUCROMALT™ (from Cargill Inc., Minneapolis, MN), pullulan, resistant starch, inulin, fructooligosaccharides (FOS), galactooligosaccharides (GOS), xylooligosaccharides, arabinoxylooligosaccharides, nigerooligosaccharides, gentiooligosaccharides, hem icellulose and fructose oligomer syrup.

The present soluble α-glucan fiber can be added to foods as a replacement or supplement for conventional carbohydrates. As such, another embodiment of the invention is a food product comprising the present soluble α-glucan fiber. In another aspect, the food product comprises the soluble α-glucan fiber composition produced by the present process.

The soluble α-glucan fiber composition may be used in a carbohydrate composition and/or food product comprising one or more high intensity artificial sweeteners including, but not limited to stevia, aspartame, sucralose, neotame, acesulfame potassium, saccharin, and combinations thereof. The present soluble α-glucan fiber may be blended with sugar substitutes such as brazzein, curculin, erythritol, glycerol, glycyrrhizin, hydrogenated starch hydrolysates, inulin, isomalt, lactitol, mabinlin, maltitol, maltooligosaccharide, maltoalternan oligosaccharides (such as XTEND® SUCROMALT™, available from Cargill Inc., Minneapolis, MN), mannitol, miraculin, a mogroside mix, monatin, monellin, osladin, pentadin, sorbitol, stevia, tagatose, thaumatin, xylitol, and any combination thereof.

A food product containing the soluble α-glucan fiber composition will have a lower glycemic response, lower glycemic index, and lower glycemic load than a similar food product in which a conventional carbohydrate is used. Further, because the soluble α-glucan fiber is characterized by very low to no digestibility in the human stomach or small intestine, the caloric content of the food product is reduced. The present soluble α-glucan fiber may be used in the form of a powder, blended into a dry powder with other suitable food ingredients or may be blended or used in the form of a liquid syrup comprising the present dietary fiber (also referred to herein as an "soluble fiber syrup", "fiber syrup" or simply the "syrup"). The "syrup" can be added to food products as a source of soluble fiber. It can increase the fiber content of food products without having a negative impact on flavor, mouth feel, or texture.

The fiber syrup can be used in food products alone or in combination with bulking agents, such as sugar alcohols or maltodextrins, to reduce caloric content and/or to enhance nutritional profile of the product. The fiber syrup can also be used as a partial replacement for fat in food products.

The fiber syrup can be used in food products as a tenderizer or texturizer, to increase crispness or snap, to improve eye appeal, and/or to improve the rheology of dough, batter, or other food compositions. The fiber syrup can also be used in food products as a humectant, to increase product shelf life, and/or to produce a softer, moister texture. It can also be used in food products to reduce water activity or to immobilize and manage water. Additional uses of the fiber syrup may include: replacement of an egg wash and/or to enhance the surface sheen of a food product, to alter flour starch gelatinization temperature, to modify the texture of the product, and to enhance browning of the product.

The fiber syrup can be used in a variety of types of food products. One type of food product in which the present syrup can be very useful is bakery products (i.e., baked foods), such as cakes, brownies, cookies, cookie crisps, muffins, breads, and sweet doughs. Conventional bakery products can be relatively high in sugar and high in total carbohydrates. The use of the present syrup as an ingredient in bakery products can help lower the sugar and carbohydrate levels, as well as reduce the total calories, while increasing the fiber content of the bakery product.

There are two main categories of bakery products: yeast-raised and chemically-leavened. In yeast-raised products, like donuts, sweet doughs, and breads, the present fiber-containing syrup can be used to replace sugars, but a small amount of sugar may still be desired due to the need for a fermentation substrate for the yeast or for crust browning. The fiber syrup can be added with other liquids as a direct replacement for non-fiber containing syrups or liquid sweeteners. The dough would then be processed under conditions commonly used in the baking industry including being mixed, fermented, divided, formed or extruded into loaves or shapes, proofed, and baked or fried. The product can be baked or fried using conditions similar to traditional products. Breads are commonly baked at temperatures ranging from 420° F. to 520° F. (216-271° C.). for 20 to 23 minutes and doughnuts can be fried at temperatures ranging from 400415° F. (204-213° C.), although other temperatures and times could also be used.

Chemically leavened products typically have more sugar and may contain have a higher level of the carbohydrate compositions and/or edible syrups comprising the present soluble α-glucan fiber. A finished cookie can contain 30% sugar, which could be replaced, entirely or partially, with carbohydrate compositions and/or syrups comprising the present glucan fiber composition. These products could have a pH of 4-9.5, for example. The moisture content can be between 2-40%, for example.

The present carbohydrate compositions and/or fiber-containing syrups are readily incorporated and may be added to the fat at the beginning of mixing during a creaming step or in any method similar to the syrup or dry sweetener that it is being used to replace. The product would be mixed and then formed, for example by being sheeted, rotary cut, wire cut, or through another forming process. The products would then be baked under typical baking conditions, for example at 200-450° F. (93-232° C.).

Another type of food product in which the carbohydrate compositions and/or fiber-containing syrups can be used is breakfast cereal. For example, fiber-containing syrups could be used to replace all or part of the sugar in extruded cereal pieces and/or in the coating on the outside of those pieces. The coating is typically 30-60% of the total weight of the finished cereal piece. The syrup can be applied in a spray or drizzled on, for example.

Another type of food product in which the present α-glucan fiber composition (optionally used in the form of a carbohydrate composition and/or fiber-containing syrup) can be used is dairy products. Examples of dairy products in which it can be used include yogurt, yogurt drinks, milk drinks, flavored milks, smoothies, ice cream, shakes, cottage cheese, cottage cheese dressing, and dairy desserts, such as quarg and the whipped mousse-type products. This would include dairy products that are intended to be consumed directly (such as packaged smoothies) as well as those that are intended to be blended with other ingredients (such as blended smoothies). It can be used in pasteurized dairy products, such as ones that are pasteurized at a temperature from 160° F. to 285° F. (71-141° C.).

Another type of food product in which the composition comprising the α-glucan fiber composition can be used is confections. Examples of confections in which it can be used include hard candies, fondants, nougats and marshmallows, gelatin jelly candies or gummies, jellies, chocolate, licorice, chewing gum, caramels and toffees, chews, mints, tableted confections, and fruit snacks. In fruit snacks, a composition comprising the present α-glucan fiber could be used in combination with fruit juice. The fruit juice would provide the majority of the sweetness, and the composition comprising the glucan fiber would reduce the total sugar content and add fiber. The present compositions comprising the glucan fiber can be added to the initial candy slurry and heated to the finished solids content. The slurry could be heated from 200-305° F. (93-152° C.). to achieve the finished solids content. Acid could be added before or after heating to give a finished pH of 2-7. The composition comprising the glucan fiber could be used as a replacement for 0-100% of the sugar and 1-100% of the corn syrup or other sweeteners present.

Another type of food product in which a composition comprising the α-glucan fiber composition can be used is jams and jellies. Jams and jellies are made from fruit. A jam contains fruit pieces, while jelly is made from fruit juice. The composition comprising the present fiber can be used in place of sugar or other sweeteners as follows: weigh fruit and juice into a tank; premix sugar, the fiber-containing composition and pectin; add the dry composition to the liquid and cook to a temperature of 214-220° F. (101-104° C.); hot fill into jars and retort for 5-30 minutes.

Another type of food product in which a composition comprising the present α-glucan fiber composition (such as a fiber-containing syrup) can be used is beverages. Examples of beverages in which it can be used include carbonated beverages, fruit juices, concentrated juice mixes (e.g., margarita mix), clear waters, and beverage dry mixes. The use of the present α-glucan fiber may overcome the clarity problems that result when other types of fiber are added to beverages. A complete replacement of sugars may be possible (which could be, for example, being up to 12% or more of the total formula).

Another type of food product is high solids fillings. Examples of high solids fillings include fillings in snack bars, toaster pastries, donuts, and cookies. The high solids filling could be an acid/fruit filling or a savory filling, for example. The fiber composition could be added to products that would be consumed as is, or products that would undergo further processing, by a food processor (additional baking) or by a consumer (bake stable filling). In some embodiments of the invention, the high solids fillings would have a solids concentration between 67-90%. The solids could be entirely replaced with a composition comprising the present α-glucan fiber or it could be used for a partial replacement of the other sweetener solids present (e.g., replacement of current solids from 5-100%). Typically fruit fillings would have a pH of 2-6, while savory fillings would be between 4-8 pH. Fillings could be prepared cold or heated at up to 250° F. (121° C.) to evaporate to the desired finished solids content.

Another type of food product in which the α-glucan fiber composition or a carbohydrate composition (comprising the α-glucan fiber composition) can be used is extruded and sheeted snacks. Examples of extruded and sheeted can be used include puffed snacks, crackers, tortilla chips, and corn chips. In preparing an extruded piece, a composition comprising the present glucan fiber would be added directly with the dry products. A small amount of water would be added in the extruder, and then it would pass through various zones ranging from 100° F. to 300° F. (38-149° C.). The dried product could be added at levels from 0-50% of the dry products mixture. A syrup comprising the present glucan fiber could also be added at one of the liquid ports along the extruder. The product would come out at either a low moisture content (5%) and then baked to remove the excess moisture, or at a slightly higher moisture content (10%) and then fried to remove moisture and cook out the product. Baking could be at temperatures up to 500° F. (260° C.). for 20 minutes. Baking would more typically be at 350° F. (177° C.) for 10 minutes. Frying would typically be at 350° F. (177° C.) for 2-5 minutes. In a sheeted snack, the composition comprising the present glucan fiber could be used as a partial replacement of the other dry ingredients (for example, flour). It could be from 0-50% of the dry weight. The product would be dry mixed, and then water added to form cohesive dough. The product mix could have a pH from 5 to 8. The dough would then be sheeted and cut and then baked or fried. Baking could be at temperatures up to 500° F. (260° C.) for 20 minutes. Frying would typically be at 350° F. (177° C.) for 2-5 minutes. Another potential benefit from the use of a composition comprising the present glucan fiber is a reduction of the fat content of fried snacks by as much as 15% when it is added as an internal ingredient or as a coating on the outside of a fried food.

Another type of food product in which a fiber-containing syrup can be used is gelatin desserts. The ingredients for gelatin desserts are often sold as a dry mix with gelatin as a gelling agent. The sugar solids could be replaced partially or entirely with a composition comprising the present glucan fiber in the dry mix. The dry mix can then be mixed with water and heated to 212° F. (100° C.). to dissolve the gelatin and then more water and/or fruit can be added to complete the gelatin dessert. The gelatin is then allowed to cool and set. Gelatin can also be sold in shelf stable packs. In that case the stabilizer is usually carrageenan-based. As stated above, a composition comprising the present glucan fiber could be used to replace up to 100% of the other sweetener solids. The dry ingredients are mixed into the liquids and then pasteurized and put into cups and allowed to cool and set.

Another type of food product in which a composition comprising the present glucan fiber can be used is snack bars. Examples of snack bars in which it can be used include breakfast and meal replacement bars, nutrition bars, granola bars, protein bars, and cereal bars. It could be used in any part of the snack bars, such as in the high solids filling, the binding syrup or the particulate portion. A complete or partial replacement of sugar in the binding syrup may be possible. The binding syrup is typically from 50-90% solids and applied at a ratio ranging from 10% binding syrup to 90% particulates, to 70% binding syrup to 30% particulates. The binding syrup is made by heating a solution of sweeteners, bulking agents and other binders (like starch) to 160-230° F. (71-110° C.) (depending on the finished solids needed in the syrup). The syrup is then mixed with the particulates to coat the particulates, providing a coating throughout the matrix. A composition comprising the present glucan fiber could also be used in the particulates themselves. This could be an extruded piece, directly expanded or gun puffed. It could be used in combination with another grain ingredient, corn meal, rice flour or other similar ingredient.

Another type of food product in which the composition comprising the present glucan fiber syrup can be used is cheese, cheese sauces, and other cheese products. Examples of cheese, cheese sauces, and other cheese products in which it can be used include lower milk solids cheese, lower fat cheese, and calorie reduced cheese. In block cheese, it can help to improve the melting characteristics, or to decrease the effect of the melt limitation added by other ingredients such as starch. It could also be used in cheese sauces, for example as a bulking agent, to replace fat, milk solids, or other typical bulking agents.

Another type of food product in which a composition comprising the present glucan fiber can be used is films that are edible and/or water soluble. Examples of films in which it can be used include films that are used to enclose dry mixes for a variety of foods and beverages that are intended to be dissolved in water, or films that are used to deliver color or flavors such as a spice film that is added to a food after cooking while still hot. Other film applications include, but are not limited to, fruit and vegetable leathers, and other flexible films.

In another embodiment, compositions comprising the present glucan fiber can be used is soups, syrups, sauces, and dressings. A typical dressing could be from 0-50% oil, with a pH range of 2-7. It could be cold processed or heat processed. It would be mixed, and then stabilizer would be added. The composition comprising the present glucan fiber could easily be added in liquid or dry form with the other ingredients as needed. The dressing composition may need to be heated to activate the stabilizer. Typical heating conditions would be from 170-200° F. (77-93° C.) for 1-30 minutes. After cooling, the oil is added to make a pre-emulsion. The product is then emulsified using a homogenizer, colloid mill, or other high shear process.

Sauces can have from 0-10% oil and from 10-50% total solids, and can have a pH from 2-8. Sauces can be cold processed or heat processed. The ingredients are mixed and then heat processed. The composition comprising the present glucan fiber could easily be added in liquid or dry form with the other ingredients as needed. Typical heating would be from 170-200° F. (77-93° C.) for 1-30 minutes.

Soups are more typically 20-50% solids and in a more neutral pH range (4-8). They can be a dry mix, to which a dry composition comprising the present glucan fiber could be added, or a liquid soup which is canned and then retorted. In soups, resistant corn syrup could be used up to 50% solids, though a more typical usage would be to deliver 5 g of fiber/serving.

Another type of food product in which a composition comprising the present α-glucan fiber composition can be used is coffee creamers. Examples of coffee creamers in which it can be used include both liquid and dry creamers. A dry blended coffee creamer can be blended with commercial creamer powders of the following fat types: soybean, coconut, palm, sunflower, or canola oil, or butterfat. These fats can be non-hydrogenated or hydrogenated. The composition comprising the present α-glucan fiber composition can be added as a fiber source, optionally together with fructo-oligosaccharides, polydextrose, inulin, maltodextrin, resistant starch, sucrose, and/or conventional corn syrup solids. The composition can also contain high intensity sweeteners, such as sucralose, acesulfame potassium, aspartame, or combinations thereof. These ingredients can be dry blended to produce the desired composition.

A spray dried creamer powder is a combination of fat, protein and carbohydrates, emulsifiers, emulsifying salts, sweeteners, and anti-caking agents. The fat source can be one or more of soybean, coconut, palm, sunflower, or canola oil, or butterfat. The protein can be sodium or calcium caseinates, milk proteins, whey proteins, wheat proteins, or soy proteins. The carbohydrate could be a composition comprising the present α-glucan fiber composition alone or in combination with fructooligosaccharides, polydextrose, inulin, resistant starch, maltodextrin, sucrose, corn syrup or any combination thereof. The emulsifiers can be mono- and diglycerides, acetylated mono- and diglycerides, or propylene glycol monoesters. The salts can be trisodium citrate, monosodium phosphate, disodium phosphate, trisodium phosphate, tetrasodium pyrophosphate, monopotassium phosphate, and/or dipotassium phosphate. The composition can also contain high intensity sweeteners, such as those describe above. Suitable anti-caking agents include sodium silicoaluminates or silica dioxides. The products are combined in slurry, optionally homogenized, and spray dried in either a granular or agglomerated form.

Liquid coffee creamers are simply a homogenized and pasteurized emulsion of fat (either dairy fat or hydrogenated vegetable oil), some milk solids or caseinates, corn syrup, and vanilla or other flavors, as well as a stabilizing blend. The product is usually pasteurized via HTST (high temperature short time) at 185° F. (85° C.) for 30 seconds, or UHT (ultra-high temperature), at 285° F. (141° C.) for 4 seconds, and homogenized in a two stage homogenizer at 500-3000 psi (3.45-20.7 MPa) first stage, and 200-1000 psi (1.38-6.89 MPa) second stage. The coffee creamer is usually stabilized so that it does not break down when added to the coffee.

Another type of food product in which a composition comprising the present α-glucan fiber composition (such as a fiber-containing syrup) can be used is food coatings such as icings, frostings, and glazes. In icings and frostings, the fiber-containing syrup can be used as a sweetener replacement (complete or partial) to lower caloric content and increase fiber content. Glazes are typically about 70-90% sugar, with most of the rest being water, and the fiber-containing syrup can be used to entirely or partially replace the sugar. Frosting typically contains about 2-40% of a liquid/solid fat combination, about 20-75% sweetener solids, color, flavor, and water. The fiber-containing syrup can be used to replace all or part of the sweetener solids, or as a bulking agent in lower fat systems.

Another type of food product in which the fiber-containing syrup can be used is pet food, such as dry or moist dog food. Pet foods are made in a variety of ways, such as extrusion, forming, and formulating as gravies. The fiber-containing syrup could be used at levels of 0-50% in each of these types.

Another type of food product in which a composition comprising the present α-glucan fiber composition, such as a syrup, can be used is fish and meat. Conventional corn syrup is already used in some meats, so a fiber-containing syrup can be used as a partial or complete substitute. For example, the syrup could be added to brine before it is vacuum tumbled or injected into the meat. It could be added with salt and phosphates, and optionally with water binding ingredients such as starch, carrageenan, or soy proteins. This would be used to add fiber, a typical level would be 5 g/serving which would allow a claim of excellent source of fiber.

Personal Care and/or Pharmaceutical Compositions Comprising the Present Soluble Fiber The present glucan fiber and/or compositions comprising the present glucan fiber may be used in personal care products. For example, one may be able to use such materials as a humectants, hydrocolloids or possibly thickening agents. The present fibers and/or compositions comprising the present fibers may be used in conjunction with one or more other types of thickening agents if desired, such as those disclosed in U.S. Pat. No. 8,541,041, the disclosure of which is incorporated herein by reference in its entirety.

Personal care products herein are not particularly limited and include, for example, skin care compositions, cosmetic compositions, antifungal compositions, and antibacterial compositions. Personal care products herein may be in the form of, for example, lotions, creams, pastes, balms, ointments, pomades, gels, liquids, combinations of these and the like. The personal care products disclosed herein can include at least one active ingredient. An active ingredient is generally recognized as an ingredient that produces an intended pharmacological or cosmetic effect.

In certain embodiments, a skin care product can be applied to skin for addressing skin damage related to a lack of moisture. A skin care product may also be used to address the visual appearance of skin (e.g., reduce the appearance of flaky, cracked, and/or red skin) and/or the tactile feel of the skin (e.g., reduce roughness and/or dryness of the skin while improved the softness and subtleness of the skin). A skin care product typically may include at least one active ingredient for the treatment or prevention of skin ailments, providing a cosmetic effect, or for providing a moisturizing benefit to skin, such as zinc oxide, petrolatum, white petrolatum, mineral oil, cod liver oil, lanolin, dimethicone, hard fat, vitamin A, allantoin, calamine, kaolin, glycerin, or colloidal oatmeal, and combinations of these. A skin care product may include one or more natural moisturizing factors such as ceramides, hyaluronic acid, glycerin, squalane, amino acids, cholesterol, fatty acids, triglycerides, phospholipids, glycosphingolipids, urea, linoleic acid, glycosaminoglycans, mucopolysaccharide, sodium lactate, or sodium pyrrolidone carboxylate, for example. Other ingredients that may be included in a skin care product include, without limitation, glycerides, apricot kernel oil, canola oil, squalane, squalene, coconut oil, corn oil, jojoba oil, jojoba wax, lecithin, olive oil, safflower oil, sesame oil, shea butter, soybean oil, sweet almond oil, sunflower oil, tea tree oil, shea butter, palm oil, cholesterol, cholesterol esters, wax esters, fatty acids, and orange oil.

A personal care product herein can also be in the form of makeup or other product including, but not limited to, a lipstick, mascara, rouge, foundation, blush, eyeliner, lip liner, lip gloss, other cosmetics, sunscreen, sun block, nail polish, mousse, hair spray, styling gel, nail conditioner, bath gel, shower gel, body wash, face wash, shampoo, hair conditioner (leave-in or rinse-out), cream rinse, hair dye, hair coloring product, hair shine product, hair serum, hair anti-frizz product, hair split-end repair product, lip balm, skin conditioner, cold cream, moisturizer, body spray, soap, body scrub, exfoliant, astringent, scruffing lotion, depilatory, permanent waving solution, antidandruff formulation, antiperspirant composition, deodorant, shaving product, preshaving product, after-shaving product, cleanser, skin gel, rinse, toothpaste, or mouthwash, for example.

A pharmaceutical product herein can be in the form of an emulsion, liquid, elixir, gel, suspension, solution, cream, capsule, tablet, sachet or ointment, for example. Also, a pharmaceutical product herein can be in the form of any of the personal care products disclosed herein. A pharmaceutical product can further comprise one or more pharmaceutically acceptable carriers, diluents, and/or pharmaceutically acceptable salts. The present fibers and/or compositions comprising the present fibers can also be used in capsules, encapsulants, tablet coatings, and as an excipients for medicaments and drugs.

Gas Production

A rapid rate of gas production in the lower gastrointestinal tract gives rise to gastrointestinal discomfort such as flatulence and bloating, whereas if gas production is gradual and low the body can more easily cope. For example, inulin gives a boost of gas production which is rapid and high when compared to the present glucan fiber composition at an equivalent dosage (grams soluble fiber), whereas the present glucan fiber composition preferable preferably has a rate of gas release that is lower than that of inulin at an equivalent dosage.

In one embodiment, the soluble α-glucan fiber composition of the invention comprises a rate of gas production that is well tolerated for food applications. In one embodiment, the relative rate of gas production is no more than the rate observed for inulin under similar conditions, preferably the same or less than inulin, more preferably less than inulin, and most preferably much less than inulin at an equivalent dosage. In another embodiment, the relative rate of gas formation is measured over 3 hours or 24 hours using the methods described herein. In a preferred aspect, the rate of gas formulation formation is at least 1%, preferably 2%, 3%, 4%, 5%, 6%, 7%, 8%, 9%, 10%, 15%, 20%, 25% or at least 30% less than the rate observed for inulin under the same reaction conditions.

Beneficial Physiological Properties

Short Chain Fatty Acid Production

Use of the compounds according to the present invention may facilitate the production of energy yielding metabolites through colonic fermentation. Use of compounds according to the invention may facilitate the production of short chain fatty acids, such as propionate and/or butyrate. SCFAs are known to lower cholesterol. Consequently, the compounds of the invention may lower the risk of developing high cholesterol. The present glucan fiber composition may stimulate the production of short chain fatty acids, especially proprionate and/or butyrate, in fermentation studies. As the production of short chain fatty acids (SCFA) or the increased ratio of SCFA to acetate is beneficial for the control of cholesterol levels in a mammal in need thereof, the current invention may be of particular interest to nutritionists and consumers for the prevention and/or treatment of cardiovascular risks. Thus, another aspect of the invention provides a method for improving the health of a subject comprising administering a composition comprising the present α-glucan fiber composition to a subject in an effective amount to exert a beneficial effect on the health of said subject, such as for treating cholesterol-related diseases. In addition, it is generally known that short chain fatty acids lower the pH in the gut and this helps calcium absorption. Thus, compounds according to the present invention may also affect mineral absorption. This means that they may also improve bone health, or prevent or treat osteoporosis by lowering the pH due to SCFA increases in the gut. The production of SCFA may increase viscosity in small intestine which reduces the re-absorption of bile acids; increasing the synthesis of bile acids from cholesterol and reduces circulating low density lipoprotein (LDL) cholesterol.

In terms of beneficial physiological effect, an effective amount of a compound or composition refers to an amount effective, at dosages and for periods of time necessary, to achieve a desired beneficial physiological effect, such as lowering of blood cholesterol, increasing short chain fatty acid production or preventing or treating a gastrointestinal disorder. For instance, the amount of a composition administered to a subject will vary depending upon factors such as the subject's condition, the subject's body weight, the age of the subject, and whether a composition is the sole source of nutrition. The effective amount may be readily set by a medical practitioner or dietician. In general, a sufficient amount of the composition is administered to provide the subject with up to about 50 g of dietary fiber (insoluble and soluble) per day; for example about 25 g to about 35 g of dietary fiber per day. The amount of the present soluble α-glucan fiber composition that the subject receives is preferably in the range of about 0.1 g to about 50 g per day, more preferably in the rate of 0.5 g to 20 g per day, and most preferably 1 to 10 g per day. A compound or composition as defined herein may be taken in multiple doses, for example 1 to 5 times, spread out over the day or acutely, or may be taken in a single dose. A compound or composition as defined herein may also be fed continuously over a desired period. In certain embodiments, the desired period is at least one week or at least two weeks or at least three weeks or at least one month or at least six months.

In a preferred embodiment, the present invention provides a method for decreasing blood triglyceride levels in a subject in need thereof by administering a compound or a composition as defined herein to a subject in need thereof. In another preferred embodiment, the invention provides a method for decreasing low density lipoprotein levels in a subject in need thereof by administering a compound or a composition as defined herein to a subject in need thereof. In another preferred embodiment, the invention provides a method for increasing high density lipoprotein levels in a subject in need thereof by administering a compound or a composition as defined herein to a subject in need thereof.

Attenuation of Postprandial Blood Glucose Concentrations/Glycemic Response

The presence of bonds other than α-(1,4) backbone linkages in the present α-glucan fiber composition provides improved digestion resistance as enzymes of the human digestion track may have difficultly hydrolyzing such bonds and/or branched linkages. The presence of branches provides partial or complete indigestibility to glucan fibers, and therefore virtually no or a slower absorption of glucose into the body, which results in a lower glycemic response. Accordingly, the present invention provides an α-glucan fiber composition for the manufacture of food and drink compositions resulting in a lower glycemic response. For example, these compounds can be used to replace sugar or other rapidly digestible carbohydrates, and thereby lower the glycemic load of foods, reduce calories, and/or lower the energy density of foods. Also, the stability of the present α-glucan fiber composition possessing these types of bonds allows them to be easily passed through into the large intestine where they may serve as a substrate specific for the colonic microbial flora.

Improvement of Gut Health

In a further embodiment, compounds of the present invention may be used for the treatment and/or improvement of gut health. The present α-glucan fiber composition is preferably slowly fermented in the gut by the gut microflora. Preferably, the present compounds exhibit in an in vitro gut model a tolerance no worse than inulin or other commercially available fibers such as PROMITOR® (soluble corn fiber, Tate & Lyle), NUTRIOSE® (soluble corn fiber or resistant dextrin, Roquette), or FIBERSOL®-2 (digestion-resistant maltodextrin, Archer Daniels Midland Company & Matsutani Chemical), (i.e., a similar level of gas production), preferably an improved tolerance over one or more of the commercially available fibers, i.e. the fermentation of the present glucan fiber results in less gas production than inulin in 3 hours or 24 hours, thereby lowering discomfort, such as flatulence and bloating, due to gas formation. In one aspect, the present invention also relates to a method for moderating gas formation in the gastrointestinal tract of a subject by administering a compound or a composition as defined herein to a subject in need thereof, so as to decrease gut pain or gut discomfort due to flatulence and bloating. In further embodiments, compositions of the present invention provide subjects with improved tolerance to food fermentation, and may be combined with fibers, such as inulin or FOS, GOS, or lactulose to improve tolerance by lowering gas production.

In another embodiment, compounds of the present invention may be administered to improve laxation or improve regularity by increasing stool bulk.

Prebiotics and Probiotics

The soluble α-glucan fiber composition(s) may be useful as prebiotics, or as "synbiotics" when used in combination with probiotics, as discussed below. By "prebiotic" it is meant a food ingredient that beneficially affects the subject by selectively stimulating the growth and/or activity of one or a limited number of bacteria in the gastrointestinal tract, particularly the colon, and thus improves the health of the host. Examples of prebiotics include fructooligosaccharides, inulin, polydextrose, resistant starch, soluble corn fiber, glucooligosaccharides and galactooligosaccharides, arabinoxylan-oligosaccharides, lactitol, and lactulose.

In another embodiment, compositions comprising the soluble α-glucan fiber composition further comprise at least one probiotic organism. By "probiotic organism" it is meant living microbiological dietary supplements that provide beneficial effects to the subject through their function in the digestive tract. In order to be effective the probiotic microorganisms must be able to survive the digestive conditions, and they must be able to colonize the gastrointestinal tract at least temporarily without any harm to the subject. Only certain strains of microorganisms have these properties. Preferably, the probiotic microorganism is selected from the group comprising *Lactobacillus* spp., *Bifidobacterium* spp., *Bacillus* spp., *Enterococcus* spp., *Escherichia* spp., *Streptococcus* spp., and *Saccharomyces* spp. Specific microorganisms include, but are not limited to *Bacillus subtilis, Bacillus cereus, Bifidobacterium bificum, Bifidobacterium breve, Bifidobacterium infantis, Bifidobacterium lactis, Bifidobacterium longum, Bifidobacterium thermophilum, Enterococcus faecium, Enterococcus faecium, Lactobacillus acidophilus, Lactobacillus bulgaricus, Lactobacillus casei, Lactobacillus lactis, Lactobacillus plantarum, Lactobacillus reuteri, Lactobacillus rhamnosus, Streptococcus faecium, Streptococcus mutans, Streptococcus thermophilus, Saccharomyces boulardii, Torulopsia, Aspergillus oryzae*, and *Streptomyces* among others, including their vegetative spores, non-vegetative spores (*Bacillus*) and synthetic derivatives. More preferred probiotic microorganisms include, but are not limited to members of three bacterial genera: *Lactobacillus, Bifidobacterium* and *Saccharomyces*. In a preferred embodiment, the probiotic microorganism is *Lactobacillus, Bifidobacterium*, and a combination thereof.

The probiotic organism can be incorporated into the composition as a culture in water or another liquid or semisolid medium in which the probiotic remains viable. In another technique, a freeze-dried powder containing the probiotic organism may be incorporated into a particulate material or liquid or semi-solid material by mixing or blending.

In a preferred embodiment, the composition comprises a probiotic organism in an amount sufficient to delivery at least 1 to 200 billion viable probiotic organisms (colony forming units; "CFUs"), preferably 1 to 100 billion, and most preferably 1 to 50 billion viable probiotic organisms. The amount of probiotic organisms delivery as describe above is may be per dosage and/or per day, where multiple dosages per day may be suitable for some applications. Two or more probiotic organisms may be used in a composition.

Enzymatic Synthesis of the Soluble α-Glucan Fiber Composition

Methods are provided to enzymatically produce a soluble α-glucan fiber composition comprising α-(1,2) glycosidic linkages. More specifically, a polypeptide having α-(1,2) branching activity is used to add, in the presence of sucrose, α-(1,2) glycosidic linkages to an α-glucan substrate backbone having an effective amount of α-(1,6) glycosidic linkages.

In one embodiment, the polypeptide having α-(1,2) branching activity comprises an amino acid sequence having at least 90%, preferably at least 91, 92, 93, 94, 95, 96, 97, 98, 99 or 100% to SEQ ID NO: 6 with the proviso that the polypeptide does not comprise a second catalytic domain capable of synthesizing α-glycosidic linkages other than α-(1,2) glycosidic linkages.

Synthesis of the α-Glucan Substrate Backbone

The present soluble fiber is obtained by the addition of α-(1,2) glycosidic linkages to an α-glucan substrate ("backbone") comprising an effective amount of α-(1,6) glycosidic linkages in the backbone. In one embodiment, the effective amount of α-(1,6) linkages in the α-(1,6) glucan substrate backbone is at least 50%, 60%, 70%, 80%, 90%, 95% or 98% or all α-glycosidic linkages in the molecule. A variety of enzymes may be used to produce a suitable α-glucan substrate backbone (i.e., having an effective amount of α-(1,6) glycosidic linkages suitable for the enzymatic addition of α-(1,2) branching) from sucrose and/or maltodextrin. The enzymes used to prepare the glucan backbone may include glucosyltransferases (typically from the GH70 family of glycoside hydrolases), dextrin dextranases, 4,6-α-glucosyltransferases ("Gtf-B type" from family GH70), and combinations thereof; optionally in combination with at least one α-glucosidase; preferably wherein the α-glucosidase is an dextranase, a mutanase, or a combination thereof.

Glycoside Hydrolase Family 70

Glycoside hydrolase family 70 enzymes ("GH70") are transglucosidases produced by lactic acid bacteria such as *Streptococcus, Leuconostoc, Weisella* or *Lactobacillus* genera (see Carbohydrate Active Enzymes database; "CAZy"; Cantarel et al., (2009) *Nucleic Acids Res* 37:D233-238). The recombinantly expressed glucosyltransferases preferably have an amino acid sequence identical to that found in nature (i.e., the same as the full length sequence as found in the source organism or a catalytically active truncation thereof).

The GTF enzymes are able to polymerize the D-glucosyl units of sucrose to form homooligosaccharides or homopolysaccharides. Depending upon the specificity of the GTF enzyme, linear and/or branched glucans comprising various glycosidic linkages may be formed such as α-(1,2), α-(1,3), α-(1,4) and α-(1,6). Glucosyltransferases may also transfer the D-glucosyl units onto hydroxyl acceptor groups. A non-limiting list of acceptors may include carbohydrates, alcohols, polyols or flavonoids. The structure of the resultant glucosylated product is dependent upon the enzyme specificity.

In one embodiment, the D-glucopyranosyl donor is sucrose. As such the reaction is:

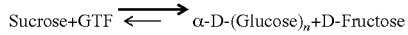

The type of glycosidic linkage predominantly formed is used to name/classify the glucosyltransferase enzyme. Examples include dextransucrases (α-(1,6) linkages; EC 2.4.1.5), mutansucrases (α-(1,3) linkages; EC 2.4.1.-), alternansucrases (alternating α(1,3)-α(1,6) backbone; EC 2.4.1.140), and reuteransucrases (mix of α-(1,4) and α-(1,6) linkages; EC 2.4.1.-).

In one embodiment, the soluble α-glucan substrate is enzymatically synthesized from sucrose (α-D-Glucopyranosyl β-D-fructofuranoside; CAS #57-50-1) obtainable from sugarcane or sugar beet. In one embodiment, the method comprises the use of at least one recombinantly produced glucosyltransferase belong to glucoside hydrolase type 70 (E.C. 2.4.1.-) capable of catalyzing the synthesis of a suitable α-glucan substrate backbone using sucrose as a substrate. In a preferred aspect, the resulting α-glucan substrate backbone is water soluble.

In one aspect, the backbone-synthesizing glucosyltransferase (GTF) is capable of forming glucans having at least 50% or more α-(1,6) glycosidic linkages with the proviso that that glucan product is not alternan (i.e., the enzyme is not an alternansucrase).

In one aspect, the glucosyltransferase comprises an amino acid sequence having at least 90%, preferably 91, 92, 93, 94, 95, 96, 97, 98, 99 or 100% identity to an amino acid sequence SEQ ID NOs: 7, 9, 10, 11, 12, 13, 14 or 16. In another aspect, the glucosyltransferase comprises an amino acid sequence having at least 90%, preferably 91, 92, 93, 94, 95, 96, 97, 98, 99 or 100% identity to an amino acid sequence selected from the group consisting of SEQ ID NOs: 7, 9, 10, 11, 12, and 13. However, it should be noted that some wild type sequences may be found in nature in a truncated form. As such, and in a further embodiment, the glucosyltransferase suitable for use may be a truncated form of the wild type sequence. In a further embodiment, the truncated glucosyltransferase comprises a sequence derived from the full length wild type amino acid sequence.

GH70 Glucosyltransferase/α-Glucanohydrolase Combinations to Produce the α-Glucan Substrate Backbone In another embodiment, a combination of a glucosyltransferase (GH70) and an α-glucanohydrolase (for example, a dextranase or mutanase) are used to produce the suitable α-glucan substrate backbone. In a preferred aspect, the glucosyltransferase and the α-glucanohydrolase are used concomitantly to produce the α-glucan substrate backbone.

The α-glucanohydrolase used to synthesize (in combination with at least one glucosyltransferase) is preferably a dextranase or mutanase; preferably and endomutanase or endodextranase. In one embodiment, the α-glucanohydrolase is a dextranase (EC 2.1.1.11), a mutanase (EC 3.1.1.59) or a combination thereof. In one embodiment, the dextranase is a food grade dextranase from *Chaetomium erraticum*. In a further embodiment, the dextranase from *Chaetomium erraticum* is DEXTRANASE® PLUS L, available from Novozymes A/S, Denmark.

In another embodiment, the α-glucanohydrolase is at least one mutanase (EC 3.1.1.59). In one embodiment, the mutanase is one obtainable from the genera *Penicillium, Paenibacillus, Hypocrea, Aspergillus,* and *Trichoderma*. In a further embodiment, the mutanase is from *Penicillium marneffei* ATCC 18224 or *Paenibacillus humicus*. In yet a further embodiment, the mutanase comprises an amino acid having at least 90% identity, preferably at least 91, 92, 93, 94, 95, 96, 97, 98, 99 or 100% identity to an amino acid sequence selected from SEQ ID NO: 21, 23, and any combination thereof. In another embodiment, the above mutanases may be a catalytically active truncation so long as the mutanase activity is retained. In yet a further preferred embodiment, the mutanase comprises SEQ ID NO: 21, 23 or a combination thereof.

In a further embodiment, a combination of a glucosyltransferase having at least 90% identity, preferably 91, 92, 93, 94, 95, 96, 97, 98, 99 or 100% identity to SEQ ID NO: 14 or 16 is used concomitantly with a mutanase having at least 90% identity, preferably 91, 92, 93, 94, 95, 96, 97, 98, 99 or 100% identity to SEQ ID NO: 21 or 23. In a preferred embodiment, a combination of a glucosyltransferase having amino acid SEQ ID NO: 14 or 16 is used concomitantly with a mutanase having amino acid sequence SEQ ID NO: 21 or 23. In a further preferred embodiment, the a combination of a glucosyltransferase having amino acid SEQ ID NO: 16 is used concomitantly with a mutanase of SEQ ID NO: 21 to produce the desired α-glucan substrate backbone (i.e., GTF0544/MUT3264).

Production of α-Glucan Substrate Backbone from Maltodextrin

The α-glucan substrate backbone may be synthesized from a maltodextrin substrate. In one embodiment, at least one polypeptide having dextrin dextranase activity (E.C. 2.4.1.2) is used to synthesize the α-glucan substrate backbone. The maltodextrin substrate/maltooligosaccharide is obtainable from processed starch or may be obtained enzymatically from sucrose using an amylosucrase (an example is provided as SEQ ID NO: 71).

The polypeptide having dextrin dextranase activity may be used in combination with at least one α-glucanohydrolase to produce the α-glucan substrate backbone. In one embodiment, the polypeptide having dextrin dextranase activity is used concomitantly with at least one α-glucanohydrolase to produce a suitable α-glucan substrate backbone. In a preferred embodiment, the α-glucanohydrolase is a dextranase, preferably an endodextranase. The enzymes used preferably have an amino acid sequence identical to that found in nature (i.e., the same as the full length sequence as found in the source organism or a catalytically active truncation thereof).

In one aspect, the polypeptide having dextrin dextranase activity comprises an amino acid sequence having at least 90%, preferably 91, 92, 93, 94, 95, 96, 97, 98, 99 or 100% identity to SEQ ID NO: 26. However, it should be noted that some wild type sequences may be found in nature in a truncated form. As such, and in a further embodiment, the dextrin dextranase suitable for use may be a truncated form of the wild type sequence. In a further embodiment, the truncated glucosyltransferase comprises a sequence derived from SEQ ID NO: 26.

In one aspect, the endodextranase is obtained from Chaetomium, preferably Chaetomium erraticum. In a further preferred aspect, the endodextranase is Dextranase L from Chaetomium erraticum. In a preferred embodiment, the endodextranase does not have significant maltose hydrolyzing activity, preferably no maltose hydrolyzing activity.

The ratio of dextrin dextranase activity to α-glucanohydrolase (i.e., endodextranase) activity may vary depending upon the selected enzymes. In one embodiment, the ratio of dextrin dextranase activity to α-glucanohydrolase activity ranges from 1:0.01 to 0.01:1.0.

In one embodiment, at least one polypeptide having 4,6-α-glucosyltransferase activity ("Gtf-B type" GH70) is used to synthesize the α-glucan substrate backbone. The maltodextrin substrate/maltooligosaccharide is obtainable from processed starch or may be obtained enzymatically from sucrose using an amylosucrase (an example is provided as SEQ ID NO: 71).

The polypeptide having 4,6-α-glucosyltransferase activity may be used in combination with at least one α-glucanohydrolase to produce the α-glucan substrate backbone. In one embodiment, the polypeptide having 4,6-α-glucosyltransferase activity is used concomitantly with at least one α-glucanohydrolase to produce a suitable α-glucan substrate backbone. In a preferred embodiment, the α-glucanohydrolase is a dextranase, preferably an endodextranase. The enzymes used preferably have an amino acid sequence identical to that found in nature (i.e., the same as the full length sequence as found in the source organism or a catalytically active truncation thereof).

In one aspect, the polypeptide having 4,6-α-glucosyltransferase activity comprises an amino acid sequence having at least 90%, preferably 91, 92, 93, 94, 95, 96, 97, 98, 99 or 100% identity to SEQ ID NO: 68, 69, or 70. However, it should be noted that some wild type sequences may be found in nature in a truncated form. As such, and in a further embodiment, the 4,6-α-glucosyltransferase may be a truncated form of the wild type sequence. In a further embodiment, the truncated 4,6-α-glucosyltransferase comprises a sequence derived from SEQ ID NO: 68, 69 or 70.

In one aspect, the endodextranase is obtained from Chaetomium, preferably Chaetomium erraticum. In a further preferred aspect, the endodextranase is Dextranase L from Chaetomium erraticum.

The ratio of 4,6-α-glucosyltransferase activity to α-glucanohydrolase (i.e., endodextranase) activity may vary depending upon the selected enzymes. In one embodiment, the ratio of 4,6-α-glucosyltransferase activity to α-glucanohydrolase activity ranges from 1:0.01 to 0.01:1.0.

The maltodextrin substrate concentration (when synthesizing the α-glucan substrate backbone) initially present when the reaction components are combined is at least 10 g/L, preferably 50 g/L to 500 g/L, more preferably 100 g/L to 500 g/L, more preferably 150 g/L to 450 g/L, and most preferably 250 g/L to 450 g/L. The maltodextrin substrate will typically have a DE ranging from 3 to 40, preferably 3 to 20; corresponding to a DP range of 3 to about 40, preferably 6 to 40, and most preferably 6 to 25).

When present in the α-glucan substrate backbone synthesis reaction, the substrate for the α-glucanohydrolase will be the members of the glucose oligomer population formed by the backbone synthesis enzymes (glucosyltransferases, dextrin dextranases, 4,6-α-glucosyltransferase, etc.). The exact concentration of each species present in the reaction system will vary.

Enzymatic Synthesis of α-(1, 2) branched Soluble Glucan Fiber Compositions

A method is provided to synthesize the present soluble α-glucan fiber compositions by enzymatically adding α-(1, 2) branching to an α-glucan substrate backbone having at least 50% α-(1,6) glycosidic linkages. Methods to produce an α-glucan substrate backbone are described above.

In one aspect, the suitable reaction components comprises at least one polypeptide having α-(1,2) branching activity, sucrose, and at least one α-glucan substrate having an effective amount of α-(1,6) glycosidic linkages. The α-glucan substrate having an effective amount of α-(1,6) glycosidic linkages in the "backbone" may be synthesized from (1) sucrose using at least one glucansucrase enzyme, (2) maltodextrins obtainable from processed starch or sucrose that have been contacted with at least one dextrin dextranase, at least one "Gtf-B type" 4,6-α-glucosyltransferase, and combinations thereof or (3) any combination thereof. The α-glucan substrate "backbone" having an effective amount of α-(1,6) glycosidic linkages may be synthesized prior to enzymatically adding the α-(1,2) branching or may be synthesized concomitantly in the same reaction mixture comprising at least one polypeptide having α-(1,2) branching activity with the proviso that the polypeptide having α-(1,2) branching activity is not the same as the enzyme(s) used to synthesize the α-glucan substrate "backbone" having an effective amount of α-(1,6) glycosidic linkages. In a further aspect, the α-glucan substrate "backbone" to which α-(1,2) branching is added is produced using a single glucansucrase, a combination of glucansucrases, a combination of at least glucansucrase and at least one α-glucanohydrolase, a dextran dextrinase, a "GtfB type" glucosyltransferase (i.e., a 4,6-α-glucosyltransferase; Kralj et al., Appl. Env. Microbiol. (2011) 77(22): 8154-8163), a combination of a dextrin dextranase and at least one α-glucanohydrolase, a combination of a "GtfB-type" glucosyltransferase and at least one α-glucanohydrolase, and any combination thereof.

In one embodiment, the polypeptide having α-(1,2) branching activity is a truncated glucosyltransferase comprising a catalytic domain capable of adding α-(1,2) branching to an α-glucan substrate backbone. In one embodiment, the catalytic domain capable of adding α-(1,2) branching further comprises at least one glucan binding domain. Preferably, the polypeptide having α-(1,2) branching activity is a truncated glucosyltransferase wherein the domain capable of synthesizing linkages other than α-(1,2) glycosidic linkage is not present (i.e., the backbone synthesizing domain or "CD1" domain found in enzymes such as the GtfJ18 glucosyltransferase from *Leuconostoc mesenteroides* subsp. *mesenteroides* J18, see GENBANK® gi:356644413 (SEQ ID NO: 1) and the DsrE glucosyltransferase from *Leuconostoc mesenteroides* NRRL B-1299 as reported in GENBANK® gi:23320943; SEQ ID NO: 2). In a preferred embodiment, the polypeptide having α-(1,2) branching activity comprises an amino acid sequence having at least 80%, 85%, 90%, 91%, 92%, 93%, 94%, 95%, 96%, 97%, 98%, 99% or 100% amino acid identity to SEQ ID NO: 6. In a further preferred aspect, the polypeptide having α-(1,2) branching activity consists essentially of an amino acid sequence having at least 80%, 85%, 90%, 91%, 92%, 93%, 94%, 95%, 96%, 97%, 98%, 99% or 100% amino acid identity to SEQ ID NO: 6. The concentration of the catalysts in the aqueous reaction formulation depends on the specific catalytic activity of each catalyst, and are chosen to obtain the desired overall rate of reaction. The weight of each catalyst typically ranges from 0.0001 mg to 20 mg per mL of total reaction volume, preferably from 0.001 mg to 10 mg per mL. The catalyst(s) may also be immobilized on a soluble or insoluble support using methods well-known to those skilled in the art; see for example, *Immobilization of Enzymes and Cells*; Gordon F. Bickerstaff, Editor; Humana Press, Totowa, NJ, USA; 1997. The use of immobilized catalysts permits the recovery and reuse of the catalyst in subsequent reactions. The enzyme catalyst(s) may be in the form of whole microbial cells, permeabilized microbial cells, microbial cell extracts, partially-purified or purified enzymes, and mixtures thereof.

The pH of the final reaction formulation is from about 3 to about 8, preferably from about 4 to about 8, more preferably from about 5 to about 8, even more preferably about 5.5 to about 7.5, and yet even more preferably about 5.5 to about 6.5. The pH of the reaction may optionally be controlled by the addition of a suitable buffer including, but not limited to, phosphate, pyrophosphate, bicarbonate, acetate, or citrate. The concentration of buffer, when employed, is typically from 0.1 mM to 1.0 M, preferably from 1 mM to 300 mM, most preferably from 10 mM to 100 mM.

The α-glucan substrate backbone concentration may range depending if the backbone is synthesized prior to enzymatic α-(1,2) branching or if the backbone is synthesize concomitantly with the enzymatic α-(1,2) branching. In one embodiment, the α-glucan substrate backbone concentration at the initiation of α-(1,2) branching is least 10 g/L, preferably 50 g/L to 500 g/L, more preferably 100 g/L to 500 g/L, more preferably 150 g/L to 450 g/L, and most preferably 250 g/L to 450 g/L.

The sucrose substrate concentration used during the α-(1,2) branching reaction may vary. In one embodiment, the sucrose concentration initially present when the reaction components are combined is at least 50 g/L, preferably 50 g/L to 600 g/L, more preferably 100 g/L to 500 g/L, more preferably 150 g/L to 450 g/L, and most preferably 250 g/L to 450 g/L. Higher concentrations of sucrose may be necessary if the α-(1,2) branching reaction occurs concomitantly with α-glucan backbone synthesis reaction.

The weight ratio of sucrose to α-glucan substrate backbone during the branching reaction may vary. In one embodiment, the weight ration of sucrose to α-glucan substrate backbone may range from 0.01:1.0 to 1.0:0.01.

The length of the reaction may vary and may often be determined by the amount of time it takes to use all of the available sucrose substrate. In one embodiment, the reaction is conducted until at least 90%, preferably at least 95% and most preferably at least 99% of the sucrose initially present in the reaction mixture is consumed. In another embodiment, the reaction time is 1 hour to 168 hours, preferably 1 hour to 72 hours, and most preferably 1 hour to 24 hours.

The maltodextrin substrate concentration initially present (when synthesizing the α-glucan substrate backbone from maltodextrin concomitantly with the enzymatic addition of α-(1,2) branching using sucrose) when the reaction components are combined is at least 10 g/L, preferably 50 g/L to 500 g/L, more preferably 100 g/L to 500 g/L, more preferably 150 g/L to 450 g/L, and most preferably 250 g/L to 450 g/L. The maltodextrin substrate will typically have a DE ranging from 3 to 40, preferably 3 to 20; corresponding to a DP range of 3 to about 40, preferably 6 to 40, and most preferably 6 to 25).

The length of the reaction may vary and may often be determined by the amount of time it takes to use all of the available sucrose substrate. In one embodiment, the reaction is conducted until at least 90%, preferably at least 95% and most preferably at least 99% of the maltodextrin substrate initially present in the reaction mixture is consumed. In another embodiment, the reaction time is 1 hour to 168 hours, preferably 1 hour to 120 hours, and most preferably 1 hour to 72 hours.

The temperature of the enzymatic reaction system may be chosen to control both the reaction rate and the stability of the enzyme catalyst(s) used. The temperature of the reaction may range from just above the freezing point of the reaction formulation (approximately 0° C.) to about 60° C., with a preferred range of 5° C. to about 55° C., and a more preferred range of reaction temperature of from about 20° C. to about 47° C.

In a "first" embodiment, a method is provided to produce a soluble α-glucan fiber composition comprising:
a. providing a set of reaction components comprising:
   i. sucrose;
   ii. an α-glucan substrate backbone having a weight average molecular weight of at least 0.5 kDa, said α-glucan substrate backbone comprising at least 50% α-(1,6) glycosidic linkages;
   iii. a polypeptide having α-(1,2) branching activity, said polypeptide comprising an amino acid sequence having at least 90% identity to SEQ ID NO: 6; said polypeptide capable of catalyzing the synthesis of α-(1,2) glycosidic linkages on the α-glucan substrate backbone; and
   iv. optionally one or more acceptors;
b. combining the set of reaction component under suitable aqueous reaction conditions whereby the polypeptide catalyzing the synthesis of an α-glucan fiber composition comprising 1 to 50% of a combination of α-(1,2) and α-(1,2,6) glycosidic linkages; and
c. optionally isolating the α-glucan fiber composition.

In a further embodiment to the above, the method further comprises a step of: (d) concentrating the α-glucan fiber composition.

In a further embodiment to any of the above embodiments, the α-glucan substrate comprises 1% to 50% of α-(1,3) glycosidic linkages.

In a further embodiment to any of the above embodiments, the α-glucan substrate backbone comprises more than 10% but less than 40% α-(1,4) glycosidic linkages.

In a further embodiment to any of the above embodiments, the α-glucan fiber composition comprises
a. a viscosity of less than 10 cps at 12 wt % in water;
b. a digestibility of less than 20% as measured by the Association of Analytical Communities (AOAC) method 2009.01;
c. a solubility of at least 20% (w/w) in water at 25° C.; and
d. a polydispersity index of less than 5.

In another embodiment, a method is provided to produce an α-glucan fiber composition comprising:
a. contacting sucrose with at least one glucosyltransferase or a combination of at least one glucosyltransferase and at least one α-glucanohydrolase under suitable reaction conditions whereby an α-glucan substrate backbone is produced having a weight average molecular weight of at least 0.5 kDa, said α-glucan substrate backbone comprising at least 50% α-(1,6) glycosidic linkages; wherein said α-glucan substrate comprises less than 1% α-(1,2) glycosidic linkages;
b. contacting the α-glucan substrate backbone produced in (a) with a set of reaction components comprising
   i. a polypeptide having α-(1,2) branching activity comprising an amino acid sequence having at least 90% identity to SEQ ID NO: 6; said polypeptide capable of catalyzing the synthesis of α-(1,2) glycosidic linkages on the α-glucan substrate;
   ii. sucrose; and
   iii. optionally one or more acceptors;
c. combining the set of reaction components of (b) under suitable aqueous reaction conditions whereby the polypeptide catalyzing the synthesis of an α-glucan fiber composition comprises 1 to 50% α-(1,2) glycosidic linkages; and
d. optionally isolating the α-glucan fiber composition of step (c).

In a further embodiment, the at least one glucosyltransferase of step (a) comprises an amino acid sequence having at least 90% identity to an amino acid sequence selected from the group consisting of SEQ ID NOs: 7, 9, 10, 11, 12, 13, 14 and 16.

In a further embodiment, wherein the combination of at least one glucosyltransferase and at least one α-glucanohydrolase of step (a) is:
a. the at least one glucosyltransferase comprises an amino acid sequence SEQ ID NO: 14, 16 or a combination thereof; and
b. The at least one α-glucanohydrolase comprises an amino acid sequence selected from the group consisting of SEQ ID NOs: 21, 23 or a combination thereof.

In another embodiment, a method to produce an α-glucan fiber composition comprising:
a. contacting a maltodextrin substrate with
   i. a dextrin dextranase or
   ii. a combination of a dextrin dextranase and at least one α-glucanohydrolase under suitable aqueous reaction conditions; whereby an α-glucan substrate backbone is produced having a weight average molecular weight of at least 0.5 kDa, said α-glucan substrate backbone comprising at least 50% α-(1,6) glycosidic linkages; wherein said α-glucan substrate comprises less than 1% α-(1,2) glycosidic linkages;
b. contacting the α-glucan substrate backbone produced in (a) with a set of reaction components comprising
   i. a polypeptide comprising an amino acid sequence having at least 90% identity to SEQ ID NO: 6; said polypeptide capable of catalyzing the synthesis of α-(1,2) glycosidic linkages on the α-glucan substrate backbone;
   ii. sucrose; and
   iii. optionally one or more acceptors;
c. combining the set of reaction components of (b) under suitable aqueous reaction conditions whereby the polypeptide catalyzing the synthesis of an α-glucan fiber composition comprising 1 to 50% of a combination of α-(1,2) and α-(1,2,6) glycosidic linkages; and
d. optionally isolating the α-glucan fiber composition of step (c).

In another embodiment, a method is provided to produce an α-glucan fiber composition comprising:
a. providing a set of reaction components comprising
   i. a maltodextrin substrate;
   ii. a 4,6-α-glucosyltransferase or a combination of a 4,6-α-glucosyltransferase and at least one α-glucanohydrolase under suitable aqueous reaction conditions;
   iii. a polypeptide comprising an amino acid sequence having at least 90% identity to SEQ ID NO: 6; said polypeptide capable of catalyzing the synthesis of α-(1,2) glycosidic linkages on an α-glucan substrate;
   iv. sucrose; and
   v. optionally one or more acceptors;
b. combining the set of reaction components of (a) under suitable aqueous reaction conditions whereby an α-glucan fiber composition comprising 1 to 50% of a combination of α-(1,2) and α-(1,2,6) glycosidic linkages is produced; and
c. optionally isolating the α-glucan fiber composition of step (b).

In a further embodiment to any of the above methods, the soluble α-glucan fiber composition is isolated comprising at least one of centrifugation, filtration, fractionation, chromatographic separation, dialysis, evaporation, dilution or any combination thereof.

Methods to Identify Substantially Similar Enzymes Having the Desired Activity

The skilled artisan recognizes that substantially similar enzyme sequences may also be used in the present compositions and methods so long as the desired activity is retained (i.e., glucosyltransferase activity capable of forming glucans having the desired glycosidic linkages or α-glucanohydrolases having endohydrolytic activity towards the target glycosidic linkage(s)). For example, it has been demonstrated that catalytically activity truncations may be prepared and used so long as the desired activity is retained (or even improved in terms of specific activity). In one embodiment, substantially similar sequences are defined by their ability to hybridize, under highly stringent conditions with the nucleic acid molecules associated with sequences exemplified herein. In another embodiment, sequence alignment algorithms may be used to define substantially similar enzymes based on the percent identity to the DNA or amino acid sequences provided herein.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J. and Russell, D., T. *Molecular Cloning: A Laboratory Manual*, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms. Post-hybridization washes typically determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of conditions uses higher temperatures in which the washes are identical to those above except for the temperature of the final two 30 min washes in 0.2×SSC, 0.5% SDS was increased to 60° C. Another preferred set of highly stringent hybridization conditions is 0.1×SSC, 0.1% SDS, 65° C. and washed with 2×SSC, 0.1% SDS followed by a final wash of 0.1×SSC, 0.1% SDS, 65° C.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (Sambrook, J. and Russell, D., T., supra). For hybridizations with shorter nucleic acids, i.e., oligonucleotides, the position of mismatches becomes more important, and the length of the oligonucleotide determines its specificity. In one aspect, the length for a hybridizable nucleic acid is at least about 10 nucleotides. Preferably, a minimum length for a hybridizable nucleic acid is at least about 15 nucleotides in length, more preferably at least about 20 nucleotides in length, even more preferably at least 30 nucleotides in length, even more preferably at least 300 nucleotides in length, and most preferably at least 800 nucleotides in length. Furthermore, the skilled artisan will recognize that the temperature and wash solution salt concentration may be adjusted as necessary according to factors such as length of the probe.

As used herein, the term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the number of matching nucleotides or amino acids between strings of such sequences. "Identity" and "similarity" can be readily calculated by known methods, including but not limited to those described in: *Computational Molecular Biology* (Lesk, A. M., ed.) Oxford University Press, N Y (1988); *Biocomputing: Informatics and Genome Projects* (Smith, D. W., ed.) Academic Press, N Y (1993); *Computer Analysis of Sequence Data, Part I* (Griffin, A. M., and Griffin, H. G., eds.) Humana Press, N J (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs. Sequence alignments and percent identity calculations may be performed using the Megalign program of the LASERGENE bioinformatics computing suite (DNASTAR Inc., Madison, WI), the AlignX program of Vector NTI v. 7.0 (Informax, Inc., Bethesda, MD), or the EMBOSS Open Software Suite (EMBL-EBI; Rice et al., *Trends in Genetics* 16, (6):276-277 (2000)). Multiple alignment of the sequences can be performed using the CLUSTAL method (such as CLUSTALW; for example version 1.83) of alignment (Higgins and Sharp, *CABIOS*, 5:151-153 (1989); Higgins et al., *Nucleic Acids Res.* 22:4673-4680 (1994); and Chenna et al., *Nucleic Acids Res* 31 (13):3497-500 (2003)), available from the European Molecular Biology Laboratory via the European Bioinformatics Institute) with the default parameters. Suitable parameters for CLUSTALW protein alignments include GAP Existence penalty=15, GAP extension=0.2, matrix=Gonnet (e.g., Gonnet250), protein ENDGAP=-1, protein GAPDIST=4, and KTUPLE=1. In one embodiment, a fast or slow alignment is used with the default settings where a slow alignment is preferred. Alternatively, the parameters using the CLUSTALW method (e.g., version 1.83) may be modified to also use KTUPLE=1, GAP PENALTY=10, GAP extension=1, matrix=BLOSUM (e.g., BLOSUM64), WINDOW=5, and TOP DIAGONALS SAVED=5.

In one aspect, suitable isolated nucleic acid molecules encode a polypeptide having an amino acid sequence that is at least about 20%, preferably at least 30%, 40%, 50%, 60%, 70%, 80%, 85%, 90%, 91%, 92%, 93%, 94%, 95%, 96%, 97%, 98%, or 99% identical to the amino acid sequences reported herein. In another aspect, suitable isolated nucleic acid molecules encode a polypeptide having an amino acid sequence that is at least about 20%, preferably at least 30%, 40%, 50%, 60%, 70%, 80%, 85%, 90%, 91%, 92%, 93%, 94%, 95%, 96%, 97%, 98%, or 99% identical to the amino acid sequences reported herein; with the proviso that the polypeptide retains the respective activity (i.e., glucosyltransferase or α-glucanohydrolase activity).

Methods to Obtain the Enzymatically-Produced Soluble α-Glucan Fiber Composition

Any number of common purification techniques may be used to obtain the present soluble α-glucan fiber composition from the reaction system including, but not limited to centrifugation, filtration, fractionation, chromatographic separation, dialysis, evaporation, precipitation, dilution or any combination thereof, preferably by dialysis or chromatographic separation, most preferably by dialysis (ultrafiltration).

Recombinant Microbial Expression

The genes and gene products of the instant sequences may be produced in heterologous host cells, particularly in the cells of microbial hosts. Preferred heterologous host cells for expression of the instant genes and nucleic acid molecules are microbial hosts that can be found within the fungal or bacterial families and which grow over a wide range of temperature, pH values, and solvent tolerances. For example, it is contemplated that any of bacteria, yeast, and filamentous fungi may suitably host the expression of the present nucleic acid molecules. The enzyme(s) may be expressed intracellularly, extracellularly, or a combination of both intracellularly and extracellularly, where extracellular expression renders recovery of the desired protein from a fermentation product more facile than methods for recovery of protein produced by intracellular expression. Transcription, translation and the protein biosynthetic apparatus remain invariant relative to the cellular feedstock used to generate cellular biomass; functional genes will be expressed regardless. Examples of host strains include, but are not limited to, bacterial, fungal or yeast species such as *Aspergillus, Trichoderma, Saccharomyces, Pichia, Phaffia, Kluyveromyces, Candida, Hansenula, Yarrowia, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. In one embodiment, the fungal host cell is *Trichoderma*, preferably a strain of *Trichoderma reesei*. In one embodiment, bacterial host strains include *Escherichia, Bacillus, Kluyveromyces*, and *Pseudomonas*. In a preferred embodiment, the bacterial host cell is *Bacillus subtilis* or *Escherichia coli*.

Large-scale microbial growth and functional gene expression may use a wide range of simple or complex carbohydrates, organic acids and alcohols or saturated hydrocarbons, such as methane or carbon dioxide in the case of photosynthetic or chemoautotrophic hosts, the form and amount of nitrogen, phosphorous, sulfur, oxygen, carbon or any trace micronutrient including small inorganic ions. The regulation of growth rate may be affected by the addition, or not, of specific regulatory molecules to the culture and which are not typically considered nutrient or energy sources.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell and/or native to the production host, although such control regions need not be so derived.

Initiation control regions or promoters which are useful to drive expression of the present cephalosporin C deacetylase coding region in the desired host cell are numerous and familiar to those skilled in the art. Virtually any promoter capable of driving these genes is suitable for the present invention including but not limited to, CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, araB, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred host cell. In one embodiment, the inclusion of a termination control region is optional. In another embodiment, the chimeric gene includes a termination control region derived from the preferred host cell.

Industrial Production

A variety of culture methodologies may be applied to produce the enzyme(s). For example, large-scale production of a specific gene product over-expressed from a recombinant microbial host may be produced by batch, fed-batch, and continuous culture methodologies. Batch and fed-batch culturing methods are common and well known in the art and examples may be found in *Biotechnology: A Textbook of Industrial Microbiology* by Wulf Crueger and Anneliese Crueger (authors), Second Edition, (Sinauer Associates, Inc., Sunderland, MA (1990) and *Manual of Industrial Microbiology and Biotechnology*, Third Edition, Richard H. Baltz, Arnold L. Demain, and Julian E. Davis (Editors), (ASM Press, Washington, DC (2010).

Commercial production of the desired enzyme(s) may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added and valuable products, by-products or waste products are continuously removed from the cell mass. Cell immobilization may be performed using a wide range of solid supports composed of natural and/or synthetic materials.

Recovery of the desired enzyme(s) from a batch fermentation, fed-batch fermentation, or continuous culture, may be accomplished by any of the methods that are known to those skilled in the art. For example, when the enzyme catalyst is produced intracellularly, the cell paste is separated from the culture medium by centrifugation or membrane filtration, optionally washed with water or an aqueous buffer at a desired pH, then a suspension of the cell paste in an aqueous buffer at a desired pH is homogenized to produce a cell extract containing the desired enzyme catalyst. The cell extract may optionally be filtered through an appropriate filter aid such as celite or silica to remove cell debris prior to a heat-treatment step to precipitate undesired protein from the enzyme catalyst solution. The solution containing the desired enzyme catalyst may then be separated from the precipitated cell debris and protein by membrane filtration or centrifugation, and the resulting partially-purified enzyme catalyst solution concentrated by additional membrane filtration, then optionally mixed with an appropriate carrier (for example, maltodextrin, phosphate buffer, citrate buffer, or mixtures thereof) and spray-dried to produce a solid powder comprising the desired enzyme catalyst. Alternatively, the resulting partially-purified enzyme catalyst solution can be stabilized as a liquid formulation by the addition of polyols such as maltodextrin, sorbitol, or propylene glycol, to which is optionally added a preservative such as sorbic acid, sodium sorbate or sodium benzoate.

The production of the soluble α-glucan fiber can be carried out by combining the obtained enzyme(s) under any suitable aqueous reaction conditions which result in the production of the soluble α-glucan fiber such as the conditions disclosed herein. The reaction may be carried out in water solution, or, in certain embodiments, the reaction can be carried out in situ within a food product. Methods for producing a fiber using an enzyme catalyst in situ in a food product are known in the art. In certain embodiments, the enzyme catalyst is added to a sucrose-containing liquid food product. The enzyme catalyst can reduce the amount of sucrose in the liquid food product while increasing the amount of soluble α-glucan fiber and fructose. A suitable method for in situ production of fiber using a polypeptide material (i.e., an enzyme catalyst) within a food product can be found in WO2013/182686, the contents of which are herein incorporated by reference for the disclosure of a method for in situ production of fiber in a food product using an enzyme catalyst.

When an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope be limited to the specific values recited when defining a range.

Description of Certain Embodiments

In a first embodiment (the "first embodiment"), a soluble α-glucan fiber composition is provided, said soluble α-glucan fiber composition comprising:
a. a range of
   i. 0% to 50%, α-(1,3) glycosidic linkages, preferably 3% to 50% or
   ii. 0% to less than 40% α-(1,4) glycosidic linkages; preferably 15% to 35% α-(1,4) glycosidic linkages; or
   iii. any combination of (i) and (ii);
b. 1 to 50% of a combination of α-(1,2) and α-(1,2,6) glycosidic linkages, preferably 1 to 40%, more preferably 2 to 30%;
c. 0-25% α-(1,3,6) glycosidic linkages; preferably wherein the combination of α-(1,3) glycosidic linkages and α-(1,3,6) glycosidic linkages is 3% to 50%;
d. less than 99% α-(1,6) glycosidic linkages;
e. a weight average molecular weight of less than 300000 Daltons, preferably in the range of 1500 to 300000 Da, more preferably 1500 to 150000 Da, more preferably 1500 to 40000 Da, and even more preferably 1500 to 20000 Da;
f. a viscosity of less than 0.25 Pascal second (Pa·s); preferably 0.01 Pascal second (Pa·s); preferably less than 0.007 Pascal second (Pa·s) at 12 wt % in water;
g. a digestibility of less than 20%, preferably less than 15, 10, 9, 8, 7, 6, 5, 4, 3, 2, or 1%, as measured by the Association of Analytical Communities (AOAC) method 2009.01;
h. a solubility of at least 20% (w/w), preferably at least 30%, 40%, 50%, 60%, or 70% in pH 7 water at 25° C.; and
i. a polydispersity index of less than 26; preferably less than 5.

In second embodiment, a carbohydrate composition is provided comprising 0.01 to 99 wt % (dry solids basis), preferably 10 to 90% wt %, of the soluble α-glucan fiber composition described above in the first embodiment.

In a third embodiment, a food product, personal care product or pharmaceutical product is provided comprising the soluble α-glucan fiber composition of the first embodiment or a carbohydrate composition comprising the soluble α-glucan fiber composition of the second embodiment.

In a fourth embodiment, a low cariogenicity composition is provided comprising the soluble α-glucan fiber composition of the first embodiment and at least one polyol.

In a fifth embodiment, a method is provided to produce a soluble α-glucan fiber composition comprising:
a. providing a set of reaction components comprising:
   i. sucrose;
   ii. an α-glucan substrate backbone having a weight average molecular weight of at least 0.5 kDa, said α-glucan substrate comprising at least 50% α-(1,6) glycosidic linkages; preferably wherein the α-glucan substrate backbone further comprises 1 to 50% α-(1,3) glycosidic linkages;
   iii. a polypeptide comprising an amino acid sequence having at least 90% identity to SEQ ID NO: 6; said polypeptide capable of catalyzing the synthesis of α-(1,2) glycosidic linkages on the α-glucan substrate backbone; and
   iv. optionally one or more acceptors;
b. combining the set of reaction components under suitable aqueous reaction conditions whereby the polypeptide catalyzes the synthesis of an α-glucan fiber composition comprising 1 to 50% α-(1,2) glycosidic linkages; preferably 1 to 40%, and most preferably 2 to 30% of a combination of α-(1,2) and α-(1,2,6) glycosidic linkages; and
c. optionally isolating the α-glucan fiber composition.

In a further embodiment to the above, the α-glucan substrate backbone comprises more than 10% but less than 40% α-(1,4) glycosidic linkages.

In a further embodiment to any of the above embodiments, the α-glucan fiber composition formed by the above method comprises
a. a viscosity of less than 0.01 10 cps Pascal second (Pa·s) at 12 wt % in water at 20° C.;
b. a digestibility of less than 20% as measured by the Association of Analytical Communities (AOAC) method 2009.01;
c. a solubility of at least 20% (w/w) in pH 7 water at 25° C.; and
d. a polydispersity index of less than 5.

In a sixth embodiment, a method to produce an α-glucan fiber composition is provided comprising:
a. contacting sucrose with at least one glucosyltransferase or a combination of at least one glucosyltransferase and at least one α-glucanohydrolase under suitable reaction conditions whereby an α-glucan substrate is produced having a weight average molecular weight of at least 0.5 kDa, said α-glucan substrate comprising at least 50% α-(1,6) glycosidic linkages; wherein said α-glucan substrate comprises less than 1% α-(1,2) glycosidic linkages;
b. contacting the α-glucan substrate produced in (a) with a set of reaction components comprising
   i. a polypeptide comprising an amino acid sequence having at least 90% identity to SEQ ID NO: 6; said polypeptide capable of catalyzing the synthesis of α-(1,2) glycosidic linkages on the α-glucan substrate;
   ii. sucrose; and
   iii. optionally one or more acceptors;
c. combining the set of reaction components under suitable aqueous reaction conditions whereby the polypeptide catalyzes the synthesis of an α-glucan fiber composition comprising 1 to 50% of a combination of α-(1,2) and α-(1,2,6) glycosidic linkages; and
d. optionally isolating the α-glucan fiber composition of step (c).

In a seventh embodiment, a method to produce an α-glucan fiber composition is provided comprising:
a. contacting a maltodextrin substrate with
   i. a dextrin dextranase or
   ii. a combination of a dextrin dextranase and at least one α-glucanohydrolase under suitable aqueous reaction conditions; whereby an α-glucan substrate backbone is produced having a weight average molecular weight of at least 0.5 kDa, said α-glucan substrate comprising at least 50% α-(1,6) glycosidic linkages; wherein said α-glucan substrate comprises less than 1% α-(1,2) glycosidic linkages;
b. contacting the α-glucan substrate backbone produced in (a) with a set of reaction components comprising
   i. a polypeptide comprising an amino acid sequence having at least 90% identity to SEQ ID NO: 6; said polypeptide capable of catalyzing the synthesis of α-(1,2) glycosidic linkages on the α-glucan substrate;
   ii. sucrose; and
   iii. optionally one or more acceptors;
c. combining the set of reaction components under suitable aqueous reaction conditions whereby the polypeptide catalyzes the synthesis of an α-glucan fiber composition comprising 1 to 50% of a combination of α-(1,2) and α-(1,2,6) glycosidic linkages; and
d. optionally isolating the α-glucan fiber composition of step (c).

In another embodiment, a method to produce an α-glucan fiber composition is provided comprising:
a. providing a set of reaction components comprising
   i. a maltodextrin substrate;
   ii. a dextrin dextrinase;
   iii. a polypeptide comprising an amino acid sequence having at least 90% identity to SEQ ID NO: 6; said polypeptide capable of catalyzing the synthesis of α-(1,2) glycosidic linkages on an α-glucan substrate;
   iv. sucrose; and
   v. optionally one or more acceptors;
b. combining the set of reaction components under suitable aqueous reaction conditions whereby an α-glucan fiber composition comprising 1 to 50% α-(1,2) glycosidic linkages is formed; and
c. optionally isolating the α-glucan fiber composition of step (b).

In some embodiments of any of the methods, the step of combining the set of reaction components under suitable aqueous reaction conditions comprises combining the set of reaction components within a food product.

In addition to any of the above method embodiments, the method to produce an α-glucan fiber composition further comprises step (d) concentrating the α-glucan fiber composition.

In addition to any of the above embodiments, the sucrose concentration is initially at least 50 g/L; preferably at least 200 g/L when the set of reaction components are combined.

In addition to any of the above embodiments, the weight ratio of the α-glucan substrate backbone to sucrose present in the reaction ranges from 0.01:1 to 1:0.01.

In another embodiment, a method is provided to make a blended carbohydrate composition comprising combining the soluble α-glucan fiber composition of the first embodiment with: a monosaccharide, a disaccharide, glucose, sucrose, fructose, leucrose, corn syrup, high fructose corn syrup, isomerized sugar, maltose, trehalose, panose, raffinose, cellobiose, isomaltose, honey, maple sugar, a fruit-derived sweetener, sorbitol, maltitol, isomaltitol, lactose, nigerose, kojibiose, xylitol, erythritol, dihydrochalcone, stevioside, α-glycosyl stevioside, acesulfame potassium, alitame, neotame, glycyrrhizin, thaumantin, sucralose, L-aspartyl-L-phenylalanine methyl ester, saccharine, maltodextrin, starch, potato starch, tapioca starch, dextran, soluble corn fiber, a resistant maltodextrin, a branched maltodextrin, inulin, polydextrose, a fructooligosaccharide, a galactooligosaccharide, a xylooligosaccharide, an arabinoxylooligosaccharide, a nigerooligosaccharide, a gentiooligosaccharide, hemicellulose, fructose oligomer syrup, an isomaltooligosaccharide, a filler, an excipient, a binder, or any combination thereof.

In another embodiment, a method to make a food product, personal care product, or pharmaceutical product is provided comprising mixing one or more edible food ingredients, cosmetically acceptable ingredients or pharmaceutically acceptable ingredients; respectively, with the soluble α-glucan fiber composition of the first embodiment, the carbohydrate composition of the second embodiment, or a combination thereof.

In another embodiment, a method to reduce the glycemic index of a food or beverage is provided comprising incorporating into the food or beverage the soluble α-glucan fiber composition of the first embodiment.

In another embodiment, a method of inhibiting the elevation of blood-sugar level, lowering lipids in the living body, treating constipation or reducing gastrointestinal transit time in a mammal is provided comprising a step of administering the soluble α-glucan fiber composition of the first embodiment to the mammal.

In another embodiment, a method to alter fatty acid production in the colon of a mammal is provided the method comprising a step of administering the present soluble α-glucan fiber composition of to the mammal; preferably wherein the short chain fatty acid production is increased and/or the branched chain fatty acid production is decreased.

In another embodiment, a use of the soluble α-glucan fiber composition of the first embodiment in a food composition suitable for consumption by animals, including humans is also provided.

A composition or method according to any of the above embodiments wherein the α-glucan fiber composition comprises less than 10%, preferably less than 5 wt %, and most preferably 1 wt % or less reducing sugars.

A composition or method according to any of the above embodiments wherein the soluble α-glucan fiber composition is characterized by a number average molecular weight (Mn) between 1500 and 90,000 g/mol, preferably 1500 to 30,000 g/mol, more preferably 1500 to 20,000, and more preferably 3000 to 16000 g/mol.

A composition or method according to any of the above embodiments wherein the carbohydrate composition comprises: a monosaccharide, a disaccharide, glucose, sucrose, fructose, leucrose, corn syrup, high fructose corn syrup, isomerized sugar, maltose, trehalose, panose, raffinose, cellobiose, isomaltose, honey, maple sugar, a fruit-derived sweetener, sorbitol, maltitol, isomaltitol, lactose, nigerose, kojibiose, xylitol, erythritol, dihydrochalcone, stevioside, α-glycosyl stevioside, acesulfame potassium, alitame, neotame, glycyrrhizin, thaumantin, sucralose, L-aspartyl-L-phenylalanine methyl ester, saccharine, maltodextrin, starch, potato starch, tapioca starch, dextran, soluble corn fiber, a resistant maltodextrin, a branched maltodextrin, inulin, polydextrose, a fructooligosaccharide, a galactooligosaccharide, a xylooligosaccharide, an arabinoxylooligosaccharide, a nigerooligosaccharide, a gentiooligosaccharide, hem icellulose, fructose oligomer syrup, an isomaltooligosaccharide, a filler, an excipient, a binder, or any combination thereof.

A composition or method according to any of the above embodiments wherein the carbohydrate composition is in the form of a liquid, a syrup, a powder, granules, shaped spheres, shaped sticks, shaped plates, shaped cubes, tablets, powders, capsules, sachets, or any combination thereof.

A composition or method according to any of the above embodiments wherein the food product is
 a. a bakery product selected from the group consisting of cakes, brownies, cookies, cookie crisps, muffins, breads, and sweet doughs, extruded cereal pieces, and coated cereal pieces;
 b. a dairy product selected from the group consisting of yogurt, yogurt drinks, milk drinks, flavored milks, smoothies, ice cream, shakes, cottage cheese, cottage cheese dressing, quarg, and whipped mousse-type products;
 c. confections selected from the group consisting of hard candies, fondants, nougats and marshmallows, gelatin jelly candies, gummies, jellies, chocolate, licorice, chewing gum, caramels, toffees, chews, mints, tableted confections, and fruit snacks;
 d. beverages selected from the group consisting of carbonated beverages, fruit juices, concentrated juice mixes, clear waters, and beverage dry mixes;
 e. high solids fillings for snack bars, toaster pastries, donuts, or cookies;
 f. extruded and sheeted snacks selected from the group consisting of puffed snacks, crackers, tortilla chips, and corn chips;
 g. snack bars, nutrition bars, granola bars, protein bars, and cereal bars;
 h. cheeses, cheese sauces, and other edible cheese products;
 i. edible films;
 j. water soluble soups, syrups, sauces, dressings, or coffee creamers; or
 k. dietary supplements; preferably in the form of tablets, powders, capsules or sachets.

A composition comprising 0.01 to 99 wt % (dry solids basis) of the present soluble α-glucan fiber composition and: a synbiotic, a peptide, a peptide hydrolysate, a protein, a protein hydrolysate, a soy protein, a dairy protein, an amino acid, a polyol, a polyphenol, a vitamin, a mineral, an herbal, an herbal extract, a fatty acid, a polyunsaturated fatty acid (PUFAs), a phytosteroid, betaine, a carotenoid, a digestive enzyme, a probiotic organism or any combination thereof.

A method according to any of the above embodiments wherein the isolating step comprises at least one of centrifugation, filtration, fractionation, chromatographic separation, dialysis, evaporation, dilution or any combination thereof.

A method according to any of the above embodiments wherein the glucosyltransferase used to synthesize the α-glucan substrate backbone comprises an amino acid sequence having at least 90% identity to SEQ ID NO: 7, 9, 10, 11, 12, 13, 14 or 16; preferably 7, 9, 10, 11, 12 or 13 when not used with an α-glucanohydrolase.

A method according to any of the above embodiments wherein the α-glucanohydrolase is a dextranase or mutanase.

A method according to any of the above embodiments wherein the maltodextrin substrate concentration is initially at least 20 g/L when the set of reaction components are combined.

A method according to any of the above embodiments wherein the ratio of dextrin dextranase activity to endodextranase activity ranges from 0.01:1 to 1:0.01.

A method according to any of the above embodiments wherein the suitable aqueous reaction conditions comprise a reaction temperature between 0° C. and 45° C.

A method according to any of the above embodiments wherein the suitable aqueous reaction conditions comprise a pH range of 3 to 8; preferably 4 to 8.

A method according to any of the above embodiments wherein the suitable aqueous reaction conditions comprise including a buffer selected from the group consisting of phosphate, pyrophosphate, bicarbonate, acetate, and citrate.

A method according to any of the above embodiments wherein said polypeptide having dextrin dextranase activity comprises an amino acid sequence having at least 90%, preferably at least 91, 92, 93, 94, 95, 96, 97, 98, 99 or 100% identity to SEQ ID NO:26.

A method according to any of the above embodiments wherein said at least one polypeptide comprising α-glucanohydrolase activity comprises dextrinase activity, preferably endodextranase activity, preferably an endodextranase from *Chaetomium erraticum*, more preferably Dextrinase L from *Chaetomium erraticum*, and most preferably DEXTRANASE® Plus L. In a preferred embodiment, the dextranase is suitable for use in foods and is generally recognized as safe (GRAS).

A method according to any of the above embodiments wherein said at least one polypeptide comprising α-glucanohydrolase activity comprises mutanase activity, preferable endomutanase activity, preferably comprising an amino acid sequence having at least 90% identity, preferably 91, 92, 93, 94, 95, 96, 97, 98, 99 or 100% identity to SEQ ID NO: 21 or 23.

A method according to any of the above embodiments wherein said glucosyltransferase comprises an amino acid sequence having at least 90%, preferably at least 91, 92, 93, 94, 95, 96, 97, 98, 99 or 100% identity to SEQ ID NO: 14 or 16 and said endomutanase comprises an amino acid sequence having at least 90%, preferably 91, 92, 93, 94, 95, 96, 97, 98, 99 or 100% identity to SEQ ID NO: 21 or 23.

A method according to any of the above embodiments where the α-glucan substrate backbone is synthesized from maltodextrin using a 4,6-α-glucosyltransferase (Gtf-B type) comprising an amino acid sequence having at least 90% identity; preferably at least 91, 92, 93, 94, 95, 96, 97, 98, 99 or 100% identity to SEQ ID NO: 68, 69 or 70.

A method according to any of the above embodiments wherein the maltodextrin substrate is synthesized using an polypeptide having amylosucrase activity, preferably comprising an amino acid sequence having at least 90% identity, more preferably at least 91, 92, 93, 94, 95, 96, 97, 98, 99 or 100% identity to SEQ ID NO: 71.

A product produced by any of the above process embodiments; preferably wherein the product produced is the soluble α-glucan fiber composition of the first embodiment.

EXAMPLES

Unless defined otherwise herein, all technical and scientific terms used herein have the same meaning as commonly understood by one of ordinary skill in the art to which this invention belongs. Singleton, et al., *DICTIONARY OF MICROBIOLOGY AND MOLECULAR BIOLOGY, 2D ED.*, John Wiley and Sons, New York (1994), and Hale & Marham, *THE HARPER COLLINS DICTIONARY OF BIOLOGY*, Harper Perennial, N.Y. (1991) provide one of skill with a general dictionary of many of the terms used in this invention.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations is as follows: "sec" or "s" means second(s), "ms" mean milliseconds, "min" means minute(s), "h" or "hr" means hour(s), "µL" means microliter(s), "mL" means milliliter(s), "L" means liter(s); "mL/min" is milliliters per minute; "µg/mL" is microgram(s) per milliliter(s); "LB" is Luria broth; "µm" is micrometers, "nm" is nanometers; "OD" is optical density; "IPTG" is isopropyl-β-D-thio-galactoside; "g" is gravitational force; "mM" is millimolar; "SDS-PAGE" is sodium dodecyl sulfate polyacrylamide; "mg/mL" is milligrams per milliliters; "N" is normal; "w/v" is weight for volume; "DTT" is dithiothreitol; "BCA" is bicinchoninic acid; "DMAc" is N, N'-dimethyl acetamide; "LiCl" is Lithium chloride' "NMR" is nuclear magnetic resonance; "DMSO" is dimethylsulfoxide; "SEC" is size exclusion chromatography; "GI" or "gi" means GenInfo Identifier, a system used by GENBANK® and other sequence databases to uniquely identify polynucleotide and/or polypeptide sequences within the respective databases; "DPx" means glucan degree of polymerization having "x" units in length; "ATCC" means American Type Culture Collection (Manassas, VA), "DSMZ" and "DSM" will refer to Leibniz Institute DSMZ-German Collection of Microorganisms and Cell Cultures, (Braunschweig, Germany); "EELA" is the Finish Food Safety Authority (Helsinki, Finland;)"CCUG" refer to the Culture Collection, University of Göteborg, Sweden; "Suc." means sucrose; "Gluc." means glucose; "Fruc." means fructose; "Leuc." means leucrose; and "Rxn" means reaction.

General Methods

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, NY (2001); and by Silhavy, T. J., Bennan, M. L. and Enquist, L. W., *Experiments with Gene Fusions*, Cold Spring Harbor Laboratory Cold Press Spring Harbor, N Y (1984); and by Ausubel, F. M. et. al., *Short Protocols in Molecular Biology*, 5th Ed. Current Protocols and John Wiley and Sons, Inc., N.Y., 2002.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., (American Society for Microbiology Press, Washington, DC (1994)), *Biotechnology: A Textbook of Industrial Microbiology* by Wulf Crueger and Anneliese Crueger (authors), Second Edition, (Sinauer Associates, Inc., Sunderland, MA (1990)), and *Manual of Industrial Microbiology and Biotechnology*, Third Edition, Richard H. Baltz, Arnold L. Demain, and Julian E. Davis (Editors), (American Society of Microbiology Press, Washington, DC (2010).

All reagents, restriction enzymes and materials used for the growth and maintenance of bacterial cells were obtained from BD Diagnostic Systems (Sparks, MD), Invitrogen/Life Technologies Corp. (Carlsbad, CA), Life Technologies (Rockville, MD), QIAGEN (Valencia, CA), Sigma-Aldrich Chemical Company (St. Louis, MO) or Pierce Chemical Co. (A division of Thermo Fisher Scientific Inc., Rockford, IL) unless otherwise specified. IPTG, (cat #16758) and triphenyltetrazolium chloride were obtained from the Sigma Co., (St. Louis, MO). Bellco spin flask was from the Bellco Co., (Vineland, NJ). LB medium was from Becton, Dickinson and Company (Franklin Lakes, New Jersey). BCA protein assay was from Sigma-Aldrich (St Louis, MO).

Growth of Recombinant *E. coli* Strains for Production of GTF Enzymes

*Escherichia coli* strains expressing a functional GTF enzyme were grown in shake flask using LB medium with ampicillin (100 µg/mL) at 37° C. and 220 rpm to $OD_{600nm}$=0.4-0.5, at which time isopropyl-β-D-thio-galactoside (IPTG) was added to a final concentration of 0.5 mM and incubation continued for 2-4 hr at 37° C. Cells were harvested by centrifugation at 5,000×g for 15 min and resuspended (20%-25% wet cell weight/v) in 50 mM phosphate buffer pH 7.0). Resuspended cells were passed through a French Pressure Cell (SLM Instruments, Rochester, NY) twice to ensure >95% cell lysis. Cell lysate was centrifuged for 30 min at 12,000×g and 4° C. The resulting supernatant (cell extract) was analyzed by the BCA protein assay and SDS-PAGE to confirm expression of the GTF enzyme, and the cell extract was stored at −80° C.

pHYT Vector

The pHYT vector backbone is a replicative *Bacillus subtilis* expression plasmid containing the *Bacillus subtilis* aprE promoter. It was derived from the *Escherichia coli-Bacillus subtilis* shuttle vector pHY320PLK (GENBANK® Accession No. D00946 and is commercially available from Takara Bio Inc. (Otsu, Japan)). The replication origin for *Escherichia coli* and ampicillin resistance gene are from pACYC177 (GENBANK® X06402 and is commercially available from New England Biolabs Inc., Ipswich, MA). The replication origin for *Bacillus subtilis* and tetracycline resistance gene were from pAMalpha-1 (Francia et al., *J Bacteriol.* 2002 September; 184(18):5187-93)).

To construct pHYT, a terminator sequence: 5'-ATAAAAAACGCTCGGTTGCCGCCGGGCGTTTTT-TAT-3' (SEQ ID NO: 32) from phage lambda was inserted after the tetracycline resistance gene. The entire expression cassette (EcoRI-BamHI fragment) containing the aprE promoter-AprE signal peptide sequence-coding sequence encoding the enzyme of interest (e.g., coding sequences for various GTFs)-BPN' terminator was cloned into the EcoRI and HindIII sites of pHYT using a BamHI-HindIII linker that destroyed the HindIII site. The linker sequence is 5'-GGATCCTGACTGCCTGAGCTT-3' (SEQ ID NO: 33). The aprE promoter and AprE signal peptide sequence (SEQ ID NO: 34) are native to Bacillus subtilis. The BPN' terminator is from subtilisin of Bacillus amyloliquefaciens. In the case when native signal peptide was used, the AprE signal peptide was replaced with the native signal peptide of the expressed gene.

Biolistic Transformation of T. reesei

A Trichoderma reesei spore suspension was spread onto the center ~6 cm diameter of an acetamidase transformation plate (150 µL of a $5 \times 10^7$-$5 \times 10^8$ spore/mL suspension). The plate was then air dried in a biological hood. The stopping screens (BioRad 165-2336) and the macrocarrier holders (BioRad 1652322) were soaked in 70% ethanol and air dried. DRIERITE® desiccant (calcium sulfate desiccant; W.A. Hammond DRIERITE® Company, Xenia, OH) was placed in small Petri dishes (6 cm Pyrex) and overlaid with Whatman filter paper (GE Healthcare Bio-Sciences, Pittsburgh, PA). The macrocarrier holder containing the macrocarrier (BioRad 165-2335; Bio-Rad Laboratories, Hercules, CA) was placed flatly on top of the filter paper and the Petri dish lid replaced. A tungsten particle suspension was prepared by adding 60 mg tungsten M-10 particles (microcarrier, 0.7 micron, BioRad #1652266, Bio-Rad Laboratories) to an Eppendorf tube. Ethanol (1 mL) (100%) was added. The tungsten was vortexed in the ethanol solution and allowed to soak for 15 minutes. The Eppendorf tube was microfuged briefly at maximum speed to pellet the tungsten. The ethanol was decanted and washed three times with sterile distilled water. After the water wash was decanted the third time, the tungsten was resuspended in 1 mL of sterile 50% glycerol. The transformation reaction was prepared by adding 25 µL suspended tungsten to a 1.5 mL-Eppendorf tube for each transformation. Subsequent additions were made in order, 2 µL DNA pTrex3 expression vectors (SEQ ID NO: 24; see U.S. Pat. No. 6,426,410), 25 µL 2.5M $CaCl_2$), 10 µL 0.1M spermidine. The reaction was vortexed continuously for 5-10 minutes, keeping the tungsten suspended. The Eppendorf tube was then microfuged briefly and decanted. The tungsten pellet was washed with 200 µL of 70% ethanol, microfuged briefly to pellet and decanted. The pellet was washed with 200 µL of 100% ethanol, microfuged briefly to pellet, and decanted. The tungsten pellet was resuspended in 24 µL 100% ethanol. The Eppendorf tube was placed in an ultrasonic water bath for 15 seconds and 8 µL aliquots were transferred onto the center of the desiccated macrocarriers. The macrocarriers were left to dry in the desiccated Petri dishes.

A Helium tank was turned on to 1500 psi (~10.3 MPa). 1100 psi (~7.58 MPa) rupture discs (BioRad 165-2329) were used in the Model PDS-1000/He™ BIOLISTIC® Particle Delivery System (BioRad). When the tungsten solution was dry, a stopping screen and the macrocarrier holder were inserted into the PDS-1000. An acetamidase plate, containing the target T. reesei spores, was placed 6 cm below the stopping screen. A vacuum of 29 inches Hg (~98.2 kPa) was pulled on the chamber and held. The He BIOLISTIC® Particle Delivery System was fired. The chamber was vented and the acetamidase plate removed for incubation at 28° C. until colonies appeared (5 days).

Modified amdS Biolistic Agar (MABA) Per Liter
Part I, make in 500 mL distilled water ($dH_2O$)
1000× salts 1 mL
Noble agar 20 g
pH to 6.0, autoclave
Part II, make in 500 mL $dH_2O$
Acetamide 0.6 g
CsCl 1.68 g
Glucose 20 g
$KH_2PO_4$ 15 g
$MgSO_4 \cdot 7H_2O$ 0.6 g
$CaCl_2 \cdot 2H_2O$ 0.6 g
pH to 4.5, 0.2 micron filter sterilize; leave in 50° C. oven to warm, add to agar, mix, pour plates. Stored at room temperature (~21° C.)

1000× Salts Per Liter
$FeSO_4 \cdot 7H_2O$ 5 g
$MnSO_4 \cdot H_2O$ 1.6 g
$ZnSO_4 \cdot 7H_2O$ 1.4 g
$CoCl_2 \cdot 6H_2O$ 1 g
Bring up to 1 L $dH_2O$.
0.2 micron filter sterilize Determination of the Glucosyltransferase Activity Glucosyltransferase activity assay was performed by incubating 1-10% (v/v) crude protein extract containing GTF enzyme with 200 g/L sucrose in 25 mM or 50 mM sodium acetate buffer at pH 5.5 in the presence or absence of 25 g/L dextran (MW ~1500, Sigma-Aldrich, Cat. #31394) at 37° C. and 125 rpm orbital shaking. One aliquot of reaction mixture was withdrawn at 1 h, 2 h and 3 h and heated at 90° C. for 5 min to inactivate the GTF. The insoluble material was removed by centrifugation at 13,000×g for 5 min, followed by filtration through 0.2 µm RC (regenerated cellulose) membrane. The resulting filtrate was analyzed by HPLC using two Aminex HPX-87C columns series at 85° C. (Bio-Rad, Hercules, CA) to quantify sucrose concentration. The sucrose concentration at each time point was plotted against the reaction time and the initial reaction rate was determined from the slope of the linear plot.

One unit of GTF activity was defined as the amount of enzyme needed to consume one micromole of sucrose in one minute under the assay condition.

Determination of the α-Glucanohydrolase Activity

Insoluble mutan polymers required for determining mutanase activity were prepared using secreted enzymes produced by Streptococcus sobrinus ATCC® 33478™. Specifically, one loop of glycerol stock of S. sobrinus ATCC® 33478™ was streaked on a BHI agar plate (Brain Heart Infusion agar, Teknova, Hollister, CA), and the plate was incubated at 37° C. for 2 days; A few colonies were picked using a loop to inoculate 2×100 mL BHI liquid medium in the original medium bottle from Teknova, and the culture was incubated at 37° C., static for 24 h. The resulting cells were removed by centrifugation and the resulting supernatant was filtered through 0.2 µm sterile filter; 2×101 mL of filtrate was collected. To the filtrate was added 2×11.2 mL of 200 g/L sucrose (final sucrose 20 g/L). The reaction was incubated at 37° C., with no agitation for 67 h. The resulting polysaccharide polymers were collected by centrifugation at 5000×g for 10 min. The supernatant was carefully decanted. The insoluble polymers were washed 4 times with 40 mL of sterile water. The resulting mutan polymers were lyophilized for 48 h. Mutan polymer (390 mg) was suspended in 39 mL of sterile water to make suspension of 10 mg/mL. The mutan suspension was homogenized by sonication (40% amplitude until large lumps disappear, ~10 min in total). The homogenized suspension was aliquoted and stored at 4° C.

A mutanase assay was initiated by incubating an appropriate amount of enzyme with 0.5 mg/mL mutan polymer (prepared as described above) in 25 mM KOAc buffer at pH 5.5 and 37° C. At various time points, an aliquot of reaction mixture was withdrawn and quenched with equal volume of 100 mM glycine buffer (pH 10). The insoluble material in each quenched sample was removed by centrifugation at 14,000×g for 5 min. The reducing ends of oligosaccharide and polysaccharide polymer produced at each time point were quantified by the p-hydroxybenzoic acid hydrazide solution (PAHBAH) assay (Lever M., *Anal. Biochem.*, (1972) 47:273-279) and the initial rate was determined from the slope of the linear plot of the first three or four time points of the time course. The PAHBAH assay was performed by adding 10 µL of reaction sample supernatant to 100 µL of PAHBAH working solution and heated at 95° C. for 5 min. The working solution was prepared by mixing one part of reagent A (0.05 g/mL p-hydroxy benzoic acid hydrazide and 5% by volume of concentrated hydrochloric acid) and four parts of reagent B (0.05 g/mL NaOH, 0.2 g/mL sodium potassium tartrate). The absorption at 410 nm was recorded and the concentration of the reducing ends was calculated by subtracting appropriate background absorption and using a standard curve generated with various concentrations of glucose as standards.

Determination of Glycosidic Linkages

One-dimensional $^1$H NMR data were acquired on a Varian Unity Inova system (Agilent Technologies, Santa Clara, CA) operating at 500 MHz using a high sensitivity cryoprobe. Water suppression was obtained by carefully placing the observe transmitter frequency on resonance for the residual water signal in a "presat" experiment, and then using the "tnnoesy" experiment with a full phase cycle (multiple of 32) and a mix time of 10 ms.

Typically, dried samples were taken up in 1.0 mL of D20 and sonicated for 30 min. From the soluble portion of the sample, 1004 was added to a 5 mm NMR tube along with 3504 D20 and 1004 of D20 containing 15.3 mM DSS (4,4-dimethyl-4-silapentane-1-sulfonic acid sodium salt) as internal reference and 0.29% $NaN_3$ as bactericide. The abundance of each type of anomeric linkage was measured by the integrating the peak area at the corresponding chemical shift. The percentage of each type of anomeric linkage was calculated from the abundance of the particular linkage and the total abundance anomeric linkages from oligosaccharides.

Methylation Analysis

The distribution of glucosidic linkages in glucans was determined by a well-known technique generally named "methylation analysis," or "partial methylation analysis" (see: F. A. Pettolino, et al., *Nature Protocols*, (2012) 7(9): 1590-1607). The technique has a number of minor variations but always includes: 1. methylation of all free hydroxyl groups of the glucose units, 2. hydrolysis of the methylated glucan to individual monomer units, 3. reductive ring-opening to eliminate anomers and create methylated glucitols; the anomeric carbon is typically tagged with a deuterium atom to create distinctive mass spectra, 4. acetylation of the free hydroxyl groups (created by hydrolysis and ring opening) to create partially methylated glucitol acetates, also known as partially methylated products, 5. analysis of the resulting partially methylated products by gas chromatography coupled to mass spectrometry and/or flame ionization detection.

The partially methylated products include non-reducing terminal glucose units, linked units and branching points. The individual products are identified by retention time and mass spectrometry. The distribution of the partially-methylated products is the percentage (area %) of each product in the total peak area of all partially methylated products. The gas chromatographic conditions were as follows: RTx-225 column (30 m×250 µm ID×0.1 µm film thickness, Restek Corporation, Bellefonte, PA, USA), helium carrier gas (0.9 mL/min constant flow rate), oven temperature program starting at 80° C. (hold for 2 min) then 30° C./min to 170° C. (hold for 0 min) then 4° C./min to 240° C. (hold for 25 min), 1 µL injection volume (split 5:1), detection using electron impact mass spectrometry (full scan mode)

Viscosity Measurement

The viscosity of 12 wt % aqueous solutions of soluble fiber was measured using a TA Instruments AR-G2 controlled-stress rotational rheometer (TA Instruments—Waters, LLC, New Castle, DE) equipped with a cone and plate geometry. The geometry consists of a 40 mm 2° upper cone and a peltier lower plate, both with smooth surfaces. An environmental chamber equipped with a water-saturated sponge was used to minimize solvent (water) evaporation during the test. The viscosity was measured at 20° C. The peltier was set to the desired temperature and 0.65 mL of sample was loaded onto the plate using an Eppendorf pipette (Eppendorf North America, Hauppauge, NY). The cone was lowered to a gap of 50 µm between the bottom of the cone and the plate. The sample was thermally equilibrated for 3 minutes. A shear rate sweep was performed over a shear rate range of 500-10 $s^{-1}$. Sample stability was confirmed by running repeat shear rate points at the end of the test.

Determination of the Concentration of Sucrose, Glucose, Fructose and Leucrose

Sucrose, glucose, fructose, and leucrose were quantitated by HPLC with two tandem Aminex HPX-87C Columns (Bio-Rad, Hercules, CA). Chromatographic conditions used were 85° C. at column and detector compartments, 40° C. at sample and injector compartment, flow rate of 0.6 mL/min, and injection volume of 10 µL. Software packages used for data reduction were EMPOWER™ version 3 from Waters (Waters Corp., Milford, MA). Calibrations were performed with various concentrations of standards for each individual sugar.

Determination of the Concentration of Oligosaccharides

Soluble oligosaccharides were quantitated by HPLC with two tandem Aminex HPX-42A columns (Bio-Rad). Chromatographic conditions used were 85° C. column temperature and 40° C. detector temperature, water as mobile phase (flow rate of 0.6 mL/min), and injection volume of 10 µL. Software package used for data reduction was EMPOWER™ version 3 from Waters Corp. Oligosaccharide samples from DP2 to DP7 were obtained from Sigma-Aldrich: maltoheptanose (DP7, Cat. #47872), maltohexanose (DP6, Cat. #47873), maltopentose (DP5, Cat. #47876), maltotetraose (DP4, Cat. #47877), isomaltotriose (DP3, Cat. #47884) and maltose (DP2, Cat. #47288). Calibration was performed for each individual oligosaccharide with various concentrations of the standard.

Determination of Digestibility

The digestibility test protocol was adapted from the Megazyme Integrated Total Dietary Fiber Assay (AOAC method 2009.01, Ireland). The final enzyme concentrations were kept the same as the AOAC method: 50 Unit/mL of pancreatic α-amylase (PAA), 3.4 Units/mL for amyloglucosidase (AMG). The substrate concentration in each reaction was 25 mg/mL as recommended by the AOAC method.

The total volume for each reaction was 1 mL instead of 40 mL as suggested by the original protocol. Every sample was analyzed in duplicate with and without the treatment of the two digestive enzymes. The detailed procedure is described below:

The enzyme stock solution was prepared by dissolving 20 mg of purified porcine pancreatic α-amylase (150,000 Units/g; AOAC Method 2002.01) from the Integrated Total Dietary Fiber Assay Kit in 29 mL of sodium maleate buffer (50 mM, pH 6.0 plus 2 mM $CaCl_2$)) and stir for 5 min, followed by the addition of 60 uL amyloglucosidase solution (AMG, 3300 Units/mL) from the same kit. 0.5 mL of the enzyme stock solution was then mixed with 0.5 mL soluble fiber sample (50 mg/mL) in a glass vial and the digestion reaction mixture was incubated at 37° C. and 150 rpm in orbital motion in a shaking incubator for exactly 16 h. Duplicated reactions were performed in parallel for each fiber sample. The control reactions were performed in duplicate by mixing 0.5 mL maleate buffer (50 mM, pH 6.0 plus 2 mM $CaCl_2$)) and 0.5 mL soluble fiber sample (50 mg/mL) and reaction mixtures was incubated at 37° C. and 150 rpm in orbital motion in a shaking incubator for exactly 16 h. After 16 h, all samples were removed from the incubator and immediately 75 μL of 0.75 M TRIZMA® base solution was added to terminate the reaction. The vials were immediately placed in a heating block at 95-100° C., and incubate for 20 min with occasional shaking (by hand). The total volume of each reaction mixture is 1.075 mL after quenching. The amount of released glucose in each reaction was quantified by HPLC with the Aminex HPX-87C Columns (BioRad) as described in the General Methods. Maltodextrin (DE4-7, Sigma) was used as the positive control for the enzymes. To calculate the digestibility, the following formula was used:

Digestibility=100%*[amount of glucose (mg) released after treatment with enzyme–amount of glucose (mg) released in the absence of enzyme]/1.1*amount of total fiber (mg)"

Purification of Soluble Oligosaccharide Fiber

Soluble oligosaccharide fiber present in product mixtures produced by the conversion of sucrose using glucosyltransferase enzymes with or without added mutanases as described in the following examples were purified and isolated by size-exclusion column chromatography (SEC). In a typical procedure, product mixtures were heat-treated at 60° C. to 90° C. for between 15 min and 30 min and then centrifuged at 4000 rpm for 10 min. The resulting supernatant was injected onto an ÄKTAprime purification system (SEC; GE Healthcare Life Sciences) (10 mL-50 mL injection volume) connected to a GE HK 50/60 column packed with 1.1 L of Bio-Gel P2 Gel (Bio-Rad, Fine 45-90 μm) using water as eluent at 0.7 mL/min. The SEC fractions (~5 mL per tube) were analyzed by HPLC for oligosaccharides using a Bio-Rad HPX-47A column. Fractions containing >DP2 oligosaccharides were combined and the soluble fiber isolated by rotary evaporation of the combined fractions to produce a solution containing between 3% and 6% (w/w) solids, where the resulting solution was lyophilized to produce the soluble fiber as a solid product.

Pure Culture Growth on Specific Carbon Sources

To test the capability of microorganisms to grow on specific carbon sources (oligosaccharide or polysaccharide soluble fibers), selected microbes were grown in appropriate media free from carbon sources other than the ones under study. Growth was evaluated by regular (every 30 min) measurement of optical density at 600 nm in an anaerobic environment (80% $N_2$, 10% $CO_2$, 10% $H_2$). Growth was expressed as area under the curve and compared to a positive control (glucose) and a negative control (no added carbon source).

Stock solutions of oligosaccharide soluble fibers (10% w/w) were prepared in demineralised water. The solutions were either sterilised by UV radiation or filtration (0.2 μm). Stocks were stored frozen until used. Appropriate carbon source-free medium was prepared from single ingredients. Test organisms were pre-grown anaerobically in the test medium with the standard carbon source. In honeycomb wells, 20 μL of stock solution was pipetted and 180 μL carbon source-free medium with 1% test microbe was added. As positive control, glucose was used as carbon source, and as negative control, no carbon source was used. To confirm sterility of the stock solutions, uninocculated wells were used. At least three parallel wells were used per run.

The honeycomb plates were placed in a Bioscreen and growth was determined by measuring absorbance at 600 nm. Measurements were taken every 30 min and before measurements, the plates were shaken to assure an even suspension of the microbes. Growth was followed for 24 h. Results were calculated as area under the curve (i.e., $OD_{600}$/24 h). Organisms tested (and their respective growth medium) were: *Clostridium perfringens* ATCC® 3626™ (anaerobic Reinforced Clostridial Medium (from Oxoid Microbiology Products, ThermoScientific) without glucose), *Clostridium difficile* DSM 1296 (Deutsche Sammlung von Mikroorganismen and Zellkulturen DSMZ, Braunschweig, Germany) (anaerobic Reinforced Clostridial Medium (from Oxoid Microbiology Products, Thermo Fisher Scientific Inc., Waltham, MA) without glucose), *Escherichia coli* ATCC® 11775™ (anaerobic Trypticase Soy Broth without glucose), *Salmonella typhimurium* EELA (available from DSMZ, Brauchschweig, Germany) (anaerobic Trypticase Soy Broth without glucose), *Lactobacillus acidophilus* NCFM 145 (anaerobic de Man, Rogosa and Sharpe Medium (from DSMZ) without glucose), *Bifidobacterium animalis* subsp. *Lactis* Bi-07 (anaerobic Deutsche Sammlung vom Mikroorgnismen and Zellkulturen medium 58 (from DSMZ), without glucose).

In Vitro Gas Production

To measure the formation of gas by the intestinal microbiota, a pre-conditioned faecal slurry was incubated with test prebiotic (oligosaccharide or polysaccharide soluble fibers) and the volume of gas formed was measured. Fresh faecal material was pre-conditioned by dilution with 3 parts (w/v) of anaerobic simulator medium, stirring for 1 h under anaerobic conditions and filtering through 0.3-mm metal mesh after which it was incubated anaerobically for 24 h at 37° C.

The simulator medium used was composed as described by G. T. Macfarlane et al. (*Microb. Ecol.* 35(2):180-7 (1998)) containing the following constituents (g/L) in distilled water: starch (BDH Ltd.), 5.0; peptone, 0.05; tryptone, 5.0; yeast extract, 5.0; NaCl, 4.5; KCl, 4.5; mucin (porcine gastric type III), 4.0; casein (BDH Ltd.), 3.0; pectin (citrus), 2.0; xylan (oatspelt), 2.0; arabinogalactan (larch wood), 2.0; $NaHCO_3$, 1.5; $MgSO_4$, 1.25; guar gum, 1.0; inulin, 1.0; cysteine, 0.8; $KH_2PO_4$, 0.5; $K_2HPO_4$, 0.5; bile salts No. 3, 0.4; $CaCl_2\times6H_2O$, 0.15; $FeSO_4\times7H_2O$, 0.005; hemin, 0.05; and Tween 80, 1.0; cysteine hydrochloride, 6.3; $Na_2S\times9H_2O$, and 0.1% resazurin as an indication of sustained anaerobic conditions. The simulation medium was filtered through 0.3 mm metal mesh and divided into sealed serum bottles.

Test prebiotics were added from 10% (w/w) stock solutions to a final concentration of 1%. The incubation was performed at 37° C. while maintaining anaerobic conditions. Gas production due to microbial activity was measured manually after 24 h incubation using a scaled, airtight glass syringe, thereby also releasing the overpressure from the simulation unit.

Example 1

Expression of Truncated Glucosyltransferase in *E. coli* Having α-(1,2) Branching Activity The following example describes expression of a full length glucosyltransferase and a truncated version of this enzyme in *E. coli* and tested their α-(1,2) branching activity on a glucan backbone. The full length glucosyltransferase produced glucan with little α-(1,2) branching. The truncated version of the glucosyltransferase produced glucan with significant amount of α-(1,2) branching.

The putative glucosyltransferase (GENBANK® gi: 356644413) from *Leuconostoc mesenteroides* subsp. *mesenteroides* J18 (designated as GtfJ18) has 2771 amino acids (SEQ ID NO: 1). It was identified as a glycosyl hydrolase from complete genome sequencing of the J18 strain isolated from Kimchi (Jung et al., *J. Bacteriol.* 194:730 (2012)). The full length sequence of GtfJ18 (2771 amino acids in length) has 68.6% amino acid identity to the DsrE protein (2835 amino acids in length; SEQ ID NO: 2) from *Leuconostoc mesenteroides* NRRL B-1299 (GENBANK® gi: 23320943). The DsrE protein was previously the only enzyme in the GH70 family of glucosyltransferases shown to be a bifunctional protein with two catalytic domains (Bozonnet et al., *J. Bacteriol.* 184:5763 (2002)). The first catalytic domain "CD1" catalyzes the synthesis of the α-(1,6) linkages and the second catalytic domain "CD2" catalyzes the synthesis of the α-(1,2) linkages. The CD1 and CD2 domains were separated by a glucan binding domain "GBD" (Fabre et al., *J. Bacteriol.* 187:296 (2005)). The CD1 domains of the DsrE and GtfJ18 share 79.3% amino acid identity and the CD2 domains of the two proteins share 76.6% amino acid identity.

The N-terminal 20 amino acids segment of GtfJ18 was deduced as the signal peptide by the SignalP 4.0 program (Petersen et al., *Nature Methods*, 8:785-786, (2011)). To construct the full length gtfJ18 expression plasmid, the DNA (SEQ ID NO: 3) encoding the mature protein without the signal peptide (SEQ ID NO: 4) was synthesized by GenScript USA Inc. (Piscataway, NJ). The synthesized gene was subcloned into the NheI and HindIII sites of the pET23D+ vector (NOVAGEN®; Merck KGaA, Darmstadt, Germany). A polynucleotide (SEQ ID NO: 5) encoding a truncated version of gtfJ18 (SEQ ID NO: 6) containing the C-terminal CD2 domain and part of a GBD domain (amino acid residues 1664-2771 of SEQ ID NO: 1) was also subcloned into the pET23D+ vector. The plasmids expressing the full length gtfJ18 gene and the truncated gtfJ18T1 gene were transformed into *E. coli* BL21 DE3 host resulting strains EC0059 and EC0059T1. Cells of EC0059 and EC0059T1 were grown to OD ~0.5 and induced with 1 mM IPTG at 37° C. for 3 hours or alternatively they were induced at 23° C. overnight. The cells were collected by centrifugation at 4000×g for 10 min and resuspended in PBS buffer pH 6.8. The cells were broken by passing through French Press at 14,000 psi (~96.53 MPa) twice and the cell debris was pelleted by centrifugation at 15,000×g for 20 min. The supernatant of the crude enzyme extract was aliquoted and frozen at −80° C.

The activity of each enzyme (EC0059; SEQ ID NO:4) and EC0059T1 (SEQ ID NO: 6) was individually tested with the glucan backbone produced by SG1018. SG1018 is a *Bacillus subtilis* BG6006 strain with 9 protease deletions (amyE:: xylRPxylAcomK-ermC, degUHy32, oppA, ΔspoIIE3501, ΔaprE, ΔnprE, Δepr, ΔispA, Δbpr, Δvpr, ΔwprA, Δmpr-ybfJ, ΔnprB) expressing a glucosyltransferase (GENBANK® gi:357235604) from *Streptococcus criceti* HS-6 (GtfHS-6). The putative glucosyltransferase (GENBANK® gi:357235604; SEQ ID NO: 7) from *Streptococcus criceti* HS-6 (designated as GtfHS6) has 1338 amino acids with the N terminal 36 amino acids deduced as the signal peptide by the SignalP 4.0 program. The full length native coding sequence (SEQ ID NO: 8) with its native signal peptide encoding sequence was synthesized by GenScript and cloned into the SpeI and HindIII sites of the replicative *Bacillus* expression plasmid pHYT (Takara Bio Inc., Otsu, Japan) under the *B. subtilis* aprE promoter. The construct was first transformed into *E. coli* DH10B and selected on ampicillin (100 μg/mL) plates. The confirmed clone pDCQ918 was then transformed into *Bacillus subtilis* BG6006 strain and selected on tetracycline (12.5 μg/mL) plates. SG1018 strain was grown in LB containing 10 μg/mL tetracycline first, and then subcultured into GrantsII medium containing 12.5 μg/mL tetracycline grown at 37° C. for 2-3 days. The cultures were spun at 15,000×g for 30 min at 4° C. and the supernatant was filtered through 0.22 μm filters. The glucan backbone reaction was set up using 10% of the SG1018 supernatant with 100 g/L sucrose, 10 mM sodium citrate pH 5 and 1 mM CaCl$_2$). All sucrose was consumed after 6 hours at 37° C. and the glucan produced by the glucosyltransferase GtfHS-6 from SG1018 (SEQ ID NO: 7) had molecular weight about 3000 and consisting of almost 100% α-(1,6) linkages. The branching reaction was set up with 70% of the glucan backbone after heat inactivation of the GtfHS-6 at 95° C. for 30 min. The branching enzyme provided as 10% (v/v) of the crude cell extract from EC0059 or EC0059T1 was added with 40 g/L sucrose. The branching reaction was incubated at 37° C. or 30° C. for 22 hours and the products were analyzed by HPLC for sucrose consumption and NMR for linkage profile.

NMR data were acquired on an Agilent DD2 spectrometer (Agilent Technologies, Inc., Santa Clara, CA) operating at 500 MHz for $^1$H using a 5 mm cryogenic triple-resonance pulsed-field gradient probe. Water suppression was obtained by carefully placing the observe transmitter frequency on resonance for the residual water signal in a "presat" experiment, and then using the first slice of a NOESY experiment with a full phase cycle (multiple of 32) and a mix time of 10 ms. One-dimensional $^1$H spectra were acquired with a spectral width of 6410 Hz, acquisition time of 5.1 s, 65536 data points, 4 s pre-saturation and a 90-degree observe pulse. Signal averaging typically involved accumulation of 64 scans. Sample temperature was maintained at 25° C.

Liquid samples were prepared by adding either 50 or 1004 to a 5 mm NMR tube along with 604 of D20 containing 12.4 mM 4,4-dimethyl-4-silapentane-1-sulfonic acid sodium salt (DSS) as internal chemical shift reference, and the balance (450 or 400 μL) of D20 for a total volume of 560 μL. The DSS methyl resonance was set to 0 ppm.

Chemical shift assignments for different anomeric linkages were taken from Goffin et al. (*Bull Korean Chem. Soc.* 30:2535 (2009)). Assignments specific to α-(1,2) branching on an α-(1,6) backbone were taken from Maina et al., (*Carb. Res.* 343:1446 (2008)). Alpha-(1,2) substitution on the (1,6) backbone (alpha 1-2,6 linkage) leads to a characteristic chemical shift (5.18 ppm) for the anomeric H adjacent the substitution site. The anomeric H of the (1-2) linked sugar (5.10 ppm) is obscured by leucrose in reaction mixtures but is directly observed in purified samples.

The product with EC0059 extract (comprising GtfJ18; SEQ ID NO: 4) contained 97% α-(1,6) linkages and only 0.6% α-(1,2) linkages. The product with EC0059T1 extract contained 82% α-(1,6) linkages and 18% α-(1,2) linkages. The truncated GtfJ18T1 (SEQ ID NO: 6) in EC0059T1 showed much higher α-(1,2) branching activity comparing to the full length GtfJ18 in EC0059. Although not bound by theory, it may be that the CD1 domain in the full length GtfJ18 was very active and competed with CD2 branching domain for the needed sucrose.

Example 2

Optimization of the α-(1,2) Branching Activity

The following example describes optimization of the α-(1,2) branching activity of EC0059T1 (SEQ ID NO: 6) with regards to temperature and sucrose concentrations.

The branching enzyme reaction described above with the glucan backbone produced by SG1018 (comprising GTF5604; SEQ ID NO: 7) was set up at 30° C. and at 37° C. with 40 g/L sucrose. The branched products were analyzed by HPLC for sugar concentrations and NMR for linkages. Table 1 shows that at 30° C. almost all sucrose was consumed and achieved 27% α-(1,2) branching on the backbone produced by SG1018, whereas about half of sucrose was not consumed at 37° C. and achieved 18% α-(1,2) branching on the SG1018 backbone. The sucrose control was the negative control with all reaction components except for the branching enzyme. The data indicated that the branching enzyme GTFJ18T1 (SEQ ID NO: 6) is more active at 30° C. than at 37° C.

TABLE 1

Analysis of the α-(1,2) branching reaction products of the SG1018 produced glucan backbone with 40 g/L sucrose at different temperatures

| | HPLC analysis | | | | NMR Analysis (%) | | | |
|---|---|---|---|---|---|---|---|---|
| Samples | Sucrose (g/L) | Leucrose (g/L) | Glucose (g/L) | Fructose (g/L) | α-1,2,6 | α-1,6 | α-1,3 | α-1,3,6 |
| Sucrose control | 43.1 | 16.5 | 6.3 | 50.8 | 0 | 100 | 0 | 0 |
| EC0059T1-37° C. (SEQ ID NO: 6) | 18.6 | 18.7 | 5.6 | 61.5 | 18.4 | 81.6 | 0 | 0 |
| EC0059T1-30° C. (SEQ ID NO: 6) | 0.18 | 20.9 | 6.8 | 67.6 | 27.4 | 72.1 | 0.47 | 0 |

Another experiment was set up with various sucrose concentrations ranging from 2.5 g/L to 40 g/L in the branching reaction at 30° C. Table 2 shows that a higher percentage of α-(1,2) branching was reached with higher sucrose concentrations in the branching reaction. In the case of 40 g/L sucrose, 21.4% of α-(1,2) branching was achieved even though there was still 14.7 g/L sucrose left at the end of the reaction. A new batch of more active branching enzyme was prepared from EC0059T1 (SEQ ID NO: 6) and the branching reaction was repeated with 40 g/L and 80 g/L sucrose. Table 3 shows that when 40 g/L sucrose was all consumed, 24.5% α-(1,2) branching was achieved with SG1018-derived (i.e., glucan background produced using SEQ ID NO: 7) glucan backbone. When 80 g/L sucrose was used, as high as 40% α-(1,2) branching was achieved.

TABLE 2

Analysis of the α-(1,2) branching reaction products of the SG1018 produced glucan backbone at 30° C. with different sucrose concentrations (2.5 g/L-40 g/L)

| | | | HPLC analysis | | | NMR Analysis (%) | | | |
|---|---|---|---|---|---|---|---|---|---|
| Samples | Initial Sucrose (g/L) | Final Sucrose (g/L) | Leucrose (g/L) | Glucose (g/L) | Fructose (g/L) | α-1,2,6 | α-1,6 | α-1,3 | α-1,3,6 |
| EC0059T1 | 40 | 14.7 | 19.2 | 6.6 | 62.6 | 21.4 | 78.6 | 0 | 0 |
| EC0059T1 | 20 | 7.1 | 17.7 | 3 | 63.7 | 13.1 | 86.9 | 0 | 0 |
| EC0059T1 | 10 | 3.4 | 17.5 | 5.2 | 53.7 | 6.1 | 93.9 | 0 | 0 |
| EC0059T1 | 5 | 1.3 | 17.2 | 5.4 | 51.5 | 3.4 | 96.6 | 0 | 0 |
| EC0059T1 | 2.5 | 0.7 | 17 | 5.2 | 50.1 | 1.8 | 98.2 | 0 | 0 |
| Sucrose control | 40 | 43.1 | 16.5 | 6.3 | 50.8 | 0 | 100 | 0 | 0 |

TABLE 3

Analysis of the α-(1,2) branching reaction products of the SG1018
produced glucan backbone at 30° C. with different sucrose concentrations
(40 g/L-80 g/L) using a new batch of the branching enzyme

| | HPLC analysis | | | | | NMR Analysis (%) | | | |
|---|---|---|---|---|---|---|---|---|---|
| Samples | Initial Sucrose (g/L) | Final Sucrose (g/L) | Leucrose (g/L) | Glucose (g/L) | Fructose (g/L) | α-1,2,6 | α-1,6 | α-1,3 | α-1,3,6 |
| EC0059T1 | 80 | 2 | 33.1 | 9.2 | 81.3 | 40.1 | 59.9 | 0 | 0 |
| EC0059T1 | 40 | 0.6 | 21.6 | 7.1 | 69.0 | 24.5 | 75.5 | 0 | 0 |
| Sucrose control | 80 | 86.3 | 17.8 | 4.8 | 52.2 | 0 | 100 | 0 | 0 |

Example 3

Addition of α-(1,2) Branching to Different Glucan Backbones Generated from Sucrose The following example describes the evaluation of the α-(1,2) branching activity of EC0059T1 (SEQ ID NO: 6) on different glucan backbones generated from sucrose. The glucan backbones generated from glucosyltransferases and combinations of glucosyltransferases/mutanases have a wide range of different linkages and molecular weights. The α-(1,2) branching enzyme is active on glucans of different molecular weights having predominantly α-(1,6) linkages as well as glucans comprising mixtures of α-(1,6) and α-(1,3) linkages. The α-(1,2) branching enzyme is not active on the glucans having predominantly α-(1,3) linkages.

Six glucan backbones were generated using glucosyltransferases derived from GENBANK® gi numbers as listed in Table 4. The sequences of the glucosyltransferases are provided as follows: SG1006 ("GTF1729"; SEQ ID NO: 9), SG1018 ("GTF1428"; also referred to herein as "GTF5604"; SEQ ID NO: 7), SG1031 ("GTF6831"; SEQ ID NO: 10), SG1051 ("GTF8845"; SEQ ID NO: 11), SG1066 ("GTF0088"; SEQ ID NO: 12), and SG1115 ("GTF8117"; SEQ ID NO: 13). The glucosyltransferases were expressed in *Bacillus subtilis* BG6006 and the glucan backbone synthesis reactions were set up as described in Example 1 for SG1018. All GTFs were expressed as full length mature proteins except for GTF0088 which had an N-terminal truncation. The GTF1729 (SEQ ID NO: 9) (SG1006) and GTF1428 (SEQ ID NO: 7) (SG1018) were expressed with their native signal sequences. The other four GTFs were expressed with the *Bacillus subtilis* derived AprE signal sequence (SEQ ID NO: 34). The reactions started with 200 g/L sucrose at 37° C. and monitored for 1-3 days until sucrose was all consumed. The HPLC analysis of the backbone reactions were shown in Table 4. The backbone reaction products were also analyzed for linkages by NMR and molecular weight by size exclusion chromatography. As shown in Table 4, the backbones generated range from about 1 kD to 40 kD. Some backbones contain predominantly α-(1,6) linkages and some contain mixtures of α-(1,6) and α-(1,3) linkages.

TABLE 4

Analysis of different glucan backbones generated using different glucosyltransferases with 200 g/L sucrose

| Samples | GENBANK® GI number (SEQ ID NO.) | HPLC analysis of glucan backbone | | | | MW (Da) | NMR analysis of glucan backbone (%) | | | |
|---|---|---|---|---|---|---|---|---|---|---|
| | | Sucrose (g/L) | Leucrose (g/L) | Glucose (g/L) | Fructose (g/L) | | α-1,2,6 | α-1,6 | α-1,3 | α-1,3,6 |
| SG1006 | 121729 (SEQ ID NO: 9) | 0.4 | 9.9 | 7.4 | 84.0 | 6322 | 0 | 100 | 0 | 0 |
| SG1018 | 4691428 (SEQ ID NO: 7) | 0.9 | 25.6 | 7.7 | 80.5 | 2964 | 0 | 100 | 0 | 0 |
| SG1031 | 345526831 (SEQ ID NO: 10) | 0.6 | 8.5 | 9.8 | 88.1 | 43232 | 0 | 100 | 0 | 0 |
| SG1051 | 22138845 (SEQ ID NO: 11) | 0.8 | 42.6 | 16.3 | 63.2 | 18938 | 0 | 80.0 | 2.9 | 17.1 |
| SG1066 | 3130088 (SEQ ID NO: 12) | 0.7 | 30.7 | 13 | 77.0 | 1265 | 0 | 85.9 | 12.2 | 1.9 |
| SG1115 | 335358117 (SEQ ID NO: 13) | 0.2 | 6.5 | 7.6 | 0.0 | 25300 | 0 | 100 | 0 | 0 |

Two glucan backbones were generated using reaction mixtures comprising combinations of at least one glucosyltransferase and at least one mutanase (concomitant GTF/mutanase). The glucans produced by these glucosyltransferases reactions contain a significant amount of α-(1,3) linkages and are usually insoluble. Mutanases with endohydrolytic activity were used to decrease the molecular weights of the α-(1,3) containing glucans to DP<10 to help make them soluble in water. The soluble DP<10 oligosaccharides containing α-(1,3) linkages were purified and used as backbones for the α-(1,2) branching reaction.

The two glucosyltransferases used in the GTF/mutanase reactions were expressed in *E. coli*. The truncated version of a glucosyltransferase enzyme identified in GENBANK® gi:290580544 (GtfB from *Streptococcus mutans* NN2025; full length sequence provided as SEQ ID NO: 14) and a mature form of GENBANK® gi:47527 (full length sequence with signal sequence provided as SEQ ID NO: 17)

(GtfJ from *Streptococcus salivarius* ATCC® 25975; signal sequence removed and start codon added) were synthesized using codons optimized for expression in *E. coli* (DNA 2.0 Inc., Menlo Park, CA). The polynucleotide (SEQ ID NO: 15) encoding truncated protein derived from GENBANK® gi:290580544 ("GTF0544"; SEQ ID NO: 16) and the polynucleotide (SEQ ID NO: 18) encoding the protein derived from GENBANK® gi:47527 ("GTF7527"; SEQ ID NO: 19) were subcloned into plasmid pJEXPRESS404® to generate the plasmid identified as pMP67 and pMP52, respectively. The plasmid pMP67 was used to transform *E. coli* TOP10 (Thermo Fisher Scientific Inc., Waltham, MA). *E. coli* strains TOP10/pMP67 expressing the GtfB enzyme "GTF0544" was grown in LB medium with ampicillin (100 µg/mL) at 37° C. with shaking to $OD_{600nm}$=0.4-0.5, at which time isopropyl-β-D-thio-galactoside (IPTG) was added to a final concentration of 0.5 mM and incubation continued for 2-4 hr at 37° C. Cells were harvested by centrifugation at 5,000×g for 15 min and resuspended (20% w/v) in 50 mM phosphate buffer pH 7.0. Resuspended cells were passed through a French Pressure Cell (SLM Instruments, Rochester, NY) twice to ensure >95% cell lysis. Lysed cells were centrifuged for 30 min at 12,000×g at 4° C. The resulting supernatants were stored at –80° C. The pMP52 plasmid was transformed into *E. coli* MG1655 and the resulting MG1655/pMP52 was grown in fermentor to produce GtfJ as follows:

Production of Recombinant GTF by Fermentation

Production of the recombinant mature glucosyltransferase Gtf-J in a fermentor was initiated by preparing a pre-seed culture of the *E. coli* strain MG1655/pMP52, expressing the mature Gtf-J enzyme (GI:47527; "GTF7527"; SEQ ID NO: 19). A 10-mL aliquot of the seed medium was added into a 125-mL disposable baffled flask and was inoculated with a 1.0 mL culture of *E. coli* MG1655/pMP52 in 20% glycerol. This culture was allowed to grow at 37° C. while shaking at 300 rpm for 3 h.

A seed culture for starting the fermentor was prepared by charging a 2-L shake flask with 0.5 L of the seed medium. 1.0 mL of the pre-seed culture was aseptically transferred into 0.5 L seed medium in the flask and cultivated at 37° C. and 300 rpm for 5 h. The seed culture was transferred at optical density >2 ($OD_{550}$) to a 14-L fermentor (Braun, Perth Amboy, NJ) containing 8 L of the fermentor medium described above at 37° C.

Cells of *E. coli* MG1655/pMP52 were allowed to grow in the fermentor and glucose feed (50% w/w glucose solution containing 1% w/w $MgSO_4 \cdot 7H_2O$) was initiated when glucose concentration in the medium decreased to 0.5 g/L. The feed was started at 0.36 grams feed per minute (g feed/min) and increased progressively each hour to 0.42, 0.49, 0.57, 0.66, 0.77, 0.90, 1.04, 1.21, 1.41 1.63, 1.92, 2.2 g feed/min respectively. The rate remained constant afterwards. Glucose concentration in the medium was monitored using an YSI glucose analyzer (YSI, Yellow Springs, Ohio). When glucose concentration exceeded 0.1 g/L the feed rate was decreased or stopped temporarily. Induction of glucosyltransferase enzyme activity was initiated, when cells reached an $OD_{550}$ of 70, with the addition of 9 mL of 0.5 M IPTG (isopropyl β-D-1-thiogalacto-pyranoside). The dissolved oxygen (DO) concentration was controlled at 25% of air saturation. The DO was controlled first by impeller agitation rate (400 to 1200 rpm) and later by aeration rate (2 to 10 standard liters per minute, slpm). The pH was controlled at 6.8. $NH_4OH$ (14.5% weight/volume, w/v) and $H_2SO_4$ (20% w/v) were used for pH control. The back pressure was maintained at 0.5 bar. At various intervals (20, 25 and 30 hours), 5 mL of Suppressor 7153 antifoam (Cognis Corporation, Cincinnati, OH) was added into the fermentor to suppress foaming. Cells were harvested by centrifugation 8 h post IPTG addition and were stored at –80° C. as a cell paste.

Mutanases

A gene encoding a mutanase from *Paenibacillus humicus* identified in GENBANK® gi:257153264 was synthesized by GenScript (Piscataway, NJ). The nucleotide sequence (SEQ ID NO: 20) encoding protein sequence (SEQ ID NO: 21) was subcloned into pET24a (Novagen; Merck KGaA, Darmstadt, Germany). The resulting plasmid was transformed into *E. coli* BL21(DE3) (Invitrogen, Carlsbad, CA) to generate the strain identified as "SGZY6". The strain was grown at 37° C. with shaking at 220 rpm to $OD_{600}$ of ~0.7, then the temperature was lowered to 18° C. and IPTG was added to a final concentration of 0.4 mM. The culture was grown overnight before harvest by centrifugation at 4000×g. The cell pellet from 600 mL of culture was suspended in 22 mL 50 mM KPi buffer, pH 7.0. Cells were disrupted by French Cell Press (2 passages @ 15,000 psi (103.4 MPa)); Cell debris was removed by centrifugation (Sorvall SS34 rotor, @13,000 rpm) for 40 min. The supernatant was analyzed by SDS-PAGE to confirm the expression of the mutanase and the crude extract was used for activity assay. The crude extract was stored at –80° C.

A gene encoding the *Penicillium marneffei* ATCC® 18224 mutanase identified in GENBANK® gi:212533325 was synthesized by GenScript (Piscataway, NJ). The nucleotide sequence (SEQ ID NO: 22) encoding protein sequence (SEQ ID NO: 23) was subcloned into plasmid pTrex3 (SEQ ID NO: 24) at SacII and AscI restriction sites, a vector designed to express the gene of interest in *Trichoderma reesei*, under control of CBHI promoter and terminator, with *Aspergillus niger* acetamidase for selection. The resulting plasmid was transformed into *T. reesei* by biolistic injections. The detailed method of biolistic transformation is described in International PCT Patent Application Publication WO2009/126773 A1. A 1 cm2 agar plug with spores from a stable clone TRM05-3 was used to inoculate the production media (described below). The culture was grown in the shake flasks for 4-5 days at 28° C. and 220 rpm. To harvest the secreted proteins, the cell mass was first removed by centrifugation at 4000×g for 10 min and the supernatant was filtered through 0.2 µm sterile filters. The expression of mutanase "MUT3325" (SEQ ID NO: 23) was confirmed by SDS-PAGE.

The production media component is listed below.

| NREL-Trich Lactose Defined | | |
| --- | --- | --- |
| Formula | Amount | Units |
| ammonium sulfate | 5 | g |
| PIPPS | 33 | g |
| BD Bacto casamino acid | 9 | g |
| $KH_2PO_4$ | 4.5 | g |
| $CaCl_2 \cdot 2H_2O$ | 1.32 | g |
| $MgSO_4 \cdot 7H_2O$ | 1 | g |
| *T. reesei* trace elements | 2.5 | mL |
| NaOH pellet | 4.25 | g |
| Adjust pH to 5.5 with 50% NaOH | | |
| Bring volume to | 920 | mL |
| Add to each aliquot: Foamblast | 5 | Drops |
| Autoclave, then add 20% lactose filter sterilized | 80 | mL |

| T. reesei trace elements | | |
|---|---|---|
| Formula | Amount | Units |
| citric acid•H$_2$O | 191.41 | g |
| FeSO$_4$•7H$_2$O | 200 | g |
| ZnSO$_4$•7H$_2$O | 16 | g |
| CuSO$_4$•5H$_2$O | 3.2 | g |
| MnSO$_4$•H$_2$O | 1.4 | g |
| H$_3$BO$_3$ (boric acid) | 0.8 | g |
| Bring volume to | 1 | L |

Production of MUT3325 BY Fermentation

Fermentation seed culture was prepared by inoculating 0.5 L of minimal medium in a 2-L baffled flask with 1.0 mL frozen spore suspension of the MUT3325 expression strain TRM05-3 (The minimal medium was composed of 5 g/L ammonium sulfate, 4.5 g/L potassium phosphate monobasic, 1.0 g/L magnesium sulfate heptahydrate, 14.4 g/L citric acid anhydrous, 1 g/L calcium chloride dihydrate, 25 g/L glucose and trace elements including 0.4375 g/L citric acid, 0.5 g/L ferrous sulfate heptahydrate, 0.04 g/L zinc sulfate heptahydrate, 0.008 g/L cupric sulfate pentahydrate, 0.0035 manganese sulfate monohydrate and 0.002 g/L boric acid. The pH was 5.5.). The culture was grown at 32° C. and 170 rpm for 48 hours before transferred to 8 L of the production medium in a 14-L fermentor. The production medium was composed of 75 g/L glucose, 4.5 g/L potassium phosphate monobasic, 0.6 g/L calcium chloride dehydrate, 1.0 g/L magnesium sulfate heptahydrate, 7.0 g/L ammonium sulfate, 0.5 g/L citric acid anhydrous, 0.5 g/L ferrous sulfate heptahydrate, 0.04 g/L zinc sulfate heptahydrate, 0.00175 g/L cupric sulfate pentahydrate, 0.0035 g/L manganese sulfate monohydrate, 0.002 g/L boric acid and 0.3 mL/L foam blast 882.

The fermentation was first run with batch growth on glucose at 34° C., 500 rpm for 24 h. At the end of 24 h, the temperature was lowered to 28° C. and agitation speed was increased to 1000 rpm. The fermentor was then fed with a mixture of glucose and sophorose (62% w/w) at specific feed rate of 0.030 g glucose-sophorose solids/g biomass/hr. At the end of run, the biomass was removed by centrifugation and the supernatant containing the mutanase was concentrated about 10-fold by ultrafiltration using 10-kD Molecular Weight Cut-Off ultrafiltration cartridge (UFP-10-E-35: GEHealthcare, Little Chalfont, Buckinghamshire, UK). The concentrated protein was stored at −80° C.

Glucan Backbones Generated Using Reaction Mixtures Comprising Combinations Glucosyltransferases and Mutanases The GTF0544/MUT3264 reaction comprised sucrose (100 g/L), GTF0544 (SEQ ID NO: 16) (10% v/v) and MUT3264 (SEQ ID NO: 21) (10% v/v) in deionized water with total volume of 200 mL was performed at 37° C. with shaking at 125 rpm. The GTF7527/MUT3325 reaction comprised sucrose (210 g/L), concentrated GTF7527 produced in the fermenter (0.3% v/v) and MUT3325 (SEQ ID NO: 23) produced in shake flask (20% v/v) in deionized water with total volume of 100 mL was performed at 37° C. with shaking at 125 rpm. The reactions were quenched by heating at 95° C. for 5 min after 24 h. The insoluble materials were removed by centrifugation at 13,000×g for 10 min and filtration through 0.2 μm RC membrane filters. The soluble product mixtures were analyzed by HPLC to determine the concentrations of sucrose, glucose, fructose, leucrose and oligosaccharides (Table 5). The soluble products were purified and the purified samples were analyzed by $^1$HNMR to determine the linkage of the oligosaccharides.

TABLE 5

The mono-, di- and oligosaccharide profile from reactions of GTF0544/MUT3264 and GTF7527/MUT3325

| | | Product Concentration (g/L) | | | | | | | | | | | Linkage Profile of Oligosaccharides (%) | | | | | |
|---|---|---|---|---|---|---|---|---|---|---|---|---|---|---|---|---|---|---|
| GTF | Mutanase | Suc | Leu | Glu | Fru | DP ≥ 8 | DP7 | DP6 | DP5 | DP4 | DP3 | DP2 | α-1,4 | α-1,3 | α-1,3,6 | α-1,2,6 | α-1,2 | α-1,6 |
| GTF0544 | MUT3264 | 2.0 | 14.8 | 2.0 | 41.7 | 9.2 | 2.3 | 3.5 | 3.3 | 8.0 | 3.6 | 3.5 | 0.0 | 32.3 | 3.4 | 0.0 | 0.0 | 64.1 |
| GTF7527 | MUT3325 | 3.3 | 53.1 | 4.7 | 80.6 | 0.0 | 0.0 | 0.2 | 11.6 | 14.8 | 12.8 | 8.5 | 0.0 | 95.9 | 0.6 | 0.0 | 0.0 | 3.4 |

Suc = sucrose;
Leu = leucrose;
Fru = fructose;
DP = degree of polymerization

The α-(1,2) branching reactions were set up with six crude backbones from the glucosyltransferases reactions and two purified backbones from the glucosyltransferases/mutanases reactions. The branching reaction was set up with 70% of the glucan backbones after heat inactivation of the enzymes. The branching enzyme, provided as 10% (v/v) of the EC0059T1 crude cell extract, was added with 80 g/L sucrose. For the four glucan backbones produced by the following 4 strains (SG1006, SG1018, SG1031, and SG1115) with all α-(1,6) linkages, sucrose was almost all consumed and about 40% α-(1,2) branching was achieved. For three backbones (SG1051 and SG1066 from GTF reactions, GTF0544/MUT3264 from GTF/mutanase reaction) contain significant α-(1,3) or α-(1,3,6) linkages, sucrose was partially consumed and about 20-30% of α-(1,2) branching was achieved. For the backbone from the GTF7527/MUT3325 (GTF/mutanase reaction) that is predominantly α-(1,3) linkages, sucrose was not consumed and no α-(1,2) branching was achieved. Table 6 summarizes the HPLC and NMR analysis of the branching reaction products. These data demonstrates that the α-(1,2) branching enzyme is active on glucans of different molecular weights comprising predominantly α-(1,6) linkages as well as mixtures of α-(1,6) and α-(1,3) linkages. The α-(1,2) branching enzyme is not active on the glucans comprising predominantly α-(1,3) linkages.

TABLE 6

Analysis of α-(1,2) branching reaction products with different glucan backbones generated from 80 g/L sucrose at 30° C.

| | HPLC | | | | | | | |
|---|---|---|---|---|---|---|---|---|
| | Final Sucrose | Leucrose | Glucose | Fructose | NMR Linkage (%) | | | |
| Samples | (g/L) | (g/L) | (g/L) | (g/L) | α-1,2,6 | α-1,6 | α-1,3 | α-1,3,6 |
| EC0059T1-1006 | 1.8 | 21.4 | 8.2 | 88.4 | 38.3 | 61.7 | 0.0 | 0.0 |
| EC0059T1-1018 | 2 | 33.1 | 9.2 | 81.3 | 40.1 | 59.9 | 0.0 | 0.0 |
| EC0059T1-1031 | 2 | 18.4 | 6.6 | 99.3 | 39.6 | 60.4 | 0.0 | 0.0 |
| EC0059T1-1051 | 39.6 | 44.4 | 16.4 | 58.5 | 28.6 | 51.3 | 3.2 | 16.8 |
| EC0059T1-1066 | 8.6 | 44.2 | 14.6 | 69.3 | 33.5 | 52.3 | 11.3 | 2.9 |
| EC0059T1-1115 | 1.2 | 17.2 | 8.5 | 92.3 | 39.0 | 61.0 | 0.0 | 0.0 |
| EC0059T1-0544/3264 | 66.6 | 0 | 0.5 | 7 | 22.8 | 58.2 | 15.4 | 3.6 |
| EC0059T1-7527/3325 | 79.8 | 0.2 | 2.7 | 2.8 | 0.0 | 2.6 | 95.9 | 1.6 |

Example 4

Expression of Dextrin Dextranase from *Gluconobacter oxydans* in *Escherichia coli*

The following example describes expression of dextrin dextranase (DDase) from *Gluconobacter oxydans* NCIMB4943 in *E. coli* BL21 DE3. The malQ gene encoding the amylomaltase in the native *E. coli* predominantly contributed to the background activity of maltodextrin conversion. The dextrin dextranase was subsequently expressed in an *E. coli* BL21 DE3 ΔmalQ host.

Dextrin dextranase (DDase) (SEQ ID NO: 26) uses α-(1, 4) linked maltodextrins as substrates to make α-(1,6) linked dextrans by sequential transfer of a glucose unit from the non-reducing end. The DDase coding sequence (SEQ ID NO: 25) from *Gluconobacter oxydans* NCIMB4943 was amplified by PCR and cloned into the NheI and HindIII sites of pET23D vector. The sequence confirmed DDase gene expressed by the T7 promoter on plasmid pDCQ863 was transformed into *E. coli* BL21 DE3 host. The resulting strain together with the BL21 DE3 host control were grown at 37° C. with shaking at 220 rpm to $OD_{600}$ of ~0.5 and IPTG was added to a final concentration of 0.5 mM for induction. The cultures were grown for additional 2-3 hours before harvest by centrifugation at 4000×g. The cell pellets from 1 L of culture were suspended in 30 mL 20 mM KPi buffer, pH 6.8. Cells were disrupted by French Cell Press (2 passages @ 15,000 psi (103.4 MPa)); Cell debris was removed by centrifugation (Sorvall SS34 rotor, @13,000 rpm) for 40 min. The supernatant (10%) was incubated with maltotetraose (DP4) substrate (Sigma) at 16 g/L final concentration in 25 mM sodium acetate buffer pH4.8 at 37° C. overnight. The oligosaccharides profile was analyzed on HPLC. The maltotetraose (DP4) substrate was converted in the BL21 DE3 host without the expression plasmid, suggesting a background activity in the host to utilize DP4.

To check which enzyme predominantly contributed to the background activity, a set of strains from "Keio collection" (Baba et al., (2006) *Mol. Syst. Biol.*, article number 2006.0008; pages 1-11) with a single gene deletion was tested (Table 7) in the maltotetraose assay as described above. *Escherichia coli* K-12 strain BW25113 was the parental strain for the Keio collection. JW3543 contains a deletion of the malS (SEQ ID NO: 28) encoding a periplasmic α-amylase. JW1912 contains a deletion of amyA (SEQ ID NO: 31) encoding a cytoplasmic α-amylase. JW3379 contains a deletion of malQ (SEQ ID NO: 27) encoding an amylomaltase. JW5689 contains a deletion of malP (SEQ ID NO: 29) encoding a maltodextrin phosphorylase. JW0393 contains a deletion of malZ (SEQ ID NO: 30) encoding a maltodextrin glucosidase. The maltotetraose control (G4 control) does not contain any cell extract, When BW25113 cell extract was added, most maltotetraose was converted, indicating the background activity in BW25113. For the five Keio deletion strains tested, four of them still showed the background activity as the BW25113 parental strain. Only JW3379 with malQ deletion showed that most of the background activity was abolished and maltotetraose was retained as the G4 control. This experiment suggested that malQ predominantly contributed to the background activity. The malQ:kanR deletion in the JW3379 was transferred to the BL21 DE3 strain by standard P1 transduction to make the BL21 DE3 ΔmalQ expression host.

The pDCQ863 expressing the DDase and the pET23D vector control was transformed into the BL21 DE3 ΔmalQ expression host resulting EC0063 expression host. The cell extracts were prepared and assayed with maltotetraose substrate ad describe above. The result in Table 8 showed that pET23D in BL21 DE3 had background activity for maltotetraose conversion, but no background activity in the BL21 DE3 ΔmalQ host. When pDCQ863 encoding the DDase was expressed in the BL21 DE3 ΔmalQ host, maltotetraose was converted due to activity of the DDase. The EC0063 expressing DDase was used as the source of DDase enzyme for glucan production.

TABLE 7

Test background activity in *E. coli* hosts with single gene knockout from Keio collection

| Sample | Gene deleted | DP8 & up est. (g/L) | DP7 (g/L) | DP6 (g/L) | DP5 (g/L) | DP4 (g/L) | DP3 (g/L) | DP2 (g/L) | Glucose (g/L) |
|---|---|---|---|---|---|---|---|---|---|
| BW25113 | none | 4.8 | 1.1 | 1.5 | 1.8 | 2.2 | 1.9 | 1.6 | 1.1 |
| JW3543 | ΔmalS | 4.8 | 1.1 | 1.4 | 1.8 | 2.2 | 1.9 | 1.6 | 1.2 |
| JW3379 | ΔmalQ | 0.2 | 0.0 | 0.1 | 0.3 | 16.2 | 0.7 | 0.3 | 0.0 |
| JW1912 | ΔamyA | 5.6 | 1.3 | 1.3 | 1.8 | 1.9 | 1.6 | 1.4 | 0.8 |

TABLE 7-continued

Test background activity in E. coli hosts with
single gene knockout from Keio collection

| Sample | Gene deleted | DP8 & up est. (g/L) | DP7 (g/L) | DP6 (g/L) | DP5 (g/L) | DP4 (g/L) | DP3 (g/L) | DP2 (g/L) | Glucose (g/L) |
|---|---|---|---|---|---|---|---|---|---|
| JW0393 | ΔmalZ | 4.4 | 1.1 | 1.4 | 1.9 | 2.2 | 2.0 | 1.8 | 0.0 |
| JW5689 | ΔmalP | 4.9 | 1.2 | 1.5 | 1.8 | 2.6 | 1.7 | 1.4 | 1.0 |
| G4 cntl |  | 0.2 | 0.0 | 0.0 | 0.0 | 17.0 | 0.9 | 0.0 | 0.0 |

TABLE 8

Expression of DDase in the BL21 DE3 ΔmalQ host

| Sample | Host | Gene expressed | DP8 & up est. (g/L) | DP7 (g/L) | DP6 (g/L) | DP5 (g/L) | DP4 (g/L) | DP3 (g/L) | DP2 (g/L) | Glucose (g/L) |
|---|---|---|---|---|---|---|---|---|---|---|
| EC0063-ΔmalQ | BL21-DE3ΔmalQ | DDase | 0.2 | 0.2 | 0.3 | 0.7 | 1.1 | 2.5 | 5.5 | 0.4 |
| BL21-DE3ΔmalQ pET23D | BL21-DE3ΔmalQ | None | 0.2 | 0.0 | 0.0 | 0.0 | 16.6 | 0.6 | 0.3 | 0.0 |
| BL21-DE3 pET23D | BL21-DE3 | None | 3.3 | 1.1 | 1.3 | 2.1 | 3.6 | 2.0 | 1.6 | 1.5 |
| G4 control |  |  | 0.2 | 0.00 | 0.00 | 0.00 | 17.3 | 0.3 | 0.00 | 0.00 |

Example 5

Addition of α-(1,2) Branching to Different Glucan Backbones Generated from Maltodextrin The following example describes the evaluation of the α-(1,2) branching activity of EC0059T1 (SEQ ID NO: 6) on glucan backbones generated from maltodextrins (MD). The results demonstrate that the α-(1,2) branching enzyme is also active on glucans with mixtures of α-(1,6) and α-(1,4) linkages generated using a DDase reaction from maltodextrin substrates. The branching reaction could be performed sequentially after the glucan backbone reaction or concurrently with the glucan backbone reaction.

The EC0063 strain expressing the active DDase (SEQ ID ON: 26) was used to convert maltodextrins to nondigestible glucan fibers. Two types of maltodextrins with DE13-17 and DE 4-7 were used as substrates. The 10% (v/v) of EC0063 extract was incubated with 100 g/L MD substrate in 25 mM sodium acetate buffer pH4.8 at 37° C. overnight. The linkage profile of the products was analyzed by NMR. The digestibility of the products was analyzed by Megazyme digestibility assay. Both types of substrates behaved similarly that there are about 95% α-(1,4) linkages and 5% α-(1,6) linkages in the substrates. The non-digestibility of the maltodextrin substrates was about 5-10% (i.e., a digestibility of approximately 90-95%). After the maltodextrin substrates were reacted with DDase, the reaction products of the DDase had about 65-75% α-(1,6) linkages with remaining as α-(1,4) linkages. The nondigestibility of the products also increased to about 65-75%.

For the branching of the DDase product, the branching enzyme extract could be added to the DDase reaction sequentially or concurrently. In the sequential reaction, the 10% EC0063 extract containing DDase was reacted with 100 g/L maltodextrin substrate first as described above. The reaction was heat killed for 5 min at 95° C. Eighty percent of the DDase reaction product was used to set up the branching reaction by adding 40 g/L sucrose and 10% of the EC0059T1 extract containing the GtfJ18T1 branching enzyme. This branching reaction was incubated at 30° C. for 24-48 hours and then heat killed for analysis by HPLC, NMR and Megazyme digestibility. In the concurrent reaction, 80 g/L maltodextrin substrate (DE13-17) was reacted with 10% of EC0063 extract containing DDase and 10% of EC0059T1 extract containing GtfJ18T1 concomitantly in 25 mM sodium acetate buffer pH4.8 with 40 g/L sucrose. The reaction was incubated at 30° C. for 24-48 hours and reaction products analyzed the same way as the sequential reaction products. Data in table 9 showed that sequential reaction and concurrent reaction produced similar products. Both reactions generated glucans with about 15% α-(1,2) linkages. The nondigestibility of the products also increased with the introduction of the branching.

TABLE 9

Analysis of sequential and concurrent reaction
products of DDase and branching enzyme GtfJ18T1
using maltodextrin DE13-17 as substrate

| Rxn | Enzyme 1 | Enzyme 2 | % Not digestible | 1,4 | 1,2,6 | 1,3 | 1,6 |
|---|---|---|---|---|---|---|---|
| Backbone only | DDase | none | 75.3% | 24.8 | 0.0 | 0.0 | 75.2 |
| Sequential | DDase | GtfJ18T1 | 81.3% | 22.6 | 15.8 | 0.0 | 61.6 |
| Concurrent | DDase | GtfJ18T1 | 83.1% | 24.8 | 13.5 | 0.0 | 61.6 |
| MD control | none | none | 11.1% | 95.2 | 0.0 | 0.0 | 4.8 |

Example 6

Purification and Isolation of Soluble Fiber Produced by α-(1,2) Branching Reactions The α-(1,2) branching reactions were set up with six crude backbones from the glucosyltransferases reactions and one purified backbone from a glucosyltransferases/mutanase reaction as described in Example 3. The 400-mL reactions started with 200 g/L sucrose and 5% (v/v) enzyme solution (0.22 micron sterile filtered) in 10 mM sodium citrate buffer (pH 5.0) and 0.1 mM calcium chloride at 37° C. with shaking. The reactions were monitored by HPLC for 1-3 days until sucrose was all consumed. At completion of sucrose conversion, the enzymes were inactivated by heating the reaction mixture to 95° C. for 30 minutes, followed by cooling to room temperature. The resulting mixture was centrifuged to remove any precipitates, and the glucan backbone-containing supernatant was employed in the branching reaction.

The 600-mL branching reactions were set up starting with 420 mL (70% v/v) of the glucan backbone-containing supernatant prepared as described above. The branching enzyme, provided as 5% (v/v) of the EC0059T1 crude cell extract (30 mL, (0.22 micron sterile filtered)), was added with 120 mL of 40 wt % sucrose in water (final concentration of 80 g/L sucrose) and 30 mL of deionized water. The reactions were run at 30° C. and between pH 5.0-6.0 with shaking at 180-200 rpm, and sucrose conversion was monitored by HPLC. At completion of sucrose conversion, the enzyme was inactivated by heating the reaction mixture to 95° C. for 30 minutes, followed by cooling to room temperature. The resulting mixture was centrifuged to remove any precipitates, then the supernatant was purified by SEC using BioGel P2 resin (BioRad). The SEC fractions that contained oligosaccharides ≥DP3 were combined and concentrated by rotary evaporation for analysis by HPLC (Table 10).

TABLE 10

HPLC analysis of soluble oligosaccharide fiber produced by α-(1,2) branching reactions.

| | DP8+ g/L | DP7 g/L | DP6 g/L | DP5 g/L | DP4 g/L | DP3 g/L | DP2 g/L | Sucrose g/L | Leucrose g/L | Glucose g/L | Fructose g/L |
|---|---|---|---|---|---|---|---|---|---|---|---|
| EC59T-1006 | 167 | 0.0 | 0.0 | 0.0 | 0.0 | 0.0 | 0.0 | 0.0 | 0.0 | 0.0 | 0.0 |
| EC59T-1018 | 196 | 1.2 | 0.0 | 0.6 | 0.5 | 0.0 | 0.0 | 0.0 | 0.0 | 0.0 | 0.0 |
| EC59T-1031 | 167 | 0.0 | 0.0 | 0.0 | 0.0 | 0.0 | 0.0 | 3.5 | 0.4 | 0.1 | 1.4 |
| EC59T-1051 | 196 | 1.2 | 0.0 | 0.6 | 0.5 | 0.0 | 0.0 | 1.7 | 1.0 | 0.0 | 0.7 |
| EC59T-1066 | 120 | 23.0 | 19.5 | 15.7 | 6.3 | 1.8 | 0.0 | 0.7 | 0.1 | 0.1 | 0.1 |
| EC59T-1115 | 183 | 0.0 | 0.0 | 0.0 | 0.0 | 0.0 | 0.0 | 1.6 | 0.2 | 0.0 | 1.3 |
| EC59T-0544/3486 | 119 | 18.0 | 12.7 | 11.9 | 14.8 | 6.1 | 2.9 | 1.4 | 0.4 | 1.9 | 1.8 |

Example 7

Anomeric Linkage Analysis of Soluble Fiber Produced by α-(1,2) Branching Reactions Solutions of soluble fibers purified by SEC as described in Example 6 were dried to a constant weight by lyophilization, and the resulting solids analyzed by $^1$H NMR spectroscopy and by GC/MS as described in the General Methods section (above). The anomeric linkages for each of these soluble oligosaccharide fiber mixtures are reported in Tables 11 and 12.

TABLE 11

Anomeric linkage analysis of soluble oligosaccharides by $^1$H NMR spectroscopy.

| GTF | % α-(1,3) | % α-(1,2) | % α-(1,3,6) | % α-(1,2,6) | % α-(1,6) |
|---|---|---|---|---|---|
| EC0059T1-1006 | 0.00 | 6.10 | 0.80 | 6.10 | 87.00 |
| EC0059T1-1018 | 0.00 | 6.79 | 0.00 | 6.79 | 86.42 |
| EC0059T1-1031 | 0.00 | 9.68 | 0.00 | 9.68 | 80.65 |
| EC0059T1-1051 | 0.00 | 3.92 | 18.51 | 3.92 | 73.65 |
| EC0059T1-1066 | 8.87 | 6.52 | 1.06 | 6.52 | 77.02 |
| EC0059T1-1115 | 0.00 | 2.63 | 0.00 | 2.63 | 94.74 |
| EC0059T1-0544/3264 | 15.05 | 11.32 | 3.31 | 11.32 | 59.01 |

TABLE 12

Anomeric linkage analysis of soluble oligosaccharides by GC/MS.

| GTF | % α-(1,4) | % α-(1,3) | % α-(1,3,6) | % 2,1 Fruc | % α-(1,2) | % α-(1,6) | % α-(1,2,6) | % α-(1,4,6) |
|---|---|---|---|---|---|---|---|---|
| EC0059T1-1006 | 1.4 | 1.4 | 0.6 | 0.0 | 0.7 | 89.3 | 6.5 | 0.0 |
| EC0059T1-1018 | 1.6 | 0.0 | 0.0 | 0.0 | 0.7 | 90.6 | 7.1 | 0.0 |
| EC0059T1-1031 | 0.5 | 0.0 | 0.0 | 0.0 | 0.7 | 88.0 | 10.7 | 0.0 |
| EC0059T1-1051 | 0.0 | 0.5 | 16.9 | 0.0 | 0.0 | 78.6 | 4.0 | 0.0 |
| EC0059T1-1066 | 0.3 | 13.7 | 0.4 | 1.4 | 1.6 | 78.3 | 4.2 | 0.0 |

TABLE 12-continued

Anomeric linkage analysis of soluble oligosaccharides by GC/MS.

| GTF | % α-(1,4) | % α-(1,3) | % α-(1,3,6) | % 2,1 Fruc | % α-(1,2) | % α-(1,6) | % α-(1,2,6) | % α-(1,4,6) |
|---|---|---|---|---|---|---|---|---|
| EC0059T1-1115 | 0.0 | 0.0 | 0.0 | 0.0 | 0.0 | 98.0 | 2.0 | 0.0 |
| EC0059T1-0544/3264 | 1.6 | 28.7 | 1.9 | 1.0 | 3.1 | 56.8 | 6.9 | 0 |

Example 8

Viscosity of Soluble Fiber Produced by α-(1,2) Branching Reactions

Solutions of soluble fibers purified by SEC as described in Example 6 were dried to a constant weight by lyophilization, and the resulting solids were used to prepare a 12 wt % solution of soluble fiber in distilled, deionized water. The viscosity of the soluble fiber solutions (reported in centipoise (cP), where 1 cP=1 millipascal-s (mPa-s)) (Table 13) was measured at 20° C. as described in the General Methods section.

TABLE 13

Viscosity of 12% (w/w) soluble oligosaccharide fiber solutions measured at 20° C.

| GTF | viscosity (cP) |
|---|---|
| EC0059T1-1006 | 2.9 |
| EC0059T1-1018 | 2.1 |
| EC0059T1-1031 | 28.3 |
| EC0059T1-1051 | 6.1 |
| EC0059T1-1066 | 1.8 |
| EC0059T1-1115 | 4.7 |
| EC0059T1-0544/3264 | 4.7 |

Example 9

Digestibility of Soluble Fiber Produced by α-(1,2) Branching Reactions

Solutions of soluble fibers purified by SEC as described in Example 6 were dried to a constant weight by lyophilization. The digestibility test protocol was adapted from the Megazyme Integrated Total Dietary Fiber Assay (AOAC method 2009.01, Ireland). The final enzyme concentrations were kept the same as the AOAC method: 50 Unit/mL of pancreatic α-amylase (PAA), 3.4 Units/mL for amyloglucosidase (AMG). The substrate concentration in each reaction was 25 mg/mL as recommended by the AOAC method. The total volume for each reaction was 1 mL. Every sample was analyzed in duplicate with and without the treatment of the two digestive enzymes. The amount of released glucose was quantified by HPLC with the Aminex HPX-87C Columns (BioRad) as described in the General Methods. Maltodextrin (DE4-7, Sigma) was used as the positive control for the enzymes (Table 14).

TABLE 14

Digestibility of soluble oligosaccharide fiber.

| GTF | Digestibility (%) |
|---|---|
| EC0059T1-1006 | 2 |
| EC0059T1-1018 | 3 |
| EC0059T1-1031 | 0 |
| EC0059T1-1051 | 5 |
| EC0059T1-1066 | 7 |
| EC0059T1-1115 | 0 |
| EC0059T1-0544/3264 | 0 |

Example 10

Molecular Weight of Soluble Fiber Produced by α-(1,2) Branching Reactions

Solutions of soluble fibers purified by SEC as described in Example 6 were dried to a constant weight by lyophilization, and the resulting solids were analyzed by SEC chromatography for number average molecular weight ($M_n$), weight average molecular weight ($M_w$), peak molecular weight ($M_p$), z-average molecular weight ($M_z$), and polydispersity index (PDI=$M_w/M_n$) as described in the General Methods section (Table 15)

TABLE 15

Characterization of soluble oligosaccharide fiber by SEC.

| GTF | $M_n$ (Daltons) | $M_w$ (Daltons) | $M_p$ (Daltons) | $M_z$ (Daltons) | PDI |
|---|---|---|---|---|---|
| EC0059T1-1006 | 9715 | 12076 | 15000 | 13963 | 1.243 |
| EC0059T1-1018 | 4595 | 4874 | 5200 | 5116 | 1.061 |
| EC0059T1-1031 | 88298 | 140829 | 90900 | 307162 | 1.595 |
| EC0059T1-1051 | 7486 | 33153 | 16800 | 4393313 | 4.428 |
| EC0059T1-1066 | 1914 | 1952 | 2100 | 1988 | 1.02 |
| EC0059T1-1115 | 15228 | 15759 | 16700 | 16218 | 1.035 |
| EC0059T1-0544/3264 | 29614 | 269657 | 19300 | 3977773 | 25.385 |

Example 11

In Vitro Gas Production Using Soluble Oligosaccharide/Polysaccharide Fiber as Carbon Source Solutions of chromatographically-purified soluble oligosaccharide/polysaccharide fibers were dried to a constant weight by lyophilization. The individual soluble oligosaccharide/polysaccharide soluble fiber samples were subsequently evaluated as carbon source for in vitro gas production using the method described in the General Methods. PROMITOR® 85 (soluble corn fiber, Tate & Lyle), NUTRIOSE® FM06 (soluble corn fiber or dextrin, Roquette), FIBERSOL-2® 600F (digestion-resistant maltodextrin, Archer Daniels Midland Company & Matsutani Chemical), ORAFTI® GR (inulin from Beneo, Mannheim, Germany), LITESSE® Ultra™ (polydextrose, Danisco), GOS (galactooligosaccharide, Clasado Inc., Reading, UK), ORAFTI® P95 (oligofructose (fructooligosaccharide, FOS, Beneo), LACTITOL MC (4-O-β-D-Galactopyranosyl-D-glucitol monohydrate, Danisco) and glucose were included as control carbon sources. Table 16 lists the In vitro gas production by intestinal microbiota at 3 h and 24 h.

TABLE 16

In vitro gas production by intestinal microbiota.

| Sample | mL gas formation in 3 h | mL gas formation in 24 h |
|---|---|---|
| PROMITOR ® 85 | 2.6 | 8.5 |
| NUTRIOSE ® FM06 | 3.0 | 9.0 |
| FIBERSOL-2 ® 600F | 2.8 | 8.8 |
| ORAFTI ® GR | 3.0 | 7.3 |
| LITESSE ® ULTRA ™ | 2.3 | 5.8 |
| GOS | 2.6 | 5.2 |
| ORAFTI ® P95 | 2.6 | 7.5 |
| LACTITOL ® MC | 2.0 | 4.8 |
| Glucose | 2.4 | 5.2 |
| EC0059T1-1006 | 3.3 | 10.0 |
| EC0059T1-1018 | 3.8 | 14.8 |
| EC0059T1-1031 | 3.0 | 5.0 |
| EC0059T1-1051 | 3.5 | 8.5 |
| EC0059T1-1066 | 4.0 | 9.5 |
| EC0059T1-1115 | 3.0 | 6.5 |
| EC0059T1-0544/3264 | 3.0 | 8.3 |

Example 12

Colonic Fermentation Modeling and Measurement of Fatty Acids

Colonic fermentation was modeled using a semi-continuous colon simulator as described by Mäkivuokko et al. (*Nutri. Cancer* (2005) 52(1):94-104); in short; a colon simulator consists of four glass vessels which contain a simulated ileal fluid as described by Macfarlane et al. (*Microb. Ecol.* (1998) 35(2):180-187). The simulator is inoculated with a fresh human faecal microbiota and fed every third hour with new ileal liquid and part of the contents is transferred from one vessel to the next. The ileal fluid contains one of the described test components at a concentration of 1%. The simulation lasts for 48 h after which the content of the four vessels is harvested for further analysis. The further analysis involves the determination of microbial metabolites such as short chain fatty acids (SCFA); also referred to as volatile fatty acids (VFA) and branched chain fatty acids (BCFA). Analysis was performed as described by Holben et al. (*Microb. Ecol.* (2002) 44:175-185); in short; simulator content was centrifuged and the supernatant was used for SCFA and BCFA analysis. Pivalic acid (internal standard) and water were mixed with the supernatant and centrifuged. After centrifugation, oxalic acid solution was added to the supernatant and then the mixture was incubated at 4° C., and then centrifuged again. The resulting supernatant was analyzed by gas chromatography using a flame ionization detector and helium as the carrier gas. Comparative data generated from samples of LITESSE® ULTRA™ (polydextrose, Danisco), ORAFTI® P95 (oligofructose; fructooligosaccharide, "FOS", Beneo), lactitol (Lactitol MC (4-O-β-D-galactopyranosyl-D-glucitol monohydrate, Danisco), and a negative control is also provided. The concentration of acetic, propionic, butyric, isobutyric, valeric, isovaleric, 2-methylbutyric, and lactic acid was determined (Table 17).

TABLE 17

Simulator metabolism and measurement of fatty acid production.

| Sample | Acetic (mM) | Propionic (mM) | Butyric (mM) | Lactic (mM) | Valeric (mM) | Short Chain Fatty Acids (SCFA) (mM) | Branched Chain Fatty Acids (BCFA) (mM) |
|---|---|---|---|---|---|---|---|
| EC0059T1-1115 | 199 | 95 | 88 | 0 | 4 | 386 | 5.1 |
| Control | 83 | 31 | 40 | 3 | 6 | 163 | 7.2 |
| LITESSE ® polydextrose | 256 | 76 | 84 | 1 | 6 | 423 | 5.3 |
| FOS | 91 | 9 | 8 | 14 | — | 152 | 2.1 |
| Lactitol | 318 | 42 | 94 | 52 | — | 506 | 7.5 |

Example 13

Preparation of a Yogurt—Drinkable Smoothie

The following example describes the preparation of a yogurt—drinkable smoothie with the present fibers.

TABLE 18

| Ingredients | wt % |
|---|---|
| Distilled Water | 49.00 |
| Supra XT40 Soy Protein Isolate | 6.50 |
| Fructose | 1.00 |
| Grindsted ASD525, Danisco | 0.30 |
| Apple Juice Concentrate (70 Brix) | 14.79 |
| Strawberry Puree, Single Strength | 4.00 |
| Banana Puree, Single Strength | 6.00 |
| Plain Lowfat Yogurt - Greek Style, Cabot | 9.00 |
| 1% Red 40 Soln | 0.17 |
| Strawberry Flavor (DD-148-459-6) | 0.65 |
| Banana Flavor (#29513) | 0.20 |
| 75/25 Malic/Citric Blend | 0.40 |
| Present Soluble Fiber Sample | 8.00 |
| Total | 100.00 |

| Step No. | Procedure |
|---|---|
| | Pectin Solution Formation |
| 1 | Heat 50% of the formula water to 160° F. (~71.1° C.). |
| 2 | Disperse the pectin with high shear; mix for 10 minutes. |
| 3 | Add the juice concentrates and yogurt; mix for 5-10 minutes until the yogurt is dispersed. |
| | Protein Slurry |
| 1 | Into 50% of the batch water at 140° F. (60° C.), add the Supro XT40 and mix well. |
| 2 | Heat to 170° F. (~76.7° C.) and hold for 15 minutes. |
| 3 | Add the pectin/juice/yogurt slurry to the protein solution; mix for 5 minutes. |
| 4 | Add the fructose, fiber, flavors and colors; mix for 3 minutes. |
| 5 | Adjust the pH using phosphoric acid to the desired range (pH range 4.0-4.1). |
| 6 | Ultra High Temperature (UHT) process at 224° F. (~106.7° C.) for 7 seconds with UHT homogenization after heating at 2500/500 psig (17.24/3.45 MPa) using the indirect steam (IDS) unit. |
| 7 | Collect bottles and cool in ice bath. |
| 8 | Store product in refrigerated conditions. |

Example 14

Preparation of a Fiber Water Formulation

The following example describes the preparation of a fiber water with the present fibers.

TABLE 19

| Ingredient | wt % |
|---|---|
| Water, deionized | 86.41 |
| Pistachio Green #06509 | 0.00 |
| Present Soluble Fiber Sample | 8.00 |
| Sucrose | 5.28 |
| Citric Acid | 0.08 |
| Flavor (M748699M) | 0.20 |
| Vitamin C, ascorbic acid | 0.02 |
| TOTAL | 100.00 |

| Step No. | Procedure |
|---|---|
| 1 | Add dry ingredients and mix for 15 minutes. |
| 2 | Add remaining dry ingredients; mix for 3 minutes |
| 3 | Adjust pH to 3.0 +/− 0.05 using citric acid as shown in formulation. |
| 4 | Ultra High Temperature (UHT) processing at 224° F. (~106.7° C.) for 7 seconds with homogenization at 2500/500 psig (17.24/3.45 MPa). |
| 5 | Collect bottles and cool in ice bath. |
| 6 | Store product in refrigerated conditions. |

Example 15

Preparation of a Spoonable Yogurt Formulation

The following example describes the preparation of a spoonable yogurt with the present fibers.

TABLE 20

| Ingredient | wt % |
|---|---|
| Skim Milk | 84.00 |
| Sugar | 5.00 |
| Yogurt (6051) | 3.00 |
| Cultures (add to pH break point) | |
| Present Soluble Fiber | 8.00 |
| TOTAL | 100.00 |

| Step No. | Procedure |
|---|---|
| 1 | Add dry ingredients to base milk liquid; mix for 5 min. |
| 2 | Pasteurize at 195° F. (~90.6° C.) for 30 seconds, homogenize at 2500 psig (~17.24 MPa), and cool to 105-110° F. (~40.6-43.3° C.). |
| 3 | Inoculate with culture; mix gently and add to water batch or hot box at 108° F. (~42.2° C.) until pH reaches 4.5-4.6. |
| | Fruit Prep Procedure |
| 1 | Add water to batch tank, heat to 140° F. (~60° C.). |
| 2 | Pre-blend carbohydrates and stabilizers. Add to batch tank and mix well. |
| 3 | Add Acid to reduce the pH to the desired range (target pH 3.5-4.0). |
| 4 | Add Flavor. |
| 5 | Cool and refrigerate. |

Example 16

Preparation of a Model Snack Bar Formulation

The following example describes the preparation of a model snack bar with the present fibers.

TABLE 21

| Ingredients | wt % |
|---|---|
| Corn Syrup 63 DE | 15.30 |
| Present Fiber solution (70 Brix) | 16.60 |
| Sunflower Oil | 1.00 |
| Coconut Oil | 1.00 |
| Vanilla Flavor | 0.40 |
| Chocolate Chips | 7.55 |
| SUPRO ® Nugget 309 | 22.10 |

TABLE 21-continued

| Ingredients | wt % |
| --- | --- |
| Rolled Oats | 18.00 |
| Arabic Gum | 2.55 |
| Alkalized Cocoa Powder | 1.00 |
| Milk Chocolate Coating Compound | 14.50 |
| TOTAL | 100.00 |

| Step No. | Procedure |
| --- | --- |
| 1 | Combine corn syrup with liquid fiber solution. Warm syrup in microwave for 10 seconds. |
| 2 | Combine syrup with oils and liquid flavor in mixing bowl. Mix for 1 minute at speed 2. |
| 3 | Add all dry ingredient in bowl and mix for 45 seconds at speed 1. |
| 4 | Scrape and mix for another 30 seconds or till dough is mixed. |
| 5 | Melt chocolate coating. |
| 6 | Fully coat the bar with chocolate coating. |

Example 17

Preparation of a High Fiber Wafer

The following example describes the preparation of a high fiber wafer with the present fibers.

TABLE 22

| Ingredients | wt % |
| --- | --- |
| Flour, white plain | 38.17 |
| Present fiber | 2.67 |
| Oil, vegetable | 0.84 |
| GRINSTED ® CITREM 2-in-1 [1] citric acid ester made from sunflower or palm oil (emulsifier) | 0.61 |
| Salt | 0.27 |
| Sodium bicarbonate | 0.11 |
| Water | 57.33 |

[1] Danisco.

| Step No. | Procedure |
| --- | --- |
| 1. | High shear the water, oil and CITREM for 20 seconds. |
| 2. | Add dry ingredients slowly, high shear for 2-4 minutes. |
| 3. | Rest batter for 60 minutes. |
| 4. | Deposit batter onto hot plate set at 200° C. top and bottom, bake for 1 minute 30 seconds |
| 5. | Allow cooling pack as soon as possible. |

Example 18

Preparation of a Soft Chocolate Chip Cookie

The following example describes the preparation of a soft chocolate chip cookie with the present fibers.

TABLE 23

| Ingredients | wt % |
| --- | --- |
| Stage 1 | |
| Lactitol, C | 16.00 |
| Cake margarine | 17.70 |

TABLE 23-continued

| Ingredients | wt % |
| --- | --- |
| Salt | 0.30 |
| Baking powder | 0.80 |
| Eggs, dried whole | 0.80 |
| Bicarbonate of soda | 0.20 |
| Vanilla flavor | 0.26 |
| Caramel flavor | 0.03 |
| Sucralose powder | 0.01 |
| Stage 2 | |
| Present Fiber Solution (70 brix) | 9.50 |
| water | 4.30 |
| Stage 3 | |
| Flour, pastry | 21.30 |
| Flour, high ratio cake | 13.70 |
| Stage Four | |
| Chocolate chips, 100% lactitol, sugar free | 15.10 |

| Step No. | Procedure |
| --- | --- |
| 1. | Cream together stage one, fast speed for 1 minute. |
| 2. | Blend stage two to above, slow speed for 2 minutes. |
| 3. | Add stage three, slow speed for 20 seconds. |
| 4. | Scrape down bowl; add stage four, slow speed for 20 seconds. |
| 5. | Divide into 30 g pieces, flatten, and place onto silicone lined baking trays. |
| 6. | Bake at 190° C. for 10 minutes approximately. |

Example 19

Preparation of a Reduced Fat Short-Crust Pastry

The following example describes the preparation of a reduced fat short-crust pastry with the present fibers.

TABLE 24

| Ingredients | wt % |
| --- | --- |
| Flour, plain white | 56.6 |
| Water | 15.1 |
| Margarine | 11.0 |
| Shortening | 11.0 |
| Present fiber | 6.0 |
| Salt | 0.3 |

| Step No. | Procedure |
| --- | --- |
| 1. | Dry blend the flour, salt and present glucan fiber (dry) |
| 2. | Gently rub in the fat until the mixture resembles fine breadcrumbs. |
| 3. | Add enough water to make a smooth dough. |

Example 20

Preparation of a Low Sugar Cereal Cluster

The following example describes the preparation of a low sugar cereal cluster with one of the present fibers.

TABLE 25

| Ingredients | wt % |
|---|---|
| Syrup Binder | 30.0 |
| Lactitol, MC 50% | |
| Present Fiber Solution (70 brix) 25% | |
| Water 25% | |
| Cereal Mix | 60.0 |
| Rolled Oats 70% | |
| Flaked Oats 10% | |
| Crisp Rice 10% | |
| Rolled Oats 10% | |
| Vegetable oil | 10.0 |

| Step No. | Procedure |
|---|---|
| 1. | Chop the fines. |
| 2. | Weight the cereal mix and add fines. |
| 3. | Add vegetable oil on the cereals and mix well. |
| 4. | Prepare the syrup by dissolving the ingredients. |
| 5. | Allow the syrup to cool down. |
| 6. | Add the desired amount of syrup to the cereal mix. |
| 7. | Blend well to ensure even coating of the cereals. |
| 8. | Spread onto a tray. |
| 9. | Place in a dryer/oven and allow to dry out. |
| 10. | Leave to cool down completely before breaking into clusters. |

Example 21

Preparation of a Pectin Jelly

The following example describes the preparation of a pectin jelly with the present fibers.

TABLE 26

| Ingredients | wt % |
|---|---|
| Component A | |
| Xylitol | 4.4 |
| Pectin | 1.3 |
| Component B | |
| Water | 13.75 |
| Sodium citrate | 0.3 |
| Citric Acid, anhydrous | 0.3 |
| Component C | |
| Present Fiber Solution (70 brix) | 58.1 |
| Xylitol | 21.5 |
| Component D | |
| Citric acid | 0.35 |
| Flavor, Color | q.s. |

| Step No. | Procedure |
|---|---|
| 1. | Dry blend the pectin with the xylitol (Component A). |
| 2. | Heat Component B until solution starts to boil. |
| 3. | Add Component A gradually, and then boil until completely dissolved. |
| 4. | Add Component C gradually to avoid excessive cooling of the batch. |
| 5. | Boil to 113° C. |
| 6. | Allow to cool to <100° C. and then add colour, flavor and acid (Component D). Deposit immediately into starch molds. |
| 7. | Leave until firm, then de-starch. |

Example 22

Preparation of a Chewy Candy

The following example describes the preparation of a chewy candy with the present fibers.

TABLE 27

| Ingredients | wt % |
|---|---|
| Present glucan fiber | 35 |
| Xylitol | 35 |
| Water | 10 |
| Vegetable fat | 4.0 |
| Glycerol Monostearate (GMS) | 0.5 |
| Lecithin | 0.5 |
| Gelatin 180 bloom (40% solution) | 4.0 |
| Xylitol, CM50 | 10.0 |
| Flavor, color & acid | q.s. |

| Step No. | Procedure |
|---|---|
| 1. | Mix the present glucan fiber, xylitol, water, fat, GMS and lecithin together and then cook gently to 158° C. |
| 2. | Cool the mass to below 90° C. and then add the gelatin solution, flavor, color and acid. |
| 3. | Cool further and then add the xylitol CM. Pull the mass immediately for 5 minutes. |
| 4. | Allow the mass to cool again before processing (cut and wrap or drop rolling). |

Example 23

Preparation of a Coffee—Cherry Ice Cream

The following example describes the preparation of a coffee-cherry ice cream with the present fibers.

TABLE 28

| Ingredients | wt % |
|---|---|
| Fructose, C | 8.00 |
| Present glucan fiber | 10.00 |
| Skimmed milk powder | 9.40 |
| Anhydrous Milk Fat (AMF) | 4.00 |
| CREMODAN ® SE 709 | 0.65 |
| Emulsifier & Stabilizer System[1] | |
| Cherry Flavoring U35814[1] | 0.15 |
| Instant coffee | 0.50 |
| Tri-sodium citrate | 0.20 |
| Water | 67.10 |

[1]Danisco.

| Step No. | Procedure |
|---|---|
| 1. | Add the dry ingredients to the water, while agitating vigorously. |
| 2. | Melt the fat. |
| 3. | Add the fat to the mix at 40° C. |
| 4. | Homogenize at 200 bar/70-75° C. |
| 5. | Pasteurize at 80-85° C./20-40 seconds. |
| 6. | Cool to ageing temperature (5° C.). |
| 7. | Age for minimum 4 hours. |
| 8. | Add flavor to the mix. |
| 9. | Freeze in continuous freezer to desired overrun (100% is recommended). |
| 10. | Harden and storage at −25° C. |

What is claimed is:

1. A method of producing alpha-glucan, said method comprising:
   combining a food that has at least water and sucrose with a glucosyltransferase enzyme comprising an amino acid sequence that is at least 91% identical to SEQ ID NO: 10,
   wherein alpha-glucan comprising 100% alpha-1,6 glycosidic linkages is produced by the glucosyltransferase enzyme in the food and the method increases the amounts of soluble alpha-glucan and fructose in the food as measured.

2. The method of claim 1, wherein the food is a liquid food product.

3. The method of claim 1, wherein the food is a dairy product.

4. The method of claim 1, wherein the food is a beverage.

5. The method of claim 4, wherein the beverage is a carbonated beverage.

6. The method of claim 4, wherein the beverage is a fruit juice.

7. The method of claim 4, wherein the beverage is a concentrated juice.

8. The method of claim 4, wherein the beverage is a milk-based drink.

9. The method of claim 1, wherein the food is selected from the group consisting of yogurt, yogurt drinks, milk drinks, flavored milks, smoothies, ice cream, shakes, quarg, whipped mousse, fondants, nougats, soups, syrups, sauces, dressings, and coffee creamers.

10. The method of claim 1, wherein the food is a bakery product.

11. The method of claim 1, wherein the glucosyltransferase enzyme comprises an amino acid sequence that is at least 95% identical to SEQ ID NO:10.

12. The method of claim 1, wherein the glucosyltransferase enzyme is immobilized on a support.

13. A method of producing alpha-glucan, said method comprising:
   combining a food that has at least water and sucrose with a glucosyltransferase enzyme comprising an amino acid sequence that is at least 90% identical to SEQ ID NO:43,
   wherein the food is a dairy product, carbonated beverage, fruit juice, bakery product, or is selected from the group consisting of yogurt, yogurt drinks, milk drinks, flavored milks, smoothies, ice cream, shakes, quarg, whipped mousse, fondants, nougats, soups, sauces, dressings, and coffee creamers,
   wherein alpha-glucan is produced by the glucosyltransferase enzyme in the food and the method increases the amounts of soluble alpha-glucan and fructose in the food as measured.

14. The method of claim 13, wherein the glucosyltransferase enzyme comprises an amino acid sequence that is at least 95% identical to SEQ ID NO:43.

15. The method of claim 13, wherein the glucosyltransferase enzyme is immobilized on a support.

16. The method of claim 13, wherein the food is the dairy product.

17. The method of claim 13, wherein the food is the carbonated beverage.

18. The method of claim 13, wherein the food is the fruit juice.

19. The method of claim 13, wherein the food is the bakery product.

20. The method of claim 13, wherein the food is selected from the group consisting of yogurt, yogurt drinks, milk drinks, flavored milks, smoothies, ice cream, shakes, quarg, whipped mousse, fondants, nougats, soups, sauces, dressings, and coffee creamers.

* * * * *

SEQUENCE LISTING

<160> NUMBER OF SEQ ID NOS: 71

<210> SEQ ID NO 1
<211> LENGTH: 2771
<212> TYPE: PRT
<213> ORGANISM: Leuconostoc mesenteroides

<400> SEQUENCE: 1

```
Met Thr Ala Gly Ile Phe Ser Ala Val Ile Phe Gly Val Ser Thr Thr
1               5                   10                  15

Asn Val Ser Ala Asp Ser Thr Asn Asn Thr Gly Val Thr Val Ser Gln
            20                  25                  30

Ala Thr Asp Lys Val Ala Asp Thr Thr Ala Thr Thr Asp Lys Val Ala
        35                  40                  45

Asp Thr Thr Ala Thr Thr Asp Lys Val Ala Asp Thr Ala Ala Thr Thr
    50                  55                  60

Asp Lys Val Ala Asp Thr Thr Ala Thr Thr Asp Lys Val Ala Asp Thr
65                  70                  75                  80

Ala Ala Thr Thr Asp Lys Val Ala Asp Thr Thr Ala Thr Thr Asp Lys
                85                  90                  95

Val Ala Asp Thr Ala Ala Thr Asp Lys Ala Ala Asp Thr Ala Ala
            100                 105                 110

Thr Thr Asp Lys Val Ala Asp Thr Ala Ala Thr Asp Lys Val Ala
        115                 120                 125

Asp Thr Val Ala Ala Thr Asp Lys Val Ala Asp Thr Thr Ala Thr Thr
    130                 135                 140

Asp Lys Ala Ala Asp Thr Ala Ala Thr Thr Asp Lys Val Thr Asp Thr
145                 150                 155                 160

Thr Ala Ala Thr Asp Lys Ala Ala Asp Thr Thr Ala Thr Thr Asp Lys
                165                 170                 175

Val Ala Asp Thr Thr Ala Thr Thr Ser Glu Lys Ser Lys Ser Ile Lys
            180                 185                 190

Gln Ile Asp Gly Lys Thr Tyr Phe Ile Gly Asn Asp Gly Gln Pro Lys
        195                 200                 205

Lys Asn Phe Thr Ala Ile Val Asp Gly Gln Val Leu Tyr Phe Asp Lys
    210                 215                 220

Asp Thr Gly Ala Leu Thr Ser Asn Ser Ser Gln Tyr Thr Asp Gly Leu
225                 230                 235                 240

Ala Asn Ile Gly Asn Glu His Asn Ala Ala Tyr Ser Leu Ser Ser Asp
                245                 250                 255

Ser Phe Thr Gln Val Asp Gly Tyr Leu Thr Ala Asn Ser Trp Tyr Arg
            260                 265                 270

Pro Lys Asp Ile Leu Lys Asn Gly Thr Thr Trp Thr Ala Ala Thr Ala
        275                 280                 285

Asn Asp Phe Arg Pro Leu Leu Met Ser Trp Trp Pro Asp Lys Asp Thr
    290                 295                 300

Gln Val Ser Tyr Leu Lys Tyr Met Gln Ser Ala Gly Leu Leu Ser Asp
305                 310                 315                 320

Asp Val Ala Leu Ser Asn Asn Asp Ser Met Asn Ser Leu Thr Asp Thr
                325                 330                 335

Ala Met Thr Val Gln Lys Lys Ile Glu Glu Lys Ile Gly Leu Leu Gly
            340                 345                 350

Ser Thr Asp Trp Leu Lys Ala Asp Met Asn Gln Met Val Asp Ser Gln
        355                 360                 365
```

```
Ser Asn Trp Asn Ile Ser Ser Glu Ser Lys Gly Thr Asp His Leu Gln
370                 375                 380

Gly Gly Ala Leu Leu Tyr Val Asn Ser Asp Leu Thr Pro Asn Ala Asn
385                 390                 395                 400

Ser Asp Tyr Arg Leu Leu Asn Arg Thr Pro Thr Asn Gln Lys Gly Gln
                405                 410                 415

Ile Thr Thr Asn Gly Asn Gln Gly Gly Tyr Glu Met Leu Leu Ala Asn
            420                 425                 430

Asp Val Asp Asn Ser Asn Pro Ile Val Gln Ala Glu Gln Leu Asn Trp
                435                 440                 445

Leu Tyr Tyr Met Met Asn Ile Gly Ser Ile Ala Gln Asn Asp Pro Thr
        450                 455                 460

Ala Asn Phe Asp Gly Tyr Arg Val Asp Ala Val Asp Asn Val Asn Ala
465                 470                 475                 480

Asp Leu Leu Gln Ile Ala Gly Asp Tyr Phe Lys Ala Ala Tyr Gly Thr
                485                 490                 495

Asn Gln Ser Asp Ala Asn Ala Asn Asn His Ile Ser Ile Leu Glu Asp
                500                 505                 510

Trp Asp Asn Asn Asp Pro Ala Tyr Val Lys Ala Gln Gly Asn Asn Gln
                515                 520                 525

Leu Thr Met Asp Phe Pro Met His Leu Ala Leu Lys Tyr Ser Leu Asn
        530                 535                 540

Met Pro Ser Ser Ala Arg Ser Gly Leu Glu Pro Ala Ile Ser Thr Ser
545                 550                 555                 560

Leu Val Asn Arg Ala Ala Asp Ala Thr Glu Asn Glu Ala Gln Pro Asn
                565                 570                 575

Tyr Ser Phe Ile Arg Ala His Asp Ser Glu Val Gln Thr Val Ile Ala
                580                 585                 590

Gln Ile Ile Lys Asp Lys Ile Asn Pro Ser Ser Asp Gly Leu Thr Val
            595                 600                 605

Ser Thr Asp Glu Ile Ala Lys Ala Phe Glu Ile Tyr Asn Ala Asp Glu
        610                 615                 620

Leu Lys Ala Asp Lys Glu Tyr Thr Ala Tyr Asn Ile Pro Ser Ser Tyr
625                 630                 635                 640

Ala Leu Met Leu Thr Asn Lys Asp Thr Ile Pro Arg Val Tyr Tyr Gly
                645                 650                 655

Asp Leu Phe Thr Asp Asp Gly Gln Tyr Met Ser Ala Lys Ser Pro Tyr
                660                 665                 670

Tyr Asp Ala Leu Thr Ser Leu Leu Gln Ser Arg Val Lys Tyr Val Ser
                675                 680                 685

Gly Gly Gln Ser Met Asn Met Thr Tyr Leu His Asn Asn Gln Gly Leu
690                 695                 700

Leu Thr Ser Val Arg Tyr Gly Lys Asp Ala Met Thr Ala Asn Asp Thr
705                 710                 715                 720

Gly Thr Ser Glu Thr Arg Thr Gln Gly Ile Gly Leu Ile Val Gly Asn
                725                 730                 735

Lys Thr Asp Leu Asn Leu Asn Asn Asp Glu Gln Ile Val Leu Asn Met
                740                 745                 750

Gly Ala Ala His Lys Asn Gln Ala Tyr Arg Ala Leu Met Leu Ser Thr
                755                 760                 765

Lys Asp Gly Leu Lys Ile Tyr Asn Asn Asp Glu Ala Pro Val Ser
770                 775                 780

Tyr Thr Asp Asp Gln Gly Arg Leu Ile Phe Lys Ser Asp Val Val Tyr
```

-continued

```
            785                 790                 795                 800
        Gly Val Ser Asp Ala Gln Val Ser Gly Tyr Leu Ala Ala Trp Val Pro
                        805                 810                 815
        Val Gly Ala Asn Asp Ser Gln Asp Ala Arg Thr Glu Ser Ser Thr Thr
                        820                 825                 830
        Ala Ser Thr Asp Gly Asn Thr Tyr His Ser Asn Ser Ala Leu Asp Ser
                        835                 840                 845
        Gln Leu Ile Tyr Glu Gly Phe Ser Asn Phe Gln Ala Met Pro Thr Gln
            850                 855                 860
        Ala Asp Glu Tyr Thr Asn Ile Lys Ile Ala Glu Asn Ala Gln Leu Phe
        865                 870                 875                 880
        Lys Ser Leu Gly Ile Thr Ser Phe Glu Leu Ala Pro Gln Tyr Arg Ser
                        885                 890                 895
        Ser Thr Asp Asn Ser Phe Leu Asp Ser Val Ile Gln Asn Gly Tyr Ala
                        900                 905                 910
        Phe Thr Asp Arg Tyr Asp Ile Gly Tyr Asn Thr Pro Thr Lys Tyr Gly
                        915                 920                 925
        Thr Val Asp Gln Leu Leu Asp Ala Leu Arg Ala Leu His Ala Gln Gly
                        930                 935                 940
        Ile Gln Ala Ile Asn Asp Trp Val Pro Asp Gln Ile Tyr Asn Leu Pro
        945                 950                 955                 960
        Gly Glu Glu Ile Val Thr Ala Ser Arg Thr Asn Gly Ser Gly Lys Val
                        965                 970                 975
        Asn Glu Ser Ser Val Ile Asn Asn Thr Leu Tyr Asp Ser Arg Thr Val
                        980                 985                 990
        Gly Gly Gly Glu Tyr Gln Ala Ile Tyr Gly Gly Ala Phe Leu Asp Lys
                        995                 1000                1005
        Leu Lys Gln Asp Tyr Pro Glu Leu Phe Glu Thr Lys Gln Ile Ser
                1010                1015                1020
        Thr Gly Glu Ala Met Asn Pro Asp Val Lys Ile Thr Glu Trp Ser
                1025                1030                1035
        Ala Lys Tyr Phe Asn Gly Ser Asn Ile Gln Gly Arg Gly Ala Trp
                1040                1045                1050
        Tyr Val Leu Lys Asp Trp Ser Thr Asn Gln Tyr Phe Asn Val Ser
                1055                1060                1065
        Ser Gly Ser Glu Phe Leu Pro Lys Gln Leu Leu Gly Glu Lys Thr
                1070                1075                1080
        Ser Thr Gly Phe Thr Asn Val Asp Asn Gly Lys Thr Glu Phe Tyr
                1085                1090                1095
        Ser Thr Ser Gly Tyr Gln Ala Lys Asn Thr Phe Ile Gln Asp Asn
                1100                1105                1110
        Asp Asn Trp Tyr Tyr Phe Asp Asn Asp Gly Tyr Met Val Val Gly
                1115                1120                1125
        Gly Gln Glu Ile Asn Gly Lys Lys Tyr Tyr Phe Leu Pro Asn Gly
                1130                1135                1140
        Val Glu Leu Gln Asp Ala Tyr Leu Ser Asp Gly Thr Ser Glu Tyr
                1145                1150                1155
        Tyr Tyr Ser Ser Asp Gly Arg Gln Ile Ser Asn Gln Tyr Tyr Gln
                1160                1165                1170
        Gly Ser Asp Asn Asn Trp Arg Tyr Phe Phe Ala Asp Gly His Met
                1175                1180                1185
        Ala Val Gly Leu Ala Thr Ile Thr Thr Glu Asn Gly Thr Thr Asn
                1190                1195                1200
```

```
Gln Gln Tyr Phe Asp Ala Asn Gly Val Gln Leu Lys Gly Val Ala
1205                1210                1215

Ile Lys Asp Thr Asp Gly Asn Val His Tyr Phe Asp Gly Lys Thr
1220                1225                1230

Gly Asn Met Val Ile Asn Ser Trp Gly Lys Ile Ser Asp Gly Ser
1235                1240                1245

Trp Leu Tyr Leu Asn Asp Ser Gly Val Ala Val Thr Gly Pro Gln
1250                1255                1260

Asn Ile Asn Gly Gln Asn Leu Tyr Phe Asn Glu Asp Gly Ile Gln
1265                1270                1275

Val Lys Gly Glu Ala Ile Thr Asp Asn Ser Gly Asn Ile His Tyr
1280                1285                1290

Tyr Asp Arg Ser Thr Gly Asn Met Val Val Asn Ser Trp Gly Glu
1295                1300                1305

Thr Asn Asn Gly Ser Trp Leu Tyr Leu Asn Asp Lys Gly Asp Ala
1310                1315                1320

Val Thr Gly Glu Gln Val Ile Asp Gly Gln Lys Leu Tyr Phe Ser
1325                1330                1335

Ser Asn Gly Ile Gln Leu Lys Asn Thr Phe Lys Lys Leu Ser Asp
1340                1345                1350

Gly Ser Trp Leu Tyr Leu Asn Asp Lys Gly Leu Pro Val Thr Gly
1355                1360                1365

Ala Gln Val Ile Asp Gly Gln Asn Leu Tyr Phe Asp Gln Asp Gly
1370                1375                1380

Lys Gln Val Lys Gly Asp Val Ala Thr Asp Gly Gln Gly Asn Thr
1385                1390                1395

His Tyr Tyr Asp Gly Asn Thr Gly Asn Met Val Thr Asn Ser Trp
1400                1405                1410

Ala Glu Leu Pro Asp Gly Ser Trp Met Tyr Leu Asp Asn Asp Gly
1415                1420                1425

Asn Pro Leu Thr Gly Gln Gln Lys Ile Asp Gly Gln Ser Leu Tyr
1430                1435                1440

Phe Asn Asp Ala Gly Lys Gln Ile Lys Asn Ala Leu Val Lys Leu
1445                1450                1455

Asp Asp Gly Ser Thr Ile Tyr Leu Asp Asp Lys Gly Val Ser Ser
1460                1465                1470

Thr Gly Ile Gln Arg Ile Asp Asp Lys Ile Tyr Tyr Phe Asp Pro
1475                1480                1485

Asp Gly Lys Gln Val Val Cys Arg Phe Glu Glu Leu Pro Asp Gly
1490                1495                1500

Ser Trp Met Tyr Leu Asp Asp Asp Gly Val Ala Ala Thr Gly Ala
1505                1510                1515

Gln Lys Ile Asn Gly Gln Glu Leu Tyr Phe Asp Asn Ser Gly Lys
1520                1525                1530

Gln Val Lys Asn Asp Lys Val Ile Asn Asp Asp Gly Thr Ile Asn
1535                1540                1545

Tyr Tyr Thr Gly Met Ser Gly Glu Lys Leu Lys Asn Asp Phe Gly
1550                1555                1560

Glu Leu Pro Asp Gly Ser Trp Met Tyr Leu Asp Asn Gln Gly Asn
1565                1570                1575

Ala Val Ile Gly Ala Gln Lys Ile Asn Gly Gln Asn Leu Tyr Phe
1580                1585                1590
```

```
Lys Thr Asp Gly Arg Gln Val Lys Gly Glu Ala Asn Val Asp Ser
1595                1600                1605

Ser Gly Glu Met His Phe Tyr Asp Pro Asp Ser Gly Glu Leu Ile
1610                1615                1620

Thr Asn Arg Phe Glu Gln Val Ala Ser Gly Val Trp Ala Tyr Phe
1625                1630                1635

Asp Ala Lys Gly Val Ala Val Thr Gly Glu Gln Arg Ile Gly Lys
1640                1645                1650

Gln Asn Leu Phe Phe Asp Pro Thr Gly Tyr Gln Val Lys Gly Asp
1655                1660                1665

Lys Arg Thr Ile Asp Gly Val Leu Tyr Thr Phe Asp Lys Glu Ser
1670                1675                1680

Gly Glu Arg Lys Gly Leu Asp Ser Ile Ser Val Leu Pro Thr Asn
1685                1690                1695

Gly Gln Tyr Thr Thr Asp Lys Ala Gln Asn Trp Tyr Tyr Gln Val
1700                1705                1710

Asp Gly Glu Asn Val Lys Gly Leu Tyr Thr Asn Asn Asp Gly Gln
1715                1720                1725

Leu Arg Tyr Phe Asp Leu Thr Thr Gly Val Gln Thr Lys Gly Asn
1730                1735                1740

Phe Val Thr Ile Gly Asn Asp Thr Tyr Tyr Phe Thr Lys Glu Gln
1745                1750                1755

Gly Asp Gly Gln Ile Val Ser Glu Val Val Ser Gly His Tyr Gly
1760                1765                1770

Thr Val Gln Leu Ser Asp Asn Ser Ser Ala Trp Val Tyr Arg Gly
1775                1780                1785

Ala Asn Asp Gln Ile Leu Lys Gly Leu Gln Asn Ile Asn Gly Arg
1790                1795                1800

Leu Gln Tyr Phe Asp Leu Thr Thr Gly Ala Gln Leu Lys Gly Gly
1805                1810                1815

Ala Ala Asn Tyr Asp Gly Asn Leu Tyr Tyr Phe Glu Ser Ser Asp
1820                1825                1830

Gly Asn Leu Val Ser Lys Ile Gln Gln Ser Tyr Ser Thr Gly Asn
1835                1840                1845

Tyr Val Thr Asp Gly Asp Lys Val Thr Tyr Ala Asp Glu Gln Asn
1850                1855                1860

Asn Gln Val Thr Gly Leu Ala Leu Ile Asp Asp Gln Leu Gln Tyr
1865                1870                1875

Phe Asp Pro Ser Asp Gly Arg Gln Val Lys Asn Glu Gln Val Ile
1880                1885                1890

Val Asp Gly Val Thr Tyr Tyr Phe Asp Lys Asn Gly Asn Gly Gln
1895                1900                1905

Tyr Leu Phe Thr Asn Thr Ala Thr Met Ser Thr Asn Glu Phe Ala
1910                1915                1920

Lys His Ser Ala Ala Tyr Ser Asn Asp Ser Ser Phe Lys Asn
1925                1930                1935

Thr Ile Asp Gly Phe Leu Thr Ala Asp Thr Trp Tyr Arg Pro Lys
1940                1945                1950

Asp Ile Leu Glu Asn Gly Gln Thr Trp Val Val Ser Ser Thr Asn
1955                1960                1965

Asp Val Arg Pro Leu Ile Thr Val Trp Trp Leu Asn Lys Asp Val
1970                1975                1980

Gln Val Asn Tyr Ser Asn Phe Met Lys Gln Asn Gly Leu Leu Asp
```

```
                    1985                1990                1995
Thr Ser Ser Gln Phe Asn Leu Gln Ser Asp Gln Tyr Asp Leu Asn
                    2000                2005                2010

Val Ala Ala Gln Lys Val Gln Val Ala Ile Glu Lys Arg Ile Ser
                    2015                2020                2025

Lys Glu Lys Ser Thr Asp Trp Leu Lys Asp Leu Leu Phe Glu Ala
                    2030                2035                2040

His Glu Asp Thr Pro Ser Phe Val Lys Gln Gln Phe Ile Trp Asn
                    2045                2050                2055

Lys Asp Ser Glu Tyr Gln Gly Gln Gly Asp Ala Trp Phe Gln Gly
                    2060                2065                2070

Gly Tyr Leu Lys Tyr Gly Asn Asn Glu Leu Thr Pro Thr Thr Asn
                    2075                2080                2085

Ser Asp Tyr Arg Glu Ser Gly Asn Thr Leu Asp Phe Leu Leu Ala
                    2090                2095                2100

Asn Asp Val Asp Asn Ser Asn Pro Ala Val Gln Ala Glu Asn Leu
                    2105                2110                2115

Asn Trp Leu His Tyr Leu Met Asn Phe Gly Thr Ile Thr Ala Asn
                    2120                2125                2130

Asp Asp Asp Ala Asn Phe Asp Ser Ile Arg Ile Asp Ala Val Asp
                    2135                2140                2145

Phe Ile Asp Asn Asp Ala Ile Gln Arg Thr Tyr Asp Tyr Met Arg
                    2150                2155                2160

Asp Ala Tyr Lys Val Asp Ala Ser Glu Asp Asn Ala Asn Lys His
                    2165                2170                2175

Ile Ser Leu Val Glu Ala Gly Leu Asp Ala Gly Thr Ser Thr Ile
                    2180                2185                2190

Lys Ser Asp Ala Leu Val Glu Ser Asn Phe Arg Glu Ala Ala Thr
                    2195                2200                2205

Leu Ser Leu Ala Asn Gln Ser Gly Glu Asn Ser Leu Thr Asn
                    2210                2215                2220

Met Leu Gln Asp Ile Asp Gly Gly Gln Ile Ile Ala Asp His Ala
                    2225                2230                2235

Asn Asn Ala Thr Glu Asn Glu Ser Thr Pro Asn Tyr Ser Ile Ile
                    2240                2245                2250

His Ala His Asp Lys Gly Ile Gln Glu Lys Val Gly Ala Ala Ile
                    2255                2260                2265

Thr Asp Val Thr Gly Ala Asp Trp Thr Asn Phe Thr Asp Asp Gln
                    2270                2275                2280

Leu Lys Glu Gly Leu Ala Ala Tyr Tyr Gln Asp Gln Arg Ser Thr
                    2285                2290                2295

Asn Lys Lys Tyr Asn Ile Tyr Asn Leu Pro Ser Ile Tyr Ala Leu
                    2300                2305                2310

Met Leu Thr Asn Lys Asp Thr Val Pro Arg Val Tyr Tyr Gly Asp
                    2315                2320                2325

Met Tyr Gln Asp Asp Gly Gln Tyr Met Glu Lys Gln Ser Ile Tyr
                    2330                2335                2340

Tyr Asp Ala Ile Val Ser Leu Met Asn Thr Arg Lys Ser Tyr Val
                    2345                2350                2355

Ser Gly Gly Gln Thr Met Asp Val Asp Glu His Gly Leu Leu Lys
                    2360                2365                2370

Ser Val Arg Phe Gly Lys Asp Ala Met Thr Ala Ser Asp Leu Gly
                    2375                2380                2385
```

-continued

```
Thr Asn Glu Thr Arg Thr Glu Gly Val Gly Val Leu Val Gly Asn
    2390            2395                2400

Asp Ser Ser Leu Lys Leu Asn Asp Ser Asp Thr Val Thr Leu Glu
    2405            2410                2415

Met Gly Ala Ala His Lys Asn Gln Lys Tyr Arg Ala Ala Leu Leu
    2420            2425                2430

Thr Thr Ser Asp Gly Ile Val Thr Tyr Asp Ala Asp Asn Asp Ala
    2435            2440                2445

Pro Thr Ile Trp Thr Asp Arg Gly Thr Leu Thr Phe Ser Asn
    2450            2455                2460

Lys Glu Ile Ala Gly Gln Asp Tyr Thr Ser Val Gln Gly Phe Ala
    2465            2470                2475

Asn Ser Gln Val Ser Gly Tyr Leu Ala Val Trp Val Pro Val Gly
    2480            2485                2490

Ala Ser Asp Asp Gln Asp Val Arg Thr Ala Ala Leu Thr Asp Ala
    2495            2500                2505

Asn Leu Asp Asp Lys Val Leu His Ser Asn Ala Ala Leu Asp Ser
    2510            2515                2520

Asn Leu Ile Tyr Glu Gly Phe Ser Asn Phe Gln Pro Lys Ala Thr
    2525            2530                2535

Thr Asn Asp Glu Leu Thr Asn Val Val Ile Ala Lys Asn Ala Asn
    2540            2545                2550

Leu Phe Glu Lys Trp Gly Ile Thr Ser Phe Glu Met Ala Pro Gln
    2555            2560                2565

Tyr Arg Ser Ser Gly Asp His Thr Phe Leu Asp Ser Thr Ile Asp
    2570            2575                2580

Asn Gly Tyr Ala Phe Thr Asp Arg Tyr Asp Leu Gly Phe Glu Thr
    2585            2590                2595

Pro Thr Lys Tyr Gly Thr Asp Lys Asp Leu Arg Thr Ala Ile Lys
    2600            2605                2610

Ala Leu His Gln Ser Asn Met Gln Val Met Ala Asp Val Val Asp
    2615            2620                2625

Asn Gln Val Tyr Asn Leu Ser Gly Gln Glu Val Val Ser Ala Ser
    2630            2635                2640

Arg Ala Gly Val Tyr Gly Asn Asp Val Ser Thr Gly Phe Gly Thr
    2645            2650                2655

Gln Leu Tyr Ala Val Asn Ser Val Gly Gly Lys Tyr Gln Ala
    2660            2665                2670

Gln Tyr Gly Gly Glu Tyr Leu Asn Glu Leu Lys Gln Gln Tyr Pro
    2675            2680                2685

Asp Leu Phe Glu Ala Lys Thr Tyr Asp Tyr Trp Val Lys Asn Tyr
    2690            2695                2700

Ser Asn Asp Gly Ser Asp Pro Tyr Tyr Thr Leu Ser Gln Asn Thr
    2705            2710                2715

Arg Lys Asp Met Pro Ser Ser Glu Val Ile Lys Gln Trp Ser Ala
    2720            2725                2730

Lys Tyr Met Asn Gly Thr Asn Val Leu Gly Asn Gly Met Gly Tyr
    2735            2740                2745

Val Leu Lys Asp Trp Asn Thr Gly Glu Tyr Phe Lys Ile Gly Glu
    2750            2755                2760

Lys Asn Ala Asp Phe Ile Thr Asn
    2765            2770
```

```
<210> SEQ ID NO 2
<211> LENGTH: 2835
<212> TYPE: PRT
<213> ORGANISM: Leuconostoc mesenteroides

<400> SEQUENCE: 2

Met Arg Asp Met Arg Val Ile Cys Asp Arg Lys Lys Leu Tyr Lys Ser
1               5                   10                  15

Gly Lys Val Leu Val Thr Ala Gly Ile Phe Ala Leu Met Met Phe Gly
                20                  25                  30

Val Thr Thr Ala Ser Val Ser Ala Asn Thr Ile Ala Val Asp Thr Asn
                35                  40                  45

His Ser Arg Thr Ser Ala Gln Ile Asn Lys Ser Ala Val Asp Lys Val
        50                  55                  60

Asn Asp Asp Lys Thr Thr Leu Gly Ala Ala Lys Val Val Ala Val Ala
65                  70                  75                  80

Thr Thr Pro Ala Thr Pro Val Ala Asp Lys Thr Val Ser Ala Pro Ala
                85                  90                  95

Ala Asp Lys Ala Val Asp Thr Thr Ser Ser Thr Thr Pro Ala Thr Asp
                100                 105                 110

Lys Ala Val Asp Thr Thr Pro Thr Pro Ala Ala Asp Lys Ala Val
                115                 120                 125

Asp Thr Thr Pro Thr Thr Pro Ala Ala Asp Lys Ala Val Asp Thr Thr
                130                 135                 140

Pro Thr Thr Pro Ala Ala Asn Lys Ala Val Asp Thr Thr Pro Ala Thr
145                 150                 155                 160

Ala Ala Thr Asp Lys Ala Val Ala Thr Pro Ala Thr Pro Ala Ala Asp
                165                 170                 175

Lys Leu Ala Asn Thr Thr Pro Ala Thr Asp Lys Ala Val Ala Thr Thr
                180                 185                 190

Pro Ala Thr Pro Val Ala Asn Lys Ala Ala Asp Thr Ser Ser Ile His
                195                 200                 205

Asp Gln Pro Leu Asp Thr Asn Val Pro Thr Asp Lys Ser Ala Asn Leu
        210                 215                 220

Val Ser Thr Thr Gln Lys Ser Thr Asp Asn Gln Gln Val Lys Ser Thr
225                 230                 235                 240

Glu Thr Ser His Leu Gln Glu Ile Asn Gly Lys Thr Tyr Phe Leu Asp
                245                 250                 255

Asp Asn Gly Gln Val Lys Lys Asn Phe Thr Ala Ile Ile Asp Gly Lys
                260                 265                 270

Val Leu Tyr Phe Asp Lys Thr Ser Gly Glu Leu Thr Ala Asn Ala Pro
                275                 280                 285

Gln Val Thr Lys Gly Leu Val Asn Ile Asp Asn Ala His Asn Ala Ala
                290                 295                 300

His Asp Leu Thr Ala Asp Asn Phe Thr Asn Val Asp Gly Tyr Leu Thr
305                 310                 315                 320

Ala Asn Ser Trp Tyr Arg Pro Lys Asp Ile Leu Lys Asn Gly Thr Thr
                325                 330                 335

Trp Thr Pro Thr Thr Ala Glu Asp Phe Arg Pro Leu Leu Met Ser Trp
                340                 345                 350

Trp Pro Asp Lys Asn Thr Gln Val Ala Tyr Leu Gln Tyr Met Gln Ser
                355                 360                 365

Val Gly Met Leu Pro Asp Asp Val Lys Val Ser Asn Asp Asp Asn Met
                370                 375                 380
```

```
Ser Thr Leu Thr Asp Ala Ala Met Thr Val Gln Lys Asn Ile Glu Ser
385                 390                 395                 400

Arg Ile Gly Val Ser Gly Lys Thr Asp Trp Leu Lys Gln Asp Met Asn
            405                 410                 415

Lys Leu Ile Asp Ser Gln Ala Asn Trp Asn Ile Asp Ser Glu Ser Lys
            420                 425                 430

Gly Asn Asp His Leu Gln Gly Gly Ala Leu Leu Tyr Val Asn Asp Asp
            435                 440                 445

Lys Thr Pro Asn Ala Asn Ser Asp Tyr Arg Leu Leu Asn Arg Thr Pro
            450                 455                 460

Thr Asn Gln Thr Gly Gln Ile Thr Asp Pro Ser Lys Gln Gly Gly Tyr
465                 470                 475                 480

Glu Met Leu Leu Ala Asn Asp Val Asp Asn Ser Asn Pro Val Val Gln
                485                 490                 495

Ala Glu Gln Leu Asn Trp Leu His Tyr Met Met Asn Ile Gly Thr Ile
                500                 505                 510

Ala Gln Asn Asp Pro Thr Ala Asn Phe Asp Gly Tyr Arg Val Asp Ala
            515                 520                 525

Val Asp Asn Val Asp Ala Asp Leu Leu Gln Ile Ala Gly Asp Tyr Phe
530                 535                 540

Lys Ala Ala Tyr Gly Thr Gly Lys Thr Glu Ala Asn Ala Asn Asn His
545                 550                 555                 560

Ile Ser Ile Leu Glu Asp Trp Asp Asn Asn Asp Ser Ala Tyr Ile Lys
            565                 570                 575

Ala His Gly Asn Asn Gln Leu Thr Met Asp Phe Pro Ala His Leu Ala
            580                 585                 590

Leu Lys Tyr Ala Leu Asn Met Pro Leu Ala Ala Gln Ser Gly Leu Glu
            595                 600                 605

Pro Leu Ile Asn Thr Ser Leu Val Lys Arg Gly Lys Asp Ala Thr Glu
            610                 615                 620

Asn Glu Ala Gln Pro Asn Tyr Ala Phe Ile Arg Ala His Asp Ser Glu
625                 630                 635                 640

Val Gln Thr Val Ile Ala Gln Ile Ile Lys Asp Lys Ile Asn Thr Lys
                645                 650                 655

Ser Asp Gly Leu Thr Val Thr Pro Asp Glu Ile Lys Gln Ala Phe Thr
            660                 665                 670

Ile Tyr Asn Ala Asp Glu Leu Lys Ala Asp Lys Glu Tyr Thr Ala Tyr
            675                 680                 685

Asn Ile Pro Ala Ser Tyr Ala Val Leu Leu Thr Asn Lys Asp Thr Val
            690                 695                 700

Pro Arg Val Tyr Tyr Gly Asp Leu Phe Ser Asp Gly Gln Tyr Met
705                 710                 715                 720

Ser Gln Lys Ser Pro Tyr Tyr Asp Ala Ile Thr Ser Leu Leu Lys Ser
            725                 730                 735

Arg Ile Lys Tyr Val Ala Gly Gly Gln Ser Met Asn Met Thr Tyr Leu
            740                 745                 750

His Glu Cys Phe Asp Pro Ala Lys Asn Glu Thr Lys Pro Gln Gly Val
            755                 760                 765

Leu Thr Ser Val Arg Tyr Gly Lys Gly Ala Met Thr Ala Asp Asp Leu
            770                 775                 780

Gly Asn Ser Asp Thr Arg Gln Gln Gly Ile Gly Leu Val Ile Asn Asn
785                 790                 795                 800
```

-continued

```
Lys Pro Phe Leu Asn Leu Asn Asp Asp Glu Gln Ile Val Leu Asn Met
            805                 810                 815

Gly Ala Ala His Lys Asn Gln Ala Tyr Arg Pro Leu Met Leu Thr Thr
        820                 825                 830

Lys Ser Gly Leu Gln Ile Tyr Asp Lys Asp Ala Gly Ala Pro Val Val
    835                 840                 845

Tyr Thr Asn Asp Ala Gly Gln Leu Ile Phe Lys Ser Asp Met Val Tyr
850                 855                 860

Gly Val Ser Asn Pro Gln Val Ser Gly Tyr Phe Ala Ala Trp Val Pro
865                 870                 875                 880

Val Gly Ala Ser Asp Ser Gln Asp Ala Arg Thr Gln Ser Ser Gln Ser
            885                 890                 895

Glu Thr Lys Asp Gly Asp Val Tyr His Ser Asn Ala Ala Leu Asp Ser
        900                 905                 910

Asn Val Ile Tyr Glu Gly Phe Ser Asn Phe Gln Ala Met Pro Glu Lys
    915                 920                 925

Asn Asp Asp Phe Thr Asn Val Lys Ile Ala Gln Asn Ala Lys Leu Phe
930                 935                 940

Lys Asp Leu Gly Ile Thr Ser Phe Glu Leu Ala Pro Gln Tyr Arg Ser
945                 950                 955                 960

Ser Thr Asp Asn Ser Phe Leu Asp Ser Val Ile Gln Asn Gly Tyr Ala
            965                 970                 975

Phe Thr Asp Arg Tyr Asp Val Gly Tyr Asn Thr Pro Thr Lys Tyr Gly
        980                 985                 990

Thr Val Asp Gln Leu Leu Asp Ser Leu Arg Ala Leu His Ala Gln Gly
    995                 1000                1005

Ile Gln Ala Ile Asn Asp Trp Val Pro Asp Gln Ile Tyr Asn Leu
    1010                1015                1020

Pro Gly Glu Gln Ile Val Thr Ala Val Arg Thr Asn Gly Ser Gly
    1025                1030                1035

Lys Tyr Asp Tyr Asp Ser Val Ile Asn Asn Thr Leu Tyr Asp Ser
    1040                1045                1050

Arg Thr Val Gly Gly Gly Glu Tyr Gln Glu Lys Phe Gly Gly Leu
    1055                1060                1065

Phe Leu Asp Gln Leu Lys Lys Asp Tyr Pro Ser Leu Phe Glu Thr
    1070                1075                1080

Lys Gln Ile Ser Thr Asn Gln Pro Met Asn Pro Asp Val Lys Ile
    1085                1090                1095

Lys Glu Trp Ser Ala Lys Tyr Phe Asn Gly Ser Asn Ile Gln Gly
    1100                1105                1110

Arg Gly Ala Trp Tyr Val Leu Lys Asp Trp Ala Thr Asn Gln Tyr
    1115                1120                1125

Phe Asn Val Ser Ser Asp Asn Gly Phe Leu Pro Lys Gln Leu Leu
    1130                1135                1140

Gly Glu Lys Thr Ser Thr Gly Phe Ile Thr Glu Asn Gly Lys Thr
    1145                1150                1155

Ser Phe Tyr Ser Thr Ser Gly Tyr Gln Ala Lys Asp Thr Phe Ile
    1160                1165                1170

Gln Asp Gly Thr Asn Trp Tyr Tyr Phe Asp Asn Ala Gly Tyr Met
    1175                1180                1185

Leu Thr Gly Lys Gln Asn Ile His Asp Lys Asn Tyr Tyr Phe Leu
    1190                1195                1200

Pro Asn Gly Val Glu Leu Gln Asp Ala Tyr Leu Phe Asp Gly Asn
```

-continued

|      |      |      | 1205 |      |      |      | 1210 |      |      |      | 1215 |
|------|------|------|------|------|------|------|------|------|------|------|------|

Gln Glu Phe Tyr Tyr Asn Lys Ala Gly Glu Gln Val Met Asn Gln
        1220                1225                1230

Tyr Tyr Gln Asp Ser Gln Asn Gln Trp His Tyr Phe Phe Glu Asn
        1235                1240                1245

Gly Arg Met Ala Ile Gly Leu Thr Glu Val Pro Asn Ala Asp Gly
        1250                1255                1260

Thr His Val Thr Gln Tyr Phe Asp Ala Asn Gly Val Gln Ile Lys
        1265                1270                1275

Gly Thr Ala Ile Lys Asp Gln Asn Asn Gln Leu Arg Tyr Phe Asp
        1280                1285                1290

Glu Ala Thr Gly Asn Met Val Val Asn Ser Trp Gly Gln Leu Ala
        1295                1300                1305

Asp Lys Ser Trp Leu Tyr Leu Asn Ala Gln Gly Val Ala Val Thr
        1310                1315                1320

Gly Asn Gln Lys Ile Asp Gly Glu Glu Tyr Tyr Phe Asn Ala Asp
        1325                1330                1335

Gly Lys Gln Val Lys Gly Asn Ala Ile Ile Asp Asn Asn Gly Asp
        1340                1345                1350

Gln Arg Tyr Tyr Asp Gly Asp Lys Gly Val Met Val Val Asn Ser
        1355                1360                1365

Trp Gly Glu Leu Pro Asp Gly Ser Trp Leu Tyr Leu Asn Asp Lys
        1370                1375                1380

Gly Ile Ala Val Thr Gly Arg Gln Val Ile Asn Asn Gln Val Asn
        1385                1390                1395

Phe Phe Gly Asn Asp Gly Lys Gln Ile Lys Asp Ala Phe Lys Leu
        1400                1405                1410

Leu Ser Asp Gly Ser Trp Val Tyr Leu Asp Asp Lys Gly Leu Ile
        1415                1420                1425

Thr Thr Gly Ala Lys Val Ile Asn Gly Leu Asn Met Phe Phe Asp
        1430                1435                1440

Lys Asp Gly His Gln Ile Lys Gly Asp Ala Ser Thr Asp Ala Asn
        1445                1450                1455

Gly Lys Arg His Tyr Tyr Asp Lys Asn Asp Gly His Leu Val Thr
        1460                1465                1470

Asn Ser Trp Gly Glu Leu Pro Asp Gly Ser Trp Leu Tyr Leu Glu
        1475                1480                1485

Glu Gln Gly Asp Ala Val Thr Gly Gln Arg Val Ile Asp Gly Lys
        1490                1495                1500

Thr Arg Tyr Phe Asp Glu Asp Gly Lys Gln Ile Lys Asn Ser Leu
        1505                1510                1515

Lys Thr Leu Ala Asn Gly Asp Lys Ile Tyr Leu Asp Gly Asp Gly
        1520                1525                1530

Val Ala Ala Thr Gly Leu Gln His Val Gly Asp Lys Ile Met Tyr
        1535                1540                1545

Phe Asp Glu Asp Gly Lys Gln Val Val Gly Lys Phe Val Ser Ala
        1550                1555                1560

Lys Asp Gly Ser Trp Tyr Tyr Leu Asn Gln Asp Gly Val Ala Ala
        1565                1570                1575

Val Gly Pro Ser Ser Ile Asn Gly Gln Ser Leu Tyr Phe Asp Gln
        1580                1585                1590

Asp Gly Lys Gln Val Lys Tyr Asn Glu Val Arg Asn Ser Asp Gly
        1595                1600                1605

```
Thr Thr Asn Tyr Tyr Thr Gly Leu Thr Gly Glu Lys Leu Thr Gln
    1610                1615                1620

Asp Phe Gly Glu Leu Pro Asp Gly Ser Trp Ile Tyr Leu Asp Ala
    1625                1630                1635

Gln Gly His Thr Val Thr Gly Ala Gln Ile Ile Asn Gly Gln Asn
    1640                1645                1650

Leu Tyr Phe Lys Ala Asp Gly Gln Gln Val Lys Gly His Ala Tyr
    1655                1660                1665

Thr Asp Gln Leu Gly His Met Arg Phe Tyr Asp Pro Asp Ser Gly
    1670                1675                1680

Asp Met Leu Ser Asn Arg Phe Glu Gln Ile Thr Pro Gly Val Trp
    1685                1690                1695

Ala Tyr Phe Gly Ala Asp Gly Val Ala Ile Thr Gly Gln His Asp
    1700                1705                1710

Ile Asn Gly Gln Lys Leu Phe Phe Asp Glu Thr Gly Tyr Gln Val
    1715                1720                1725

Lys Gly Ser Gln Arg Thr Ile Asp Gly Thr Leu Tyr Ser Phe Asp
    1730                1735                1740

Ser Gln Thr Gly Asn Gln Lys Arg Val Gln Thr Thr Leu Leu Pro
    1745                1750                1755

Gln Ala Gly His Tyr Ile Thr Lys Asn Gly Asn Asp Trp Gln Tyr
    1760                1765                1770

Asp Thr Asn Gly Glu Leu Ala Lys Gly Leu Arg Gln Asp Ser Asn
    1775                1780                1785

Gly Lys Leu Arg Tyr Phe Asp Leu Thr Thr Gly Ile Gln Ala Lys
    1790                1795                1800

Gly Gln Phe Val Thr Ile Gly Gln Glu Thr Tyr Tyr Phe Ser Lys
    1805                1810                1815

Asp His Gly Asp Ala Gln Leu Leu Pro Met Val Thr Glu Gly His
    1820                1825                1830

Tyr Gly Thr Ile Thr Leu Lys Gln Gly Gln Asp Thr Lys Thr Ala
    1835                1840                1845

Trp Val Tyr Arg Asp Gln Asn Asn Thr Ile Leu Lys Gly Leu Gln
    1850                1855                1860

Asn Ile Asn Gly Thr Leu Gln Phe Phe Asp Pro Tyr Thr Gly Glu
    1865                1870                1875

Gln Leu Lys Gly Gly Val Ala Lys Tyr Asp Asp Lys Leu Phe Tyr
    1880                1885                1890

Phe Glu Ser Gly Lys Gly Asn Leu Val Ser Thr Val Ala Gly Asp
    1895                1900                1905

Tyr Gln Asp Gly His Tyr Ile Ser Gln Asp Gly Gln Thr Arg Tyr
    1910                1915                1920

Ala Asp Lys Gln Asn Gln Leu Val Lys Gly Leu Val Thr Val Asn
    1925                1930                1935

Gly Ala Leu Gln Tyr Phe Asp Asn Ala Thr Gly Asn Gln Ile Lys
    1940                1945                1950

Asn Gln Gln Val Ile Val Asp Gly Lys Thr Tyr Tyr Phe Asp Asp
    1955                1960                1965

Lys Gly Asn Gly Glu Tyr Leu Phe Thr Asn Thr Leu Asp Met Ser
    1970                1975                1980

Thr Asn Ala Phe Ser Thr Lys Asn Val Ala Phe Asn His Asp Ser
    1985                1990                1995
```

-continued

Ser Ser Phe Asp His Thr Val Asp Gly Phe Leu Thr Ala Asp Thr
2000            2005            2010

Trp Tyr Arg Pro Lys Ser Ile Leu Ala Asn Gly Thr Thr Trp Arg
2015            2020            2025

Asp Ser Thr Asp Lys Asp Met Arg Pro Leu Ile Thr Val Trp Trp
2030            2035            2040

Pro Asn Lys Asn Val Gln Val Asn Tyr Leu Asn Phe Met Lys Ala
2045            2050            2055

Asn Gly Leu Leu Thr Thr Ala Ala Gln Tyr Thr Leu His Ser Asp
2060            2065            2070

Gln Tyr Asp Leu Asn Gln Ala Ala Gln Asp Val Gln Val Ala Ile
2075            2080            2085

Glu Arg Arg Ile Ala Ser Glu His Gly Thr Asp Trp Leu Gln Lys
2090            2095            2100

Leu Leu Phe Glu Ser Gln Asn Asn Pro Ser Phe Val Lys Gln
2105            2110            2115

Gln Phe Ile Trp Asn Lys Asp Ser Glu Tyr His Gly Gly Gly Asp
2120            2125            2130

Ala Trp Phe Gln Gly Gly Tyr Leu Lys Tyr Gly Asn Asn Pro Leu
2135            2140            2145

Thr Pro Thr Thr Asn Ser Asp Tyr Arg Gln Pro Gly Asn Ala Phe
2150            2155            2160

Asp Phe Leu Leu Ala Asn Asp Val Asp Asn Ser Asn Pro Val Val
2165            2170            2175

Gln Ala Glu Asn Leu Asn Trp Leu His Tyr Leu Met Asn Phe Gly
2180            2185            2190

Thr Ile Thr Ala Gly Gln Asp Asp Ala Asn Phe Asp Ser Ile Arg
2195            2200            2205

Ile Asp Ala Val Asp Phe Ile His Asn Asp Thr Ile Gln Arg Thr
2210            2215            2220

Tyr Asp Tyr Leu Arg Asp Ala Tyr Gln Val Gln Gln Ser Glu Ala
2225            2230            2235

Lys Ala Asn Gln His Ile Ser Leu Val Glu Ala Gly Leu Asp Ala
2240            2245            2250

Gly Thr Ser Thr Ile His Asn Asp Ala Leu Ile Glu Ser Asn Leu
2255            2260            2265

Arg Glu Ala Ala Thr Leu Ser Leu Thr Asn Glu Pro Gly Lys Asn
2270            2275            2280

Lys Pro Leu Thr Asn Met Leu Gln Asp Val Asp Gly Gly Thr Leu
2285            2290            2295

Ile Thr Asp His Thr Gln Asn Ser Thr Glu Asn Gln Ala Thr Pro
2300            2305            2310

Asn Tyr Ser Ile Ile His Ala His Asp Lys Gly Val Gln Glu Lys
2315            2320            2325

Val Gly Ala Ala Ile Thr Asp Ala Thr Gly Ala Asp Trp Thr Asn
2330            2335            2340

Phe Thr Asp Glu Gln Leu Lys Ala Gly Leu Glu Leu Phe Tyr Lys
2345            2350            2355

Asp Gln Arg Ala Thr Asn Lys Lys Tyr Asn Ser Tyr Asn Ile Pro
2360            2365            2370

Ser Ile Tyr Ala Leu Met Leu Thr Asn Lys Asp Thr Val Pro Arg
2375            2380            2385

Met Tyr Tyr Gly Asp Met Tyr Gln Asp Asp Gly Gln Tyr Met Ala

```
                2390                2395                2400

Asn Lys Ser Ile Tyr Tyr Asp Ala Leu Val Ser Leu Met Thr Ala
    2405                2410                2415

Arg Lys Ser Tyr Val Ser Gly Gly Gln Thr Met Ser Val Asp Asn
    2420                2425                2430

His Gly Leu Leu Lys Ser Val Arg Phe Gly Lys Asp Ala Met Thr
    2435                2440                2445

Ala Asn Asp Leu Gly Thr Ser Ala Thr Arg Thr Glu Gly Leu Gly
    2450                2455                2460

Val Ile Ile Gly Asn Asp Pro Lys Leu Gln Leu Asn Asp Ser Asp
    2465                2470                2475

Lys Val Thr Leu Asp Met Gly Ala Ala His Lys Asn Gln Lys Tyr
    2480                2485                2490

Arg Ala Val Ile Leu Thr Thr Arg Asp Gly Leu Ala Thr Phe Asn
    2495                2500                2505

Ser Asp Gln Ala Pro Thr Ala Trp Thr Asn Asp Gln Gly Thr Leu
    2510                2515                2520

Thr Phe Ser Asn Gln Glu Ile Asn Gly Gln Asp Asn Thr Gln Ile
    2525                2530                2535

Arg Gly Val Ala Asn Pro Gln Val Ser Gly Tyr Leu Ala Val Trp
    2540                2545                2550

Val Pro Val Gly Ala Ser Asp Asn Gln Asp Ala Arg Thr Ala Ala
    2555                2560                2565

Thr Thr Thr Glu Asn His Asp Gly Lys Val Leu His Ser Asn Ala
    2570                2575                2580

Ala Leu Asp Ser Asn Leu Ile Tyr Glu Gly Phe Ser Asn Phe Gln
    2585                2590                2595

Pro Lys Ala Thr Thr His Asp Glu Leu Thr Asn Val Val Ile Ala
    2600                2605                2610

Lys Asn Ala Asp Val Phe Asn Asn Trp Gly Ile Thr Ser Phe Glu
    2615                2620                2625

Met Ala Pro Gln Tyr Arg Ser Ser Gly Asp His Thr Phe Leu Asp
    2630                2635                2640

Ser Thr Ile Asp Asn Gly Tyr Ala Phe Thr Asp Arg Tyr Asp Leu
    2645                2650                2655

Gly Phe Asn Thr Pro Thr Lys Tyr Gly Thr Asp Gly Asp Leu Arg
    2660                2665                2670

Ala Thr Ile Gln Ala Leu His His Ala Asn Met Gln Val Met Ala
    2675                2680                2685

Asp Val Val Asp Asn Gln Val Tyr Asn Leu Pro Gly Lys Glu Val
    2690                2695                2700

Val Ser Ala Thr Arg Ala Gly Val Tyr Gly Asn Asp Asp Ala Thr
    2705                2710                2715

Gly Phe Gly Thr Gln Leu Tyr Val Thr Asn Ser Val Gly Gly Gly
    2720                2725                2730

Gln Tyr Gln Glu Lys Tyr Ala Gly Gln Tyr Leu Glu Ala Leu Lys
    2735                2740                2745

Ala Lys Tyr Pro Asp Leu Phe Glu Gly Lys Ala Tyr Asp Tyr Trp
    2750                2755                2760

Tyr Lys Asn Tyr Ala Asn Asp Gly Ser Asn Pro Tyr Tyr Thr Leu
    2765                2770                2775

Ser His Gly Asp Arg Glu Ser Ile Pro Ala Asp Val Ala Ile Lys
    2780                2785                2790
```

```
Gln Trp Ser Ala Lys Tyr Met Asn Gly Thr Asn Val Leu Gly Asn
    2795             2800                 2805

Gly Met Gly Tyr Val Leu Lys Asp Trp His Asn Gly Gln Tyr Phe
    2810             2815                 2820

Lys Leu Asp Gly Asp Lys Ser Thr Leu Pro Gln Ile
    2825             2830                 2835

<210> SEQ ID NO 3
<211> LENGTH: 8268
<212> TYPE: DNA
<213> ORGANISM: Leuconostoc mesenteroides

<400> SEQUENCE: 3
atggctagcg ctgatagcac taacaacact ggtgttacgg tgtcacaagc aacagataaa      60
gtagcagaca cgacggctac aacgacaaa gtagcggaca caacagctac aacagataaa     120
```

(Note: the sequence continues with lines ending at 180, 240, 300, 360, 420, 480, 540, 600, 660, 720, 780, 840, 900, 960, 1020, 1080, 1140, 1200, 1260, 1320, 1380, 1440, 1500, 1560, 1620, 1680, 1740, 1800, 1860)

```
gtggccgaca cagcagctac aacggacaaa gtagcggaca caacagctac aacagataaa     180
gtggccgaca cagcagctac aacggacaaa gtagcggaca caacagctac aacagataaa     240
gtggccgaca cagcagctgc aacagataaa gcagccgata cagcggctac aacggataaa     300
gtggccgaca cagcagctgc aacggataaa gtagcggaca cagtagctgc aacggacaaa     360
gtagcggaca caacagctac aacagataaa gcagccgata cagcggctac aacggataaa     420
gtaaccgaca caacagctgc aacggataaa gcagcggaca cgacggctac aacagataaa     480
gtggccgaca caacagccac aacatcagaa aaatcaaaaa gtattaaaca aattgatggt     540
aaaacttatt tcattggtaa tgatggtcag cctaagaaaa attttacagc cattgttgac     600
ggtcaagtat tatatttcga caaagatact ggtgctttga catcaaatag tagtcaatat     660
accgatggtt tagccaatat aggaaatgag cataatgcgg cttattcatt gtcttcggat     720
agttttacac aagttgatgg ctatctaacg gctaacagtt ggtaccgacc taaagatata     780
ttaaaaaatg gtacaacttg gacggctgca acagcaaacg attttcgacc attgttaatg     840
tcttggtggc cagataaaga tacccaagtt tcatacttaa aatatatgca atctgcggga     900
ttattatcag atgacgttgc attatcaaac aatgatagta tgaacagttt gacggatacg     960
gctatgactg ttcaaaaaaa aattgaagaa aaaattggct tattgggcag tactgactgg    1020
cttaaggccg atatgaacca aatggttgat tcacaatcga attggaacat tagtagtgag    1080
tctaaaggaa cagatcattt gcaaggtggt gcgctcctat acgttaatag tgatttaaca    1140
ccaaatgcca attctgatta tcgttttatta aatcgaacgc caactaacca aaaaggtcaa    1200
attacaacaa atggtaatca aggtggctat gagatgctgt tggccaacga tgttgataat    1260
tctaacccaa ttgttcaagc tgaacaatta aattggttat actacatgat gaatatcggt    1320
agcatcgccc aaaatgatcc aacagcaaat tttgacggtt acagagttga tgctgttgat    1380
aacgtgaatg ctgacttgtt gcaaattgct ggagattatt ttaaagcagc atatggaaca    1440
aatcaaagtg acgctaatgc aaacaatcac atttccatct tagaagactg ggacaataat    1500
gatccagcgt atgtaaaagc acaggggaac aaccaattaa ccatggattt tccaatgcat    1560
ttggcattga gtattcatt gaatatgcca agtagtgctc gtagcggttt ggaaccagca    1620
atttcaacaa gcctagtaaa tcgtgcagca gacgccacag aaaatgaagc ccaaccgaac    1680
tattcattta ttcgtgcaca tgatagtgaa gtacaaacgg ttattgctca aattattaaa    1740
gataaaatta tcctagttc cgatggattg actgtctcaa cagatgaaat tgccaaagca    1800
ttcgaaatat ataatgctga cgaattaaag gctgataaag agtataccgc atataatata    1860
```

```
ccctcatcat atgcattgat gttaactaac aaagatacaa ttcctcgtgt gtattatggt    1920
gatttgttta cggatgatgg acaatatatg tctgcaaaat caccatatta tgatgcactt    1980
acttcattgc ttcaatcgcg agtaaaatat gtttcaggtg gtcaatctat gaatatgact    2040
taccttcata taatcaagg cctttgacg tcagttcgct atggaaaaga cgccatgaca    2100
gctaacgaca ctggtacaag tgaaacgcgc acacaaggta ttggattaat tgtcggcaac    2160
aaaactgatt taaacctgaa taatgatgag caaattgtac ttaacatggg ggccgcacac    2220
aaaaatcaag cataccgtgc attaatgtta agtactaaag atggcttgaa aatttataat    2280
aatgatgacg aggcaccggt atcgtataca gatgaccaag gccgtttgat ttttaaatct    2340
gatgtggttt atggtgtgag tgatgctcag gtttctggtt atttagcagc ttgggtgcca    2400
gtcggtgcaa acgatagcca agatgctaga acagaaagta gtacaacagc gtcaacagat    2460
ggtaatacct atcattcaaa tagtgcctta gattctcaac ttatatatga aggcttttca    2520
aacttccaag ccatgccaac acaggccgat gagtatacca atatcaagat tgccgaaaat    2580
gcacaattat tcaagagcct tgggataaca tcatttgaat tggcacctca ataccgttca    2640
agtacggata cagtttcttt agattcagtt attcaaaatg ctatgccttt cacggatcgc    2700
tacgacattg gttataatac gcctacaaag tacggtacag ttgaccaact attagatgct    2760
ttaagagcat tgcatgctca aggcattcag gctatcaatg attgggtccc agaccaaatt    2820
tataatttgc ctggggaaga aatagtgaca gccagtcgaa caaacggttc gggaaaggtg    2880
aatgaaagtt cagttattaa taatacgcta tatgattctc gtactgttgg tggcggagag    2940
tatcaagcaa tatatggagg tgctttctta gataagttaa aacaagatta tcctgagtta    3000
tttgaaacaa aacaaatttc aacaggtgaa gcaatgaacc ctgatgtcaa aatcacagaa    3060
tggtcagcta agtattttaa tggctcaaac attcaaggac gtggtgcatg gtatgttctc    3120
aaggattggt caacaaatca atactttaat gtttcaagtg gtagtgaatt tttacctaag    3180
caactgttag gcgaaaaaac aagtacaggg tttaccaacg tggacaatgg caagactgag    3240
ttttattcta cgagtggcta ccaagcaaag aatacattta ttcaagataa tgacaattgg    3300
tattattttg ataatgatgg ctatatggtt gttggcggtc aagaaattaa tggtaaaaaa    3360
tattatttcc taccaaatgg tgtagagtta caagatgctt atttgtctga tgggacaagt    3420
gagtattact acagtagtga tggtcgtcaa atttctaatc aatattatca aggatcagac    3480
aacaactggc gttatttctt tgcagatggt catatggctg taggttagc aacaattact    3540 acagaaaatg gtacaacaaa tcaacaatat ttcgatgcaa atggtgtgca acttaagggc    3600
gtagctataa aggatactga tggcaatgtg cactattttg atggcaagac aggaaacatg    3660
gttataaatt cctggggtaa aataagcgat ggttcatggt tatacttaaa tgatagcggt    3720
gtagcggtca caggaccgca aaatattaac ggccaaaatc tttacttcaa cgaagacggt    3780
attcaagtaa agggtgaagc cattactgat aatagtggaa acatacatta ttatgatcgc    3840
agcacaggaa atatggttgt gaactcatgg ggtgaaacga taatggttc atggctatac    3900 ttgaacgaca agggtgatgc cgttacagga gaacaagtta ttgacggtca aaaactatat    3960
ttcagtagta atggaatcca acttaaaaat acattcaaga agctatccga tggttcatgg    4020
ctatatttga acgataaagg tcttccagtg acaggagcac aggtcattga tggacaaaac    4080
ttgtatttcg accaagatgg gaagcaagtc aagggtgacg ttgctacaga tggacaaggt    4140
aacactcatt attatgatgg caacacagga aatatggtta ctaattcatg ggcagagtta    4200
```

```
ccggacggtt catggatgta tctggacaat gatggcaatc ctttaacagg acagcaaaag    4260
attgatggcc agtcactcta ctttaatgat gctggtaagc aaatcaaaaa cgcattggtt    4320
aaactagatg atgggtcaac aatttacctc gatgataaag gtgtttcatc aactggtatt    4380
caaagaattg atgataagat atattatttt gatcctgatg gtaaacaagt agtatgtcgt    4440
tttgaagaat taccagatgg ttcatggatg tatctagatg atgacggtgt tgctgctacg    4500
ggcgctcaaa aaattaatgg ccaggaatta tatttcgaca atagcgggaa acaagtcaag    4560
aacgacaaag taattaatga cgatggaaca ataaactatt acacaggtat gagcggtgaa    4620
aaactaaaaa atgattttgg tgaattacca gacggttcat ggatgtactt ggataatcaa    4680
ggtaatgctg taataggtgc ccaaaaaatt aatggccaga atctttactt caagacagac    4740
ggacgacagg ttaagggtga agcaaatgtt gattcatcag gtgaaatgca cttctatgat    4800
cctgattctg gcgagctaat tacaaataga tttgaacaag ttgctagtgg tgtatgggct    4860
tactttgatg ccaaaggtgt tgctgtaact ggtgagcaac gcattggtaa gcaaaattta    4920
ttttttgatc caactggtta tcaagttaaa ggcgacaaac gaacaattga cggcgttctc    4980 tataccttg ataaagaaag tggtgagaga aagggtttag attctatatc ggtattaccc    5040
accaatggac aatacacaac cgataaggcc caaaattggt attaccaagt cgatggtgaa    5100
aatgtaaaag ggctatatac aaataatgat ggtcaattac gttacttcga tttgacaact    5160
ggcgtgcaga ctaaaggtaa ttttgtgaca attggcaatg ataccatact tttcaccaag    5220
gaacaagggg atggacagat agttctgag gttgtgtcag acactatgg tactgtccag    5280 ttgagtgaca attcgtctgc atgggtttat cgcggtgcaa atgatcaaat tttgaaaggc    5340
ctacagaata taaacggtcg tctgcaatat tttgatctaa ccaccggtgc gcaattaaaa    5400
ggcggtgctg caaactatga tggcaacctt tattattttg aatcatcaga tggtaaccta    5460
gtcagtaaaa ttcagcaatc ttattctact gggaattatg tgaccgatgg tgataaagta    5520
acatatgctg atgagcaaaa caaccaagtc acgggattag cgttgattga tgatcaacta    5580
caatacttcg atccaagtga cggtcgtcaa gtcaagaatg agcaggttat cgttgatggc    5640
gtcacatact actttgataa aaatggtaat ggacaatact tgtttacaaa tactgcaacg    5700
atgtcaacta atgaatttgc caaacatagt gctgcttata gcaatgatag ttctagcttc    5760
aagaatacga tagatggttt cttgacggcc gataccggt atcgccctaa agatatcttg    5820
gaaaacggac aaacgtgggt agtttcttca acaaatgacg tgcgaccact gataacagtt    5880
tggtggctaa ataagatgt tcaagttaat tattcaaatt ttatgaagca aaatggtttg    5940
ctagatacaa gtagtcaatt taatctacaa tctgatcaat atgacttgaa tgtcgccgcg    6000
caaaaagttc aagtggctat tgaaaaacgc atttcgaaag aaaagagtac agattggttg    6060
aaagatcttt tgtttgaagc tcatgaagat acgccttcat ttgtgaaaca acaatttatt    6120
tggaataaag attctgaata tcaaggtcaa ggggatgcgt ggttccaagg tggttatctg    6180
aaatatggta caatgaatt aaccccaaca acgaactcag attatcgtga atccggtaat    6240
acattagact tcttgcttgc taatgatgtc gacaattcta acccagcggt tcaagctgaa    6300
aatttgaatt ggttacatta tttaatgaac tttggcacga ttacagctaa tgatgatgat    6360
gctaattttg acagtattcg tattgatgcc gttgacttta ttgataatga tgccattcag    6420
agaacctacg attacatgcg tgatgcttat aaagttgatg caagtgaaga caacgctaat    6480 aagcatatttt cactggtgga agctggatta gatgctggta cctctacaat taagagtgat    6540
gctttagttg aatctaactt tagagaggca gctacactat cgctggcaaa tcaatcaggg    6600
```

| | | | | |
|---|---|---|---|---|
| gaaaatagtt | ccttgactaa | tatgttgcaa | gacattgatg | gtggccagat tatagctgat | 6660 |
| cacgccaaca | atgcaacaga | aaatgaatca | acgccaaatt | attcaattat tcatgctcat | 6720 |
| gataagggga | ttcaagaaaa | ggttggtgca | gcaattaccg | acgttactgg tgcagactgg | 6780 |
| acgaatttca | ccgatgacca | attaaaagaa | ggattagcag | cttattatca agatcaacgt | 6840 |
| tcaacgaata | aaaagtataa | catctataac | ttacctagta | tctatgcttt aatgttgacc | 6900 |
| aataaggaca | cagttcctcg | tgtttattac | ggtgatatgt | atcaagatga tggccagtat | 6960 |
| atggaaaagc | aaagtattta | ttatgatgcc | attgtttcct | tgatgaacac tagaaagagt | 7020 |
| tatgtgagtg | gtgggcaaac | tatggatgta | gatgaacatg | gtttgttgaa gagtgttcgt | 7080 |
| tttggtaaag | acgcaatgac | agctagtgac | cttggtacga | atgaaacacg cactgaaggt | 7140 |
| gttggtgtgc | tggtcggcaa | tgattcttca | ctaaaactaa | atgattcaga tacagttact | 7200 |
| ttagagatgg | gggcggctca | taaaaaccaa | aagtaccgag | ctgcattgtt gacaacaagc | 7260 |
| gatggtattg | ttacgtatga | tgctgataat | gatgcaccaa | caatctggac agatgaccgt | 7320 |
| ggtacattga | cgttctcaaa | taaggagatt | gctggtcaag | attatacaag cgtgcaagga | 7380 |
| ttcgctaatt | cacaagtatc | aggttactta | gcagtttggg | tgcccgtagg agctagtgac | 7440 |
| gatcaagatg | tccgaacagc | agcattaaca | gatgcaaatc | ttgatgacaa agtactgcat | 7500 |
| tctaatgctg | cattagattc | gaacttgatt | tacgaaggct | tttctaactt tcaacctaaa | 7560 |
| gcaaccacca | atgatgaatt | gactaacgta | gtaattgcta | aaaatgctaa tttatttgaa | 7620 |
| aagtggggaa | tcacaagttt | tgagatggca | ccacaatatc | gttcaagtgg ggaccacacg | 7680 |
| ttcttagatt | caacgattga | taatggttat | gcatttactg | accgatacga tttgggattt | 7740 |
| gaaacaccaa | ctaagtacgg | tactgataag | gatttgcgta | ctgcaattaa agcattgcac | 7800 |
| caatcaaata | tgcaggttat | ggctgatgta | gttgataacc | aagtttataa tttatctgga | 7860 |
| caggaggtcg | tatcagcttc | acgtgccggt | gtttacggca | atgatgtgtc aactggatttt | 7920 |
| gggacacaac | tctatgcggt | taatagtgtt | ggtggtggta | aatatcaagc ccaatacggt | 7980 |
| ggtgaatatt | tgaatgaatt | gaagcaacaa | tacccagatt | tgttcgaagc taagacgtat | 8040 |
| gactattggg | ttaaaaatta | ttcaaatgac | ggatcggatc | cgtattacac actgtcgcaa | 8100 |
| aacacacgaa | aagatatgcc | aagtagtgag | gtcattaaac | aatggtcagc taaatatatg | 8160 |
| aatggtacta | atgtattagg | aaacggtatg | ggatatgttt | tgaaagattg gaatacaggt | 8220 |
| gagtatttca | aaattggaga | aaagaatgct | gattttataa | caaattaa | 8268 |

<210> SEQ ID NO 4
<211> LENGTH: 2755
<212> TYPE: PRT
<213> ORGANISM: Leuconostoc mesenteroides

<400> SEQUENCE: 4

Met Ala Ser Ala Asp Ser Thr Asn Thr Gly Val Thr Val Ser Gln
1               5                   10                  15

Ala Thr Asp Lys Val Ala Asp Thr Thr Ala Thr Thr Asp Lys Val Ala
            20                  25                  30

Asp Thr Thr Ala Thr Thr Asp Lys Val Ala Asp Thr Ala Ala Thr Thr
        35                  40                  45

Asp Lys Val Ala Asp Thr Thr Ala Thr Thr Asp Lys Val Ala Asp Thr
    50                  55                  60

Ala Ala Thr Thr Asp Lys Val Ala Asp Thr Thr Ala Thr Thr Asp Lys
65                  70                  75                  80

```
Val Ala Asp Thr Ala Ala Thr Asp Lys Ala Ala Asp Thr Ala Ala
                 85                  90                  95

Thr Thr Asp Lys Val Ala Asp Thr Ala Ala Thr Asp Lys Val Ala
                100                 105                 110

Asp Thr Val Ala Ala Thr Asp Lys Val Ala Asp Thr Thr Ala Thr Thr
                115                 120                 125

Asp Lys Ala Ala Asp Thr Ala Ala Thr Thr Asp Lys Val Thr Asp Thr
            130                 135                 140

Thr Ala Ala Thr Asp Lys Ala Ala Asp Thr Thr Ala Thr Thr Asp Lys
145                 150                 155                 160

Val Ala Asp Thr Thr Ala Thr Thr Ser Glu Lys Ser Lys Ser Ile Lys
                165                 170                 175

Gln Ile Asp Gly Lys Thr Tyr Phe Ile Gly Asn Asp Gly Gln Pro Lys
                180                 185                 190

Lys Asn Phe Thr Ala Ile Val Asp Gly Gln Val Leu Tyr Phe Asp Lys
                195                 200                 205

Asp Thr Gly Ala Leu Thr Ser Asn Ser Ser Gln Tyr Thr Asp Gly Leu
                210                 215                 220

Ala Asn Ile Gly Asn Glu His Asn Ala Ala Tyr Ser Leu Ser Ser Asp
225                 230                 235                 240

Ser Phe Thr Gln Val Asp Gly Tyr Leu Thr Ala Asn Ser Trp Tyr Arg
                245                 250                 255

Pro Lys Asp Ile Leu Lys Asn Gly Thr Thr Trp Thr Ala Ala Thr Ala
                260                 265                 270

Asn Asp Phe Arg Pro Leu Leu Met Ser Trp Trp Pro Asp Lys Asp Thr
                275                 280                 285

Gln Val Ser Tyr Leu Lys Tyr Met Gln Ser Ala Gly Leu Leu Ser Asp
                290                 295                 300

Asp Val Ala Leu Ser Asn Asn Asp Ser Met Asn Ser Leu Thr Asp Thr
305                 310                 315                 320

Ala Met Thr Val Gln Lys Lys Ile Glu Glu Lys Ile Gly Leu Leu Gly
                325                 330                 335

Ser Thr Asp Trp Leu Lys Ala Asp Met Asn Gln Met Val Asp Ser Gln
                340                 345                 350

Ser Asn Trp Asn Ile Ser Ser Glu Ser Lys Gly Thr Asp His Leu Gln
                355                 360                 365

Gly Gly Ala Leu Leu Tyr Val Asn Ser Asp Leu Thr Pro Asn Ala Asn
                370                 375                 380

Ser Asp Tyr Arg Leu Leu Asn Arg Thr Pro Thr Asn Gln Lys Gly Gln
385                 390                 395                 400

Ile Thr Thr Asn Gly Asn Gln Gly Gly Tyr Glu Met Leu Leu Ala Asn
                405                 410                 415

Asp Val Asp Asn Ser Asn Pro Ile Val Gln Ala Glu Gln Leu Asn Trp
                420                 425                 430

Leu Tyr Tyr Met Met Asn Ile Gly Ser Ile Ala Gln Asn Asp Pro Thr
                435                 440                 445

Ala Asn Phe Asp Gly Tyr Arg Val Asp Ala Val Asp Asn Val Asn Ala
                450                 455                 460

Asp Leu Leu Gln Ile Ala Gly Asp Tyr Phe Lys Ala Ala Tyr Gly Thr
465                 470                 475                 480

Asn Gln Ser Asp Ala Asn Ala Asn Asn His Ile Ser Ile Leu Glu Asp
                485                 490                 495
```

-continued

Trp Asp Asn Asn Asp Pro Ala Tyr Val Lys Ala Gln Gly Asn Asn Gln
            500                 505                 510

Leu Thr Met Asp Phe Pro Met His Leu Ala Leu Lys Tyr Ser Leu Asn
        515                 520                 525

Met Pro Ser Ser Ala Arg Ser Gly Leu Glu Pro Ala Ile Ser Thr Ser
    530                 535                 540

Leu Val Asn Arg Ala Ala Asp Ala Thr Glu Asn Glu Ala Gln Pro Asn
545                 550                 555                 560

Tyr Ser Phe Ile Arg Ala His Asp Ser Glu Val Gln Thr Val Ile Ala
                565                 570                 575

Gln Ile Ile Lys Asp Lys Ile Asn Pro Ser Ser Asp Gly Leu Thr Val
            580                 585                 590

Ser Thr Asp Glu Ile Ala Lys Ala Phe Glu Ile Tyr Asn Ala Asp Glu
        595                 600                 605

Leu Lys Ala Asp Lys Glu Tyr Thr Ala Tyr Asn Ile Pro Ser Ser Tyr
    610                 615                 620

Ala Leu Met Leu Thr Asn Lys Asp Thr Ile Pro Arg Val Tyr Tyr Gly
625                 630                 635                 640

Asp Leu Phe Thr Asp Asp Gly Gln Tyr Met Ser Ala Lys Ser Pro Tyr
                645                 650                 655

Tyr Asp Ala Leu Thr Ser Leu Leu Gln Ser Arg Val Lys Tyr Val Ser
            660                 665                 670

Gly Gly Gln Ser Met Asn Met Thr Tyr Leu His Asn Asn Gln Gly Leu
        675                 680                 685

Leu Thr Ser Val Arg Tyr Gly Lys Asp Ala Met Thr Ala Asn Asp Thr
    690                 695                 700

Gly Thr Ser Glu Thr Arg Thr Gln Gly Ile Gly Leu Ile Val Gly Asn
705                 710                 715                 720

Lys Thr Asp Leu Asn Leu Asn Asp Glu Gln Ile Val Leu Asn Met
                725                 730                 735

Gly Ala Ala His Lys Asn Gln Ala Tyr Arg Ala Leu Met Leu Ser Thr
            740                 745                 750

Lys Asp Gly Leu Lys Ile Tyr Asn Asn Asp Asp Glu Ala Pro Val Ser
        755                 760                 765

Tyr Thr Asp Asp Gln Gly Arg Leu Ile Phe Lys Ser Asp Val Val Tyr
    770                 775                 780

Gly Val Ser Asp Ala Gln Val Ser Gly Tyr Leu Ala Ala Trp Val Pro
785                 790                 795                 800

Val Gly Ala Asn Asp Ser Gln Asp Ala Arg Thr Glu Ser Ser Thr Thr
                805                 810                 815

Ala Ser Thr Asp Gly Asn Thr Tyr His Ser Asn Ser Ala Leu Asp Ser
            820                 825                 830

Gln Leu Ile Tyr Glu Gly Phe Ser Asn Phe Gln Ala Met Pro Thr Gln
        835                 840                 845

Ala Asp Glu Tyr Thr Asn Ile Lys Ile Ala Glu Asn Ala Gln Leu Phe
    850                 855                 860

Lys Ser Leu Gly Ile Thr Ser Phe Glu Leu Ala Pro Gln Tyr Arg Ser
865                 870                 875                 880

Ser Thr Asp Asn Ser Phe Leu Asp Ser Val Ile Gln Asn Gly Tyr Ala
                885                 890                 895

Phe Thr Asp Arg Tyr Asp Ile Gly Tyr Asn Thr Pro Thr Lys Tyr Gly
            900                 905                 910

Thr Val Asp Gln Leu Leu Asp Ala Leu Arg Ala Leu His Ala Gln Gly

```
             915                 920                 925
Ile Gln Ala Ile Asn Asp Trp Val Pro Asp Gln Ile Tyr Asn Leu Pro
            930                 935                 940

Gly Glu Glu Ile Val Thr Ala Ser Arg Thr Asn Gly Ser Gly Lys Val
945                 950                 955                 960

Asn Glu Ser Ser Val Ile Asn Asn Thr Leu Tyr Asp Ser Arg Thr Val
                965                 970                 975

Gly Gly Gly Glu Tyr Gln Ala Ile Tyr Gly Gly Ala Phe Leu Asp Lys
            980                 985                 990

Leu Lys Gln Asp Tyr Pro Glu Leu Phe Glu Thr Lys Gln Ile Ser Thr
                995                1000                1005

Gly Glu Ala Met Asn Pro Asp Val Lys Ile Thr Glu Trp Ser Ala
           1010                1015                1020

Lys Tyr Phe Asn Gly Ser Asn Ile Gln Gly Arg Gly Ala Trp Tyr
           1025                1030                1035

Val Leu Lys Asp Trp Ser Thr Asn Gln Tyr Phe Asn Val Ser Ser
           1040                1045                1050

Gly Ser Glu Phe Leu Pro Lys Gln Leu Leu Gly Glu Lys Thr Ser
           1055                1060                1065

Thr Gly Phe Thr Asn Val Asp Asn Gly Lys Thr Glu Phe Tyr Ser
           1070                1075                1080

Thr Ser Gly Tyr Gln Ala Lys Asn Thr Phe Ile Gln Asp Asn Asp
           1085                1090                1095

Asn Trp Tyr Tyr Phe Asp Asn Asp Gly Tyr Met Val Val Gly Gly
           1100                1105                1110

Gln Glu Ile Asn Gly Lys Lys Tyr Tyr Phe Leu Pro Asn Gly Val
           1115                1120                1125

Glu Leu Gln Asp Ala Tyr Leu Ser Asp Gly Thr Ser Glu Tyr Tyr
           1130                1135                1140

Tyr Ser Ser Asp Gly Arg Gln Ile Ser Asn Gln Tyr Tyr Gln Gly
           1145                1150                1155

Ser Asp Asn Asn Trp Arg Tyr Phe Phe Ala Asp Gly His Met Ala
           1160                1165                1170

Val Gly Leu Ala Thr Ile Thr Thr Glu Asn Gly Thr Thr Asn Gln
           1175                1180                1185

Gln Tyr Phe Asp Ala Asn Gly Val Gln Leu Lys Gly Val Ala Ile
           1190                1195                1200

Lys Asp Thr Asp Gly Asn Val His Tyr Phe Asp Gly Lys Thr Gly
           1205                1210                1215

Asn Met Val Ile Asn Ser Trp Gly Lys Ile Ser Asp Gly Ser Trp
           1220                1225                1230

Leu Tyr Leu Asn Asp Ser Gly Val Ala Val Thr Gly Pro Gln Asn
           1235                1240                1245

Ile Asn Gly Gln Asn Leu Tyr Phe Asn Glu Asp Gly Ile Gln Val
           1250                1255                1260

Lys Gly Glu Ala Ile Thr Asp Asn Ser Gly Asn Ile His Tyr Tyr
           1265                1270                1275

Asp Arg Ser Thr Gly Asn Met Val Val Asn Ser Trp Gly Glu Thr
           1280                1285                1290

Asn Asn Gly Ser Trp Leu Tyr Leu Asn Asp Lys Gly Asp Ala Val
           1295                1300                1305

Thr Gly Glu Gln Val Ile Asp Gly Gln Lys Leu Tyr Phe Ser Ser
           1310                1315                1320
```

```
Asn Gly Ile Gln Leu Lys Asn Thr Phe Lys Lys Leu Ser Asp Gly
    1325                1330                1335

Ser Trp Leu Tyr Leu Asn Asp Lys Gly Leu Pro Val Thr Gly Ala
    1340                1345                1350

Gln Val Ile Asp Gly Gln Asn Leu Tyr Phe Asp Gln Asp Gly Lys
    1355                1360                1365

Gln Val Lys Gly Asp Val Ala Thr Asp Gly Gln Gly Asn Thr His
    1370                1375                1380

Tyr Tyr Asp Gly Asn Thr Gly Asn Met Val Thr Asn Ser Trp Ala
    1385                1390                1395

Glu Leu Pro Asp Gly Ser Trp Met Tyr Leu Asp Asn Asp Gly Asn
    1400                1405                1410

Pro Leu Thr Gly Gln Gln Lys Ile Asp Gly Gln Ser Leu Tyr Phe
    1415                1420                1425

Asn Asp Ala Gly Lys Gln Ile Lys Asn Ala Leu Val Lys Leu Asp
    1430                1435                1440

Asp Gly Ser Thr Ile Tyr Leu Asp Asp Lys Gly Val Ser Ser Thr
    1445                1450                1455

Gly Ile Gln Arg Ile Asp Asp Lys Ile Tyr Tyr Phe Asp Pro Asp
    1460                1465                1470

Gly Lys Gln Val Val Cys Arg Phe Glu Glu Leu Pro Asp Gly Ser
    1475                1480                1485

Trp Met Tyr Leu Asp Asp Asp Gly Val Ala Ala Thr Gly Ala Gln
    1490                1495                1500

Lys Ile Asn Gly Gln Glu Leu Tyr Phe Asp Asn Ser Gly Lys Gln
    1505                1510                1515

Val Lys Asn Asp Lys Val Ile Asn Asp Asp Gly Thr Ile Asn Tyr
    1520                1525                1530

Tyr Thr Gly Met Ser Gly Glu Lys Leu Lys Asn Asp Phe Gly Glu
    1535                1540                1545

Leu Pro Asp Gly Ser Trp Met Tyr Leu Asp Asn Gln Gly Asn Ala
    1550                1555                1560

Val Ile Gly Ala Gln Lys Ile Asn Gly Gln Asn Leu Tyr Phe Lys
    1565                1570                1575

Thr Asp Gly Arg Gln Val Lys Gly Glu Ala Asn Val Asp Ser Ser
    1580                1585                1590

Gly Glu Met His Phe Tyr Asp Pro Asp Ser Gly Glu Leu Ile Thr
    1595                1600                1605

Asn Arg Phe Glu Gln Val Ala Ser Gly Val Trp Ala Tyr Phe Asp
    1610                1615                1620

Ala Lys Gly Val Ala Val Thr Gly Glu Gln Arg Ile Gly Lys Gln
    1625                1630                1635

Asn Leu Phe Phe Asp Pro Thr Gly Tyr Gln Val Lys Gly Asp Lys
    1640                1645                1650

Arg Thr Ile Asp Gly Val Leu Tyr Thr Phe Asp Lys Glu Ser Gly
    1655                1660                1665

Glu Arg Lys Gly Leu Asp Ser Ile Ser Val Leu Pro Thr Asn Gly
    1670                1675                1680

Gln Tyr Thr Thr Asp Lys Ala Gln Asn Trp Tyr Tyr Gln Val Asp
    1685                1690                1695

Gly Glu Asn Val Lys Gly Leu Tyr Thr Asn Asn Asp Gly Gln Leu
    1700                1705                1710
```

```
Arg Tyr Phe Asp Leu Thr Thr Gly Val Gln Thr Lys Gly Asn Phe
1715                    1720                1725

Val Thr Ile Gly Asn Asp Thr Tyr Tyr Phe Thr Lys Glu Gln Gly
1730                    1735                1740

Asp Gly Gln Ile Val Ser Glu Val Val Ser Gly His Tyr Gly Thr
1745                    1750                1755

Val Gln Leu Ser Asp Asn Ser Ala Trp Val Tyr Arg Gly Ala
1760                    1765                1770

Asn Asp Gln Ile Leu Lys Gly Leu Gln Asn Ile Asn Gly Arg Leu
1775                    1780                1785

Gln Tyr Phe Asp Leu Thr Thr Gly Ala Gln Leu Lys Gly Gly Ala
1790                    1795                1800

Ala Asn Tyr Asp Gly Asn Leu Tyr Tyr Phe Glu Ser Ser Asp Gly
1805                    1810                1815

Asn Leu Val Ser Lys Ile Gln Gln Ser Tyr Ser Thr Gly Asn Tyr
1820                    1825                1830

Val Thr Asp Gly Asp Lys Val Thr Tyr Ala Asp Glu Gln Asn Asn
1835                    1840                1845

Gln Val Thr Gly Leu Ala Leu Ile Asp Asp Gln Leu Gln Tyr Phe
1850                    1855                1860

Asp Pro Ser Asp Gly Arg Gln Val Lys Asn Glu Gln Val Ile Val
1865                    1870                1875

Asp Gly Val Thr Tyr Tyr Phe Asp Lys Asn Gly Asn Gly Gln Tyr
1880                    1885                1890

Leu Phe Thr Asn Thr Ala Thr Met Ser Thr Asn Glu Phe Ala Lys
1895                    1900                1905

His Ser Ala Ala Tyr Ser Asn Asp Ser Ser Ser Phe Lys Asn Thr
1910                    1915                1920

Ile Asp Gly Phe Leu Thr Ala Asp Thr Trp Tyr Arg Pro Lys Asp
1925                    1930                1935

Ile Leu Glu Asn Gly Gln Thr Trp Val Val Ser Ser Thr Asn Asp
1940                    1945                1950

Val Arg Pro Leu Ile Thr Val Trp Trp Leu Asn Lys Asp Val Gln
1955                    1960                1965

Val Asn Tyr Ser Asn Phe Met Lys Gln Asn Gly Leu Leu Asp Thr
1970                    1975                1980

Ser Ser Gln Phe Asn Leu Gln Ser Asp Gln Tyr Asp Leu Asn Val
1985                    1990                1995

Ala Ala Gln Lys Val Gln Val Ala Ile Glu Lys Arg Ile Ser Lys
2000                    2005                2010

Glu Lys Ser Thr Asp Trp Leu Lys Asp Leu Leu Phe Glu Ala His
2015                    2020                2025

Glu Asp Thr Pro Ser Phe Val Lys Gln Gln Phe Ile Trp Asn Lys
2030                    2035                2040

Asp Ser Glu Tyr Gln Gly Gln Gly Asp Ala Trp Phe Gln Gly Gly
2045                    2050                2055

Tyr Leu Lys Tyr Gly Asn Asn Glu Leu Thr Pro Thr Thr Asn Ser
2060                    2065                2070

Asp Tyr Arg Glu Ser Gly Asn Thr Leu Asp Phe Leu Leu Ala Asn
2075                    2080                2085

Asp Val Asp Asn Ser Asn Pro Ala Val Gln Ala Glu Asn Leu Asn
2090                    2095                2100

Trp Leu His Tyr Leu Met Asn Phe Gly Thr Ile Thr Ala Asn Asp
```

```
                2105                2110                2115

Asp Asp Ala Asn Phe Asp Ser Ile Arg Ile Asp Ala Val Asp Phe
    2120                2125                2130

Ile Asp Asn Asp Ala Ile Gln Arg Thr Tyr Asp Tyr Met Arg Asp
    2135                2140                2145

Ala Tyr Lys Val Asp Ala Ser Glu Asp Asn Ala Asn Lys His Ile
    2150                2155                2160

Ser Leu Val Glu Ala Gly Leu Asp Ala Gly Thr Ser Thr Ile Lys
    2165                2170                2175

Ser Asp Ala Leu Val Glu Ser Asn Phe Arg Glu Ala Ala Thr Leu
    2180                2185                2190

Ser Leu Ala Asn Gln Ser Gly Glu Asn Ser Ser Leu Thr Asn Met
    2195                2200                2205

Leu Gln Asp Ile Asp Gly Gln Ile Ile Ala Asp His Ala Asn
    2210                2215                2220

Asn Ala Thr Glu Asn Glu Ser Thr Pro Asn Tyr Ser Ile Ile His
    2225                2230                2235

Ala His Asp Lys Gly Ile Gln Glu Lys Val Gly Ala Ala Ile Thr
    2240                2245                2250

Asp Val Thr Gly Ala Asp Trp Thr Asn Phe Thr Asp Asp Gln Leu
    2255                2260                2265

Lys Glu Gly Leu Ala Ala Tyr Tyr Gln Asp Gln Arg Ser Thr Asn
    2270                2275                2280

Lys Lys Tyr Asn Ile Tyr Asn Leu Pro Ser Ile Tyr Ala Leu Met
    2285                2290                2295

Leu Thr Asn Lys Asp Thr Val Pro Arg Val Tyr Tyr Gly Asp Met
    2300                2305                2310

Tyr Gln Asp Asp Gly Gln Tyr Met Glu Lys Gln Ser Ile Tyr Tyr
    2315                2320                2325

Asp Ala Ile Val Ser Leu Met Asn Thr Arg Lys Ser Tyr Val Ser
    2330                2335                2340

Gly Gly Gln Thr Met Asp Val Asp Glu His Gly Leu Leu Lys Ser
    2345                2350                2355

Val Arg Phe Gly Lys Asp Ala Met Thr Ala Ser Asp Leu Gly Thr
    2360                2365                2370

Asn Glu Thr Arg Thr Glu Gly Val Gly Val Leu Val Gly Asn Asp
    2375                2380                2385

Ser Ser Leu Lys Leu Asn Asp Ser Asp Thr Val Thr Leu Glu Met
    2390                2395                2400

Gly Ala Ala His Lys Asn Gln Lys Tyr Arg Ala Ala Leu Leu Thr
    2405                2410                2415

Thr Ser Asp Gly Ile Val Thr Tyr Asp Ala Asp Asn Asp Ala Pro
    2420                2425                2430

Thr Ile Trp Thr Asp Arg Gly Thr Leu Thr Phe Ser Asn Lys
    2435                2440                2445

Glu Ile Ala Gly Gln Asp Tyr Thr Ser Val Gln Gly Phe Ala Asn
    2450                2455                2460

Ser Gln Val Ser Gly Tyr Leu Ala Val Trp Val Pro Val Gly Ala
    2465                2470                2475

Ser Asp Asp Gln Asp Val Arg Thr Ala Ala Leu Thr Asp Ala Asn
    2480                2485                2490

Leu Asp Asp Lys Val Leu His Ser Asn Ala Ala Leu Asp Ser Asn
    2495                2500                2505
```

-continued

```
Leu Ile Tyr Glu Gly Phe Ser Asn Phe Gln Pro Lys Ala Thr Thr
2510                2515                2520

Asn Asp Glu Leu Thr Asn Val Val Ile Ala Lys Asn Ala Asn Leu
    2525                2530                2535

Phe Glu Lys Trp Gly Ile Thr Ser Phe Glu Met Ala Pro Gln Tyr
2540                2545                2550

Arg Ser Ser Gly Asp His Thr Phe Leu Asp Ser Thr Ile Asp Asn
    2555                2560                2565

Gly Tyr Ala Phe Thr Asp Arg Tyr Asp Leu Gly Phe Glu Thr Pro
2570                2575                2580

Thr Lys Tyr Gly Thr Asp Lys Asp Leu Arg Thr Ala Ile Lys Ala
    2585                2590                2595

Leu His Gln Ser Asn Met Gln Val Met Ala Asp Val Val Asp Asn
2600                2605                2610

Gln Val Tyr Asn Leu Ser Gly Gln Glu Val Val Ser Ala Ser Arg
    2615                2620                2625

Ala Gly Val Tyr Gly Asn Asp Val Ser Thr Gly Phe Gly Thr Gln
2630                2635                2640

Leu Tyr Ala Val Asn Ser Val Gly Gly Gly Lys Tyr Gln Ala Gln
    2645                2650                2655

Tyr Gly Gly Glu Tyr Leu Asn Glu Leu Lys Gln Gln Tyr Pro Asp
2660                2665                2670

Leu Phe Glu Ala Lys Thr Tyr Asp Tyr Trp Val Lys Asn Tyr Ser
    2675                2680                2685

Asn Asp Gly Ser Asp Pro Tyr Tyr Thr Leu Ser Gln Asn Thr Arg
2690                2695                2700

Lys Asp Met Pro Ser Ser Glu Val Ile Lys Gln Trp Ser Ala Lys
    2705                2710                2715

Tyr Met Asn Gly Thr Asn Val Leu Gly Asn Gly Met Gly Tyr Val
2720                2725                2730

Leu Lys Asp Trp Asn Thr Gly Glu Tyr Phe Lys Ile Gly Glu Lys
    2735                2740                2745

Asn Ala Asp Phe Ile Thr Asn
2750                2755
```

<210> SEQ ID NO 5
<211> LENGTH: 3324
<212> TYPE: DNA
<213> ORGANISM: Leuconostoc mesenteroides

<400> SEQUENCE: 5

```
gttaaaggcg acaaacgaac aattgacggc gttctctata cctttgataa agaaagtggt    60
gagagaaagg gtttagattc tatatcggta ttacccacca atggacaata cacaaccgat   120
aaggcccaaa attggtatta ccaagtcgat ggtgaaaatg taaaagggct atatacaaat   180
aatgatggtc aattacgtta cttcgatttg acaactggcg tgcagactaa aggtaatttt   240
gtgacaattg gcaatgatac ctactatttc accaaggaac aaggggatgg acagatagtt   300
tctgaggttg tgtcaggaca ctatggtact gtccagttga gtgacaattc gtctgcatgg   360
gtttatcgcg gtgcaaatga tcaaattttg aaaggcctac agaatataaa cggtcgtctg   420
caatattttg atctaaccac cggtgcgcaa ttaaaaggcg gtgctgcaaa ctatgatggc   480
aacctttatt attttgaatc atcagatggt aacctagtca gtaaaattca gcaatcttat   540
tctactggga attatgtgac cgatggtgat aaagtaacat atgctgatga gcaaaacaac   600
```

```
caagtcacgg gattagcgtt gattgatgat caactacaat acttcgatcc aagtgacggt    660
cgtcaagtca agaatgagca ggttatcgtt gatggcgtca catactactt tgataaaaat    720
ggtaatggac aatacttgtt tacaaatact gcaacgatgt caactaatga atttgccaaa    780
catagtgctg cttatagcaa tgatagttct agcttcaaga atacgataga tggtttcttg    840
acggccgata cctggtatcg ccctaaagat atcttggaaa acggacaaac gtgggtagtt    900
tcttcaacaa atgacgtgcg accactgata acagtttggt ggctaaataa agatgttcaa    960
gttaattatt caaattttat gaagcaaaat ggtttgctag atacaagtag tcaatttaat    1020
ctacaatctg atcaatatga cttgaatgtc gccgcgcaaa aagttcaagt ggctattgaa    1080
aaacgcattt cgaaagaaaa gagtacagat tggttgaaag atcttttgtt tgaagctcat    1140
gaagatacgc cttcatttgt gaaacaacaa tttatttgga ataaagattc tgaatatcaa    1200
ggtcaagggg atgcgtggtt ccaaggtggt tatctgaaat atggtaacaa tgaattaacc    1260
ccaacaacga actcagatta tcgtgaatcc ggtaatacat tagacttctt gcttgctaat    1320
gatgtcgaca attctaaccc agcggttcaa gctgaaaatt tgaattggtt acattattta    1380
atgaactttg gcacgattac agctaatgat gatgatgcta attttgacag tattcgtatt    1440
gatgccgttg actttattga taatgatgcc attcagagaa cctacgatta catgcgtgat    1500
gcttataaag ttgatgcaag tgaagacaac gctaataagc atatttcact ggtgaagct    1560 ggattagatg ctggtacctc tacaattaag agtgatgctt tagttgaatc taactttaga    1620
gaggcagcta cactatcgct ggcaaatcaa tcagggggaaa atagttcctt gactaatatg    1680
ttgcaagaca ttgatggtgg ccagattata gctgatcacg ccaacaatgc aacagaaaat    1740
gaatcaacgc caaattattc aattattcat gctcatgata aggggattca agaaaaggtt    1800
ggtgcagcaa ttaccgacgt tactggtgca gactggacga atttcaccga tgaccaatta    1860
aaagaaggat tagcagctta ttatcaagat caacgttcaa cgaataaaaa gtataacatc    1920
tataacttac ctagtatcta tgctttaatg ttgaccaata aggacacagt tcctcgtgtt    1980
tattacggtg atatgtatca agatgatggc cagtatatgg aaaagcaaag tatttattat    2040
gatgccattg tttccttgat gaacactaga aagagttatg tgagtggtgg gcaaactatg    2100
gatgtagatg aacatggttt gttgaagagt gttcgttttg gtaaagacgc aatgacagct    2160
agtgaccttg gtacgaatga aacacgcact gaaggtgttg gtgtgctggt cggcaatgat    2220
tcttcactaa aactaaatga ttcagataca gttactttag agatgggggc ggctcataaa    2280
aaccaaaagt accgagctgc attgttgaca acaagcgatg gtattgttac gtatgatgct    2340
gataatgatg caccaacaat ctggacagat gaccgtggta cattgacgtt ctcaaataag    2400
gagattgctg gtcaagatta tacaagcgtg caaggattcg ctaattcaca agtatcaggt    2460
tacttagcag tttgggtgcc cgtaggagct agtgacgatc aagatgtccg aacagcagca    2520
ttaacagatg caaatcttga tgacaaagta ctgcattcta atgctgcatt agattcgaac    2580
ttgatttacg aaggcttttc taactttcaa cctaaagcaa ccaccaatga tgaattgact    2640
aacgtagtaa ttgctaaaaa tgctaattta tttgaaaagt ggggaatcac aagttttgag    2700
atggcaccac aatatcgttc aagtggggac cacacgttct tagattcaac gattgataat    2760
ggttatgcat ttactgaccg atacgatttg ggatttgaaa caccaactaa gtacggtact    2820
gataaggatt tgcgtactgc aattaaagca ttgcaccaat caaatatgca ggttatggct    2880
gatgtagttg ataaccaagt ttataattta tctggacagg aggtcgtatc agcttcacgt    2940
```

-continued

```
gccggtgttt acggcaatga tgtgtcaact ggatttggga cacaactcta tgcggttaat    3000
agtgttggtg gtggtaaata tcaagcccaa tacggtggtg aatatttgaa tgaattgaag    3060
caacaatacc cagatttgtt cgaagctaag acgtatgact attgggttaa aaattattca    3120
aatgacggat cggatccgta ttacacactg tcgcaaaaca cacgaaaaga tatgccaagt    3180
agtgaggtca ttaaacaatg gtcagctaaa tatatgaatg gtactaatgt attaggaaac    3240
ggtatgggat atgttttgaa agattggaat acaggtgagt atttcaaaat tggagaaaag    3300
aatgctgatt ttataacaaa ttaa                                           3324
```

```
<210> SEQ ID NO 6
<211> LENGTH: 1107
<212> TYPE: PRT
<213> ORGANISM: Leuconostoc mesenteroides

<400> SEQUENCE: 6

Met Lys Gly Asp Lys Arg Thr Ile Asp Gly Val Leu Tyr Thr Phe Asp
1               5                   10                  15

Lys Glu Ser Gly Glu Arg Lys Gly Leu Asp Ser Ile Ser Val Leu Pro
                20                  25                  30

Thr Asn Gly Gln Tyr Thr Thr Asp Lys Ala Gln Asn Trp Tyr Tyr Gln
            35                  40                  45

Val Asp Gly Glu Asn Val Lys Gly Leu Tyr Thr Asn Asp Gly Gln
        50                  55                  60

Leu Arg Tyr Phe Asp Leu Thr Gly Val Gln Thr Lys Gly Asn Phe
65                  70                  75                  80

Val Thr Ile Gly Asn Asp Thr Tyr Tyr Phe Thr Lys Glu Gln Gly Asp
                85                  90                  95

Gly Gln Ile Val Ser Glu Val Val Ser Gly His Tyr Gly Thr Val Gln
            100                 105                 110

Leu Ser Asp Asn Ser Ser Ala Trp Val Tyr Arg Gly Ala Asn Asp Gln
        115                 120                 125

Ile Leu Lys Gly Leu Gln Asn Ile Asn Gly Arg Leu Gln Tyr Phe Asp
    130                 135                 140

Leu Thr Thr Gly Ala Gln Leu Lys Gly Gly Ala Ala Asn Tyr Asp Gly
145                 150                 155                 160

Asn Leu Tyr Tyr Phe Glu Ser Ser Asp Gly Asn Leu Val Ser Lys Ile
                165                 170                 175

Gln Gln Ser Tyr Ser Thr Gly Asn Tyr Val Thr Asp Gly Asp Lys Val
            180                 185                 190

Thr Tyr Ala Asp Glu Gln Asn Asn Gln Val Thr Gly Leu Ala Leu Ile
        195                 200                 205

Asp Asp Gln Leu Gln Tyr Phe Asp Pro Ser Asp Gly Arg Gln Val Lys
    210                 215                 220

Asn Glu Gln Val Ile Val Asp Gly Val Thr Tyr Tyr Phe Asp Lys Asn
225                 230                 235                 240

Gly Asn Gly Gln Tyr Leu Phe Thr Asn Thr Ala Thr Met Ser Thr Asn
                245                 250                 255

Glu Phe Ala Lys His Ser Ala Ala Tyr Ser Asn Asp Ser Ser Ser Phe
            260                 265                 270

Lys Asn Thr Ile Asp Gly Phe Leu Thr Ala Asp Thr Trp Tyr Arg Pro
        275                 280                 285

Lys Asp Ile Leu Glu Asn Gly Gln Thr Trp Val Val Ser Ser Thr Asn
    290                 295                 300
```

```
Asp Val Arg Pro Leu Ile Thr Val Trp Trp Leu Asn Lys Asp Val Gln
305                 310                 315                 320

Val Asn Tyr Ser Asn Phe Met Lys Gln Asn Gly Leu Leu Asp Thr Ser
            325                 330                 335

Ser Gln Phe Asn Leu Gln Ser Asp Gln Tyr Asp Leu Asn Val Ala Ala
            340                 345                 350

Gln Lys Val Gln Val Ala Ile Glu Lys Arg Ile Ser Lys Glu Lys Ser
            355                 360                 365

Thr Asp Trp Leu Lys Asp Leu Leu Phe Glu Ala His Glu Asp Thr Pro
370                 375                 380

Ser Phe Val Lys Gln Gln Phe Ile Trp Asn Lys Asp Ser Glu Tyr Gln
385                 390                 395                 400

Gly Gln Gly Asp Ala Trp Phe Gln Gly Gly Tyr Leu Lys Tyr Gly Asn
            405                 410                 415

Asn Glu Leu Thr Pro Thr Thr Asn Ser Asp Tyr Arg Glu Ser Gly Asn
            420                 425                 430

Thr Leu Asp Phe Leu Leu Ala Asn Asp Val Asp Asn Ser Asn Pro Ala
            435                 440                 445

Val Gln Ala Glu Asn Leu Asn Trp Leu His Tyr Leu Met Asn Phe Gly
450                 455                 460

Thr Ile Thr Ala Asn Asp Asp Ala Asn Phe Asp Ser Ile Arg Ile
465                 470                 475                 480

Asp Ala Val Asp Phe Ile Asp Asn Asp Ala Ile Gln Arg Thr Tyr Asp
            485                 490                 495

Tyr Met Arg Asp Ala Tyr Lys Val Asp Ala Ser Glu Asp Asn Ala Asn
            500                 505                 510

Lys His Ile Ser Leu Val Glu Ala Gly Leu Asp Ala Gly Thr Ser Thr
            515                 520                 525

Ile Lys Ser Asp Ala Leu Val Glu Ser Asn Phe Arg Glu Ala Ala Thr
530                 535                 540

Leu Ser Leu Ala Asn Gln Ser Gly Glu Asn Ser Ser Leu Thr Asn Met
545                 550                 555                 560

Leu Gln Asp Ile Asp Gly Gly Gln Ile Ile Ala Asp His Ala Asn Asn
            565                 570                 575

Ala Thr Glu Asn Glu Ser Thr Pro Asn Tyr Ser Ile Ile His Ala His
            580                 585                 590

Asp Lys Gly Ile Gln Glu Lys Val Gly Ala Ala Ile Thr Asp Val Thr
            595                 600                 605

Gly Ala Asp Trp Thr Asn Phe Thr Asp Gln Leu Lys Glu Gly Leu
610                 615                 620

Ala Ala Tyr Tyr Gln Asp Gln Arg Ser Thr Asn Lys Lys Tyr Asn Ile
625                 630                 635                 640

Tyr Asn Leu Pro Ser Ile Tyr Ala Leu Met Leu Thr Asn Lys Asp Thr
            645                 650                 655

Val Pro Arg Val Tyr Tyr Gly Asp Met Tyr Gln Asp Asp Gly Gln Tyr
            660                 665                 670

Met Glu Lys Gln Ser Ile Tyr Tyr Asp Ala Ile Val Ser Leu Met Asn
            675                 680                 685

Thr Arg Lys Ser Tyr Val Ser Gly Gly Gln Thr Met Asp Val Asp Glu
            690                 695                 700

His Gly Leu Leu Lys Ser Val Arg Phe Gly Lys Asp Ala Met Thr Ala
705                 710                 715                 720

Ser Asp Leu Gly Thr Asn Glu Thr Arg Thr Glu Gly Val Gly Val Leu
```

```
                725                 730                 735
Val Gly Asn Asp Ser Ser Leu Lys Leu Asn Asp Ser Asp Thr Val Thr
            740                 745                 750
Leu Glu Met Gly Ala Ala His Lys Asn Gln Lys Tyr Arg Ala Ala Leu
        755                 760                 765
Leu Thr Thr Ser Asp Gly Ile Val Thr Tyr Asp Ala Asp Asn Asp Ala
    770                 775                 780
Pro Thr Ile Trp Thr Asp Asp Arg Gly Thr Leu Thr Phe Ser Asn Lys
785                 790                 795                 800
Glu Ile Ala Gly Gln Asp Tyr Thr Ser Val Gln Gly Phe Ala Asn Ser
                805                 810                 815
Gln Val Ser Gly Tyr Leu Ala Val Trp Val Pro Val Gly Ala Ser Asp
            820                 825                 830
Asp Gln Asp Val Arg Thr Ala Ala Leu Thr Asp Ala Asn Leu Asp Asp
        835                 840                 845
Lys Val Leu His Ser Asn Ala Ala Leu Asp Ser Asn Leu Ile Tyr Glu
    850                 855                 860
Gly Phe Ser Asn Phe Gln Pro Lys Ala Thr Thr Asn Asp Glu Leu Thr
865                 870                 875                 880
Asn Val Val Ile Ala Lys Asn Ala Asn Leu Phe Glu Lys Trp Gly Ile
                885                 890                 895
Thr Ser Phe Glu Met Ala Pro Gln Tyr Arg Ser Ser Gly Asp His Thr
            900                 905                 910
Phe Leu Asp Ser Thr Ile Asp Asn Gly Tyr Ala Phe Thr Asp Arg Tyr
        915                 920                 925
Asp Leu Gly Phe Glu Thr Pro Thr Lys Tyr Gly Thr Asp Lys Asp Leu
    930                 935                 940
Arg Thr Ala Ile Lys Ala Leu His Gln Ser Asn Met Gln Val Met Ala
945                 950                 955                 960
Asp Val Val Asp Asn Gln Val Tyr Asn Leu Ser Gly Gln Glu Val Val
                965                 970                 975
Ser Ala Ser Arg Ala Gly Val Tyr Gly Asn Asp Val Ser Thr Gly Phe
            980                 985                 990
Gly Thr Gln Leu Tyr Ala Val Asn Ser Val Gly Gly Lys Tyr Gln
        995                 1000                1005
Ala Gln Tyr Gly Gly Glu Tyr Leu Asn Glu Leu Lys Gln Gln Tyr
    1010                1015                1020
Pro Asp Leu Phe Glu Ala Lys Thr Tyr Asp Tyr Trp Val Lys Asn
    1025                1030                1035
Tyr Ser Asn Asp Gly Ser Asp Pro Tyr Tyr Thr Leu Ser Gln Asn
    1040                1045                1050
Thr Arg Lys Asp Met Pro Ser Ser Glu Val Ile Lys Gln Trp Ser
    1055                1060                1065
Ala Lys Tyr Met Asn Gly Thr Asn Val Leu Gly Asn Gly Met Gly
    1070                1075                1080
Tyr Val Leu Lys Asp Trp Asn Thr Gly Glu Tyr Phe Lys Ile Gly
    1085                1090                1095
Glu Lys Asn Ala Asp Phe Ile Thr Asn
    1100                1105

<210> SEQ ID NO 7
<211> LENGTH: 1338
<212> TYPE: PRT
<213> ORGANISM: Streptococcus criceti
```

<400> SEQUENCE: 7

```
Met Glu Lys Asn Leu Arg Tyr Lys Leu His Lys Val Lys Gln Trp
 1               5                  10                  15

Val Ala Ile Gly Val Thr Thr Phe Ala Val Gly Phe Leu Ala Gly
                20                  25                  30

Gly Gln Val Val Ala Ala Asp Ala Thr Asp Gly Asn Gly Gly Asn Thr Gln
                    35                  40                  45

Val Ala His Leu Ile Pro Lys Glu Pro Thr Asp Tyr Lys Phe Asp Thr
        50                  55                  60

Pro Ser Gly Ile Leu Thr Gly Leu Asn Phe Ala Asn Ala Gln Thr Ser
65                  70                  75                  80

Pro Ala Gly Asp Asn Ala Gly Ala Asn Gln Pro Ala Gly Gly Ile Glu
                85                  90                  95

Pro Gln Thr Ala Glu Asn Ala Ala Thr Asp Gly Gln Ala Val Pro Gln
            100                 105                 110

Thr Ser Asp Gln Pro Gly His Leu Glu Asn Val Asp Gly Lys Thr Tyr
            115                 120                 125

Tyr Val Asp Ala Asn Gly Gln Arg Leu Lys Asn Tyr Ser Thr Val Ile
130                 135                 140

Asp Gly Lys Thr Tyr Tyr Phe Asp Ala Gln Thr Gly Gln Ala Gln Ala
145                 150                 155                 160

Glu Thr Pro Gln Ile Asn Gln Asn Asp Asn Gln Val Ala Pro Asp Thr
                165                 170                 175

Tyr Ala Ala Asn Asn Gln Ala Phe Thr Asn Asp Val Ser Ser Phe Glu
            180                 185                 190

Thr Val Asp Asn Tyr Val Thr Ala Asp Ser Trp Tyr Arg Pro Arg Lys
            195                 200                 205

Ile Leu Lys Asn Gly Glu Ser Trp Gln Ala Ser Ala Glu Ser Asp Met
210                 215                 220

Arg Pro Ile Leu Met Thr Trp Trp Pro Asp Ala Ala Thr Lys Ala Ala
225                 230                 235                 240

Tyr Ala Asn Tyr Trp Val Lys Glu Gly Leu Ile Ser Gly Ser Tyr Ser
                245                 250                 255

Pro Asn Ser Ala Asn Leu Glu Thr Ala Val Gln Thr Ile Gln Ala Ala
            260                 265                 270

Ile Glu Lys Lys Ile Ala Ser Glu Gly Ser Thr Ala Trp Leu Arg Asp
            275                 280                 285

Lys Met Ser Gln Phe Val Lys Ser Gln Asn Gln Trp Ser Leu Ala Ser
290                 295                 300

Glu Asn Pro Thr Val Tyr Pro Asn Gln Asp His Leu Gln Gly Gly Ala
305                 310                 315                 320

Leu Leu Phe Ser Asn Asn Glu Ala Thr Ala His Ala Asn Ser Asp Trp
                325                 330                 335

Arg Leu Leu Asn Arg Asn Pro Thr Phe Gln Thr Gly Lys Gln Lys Tyr
            340                 345                 350

Phe Thr Thr Asn Tyr Ala Gly Tyr Glu Leu Leu Leu Ala Asn Asp Val
            355                 360                 365

Asp Asn Ser Asn Pro Ile Val Gln Ala Glu Gln Leu Asn His Phe His
            370                 375                 380

Tyr Leu Met Asn Trp Gly Glu Ile Val Met Gly Asp Lys Asn Ala Asn
385                 390                 395                 400

Phe Asp Gly Val Arg Val Asp Ala Val Asp Asn Val Asn Ala Asp Leu
```

```
                405                 410                 415
Leu Gln Ile Gln Arg Asp Tyr Tyr Lys Ala Lys Tyr Gly Val Asp Gln
            420                 425                 430

Asn Glu Lys Asn Ala Ile Asp His Leu Ser Ile Leu Glu Ala Trp Ser
            435                 440                 445

Gly Asn Asp Asn Asp Tyr Val Lys Asp Gln Asn Asn Phe Ser Leu Ser
        450                 455                 460

Ile Asp Asn Ser Gln Arg Ser Tyr Met Leu Ala Ala Phe Ala Tyr Pro
465                 470                 475                 480

Ala Ser Gln Arg Gly Asn Asp Tyr Ile Ser Leu Leu Pro Lys Val Gly
                485                 490                 495

Leu Lys Asp Arg Arg Tyr Ala Lys Asn Gly Asn Pro Val Pro Asn Tyr
            500                 505                 510

Val Phe Ile Arg Ala His Asp Ser Glu Val Gln Thr Arg Ile Ala Lys
            515                 520                 525

Ile Ile Arg Glu Arg Leu Gly Lys Thr Asn Ala Asp Gly Leu Thr Asn
        530                 535                 540

Ile Thr Leu Asp Asp Leu Asn Lys Ala Phe Asp Ile Tyr Asn Gln Asp
545                 550                 555                 560

Met Lys Ala Val Asp Lys Gln Tyr Tyr Pro Asn Asn Leu Pro Met Ala
                565                 570                 575

Tyr Ala Trp Met Leu Gln Asn Lys Asp Thr Val Thr Arg Val Tyr Tyr
            580                 585                 590

Gly Asp Met Tyr Thr Asp Asp Gly Gln Tyr Met Glu Thr Lys Thr Pro
        595                 600                 605

Phe His Asp Ala Ile Glu Thr Leu Leu Lys Ala Arg Ile Lys Tyr Val
610                 615                 620

Ala Gly Gly Gln Thr Ala Gly Tyr Val Gln Gly Trp Gly Ser Gly Ile
625                 630                 635                 640

Leu Thr Ser Val Arg Tyr Gly Lys Gly Ala Asp Thr Ala Ile Asp Ala
                645                 650                 655

Gly Thr Ala Glu Thr Arg Thr Ser Gly Met Ala Val Leu Ile Asn Asn
            660                 665                 670

Lys Pro Asn Phe Gln Ser Tyr Asn Gly Leu Thr Leu Asp Met Gly Ala
        675                 680                 685

Ala His Lys Asn Gln Ala Tyr Arg Pro Leu Leu Leu Ser Thr Lys Asp
            690                 695                 700

Gly Ile Ala Thr Tyr Leu Asn Asp Ser Asp Val Ser Ser Asn Gln Tyr
705                 710                 715                 720

Lys Tyr Thr Asp Gly Gln Gly Arg Leu Asn Phe Ser Ala Ser Glu Leu
                725                 730                 735

Arg Ser Val Ala Asn Val Gln Val Ser Gly Met Ile Gln Val Trp Val
            740                 745                 750

Pro Val Gly Ala Ala Asp Asn Gln Asp Val Arg Val Ala Pro Asn Thr
        755                 760                 765

Asn Arg Asn Asn Ser Ser Asn Ile Tyr Thr Gln Ser Asp Ala Leu Asp
        770                 775                 780

Ser Gln Val Ile Tyr Glu Gly Phe Ser Asn Phe Gln Ala Phe Ala Lys
785                 790                 795                 800

Thr Pro Glu Gln Tyr Thr Asn Ala Val Ile Ala Lys Asn Ala Asp Leu
                805                 810                 815

Phe Lys Ser Trp Gly Ile Thr Gln Phe Glu Met Ala Pro Gln Tyr Val
            820                 825                 830
```

```
Ser Ser Glu Asp Gly Thr Phe Leu Asp Ser Val Val Leu Asn Gly Tyr
        835                 840                 845

Ala Phe Ser Asp Arg Tyr Asp Leu Ala Met Ser Lys Asn Asn Lys Tyr
850                 855                 860

Gly Ser Lys Glu Asp Leu Ala Asn Ala Ile Lys Gly Leu His Asn Ala
865                 870                 875                 880

Gly Ile Lys Val Leu Ser Asp Trp Val Pro Asp Gln Met Tyr Asn Leu
                885                 890                 895

Pro Gly Lys Glu Val Val Thr Ala Thr Arg Val Asp Gln Tyr Gly Arg
                900                 905                 910

Pro Lys Ala Gly Ala Thr Ile Asn Arg Thr Pro Tyr Val Val Asn Thr
                915                 920                 925

Lys Thr Tyr Gly Asp Tyr Gln Glu Gln Tyr Gly Gly Lys Phe Leu Asp
            930                 935                 940

Glu Leu Gln Lys Leu Tyr Pro Ser Leu Phe Thr Thr Lys Gln Ile Ser
945                 950                 955                 960

Thr Gly Lys Pro Ile Asp Pro Ser Val Lys Ile Thr Asn Trp Ser Ala
                965                 970                 975

Lys Tyr Phe Asn Gly Ser Asn Ile Leu Gly Arg Gly Ala Lys Tyr Val
                980                 985                 990

Leu Ser Asp Asn Asn Lys Tyr Leu Asn Leu Gly Ala Gly Gln Phe Phe
            995                 1000                1005

Leu Pro Thr Asn Leu Asn Asn Thr Tyr Gly Gln Pro Gln Ala Pro
    1010                1015                1020

Ala Asn Gly Phe Ile Ser Lys Asn Gly Ile His Tyr Ile Asp
    1025                1030                1035

Asn Asn Gly Gln Glu Val Lys Asn Gln Phe Lys Glu Ile Ala Gly
    1040                1045                1050

Ser Trp Tyr Tyr Phe Asp Ala Asn Gly Lys Met Ala Thr Gly Gln
    1055                1060                1065

Thr Lys Ile Gly Asn Thr Thr Tyr Leu Phe Met Pro Asn Gly Lys
    1070                1075                1080

Gln Leu Lys Glu Gly Val Trp Tyr Asp Gly Lys Lys Ala Tyr Tyr
    1085                1090                1095

Tyr Asp Asp Asn Gly Arg Thr Trp Thr Asn Lys Gly Phe Val Glu
    1100                1105                1110

Phe Lys Val Asn Gly Gln Asp Lys Trp Arg Tyr Phe Asn Gly Asp
    1115                1120                1125

Gly Ser Ile Ala Val Gly Leu Val Ser Leu Asp Asn Arg Thr Leu
    1130                1135                1140

Tyr Phe Asp Ala Tyr Gly Tyr Gln Val Lys Gly Gln Thr Leu Thr
    1145                1150                1155

Ile Asn Gly Lys Thr Tyr Ser Phe Asp Ala Asn Glu Gly Asp Leu
    1160                1165                1170

Ile Thr Gly Asn Thr Pro Ser Pro Glu Pro Asn Asn Gln Gly Ala
    1175                1180                1185

Trp Glu Ala Leu Gly Asp Asn Gln Trp Gly Tyr Arg Lys Asp Gly
    1190                1195                1200

Lys Leu Leu Thr Gly Ser Gln Thr Ile Ala Gly Gln Lys Val Phe
    1205                1210                1215

Phe Gln Pro Asn Gly Val Gln Val Lys Gly Gly Thr Ala Lys Asp
    1220                1225                1230
```

| | | | | | | | | | | | |
|---|---|---|---|---|---|---|---|---|---|---|---|
| Glu | Ala | Gly | Val | Leu | Arg | Phe | Tyr | Asp | Arg | Asp | Gln | Gly | His | Leu |
| | 1235 | | | | 1240 | | | | 1245 | | |

| Ala | Gly | Lys | Gly | Trp | Tyr | Ser | Thr | Ala | Asp | Asn | Asn | Trp | Val | Tyr |
|---|---|---|---|---|---|---|---|---|---|---|---|---|---|---|
| | 1250 | | | | 1255 | | | | 1260 | | | | | |

| Val | Asp | Asp | Ala | Gly | Arg | Val | Val | Thr | Gly | Leu | Gln | Lys | Ile | Gly |
|---|---|---|---|---|---|---|---|---|---|---|---|---|---|---|
| | 1265 | | | | 1270 | | | | 1275 | | | | | |

| Ser | Gln | Thr | Leu | Tyr | Phe | Asp | Asp | Asn | Gly | Ile | Gln | Ala | Lys | Gly |
|---|---|---|---|---|---|---|---|---|---|---|---|---|---|---|
| | 1280 | | | | 1285 | | | | 1290 | | | | | |

| Lys | Ala | Ile | Trp | Asp | Lys | Asp | Gly | Asn | Leu | Arg | Tyr | Phe | Ala | Ala |
|---|---|---|---|---|---|---|---|---|---|---|---|---|---|---|
| | 1295 | | | | 1300 | | | | 1305 | | | | | |

| Gly | Ser | Gly | Asp | Met | Ile | Thr | Asn | Arg | Trp | Tyr | Asn | Ile | Gly | Asp |
|---|---|---|---|---|---|---|---|---|---|---|---|---|---|---|
| | 1310 | | | | 1315 | | | | 1320 | | | | | |

| Asn | Gln | Trp | Tyr | Trp | Phe | Asn | Asn | Gln | Gly | Ile | Ala | Ser | Arg | Trp |
|---|---|---|---|---|---|---|---|---|---|---|---|---|---|---|
| | 1325 | | | | 1330 | | | | 1335 | | | | | |

<210> SEQ ID NO 8
<211> LENGTH: 3909
<212> TYPE: DNA
<213> ORGANISM: Streptococcus criceti

<400> SEQUENCE: 8

```
gctgacgcga ctgacggtaa cggagggaat actcaagttg cccacttgat tcctaaagag    60
cctactgact ataagttcga tactccaagt ggaattctca ctggtcttaa ttttgcgaat   120
gctcaaacaa gcccagcagg cgataatgct ggtgctaatc aaccggcggg aggaatcgag   180
cctcagactg ctgaaaatgc tgcaacagat ggccaagctg ttcctcaaac tagtgaccag   240
ccaggtcatt tggaaaatgt ggatggcaaa acctactatg tagatgctaa cggtcagcgt   300
ttgaaaaatt attcaaccgt gattgatggc aagacttact attttgatgc tcagactggt   360
caggctcagg ccgaaacacc acagattaat caaaatgata atcaggtggc accagatact   420
tatgcggcta ataatcaggc tttcaccaat gatgtttcaa gttttgaaac ggttgacaac   480
tatgtgacgg cggattcttg gtaccgtcct cgtaaaattt tgaagaatgg ggaaagttgg   540
caggctagcg ctgaatcaga catgcgcccc atcctgatga cttggtggcc tgatgcagct   600
actaaggctg cctatgctaa ttactgggtt aaggaaggtt tgatttcagg ctcctattca   660
ccaaactcag ccaatcttga cagccgtc caaactattc aggcagctat tgagaagaaa   720
attgcttcgg aaggcagcac agcttggctg cgtgacaaga tgtcgcaatt tgttaaatcg   780
caaaatcaat ggagtcttgc ctctgaaaat ccaactgtct atcctaatca ggatcacctg   840
cagggggag ccttgctctt tagcaataac gaagcaacgg ctcatgctaa ttctgattgg   900
cgtttgctca accgtaatcc taccttccaa acgggtaagc aaaaatattt cacaaccaac   960
tatgctggtt atgaactgct tttggccaac gatgttgata attccaaccc aattgttcaa  1020
gcggaacagc ttaatcattt ccactacctc atgaactggg gtgagattgt catgggagat  1080
aagaatgcta atttcgacgg cgttcgggtc gatgcagtcg ataatgttaa tgctgatttg  1140
ctacaaattc agcgggatta ctacaaggct aaatatggcg ttgatcaaaa tgaaagaat  1200
gccattgatc acttatctat tttagaggct tggtcgggta atgataatga ctatgttaag  1260
gatcagaaca acttctcgct gtctattgat aattcacaac gtagctatat gctggcagcc  1320
tttgcttatc cggccagtca acgggggaat gattacatca gcctgttacc taaagttggt  1380
ctgaaggatc gccggtatgc taaaaatggt aatccagttc caactatgt ctttattcgt  1440
gcccatgact ccgaagtcca aacgcgaatt gcgaaaatta ttcgggaacg tctgggaaaa  1500
```

```
acgaacgccg atggcctgac caatattact ttagatgatt taaataaggc ctttgatatt    1560
tacaatcaag atatgaaggc tgttgataag cagtactatc caaataattt gccaatggct    1620
tatgcttgga tgttacaaaa taaggataca gtaactcgtg tctattatgg tgatatgtac    1680
accgacgatg tcagtacat ggaaactaag acgccattcc atgatgccat gaaacgttg     1740
ctcaaggcac gcattaaata tgtggctggc ggtcaaacag ctgggtatgt acaaggctgg    1800
ggcagcggta tcttaacctc tgtgcgttat ggtaagggag ccgatactgc tattgatgct    1860
gggacagcag aaactcgcac ttctggcatg gctgtcctga ttaataataa gcctaatttc    1920
caatcctata tggtttgac gcttgatatg ggtgctgctc ataagaatca ggcctaccgc     1980
cctcttcttt tatcaactaa ggatggaatt gcaacctatc ttaatgatag tgatgttagc    2040
agcaatcagt acaaatatac tgatgggcag gtcgtttga atttcagcgc ttctgaactg     2100
cgcagcgttg ctaatgttca gtctcagga atgattcagg tttgggtacc cgtgggtgcc    2160
gctgacaatc aagatgttcg tgtagctcct aacaccaatc gcaataattc ttccaatatc    2220
tatactcaaa gtgatgctct ggattcccaa gtgatctatg aaggtttctc aaacttccaa    2280
gcttttgcta agacacctga acaatacacc aatgcggtga ttgctaagaa tgcggatctc    2340
tttaaatcat ggggcattac ccaatttgaa atggcaccgc agtacgtgtc atccgaagat    2400
ggcactttct tggattctgt tgttctcaat ggttatgcct ttagcgaccg ttatgatctg    2460
gctatgagta agaataacaa gtacggctcc aaagaagatt tggccaatgc tatcaagggt    2520
ctccataatg ctggtattaa ggtcttgtcg gactgggtac cggatcagat gtataacctg    2580
ccaggtaaag aagtcgtgac tgcaacacgg gttgaccaat acggtagacc taaggctggt    2640
gcgacgatta acaggacacc ttatgtagtt aataccaaga cttatggtga ttatcaagag    2700
cagtatggcg gtaaattctt ggatgaattg cagaagcttt atccaagtct cttcacgact    2760
aagcagattt caactggcaa accaattgac ccatcggtca aaattactaa ctggtcagct    2820
aaatatttca acggctctaa tatcttagga cgtggggcta aatatgttct cagcgataat    2880
aataagtacc tcaatttagg tgccggtcaa ttcttcttac caaccaatct caataatacc    2940
tacggtcagc acaagctcc agctaatggt ttcatttcta agaatggtgg tattcattat    3000
attgataata atggtcaaga agtcaagaat caatttaagg aaattgctgg cagctggtat    3060
tatttcgatg ccaatggtaa gatggctact ggacaaacca agattggcaa tactacctac    3120
ctcttcatgc ctaatggtaa gcagctcaaa gaaggtgttt ggtatgatgg caagaaggct    3180
tactattatg atgataacgg tcgaacttgg acaaataagg gatttgtcga gttcaaggta    3240
aacggtcaag ataaatggcg ttactttaac ggtgatggct ccatcgctgt cggtctcgtt    3300
tctcttgata tcgtacccct ctactttgac gcctatggct accaagtcaa gggtcaaact    3360
ctgactatca atggtaaaac ttatagcttt gatgccaatg aaggtgattt gattacgggg    3420
aatacgccaa gtccagaacc aaacaatcaa ggagcttggg aagcactggg tgataaccaa    3480
tggggctatc gcaaggatgg caagcttttg acaggcagcc aaacgattgc tggacaaaaa    3540
gtcttcttcc agcctaatgg tgtccaagtc aagggtggca cggctaagga tgaagcagga    3600
gttcttcgct tttacgaccg tgatcaagga catttagctg gtaagggttg gtactcaaca    3660
gctgataaca actgggttta tgtcgatgat gctggtcgtg ttgtcactgg ccttcaaaag    3720
attggaagcc aaacgctcta tttttgatgat aatggtatcc aagctaaggg taaggctatc    3780
tgggataagg acggtaatct tcgttatttt gcagcaggtt ccggtgacat gattaccaac    3840
cgttggtata atatcggtga taaccaatgg tactggttca ataaccaagg gattgcttca    3900
``` agatggtaa                                                          3909

<210> SEQ ID NO 9
<211> LENGTH: 1365
<212> TYPE: PRT
<213> ORGANISM: Streptococcus downei

<400> SEQUENCE: 9

Met Glu Lys Asn Leu Arg Tyr Lys Leu His Lys Val Lys Lys Gln Trp
1               5                   10                  15

Val Ala Ile Gly Val Thr Thr Val Thr Leu Ser Phe Leu Ala Gly Gly
            20                  25                  30

Gln Val Val Ala Ala Asp Thr Asn Asn Asn Asp Gly Thr Ser Val Gln
        35                  40                  45

Val Asn Lys Met Val Pro Ser Asp Pro Lys Phe Asp Ala Gln Ala Gln
    50                  55                  60

Asn Gly Gln Leu Ala Gln Ala Met Phe Lys Ala Ala Asn Gln Ala Asp
65                  70                  75                  80

Gln Thr Ala Thr Ser Gln Val Ser Pro Ala Thr Asp Gly Arg Val Asp
                85                  90                  95

Asn Gln Val Thr Pro Ala Ala Asn Gln Pro Ala Ala Asn Val Ala Asn
            100                 105                 110

Gln Asp Val Ala Asn Pro Ala Thr Asp Ala Gly Ala Leu Asn Arg Gln
        115                 120                 125

Ser Ala Ala Asp Thr Ser Thr Asp Gly Lys Ala Val Pro Gln Thr Ser
    130                 135                 140

Asp Gln Pro Gly His Leu Glu Thr Val Asp Gly Lys Thr Tyr Tyr Val
145                 150                 155                 160

Asp Ala Asn Gly Gln Arg Leu Lys Asn Tyr Ser Met Val Ile Asp Gly
                165                 170                 175

Lys Thr Tyr Tyr Phe Asp Gly Gln Thr Gly Glu Ala Gln Thr Asp Leu
            180                 185                 190

Pro Lys Thr Gly Gln Ala Asn Gln Asp Asn Val Pro Asp Ser Tyr Gln
        195                 200                 205

Ala Asn Asn Gln Ala Tyr Ser Asn Glu Ala Ser Ser Phe Glu Thr Val
    210                 215                 220

Asp Asn Tyr Leu Thr Ala Asp Ser Trp Tyr Arg Pro Arg Lys Ile Leu
225                 230                 235                 240

Lys Asn Gly Gln Ser Trp Gln Ala Ser Ser Glu Gly Asp Leu Arg Pro
                245                 250                 255

Ile Leu Met Thr Trp Trp Pro Asp Ala Ala Thr Lys Ala Ala Tyr Ala
            260                 265                 270

Asn Phe Trp Ala Lys Glu Gly Leu Ile Ser Gly Ser Tyr Arg Gln Asn
        275                 280                 285

Ser Ala Asn Leu Asp Ala Ala Thr Gln Asn Ile Gln Ser Ala Ile Glu
    290                 295                 300

Lys Lys Ile Ala Ser Glu Gly Asn Thr Asn Trp Leu Arg Asp Lys Met
305                 310                 315                 320

Ser Gln Phe Val Lys Ser Gln Asn Gln Trp Ser Ile Ala Ser Glu Asn
                325                 330                 335

Glu Thr Val Tyr Pro Asn Gln Asp His Met Gln Gly Gly Ala Leu Leu
            340                 345                 350

Phe Ser Asn Ser Lys Asp Thr Glu His Ala Asn Ser Asp Trp Arg Leu
        355                 360                 365

```
Leu Asn Arg Asn Pro Thr Phe Gln Thr Gly Lys Gln Lys Tyr Phe Thr
    370                 375                 380

Thr Asn Tyr Ala Gly Tyr Glu Leu Leu Leu Ala Asn Asp Val Asp Asn
385                 390                 395                 400

Ser Asn Pro Val Val Gln Ala Glu Gln Leu Asn His Leu His Tyr Leu
                405                 410                 415

Met Asn Trp Gly Asp Ile Val Met Gly Asp Lys Asp Ala Asn Phe Asp
            420                 425                 430

Gly Val Arg Val Asp Ala Val Asp Asn Val Asn Ala Asp Leu Leu Gln
            435                 440                 445

Ile Gln Arg Asp Tyr Tyr Lys Ala Lys Tyr Gly Thr Asp Gln Asn Glu
    450                 455                 460

Lys Asn Ala Ile Asp His Leu Ser Ile Leu Glu Ala Trp Ser Gly Asn
465                 470                 475                 480

Asp Asn Asp Tyr Val Lys Asp Gln Asn Asn Phe Ser Leu Ser Ile Asp
                485                 490                 495

Asn Asp Gln Arg Ser Gly Met Leu Lys Ala Phe Gly Tyr Ala Ser Ala
            500                 505                 510

Tyr Arg Gly Asn Leu Ser Asn Leu Ala Thr Ala Gly Leu Lys Asn Arg
    515                 520                 525

Ser Ala Asn Pro Asp Ser Asp Pro Val Pro Asn Tyr Val Phe Ile Arg
530                 535                 540

Ala His Asp Ser Glu Val Gln Thr Arg Ile Ala Lys Ile Ile Arg Glu
545                 550                 555                 560

Lys Leu Gly Lys Thr Asn Ala Asp Gly Leu Thr Asn Leu Thr Leu Asp
                565                 570                 575

Asp Leu Asn Lys Ala Phe Asp Ile Tyr Asn Gln Asp Met Asn Ala Thr
            580                 585                 590

Asp Lys Val Tyr Tyr Pro Asn Asn Leu Pro Met Ala Tyr Ala Trp Met
    595                 600                 605

Leu Gln Asn Lys Asp Thr Val Thr Arg Val Tyr Tyr Gly Asp Met Tyr
    610                 615                 620

Thr Asp Asn Gly Gln Tyr Met Ala Thr Lys Thr Pro Phe Tyr Asn Ala
625                 630                 635                 640

Ile Glu Thr Leu Leu Lys Gly Arg Ile Lys Tyr Val Ala Gly Gly Gln
                645                 650                 655

Ala Val Ser Tyr Lys Gln Asp Trp Ser Ser Gly Ile Leu Thr Ser Val
            660                 665                 670

Arg Tyr Gly Lys Gly Ala Asn Ser Ala Ser Asp Ala Gly Asn Thr Glu
    675                 680                 685

Thr Arg Asn Ser Gly Met Ala Leu Leu Ile Asn Asn Arg Pro Asn Phe
690                 695                 700

Arg Ala Tyr Arg Asn Leu Thr Leu Asn Met Gly Ala Ala His Lys Ser
705                 710                 715                 720

Gln Ala Tyr Arg Pro Leu Leu Leu Ser Thr Lys Asp Gly Ile Ala Thr
                725                 730                 735

Tyr Leu Asn Asp Ser Asp Val Asp Ser Arg Gln Tyr Lys Tyr Thr Asp
            740                 745                 750

Ser Gln Gly Asn Leu Ser Phe Ser Ala Ser Glu Leu Gln Ser Val Ala
    755                 760                 765

Asn Ala Gln Val Ser Gly Met Ile Gln Val Trp Val Pro Val Gly Ala
    770                 775                 780
```

```
Ala Asp Asn Gln Asp Val Arg Thr Ser Pro Ser Thr Gln Ala Thr Lys
785                 790                 795                 800

Asp Gly Asn Ile Tyr His Gln Ser Asp Ala Leu Asp Ser Gln Val Ile
            805                 810                 815

Tyr Glu Gly Phe Ser Asn Phe Gln Ala Phe Gln Ser Pro Asp Gln
        820                 825                 830

Tyr Thr Asn Ala Val Ile Ala Lys Asn Gly Asp Leu Phe Lys Ser Trp
            835                 840                 845

Gly Ile Thr Gln Phe Glu Met Ala Pro Gln Tyr Val Ser Ser Glu Asp
850                 855                 860

Gly Thr Phe Leu Asp Ser Val Ile Leu Asn Gly Tyr Ala Phe Ser Asp
865                 870                 875                 880

Arg Tyr Asp Leu Ala Met Ser Lys Asn Lys Tyr Gly Ser Lys Gln
        885                 890                 895

Asp Leu Ala Asn Ala Ile Lys Gly Leu Gln Ser Ala Gly Ile Lys Val
            900                 905                 910

Leu Ser Asp Leu Val Pro Asn Gln Leu Tyr Asn Leu Pro Gly Lys Glu
        915                 920                 925

Val Val Thr Ala Thr Arg Val Asn Gln Tyr Gly Gln Ala Lys Ser Gly
930                 935                 940

Ala Thr Ile Asn Lys Thr Pro Tyr Val Ala Asn Thr Arg Ser Tyr Gly
945                 950                 955                 960

Asp Tyr Gln Glu Gln Tyr Gly Gly Lys Phe Leu Asp Asp Leu Gln Lys
            965                 970                 975

Leu Tyr Pro Arg Leu Phe Ser Thr Lys Gln Ile Ser Thr Gly Lys Pro
        980                 985                 990

Ile Asp Pro Ser Val Lys Ile Thr Asn Trp Ser Ala Lys Tyr Phe Asn
        995                 1000                1005

Gly Ser Asn Ile Leu Gly Arg Gly Ala Lys Tyr Val Leu Ser Glu
1010                1015                1020

Gly Asn Lys Tyr Leu Asn Leu Ala Asp Gly Lys Leu Phe Leu Pro
1025                1030                1035

Thr Val Leu Asn Asn Thr Tyr Gly Gln Pro Gln Val Ser Ala Asn
1040                1045                1050

Gly Phe Ile Ser Lys Asn Gly Gly Ile His Tyr Leu Asp Lys Asn
1055                1060                1065

Gly Gln Glu Val Lys Asn Arg Phe Lys Glu Ile Ser Gly Ser Trp
1070                1075                1080

Tyr Tyr Phe Asp Ser Asp Gly Lys Met Ala Thr Gly Lys Thr Lys
1085                1090                1095

Ile Gly Asn Asp Thr Tyr Leu Phe Met Pro Asn Gly Lys Gln Leu
1100                1105                1110

Lys Glu Gly Val Trp Tyr Asp Gly Lys Lys Ala Tyr Tyr Tyr Asp
1115                1120                1125

Asp Asn Gly Arg Thr Trp Thr Asn Lys Gly Phe Val Glu Phe Arg
1130                1135                1140

Val Asp Gly Gln Asp Lys Trp Arg Tyr Phe Asn Gly Asp Gly Thr
1145                1150                1155

Ile Ala Ile Gly Leu Val Ser Leu Asp Asn Arg Thr Leu Tyr Phe
1160                1165                1170

Asp Ala Tyr Gly Tyr Gln Val Lys Gly Gln Thr Val Thr Ile Asn
1175                1180                1185

Gly Lys Ser Tyr Thr Phe Asp Ala Asp Gln Gly Asp Leu Val Gln
```

```
                      1190                1195                1200

Thr  Asp  Asn  Ala  Asn  Pro  Ala  Pro  Gln  Gly  Gln  Ala  Gly  Trp  Lys
            1205                1210                1215

Leu  Leu  Gly  Asp  Asn  Gln  Trp  Gly  Tyr  Arg  Lys  Asp  Gly  Gln  Leu
       1220                1225                1230

Leu  Thr  Gly  Glu  Gln  Thr  Ile  Asp  Gly  Gln  Lys  Val  Phe  Phe  Gln
       1235                1240                1245

Asp  Asn  Gly  Val  Gln  Val  Lys  Gly  Gly  Thr  Ala  Thr  Asp  Ala  Ser
       1250                1255                1260

Gly  Val  Leu  Arg  Phe  Tyr  Asp  Arg  Asp  Gln  Gly  His  Gln  Val  Gly
       1265                1270                1275

Lys  Gly  Trp  Tyr  Ser  Thr  Ser  Asp  Asp  Asn  Trp  Val  Tyr  Val  Asn
       1280                1285                1290

Glu  Ser  Gly  Gln  Val  Leu  Thr  Gly  Leu  Gln  Thr  Ile  Asp  Gly  Gln
       1295                1300                1305

Thr  Val  Tyr  Phe  Asp  Asp  Lys  Gly  Ile  Gln  Ala  Lys  Gly  Lys  Ala
       1310                1315                1320

Val  Trp  Asp  Glu  Asn  Gly  Asn  Leu  Arg  Tyr  Phe  Asp  Ala  Asp  Ser
       1325                1330                1335

Gly  Asn  Met  Leu  Arg  Asp  Arg  Trp  Lys  Asn  Val  Asp  Gly  Asn  Trp
       1340                1345                1350

Tyr  Tyr  Phe  Asn  Arg  Asn  Gly  Leu  Ala  Thr  Arg  Trp
       1355                1360                1365

<210> SEQ ID NO 10
<211> LENGTH: 1587
<212> TYPE: PRT
<213> ORGANISM: Streptococcus salivarius

<400> SEQUENCE: 10

Met  Arg  Ser  Lys  Lys  Leu  Trp  Ile  Ser  Leu  Leu  Phe  Ala  Leu  Thr  Leu
1                5                  10                  15

Ile  Phe  Thr  Met  Ala  Phe  Ser  Asn  Met  Ser  Ala  Ser  Ala  Glu  Glu  Thr
              20                  25                  30

Asn  Asn  Ser  Asn  Gly  Ser  Pro  Ser  Thr  Thr  Val  Gly  Glu  Asn  Thr
          35                  40                  45

Asn  Pro  Val  Val  Glu  Lys  Glu  Val  Gly  Thr  Thr  Thr  Glu  Val  Ala  Asn
 50                  55                  60

Thr  Ser  Asn  Ala  Thr  Thr  Thr  Glu  Arg  Ala  Glu  Val  Thr  Ala  Asp  Lys
65                  70                  75                  80

Pro  Ala  Glu  Thr  Thr  Val  Gln  Pro  Asn  Ser  Gly  Thr  Thr  Thr  Ser  Asp
              85                  90                  95

Arg  Ala  Val  Ala  Val  Glu  Val  Glu  Ala  Lys  Pro  Glu  Thr  Thr  Ala  Lys
          100                 105                 110

Pro  Glu  Val  Ala  Thr  Lys  Pro  Glu  Thr  Ala  Thr  Thr  Ser  Glu  Val  Ala
          115                 120                 125

Ala  Asn  Ala  Gly  Val  Ala  Ala  Pro  Thr  Thr  Glu  Lys  Ser  Lys  Glu  Leu
          130                 135                 140

Ser  Glu  Ala  Glu  Ile  Lys  Ala  Ala  Val  Ser  Leu  Asp  Asn  Ile  Lys  Lys
145                 150                 155                 160

Glu  Lys  Asp  Gly  Lys  Tyr  Tyr  Tyr  Leu  Leu  Glu  Asp  Gly  Ser  His  Lys
                165                 170                 175

Lys  Asn  Phe  Ala  Ile  Thr  Val  Asn  Gly  Gln  Val  Leu  Tyr  Phe  Asp  Glu
              180                 185                 190
```

```
Asn Gly Ala Leu Ser Ser Thr Ser Thr Tyr Ser Phe Thr Gln Glu Thr
        195                 200                 205

Thr Asn Leu Val Thr Asp Phe Thr Lys Asn Asn Ala Ala Tyr Asp Ser
    210                 215                 220

Thr Lys Ala Ser Phe Glu Leu Val Asp Gly Tyr Leu Thr Ala Asp Ser
225                 230                 235                 240

Trp Tyr Arg Pro Lys Glu Ile Leu Glu Ala Gly Thr Thr Trp Lys Ala
                245                 250                 255

Ser Thr Glu Lys Asp Phe Arg Pro Leu Leu Met Ser Trp Trp Pro Asp
                260                 265                 270

Lys Asp Thr Gln Val Ala Tyr Leu Asn Tyr Met Thr Lys Ala Leu Ser
            275                 280                 285

Asn Gly Glu Glu Thr Lys Asp Val Phe Thr Ile Glu Asn Ser Gln Ala
        290                 295                 300

Ser Leu Asn Ala Ala Ala Gln Ile Leu Gln Arg Lys Ile Glu Val Lys
305                 310                 315                 320

Ile Ala Ala Asn Lys Ser Thr Asp Trp Leu Arg Gln Ser Ile Glu Ala
                325                 330                 335

Phe Val Lys Asp Gln Asp Lys Trp Asn Ile Asn Ser Glu Ser Pro Gly
            340                 345                 350

Lys Glu His Phe Gln Lys Gly Ala Leu Leu Phe Val Asn Ser Asp Ser
        355                 360                 365

Thr Lys Trp Ala Asn Ser Asp Tyr Arg Lys Leu Asn Gln Thr Ala Thr
    370                 375                 380

Ser Tyr Ile Lys Asn His Lys Ile Val Asn Gly Ser Asp Gly Gly Tyr
385                 390                 395                 400

Glu Phe Leu Leu Ser Asn Asp Ile Asp Asn Ser Asn Pro Val Val Gln
                405                 410                 415

Ala Glu Met Leu Asn Gln Leu Tyr Tyr Phe Met Asn Trp Gly Gln Ile
            420                 425                 430

Val Phe Gly Asp Lys Asp Lys Asp Ala His Phe Asp Gly Ile Arg Val
        435                 440                 445

Asp Ala Val Asp Asn Val Ser Val Asp Met Leu Gln Leu Val Ser Ser
    450                 455                 460

Tyr Met Lys Ala Ala Tyr Lys Val Asn Glu Ser Glu Ala Arg Ala Leu
465                 470                 475                 480

Ala Asn Ile Ser Ile Leu Glu Ala Trp Ser His Asn Asp Pro Tyr Tyr
                485                 490                 495

Val Asn Glu His Asn Thr Ala Ala Leu Ser Met Asp Asn Gly Leu Arg
            500                 505                 510

Leu Ser Ile Val His Gly Leu Thr Arg Pro Val Thr Asn Lys Gly Thr
        515                 520                 525

Gly Ala Arg Asn Ala Ser Met Lys Asp Leu Ile Asn Gly Gly Tyr Phe
    530                 535                 540

Gly Leu Ser Asn Arg Ala Glu Val Thr Ser Tyr Asp Gln Leu Gly Phe
545                 550                 555                 560

Ala Thr Tyr Leu Phe Val Arg Ala His Asp Ser Glu Val Gln Thr Val
                565                 570                 575

Ile Ala Asp Ile Ile Ser Lys Lys Ile Asp Pro Thr Thr Asp Gly Phe
            580                 585                 590

Thr Phe Thr Leu Asp Gln Leu Lys Gln Ala Phe Asp Ile Tyr Asn Ala
        595                 600                 605

Asp Met Leu Lys Val Asp Lys Glu Tyr Thr His Ser Asn Ile Pro Ala
```

-continued

```
            610                 615                 620
Ala Tyr Ala Leu Met Leu Gln Thr Met Gly Ala Ala Thr Arg Val Tyr
625                 630                 635                 640

Tyr Gly Asp Leu Tyr Thr Asp Asn Gly Gln Tyr Met Ala Lys Lys Ser
                645                 650                 655

Pro Tyr Phe Asp Gln Ile Thr Thr Leu Leu Lys Ala Arg Pro Lys Tyr
                660                 665                 670

Val Ala Gly Gly Gln Thr Ser Tyr Ile His Asn Leu Ala Gly Asp Gly
                675                 680                 685

Val Ser Ser Ala Lys Asp Asn Lys Glu Val Leu Val Ser Val Arg Tyr
            690                 695                 700

Gly Gln Asp Leu Met Ser Lys Thr Asp Thr Glu Gly Gly Lys Tyr Gly
705                 710                 715                 720

Arg Asn Ser Gly Met Leu Thr Leu Ile Ala Asn Asn Pro Asp Leu Lys
                725                 730                 735

Leu Ala Asp Gly Glu Thr Ile Thr Val Asn Met Gly Ala Ala His Lys
                740                 745                 750

Asn Gln Ala Tyr Arg Pro Leu Leu Gly Thr Asp Lys Gly Ile Val
            755                 760                 765

Ser Ser Leu Asn Asp Ser Asp Thr Lys Val Val Lys Tyr Thr Asp Ala
770                 775                 780

Gln Gly Asn Leu Val Phe Thr Ala Asp Glu Ile Lys Gly Phe Lys Thr
785                 790                 795                 800

Val Asp Met Ser Gly Tyr Leu Ser Val Trp Val Pro Val Gly Ala Thr
                805                 810                 815

Asp Asp Gln Asn Val Leu Ala Lys Pro Ser Thr Lys Ala Tyr Lys Glu
                820                 825                 830

Gly Asp Lys Val Tyr Ser Ser Ala Ala Leu Glu Ala Gln Val Ile
            835                 840                 845

Tyr Glu Gly Phe Ser Asn Phe Gln Asp Phe Val Lys Glu Asp Ser Gln
850                 855                 860

Tyr Thr Asn Lys Leu Ile Ala Ala Asn Ala Asp Leu Phe Lys Ser Trp
865                 870                 875                 880

Gly Ile Thr Ser Phe Glu Ile Ala Pro Gln Tyr Val Ser Ser Lys Asp
                885                 890                 895

Gly Thr Phe Leu Asp Ser Ile Ile Glu Asn Gly Tyr Ala Phe Thr Asp
                900                 905                 910

Arg Tyr Asp Phe Ala Met Ser Lys Asn Asn Lys Tyr Gly Ser Lys Glu
            915                 920                 925

Asp Leu Arg Asp Ala Leu Lys Ala Leu His Lys Gln Gly Ile Gln Val
930                 935                 940

Ile Ala Asp Trp Val Pro Asp Gln Leu Tyr Thr Leu Pro Gly Lys Glu
945                 950                 955                 960

Val Val Thr Ala Thr Arg Thr Asp Thr His Gly Lys Val Leu Asp Asp
                965                 970                 975

Thr Ser Leu Val Asn Lys Leu Tyr Val Thr Asn Thr Lys Ser Ser Gly
                980                 985                 990

Asn Asp Phe Gln Ala Gln Tyr Gly  Gly Ala Phe Leu Asp  Lys Leu Gln
            995                 1000                1005

Lys Leu  Tyr Pro Glu Ile Phe   Lys Glu Val Met Glu   Ala Ser Gly
        1010                1015                1020

Lys Thr  Ile Asp Pro Ser Val   Lys Ile Lys Gln Trp   Glu Ala Lys
        1025                1030                1035
```

-continued

```
Tyr Phe Asn Gly Thr Asn Ile Gln Lys Arg Gly Ser Asp Tyr Val
    1040                1045                1050

Leu Ser Asp Gly Lys Leu Tyr Phe Thr Val Asn Asp Lys Gly Thr
    1055                1060                1065

Phe Leu Pro Ala Ala Leu Thr Gly Asp Thr Lys Ala Lys Thr Gly
    1070                1075                1080

Phe Ala Tyr Asp Gly Thr Gly Val Thr Tyr Tyr Thr Thr Ser Gly
    1085                1090                1095

Thr Gln Ala Lys Ser Gln Phe Val Thr Tyr Asn Gly Lys Gln Tyr
    1100                1105                1110

Tyr Phe Asn Asp Lys Gly Tyr Leu Val Thr Gly Glu Gln Thr Ile
    1115                1120                1125

Asp Gly Ser Asn Tyr Phe Leu Pro Asn Gly Val Met Phe Thr
    1130                1135                1140

Asp Gly Val Arg Lys Asn Ala Lys Gly Gln Ser Leu Val Tyr Gly
    1145                1150                1155

Lys Ser Gly Lys Leu Thr Thr Gln Thr Gly Trp Lys Glu Val Thr
    1160                1165                1170

Val Lys Asp Asp Ser Gly Lys Glu Glu Lys Phe Tyr Gln Tyr Phe
    1175                1180                1185

Phe Lys Gly Gly Ile Met Ala Thr Gly Leu Thr Glu Val Glu Gly
    1190                1195                1200

Lys Glu Lys Tyr Phe Tyr Asp Asn Gly Tyr Gln Ala Lys Gly Val
    1205                1210                1215

Phe Val Pro Thr Lys Asp Gly His Leu Met Phe Phe Cys Gly Asp
    1220                1225                1230

Ser Gly Glu Arg Lys Tyr Ser Gly Phe Phe Glu Gln Asp Gly Asn
    1235                1240                1245

Trp Tyr Tyr Ala Asn Asp Lys Gly Tyr Val Ala Thr Gly Phe Thr
    1250                1255                1260

Lys Val Gly Lys Gln Asn Leu Tyr Phe Asn Glu Lys Gly Val Gln
    1265                1270                1275

Val Lys Asn Arg Phe Phe Gln Val Gly Asp Ala Thr Tyr Tyr Ala
    1280                1285                1290

Asn Asn Glu Gly Asp Val Leu Arg Gly Ala Gln Thr Ile Asn Gly
    1295                1300                1305

Asp Glu Leu Tyr Phe Asp Glu Ser Gly Lys Gln Val Lys Gly Glu
    1310                1315                1320

Phe Val Asn Asn Pro Asp Gly Thr Thr Ser Tyr Tyr Asp Ala Ile
    1325                1330                1335

Thr Gly Val Lys Leu Val Asp Thr Ser Leu Val Val Asp Gly Gln
    1340                1345                1350

Thr Phe Asn Val Asp Ala Lys Gly Val Val Thr Lys Ala His Thr
    1355                1360                1365

Pro Gly Phe Tyr Thr Thr Gly Asp Asn Asn Trp Phe Tyr Ala Asp
    1370                1375                1380

Ser Tyr Gly Arg Asn Val Thr Gly Ala Gln Val Ile Asn Gly Gln
    1385                1390                1395

His Leu Tyr Phe Asp Ala Asn Gly Arg Gln Val Lys Gly Gly Phe
    1400                1405                1410

Val Thr Asn Thr Asp Gly Ser Arg Ser Phe Tyr His Trp Asn Thr
    1415                1420                1425
```

```
Gly Asp Lys Leu Val Ser Thr Phe Phe Thr Gly His Asp Arg
    1430            1435            1440

Trp Tyr Tyr Ala Asp Asp Arg Gly Asn Val Val Thr Gly Ala Gln
    1445            1450            1455

Val Ile Asn Gly Gln Lys Leu Phe Phe Asp Thr Asp Gly Lys Gln
    1460            1465            1470

Val Lys Gly Ala Phe Ala Thr Asn Ala Asn Gly Ser Arg Ser Tyr
    1475            1480            1485

Tyr His Trp Asn Thr Gly Asn Lys Leu Val Ser Thr Phe Phe Thr
    1490            1495            1500

Ser Gly Asp Asn Asn Trp Tyr Ala Asp Ala Lys Gly Glu Val
    1505            1510            1515

Val Val Gly Glu Gln Thr Ile Asn Gly Gln His Leu Tyr Phe Asp
    1520            1525            1530

Gln Thr Gly Lys Gln Val Lys Gly Ala Thr Ala Thr Asn Pro Asp
    1535            1540            1545

Gly Ser Ile Ser Tyr Tyr Asp Val His Thr Gly Glu Lys Ala Ile
    1550            1555            1560

Asn Arg Trp Val Lys Ile Pro Ser Gly Gln Trp Val Tyr Phe Asn
    1565            1570            1575

Ala Gln Gly Lys Gly Tyr Val Ser Asn
    1580            1585

<210> SEQ ID NO 11
<211> LENGTH: 1414
<212> TYPE: PRT
<213> ORGANISM: Streptococcus sobrinus

<400> SEQUENCE: 11

Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Ser Ala Ile Asp Gly
                20                  25                  30

Lys Tyr Tyr Tyr Val Gln Ala Asp Gly Ser Tyr Lys Lys Asn Phe Ala
            35                  40                  45

Ile Thr Val Asn Gly Gln Met Leu Tyr Phe Asp Ser Asp Thr Gly Ala
        50                  55                  60

Leu Ser Ser Thr Ser Thr Tyr Ser Phe Ser Gln Gly Thr Thr Asn Leu
65                  70                  75                  80

Val Asp Asp Phe Ser Ser His Asn Lys Ala Tyr Asp Ser Thr Ala Lys
                85                  90                  95

Ser Phe Glu Leu Val Asn Gly Tyr Leu Thr Ala Asn Ser Trp Tyr Arg
                100                 105                 110

Pro Ala Gly Ile Leu Arg Asn Gly Gln Thr Trp Glu Ala Ser Asn Glu
            115                 120                 125

Asn Asp Leu Arg Pro Val Leu Met Ser Trp Trp Pro Asp Lys Asp Thr
        130                 135                 140

Gln Val Ala Tyr Val Asn Tyr Met Asn Lys Tyr Leu Ser Ala Asn Glu
145                 150                 155                 160

Thr Glu Val Thr Asn Glu Thr Ser Gln Val Asp Leu Asn Lys Glu Ala
                165                 170                 175

Gln Ser Ile Gln Thr Lys Ile Glu Gln Lys Ile Thr Ser Asp Asn Ser
                180                 185                 190

Thr Gln Trp Leu Arg Thr Ala Met Glu Ala Phe Val Ala Ala Gln Pro
            195                 200                 205
```

-continued

```
Lys Trp Asn Met Ser Thr Glu Asn Phe Asn Lys Gly Asp His Leu Gln
210                 215                 220
Gly Gly Ala Leu Leu Tyr Thr Asn Ser Asp Leu Thr Pro Trp Ala Asn
225                 230                 235                 240
Ser Asp Tyr Arg Leu Leu Asn Arg Thr Pro Thr Gln Gln Asp Gly Thr
                245                 250                 255
Lys Lys Tyr Phe Thr Glu Gly Gly Glu Gly Tyr Glu Phe Leu Leu
                260                 265                 270
Ser Asn Asp Val Asp Asn Ser Asn Pro Val Val Gln Ala Glu Gln Leu
                275                 280                 285
Asn Gln Leu His Tyr Leu Met Asn Trp Gly Asp Ile Val Met Gly Asp
                290                 295                 300
Lys Asp Ala Asn Phe Asp Gly Val Arg Val Asp Ala Val Asp Asn Val
305                 310                 315                 320
Asn Ala Asp Leu Leu Gln Val Tyr Ser Asn Tyr Phe Lys Asp Asn Tyr
                325                 330                 335
Lys Val Thr Asp Ser Glu Ala Asn Ala Leu Ala His Ile Ser Ile Leu
                340                 345                 350
Glu Ala Trp Ser Leu Asn Asp Asn Gln Tyr Asn Glu Asp Thr Asn Gly
                355                 360                 365
Thr Ala Leu Ser Ile Asp Asn Ser Ser Arg Leu Thr Ser Leu Ala Val
                370                 375                 380
Leu Thr Lys Gln Pro Gly Gln Arg Ile Asp Leu Ser Asn Leu Ile Ser
385                 390                 395                 400
Glu Ser Val Asn Lys Glu Arg Ala Asn Asp Thr Ala Tyr Gly Asp Thr
                405                 410                 415
Ile Pro Thr Tyr Ser Phe Val Arg Ala His Asp Ser Glu Val Gln Thr
                420                 425                 430
Val Ile Ala Lys Ile Val Lys Glu Lys Ile Asp Thr Asn Ser Asp Gly
                435                 440                 445
Tyr Thr Phe Thr Leu Asp Gln Leu Lys Asp Ala Phe Lys Ile Tyr Asn
                450                 455                 460
Glu Asp Met Ala Lys Val Asn Lys Thr Tyr Thr His Tyr Asn Ile Pro
465                 470                 475                 480
Ala Ala Tyr Ala Leu Leu Leu Ser Asn Met Glu Ser Val Pro Arg Val
                485                 490                 495
Tyr Tyr Gly Asp Leu Tyr Thr Asp Asp Gly Gln Tyr Met Ala Lys Lys
                500                 505                 510
Ser Pro Tyr Tyr Asp Ala Ile Ala Thr Met Leu Gln Gly Arg Ile Ala
                515                 520                 525
Tyr Val Ser Gly Gly Gln Ser Glu Glu Val His Lys Val Asn Gly Asn
                530                 535                 540
Asn Gln Ile Leu Ser Ser Val Arg Tyr Gly Gln Asp Leu Met Ser Ala
545                 550                 555                 560
Asp Asp Thr Gln Gly Thr Asp Leu Ser Arg Thr Ser Gly Leu Val Thr
                565                 570                 575
Leu Val Ser Asn Asp Pro Asn Leu Asp Leu Gly Gly Asp Ser Leu Thr
                580                 585                 590
Val Asn Met Gly Arg Ala His Ala Asn Gln Ala Tyr Arg Pro Leu Ile
                595                 600                 605
Leu Gly Thr Lys Asp Gly Val Gln Ser Tyr Leu Lys Asp Ser Asp Thr
610                 615                 620
```

```
Asn Ile Val Lys Tyr Thr Asp Ala Asn Gly Asn Leu Thr Phe Thr Ala
625                 630                 635                 640

Asp Asp Ile Lys Gly Tyr Ser Thr Val Asp Met Ser Gly Tyr Leu Ala
            645                 650                 655

Val Trp Val Pro Val Gly Ala Lys Asp Gly Gln Asp Val Arg Val Ala
                660                 665                 670

Ala Asp Thr Asn Gln Lys Ala Asp Gly Lys Ser Leu Lys Thr Ser Ala
            675                 680                 685

Ala Leu Asp Ser Gln Val Ile Tyr Glu Gly Phe Ser Asn Phe Gln Asp
690                 695                 700

Phe Ala Asn Asn Asp Ala Asp Tyr Thr Asn Lys Lys Ile Ala Glu Asn
705                 710                 715                 720

Ala Asp Phe Phe Lys Lys Leu Gly Ile Thr Ser Phe Glu Met Ala Pro
            725                 730                 735

Gln Tyr Val Ser Ala Thr Asp Gly Ser Phe Leu Asp Ser Ile Ile Gln
                740                 745                 750

Asn Gly Tyr Ala Phe Ser Asp Arg Tyr Asp Leu Ala Met Ser Lys Asn
            755                 760                 765

Asn Lys Tyr Gly Ser Lys Asp Leu Ala Asn Ala Leu Lys Ala Leu
770                 775                 780

His Ala Asn Gly Ile Gln Ala Ile Ala Asp Trp Val Pro Asp Gln Ile
785                 790                 795                 800

Tyr Gln Leu Pro Gly Glu Glu Val Val Thr Ala Lys Arg Thr Asn Ser
                805                 810                 815

Tyr Gly Asn Pro Thr Phe Asp Ala Tyr Ile Asn Asn Ala Leu Tyr Ala
            820                 825                 830

Thr Asn Thr Lys Ser Ser Gly Ser Asp Tyr Gln Ala Gln Tyr Gly Gly
            835                 840                 845

Ala Phe Leu Asp Glu Leu Lys Ala Lys Tyr Pro Asp Met Phe Thr Val
850                 855                 860

Asn Met Ile Ser Thr Gly Lys Pro Ile Asp Pro Ser Thr Lys Ile Lys
865                 870                 875                 880

Gln Trp Glu Ala Lys Tyr Phe Asn Gly Thr Asn Val Leu Gly Lys Gly
                885                 890                 895

Ala Gly Tyr Val Leu Ser Asp Asp Ala Thr Gly Lys Tyr Phe Thr Val
            900                 905                 910

Asn Glu Asn Gly Asp Phe Leu Pro Ala Ser Phe Thr Gly Asp Gln Asn
            915                 920                 925

Ala Lys Thr Gly Phe Tyr Tyr Asp Gly Thr Gly Met Ala Tyr Tyr Ser
930                 935                 940

Thr Ser Gly Asn Lys Ala Val Asn Ser Phe Ile Tyr Glu Gly Gly His
945                 950                 955                 960

Tyr Tyr Tyr Phe Asp Lys Asp Gly His Met Val Thr Gly Ser Tyr Lys
                965                 970                 975

Ala Glu Asp Gly Asn Asp Tyr Tyr Phe Leu Pro Asn Gly Ile Gln Met
            980                 985                 990

Arg Asp Ala Ile Tyr Gln Asp Ala Gln Gly Asn Ser Tyr Tyr Tyr Gly
            995                1000                1005

Arg Thr Gly Ile Leu Tyr Lys Gly Asp Asn Trp Tyr Pro Phe Val
            1010                1015                1020

Asp Pro Asn Asn Ala Asn Lys Thr Val Phe Arg Tyr Phe Asp Ala
            1025                1030                1035

Asn Asn Val Met Ala Ile Gly Tyr Arg Asn Met Tyr Gly Gln Thr
```

```
            1040                1045                1050
Tyr Tyr Phe Asp Glu Asn Gly Phe Gln Ala Lys Gly Gln Leu Leu
            1055                1060                1065

Thr Asp Asp Lys Gly Thr His Tyr Phe Asp Glu Asp Asn Gly Ala
            1070                1075                1080

Met Ala Lys Asn Lys Phe Val Asn Val Gly Asp Asp Trp Tyr Tyr
            1085                1090                1095

Met Asp Gly Asn Gly Asn Ala Val Lys Gly Gln Tyr Pro Val Asn
            1100                1105                1110

Asn Gln Ile Leu Tyr Phe Asn Pro Glu Thr Gly Val Gln Val Lys
            1115                1120                1125

Gly Gln Phe Ile Thr Asp Ala Gln Gly Arg Thr Ser Tyr Tyr Asp
            1130                1135                1140

Ala Asn Ser Gly Ala Leu Lys Ser Ser Gly Phe Phe Thr Pro Asn
            1145                1150                1155

Gly Ser Asp Trp Tyr Tyr Ala Glu Asn Gly Tyr Val Tyr Lys Gly
            1160                1165                1170

Phe Lys Gln Val Ala Glu Asn Gln Asp Gln Trp Tyr Tyr Phe Asp
            1175                1180                1185

Gln Thr Thr Gly Lys Gln Ala Lys Gly Ala Ala Lys Val Asp Gly
            1190                1195                1200

Arg Asp Leu Tyr Phe Asn Pro Asp Ser Gly Val Gln Val Lys Gly
            1205                1210                1215

Asp Phe Ala Thr Asp Glu Ser Gly Asn Thr Ser Phe Tyr His Gly
            1220                1225                1230

Asp Asn Gly Asp Lys Val Val Gly Gly Phe Phe Thr Thr Gly Asn
            1235                1240                1245

Asn Ala Trp Tyr Tyr Ala Asp Asn Asn Gly Asn Leu Val Lys Gly
            1250                1255                1260

Phe Gln Glu Ile Asp Gly Lys Trp Tyr His Phe Asp Glu Val Thr
            1265                1270                1275

Gly Gln Gln Ala Lys Gly Ala Ala Leu Val Asn Gly Gln Gln Leu
            1280                1285                1290

Tyr Phe Asp Val Asp Ser Gly Ile Gln Val Lys Gly Asp Phe Val
            1295                1300                1305

Thr Asp Gly Gln Gly Asn Thr Ser Tyr Tyr Asp Val Asn Ser Gly
            1310                1315                1320

Asp Lys Lys Val Asn Gly Phe Phe Thr Thr Gly Asp Asn Ala Trp
            1325                1330                1335

Tyr Tyr Ala Asp Gly Gln Gly Asn Leu Ala Lys Gly Arg Lys Ser
            1340                1345                1350

Ile Asp Asn Gln Asp Leu Tyr Phe Asp Pro Ala Thr Gly Lys Gln
            1355                1360                1365

Val Lys Gly Gln Leu Val Ser Ile Asp Gly Arg Asn Tyr Tyr Phe
            1370                1375                1380

Asp Ser Gly Ser Gly Asn Met Ala Lys Asn Arg Phe Val Arg Ile
            1385                1390                1395

Gly Asp Gln Trp Ile Tyr Phe Gly Asn Asp Gly Ala Ala Thr Asn
            1400                1405                1410

Leu

<210> SEQ ID NO 12
<211> LENGTH: 1267
```

```
<212> TYPE: PRT
<213> ORGANISM: Streptococcus mutans

<400> SEQUENCE: 12

Met Val Asn Gly Lys Tyr Tyr Tyr Lys Glu Asp Gly Thr Leu Gln
1               5                   10                  15

Lys Asn Tyr Ala Leu Asn Ile Asn Gly Lys Thr Phe Phe Asp Glu
                20                  25                  30

Thr Gly Ala Leu Ser Asn Thr Leu Pro Ser Lys Lys Gly Asn Ile
            35                  40                  45

Thr Asn Asn Asp Asn Thr Asn Ser Phe Ala Gln Tyr Asn Gln Val Tyr
    50                  55                  60

Ser Thr Asp Ala Ala Asn Phe Glu His Val Asp His Tyr Leu Thr Ala
65                  70                  75                  80

Glu Ser Trp Tyr Arg Pro Lys Tyr Ile Leu Lys Asp Gly Lys Thr Trp
                85                  90                  95

Thr Gln Ser Thr Glu Lys Asp Phe Arg Pro Leu Leu Met Thr Trp Trp
                100                 105                 110

Pro Asp Gln Glu Thr Gln Arg Gln Tyr Val Asn Tyr Met Asn Ala Gln
            115                 120                 125

Leu Gly Ile His Gln Thr Tyr Asn Thr Ala Thr Ser Pro Leu Gln Leu
130                 135                 140

Asn Leu Ala Ala Gln Thr Ile Gln Thr Lys Ile Glu Glu Lys Ile Thr
145                 150                 155                 160

Ala Glu Lys Asn Thr Asn Trp Leu Arg Gln Thr Ile Ser Ala Phe Val
                165                 170                 175

Lys Thr Gln Ser Ala Trp Asn Ser Asp Ser Glu Lys Pro Phe Asp Asp
                180                 185                 190

His Leu Gln Lys Gly Ala Leu Leu Tyr Ser Asn Asn Ser Lys Leu Thr
            195                 200                 205

Ser Gln Ala Asn Ser Asn Tyr Arg Ile Leu Asn Arg Thr Pro Thr Asn
210                 215                 220

Gln Thr Gly Lys Lys Asp Pro Arg Tyr Thr Ala Asp Arg Thr Ile Gly
225                 230                 235                 240

Gly Tyr Glu Phe Leu Leu Ala Asn Asp Val Asp Asn Ser Asn Pro Val
                245                 250                 255

Val Gln Ala Glu Gln Leu Asn Trp Leu His Phe Leu Met Asn Phe Gly
            260                 265                 270

Asn Ile Tyr Ala Asn Asp Pro Asp Ala Asn Phe Asp Ser Ile Arg Val
            275                 280                 285

Asp Ala Val Asp Asn Val Asp Ala Asp Leu Leu Gln Ile Ala Gly Asp
290                 295                 300

Tyr Leu Lys Ala Ala Lys Gly Ile His Lys Asn Asp Lys Ala Ala Asn
305                 310                 315                 320

Asp His Leu Ser Ile Leu Glu Ala Trp Ser Tyr Asn Asp Thr Pro Tyr
                325                 330                 335

Leu His Asp Asp Gly Asp Asn Met Ile Asn Met Asp Asn Arg Leu Arg
            340                 345                 350

Leu Ser Leu Leu Tyr Ser Leu Ala Lys Pro Leu Asn Gln Arg Ser Gly
            355                 360                 365

Met Asn Pro Leu Ile Thr Asn Ser Leu Val Asn Arg Thr Asp Asp Asn
            370                 375                 380

Ala Glu Thr Ala Ala Val Pro Ser Tyr Ser Phe Ile Arg Ala His Asp
385                 390                 395                 400
```

```
Ser Glu Val Gln Asp Leu Ile Arg Asn Ile Ile Arg Ala Glu Ile Asn
            405                 410                 415

Pro Asn Val Val Gly Tyr Ser Phe Thr Met Glu Ile Lys Lys Ala
                420                 425                 430

Phe Glu Ile Tyr Asn Lys Asp Leu Leu Ala Thr Glu Lys Lys Tyr Thr
        435                 440                 445

His Tyr Asn Thr Ala Leu Ser Tyr Ala Leu Leu Thr Asn Lys Ser
    450                 455                 460

Ser Val Pro Arg Val Tyr Tyr Gly Asp Met Phe Thr Asp Asp Gly Gln
465                 470                 475                 480

Tyr Met Ala His Lys Thr Ile Asn Tyr Glu Ala Ile Glu Thr Leu Leu
                485                 490                 495

Lys Ala Arg Ile Lys Tyr Val Ser Gly Gln Ala Met Arg Asn Gln
                500                 505                 510

Gln Val Gly Asn Ser Glu Ile Ile Thr Ser Val Arg Tyr Gly Lys Gly
                515                 520                 525

Ala Leu Lys Ala Thr Asp Thr Gly Asp Arg Thr Thr Arg Thr Ser Gly
        530                 535                 540

Val Ala Val Ile Glu Gly Asn Asn Pro Ser Leu Arg Leu Lys Ala Ser
545                 550                 555                 560

Asp Arg Val Val Asn Met Gly Ala Ala His Lys Asn Gln Ala Tyr
                565                 570                 575

Arg Pro Leu Leu Leu Thr Thr Asp Asn Gly Ile Lys Ala Tyr His Ser
                580                 585                 590

Asp Gln Glu Ala Ala Gly Leu Val Arg Tyr Thr Asn Asp Arg Gly Glu
        595                 600                 605

Leu Ile Phe Thr Ala Ala Asp Ile Lys Gly Tyr Ala Asn Pro Gln Val
        610                 615                 620

Ser Gly Tyr Leu Gly Val Trp Val Pro Val Gly Ala Ala Ala Asp Gln
625                 630                 635                 640

Asp Val Arg Val Ala Ala Ser Thr Ala Pro Ser Thr Asp Gly Lys Ser
                645                 650                 655

Val His Gln Asn Ala Ala Leu Asp Ser Arg Val Met Phe Glu Gly Phe
                660                 665                 670

Ser Asn Phe Gln Ala Phe Ala Thr Lys Lys Glu Glu Tyr Thr Asn Val
                675                 680                 685

Val Ile Ala Lys Asn Val Asp Lys Phe Ala Glu Trp Gly Val Thr Asp
        690                 695                 700

Phe Glu Met Ala Pro Gln Tyr Val Ser Ser Thr Asp Gly Ser Phe Leu
705                 710                 715                 720

Asp Ser Val Ile Gln Asn Gly Tyr Ala Phe Thr Asp Arg Tyr Asp Leu
                725                 730                 735

Gly Ile Ser Lys Pro Asn Lys Tyr Gly Thr Ala Asp Asp Leu Val Lys
                740                 745                 750

Ala Ile Lys Ala Leu His Ser Lys Gly Ile Lys Val Met Ala Asp Trp
        755                 760                 765

Val Pro Asp Gln Met Tyr Ala Phe Pro Glu Lys Glu Val Val Thr Ala
        770                 775                 780

Thr Arg Val Asp Lys Tyr Gly Thr Pro Val Ala Gly Ser Gln Ile Lys
785                 790                 795                 800

Asn Thr Leu Tyr Val Val Asp Gly Lys Ser Ser Gly Lys Asp Gln Gln
                805                 810                 815
```

```
Ala Lys Tyr Gly Gly Ala Phe Leu Glu Glu Leu Gln Ala Lys Tyr Pro
            820                 825                 830

Glu Leu Phe Ala Arg Lys Gln Ile Ser Thr Gly Val Pro Met Asp Pro
            835                 840                 845

Ser Val Lys Ile Lys Gln Trp Ser Ala Lys Tyr Phe Asn Gly Thr Asn
        850                 855                 860

Ile Leu Gly Arg Gly Ala Gly Tyr Val Leu Lys Asp Gln Ala Thr Asn
865                 870                 875                 880

Thr Tyr Phe Ser Leu Val Ser Asp Asn Thr Phe Leu Pro Lys Ser Leu
                885                 890                 895

Val Asn Pro Asn His Gly Thr Ser Ser Ser Val Thr Gly Leu Val Phe
            900                 905                 910

Asp Gly Lys Gly Tyr Val Tyr Tyr Ser Thr Ser Gly Tyr Gln Ala Lys
            915                 920                 925

Asn Thr Phe Ile Ser Leu Gly Asn Asn Trp Tyr Tyr Phe Asp Asn Asn
        930                 935                 940

Gly Tyr Met Val Thr Gly Ala Gln Ser Ile Asn Gly Ala Asn Tyr Tyr
945                 950                 955                 960

Phe Leu Ser Asn Gly Ile Gln Leu Arg Asn Ala Ile Tyr Asp Asn Gly
                965                 970                 975

Asn Lys Val Leu Ser Tyr Tyr Gly Asn Asp Gly Arg Arg Tyr Glu Asn
            980                 985                 990

Gly Tyr Tyr Leu Phe Gly Gln Gln  Trp Arg Tyr Phe Gln Asn Gly Ile
            995                 1000                1005

Met Ala Val Gly Leu Thr Arg Val His Gly Ala Val  Gln Tyr Phe
1010                1015                1020

Asp Ala Ser Gly Phe Gln Ala Lys Gly Gln Phe Ile  Thr Thr Ala
1025                1030                1035

Asp Gly Lys Leu Arg Tyr Phe Asp Arg Asp Ser Gly  Asn Gln Ile
1040                1045                1050

Ser Asn Arg Phe Val Arg Asn Ser Lys Gly Glu Trp  Phe Leu Phe
1055                1060                1065

Asp His Asn Gly Val Ala Val Thr Gly Thr Val Thr  Phe Asn Gly
1070                1075                1080

Gln Arg Leu Tyr Phe Lys Pro Asn Gly Val Gln Ala  Lys Gly Glu
1085                1090                1095

Phe Ile Arg Asp Ala Asp Gly His Leu Arg Tyr Tyr  Asp Pro Asn
1100                1105                1110

Ser Gly Asn Glu Val Arg Asn Arg Phe Val Arg Asn  Ser Lys Gly
1115                1120                1125

Glu Trp Phe Leu Phe Asp His Asn Gly Ile Ala Val  Thr Gly Ala
1130                1135                1140

Arg Val Val Asn Gly Gln Arg Leu Tyr Phe Lys Ser  Asn Gly Val
1145                1150                1155

Gln Ala Lys Gly Glu Leu Ile Thr Glu Arg Lys Gly  Arg Ile Lys
1160                1165                1170

Tyr Tyr Asp Pro Asn Ser Gly Asn Glu Val Arg Asn  Arg Tyr Val
1175                1180                1185

Arg Thr Ser Ser Gly Asn Trp Tyr Tyr Phe Gly Asn  Asp Gly Tyr
1190                1195                1200

Ala Leu Ile Gly Trp His Val Val Glu Gly Arg Arg  Val Tyr Phe
1205                1210                1215

Asp Glu Asn Gly Val Tyr Arg Tyr Ala Ser His Asp  Gln Arg Asn
```

```
                1220                1225                1230
His Trp Asn Tyr Asp Tyr Arg Arg Asp Phe Gly Arg Gly Ser Ser
            1235                1240                1245

Ser Ala Ile Arg Phe Arg His Ser Arg Asn Gly Phe Phe Asp Asn
            1250                1255                1260

Phe Phe Arg Phe
        1265

<210> SEQ ID NO 13
<211> LENGTH: 1646
<212> TYPE: PRT
<213> ORGANISM: Lactobacillus animalis

<400> SEQUENCE: 13

Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Gly Lys
                20                  25                  30

Asp Glu Thr Ser Ser Asn Glu Thr Gln Thr Glu Gln Thr Leu Asn
            35                  40                  45

Thr Asp Glu Ser Thr Asp Thr Thr Thr Asp Val Ser Asn Glu Ala Lys
50                  55                  60

Ala Thr Glu Ala Gln Leu Thr Thr Gln Asp Ala Asp Met Ala Ser Ser
65                  70                  75                  80

Glu Glu Lys Thr Thr Asn Val Glu Lys Glu Val Thr Thr Ala Glu Thr
                85                  90                  95

Asn Lys Asp Thr Thr Val Lys Asn Val Glu Ser Ser Glu Gln Asn Thr
            100                 105                 110

Thr Thr Val Ala Asp Lys Asn Ala Val Asp Ser Thr Ala Gln Val Asn
            115                 120                 125

Thr Ala Glu Lys Glu Asn Lys Tyr Thr Gln Glu Asn Val Asn Gly Asn
    130                 135                 140

Trp Tyr Leu Lys Asp Glu Gln Gly Asn Tyr Leu Thr Gly Phe Gln Glu
145                 150                 155                 160

Ile Lys Asp Gln Asn Lys Thr Val Tyr Tyr Asn Pro Asp Ser Lys Gln
                165                 170                 175

Met Val Tyr Gly Gln Gln Asn Ile Asn Gly Asn Trp Tyr Leu Phe Asp
            180                 185                 190

Thr Phe Asn Gly Ala Met Gln Thr Gly Leu Gln Tyr Ile Arg Asp Gln
            195                 200                 205

Lys Lys Leu Ala Tyr Tyr Asn Glu Gly Gln Met Gln Tyr Gly Thr
    210                 215                 220

Val Glu Ile Asp Gly Gln Lys Tyr Gln Ala Asp Thr Phe Asn Gly Ala
225                 230                 235                 240

Ile Lys Gly Lys Gly Gln Thr Lys Ile Ala Asp Asn Trp Tyr Leu Phe
                245                 250                 255

Asn Asn Ala Gly Gln Val Val Asp Gly Trp Gln Trp Ile Asn Asp Gln
            260                 265                 270

Gly Lys Thr Val Tyr Tyr Ser Thr Lys Thr Ala Gln Met Val His Gly
        275                 280                 285

Gln Gln Asn Ile Asn Gly His Trp Tyr Leu Phe Asp Lys Thr Thr Gly
    290                 295                 300

Ala Met Gln Arg Gly Phe Gln Asn Leu Lys Ala Tyr Gly Asp Asp Lys
305                 310                 315                 320
```

-continued

```
Thr Val Tyr Tyr Asn Gln Asp Gly Trp Met Leu Tyr Gly Gln Gln Lys
                325                 330                 335

Ile Asp Asn Lys Trp Tyr Asn Phe Asp Thr Phe Asn Gly Ala Met Lys
            340                 345                 350

Thr Gly Phe Val Lys Ile Pro Glu Gln Asn Lys Thr Val Tyr Tyr Ala
        355                 360                 365

Pro Asn Gly Gln Met Gln Tyr Gly Trp Gln Trp Val Asp Asn Ala Thr
370                 375                 380

Arg Tyr Phe Asp Thr Phe Asn Gly Ala Met Ala Thr Gly Gln Lys Leu
385                 390                 395                 400

Ile Thr Gly His Trp Tyr Leu Phe Asp Asn Asn Gly Ala Met Gln Arg
                405                 410                 415

Gly Phe Gln Asn Leu Lys Asn Tyr Gly Asp Asn Lys Thr Val Tyr Tyr
            420                 425                 430

Asn Gln Asp Gly Trp Met Leu Tyr Gly Trp Gln Trp Val Asn Asn Ala
        435                 440                 445

Thr Arg Tyr Phe Asp Thr Phe Asn Gly Ala Met Thr Thr Gly Gln Lys
450                 455                 460

Lys Ile Asn Asp His Trp Tyr Leu Phe Asp Lys Asp Gly Ala Met Gln
465                 470                 475                 480

Arg Gly Ile Gln Tyr Ile Pro Glu Glu Asn Lys Leu Val Tyr Tyr Asn
                485                 490                 495

Gln Asp Gly Trp Met Leu Tyr Gly Lys Gln Asn Ile Asn Gly Val Asp
            500                 505                 510

His Asn Phe Asn Thr Phe Asn Gly Ala Leu Glu Ala Lys Gly Gln Val
        515                 520                 525

Lys Val Gly Asn Asn Trp Tyr Leu Phe Asn Asn Ser Gly Thr Ile Gln
530                 535                 540

Thr Gly Phe Gln Asp Leu Lys Ala Tyr Gly Gln Asp Lys Val Val Tyr
545                 550                 555                 560

Tyr Asp Pro Lys Thr Ala Ala Met Val Tyr Gly Tyr Gln Asn Ile Asp
                565                 570                 575

Gly Asn Trp Tyr Leu Phe Ser Arg Ala Asn Gly Ser Met Gln Arg Gly
            580                 585                 590

Leu Gln Asn Val Asn Gly Val Asp Leu Leu Phe Asp Glu Lys Thr Gly
        595                 600                 605

Ala Leu Leu Thr Gly Val Gln Asn Ile Lys Gly Asn Asn Tyr Phe Val
        610                 615                 620

Asp Lys Arg Ser Gly Asn Ile Lys Lys Asn Leu Val Val Leu Gly Ala
625                 630                 635                 640

Asp Asn Lys Trp Met Tyr Phe Asp Ala Lys Thr Gly Lys Gly Thr Asn
                645                 650                 655

Thr Leu Glu Asp Gln Tyr Lys Lys Gly Val Val Ser Gly Asn Val Glu
            660                 665                 670

Phe Ile Thr Asn Asn Ala Ala Tyr Ser Phe Asp Gly Asn Ser Phe Glu
        675                 680                 685

Asn Ile Asn Gly Phe Leu Thr Ala Asp Ser Trp Tyr Arg Pro Lys Ser
        690                 695                 700

Ile Leu Lys Asp Gly Ser Thr Trp Thr Ala Thr Glu Thr Asp Leu
705                 710                 715                 720

Arg Pro Leu Leu Met Thr Trp Trp Pro Asn Glu Gln Ile Lys Ala Asn
                725                 730                 735

Tyr Leu Asn Tyr Met Lys Asp Lys Gly Phe Ile Asn Asn Ser Gly Thr
```

```
              740                 745                 750
Tyr Asn Ala Glu Ser Asp Pro Asn Tyr Met Asp Phe Ala Ala Gln Glu
                755                 760                 765

Ala Gln Arg Asn Ile Glu Arg Lys Ile Thr Lys Glu Asn Asp Thr Thr
            770                 775                 780

Trp Leu Arg Asp Leu Ile Thr Asp Phe Ile Lys Thr Gln Asp Ile Trp
785                 790                 795                 800

Asn Glu Gln Ser Glu Gly Val Ser Thr Glu Gly Leu Gln Lys Phe Gln
                805                 810                 815

Gly Gly Phe Leu Lys Tyr Val Asn Ser Glu Leu Thr Pro Tyr Ala Asn
                820                 825                 830

Ser Glu Trp Arg Lys Leu Gly Tyr Gln Pro Thr Met Leu Thr Gln Asn
            835                 840                 845

Asn Val Gly Ala Glu Phe Leu Leu Ala Asn Asp Ile Asp Asn Ser Asn
        850                 855                 860

Pro Val Gln Ala Glu Gln Leu Asn Trp Leu His Phe Leu Met Asn
865                 870                 875                 880

Phe Gly Thr Ile Thr Ala Asn Asp Pro Ser Ala Asn Phe Asp Gly Ile
                885                 890                 895

Arg Ile Asp Ala Val Asp Asn Val Asp Ala Ser Leu Leu Ser Ile Ala
                900                 905                 910

Gly Asp Tyr Phe Lys Ala Ala Tyr Lys Val Gly Gln Asn Asp Ala Thr
                915                 920                 925

Ala Asn Lys His Ile Ser Ile Leu Glu Asp Trp Asn Asp Lys Asp Pro
            930                 935                 940

Glu Tyr Val Asn Ser Ile Gly Asn Pro Gln Leu Thr Met Asp Asp Tyr
945                 950                 955                 960

Ile Val Gln Gln Leu Lys Phe Ser Leu Gly Gln Ala Pro Asp Lys Val
                965                 970                 975

Asp Arg Met Gln Arg Phe Lys Glu Trp Tyr Leu Val Ser Arg Ser Lys
            980                 985                 990

Asp Asn Thr Glu Asn Thr Ala Ile Pro Asn Tyr Ser Phe Val Arg Ala
            995                1000                1005

His Asp Ala Ser Val Gln Glu Asp Ile Leu Gln Leu Ile Gln Asp
       1010                1015                1020

Thr Thr Gly Lys Pro Trp Gly Val Tyr Thr Asn Glu Glu Leu Gln
       1025                1030                1035

Gln Gly Leu Lys Asp Tyr Met Ala Asp Gln Lys Leu Thr Asn Lys
       1040                1045                1050

Lys Tyr Asn Arg Tyr Asn Ile Pro Ser Ser Tyr Ala Ile Leu Leu
       1055                1060                1065

Thr Asn Lys Asp Thr Ile Pro Arg Val Tyr Tyr Gly Asp Leu Tyr
       1070                1075                1080

Ser Asp Ala Gly Lys Tyr Met Ala Glu Lys Ser Ile Tyr Phe Asp
       1085                1090                1095

Ala Ile Asp Asn Leu Leu Lys Thr Arg Thr Lys Tyr Val Ala Gly
       1100                1105                1110

Gly Gln Thr Leu Asp Val Asp Gly His Asp Ile Leu Thr Ser Val
       1115                1120                1125

Arg Phe Gly Lys Gly Ala Leu Asn Val Thr Asp Lys Gly Thr Ser
       1130                1135                1140

Glu Thr Arg Thr Gln Gly Met Gly Leu Ile Ile Ser Asn Asn Asn
       1145                1150                1155
```

```
Ser Leu Lys Leu Asn Asp Gly Glu Lys Val Val Leu His Met Gly
    1160                1165            1170

Ala Ala His Lys Asn Gln Ala Tyr Arg Ala Val Met Leu Ser Ser
    1175                1180            1185

Ala Asn Gly Leu Ile Asn Tyr Thr Ser Asp Ala Asn Ala Pro Val
    1190                1195            1200

Val Tyr Thr Asn Asn Asp Gly Asp Leu Ile Phe Thr Asn Lys Asp
    1205                1210            1215

Val Val Thr Asn Gly Lys Val Gln Ala Asn Thr Ala Ile Lys Gly
    1220                1225            1230

Val Met Asn Pro Tyr Val Ser Gly Tyr Leu Ala Met Trp Val Pro
    1235                1240            1245

Val Gly Ala Ser Ala Thr Gln Asp Ala Arg Thr Ala Ala Ser Thr
    1250                1255            1260

Lys Thr Thr Thr Asp Gly Ser Val Phe His Ser Asn Ala Ala Leu
    1265                1270            1275

Asp Ser Asn Leu Ile Tyr Glu Gly Phe Ser Asn Phe Gln Ala Phe
    1280                1285            1290

Pro Glu Asn Ala Ser Glu Asn Ala Asn Ala Ile Ile Ala Gln Asn
    1295                1300            1305

Val Asp Leu Phe Asn Ser Trp Gly Val Thr Ser Phe Gln Leu Ala
    1310                1315            1320

Pro Gln Tyr Val Ser Ser His Asp Gly Ser Phe Leu Asp Ser Ile
    1325                1330            1335

Ile Asp Asn Gly Tyr Ala Phe Thr Asp Arg Tyr Asp Leu Ala Met
    1340                1345            1350

Ser Lys Asn Asn Lys Tyr Gly Ser Tyr Gln Asp Leu Val Asn Val
    1355                1360            1365

Leu Lys Ala Leu His Ala Gly Ile Gln Val Ile Ala Asp Trp
    1370                1375            1380

Val Pro Asp Gln Ile Tyr Ser Leu Pro Gly Lys Glu Val Val Ser
    1385                1390            1395

Val Val Arg Ser Asp Glu Phe Gly Asn Lys Val Asp Gly Thr Gln
    1400                1405            1410

Ile Asp Asn Thr Leu Tyr Val Val Asn Thr Ile Gly Gly Gly Gln
    1415                1420            1425

Tyr Gln Lys Glu Tyr Gly Gly Arg Tyr Leu Glu Glu Leu Lys Gln
    1430                1435            1440

Lys Tyr Pro Glu Leu Phe Lys Thr Lys Gln Pro Ser Thr Gly Val
    1445                1450            1455

Thr Ile Asp Pro Ser Glu Lys Ile Thr Glu Trp Ser Ala Lys Tyr
    1460                1465            1470

Leu Asn Gly Thr Asn Ile Leu His Arg Gly Ala Glu Phe Val Leu
    1475                1480            1485

Arg Asp Gly Ala Thr Tyr Phe Arg Val Ala Glu Thr Ser Glu Val
    1490                1495            1500

Phe Leu Pro Ser Gln Leu Arg Gly Lys Ile Thr Lys Asn Gly Phe
    1505                1510            1515

Trp Lys Asn Asp Ala Gly Lys Val Asn Tyr Tyr Asn Ser Glu Gly
    1520                1525            1530

Glu Ile Met Lys Asn Ala Phe Val Lys Asp Gly Lys Asn Asn Trp
    1535                1540            1545
```

```
Tyr Tyr Phe Asp Asn Asp Gly Asn Met Val Thr Asn Thr Ala Leu
    1550                1555                1560

Thr Ile Asp Ser Asp Ala Gln Val Ala Asp Tyr Tyr Phe Leu Asn
    1565                1570                1575

Asn Gly Ile Ser Leu Arg Asp Gly Phe Val Gln Leu Ala Asn Gly
    1580                1585                1590

Asp Ile Tyr Tyr Tyr Asp Val Asn Gly Arg Lys Leu Lys Asn Gly
    1595                1600                1605

Lys Val Thr Val Asn Asn Val Glu Tyr Thr Thr Asp Lys Asn Gly
    1610                1615                1620

Lys Val Val Gly Glu Asn Val Leu Lys Lys Leu Asp Glu Ile Ile
    1625                1630                1635

Thr Thr Gly Lys Thr Thr Leu Ile
    1640            1645

<210> SEQ ID NO 14
<211> LENGTH: 1476
<212> TYPE: PRT
<213> ORGANISM: Streptococcus mutans

<400> SEQUENCE: 14

Met Asp Lys Lys Val Arg Tyr Lys Leu Arg Lys Val Lys Arg Trp
 1              5                  10                  15

Val Thr Val Ser Val Ala Ser Ala Val Met Thr Leu Thr Leu Ser
                20                  25                  30

Gly Gly Leu Val Lys Ala Asp Ser Asn Glu Ser Lys Ser Gln Ile Ser
            35                  40                  45

Asn Asp Ser Asn Thr Ser Val Val Thr Ala Asn Glu Glu Ser Asn Val
 50                  55                  60

Thr Thr Glu Ala Thr Ser Lys Gln Glu Ala Ala Ser Ser Gln Thr Asn
 65                  70                  75                  80

His Thr Val Thr Thr Ser Ser Ser Ser Thr Ser Val Val Asn Pro Lys
                85                  90                  95

Glu Val Val Ser Asn Pro Tyr Thr Val Gly Glu Thr Ala Ser Asn Gly
                100                 105                 110

Glu Lys Leu Gln Asn Gln Thr Thr Val Asp Lys Thr Ser Glu Ala
            115                 120                 125

Ala Ala Asn Asn Ile Ser Lys Gln Thr Glu Ala Asp Thr Asp Val
    130                 135                 140

Ile Asp Asp Ser Asn Ala Ala Asn Ile Gln Ile Leu Glu Lys Leu Pro
145                 150                 155                 160

Asn Val Lys Glu Ile Asp Gly Lys Tyr Tyr Tyr Asp Asn Gly
                165                 170                 175

Lys Val Arg Thr Asn Phe Thr Leu Ile Ala Asp Gly Lys Ile Leu His
                180                 185                 190

Phe Asp Glu Thr Gly Ala Tyr Thr Asp Thr Ser Ile Asp Thr Val Asn
                195                 200                 205

Lys Asp Ile Val Thr Thr Arg Ser Asn Leu Tyr Lys Lys Tyr Asn Gln
    210                 215                 220

Val Tyr Asp Arg Ser Ala Gln Ser Phe Glu His Val Asp His Tyr Leu
225                 230                 235                 240

Thr Ala Glu Ser Trp Tyr Arg Pro Lys Tyr Ile Leu Lys Asp Gly Lys
                245                 250                 255

Thr Trp Thr Gln Ser Thr Glu Lys Asp Phe Arg Pro Leu Leu Met Thr
                260                 265                 270
```

```
Trp Trp Pro Ser Gln Glu Thr Gln Arg Gln Tyr Val Asn Phe Met Asn
            275                 280                 285

Ala Gln Leu Gly Ile Asn Lys Thr Tyr Asp Asp Thr Ser Asn Gln Leu
        290                 295                 300

Gln Leu Asn Ile Ala Ala Ala Thr Ile Gln Ala Lys Ile Glu Ala Lys
305                 310                 315                 320

Ile Thr Thr Leu Lys Asn Thr Asp Trp Leu Arg Gln Thr Ile Ser Ala
                325                 330                 335

Phe Val Lys Thr Gln Ser Ala Trp Asn Ser Asp Ser Glu Lys Pro Phe
            340                 345                 350

Asp Asp His Leu Gln Asn Gly Ala Val Leu Tyr Asp Asn Glu Gly Lys
                355                 360                 365

Leu Thr Pro Tyr Ala Asn Ser Asn Tyr Arg Ile Leu Asn Arg Thr Pro
        370                 375                 380

Thr Asn Gln Thr Gly Lys Lys Asp Pro Arg Tyr Thr Ala Asp Asn Thr
385                 390                 395                 400

Ile Gly Gly Tyr Glu Phe Leu Leu Ala Asn Asp Val Asp Asn Ser Asn
                405                 410                 415

Pro Val Val Gln Ala Glu Gln Leu Asn Trp Leu His Phe Leu Met Asn
            420                 425                 430

Phe Gly Asn Ile Tyr Ala Asn Asp Pro Asp Ala Asn Phe Asp Ser Ile
        435                 440                 445

Arg Val Asp Ala Val Asp Asn Val Asp Ala Asp Leu Leu Gln Ile Ala
        450                 455                 460

Gly Asp Tyr Leu Lys Ala Ala Lys Gly Ile His Lys Asn Asp Lys Ala
465                 470                 475                 480

Ala Asn Asp His Leu Ser Ile Leu Glu Ala Trp Ser Asp Asn Asp Thr
                485                 490                 495

Pro Tyr Leu His Asp Asp Gly Asp Asn Met Ile Asn Met Asp Asn Lys
            500                 505                 510

Leu Arg Leu Ser Leu Leu Phe Ser Leu Ala Lys Pro Leu Asn Gln Arg
        515                 520                 525

Ser Gly Met Asn Pro Leu Ile Thr Asn Ser Leu Val Asn Arg Thr Asp
        530                 535                 540

Asp Asn Ala Glu Thr Ala Ala Val Pro Ser Tyr Ser Phe Ile Arg Ala
545                 550                 555                 560

His Asp Ser Glu Val Gln Asp Leu Ile Arg Asp Ile Ile Lys Ala Glu
                565                 570                 575

Ile Asn Pro Asn Val Val Gly Tyr Ser Phe Thr Met Glu Glu Ile Lys
            580                 585                 590

Lys Ala Phe Glu Ile Tyr Asn Lys Asp Leu Leu Ala Thr Glu Lys Lys
        595                 600                 605

Tyr Thr His Tyr Asn Thr Ala Leu Ser Tyr Ala Leu Leu Leu Thr Asn
        610                 615                 620

Lys Ser Ser Val Pro Arg Val Tyr Tyr Gly Asp Met Phe Thr Asp Asp
625                 630                 635                 640

Gly Gln Tyr Met Ala His Lys Thr Ile Asn Tyr Glu Ala Ile Glu Thr
                645                 650                 655

Leu Leu Lys Ala Arg Ile Lys Tyr Val Ser Gly Gly Gln Ala Met Arg
            660                 665                 670

Asn Gln Gln Val Gly Asn Ser Glu Ile Ile Thr Ser Val Arg Tyr Gly
        675                 680                 685
```

-continued

Lys Gly Ala Leu Lys Ala Met Asp Thr Gly Asp Arg Thr Thr Arg Thr
690             695                 700

Ser Gly Val Ala Val Ile Glu Gly Asn Pro Ser Leu Arg Leu Lys
705             710                 715                 720

Ala Ser Asp Arg Val Val Asn Met Gly Ala His Lys Asn Gln
                725                 730                 735

Ala Tyr Arg Pro Leu Leu Thr Thr Asp Asn Gly Ile Lys Ala Tyr
                740                 745                 750

His Ser Asp Gln Glu Ala Ala Gly Leu Val Arg Tyr Thr Asn Asp Arg
            755                 760                 765

Gly Glu Leu Ile Phe Thr Ala Ala Asp Ile Lys Gly Tyr Ala Asn Pro
770                 775                 780

Gln Val Ser Gly Tyr Leu Gly Val Trp Val Pro Val Gly Ala Ala Ala
785                 790                 795                 800

Asp Gln Asp Val Arg Val Ala Ala Ser Thr Ala Pro Ser Thr Asp Gly
                805                 810                 815

Lys Ser Val His Gln Asn Ala Ala Leu Asp Ser Arg Val Met Phe Glu
                820                 825                 830

Gly Phe Ser Asn Phe Gln Ala Phe Ala Thr Lys Lys Glu Glu Tyr Thr
            835                 840                 845

Asn Val Val Ile Ala Lys Asn Val Asp Lys Phe Ala Glu Trp Gly Val
850                 855                 860

Thr Asp Phe Glu Met Ala Pro Gln Tyr Val Ser Ser Thr Asp Gly Ser
865                 870                 875                 880

Phe Leu Asp Ser Val Ile Gln Asn Gly Tyr Ala Phe Thr Asp Arg Tyr
                885                 890                 895

Asp Leu Gly Ile Ser Lys Pro Asn Lys Tyr Gly Thr Ala Asp Asp Leu
                900                 905                 910

Val Lys Ala Ile Lys Ala Leu His Ser Lys Gly Ile Lys Val Met Ala
            915                 920                 925

Asp Trp Val Pro Asp Gln Met Tyr Ala Leu Pro Glu Lys Glu Val Val
            930                 935                 940

Thr Ala Thr Arg Val Asp Lys Tyr Gly Thr Pro Val Ala Gly Ser Gln
945                 950                 955                 960

Ile Lys Asn Thr Leu Tyr Val Val Asp Gly Lys Ser Ser Gly Lys Asp
                965                 970                 975

Gln Gln Ala Lys Tyr Gly Gly Ala Phe Leu Glu Glu Leu Gln Ala Lys
                980                 985                 990

Tyr Pro Glu Leu Phe Ala Arg Lys Gln Ile Ser Thr Gly Val Pro Met
            995                 1000                1005

Asp Pro Ser Val Lys Ile Lys Gln Trp Ser Ala Lys Tyr Phe Asn
    1010                1015                1020

Gly Thr Asn Ile Leu Gly Arg Gly Ala Gly Tyr Val Leu Lys Asp
    1025                1030                1035

Gln Ala Thr Asn Thr Tyr Phe Asn Ile Ser Asp Asn Lys Glu Ile
    1040                1045                1050

Asn Phe Leu Pro Lys Thr Leu Leu Asn Gln Asp Ser Gln Val Gly
    1055                1060                1065

Phe Ser Tyr Asp Gly Lys Gly Tyr Val Tyr Ser Thr Ser Gly
    1070                1075                1080

Tyr Gln Ala Lys Asn Thr Phe Ile Ser Glu Gly Asp Lys Trp Tyr
    1085                1090                1095

Tyr Phe Asp Asn Asn Gly Tyr Met Val Thr Gly Ala Gln Ser Ile

-continued

```
              1100                1105                1110
Asn Gly Val Asn Tyr Tyr Phe Leu Pro Asn Gly Leu Gln Leu Arg
    1115                1120                1125
Asp Ala Ile Leu Lys Asn Glu Asp Gly Thr Tyr Ala Tyr Tyr Gly
    1130                1135                1140
Asn Asp Gly Arg Arg Tyr Glu Asn Gly Tyr Tyr Gln Phe Met Ser
    1145                1150                1155
Gly Val Trp Arg His Phe Asn Asn Gly Glu Met Ser Val Gly Leu
    1160                1165                1170
Thr Val Ile Asp Gly Gln Val Gln Tyr Phe Asp Glu Met Gly Tyr
    1175                1180                1185
Gln Ala Lys Gly Lys Phe Val Thr Thr Ala Asp Gly Lys Ile Arg
    1190                1195                1200
Tyr Phe Asp Lys Gln Ser Gly Asn Met Tyr Arg Asn Arg Phe Ile
    1205                1210                1215
Glu Asn Glu Glu Gly Lys Trp Leu Tyr Leu Gly Glu Asp Gly Ala
    1220                1225                1230
Ala Val Thr Gly Ser Gln Thr Ile Asn Gly Gln His Leu Tyr Phe
    1235                1240                1245
Arg Ala Asn Gly Val Gln Val Lys Gly Glu Phe Val Thr Asp Arg
    1250                1255                1260
His Gly Arg Ile Ser Tyr Tyr Asp Gly Asn Ser Gly Asp Gln Ile
    1265                1270                1275
Arg Asn Arg Phe Val Arg Asn Ala Gln Gly Gln Trp Phe Tyr Phe
    1280                1285                1290
Asp Asn Asn Gly Tyr Ala Val Thr Gly Ala Arg Thr Ile Asn Gly
    1295                1300                1305
Gln His Leu Tyr Phe Arg Ala Asn Gly Val Gln Val Lys Gly Glu
    1310                1315                1320
Phe Val Thr Asp Arg His Gly Arg Ile Ser Tyr Tyr Asp Gly Asn
    1325                1330                1335
Ser Gly Asp Gln Ile Arg Asn Arg Phe Val Arg Asn Ala Gln Gly
    1340                1345                1350
Gln Trp Phe Tyr Phe Asp Asn Asn Gly Tyr Ala Val Thr Gly Ala
    1355                1360                1365
Arg Thr Ile Asn Gly Gln His Leu Tyr Phe Arg Ala Asn Gly Val
    1370                1375                1380
Gln Val Lys Gly Glu Phe Val Thr Asp Arg Tyr Gly Arg Ile Ser
    1385                1390                1395
Tyr Tyr Asp Gly Asn Ser Gly Asp Gln Ile Arg Asn Arg Phe Val
    1400                1405                1410
Arg Asn Ala Gln Gly Gln Trp Phe Tyr Phe Asp Asn Asn Gly Tyr
    1415                1420                1425
Ala Val Thr Gly Ala Arg Thr Ile Asn Gly Gln His Leu Tyr Phe
    1430                1435                1440
Arg Ala Asn Gly Val Gln Val Lys Gly Glu Phe Val Thr Asp Arg
    1445                1450                1455
Tyr Gly Arg Ile Ser Tyr Tyr Asp Ala Asn Ser Gly Glu Arg Val
    1460                1465                1470
Arg Ile Asn
    1475

<210> SEQ ID NO 15
```

<211> LENGTH: 3942
<212> TYPE: DNA
<213> ORGANISM: Streptococcus mutans

<400> SEQUENCE: 15

| | | | | | |
|---|---|---|---|---|---|
| atgattgacg | gcaaatacta | ctactatgac | aacaacggca | aagtacgcac | caatttcacg | 60 |
| ttgatcgcgg | acggtaaaat | cctgcatttt | gatgaaactg | gcgcgtacac | cgacactagc | 120 |
| attgataccg | tgaacaagga | tattgtcacg | acgcgtagca | acctgtataa | gaaatacaat | 180 |
| caagtgtatg | atcgcagcgc | gcagagcttc | gagcatgttg | atcactacct | gacggcggaa | 240 |
| tcttggtacc | gtccgaaata | cattctgaaa | gatggcaaga | cctggaccca | gagcaccgag | 300 |
| aaggacttcc | gtcctctgct | gatgacctgg | tggccgagcc | aggaaacgca | gcgccagtat | 360 |
| gtcaacttca | tgaacgccca | gttgggtatc | aacaaaacgt | acgacgacac | cagcaatcag | 420 |
| ctgcaattga | acatcgctgc | tgcaacgatc | caagcaaaga | tcgaagccaa | atcacgacg | 480 |
| ctgaagaaca | ccgattggct | gcgtcaaacg | atcagcgcgt | tcgtcaaaac | ccaaagcgct | 540 |
| tggaatagcg | acagcgaaaa | gccgtttgat | gaccatctgc | aaaacggtgc | ggttctgtat | 600 |
| gataacgaag | gtaaattgac | gccgtatgcc | aatagcaact | atcgtattct | gaaccgcacg | 660 |
| ccgaccaacc | agaccggtaa | gaaggacccg | cgttataccg | ccgacaacac | gatcggcggc | 720 |
| tacgagtttc | tgctggccaa | cgacgtggat | aatagcaacc | cggtggttca | ggccgagcag | 780 |
| ctgaactggc | tgcacttcct | gatgaacttt | ggtaatatct | acgcaaacga | ccctgacgct | 840 |
| aacttcgact | ccatccgcgt | tgacgctgtc | gataatgtgg | acgccgatct | gttacagatc | 900 |
| gcgggtgact | atctgaaagc | ggcaaagggc | atccataaga | tgacaaagc | ggcgaacgac | 960 |
| cacctgtcca | ttctggaagc | gtggagcgac | aatgacactc | cgtatctgca | tgatgatggc | 1020 |
| gacaacatga | ttaacatgga | taacaaactg | cgcctgagcc | tgctgttctc | cctggcgaaa | 1080 |
| ccgctgaatc | agcgtagcgg | tatgaacccg | ttgattacga | acagcctggt | caaccgtact | 1140 |
| gatgataatg | ccgaaacggc | ggcagtgcca | agctactctt | ttatccgtgc | ccacgatagc | 1200 |
| gaggtccagg | atttgattcg | tgatatcatt | aaggctgaga | ttaacccgaa | cgtcgtcggt | 1260 |
| tacagcttca | cgatggaaga | gattaagaag | gcatttgaga | tctacaataa | ggacctgttg | 1320 |
| gccacggaga | agaagtatac | ccactataac | accgcattga | gctacgcgtt | gctgctgacg | 1380 |
| aacaagagca | gcgtgccgcg | tgtctactat | ggtgatatgt | ttacggacga | tggtcaatac | 1440 |
| atggcccaca | gaccattaa | ctacgaggca | atcgaaaccc | tgctgaaagc | acgtatcaag | 1500 |
| tacgtgtccg | gtggtcaggc | tatgcgcaac | cagcaagtgg | gtaattcgga | gatcatcacc | 1560 |
| agcgtgcgtt | acggtaaagg | tgcgctgaag | gcgatggata | cgggtgaccg | cactacccgt | 1620 |
| acctctggtg | tggcggtcat | tgagggcaac | aacccgagct | gcgcctgaa | ggcttctgat | 1680 |
| cgtgtggttg | tgaatatggg | tgcggcccac | aaaaatcaag | cctatcgccc | gctgctgttg | 1740 |
| acgaccgata | acggcattaa | ggcctatcac | agcgaccaag | aagcggcagg | cctggtgcgt | 1800 |
| tacaccaacg | accgtggcga | actgatcttt | accgcagccg | acattaaggg | ctacgcaaat | 1860 |
| ccgcaagtta | gcggctacct | gggcgtctgg | gtccctgttg | gcgcagcagc | tgatcaggac | 1920 |
| gttcgtgttg | cggcgagcac | cgcgccaagc | acggacggca | agagcgttca | ccagaacgcg | 1980 |
| gctctggaca | gccgtgtgat | gttcgagggt | ttctcgaact | tccaggcatt | tgctaccaag | 2040 |
| aaagaagagt | ataccaatgt | ggtcatcgct | aagaatgtgg | ataagttcgc | ggagtggggt | 2100 |
| gtcaccgatt | tcgagatggc | tccgcaatac | gtttctagca | ccgacggtag | cttttttggat | 2160 |
| agcgtgattc | aaaacggtta | tgcttttacc | gaccgttacg | acctgggcat | cagcaagccg | 2220 |

```
aacaaatatg gcaccgcgga cgatctggtt aaagcgatta aggcattgca cagcaaaggc    2280
atcaaagtta tggcggattg ggttccggac cagatgtatg ccctgccgga aaagaggtt     2340 gtgacggcaa cccgtgttga caaataccgg acgccggtag ctggcagcca gatcaaaaac    2400
acgctgtacg tggtcgatgg taaatctagc ggtaaggacc agcaggcgaa gtacggtggt    2460
gccttcctgg aagagctgca agcgaagtat ccggaactgt tcgcgcgcaa acagattagc    2520
accggtgttc cgatggaccc gagcgtcaag attaagcaat ggagcgcaaa atacttcaac    2580
ggcacgaata tcctgggtcg tggtgctggt tacgtgctga agatcaggc  aaccaacacc    2640 tactttaaca tcagcgacaa taaagagatc aatttcctgc caaagacgtt gctgaaccag    2700
gattctcaag ttggctttag ctacgacggt aagggctatg tgtactacag cacctcgggc    2760
taccaggcta aaaacacgtt catcagcgag ggtgacaagt ggtattactt cgacaataac    2820
ggttatatgg ttaccggcgc acagagcatt aatggtgtga actattactt cctgccgaat    2880
ggtttacagc tgcgtgatgc gattctgaaa aatgaggacg gtacgtacgc gtattatggc    2940
aatgatggtc gccgctacga gaatggctat tatcagttta tgagcggtgt ttggcgccat    3000
ttcaataatg gcgagatgtc cgttggtctg accgtcattg acggtcaagt tcaatacttt    3060
gacgagatgg gttaccaggc gaaaggcaaa ttcgttacca ccgcggatgg taagatccgt    3120
tacttcgata gcagagcgg caatatgtat cgtaatcgtt tcattgagaa cgaagagggc    3180
aaatggctgt acctgggtga ggacggcgcg gcagtcaccg gtagccagac gatcaatggt    3240
cagcacctgt attttcgtgc taacggcgtt caggttaagg gtgagttcgt gaccgatcgt    3300
catggccgca tctcttatta cgacggcaac agcggtgatc agatccgcaa ccgtttcgtc    3360
cgcaatgcgc aaggccagtg gttttacttt gacaacaatg gctatgcagt aactggtgct    3420
cgtacgatca acggccagca cctgtatttc cgcgcgaacg tgttcaggt aaaaggtgag    3480 tttgttacgg accgccacgg ccgcattagc tattatgatg gtaatagcgg tgaccaaatt    3540
cgcaatcgtt tcgtgcgtaa tgcacagggt cagtggttct acttcgacaa taatggttat    3600
gcagtcacgg gtgcacgtac cattaacggc caacacctgt actttcgcgc caatggtgtg    3660
caagtgaaag gcgaatttgt tactgatcgt tatggtcgta tcagctacta tgatggcaat    3720
tctggcgacc aaattcgcaa tgctttgtt cgtaacgccc aaggtcaatg gttctatttc    3780
gacaacaacg gttacgcggt gaccggtgcc cgcacgatta tggtcaaca cttgtacttc    3840 cgtgccaacg tgtccaggt gaagggtgaa tttgtgaccg accgctatgg tcgcatttct    3900
tactacgacg caaattccgg tgaacgcgtc cgtatcaatt aa                       3942
```

<210> SEQ ID NO 16
<211> LENGTH: 1313
<212> TYPE: PRT
<213> ORGANISM: Streptococcus mutans

<400> SEQUENCE: 16

```
Met Ile Asp Gly Lys Tyr Tyr Tyr Asp Asn Gly Lys Val Arg
1               5                   10                  15

Thr Asn Phe Thr Leu Ile Ala Asp Gly Lys Ile Leu His Phe Asp Glu
            20                  25                  30

Thr Gly Ala Tyr Thr Asp Thr Ser Ile Asp Thr Val Asn Lys Asp Ile
        35                  40                  45

Val Thr Thr Arg Ser Asn Leu Tyr Lys Lys Tyr Asn Gln Val Tyr Asp
    50                  55                  60
```

```
Arg Ser Ala Gln Ser Phe Glu His Val Asp His Tyr Leu Thr Ala Glu
 65                  70                  75                  80

Ser Trp Tyr Arg Pro Lys Tyr Ile Leu Lys Asp Gly Lys Thr Trp Thr
                 85                  90                  95

Gln Ser Thr Glu Lys Asp Phe Arg Pro Leu Leu Met Thr Trp Trp Pro
            100                 105                 110

Ser Gln Glu Thr Gln Arg Gln Tyr Val Asn Phe Met Asn Ala Gln Leu
        115                 120                 125

Gly Ile Asn Lys Thr Tyr Asp Asp Thr Ser Asn Gln Leu Gln Leu Asn
    130                 135                 140

Ile Ala Ala Ala Thr Ile Gln Ala Lys Ile Glu Ala Lys Ile Thr Thr
145                 150                 155                 160

Leu Lys Asn Thr Asp Trp Leu Arg Gln Thr Ile Ser Ala Phe Val Lys
                165                 170                 175

Thr Gln Ser Ala Trp Asn Ser Asp Ser Glu Lys Pro Phe Asp Asp His
            180                 185                 190

Leu Gln Asn Gly Ala Val Leu Tyr Asp Asn Glu Gly Lys Leu Thr Pro
        195                 200                 205

Tyr Ala Asn Ser Asn Tyr Arg Ile Leu Asn Arg Thr Pro Thr Asn Gln
    210                 215                 220

Thr Gly Lys Lys Asp Pro Arg Tyr Thr Ala Asp Asn Thr Ile Gly Gly
225                 230                 235                 240

Tyr Glu Phe Leu Leu Ala Asn Asp Val Asp Asn Ser Asn Pro Val Val
                245                 250                 255

Gln Ala Glu Gln Leu Asn Trp Leu His Phe Leu Met Asn Phe Gly Asn
            260                 265                 270

Ile Tyr Ala Asn Asp Pro Asp Ala Asn Phe Asp Ser Ile Arg Val Asp
    275                 280                 285

Ala Val Asp Asn Val Asp Ala Asp Leu Leu Gln Ile Ala Gly Asp Tyr
290                 295                 300

Leu Lys Ala Ala Lys Gly Ile His Lys Asn Asp Lys Ala Ala Asn Asp
305                 310                 315                 320

His Leu Ser Ile Leu Glu Ala Trp Ser Asp Asn Asp Thr Pro Tyr Leu
                325                 330                 335

His Asp Asp Gly Asp Asn Met Ile Asn Met Asp Asn Lys Leu Arg Leu
            340                 345                 350

Ser Leu Leu Phe Ser Leu Ala Lys Pro Leu Asn Gln Arg Ser Gly Met
        355                 360                 365

Asn Pro Leu Ile Thr Asn Ser Leu Val Asn Arg Thr Asp Asp Asn Ala
    370                 375                 380

Glu Thr Ala Ala Val Pro Ser Tyr Ser Phe Ile Arg Ala His Asp Ser
385                 390                 395                 400

Glu Val Gln Asp Leu Ile Arg Asp Ile Ile Lys Ala Glu Ile Asn Pro
                405                 410                 415

Asn Val Val Gly Tyr Ser Phe Thr Met Glu Glu Ile Lys Lys Ala Phe
            420                 425                 430

Glu Ile Tyr Asn Lys Asp Leu Leu Ala Thr Glu Lys Lys Tyr Thr His
        435                 440                 445

Tyr Asn Thr Ala Leu Ser Tyr Ala Leu Leu Leu Thr Asn Lys Ser Ser
    450                 455                 460

Val Pro Arg Val Tyr Tyr Gly Asp Met Phe Thr Asp Asp Gly Gln Tyr
465                 470                 475                 480

Met Ala His Lys Thr Ile Asn Tyr Glu Ala Ile Glu Thr Leu Leu Lys
```

-continued

```
                485                 490                 495
Ala Arg Ile Lys Tyr Val Ser Gly Gly Gln Ala Met Arg Asn Gln Gln
                500                 505                 510

Val Gly Asn Ser Glu Ile Ile Thr Ser Val Arg Tyr Gly Lys Gly Ala
                515                 520                 525

Leu Lys Ala Met Asp Thr Gly Asp Arg Thr Thr Arg Thr Ser Gly Val
                530                 535                 540

Ala Val Ile Glu Gly Asn Asn Pro Ser Leu Arg Leu Lys Ala Ser Asp
545                 550                 555                 560

Arg Val Val Asn Met Gly Ala Ala His Lys Asn Gln Ala Tyr Arg
                565                 570                 575

Pro Leu Leu Leu Thr Thr Asp Asn Gly Ile Lys Ala Tyr His Ser Asp
                580                 585                 590

Gln Glu Ala Ala Gly Leu Val Arg Tyr Thr Asn Asp Arg Gly Glu Leu
                595                 600                 605

Ile Phe Thr Ala Ala Asp Ile Lys Gly Tyr Ala Asn Pro Gln Val Ser
                610                 615                 620

Gly Tyr Leu Gly Val Trp Val Pro Val Gly Ala Ala Asp Gln Asp
625                 630                 635                 640

Val Arg Val Ala Ala Ser Thr Ala Pro Ser Thr Asp Gly Lys Ser Val
                645                 650                 655

His Gln Asn Ala Ala Leu Asp Ser Arg Val Met Phe Glu Gly Phe Ser
                660                 665                 670

Asn Phe Gln Ala Phe Ala Thr Lys Lys Glu Glu Tyr Thr Asn Val Val
                675                 680                 685

Ile Ala Lys Asn Val Asp Lys Phe Ala Glu Trp Gly Val Thr Asp Phe
                690                 695                 700

Glu Met Ala Pro Gln Tyr Val Ser Ser Thr Asp Gly Ser Phe Leu Asp
705                 710                 715                 720

Ser Val Ile Gln Asn Gly Tyr Ala Phe Thr Asp Arg Tyr Asp Leu Gly
                725                 730                 735

Ile Ser Lys Pro Asn Lys Tyr Gly Thr Ala Asp Asp Leu Val Lys Ala
                740                 745                 750

Ile Lys Ala Leu His Ser Lys Gly Ile Lys Val Met Ala Asp Trp Val
                755                 760                 765

Pro Asp Gln Met Tyr Ala Leu Pro Glu Lys Glu Val Val Thr Ala Thr
                770                 775                 780

Arg Val Asp Lys Tyr Gly Thr Pro Val Ala Gly Ser Gln Ile Lys Asn
785                 790                 795                 800

Thr Leu Tyr Val Val Asp Gly Lys Ser Ser Gly Lys Asp Gln Gln Ala
                805                 810                 815

Lys Tyr Gly Gly Ala Phe Leu Glu Glu Leu Gln Ala Lys Tyr Pro Glu
                820                 825                 830

Leu Phe Ala Arg Lys Gln Ile Ser Thr Gly Val Pro Met Asp Pro Ser
                835                 840                 845

Val Lys Ile Lys Gln Trp Ser Ala Lys Tyr Phe Asn Gly Thr Asn Ile
                850                 855                 860

Leu Gly Arg Gly Ala Gly Tyr Val Leu Lys Asp Gln Ala Thr Asn Thr
865                 870                 875                 880

Tyr Phe Asn Ile Ser Asp Asn Lys Glu Ile Asn Phe Leu Pro Lys Thr
                885                 890                 895

Leu Leu Asn Gln Asp Ser Gln Val Gly Phe Ser Tyr Asp Gly Lys Gly
                900                 905                 910
```

```
Tyr Val Tyr Tyr Ser Thr Ser Gly Tyr Gln Ala Lys Asn Thr Phe Ile
        915                 920                 925

Ser Glu Gly Asp Lys Trp Tyr Phe Asp Asn Asn Gly Tyr Met Val
        930                 935                 940

Thr Gly Ala Gln Ser Ile Asn Gly Val Asn Tyr Tyr Phe Leu Pro Asn
945                 950                 955                 960

Gly Leu Gln Leu Arg Asp Ala Ile Leu Lys Asn Glu Asp Gly Thr Tyr
                965                 970                 975

Ala Tyr Tyr Gly Asn Asp Gly Arg Arg Tyr Glu Asn Gly Tyr Tyr Gln
                980                 985                 990

Phe Met Ser Gly Val Trp Arg His Phe Asn Asn Gly Glu Met Ser Val
                995                 1000                1005

Gly Leu Thr Val Ile Asp Gly Gln Val Gln Tyr Phe Asp Glu Met
        1010                1015                1020

Gly Tyr Gln Ala Lys Gly Lys Phe Val Thr Thr Ala Asp Gly Lys
        1025                1030                1035

Ile Arg Tyr Phe Asp Lys Gln Ser Gly Asn Met Tyr Arg Asn Arg
        1040                1045                1050

Phe Ile Glu Asn Glu Glu Gly Lys Trp Leu Tyr Leu Gly Glu Asp
        1055                1060                1065

Gly Ala Ala Val Thr Gly Ser Gln Thr Ile Asn Gly Gln His Leu
        1070                1075                1080

Tyr Phe Arg Ala Asn Gly Val Gln Val Lys Gly Glu Phe Val Thr
        1085                1090                1095

Asp Arg His Gly Arg Ile Ser Tyr Tyr Asp Gly Asn Ser Gly Asp
        1100                1105                1110

Gln Ile Arg Asn Arg Phe Val Arg Asn Ala Gln Gly Gln Trp Phe
        1115                1120                1125

Tyr Phe Asp Asn Asn Gly Tyr Ala Val Thr Gly Ala Arg Thr Ile
        1130                1135                1140

Asn Gly Gln His Leu Tyr Phe Arg Ala Asn Gly Val Gln Val Lys
        1145                1150                1155

Gly Glu Phe Val Thr Asp Arg His Gly Arg Ile Ser Tyr Tyr Asp
        1160                1165                1170

Gly Asn Ser Gly Asp Gln Ile Arg Asn Arg Phe Val Arg Asn Ala
        1175                1180                1185

Gln Gly Gln Trp Phe Tyr Phe Asp Asn Asn Gly Tyr Ala Val Thr
        1190                1195                1200

Gly Ala Arg Thr Ile Asn Gly Gln His Leu Tyr Phe Arg Ala Asn
        1205                1210                1215

Gly Val Gln Val Lys Gly Glu Phe Val Thr Asp Arg Tyr Gly Arg
        1220                1225                1230

Ile Ser Tyr Tyr Asp Gly Asn Ser Gly Asp Gln Ile Arg Asn Arg
        1235                1240                1245

Phe Val Arg Asn Ala Gln Gly Gln Trp Phe Tyr Phe Asp Asn Asn
        1250                1255                1260

Gly Tyr Ala Val Thr Gly Ala Arg Thr Ile Asn Gly Gln His Leu
        1265                1270                1275

Tyr Phe Arg Ala Asn Gly Val Gln Val Lys Gly Glu Phe Val Thr
        1280                1285                1290

Asp Arg Tyr Gly Arg Ile Ser Tyr Tyr Asp Ala Asn Ser Gly Glu
        1295                1300                1305
```

```
<210> SEQ ID NO 17
<211> LENGTH: 1518
<212> TYPE: PRT
<213> ORGANISM: Streptococcus salivarius

<400> SEQUENCE: 17
```

| | | | | | | | | | | | | | | |
|---|---|---|---|---|---|---|---|---|---|---|---|---|---|---|
| Arg | Val | Arg | Ile | Asn | | | | | | | | | | |
| | | | 1310 | | | | | | | | | | | |
| Met | Glu | Asn | Lys | Ile | His | Tyr | Lys | Leu | His | Lys | Val | Lys | Lys | Gln | Trp |
| 1 | | | | 5 | | | | | 10 | | | | | 15 | |
| Val | Thr | Ile | Ala | Val | Ala | Ser | Val | Ala | Leu | Ala | Thr | Val | Leu | Gly | Gly |
| | | | 20 | | | | | 25 | | | | | 30 | | |
| Leu | Ser | Val | Thr | Thr | Ser | Ser | Val | Ser | Ala | Asp | Glu | Thr | Gln | Asp | Lys |
| | | | 35 | | | | | 40 | | | | | 45 | | |
| Thr | Val | Thr | Gln | Ser | Asn | Ser | Gly | Thr | Thr | Ala | Ser | Leu | Val | Thr | Ser |
| | 50 | | | | | 55 | | | | | 60 | | | | |
| Pro | Glu | Ala | Thr | Lys | Glu | Ala | Asp | Lys | Arg | Thr | Asn | Thr | Lys | Glu | Ala |
| 65 | | | | | 70 | | | | | 75 | | | | | 80 |
| Asp | Val | Leu | Thr | Pro | Ala | Lys | Glu | Thr | Asn | Ala | Val | Glu | Thr | Ala | Thr |
| | | | | 85 | | | | | 90 | | | | | 95 | |
| Thr | Thr | Asn | Thr | Gln | Ala | Thr | Ala | Glu | Ala | Ala | Thr | Ala | Thr | Thr | Thr |
| | | | 100 | | | | | 105 | | | | | 110 | | |
| Ala | Asp | Val | Ala | Val | Ala | Val | Pro | Asn | Lys | Glu | Ala | Val | Val | Thr | |
| | | | 115 | | | | | 120 | | | | | 125 | | |
| Thr | Asp | Ala | Pro | Ala | Val | Thr | Thr | Glu | Lys | Ala | Glu | Glu | Gln | Pro | Ala |
| | | | 130 | | | | | 135 | | | | | 140 | | |
| Thr | Val | Lys | Ala | Glu | Val | Val | Asn | Thr | Glu | Val | Lys | Ala | Pro | Glu | Ala |
| 145 | | | | | 150 | | | | | 155 | | | | | 160 |
| Ala | Leu | Lys | Asp | Ser | Glu | Val | Glu | Ala | Ala | Leu | Ser | Leu | Lys | Asn | Ile |
| | | | | 165 | | | | | 170 | | | | | 175 | |
| Lys | Asn | Ile | Asp | Gly | Lys | Tyr | Tyr | Tyr | Val | Asn | Glu | Asp | Gly | Ser | His |
| | | | 180 | | | | | 185 | | | | | 190 | | |
| Lys | Glu | Asn | Phe | Ala | Ile | Thr | Val | Asn | Gly | Gln | Leu | Leu | Tyr | Phe | Gly |
| | | | 195 | | | | | 200 | | | | | 205 | | |
| Lys | Asp | Gly | Ala | Leu | Thr | Ser | Ser | Ser | Thr | Tyr | Ser | Phe | Thr | Pro | Gly |
| | 210 | | | | | 215 | | | | | 220 | | | | |
| Thr | Thr | Asn | Ile | Val | Asp | Gly | Phe | Ser | Ile | Asn | Asn | Arg | Ala | Tyr | Asp |
| 225 | | | | | 230 | | | | | 235 | | | | | 240 |
| Ser | Ser | Glu | Ala | Ser | Phe | Glu | Leu | Ile | Asp | Gly | Tyr | Leu | Thr | Ala | Asp |
| | | | | 245 | | | | | 250 | | | | | 255 | |
| Ser | Trp | Tyr | Arg | Pro | Ala | Ser | Ile | Ile | Lys | Asp | Gly | Val | Thr | Trp | Gln |
| | | | 260 | | | | | 265 | | | | | 270 | | |
| Ala | Ser | Thr | Ala | Glu | Asp | Phe | Arg | Pro | Leu | Leu | Met | Ala | Trp | Trp | Pro |
| | | | 275 | | | | | 280 | | | | | 285 | | |
| Asn | Val | Asp | Thr | Gln | Val | Asn | Tyr | Leu | Asn | Tyr | Met | Ser | Lys | Val | Phe |
| | 290 | | | | | 295 | | | | | 300 | | | | |
| Asn | Leu | Asp | Ala | Lys | Tyr | Ser | Ser | Thr | Asp | Lys | Gln | Glu | Thr | Leu | Lys |
| 305 | | | | | 310 | | | | | 315 | | | | | 320 |
| Val | Ala | Ala | Lys | Asp | Ile | Gln | Ile | Lys | Ile | Glu | Gln | Lys | Ile | Gln | Ala |
| | | | | 325 | | | | | 330 | | | | | 335 | |
| Glu | Lys | Ser | Thr | Gln | Trp | Leu | Arg | Glu | Thr | Ile | Ser | Ala | Phe | Val | Lys |
| | | | 340 | | | | | 345 | | | | | 350 | | |
| Thr | Gln | Pro | Gln | Trp | Asn | Lys | Glu | Thr | Glu | Asn | Tyr | Ser | Lys | Gly | Gly |
| | | | 355 | | | | | 360 | | | | | 365 | | |

```
Gly Glu Asp His Leu Gln Gly Ala Leu Leu Tyr Val Asn Asp Ser
    370                 375                 380

Arg Thr Pro Trp Ala Asn Ser Asp Tyr Arg Arg Leu Asn Arg Thr Ala
385                 390                 395                 400

Thr Asn Gln Thr Gly Thr Ile Asp Lys Ser Ile Leu Asp Glu Gln Ser
                405                 410                 415

Asp Pro Asn His Met Gly Gly Phe Asp Phe Leu Leu Ala Asn Asp Val
                420                 425                 430

Asp Leu Ser Asn Pro Val Val Gln Ala Glu Gln Leu Asn Gln Ile His
            435                 440                 445

Tyr Leu Met Asn Trp Gly Ser Ile Val Met Gly Asp Lys Asp Ala Asn
    450                 455                 460

Phe Asp Gly Ile Arg Val Asp Ala Val Asp Asn Val Asp Ala Asp Met
465                 470                 475                 480

Leu Gln Leu Tyr Thr Asn Tyr Phe Arg Glu Tyr Tyr Gly Val Asn Lys
                485                 490                 495

Ser Glu Ala Asn Ala Leu Ala His Ile Ser Val Leu Glu Ala Trp Ser
                500                 505                 510

Leu Asn Asp Asn His Tyr Asn Asp Lys Thr Asp Gly Ala Ala Leu Ala
            515                 520                 525

Met Glu Asn Lys Gln Arg Leu Ala Leu Leu Phe Ser Leu Ala Lys Pro
    530                 535                 540

Ile Lys Glu Arg Thr Pro Ala Val Ser Pro Leu Tyr Asn Asn Thr Phe
545                 550                 555                 560

Asn Thr Thr Gln Arg Asp Glu Lys Thr Asp Trp Ile Asn Lys Asp Gly
                565                 570                 575

Ser Lys Ala Tyr Asn Glu Asp Gly Thr Val Lys Gln Ser Thr Ile Gly
                580                 585                 590

Lys Tyr Asn Glu Lys Tyr Gly Asp Ala Ser Gly Asn Tyr Val Phe Ile
            595                 600                 605

Arg Ala His Asp Asn Asn Val Gln Asp Ile Ile Ala Glu Ile Ile Lys
    610                 615                 620

Lys Glu Ile Asn Pro Lys Ser Asp Gly Phe Thr Ile Thr Asp Ala Glu
625                 630                 635                 640

Met Lys Gln Ala Phe Glu Ile Tyr Asn Lys Asp Met Leu Ser Ser Asp
                645                 650                 655

Lys Lys Tyr Thr Leu Asn Asn Ile Pro Ala Ala Tyr Ala Val Met Leu
                660                 665                 670

Gln Asn Met Glu Thr Ile Thr Arg Val Tyr Tyr Gly Asp Leu Tyr Thr
            675                 680                 685

Asp Asp Gly His Tyr Met Glu Thr Lys Ser Pro Tyr Tyr Asp Thr Ile
    690                 695                 700

Val Asn Leu Met Lys Ser Arg Ile Lys Tyr Val Ser Gly Gly Gln Ala
705                 710                 715                 720

Gln Arg Ser Tyr Trp Leu Pro Thr Gly Lys Met Asp Asn Ser Asp
                725                 730                 735

Val Glu Leu Tyr Arg Thr Asn Glu Val Tyr Thr Ser Val Arg Tyr Gly
                740                 745                 750

Lys Asp Ile Met Thr Ala Asn Asp Thr Glu Gly Ser Lys Tyr Ser Arg
            755                 760                 765

Thr Ser Gly Gln Val Thr Leu Val Ala Asn Asn Pro Lys Leu Asn Leu
    770                 775                 780
```

```
Asp Gln Ser Ala Lys Leu Asn Val Glu Met Gly Lys Ile His Ala Asn
785                 790                 795                 800

Gln Lys Tyr Arg Ala Leu Ile Val Gly Thr Ala Asp Gly Ile Lys Asn
        805                 810                 815

Phe Thr Ser Asp Ala Asp Ala Ile Ala Ala Gly Tyr Val Lys Glu Thr
            820                 825                 830

Asp Ser Asn Gly Val Leu Thr Phe Gly Ala Asn Asp Ile Lys Gly Tyr
        835                 840                 845

Glu Thr Phe Asp Met Ser Gly Phe Val Ala Val Trp Val Pro Val Gly
    850                 855                 860

Ala Ser Asp Asn Gln Asp Ile Arg Val Ala Pro Ser Thr Glu Ala Lys
865                 870                 875                 880

Lys Glu Gly Glu Leu Thr Leu Lys Ala Thr Glu Ala Tyr Asp Ser Gln
                885                 890                 895

Leu Ile Tyr Glu Gly Phe Ser Asn Phe Gln Thr Ile Pro Asp Gly Ser
            900                 905                 910

Asp Pro Ser Val Tyr Thr Asn Arg Lys Ile Ala Glu Asn Val Asp Leu
        915                 920                 925

Phe Lys Ser Trp Gly Val Thr Ser Phe Glu Met Ala Pro Gln Phe Val
    930                 935                 940

Ser Ala Asp Asp Gly Thr Phe Leu Asp Ser Val Ile Gln Asn Gly Tyr
945                 950                 955                 960

Ala Phe Ala Asp Arg Tyr Asp Leu Ala Met Ser Lys Asn Lys Tyr
                965                 970                 975

Gly Ser Lys Glu Asp Leu Arg Asp Ala Leu Lys Ala Leu His Lys Ala
            980                 985                 990

Gly Ile Gln Ala Ile Ala Asp Trp Val Pro Asp Gln Ile Tyr Gln Leu
        995                 1000                1005

Pro Gly Lys Glu Val Val Thr Ala Thr Arg Thr Asp Gly Ala Gly
    1010                1015                1020

Arg Lys Ile Ala Asp Ala Ile Ile Asp His Ser Leu Tyr Val Ala
    1025                1030                1035

Asn Ser Lys Ser Ser Gly Lys Asp Tyr Gln Ala Lys Tyr Gly Gly
    1040                1045                1050

Glu Phe Leu Ala Glu Leu Lys Ala Lys Tyr Pro Glu Met Phe Lys
    1055                1060                1065

Val Asn Met Ile Ser Thr Gly Lys Pro Ile Asp Asp Ser Val Lys
    1070                1075                1080

Leu Lys Gln Trp Lys Ala Glu Tyr Phe Asn Gly Thr Asn Val Leu
    1085                1090                1095

Glu Arg Gly Val Gly Tyr Val Leu Ser Asp Glu Ala Thr Gly Lys
    1100                1105                1110

Tyr Phe Thr Val Thr Lys Glu Gly Asn Phe Ile Pro Leu Gln Leu
    1115                1120                1125

Thr Gly Lys Glu Lys Val Ile Thr Gly Phe Ser Ser Asp Gly Lys
    1130                1135                1140

Gly Ile Thr Tyr Phe Gly Thr Ser Gly Thr Gln Ala Lys Ser Ala
    1145                1150                1155

Phe Val Thr Phe Asn Gly Asn Thr Tyr Tyr Phe Asp Ala Arg Gly
    1160                1165                1170

His Met Val Thr Asn Ser Glu Tyr Ser Pro Asn Gly Lys Asp Val
    1175                1180                1185

Tyr Arg Phe Leu Pro Asn Gly Ile Met Leu Ser Asn Ala Phe Tyr
```

```
                1190            1195            1200
Ile Asp Ala Asn Gly Asn Thr Tyr Leu Tyr Asn Ser Lys Gly Gln
    1205            1210                1215

Met Tyr Lys Gly Gly Tyr Thr Lys Phe Asp Val Ser Glu Thr Asp
    1220            1225                1230

Lys Asp Gly Lys Glu Ser Lys Val Val Lys Phe Arg Tyr Phe Thr
    1235            1240                1245

Asn Glu Gly Val Met Ala Lys Gly Val Thr Val Ile Asp Gly Phe
    1250            1255                1260

Thr Gln Tyr Phe Gly Glu Asp Gly Phe Gln Ala Lys Asp Lys Leu
    1265            1270                1275

Val Thr Phe Lys Gly Lys Thr Tyr Tyr Phe Asp Ala His Thr Gly
    1280            1285                1290

Asn Gly Ile Lys Asp Thr Trp Arg Asn Ile Asn Gly Lys Trp Tyr
    1295            1300                1305

Tyr Phe Asp Ala Asn Gly Val Ala Ala Thr Gly Ala Gln Val Ile
    1310            1315                1320

Asn Gly Gln Lys Leu Tyr Phe Asn Glu Asp Gly Ser Gln Val Lys
    1325            1330                1335

Gly Gly Val Val Lys Asn Ala Asp Gly Thr Tyr Ser Lys Tyr Lys
    1340            1345                1350

Glu Gly Phe Gly Glu Leu Val Thr Asn Glu Phe Phe Thr Thr Asp
    1355            1360                1365

Gly Asn Val Trp Tyr Tyr Ala Gly Ala Asn Gly Lys Thr Val Thr
    1370            1375                1380

Gly Ala Gln Val Ile Asn Gly Gln His Leu Tyr Phe Asn Ala Asp
    1385            1390                1395

Gly Ser Gln Val Lys Gly Gly Val Val Lys Asn Ala Asp Gly Thr
    1400            1405                1410

Tyr Ser Lys Tyr Asn Ala Ser Thr Gly Glu Arg Leu Thr Asn Glu
    1415            1420                1425

Phe Phe Thr Thr Gly Asp Asn Asn Trp Tyr Tyr Ile Gly Ala Asn
    1430            1435                1440

Gly Lys Ser Val Thr Gly Glu Val Lys Ile Gly Asp Asp Thr Tyr
    1445            1450                1455

Phe Phe Ala Lys Asp Gly Lys Gln Val Lys Gly Gln Thr Val Ser
    1460            1465                1470

Ala Gly Asn Gly Arg Ile Ser Tyr Tyr Tyr Gly Asp Ser Gly Lys
    1475            1480                1485

Arg Ala Val Ser Thr Trp Ile Glu Ile Gln Pro Gly Val Tyr Val
    1490            1495                1500

Tyr Phe Asp Lys Asn Gly Leu Ala Tyr Pro Pro Arg Val Leu Asn
    1505            1510                1515

<210> SEQ ID NO 18
<211> LENGTH: 4434
<212> TYPE: DNA
<213> ORGANISM: Streptococcus salivarius

<400> SEQUENCE: 18
atggacgaaa cgcaggataa gaccgtgacg cagagcaaca gcggcaccac cgcttccctg    60
gtcactagcc ctgaagccac gaaagaggcg acaaacgca cgaacactaa agaggccgac   120
gttctgacgc ctgcaaaaga aacgaacgca gtcgagactg cgaccaccac taacacccag   180
```

```
gcgacggcgg aggccgccac gaccgcgacc accgcggacg tcgcggtggc tgcggtgccg    240
aacaaagaag cggtcgttac cacgcgatgct ccggcggtca cgaccgagaa agcggaagaa    300
```



```
gcgacggcgg aggccgccac gaccgcgacc accgcggacg tcgcggtggc tgcggtgccg    240
aacaaagaag cggtcgttac cacgcgatgct ccggcggtca cgaccgagaa agcggaagaa    300
cagccggcta ccgttaaagc agaagtcgtc aatacggaag tgaaagcgcc ggaagcggct    360
ctgaaagaca cgcgaggttga ggcagcgctg agcctgaaga acatcaagaa cattgatggc    420
aagtattact atgttaatga ggatggcagc cacaaagaga atttcgctat taccgtgaat    480
ggccagctgc tgtactttgg taaagacggt gcgctgacgt cctctagcac gtattctttt    540
accccaggca ctaccaatat cgtggacggt tttagcatta caaccgcgc ttacgacagc    600 agcgaggcga gctttgagct gatcgacggt tacttgaccg cagacagctg gtatcgtccg    660
gctagcatca tcaaagatgg tgttacgtgg caagcgtcca ccgccgagga ttttcgtccg    720
ctgctgatgg catggtggcc gaatgtggat acgcaggtga actatttgaa ttacatgtcc    780
aaagttttca acctggacgc gaaatactct agcaccgaca acaggaaac cctgaaagtg    840 gcagcaaaag acattcaaat caagattgaa caaaagattc aagcggagaa gagcacgcag    900
tggctgcgtg aaactatcag cgcctttgtg aaaacccagc cgcagtggaa caaagaaacc    960
gagaattaca gcaagggtgg tggtgaggac cacctgcaag gtggcgcact gctgtatgtt    1020
aacgacagcc gtaccccttg ggcgaatagc gattaccgtc gtctgaatcg caccgcaacc    1080
aatcagacgg gcacgatcga taagtctatt ctggacgagc agtctgaccc aaaccacatg    1140
ggcggtttcg actttctgct ggcgaacgac gtcgacctga gcaatccggt cgtgcaggct    1200
gagcagctga atcaaatcca ctatctgatg aattgggggtt ccattgtgat gggtgacaag    1260
gatgcgaact ttgacggcat tcgtgtcgat gcagttgaca acgtggacgc ggacatgttg    1320
caactgtata ccaattactt ccgtgagtac tacggtgtga acaagagcga agctaacgca    1380
ctggctcaca tcagcgttct ggaggcgtgg agcctgaatg ataatcatta caatgacaag    1440
accgatggtg cggcactggc aatggagaat aagcaacgtc tggcgctgtt gttttcgttg    1500
gcgaaaccga tcaaagagcg tacccccggca gtgagcccgc tgtataacaa caccttcaat    1560
accacccagc gtgatgaaaa gaccgattgg attaacaaag acggtagcaa ggcttacaac    1620
gaagatggca cggtcaaaca atcgaccatc ggtaagtaca acgagaaata cggtgacgca    1680
tccggtaact acgttttcat ccgtgcccac gataacaacg tccaggacat catcgccgag    1740
atcatcaaga aagagatcaa cccgaaaagc gacggcttca ccatcaccga cgccgaaatg    1800
aagcaagcct ttgaaatcta taacaaagat atgctgtcga gcgacaaaaa gtataccctg    1860
aataacattc cggcagcgta tgccgtgatg ttgcagaata tggaaacgat tacccgcgtc    1920
tattacggtg atctgtatac ggacgacggt cactacatgg aaaccaaatc tccgtattac    1980
gataccatcg tgaatttgat gaagagccgt atcaagtatg tttcgggtgg ccaggcgcaa    2040
cgtagctatt ggctgccgac cgacggtaag atggacaata gcgacgttga gctgtaccgc    2100
acgaatgagg tttacacgag cgtgcgctat ggtaaggata tcatgaccgc taatgatacc    2160
gaaggctcta agtattcccg caccagcggc caagtcacct tggtcgcgaa caatccgaag    2220
ctgaatctgg accaaagcgc caagttgaat gtggagatgg gcaaaatcca tgcgaatcag    2280
aagtatcgcg cactgattgt cggcactgcg gacggcatta agaactttac ttccgacgcg    2340
gacgccattg cagcgggtta tgtgaaagaa accgatagca acggcgtgct gaccttcggt    2400
gctaacgaca ttaagggcta cgaaacgttt gatatgagcg gtttcgtggc ggtgtgggtt    2460
ccggtgggtg catctgacaa tcaggacatt cgtgttgcgc cgagcaccga ggcaaagaaa    2520
gaaggtgagc tgaccttgaa ggcgacggaa gcgtatgata gccagctgat ttacgaaggc    2580
```

```
tttagcaatt tccagacgat cccagatggc agcgatccgt ccgtgtatac gaaccgcaag   2640
attgcggaga acgtggatct gttcaaaagc tggggtgtca ccagctttga gatggcaccg   2700
caatttgtct cggcggatga tggcaccttt ctggatagcg ttattcagaa tggctacgcc   2760
ttcgccgacc gttatgacct ggccatgtcc aagaacaaca agtatggtag caaagaggac   2820
ctgcgtgatg cactgaaagc actgcataag gcgggtattc aagctatcgc agactgggtt   2880
ccagaccaga tctaccagct gccgggcaaa gaagttgtca ccgccacccg tacgatggt    2940 gctggccgta agatcgcaga cgcgattatc gaccattctc tgtatgttgc aaacagcaaa   3000
agcagcggca agattatca agcaaagtac ggtggcgagt tcctggccga gctgaaagcc   3060
aaatacccgg aaatgttcaa agttaacatg attagcacgg taagccgat tgatgactcc    3120 gtgaaattga agcaatggaa agccgagtac ttcaatggca ccaacgtttt ggaacgtggt   3180
gtcggctatg ttctgagcga cgaggcgacc ggtaagtatt tcacggtgac aaagaaggc    3240 aatttcattc cgctgcaact gacgggtaaa gagaaagtta tcacgggttt ctccagcgat   3300
ggtaagggta tcacctattt cggtacgagc ggtacgcagg cgaagtctgc gtttgttacc   3360
ttcaatggta acacctacta tttcgacgcg cgtggccaca tggttaccaa tagcgaatac   3420
agcccgaatg gcaaggacgt ctaccgtttt ctgccgaacg gtatcatgct gagcaatgcg   3480
ttttacattg atgcgaacgg taatacctac ctgtacaact ctaagggtca aatgtacaaa   3540
ggcggttaca cgaaattcga tgtttctgaa acggataagg acggtaaaga gtccaaggtc   3600
gtcaagttcc gctactttac gaacgaaggc gtcatggcca agggtgttac cgtcattgat   3660
ggttttaccc aatacttcgg tgaggacggc tttcaagcga aggataagct ggtcaccttc   3720
aagggcaaga cgtattactt cgacgcacac actggtaatg gtatcaaaga tacctggcgc   3780
aatatcaatg gtaaatggta ctatttcgac gcgaatggcg ttgctgcgac cggtgcgcag   3840
gtgattaacg gccagaaact gtacttcaac gaggatggct cccaagtcaa aggcggcgtg   3900
gttaagaacg cagacggcac ctatagcaaa tacaaagaag gttttggtga gctggttact   3960
aacgagtttt tcacgactga tgcaatgtt tggtactacg ccggtgcaaa tggtaaaaacc   4020 gttaccggtg cacaagtgat caacggccaa catttgtact tcaatgcgga cggttcccag   4080
gtgaagggtg gcgttgtcaa gaacgcggat ggcaccaca gcaagtacaa tgctagcact   4140
ggtgaacgtc tgacgaacga gttctttacg accggtgata caattggta ttacattggc    4200 gcaaacggta agagcgtgac gggtgaggtc aagattggtg atgatactta cttttcgcg    4260 aaggatggca aacaagttaa aggtcaaacc gtcagcgccg taatggtcg cattagctac    4320 tactacggtg acagcggcaa gcgtgcggtt agcacctgga ttgagattca gccgggtgtt   4380
tatgtgtatt tcgacaaaaa cggtttggcg taccctccgc gtgttctgaa ttaa         4434
```

<210> SEQ ID NO 19
<211> LENGTH: 1477
<212> TYPE: PRT
<213> ORGANISM: Streptococcus salivarius

<400> SEQUENCE: 19

```
Met Asp Glu Thr Gln Asp Lys Thr Val Thr Gln Ser Asn Ser Gly Thr
1               5                   10                  15

Thr Ala Ser Leu Val Thr Ser Pro Glu Ala Thr Lys Glu Ala Asp Lys
            20                  25                  30

Arg Thr Asn Thr Lys Glu Ala Asp Val Leu Thr Pro Lys Glu Thr
        35                  40                  45
```

```
Asn Ala Val Glu Thr Ala Thr Thr Asn Thr Gln Ala Thr Ala Glu
 50                      55                      60

Ala Ala Thr Thr Ala Thr Ala Asp Val Ala Val Ala Ala Val Pro
 65                      70                      75                      80

Asn Lys Glu Ala Val Val Thr Thr Asp Ala Pro Ala Val Thr Thr Glu
                         85                      90                      95

Lys Ala Glu Glu Gln Pro Ala Thr Val Lys Ala Glu Val Val Asn Thr
                        100                     105                     110

Glu Val Lys Ala Pro Glu Ala Ala Leu Lys Asp Ser Glu Val Glu Ala
                115                     120                     125

Ala Leu Ser Leu Lys Asn Ile Lys Asn Ile Asp Gly Lys Tyr Tyr Tyr
            130                     135                     140

Val Asn Glu Asp Gly Ser His Lys Glu Asn Phe Ala Ile Thr Val Asn
145                     150                     155                     160

Gly Gln Leu Leu Tyr Phe Gly Lys Asp Gly Ala Leu Thr Ser Ser Ser
                165                     170                     175

Thr Tyr Ser Phe Thr Pro Gly Thr Thr Asn Ile Val Asp Gly Phe Ser
                180                     185                     190

Ile Asn Asn Arg Ala Tyr Asp Ser Ser Glu Ala Ser Phe Glu Leu Ile
            195                     200                     205

Asp Gly Tyr Leu Thr Ala Asp Ser Trp Tyr Arg Pro Ala Ser Ile Ile
    210                     215                     220

Lys Asp Gly Val Thr Trp Gln Ala Ser Thr Ala Glu Asp Phe Arg Pro
225                     230                     235                     240

Leu Leu Met Ala Trp Trp Pro Asn Val Asp Thr Gln Val Asn Tyr Leu
                245                     250                     255

Asn Tyr Met Ser Lys Val Phe Asn Leu Asp Ala Lys Tyr Ser Ser Thr
                260                     265                     270

Asp Lys Gln Glu Thr Leu Lys Val Ala Ala Lys Asp Ile Gln Ile Lys
            275                     280                     285

Ile Glu Gln Lys Ile Gln Ala Glu Lys Ser Thr Gln Trp Leu Arg Glu
    290                     295                     300

Thr Ile Ser Ala Phe Val Lys Thr Gln Pro Gln Trp Asn Lys Glu Thr
305                     310                     315                     320

Glu Asn Tyr Ser Lys Gly Gly Glu Asp His Leu Gln Gly Gly Ala
                325                     330                     335

Leu Leu Tyr Val Asn Asp Ser Arg Thr Pro Trp Ala Asn Ser Asp Tyr
                340                     345                     350

Arg Arg Leu Asn Arg Thr Ala Thr Asn Gln Thr Gly Thr Ile Asp Lys
            355                     360                     365

Ser Ile Leu Asp Glu Ser Asp Pro Asn His Met Gly Gly Phe Asp
    370                     375                     380

Phe Leu Leu Ala Asn Asp Val Asp Leu Ser Asn Pro Val Val Gln Ala
385                     390                     395                     400

Glu Gln Leu Asn Gln Ile His Tyr Leu Met Asn Trp Gly Ser Ile Val
                405                     410                     415

Met Gly Asp Lys Asp Ala Asn Phe Asp Gly Ile Arg Val Asp Ala Val
            420                     425                     430

Asp Asn Val Asp Ala Asp Met Leu Gln Leu Tyr Thr Asn Tyr Phe Arg
            435                     440                     445

Glu Tyr Tyr Gly Val Asn Lys Ser Glu Ala Asn Ala Leu Ala His Ile
    450                     455                     460
```

-continued

```
Ser Val Leu Glu Ala Trp Ser Leu Asn Asp Asn His Tyr Asn Asp Lys
465                 470                 475                 480

Thr Asp Gly Ala Ala Leu Ala Met Glu Asn Lys Gln Arg Leu Ala Leu
                485                 490                 495

Leu Phe Ser Leu Ala Lys Pro Ile Lys Glu Arg Thr Pro Ala Val Ser
            500                 505                 510

Pro Leu Tyr Asn Asn Thr Phe Asn Thr Thr Gln Arg Asp Glu Lys Thr
        515                 520                 525

Asp Trp Ile Asn Lys Asp Gly Ser Lys Ala Tyr Asn Glu Asp Gly Thr
    530                 535                 540

Val Lys Gln Ser Thr Ile Gly Lys Tyr Asn Glu Lys Tyr Gly Asp Ala
545                 550                 555                 560

Ser Gly Asn Tyr Val Phe Ile Arg Ala His Asp Asn Asn Val Gln Asp
                565                 570                 575

Ile Ile Ala Glu Ile Ile Lys Lys Glu Ile Asn Pro Lys Ser Asp Gly
            580                 585                 590

Phe Thr Ile Thr Asp Ala Glu Met Lys Gln Ala Phe Glu Ile Tyr Asn
        595                 600                 605

Lys Asp Met Leu Ser Ser Asp Lys Lys Tyr Thr Leu Asn Asn Ile Pro
    610                 615                 620

Ala Ala Tyr Ala Val Met Leu Gln Asn Met Glu Thr Ile Thr Arg Val
625                 630                 635                 640

Tyr Tyr Gly Asp Leu Tyr Thr Asp Asp Gly His Tyr Met Glu Thr Lys
                645                 650                 655

Ser Pro Tyr Tyr Asp Thr Ile Val Asn Leu Met Lys Ser Arg Ile Lys
            660                 665                 670

Tyr Val Ser Gly Gly Gln Ala Gln Arg Ser Tyr Trp Leu Pro Thr Asp
        675                 680                 685

Gly Lys Met Asp Asn Ser Asp Val Glu Leu Tyr Arg Thr Asn Glu Val
    690                 695                 700

Tyr Thr Ser Val Arg Tyr Gly Lys Asp Ile Met Thr Ala Asn Asp Thr
705                 710                 715                 720

Glu Gly Ser Lys Tyr Ser Arg Thr Ser Gly Gln Val Thr Leu Val Ala
                725                 730                 735

Asn Asn Pro Lys Leu Asn Leu Asp Gln Ser Ala Lys Leu Asn Val Glu
            740                 745                 750

Met Gly Lys Ile His Ala Asn Gln Lys Tyr Arg Ala Leu Ile Val Gly
        755                 760                 765

Thr Ala Asp Gly Ile Lys Asn Phe Thr Ser Asp Ala Asp Ala Ile Ala
    770                 775                 780

Ala Gly Tyr Val Lys Glu Thr Asp Ser Asn Gly Val Leu Thr Phe Gly
785                 790                 795                 800

Ala Asn Asp Ile Lys Gly Tyr Glu Thr Phe Asp Met Ser Gly Phe Val
                805                 810                 815

Ala Val Trp Val Pro Val Gly Ala Ser Asp Asn Gln Asp Ile Arg Val
            820                 825                 830

Ala Pro Ser Thr Glu Ala Lys Lys Glu Gly Glu Leu Thr Leu Lys Ala
        835                 840                 845

Thr Glu Ala Tyr Asp Ser Gln Leu Ile Tyr Glu Gly Phe Ser Asn Phe
    850                 855                 860

Gln Thr Ile Pro Asp Gly Ser Asp Pro Ser Val Tyr Thr Asn Arg Lys
865                 870                 875                 880

Ile Ala Glu Asn Val Asp Leu Phe Lys Ser Trp Gly Val Thr Ser Phe
```

-continued

```
                885                 890                 895
Glu Met Ala Pro Gln Phe Val Ser Ala Asp Asp Gly Thr Phe Leu Asp
            900                 905                 910

Ser Val Ile Gln Asn Gly Tyr Ala Phe Ala Asp Arg Tyr Asp Leu Ala
            915                 920                 925

Met Ser Lys Asn Asn Lys Tyr Gly Ser Lys Glu Asp Leu Arg Asp Ala
            930                 935                 940

Leu Lys Ala Leu His Lys Ala Gly Ile Gln Ala Ile Ala Asp Trp Val
945                 950                 955                 960

Pro Asp Gln Ile Tyr Gln Leu Pro Gly Lys Glu Val Val Thr Ala Thr
            965                 970                 975

Arg Thr Asp Gly Ala Gly Arg Lys Ile Ala Asp Ala Ile Ile Asp His
            980                 985                 990

Ser Leu Tyr Val Ala Asn Ser Lys Ser Ser Gly Lys Asp Tyr Gln Ala
            995                 1000                1005

Lys Tyr Gly Gly Glu Phe Leu Ala Glu Leu Lys Ala Lys Tyr Pro
            1010                1015                1020

Glu Met Phe Lys Val Asn Met Ile Ser Thr Gly Lys Pro Ile Asp
            1025                1030                1035

Asp Ser Val Lys Leu Lys Gln Trp Lys Ala Glu Tyr Phe Asn Gly
            1040                1045                1050

Thr Asn Val Leu Glu Arg Gly Val Gly Tyr Val Leu Ser Asp Glu
            1055                1060                1065

Ala Thr Gly Lys Tyr Phe Val Thr Lys Glu Gly Asn Phe Ile
            1070                1075                1080

Pro Leu Gln Leu Thr Gly Lys Glu Lys Val Ile Thr Gly Phe Ser
            1085                1090                1095

Ser Asp Gly Lys Gly Ile Thr Tyr Phe Gly Thr Ser Gly Thr Gln
            1100                1105                1110

Ala Lys Ser Ala Phe Val Thr Phe Asn Gly Asn Thr Tyr Tyr Phe
            1115                1120                1125

Asp Ala Arg Gly His Met Val Thr Asn Ser Glu Tyr Ser Pro Asn
            1130                1135                1140

Gly Lys Asp Val Tyr Arg Phe Leu Pro Asn Gly Ile Met Leu Ser
            1145                1150                1155

Asn Ala Phe Tyr Ile Asp Ala Asn Gly Asn Thr Tyr Leu Tyr Asn
            1160                1165                1170

Ser Lys Gly Gln Met Tyr Lys Gly Gly Tyr Thr Lys Phe Asp Val
            1175                1180                1185

Ser Glu Thr Asp Lys Asp Gly Lys Glu Ser Lys Val Val Lys Phe
            1190                1195                1200

Arg Tyr Phe Thr Asn Glu Gly Val Met Ala Lys Gly Val Thr Val
            1205                1210                1215

Ile Asp Gly Phe Thr Gln Tyr Phe Gly Glu Asp Gly Phe Gln Ala
            1220                1225                1230

Lys Asp Lys Leu Val Thr Phe Lys Gly Lys Thr Tyr Tyr Phe Asp
            1235                1240                1245

Ala His Thr Gly Asn Gly Ile Lys Asp Thr Trp Arg Asn Ile Asn
            1250                1255                1260

Gly Lys Trp Tyr Tyr Phe Asp Ala Asn Gly Val Ala Ala Thr Gly
            1265                1270                1275

Ala Gln Val Ile Asn Gly Gln Lys Leu Tyr Phe Asn Glu Asp Gly
            1280                1285                1290
```

| | | | | | | | | | | |
|---|---|---|---|---|---|---|---|---|---|---|
| Ser | Gln | Val | Lys | Gly | Gly | Val | Lys | Asn | Ala | Asp | Gly | Thr | Tyr |
| | 1295 | | | | 1300 | | | | 1305 | |

| Ser | Lys | Tyr | Lys | Glu | Gly | Phe | Gly | Glu | Leu | Val | Thr | Asn | Glu | Phe |
| | 1310 | | | | 1315 | | | | 1320 | |

| Phe | Thr | Thr | Asp | Gly | Asn | Val | Trp | Tyr | Tyr | Ala | Gly | Ala | Asn | Gly |
| | 1325 | | | | 1330 | | | | 1335 | |

| Lys | Thr | Val | Thr | Gly | Ala | Gln | Val | Ile | Asn | Gly | Gln | His | Leu | Tyr |
| | 1340 | | | | 1345 | | | | 1350 | |

| Phe | Asn | Ala | Asp | Gly | Ser | Gln | Val | Lys | Gly | Val | Val | Lys | Asn |
| | 1355 | | | | 1360 | | | | 1365 | |

| Ala | Asp | Gly | Thr | Tyr | Ser | Lys | Tyr | Asn | Ala | Ser | Thr | Gly | Glu | Arg |
| | 1370 | | | | 1375 | | | | 1380 | |

| Leu | Thr | Asn | Glu | Phe | Phe | Thr | Thr | Gly | Asp | Asn | Asn | Trp | Tyr | Tyr |
| | 1385 | | | | 1390 | | | | 1395 | |

| Ile | Gly | Ala | Asn | Gly | Lys | Ser | Val | Thr | Gly | Glu | Val | Lys | Ile | Gly |
| | 1400 | | | | 1405 | | | | 1410 | |

| Asp | Asp | Thr | Tyr | Phe | Phe | Ala | Lys | Asp | Gly | Lys | Gln | Val | Lys | Gly |
| | 1415 | | | | 1420 | | | | 1425 | |

| Gln | Thr | Val | Ser | Ala | Gly | Asn | Gly | Arg | Ile | Ser | Tyr | Tyr | Tyr | Gly |
| | 1430 | | | | 1435 | | | | 1440 | |

| Asp | Ser | Gly | Lys | Arg | Ala | Val | Ser | Thr | Trp | Ile | Glu | Ile | Gln | Pro |
| | 1445 | | | | 1450 | | | | 1455 | |

| Gly | Val | Tyr | Val | Tyr | Phe | Asp | Lys | Asn | Gly | Leu | Ala | Tyr | Pro | Pro |
| | 1460 | | | | 1465 | | | | 1470 | |

| Arg | Val | Leu | Asn |
| | 1475 |

<210> SEQ ID NO 20
<211> LENGTH: 3351
<212> TYPE: DNA
<213> ORGANISM: Paenibacillus humicus

<400> SEQUENCE: 20

| | |
|---|---|
| atggctagcg cagcaggagg cgcgaatctg acgctcggca aaaccgtcac cgccagcggc | 60 |
| cagtcgcaga cgtacagccc cgacaatgtc aaggacagca atcagggaac ttactgggaa | 120 |
| agcacgaaca acgccttccc gcagtggatc caagtcgacc ttggcgccag cacgagcatc | 180 |
| gaccagatcg tgctcaaact tccgtccgga tgggagactc gtacgcaaac gctctcgata | 240 |
| cagggcagcg cgaacggctc gacgttcacg aacatcgtcg atcggccgg gtatacattc | 300 |
| aatccatccg tcgccggcaa cagcgtcacg atcaacttca gcgctgccag cgcccgctac | 360 |
| gtccgcctga atttcacggc caatacgggc tggccagcag gccagctgtc ggagcttgag | 420 |
| atctacggag cgacggcgcc aacgcctact cccacgccta ctccaacacc aacgccaacg | 480 |
| ccaacaccaa cgccaacccc tacagtaacc cctgcgcctt cggccacgcc gactccgact | 540 |
| cctccggcag gcagcaacat cgccgtaggg aaatcgatta cagcctcttc cagcacgcag | 600 |
| acctacgtag ctgcaaatgc aaatgacaac aatacatcca cctattggga gggaggaagc | 660 |
| aacccgagca cgctgactct cgatttcggt tccaaccaga gcatcacttc cgtcgtcctc | 720 |
| aagctgaatc cggcttcgga atgggggact cgcacgcaaa cgatccaagt tcttggagcg | 780 |
| gatcagaacg ccggctcctt cagcaatctc gtctctgccc agtcctatac gttcaatccc | 840 |
| gcaaccggca atacggtgac gattccggtc tccgcgacgg tcaagcgcct ccagctgaac | 900 |
| attacggcga actccggcgc ccctgccggc cagattgccg agttccaagt gttcggcacg | 960 |

```
ccagcgccta atccggactt gaccattacc ggcatgtcct ggactccgtc ttctccggtc    1020
gagagcggcg acattacgct gaacgccgtc gtcaagaaca tcggaactgc agctgcaggc    1080
gccacgacgg tcaatttcta cctgaacaac gaactcgccg gcaccgctcc ggtaggcgcg    1140
cttgcggcag gagcttctgc aaatgtatcg atcaatgcag gcgccaaagc agccgcaacg    1200
tatgcggtaa gcgccaaagt cgacgagagc aacgccgtca tcgagcagaa tgaaggcaac    1260
aacagctact cgaacccgac taacctcgtc gtagcgccgg tgtccagctc cgacctcgtc    1320
gccgtgacgt catggtcgcc gggcacgccg tcgcaggag cggcggtcgc atttaccgtc     1380
gcgcttaaaa atcagggtac gctggcttcc gccggcggag cccatcccgt aaccgtcgtt    1440
ctgaaaaacg ctgccggagc gacgctgcaa accttcacgg gcacctacac aggttccctg    1500
gcagcaggcg catccgcgaa tatcagcgtg gcagctgga cggcagcgag cggcacctat      1560
accgtctcga cgacggtagc cgctgacggc aatgaaattc cggccaagca aagcaacaat    1620
acgagcagcg cgagcctcac ggtctactcg gcgcgcggcg ccagcatgcc gtacagccgt    1680
tacgacacgg aggatgcggt gctcggcggc ggagctgtcc tgagaacggc gccgacgttc    1740
gatcagtcgc tcatcgcttc cgaagcatcg ggacagaaat acgccgcact tccgtccaac    1800
ggctccagcc tgcagtggac cgtccgtcaa ggccagggcg gtgcaggcgt cacgatgcgc    1860
ttcacgatgc ccgacacgag cgacggcatg gccagaacg gctcgctcga cgtctatgtc      1920
aacggaacca agccaaaac ggtgtcgctg acctcttatt acagctggca gtatttctcc      1980
ggcgacatgc cggctgacgc tccgggcggc ggcaggccgc tcttccgctt cgacgaagtc    2040
cacttcaagc tggatacggc gttgaagccg ggagacacga tccgcgtcca aagggcggt     2100 gacagcctgg agtacggcgt cgacttcatc gagatcgagc cgattccggc agcggttgcc    2160
cgtccggcca actcggtgtc cgtcaccgaa tacgcgctg tcgccaatga cggcaaggat     2220
gatctcgccg ccttcaaggc tgccgtgacc gcagcggtag cggccggaaa atccctctac    2280
atcccggaag gcaccttcca cctgagcagc atgtgggaga tcggctcggc caccagcatg    2340
atcgacaact tcacggtcac gggtgccggc atctggtata cgaacatcca gttcacgaat    2400
cccaatgcat cgggcggcgg catctccctg agaatcaaag gaaagctgga tttcagcaac    2460
atctacatga actccaacct gcgttcccgt tacgggcaga acgccgtcta caaaggcttt    2520
atggacaatt tcggcactaa ttcgatcatc catgacgtct gggtcgagca tttcgaatgc    2580
ggcatgtggg tcggcgacta cgcccatact cctgcgatct atgcgagcgg gctcgtcgtg    2640
gaaaacagcc gcatccgcaa caatcttgcc gacggcatca acttctcgca gggaacgagc    2700
aactcgaccg tccgcaacag cagcatccgc aacaacggcg atgacggcct cgccgtctgg    2760
acgagcaaca cgaacggcgc tccggccggc gtgaacaaca ccttctccta caacacgatc    2820
gagaacaact ggcgcgcggc ggccatcgcc ttcttcggcg gcagcggcca caaggctgac    2880
cacaactaca tcatcgactg tgtcggcggc tccggcatcc ggatgaatac ggtgttccca    2940
ggctaccact tccagaacaa caccggcatc accttctcgg atacgacgat catcaacagc    3000
ggcaccagcc aggatctgta caacggcgag cgcggagcga ttgatctgga agcatccaac    3060
gacgcgatca aaaacgtcac cttcaccaac atcgacatca tcaatgccca gcgcgacggc    3120
gttcagatcg gctatggcgg cggcttcgag aacatcgtgt tcaacaacat cacgatcgac    3180
ggcaccggcc gcgacgggat atcgacatcc cgcttctcgg gacctcatct tggcgcagcc    3240
atctatacgt acacgggcaa cggctcggcg acgttcaaca acctggtgac ccggaacatc    3300
```
gcctatgcag gcggcaacta catccagagc gggttcaacc tgacgatcta a        3351

<210> SEQ ID NO 21
<211> LENGTH: 1116
<212> TYPE: PRT
<213> ORGANISM: Paenibacillus humicus

<400> SEQUENCE: 21

```
Met Ala Ser Ala Ala Gly Gly Ala Asn Leu Thr Leu Gly Lys Thr Val
1               5                   10                  15

Thr Ala Ser Gly Gln Ser Gln Thr Tyr Ser Pro Asp Asn Val Lys Asp
            20                  25                  30

Ser Asn Gln Gly Thr Tyr Trp Glu Ser Thr Asn Asn Ala Phe Pro Gln
        35                  40                  45

Trp Ile Gln Val Asp Leu Gly Ala Ser Thr Ser Ile Asp Gln Ile Val
    50                  55                  60

Leu Lys Leu Pro Ser Gly Trp Glu Thr Arg Thr Gln Thr Leu Ser Ile
65                  70                  75                  80

Gln Gly Ser Ala Asn Gly Ser Thr Phe Thr Asn Ile Val Gly Ser Ala
                85                  90                  95

Gly Tyr Thr Phe Asn Pro Ser Val Ala Gly Asn Ser Val Thr Ile Asn
            100                 105                 110

Phe Ser Ala Ala Ser Ala Arg Tyr Val Arg Leu Asn Phe Thr Ala Asn
        115                 120                 125

Thr Gly Trp Pro Ala Gly Gln Leu Ser Glu Leu Glu Ile Tyr Gly Ala
    130                 135                 140

Thr Ala Pro Thr Pro Thr Pro Thr Pro Thr Pro Thr Pro Thr Pro Thr
145                 150                 155                 160

Pro Thr Pro Thr Pro Thr Pro Thr Val Thr Pro Ala Pro Ser Ala Thr
                165                 170                 175

Pro Thr Pro Thr Pro Pro Ala Gly Ser Asn Ile Ala Val Gly Lys Ser
            180                 185                 190

Ile Thr Ala Ser Ser Ser Thr Gln Thr Tyr Val Ala Ala Asn Ala Asn
        195                 200                 205

Asp Asn Asn Thr Ser Thr Tyr Trp Glu Gly Ser Asn Pro Ser Thr
    210                 215                 220

Leu Thr Leu Asp Phe Gly Ser Asn Gln Ser Ile Thr Ser Val Val Leu
225                 230                 235                 240

Lys Leu Asn Pro Ala Ser Glu Trp Gly Thr Arg Thr Gln Thr Ile Gln
                245                 250                 255

Val Leu Gly Ala Asp Gln Asn Ala Gly Ser Phe Ser Asn Leu Val Ser
            260                 265                 270

Ala Gln Ser Tyr Thr Phe Asn Pro Ala Thr Gly Asn Thr Val Thr Ile
        275                 280                 285

Pro Val Ser Ala Thr Val Lys Arg Leu Gln Leu Asn Ile Thr Ala Asn
    290                 295                 300

Ser Gly Ala Pro Ala Gly Gln Ile Ala Glu Phe Gln Val Phe Gly Thr
305                 310                 315                 320

Pro Ala Pro Asn Pro Asp Leu Thr Ile Thr Gly Met Ser Trp Thr Pro
                325                 330                 335

Ser Ser Pro Val Glu Ser Gly Asp Ile Thr Leu Asn Ala Val Val Lys
            340                 345                 350

Asn Ile Gly Thr Ala Ala Ala Gly Ala Thr Thr Val Asn Phe Tyr Leu
        355                 360                 365
```

Asn Asn Glu Leu Ala Gly Thr Ala Pro Val Gly Ala Leu Ala Ala Gly
370                 375                 380

Ala Ser Ala Asn Val Ser Ile Asn Ala Gly Ala Lys Ala Ala Ala Thr
385                 390                 395                 400

Tyr Ala Val Ser Ala Lys Val Asp Glu Ser Asn Ala Val Ile Glu Gln
                405                 410                 415

Asn Glu Gly Asn Asn Ser Tyr Ser Asn Pro Thr Asn Leu Val Val Ala
                420                 425                 430

Pro Val Ser Ser Asp Leu Val Ala Val Thr Ser Trp Ser Pro Gly
                435                 440                 445

Thr Pro Ser Gln Gly Ala Ala Val Ala Phe Thr Val Ala Leu Lys Asn
450                 455                 460

Gln Gly Thr Leu Ala Ser Ala Gly Gly Ala His Pro Val Thr Val Val
465                 470                 475                 480

Leu Lys Asn Ala Ala Gly Ala Thr Leu Gln Thr Phe Thr Gly Thr Tyr
                485                 490                 495

Thr Gly Ser Leu Ala Ala Gly Ala Ser Ala Asn Ile Ser Val Gly Ser
                500                 505                 510

Trp Thr Ala Ala Ser Gly Thr Tyr Thr Val Ser Thr Val Ala Ala
                515                 520                 525

Asp Gly Asn Glu Ile Pro Ala Lys Gln Ser Asn Asn Thr Ser Ser Ala
530                 535                 540

Ser Leu Thr Val Tyr Ser Ala Arg Gly Ala Ser Met Pro Tyr Ser Arg
545                 550                 555                 560

Tyr Asp Thr Glu Asp Ala Val Leu Gly Gly Ala Val Leu Arg Thr
                565                 570                 575

Ala Pro Thr Phe Asp Gln Ser Leu Ile Ala Ser Glu Ala Ser Gly Gln
                580                 585                 590

Lys Tyr Ala Ala Leu Pro Ser Asn Gly Ser Ser Leu Gln Trp Thr Val
                595                 600                 605

Arg Gln Gly Gln Gly Gly Ala Gly Val Thr Met Arg Phe Thr Met Pro
610                 615                 620

Asp Thr Ser Asp Gly Met Gly Gln Asn Gly Ser Leu Asp Val Tyr Val
625                 630                 635                 640

Asn Gly Thr Lys Ala Lys Thr Val Ser Leu Thr Ser Tyr Tyr Ser Trp
                645                 650                 655

Gln Tyr Phe Ser Gly Asp Met Pro Ala Asp Ala Pro Gly Gly Arg
                660                 665                 670

Pro Leu Phe Arg Phe Asp Glu Val His Phe Lys Leu Asp Thr Ala Leu
                675                 680                 685

Lys Pro Gly Asp Thr Ile Arg Val Gln Lys Gly Gly Asp Ser Leu Glu
690                 695                 700

Tyr Gly Val Asp Phe Ile Glu Ile Glu Pro Ile Pro Ala Ala Val Ala
705                 710                 715                 720

Arg Pro Ala Asn Ser Val Ser Val Thr Glu Tyr Gly Ala Val Ala Asn
                725                 730                 735

Asp Gly Lys Asp Asp Leu Ala Ala Phe Lys Ala Ala Val Thr Ala Ala
                740                 745                 750

Val Ala Ala Gly Lys Ser Leu Tyr Ile Pro Glu Gly Thr Phe His Leu
                755                 760                 765

Ser Ser Met Trp Glu Ile Gly Ser Ala Thr Ser Met Ile Asp Asn Phe
770                 775                 780

Thr Val Thr Gly Ala Gly Ile Trp Tyr Thr Asn Ile Gln Phe Thr Asn

Pro Asn Ala Ser Gly Gly Gly Ile Ser Leu Arg Ile Lys Gly Lys Leu
785                 790                 795                 800
                805                 810                 815

Asp Phe Ser Asn Ile Tyr Met Asn Ser Asn Leu Arg Ser Arg Tyr Gly
                820                 825                 830

Gln Asn Ala Val Tyr Lys Gly Phe Met Asp Asn Phe Gly Thr Asn Ser
                835                 840                 845

Ile Ile His Asp Val Trp Val Glu His Phe Glu Cys Gly Met Trp Val
            850                 855                 860

Gly Asp Tyr Ala His Thr Pro Ala Ile Tyr Ala Ser Gly Leu Val Val
865                 870                 875                 880

Glu Asn Ser Arg Ile Arg Asn Asn Leu Ala Asp Gly Ile Asn Phe Ser
                885                 890                 895

Gln Gly Thr Ser Asn Ser Thr Val Arg Asn Ser Ser Ile Arg Asn Asn
                900                 905                 910

Gly Asp Asp Gly Leu Ala Val Trp Thr Ser Asn Thr Asn Gly Ala Pro
                915                 920                 925

Ala Gly Val Asn Asn Thr Phe Ser Tyr Asn Thr Ile Glu Asn Asn Trp
930                 935                 940

Arg Ala Ala Ala Ile Ala Phe Phe Gly Gly Ser Gly His Lys Ala Asp
945                 950                 955                 960

His Asn Tyr Ile Ile Asp Cys Val Gly Ser Gly Ile Arg Met Asn
                965                 970                 975

Thr Val Phe Pro Gly Tyr His Phe Gln Asn Asn Thr Gly Ile Thr Phe
                980                 985                 990

Ser Asp Thr Thr Ile Ile Asn Ser Gly Thr Ser Gln Asp Leu Tyr Asn
                995                 1000                1005

Gly Glu Arg Gly Ala Ile Asp Leu Glu Ala Ser Asn Asp Ala Ile
                1010                1015                1020

Lys Asn Val Thr Phe Thr Asn Ile Asp Ile Ile Asn Ala Gln Arg
                1025                1030                1035

Asp Gly Val Gln Ile Gly Tyr Gly Gly Gly Phe Glu Asn Ile Val
                1040                1045                1050

Phe Asn Asn Ile Thr Ile Asp Gly Thr Gly Arg Asp Gly Ile Ser
                1055                1060                1065

Thr Ser Arg Phe Ser Gly Pro His Leu Gly Ala Ala Ile Tyr Thr
                1070                1075                1080

Tyr Thr Gly Asn Gly Ser Ala Thr Phe Asn Asn Leu Val Thr Arg
                1085                1090                1095

Asn Ile Ala Tyr Ala Gly Gly Asn Tyr Ile Gln Ser Gly Phe Asn
                1100                1105                1110

Leu Thr Ile
    1115

<210> SEQ ID NO 22
<211> LENGTH: 1308
<212> TYPE: DNA
<213> ORGANISM: Penicillium marneffei

<400> SEQUENCE: 22
atgaagcaaa ccacttccct cctcctctca gccatcgcgg caaccagcag cttcagcgga      60
ctaacagccg ctcaaaaact cgcctttgcg cacgtcgtcg tcggcaacac tgcagcacac     120
acccaatcca cctgggaaag cgacattact ctcgcccata actccggtct agatgccttt     180

```
gccttgaacg gtggattccc cgatggcaac atccccgcac aaatcgccaa cgcttttgcg    240
gcttgtgaag ccctttcaaa tggcttcaag ctattcattt cgtttgacta cctcggtggt    300
ggtcagccct ggcctgcctc agaggttgtg tctatgctga agcagtatgc cagttccgat    360
tgttatttgg cctatgatgg caagcccttt gtctcaactt ttgagggcac cggaaatatt    420
gcggattggg cgcacggagg tcccattcgg tcggcgtgg atgtttactt tgtgccggat     480
tggacgagtt tggggcctgc tgggattaag tcgtatctcg acaatatcga tggattttc    540
agctggaaca tgtggcctgt aggtgcggcc gatatgaccg acgagcctga tttcgaatgg    600
ctcgatgcaa ttgggtccga caagacgtac atgatgggcg tttcgccatg gttcttccac    660
agtgcaagcg gaggcaccga ctgggtctgg cgtggtgatg acctctggga tgaccgatgg    720
attcaagtca cctgcgtcga ccctcaattt gtccaggtcg tcacatggaa cgactggggt    780
gaatcctcct acatcggccc cttcgtgacc gctagcgaag tccccgccgg ctcattagcc    840
tacgtcgaca acatgtcaca ccaaagcttc cttgacttct tgcctttcta catcgccacc    900
ttcaaaggcg acacattcaa catctcccgc gaccagatgc aatactggta ccgcctcgca    960
cccgccgcag caggcagcgc gtgcggcgta tacggcaatg atcccgatca aggccagact   1020
accgttgacg tcaactccat cgttcaggac aaggtgtttt tcagtgcttt gttgacgGct   1080
gatgctactg taacggtgca gattggtagt aatgctgcgg tttcatatga tggtgttgct   1140
ggtatgaacc actggagtca ggactttaat ggccagaccg gcgcggttac gtttagtgtt   1200
gtcaggggtg gcgctacagt taagagtggt attggagccg agattacggc ttcgacttcg   1260
ttgtcgaatg ggtgcactaa ttacaaccct tgggttggta gtttctaa                1308
```

<210> SEQ ID NO 23
<211> LENGTH: 435
<212> TYPE: PRT
<213> ORGANISM: Penicillium marneffei

<400> SEQUENCE: 23

```
Met Lys Gln Thr Thr Ser Leu Leu Leu Ser Ala Ile Ala Ala Thr Ser
1               5                   10                  15

Ser Phe Ser Gly Leu Thr Ala Ala Gln Lys Leu Ala Phe Ala His Val
            20                  25                  30

Val Val Gly Asn Thr Ala Ala His Thr Gln Ser Thr Trp Glu Ser Asp
        35                  40                  45

Ile Thr Leu Ala His Asn Ser Gly Leu Asp Ala Phe Ala Leu Asn Gly
    50                  55                  60

Gly Phe Pro Asp Gly Asn Ile Pro Ala Gln Ile Ala Asn Ala Phe Ala
65                  70                  75                  80

Ala Cys Glu Ala Leu Ser Asn Gly Phe Lys Leu Phe Ile Ser Phe Asp
                85                  90                  95

Tyr Leu Gly Gly Gly Gln Pro Trp Pro Ala Ser Glu Val Val Ser Met
            100                 105                 110

Leu Lys Gln Tyr Ala Ser Ser Asp Cys Tyr Leu Ala Tyr Asp Gly Lys
        115                 120                 125

Pro Phe Val Ser Thr Phe Glu Gly Thr Gly Asn Ile Ala Asp Trp Ala
    130                 135                 140

His Gly Gly Pro Ile Arg Ser Ala Val Asp Val Tyr Phe Val Pro Asp
145                 150                 155                 160

Trp Thr Ser Leu Gly Pro Ala Gly Ile Lys Ser Tyr Leu Asp Asn Ile
                165                 170                 175
```

Asp Gly Phe Phe Ser Trp Asn Met Trp Pro Val Gly Ala Ala Asp Met
            180                 185                 190

Thr Asp Glu Pro Asp Phe Glu Trp Leu Asp Ala Ile Gly Ser Asp Lys
        195                 200                 205

Thr Tyr Met Met Gly Val Ser Pro Trp Phe Phe His Ser Ala Ser Gly
        210                 215                 220

Gly Thr Asp Trp Val Trp Arg Gly Asp Asp Leu Trp Asp Asp Arg Trp
225                 230                 235                 240

Ile Gln Val Thr Cys Val Asp Pro Gln Phe Val Gln Val Thr Trp
                245                 250                 255

Asn Asp Trp Gly Glu Ser Ser Tyr Ile Gly Pro Phe Val Thr Ala Ser
            260                 265                 270

Glu Val Pro Ala Gly Ser Leu Ala Tyr Val Asp Asn Met Ser His Gln
        275                 280                 285

Ser Phe Leu Asp Phe Leu Pro Phe Tyr Ile Ala Thr Phe Lys Gly Asp
        290                 295                 300

Thr Phe Asn Ile Ser Arg Asp Gln Met Gln Tyr Trp Tyr Arg Leu Ala
305                 310                 315                 320

Pro Ala Ala Ala Gly Ser Ala Cys Gly Val Tyr Gly Asn Asp Pro Asp
                325                 330                 335

Gln Gly Gln Thr Thr Val Asp Val Asn Ser Ile Val Gln Asp Lys Val
            340                 345                 350

Phe Phe Ser Ala Leu Leu Thr Ala Asp Ala Thr Val Thr Val Gln Ile
        355                 360                 365

Gly Ser Asn Ala Ala Val Ser Tyr Asp Gly Val Ala Gly Met Asn His
        370                 375                 380

Trp Ser Gln Asp Phe Asn Gly Gln Thr Gly Ala Val Thr Phe Ser Val
385                 390                 395                 400

Val Arg Gly Gly Ala Thr Val Lys Ser Gly Ile Gly Ala Glu Ile Thr
                405                 410                 415

Ala Ser Thr Ser Leu Ser Asn Gly Cys Thr Asn Tyr Asn Pro Trp Val
            420                 425                 430

Gly Ser Phe
        435

<210> SEQ ID NO 24
<211> LENGTH: 8616
<212> TYPE: DNA
<213> ORGANISM: artificial sequence
<220> FEATURE:
<223> OTHER INFORMATION: plasmid pTrex

<400> SEQUENCE: 24
aagcttaact agtacttctc gagctctgta catgtccggt cgcgacgtac gcgtatcgat      60
ggcgccagct gcaggcggcc gcctgcagcc acttgcagtc ccgtggaatt ctcacggtga     120
atgtaggcct tttgtagggt aggaattgtc actcaagcac ccccaacctc cattacgcct     180
cccccataga gttcccaatc agtgagtcat ggcactgttc tcaaatagat tggggagaag     240
ttgacttccg cccagagctg aaggtcgcac aaccgcatga tatagggtcg gcaacggcaa     300
aaaagcacgt ggctcaccga aaagcaagat gtttgcgatc taacatccag gaacctggat     360
acatccatca tcacgcacga ccactttgat ctgctggtaa actcgtattc gccctaaacc     420
gaagtgcgtg gtaaatctac acgtgggccc ctttcggtat actgcgtgtg tcttctctag     480
gtgccattct tttcccttcc tctagtgttg aattgtttgt gttggagtcc gagctgtaac     540

```
tacctctgaa tctctggaga atggtggact aacgactacc gtgcacctgc atcatgtata    600
taatagtgat cctgagaagg ggggtttgga gcaatgtggg actttgatgg tcatcaaaca    660
aagaacgaag acgcctcttt tgcaaagttt tgtttcggct acggtgaaga actggatact    720
tgttgtgtct tctgtgtatt tttgtggcaa caagaggcca gagacaatct attcaaacac    780
caagcttgct cttttgagct acaagaacct gtggggtata tatctagagt tgtgaagtcg    840
gtaatcccgc tgtatagtaa tacgagtcgc atctaaatac tccgaagctg ctgcgaaccc    900
ggagaatcga gatgtgctgg aaagcttcta gcgagcggct aaattagcat gaaaggctat    960
gagaaattct ggagacggct tgttaatca tggcgttcca ttcttcgaca agcaaagcgt   1020
tccgtcgcag tagcaggcac tcattcccga aaaaactcgg agattcctaa gtagcgatgg   1080
aaccggaata atataatagg caatacattg agttgcctcg acggttgcaa tgcagggggta   1140
ctgagcttgg acataactgt tccgtacccc acctcttctc aacctttggc gtttccctga   1200
ttcagcgtac ccgtacaagt cgtaatcact attaacccag actgaccgga cgtgttttgc   1260
ccttcatttg gagaaataat gtcattgcga tgtgtaattt gcctgcttga ccgactgggg   1320
ctgttcgaag cccgaatgta ggattgttat ccgaactctg ctcgtagagg catgttgtga   1380
atctgtgtcg ggcaggacac gcctcgaagg ttcacggcaa gggaaaccac cgatagcagt   1440
gtctagtagc aacctgtaaa gccgcaatgc agcatcactg gaaaatacaa accaatggct   1500
aaaagtacat aagttaatgc ctaaagaagt catataccag cggctaataa ttgtacaatc   1560
aagtggctaa acgtaccgta atttgccaac ggcttgtggg gttgcagaag caacggcaaa   1620
gccccacttc cccacgtttg tttcttcact cagtccaatc tcagctggtg atcccccaat   1680
tgggtcgctt gtttgttccg gtgaagtgaa agaagacaga ggtaagaatg tctgactcgg   1740
agcgttttgc atacaaccaa gggcagtgat ggaagacagt gaaatgttga cattcaagga   1800
gtatttagcc agggatgctt gagtgtatcg tgtaaggagg tttgtctgcc gatacgacga   1860
atactgtata gtcacttctg atgaagtggt ccatattgaa atgtaagtcg gcactgaaca   1920
ggcaaaagat tgagttgaaa ctgcctaaga tctcgggccc tcgggccttc ggcctttggg   1980
tgtacatgtt tgtgctccgg gcaaatgcaa agtgtggtag gatcgaacac actgctgcct   2040
ttaccaagca gctgagggta tgtgataggc aaatgttcag gggccactgc atggtttcga   2100
atagaaagag aagcttagcc aagaacaata gccgataaag atagcctcat taaacggaat   2160
gagctagtag gcaaagtcag cgaatgtgta tatataaagg ttcgaggtcc gtgcctccct   2220
catgctctcc ccatctactc atcaactcag atcctccagg agacttgtac accatctttt   2280
gaggcacaga aacccaatag tcaaccgcgg actgcgcatc atgtatcgga agttggccgt   2340
catctcggcc ttcttggcca cacctcgtgc tagactaggc gcgccgcgcg ccagctccgt   2400
gcgaaagcct gacgcaccgg tagattcttg gtgagcccgt atcatgacgg cggcgggagc   2460
tacatggccc cgggtgattt atttttttttg tatctacttc tgacccttttt caaatatacg   2520
gtcaactcat ctttcactgg agatgcggcc tgcttggtat tgcgatgttg tcagcttggc   2580
aaattgtggc tttcgaaaac acaaaacgat tccttagtag ccatgcattt taagataacg   2640
gaatagaaga aagaggaaat taaaaaaaaa aaaaaaacaa acatcccgtt cataacccgt   2700
agaatcgccg ctcttcgtgt atcccagtac cagtttattt tgaatagctc gcccgctgga   2760
gagcatcctg aatgcaagta acaaccgtag aggctgacac ggcaggtgtt gctagggagc   2820
gtcgtgttct acaaggccag acgtcttcgc ggttgatata tatgtatgtt tgactgcagg   2880
ctgctcagcg acgacagtca agttcgccct cgctgcttgt gcaataatcg cagtggggaa   2940
```

-continued

```
gccacaccgt gactcccatc tttcagtaaa gctctgttgg tgtttatcag caatacacgt    3000
aatttaaact cgttagcatg gggctgatag cttaattacc gtttaccagt gccatggttc    3060
tgcagctttc cttggcccgt aaaattcggc gaagccagcc aatcaccagc taggcaccag    3120
ctaaacccta taattagtct cttatcaaca ccatccgctc ccccgggatc aatgaggaga    3180
atgaggggga tgcggggcta agaagccta cataaccctc atgccaactc ccagtttaca    3240
ctcgtcgagc caacatcctg actataagct aacacagaat gcctcaatcc tgggaagaac    3300
tggccgctga taagcgcgcc cgcctcgcaa aaaccatccc tgatgaatgg aaagtccaga    3360
cgctgcctgc ggaagacagc gttattgatt cccaaagaa atcggggatc ctttcagagg     3420
ccgaactgaa gatcacagag gcctccgctg cagatcttgt gtccaagctg gcggccggag    3480
agttgacctc ggtggaagtt acgctagcat tctgtaaacg ggcagcaatc gcccagcagt    3540
tagtagggtc ccctctacct ctcagggaga tgtaacaacg ccaccttatg ggactatcaa    3600
gctgacgctg gcttctgtgc agacaaactg cgcccacgag ttcttccctg acgccgctct    3660
cgcgcaggca agggaactcg atgaatacta cgcaaagcac aagagacccg ttggtccact    3720
ccatggcctc cccatctctc tcaaagacca gcttcgagtc aaggtacacc gttgccccta    3780
agtcgttaga tgtccctttt tgtcagctaa catatgccac cagggctacg aaacatcaat    3840
gggctacatc tcatggctaa acaagtacga cgaaggggac tcggttctga caaccatgct    3900
ccgcaaagcc ggtgccgtct tctacgtcaa gacctctgtc ccgcagaccc tgatggtctg    3960
cgagacagtc aacaacatca tcgggcgcac cgtcaaccca cgcaacaaga actggtcgtg    4020
cggcggcagt tctggtggtg agggtgcgat cgttgggatt cgtggtggcg tcatcggtgt    4080
aggaacggat atcggtggct cgattcgagt gccggccgcg ttcaacttcc tgtacggtct    4140
aaggccgagt catgggcggc tgccgtatgc aaagatggcg aacagcatgg agggtcagga    4200
gacggtgcac agcgttgtcg ggccgattac gcactctgtt gagggtgagt ccttcgcctc    4260
ttccttcttt tcctgctcta taccaggcct ccactgtcct cctttcttgc tttttatact    4320
atatacgaga ccggcagtca ctgatgaagt atgttagacc tccgcctctt caccaaatcc    4380
gtcctcggtc aggagccatg gaaatacgac tccaaggtca tccccatgcc ctggcgccag    4440
tccgagtcgg acattattgc ctccaagatc aagaacggcg ggctcaatat cggctactac    4500
aacttcgacg gcaatgtcct tccacaccct cctatcctgc gcggcgtgga aaccaccgtc    4560
gccgcactcg ccaaagccgg tcacaccgtg accccgtgga cgccatacaa gcacgatttc    4620
ggccacgatc tcatctccca tatctacgcg gctgacggca gcgccgacgt aatgcgcgat    4680
atcagtgcat ccggcgagcc ggcgattcca aatatcaaag acctactgaa cccgaacatc    4740
aaagctgtta acatgaacga gctctgggac acgcatctcc agaagtggaa ttaccagatg    4800
gagtaccttg agaaatggcg ggaggctgaa gaaaaggccg ggaaggaact ggacgccatc    4860
atcgcgccga ttacgcctac cgctgcggta cggcatgacc agttccggta ctatgggtat    4920
gcctctgtga tcaacctgct ggatttcacg agcgtggttg ttccggttac ctttgcggat    4980
aagaacatcg ataagaagaa tgagagtttc aaggcggtta gtgagcttga tgccctcgtg    5040
caggaagagt atgatccgga ggcgtaccat ggggcaccgg ttgcagtgca ggttatcgga    5100
cggagactca gtgaagagag gacgttggcg attgcagagg aagtggggaa gttgctggga    5160
aatgtggtga ctccatagct aataagtgtc agatagcaat ttgcacaaga aatcaatacc    5220
agcaactgta aataagcgct gaagtgacca tgccatgcta cgaaagagca gaaaaaaacc    5280
```

-continued

```
tgccgtagaa ccgaagagat atgacacgct tccatctctc aaaggaagaa tcccttcagg   5340
gttgcgtttc cagtctagac acgtataacg cacaagtgt ctctcaccaa atgggttata    5400
tctcaaatgt gatctaagga tggaaagccc agaatatcga tcgcgcgcag atccatatat   5460
agggcccggg ttataattac ctcaggtcga cgtcccatgg ccattcgaat tcgtaatcat   5520
ggtcatagct gtttcctgtg tgaaattgtt atccgctcac aattccacac aacatacgag   5580
ccggaagcat aaagtgtaaa gcctggggtg cctaatgagt gagctaactc acattaattg   5640
cgttgcgctc actgcccgct ttccagtcgg gaaacctgtc gtgccagctg cattaatgaa   5700
tcggccaacg cgcggggaga ggcggtttgc gtattgggcg ctcttccgct tcctcgctca   5760
ctgactcgct gcgctcggtc gttcggctgc ggcgagcggt atcagctcac tcaaaggcgg   5820
taatacggtt atccacagaa tcaggggata acgcaggaaa gaacatgtga gcaaaaggcc   5880
agcaaaaggc caggaaccgt aaaaaggccg cgttgctggc gtttttccat aggctccgcc   5940
cccctgacga gcatcacaaa aatcgacgct caagtcagag gtggcgaaac ccgacaggac   6000
tataaagata ccaggcgttt ccccctggaa gctccctcgt gcgctctcct gttccgaccc   6060
tgccgcttac cggatacctg tccgcctttc tcccttcggg aagcgtggcg ctttctcata   6120
gctcacgctg taggtatctc agttcggtgt aggtcgttcg ctccaagctg ggctgtgtgc   6180
acgaaccccc cgttcagccc gaccgctgcg ccttatccgg taactatcgt cttgagtcca   6240
acccggtaag acacgactta tcgccactgg cagcagccac tggtaacagg attagcagag   6300
cgaggtatgt aggcggtgct acagagttct tgaagtggtg gcctaactac ggctacacta   6360
gaagaacagt atttggtatc tgcgctctgc tgaagccagt taccttcgga aaaagagttg   6420
gtagctcttg atccggcaaa caaaccaccg ctggtagcgg tggtttttt gtttgcaagc   6480 agcagattac gcgcagaaaa aaaggatctc aagaagatcc tttgatcttt tctacggggt   6540
ctgacgctca gtggaacgaa aactcacgtt aagggatttt ggtcatgaga ttatcaaaaa   6600
ggatcttcac ctagatcctt ttaaattaaa aatgaagttt taaatcaatc taagtatat   6660 atgagtaaac ttggtctgac agttaccaat gcttaatcag tgaggcacct atctcagcga   6720
tctgtctatt tcgttcatcc atagttgcct gactccccgt cgtgtagata actacgatac   6780
gggagggctt accatctggc cccagtgctg caatgatacc gcgagaccca cgctcaccgg   6840
ctccagattt atcagcaata aaccagccag ccggaagggc cgagcgcaga agtggtcctg   6900
caactttatc cgcctccatc cagtctatta attgttgccg ggaagctaga gtaagtagtt   6960
cgccagttaa tagtttgcgc aacgttgttg ccattgctac aggcatcgtg gtgtcacgct   7020
cgtcgtttgg tatggcttca ttcagctccg gttcccaacg atcaaggcga gttacatgat   7080
cccccatgtt gtgcaaaaaa gcggttagct ccttcggtcc tccgatcgtt gtcagaagta   7140
agttggccgc agtgttatca ctcatggtta tggcagcact gcataattct cttactgtca   7200
tgccatccgt aagatgcttt tctgtgactg gtgagtactc aaccaagtca ttctgagaat   7260
agtgtatgcg gcgaccgagt tgctcttgcc cggcgtcaat acgggataat accgcgccac   7320
atagcagaac tttaaaagtg ctcatcattg gaaaacgttc ttcggggcga aaactctcaa   7380
ggatcttacc gctgttgaga tccagttcga tgtaacccac tcgtgcaccc aactgatctt   7440
cagcatcttt tactttcacc agcgtttctg ggtgagcaaa aacaggaagg caaaatgccg   7500
caaaaaaggg aataagggcg acacggaaat gttgaatact catactcttc ctttttcaat   7560
attattgaag catttatcag ggttattgtc tcatgagcgg atacatattt gaatgtattt   7620
agaaaaataa acaaataggg gttccgcgca catttccccg aaaagtgcca cctgacgtct   7680
```

```
aagaaaccat tattatcatg acattaacct ataaaaatag gcgtatcacg aggcccttc    7740
gtctcgcgcg tttcggtgat gacggtgaaa acctctgaca catgcagctc ccggagacgg    7800
tcacagcttg tctgtaagcg gatgccggga gcagacaagc ccgtcagggc gcgtcagcgg    7860
gtgttggcgg gtgtcgggc tggcttaact atgcggcatc agagcagatt gtactgagag    7920
tgcaccataa aattgtaaac gttaatattt tgttaaaatt cgcgttaaat ttttgttaaa    7980
tcagctcatt ttttaaccaa taggccgaaa tcggcaaaat cccttataaa tcaaaagaat    8040
agcccgagat agggttgagt gttgttccag tttggaacaa gagtccacta ttaaagaacg    8100
tggactccaa cgtcaaaggg cgaaaaaccg tctatcaggg cgatggccca ctacgtgaac    8160
catcacccaa atcaagtttt tggggtcga ggtgccgtaa agcactaaat cggaacccta    8220
aagggagccc ccgatttaga gcttgacggg gaaagccggc gaacgtggcg agaaaggaag    8280
ggaagaaagc gaaaggagcg ggcgctaggg cgctggcaag tgtagcggtc acgctgcgcg    8340
taaccaccac acccgccgcg cttaatgcgc cgctacaggg cgcgtactat ggttgctttg    8400
acgtatgcgg tgtgaaatac cgcacagatg cgtaaggaga aaataccgca tcaggcgcca    8460
ttcgccattc aggctgcgca actgttggga agggcgatcg gtgcgggcct cttcgctatt    8520
acgccagctg gcgaaagggg gatgtgctgc aaggcgatta agttgggtaa cgccagggtt    8580
ttcccagtca cgacgttgta aaacgacggc cagtgc                              8616

<210> SEQ ID NO 25
<211> LENGTH: 3855
<212> TYPE: DNA
<213> ORGANISM: Gluconobacter oxydans

<400> SEQUENCE: 25
atggctgaca actctgacga gcaattcgta gcgtccgatt acacgctgct tggtgacgcg      60
accgacgacc ccaacggtat ggtcgacatg ccggccggtc aggagccagc cacgaccaac    120
gcggttccgt cgggcgtcga atacaatttc ctcgccgcga cagcggggta ttacacggtc    180
agctttgcct atcagaatac ggcgaacgcg gctgcttacg aacagctttc catcaatggc    240
cagaacgagc ccggggtcgt cgaattcgac cagaccagcg cgcctcgac gggcacggcc     300
tatgcgtcag tctatctgaa ggcaggcctg aattcggtcg aactgaataa tcagacgacc    360
gatgagacca atggcctgac accggtgccg gaggatcagc ttcaggcaag ccccgccttc    420
cagatcggca cgtccacggt cgcggccggc gcatcgccct cccaggaaac gtcggcgcag    480
tcgctcgcga tctccaatca gacggatatg caggcgttcg ttcaaggcga gagcatggcg    540
cctaagcagc aatggacatt cggcccgagc ctgtccgaac tgcatgtcgg cagcaacgac    600
gaactcaatc agctcgactt caacgccgtc tggttccgca acgtcacgcc cggccagcag    660
gccgagactt attcgccgta tttcaaatcc aacgagtcgt tcgatgccaa cggcgtcctg    720
catgtgaact atggtgccta ctcgccgacc ggccaggcgc tgccggtgca gatccaggca    780
acctatgcca acgttccgaa cgaaaacctc atcgtcgaaa acctgtccct gaccaatcag    840
aatgcgagcg gcacccagcc gctggtctgg gacgtgatga atgccaccgg tatcaaccca    900
ggtgaagtca gcagcacgac atgggatccg acgcataacg catggatcgt taccgaggac    960
cagggaagtg gcaaatcccc gctttatcta gcgatcggtg actatcaggt cagcaacagc   1020
acgcacgcgg caggcgtcga cggcgtcaat gtgcgcggca gctattccct gtcgagcggc   1080
gcgtccggca atccgtccct gaatgctccg gaccagggcg ttatcggcgg gttcgagaac   1140
```

```
aacggcacga tggtcggcag cagttcgggc gcgtcgggca caaatctcgc ggtcggcacc   1200
accgacagcg atgtcaccct gaatcccggc cagaccgtcg acctcagcta ctatctctcg   1260
acagccacca gcctgtcgca gctcgacgcc aatctcgata aatatacgaa cacagtcggg   1320
tccacgacgt cgtcgacgcc gatgacggac gccaccggcg cttccgccgc gagttcctgg   1380
actcagcaga cggctaccgc atgggacgac acgctcaacc aggcctacaa tttggctggg   1440
tcgacagaaa caagcggaca ggctgcaact gccgccagcg ggcagacact ggatcctaca   1500
agcagcgctg cggcccagag tgcctatcgc tccagtctga tcaatatttt gcaggcacag   1560
agcccggaat acggctcgtt catggcgtcc accaacccgt cctatgaata caaggtctgg   1620
gtgcgcgaca gcgccgcaac cgcgatcggt ctggacgacg caggcctgac ccaaccggcc   1680
gacaagttct ggcgctggat ggcgtccgtc gagcagaacg gcatgaatgc gacctatagc   1740
ggcaacgctt caggcacatt ctcgacgaac tatggagaat cgaccagaa cctgccgatc   1800 gggttcgtcg cgccggaaaa cgactctcag ggcctgttcc tcatcgggtc ttaccgtcat   1860
tacgagcaga tgctcagcga gggccagact cagcaggccc agtccttcat cagcgatccg   1920
acggtgcgtc aggctctggt caactccgcg aactggatcc aggaaaatat tggtagcaac   1980
gggcttgggc cggctgacta ctcaatctgg gaggacatgt acggctatca tactttcacg   2040
caggtcacct acgcggaagg gctgaacgca gcatcgcaac tcgcctcggc catgggcgag   2100
ggcaatcagg cccagacctg ggcgaccggc gccgagacga tcaaggatgc gatcctgcgt   2160
ccgaccacgg cgtcgacgcc ggggctctgg aatgcgcagg aaggtcattt cgtcgaaatg   2220
atcaaccaga acgaacgat tgacaatacg atcgacgccg ataccaacat gccgccgtc   2280 ttcggtcttg tctcgcccac aagcatctat gcgactgaaa acgcgcaggc tgtcgaaaat   2340
gcgctgacga aggacaattt cggtctatcg cgctatcaga acgaaacatt ctaccagtcc   2400
tcgcagtgga gccctggggg cacatacgag gcgcaaggca tctcgccgtc ctggccgcag   2460
atgaccgcct atgacagcat cgtcagcatg gattccggca atacgaccca ggcaaataac   2520
gaccttagct ggatcgaaca gtcctatgac aatggcggca ctccgcccgg tgaatcctac   2580
gactgggcgc gtggccagcc gatcgaaagc acatcgtccg aaccggtgac ggcgagctgg   2640
tacgtccagg atctcctgaa cagcaccggc cagacatcga ccctgatgcc tgcgattacc   2700
gggcaggcac cgaccgctac gccgcagacc gacgtctccg tcaatacagg cacgaccggg   2760
ttcgggtcct acacccttgg actcgacagc gtgggtaaca gccaggccca ggatatgatc   2820
gtcggcacgg gcaacacctc tgccacgtcg gtcgccatgg tccgcaatga agctgctgcc   2880
ggtacaccgg aaaccatcga caacacgaac ggtgtcaacg accttctggt ctttggcaat   2940
gccggcgata cgaacgttct cgccgggcag aattccacta cgacaatcat gaacaacgcc   3000
gccggggacc atggcacggt ggaatacacc ggggctacgg gtgccagtgc gacgattctc   3060 gccgacctc tgacggaaat tcaggccgcc ggtacgacaa acctgatcat gggatcgcaa   3120
tccgatacga cgacgtccga tgcctatatc acgggtggcc agtacgacag tgccgaccag   3180
accaacatca ccactgaggg cccggcagga caactggacg cgatcgacaa tcaaggcaac   3240
gcacatacga cgcttcaggt cgcaagtccg accgacctcc tctataccgg ccgcgacacc   3300
acgttgaatc ttggcactga cggccagaag tcgaccatca actctcttgg taacgaccag   3360
attcatatga acggatcgaa cgtgaatgtg gcgtccgtca ccggagggtt cgacacgttc   3420
tatggtggca ccggcaccat gaccatcaac gccagccagt cggtcggcta tacgcaggaa   3480
acctatatcg gcagccagac gtccggcggg agcctgacct atacaggcgg caacgctgcg   3540
```

```
aaccagatca cgctgggcga cgaaagcagc gttgcgatca cggccggcgc cggggctatg    3600
aacatcaccg caaacgacag caccggtctt tgggccaacc tgacgaacgc ggcatcggcg    3660
gacctgaact ttgggtccag ccttggcaac tctatgatct acggcttcaa cggaagcact    3720
gacagtgcga ccatgcaggg tgtcaccggg acctccttct cggggggcaa cctgatggtc    3780
agcctggctg acaatcacag catcacgttc ttcgacgtcc ataccctttca gggcatgaac    3840 atcgtcggcg cctaa                                                      3855
```

<210> SEQ ID NO 26
<211> LENGTH: 1284
<212> TYPE: PRT
<213> ORGANISM: Gluconobacter oxydans

<400> SEQUENCE: 26

```
Met Ala Asp Asn Ser Asp Glu Gln Phe Val Ala Ser Asp Tyr Thr Leu
1               5                   10                  15

Leu Gly Asp Ala Thr Asp Pro Asn Gly Met Val Asp Met Pro Ala
            20                  25                  30

Gly Gln Glu Pro Ala Thr Thr Asn Ala Val Pro Ser Gly Val Glu Tyr
        35                  40                  45

Asn Phe Leu Ala Ala Thr Ala Gly Tyr Tyr Thr Val Ser Phe Ala Tyr
    50                  55                  60

Gln Asn Thr Ala Asn Ala Ala Tyr Glu Gln Leu Ser Ile Asn Gly
65                  70                  75                  80

Gln Asn Glu Pro Gly Val Val Glu Phe Asp Gln Thr Ser Gly Ala Ser
                85                  90                  95

Thr Gly Thr Ala Tyr Ala Ser Val Tyr Leu Lys Ala Gly Leu Asn Ser
            100                 105                 110

Val Glu Leu Asn Asn Gln Thr Thr Asp Glu Thr Asn Gly Leu Thr Pro
        115                 120                 125

Val Pro Glu Asp Gln Leu Gln Ala Ser Pro Ala Phe Gln Ile Gly Thr
    130                 135                 140

Ser Thr Val Ala Ala Gly Ala Ser Pro Ser Gln Glu Thr Ser Ala Gln
145                 150                 155                 160

Ser Leu Ala Ile Ser Asn Gln Thr Asp Met Gln Ala Phe Val Gln Gly
                165                 170                 175

Glu Ser Met Ala Pro Lys Gln Gln Trp Thr Phe Gly Pro Ser Leu Ser
            180                 185                 190

Glu Leu His Val Gly Ser Asn Asp Glu Leu Asn Gln Leu Asp Phe Asn
        195                 200                 205

Ala Val Trp Phe Arg Asn Val Thr Pro Gly Gln Gln Ala Glu Thr Tyr
    210                 215                 220

Ser Pro Tyr Phe Lys Ser Asn Glu Ser Phe Asp Ala Asn Gly Val Leu
225                 230                 235                 240

His Val Asn Tyr Gly Ala Tyr Ser Pro Thr Gly Gln Ala Leu Pro Val
                245                 250                 255

Gln Ile Gln Ala Thr Tyr Ala Asn Val Pro Asn Glu Asn Leu Ile Val
            260                 265                 270

Glu Asn Leu Ser Leu Thr Asn Gln Asn Ala Ser Gly Thr Gln Pro Leu
        275                 280                 285

Val Trp Asp Val Met Asn Ala Thr Gly Ile Asn Pro Gly Glu Val Ser
    290                 295                 300

Ser Thr Thr Trp Asp Pro Thr His Asn Ala Trp Ile Val Thr Glu Asp
```

```
305                 310                 315                 320
Gln Gly Ser Gly Lys Ser Pro Leu Tyr Leu Ala Ile Gly Asp Tyr Gln
                325                 330                 335
Val Ser Asn Ser Thr His Ala Ala Gly Val Asp Gly Val Asn Val Arg
                340                 345                 350
Gly Ser Tyr Ser Leu Ser Ser Gly Ala Ser Gly Asn Pro Ser Leu Asn
                355                 360                 365
Ala Pro Asp Gln Gly Val Ile Gly Gly Phe Glu Asn Gly Thr Met
        370                 375                 380
Val Gly Ser Ser Gly Ala Ser Gly Thr Asn Leu Ala Val Gly Thr
385                 390                 395                 400
Thr Asp Ser Asp Val Thr Leu Asn Pro Gly Gln Thr Val Asp Leu Ser
                405                 410                 415
Tyr Tyr Leu Ser Thr Ala Thr Ser Leu Ser Gln Leu Asp Ala Asn Leu
                420                 425                 430
Asp Lys Tyr Thr Asn Thr Val Gly Ser Thr Thr Ser Thr Pro Met
        435                 440                 445
Thr Asp Ala Thr Gly Ala Ser Ala Ala Ser Ser Trp Thr Gln Gln Thr
450                 455                 460
Ala Thr Ala Trp Asp Asp Thr Leu Asn Gln Ala Tyr Asn Leu Ala Gly
465                 470                 475                 480
Ser Thr Glu Thr Ser Gly Gln Ala Ala Thr Ala Ala Ser Gly Gln Thr
                485                 490                 495
Leu Asp Pro Thr Ser Ser Ala Ala Ala Gln Ser Ala Tyr Arg Ser Ser
                500                 505                 510
Leu Ile Asn Ile Leu Gln Ala Gln Ser Pro Glu Tyr Gly Ser Phe Met
                515                 520                 525
Ala Ser Thr Asn Pro Ser Tyr Glu Tyr Lys Val Trp Val Arg Asp Ser
                530                 535                 540
Ala Ala Thr Ala Ile Gly Leu Asp Asp Ala Gly Leu Thr Gln Pro Ala
545                 550                 555                 560
Asp Lys Phe Trp Arg Trp Met Ala Ser Val Glu Gln Asn Gly Met Asn
                565                 570                 575
Ala Thr Tyr Ser Gly Asn Ala Ser Gly Thr Phe Ser Thr Asn Tyr Gly
                580                 585                 590
Glu Phe Asp Gln Asn Leu Pro Ile Gly Phe Val Ala Pro Glu Asn Asp
                595                 600                 605
Ser Gln Gly Leu Phe Leu Ile Gly Ser Tyr Arg His Tyr Glu Gln Met
        610                 615                 620
Leu Ser Glu Gly Gln Thr Gln Gln Ala Gln Ser Phe Ile Ser Asp Pro
625                 630                 635                 640
Thr Val Arg Gln Ala Leu Val Asn Ser Ala Asn Trp Ile Gln Glu Asn
                645                 650                 655
Ile Gly Ser Asn Gly Leu Gly Pro Ala Asp Tyr Ser Ile Trp Glu Asp
                660                 665                 670
Met Tyr Gly Tyr His Thr Phe Thr Gln Val Thr Tyr Ala Glu Gly Leu
        675                 680                 685
Asn Ala Ala Ser Gln Leu Ala Ser Ala Met Gly Glu Gly Asn Gln Ala
        690                 695                 700
Gln Thr Trp Ala Thr Gly Ala Glu Thr Ile Lys Asp Ala Ile Leu Arg
705                 710                 715                 720
Pro Thr Thr Ala Ser Thr Pro Gly Leu Trp Asn Ala Gln Glu Gly His
                725                 730                 735
```

```
Phe Val Glu Met Ile Asn Pro Asn Gly Thr Ile Asp Asn Thr Ile Asp
            740                 745                 750

Ala Asp Thr Asn Ile Ala Ala Val Phe Gly Leu Val Ser Pro Thr Ser
            755                 760                 765

Ile Tyr Ala Thr Glu Asn Ala Gln Ala Val Glu Asn Ala Leu Thr Gln
770                 775                 780

Asp Asn Phe Gly Leu Ser Arg Tyr Gln Asn Glu Thr Phe Tyr Gln Ser
785                 790                 795                 800

Ser Gln Trp Ser Pro Gly Gly Thr Tyr Glu Ala Gln Gly Ile Ser Pro
                805                 810                 815

Ser Trp Pro Gln Met Thr Ala Tyr Asp Ser Ile Val Ser Met Asp Ser
            820                 825                 830

Gly Asn Thr Thr Gln Ala Asn Asn Asp Leu Ser Trp Ile Glu Gln Ser
            835                 840                 845

Tyr Asp Asn Gly Gly Thr Pro Pro Gly Glu Ser Tyr Asp Trp Ala Arg
850                 855                 860

Gly Gln Pro Ile Glu Ser Thr Ser Ser Glu Pro Val Thr Ala Ser Trp
865                 870                 875                 880

Tyr Val Gln Asp Leu Leu Asn Ser Thr Gly Gln Thr Ser Thr Leu Met
                885                 890                 895

Pro Ala Ile Thr Gly Gln Ala Pro Thr Ala Thr Pro Gln Thr Asp Val
            900                 905                 910

Ser Val Asn Thr Gly Thr Thr Gly Phe Gly Ser Tyr Thr Leu Gly Leu
            915                 920                 925

Asp Ser Val Gly Asn Ser Gln Ala Gln Asp Met Ile Val Gly Thr Gly
930                 935                 940

Asn Thr Ser Ala Thr Ser Val Ala Met Val Arg Asn Glu Ala Ala Ala
945                 950                 955                 960

Gly Thr Pro Glu Thr Ile Asp Asn Thr Asn Gly Val Asn Asp Leu Leu
                965                 970                 975

Val Phe Gly Asn Ala Gly Asp Thr Asn Val Leu Ala Gly Gln Asn Ser
            980                 985                 990

Thr Thr Thr Ile Met Asn Asn Ala Ala Gly Asp His Gly Thr Val Glu
            995                 1000                1005

Tyr Thr Gly Ala Thr Gly Ala Ser Ala Thr Ile Leu Ala Gly Pro
       1010                1015                1020

Leu Thr Glu Ile Gln Ala Ala Gly Thr Thr Asn Leu Ile Met Gly
       1025                1030                1035

Ser Gln Ser Asp Thr Thr Thr Ser Asp Ala Tyr Ile Thr Gly Gly
       1040                1045                1050

Gln Tyr Asp Ser Ala Asp Gln Thr Asn Ile Thr Thr Glu Gly Pro
       1055                1060                1065

Ala Gly Gln Leu Asp Ala Ile Asp Asn Gln Gly Asn Ala His Thr
       1070                1075                1080

Thr Leu Gln Val Ala Ser Pro Thr Asp Leu Leu Tyr Thr Gly Arg
       1085                1090                1095

Asp Thr Thr Leu Asn Leu Gly Thr Asp Gly Gln Lys Ser Thr Ile
       1100                1105                1110

Asn Ser Leu Gly Asn Asp Gln Ile His Met Asn Gly Ser Asn Val
       1115                1120                1125

Asn Val Ala Ser Val Thr Gly Gly Phe Asp Thr Phe Tyr Gly Gly
       1130                1135                1140
```

| | | | | | | | | | | |
|---|---|---|---|---|---|---|---|---|---|---|
|Thr|Gly|Thr|Met|Thr|Ile|Asn|Ala|Ser|Gln|Ser|Val|Gly|Tyr|Thr|
| |1145| | | |1150| | | | |1155| | | | |

Gln Glu Thr Tyr Ile Gly Ser Gln Thr Ser Gly Gly Ser Leu Thr
    1160                1165                1170

Tyr Thr Gly Gly Asn Ala Ala Asn Gln Ile Thr Leu Gly Asp Glu
    1175                1180                1185

Ser Ser Val Ala Ile Thr Ala Gly Ala Gly Ala Met Asn Ile Thr
    1190                1195                1200

Ala Asn Asp Ser Thr Gly Leu Trp Ala Asn Leu Thr Asn Ala Ala
    1205                1210                1215

Ser Ala Asp Leu Asn Phe Gly Ser Ser Leu Gly Asn Ser Met Ile
    1220                1225                1230

Tyr Gly Phe Asn Gly Ser Thr Asp Ser Ala Thr Met Gln Gly Val
    1235                1240                1245

Thr Gly Thr Ser Phe Ser Gly Gly Asn Leu Met Val Ser Leu Ala
    1250                1255                1260

Asp Asn His Ser Ile Thr Phe Phe Asp Val His Thr Leu Gln Gly
    1265                1270                1275

Met Asn Ile Val Gly Ala
    1280

```
<210> SEQ ID NO 27
<211> LENGTH: 2085
<212> TYPE: DNA
<213> ORGANISM: Escherichia coli

<400> SEQUENCE: 27
atggaaagca aacgtctgga taatgccgcg ctggcggcgg ggattagccc caattacatc      60
aatgcccacg gtaaaccgca gtcgattagc gccgaaacca acggcgtttg cttgacgcg     120
atgcatcaac gtaccgccac gaaagtggcg gtaacgccag tcccgaatgt catggtttat    180
accagcggca aaaaaatgcc gatggtggtg gagggcagcg gcgaatatag ctggctgctg    240
accaccgaag aaggaacgca gtacaaggc catgtaacgg ggggcaaagc gttcaatcta     300
ccgacgaagc tgccggaagg ttatcacacg ctgacactca cccaggacga ccagcgcgcg    360
cattgccggg tgattgtcgc cccgaaacgc tgttacgaac cgcaggcgtt gctgaataaa    420
caaaagctgt ggggtgcctg cgttcagctt tatacgctgc gatcggaaaa aaactgggt     480
attgggatt ttggcgatct caaagcgatg ctggtggatg tggcaaaacg tggcgggtcg     540
ttcattggcc tgaacccgat tcatgcgctc tatccggcaa atccggagag cgccagccca    600
tacagcccgt cttctcgccg ttggctgaat gtgatttata tcgacgttaa cgccgttgaa    660
gatttccatc ttagcgaaga ggctcaggcc tggtggcagt tgccgaccac gcaacagacg    720
ctgcaacagg cgcgcgatgc cgactgggtc gattactcca cggttaccgc cctaaaaatg    780
acagcattac gaatggcgtg gaaaggtttc gcgcaacgtg atgatgagca gatggccgcg    840
tttcgccagt tgttgcaga gcagggcgac agcctgttct ggcaggcagc ctttgatgcg    900
ctacatgccc agcaagtgaa agaggacgaa atgcgctggg gctggcctgc atggccagag    960
atgtatcaga acgtggattc accagaagtg cgtcagttct gcgaagaaca tcgtgatgac   1020
gtcgattttt atctctggtt gcagtggctg gcttacagcc agtttgccgc tgctgggag    1080
ataagccagg gctatgaaat gccgattggc ttgtatcgtg atctggcggt tggcgtagcg   1140
gaaggtgggg cggaaacctg tgtgaccgt gaactatatt gcctgaaagc atcggttggc   1200
gcgccgccgg atatcctcgg cccgttgggg cagaactggg gattaccgcc aatggacccg   1260
```

```
catatcatca ccgcgcgtgc ctatgaaccg tttatcgagc tgttgcgtgc caatatgcaa    1320
aactgcggcg cattacgaat tgaccatgtg atgtcgatgc tgcgtttgtg gtggataccg    1380
tatggcgaga cggcagatca gggcgcgtat gttcactatc cggtggatga tctgctctcg    1440
attctggcac tcgaaagtaa acgtcatcgc tgtatggtga ttggtgaaga tctcggtacc    1500
gtaccggtag agattgtcgg taagctgcgc agcagcggtg tgtactctta caaagtgctc    1560
tatttcgaaa acgaccacga gaagacgttc cgtgcaccga aagcgtatcc ggagcagtcg    1620
atggcggttg cggcgacaca tgacctgcca acgctgcgcg gttactggga gtgcggggat    1680
ctaacgctgg gcaaaaccct ggggctgtat ccggatgaag tggtactgcg cggtctgtat    1740
caggatcgcg aactggcgaa gcaagggctg ctggatgcac tgcataaata tggttgtctg    1800
ccgaaacgtg ccgggcataa ggcatcgttg atgtcgatga cgccgacgct gaaccgtggt    1860
ttgcagcgct acattgccga cagtaacagt gctctgttag gactacagcc ggaagactgg    1920
ctggatatgg ccgaaccggt gaatattcct ggcaccagtt accagtataa aaactggcga    1980
cgcaagcttt ccgcaacgct tgagtcgatg tttgccgatg atggcgtgaa caagttgctg    2040
aaggatttgg acagacggcg cagagctgca gcgaagaaga agtag               2085

<210> SEQ ID NO 28
<211> LENGTH: 2031
<212> TYPE: DNA
<213> ORGANISM: Escherichia coli

<400> SEQUENCE: 28
atgaaactcg ccgcctgttt tctgacactc cttcctggct tcgccgttgc cgccagctgg      60
acttctccgg ggtttcccgc ctttagcgaa caggggacag gaacatttgt cagccacgcg     120
cagttgccca aggtacgcg tccactaacg ctaaattttg accaacagtg ctggcagcct     180
gcggatgcga taaaactcaa tcagatgctt tccctgcaac cttgtagcaa cacgccgcct     240
caatggcgat tgttcaggga cggcgaatat acgctgcaaa tagacacccg ctccggtacg     300
ccaacattga tgatttccat ccagaacgcc gccgaaccgg tagcaagcct ggtccgtgaa     360
tgcccgaaat gggatggatt accgctcaca gtggatgtca cgccactttt ccggaagga    420 gccgccgtac gggattatta cagccagcaa attgcgatag tgaagaacgg tcaaataatg     480
ttacaacccg ctgccaccag caacggttta ctcctgctgg aacgggcaga aactgacaca    540
tccgcccctt tcgactggca taacgccacg gtttactttg tgctgacaga tcgtttcgaa    600
aacggcgatc ccagtaatga ccagagttac ggacgtcata aagacggtat ggcggaaatt    660 ggcactttc acggcggcga tttacgcggc ctgaccaaca aactggatta cctccagcag    720
ttgggcgtta atgctttatg gataagcgcc ccatttgagc aaattcacgg ctgggtcggc    780
ggcggtacaa aaggcgattt cccgcattat gcctaccacg ttattacac acaggactgg    840 acgaatcttg atgccaatat gggcaacgaa gccgatctac ggacgctggt tgatagcgca    900
catcagcgcg gtattcgtat tctctttgat gtcgtgatga accacaccgg ctatgccacg    960
ctggcggata tgcaggagta tcagtttggc gcgttatatc tttctggtga cgaagtgaaa   1020
aaatcgctgg gtgaacgctg gagcgactgg aaacctgccg ccgggcaaac ctggcatagc   1080
tttaacgatt acattaattt cagcgacaaa acaggctggg ataaatggtg ggaaaaaaac   1140
tggatcagaa cggatatcgg cgattacgac aatcctggat tcgacgatct cactatgtcg   1200
ctagcctttt tgccggatat caaaaccgaa tcaactaccg cttctggtct gccggtgttc   1260
```

| | |
|---|---|
| tataaaaaca aaatggatac ccacgccaaa gccattgacg gctatacgcc gcgcgattac | 1320 |
| ttaacccact ggttaagtca gtgggtccgc gactatggga ttgatggttt tcgggtcgat | 1380 |
| accgccaaac atgttgagtt gcccgcctgg cagcaactga aaaccgaagc cagcgccgcg | 1440 |
| cttcgcgaat ggaaaaaagc taaccccgac aaagcattag atgacaaacc tttctggatg | 1500 |
| accggtgaag cctggggcca cggcgtgatg caaagtgact actatcgcca cggcttcgat | 1560 |
| gcgatgatca atttcgatta tcaggagcag gcggcgaaag cagtcgactg tctggcgcag | 1620 |
| atggatacga cctggcagca aatggcggag aaattgcagg gtttcaacgt gttgagctac | 1680 |
| ctctcgtcgc atgatacccg cctgttccgt gaagggggcg acaaagcagc agagttatta | 1740 |
| ctattagcgc caggcgcggt acaaatcttt tatggtgatg aatcctcgcg tccgttcggt | 1800 |
| cctacaggtt ctgatccgct gcaaggtaca cgttcggata tgaactggca ggatgttagc | 1860 |
| ggtaaatctg ccgccagcgt cgcgcactgg cagaaaatca gccagttccg cgcccgccat | 1920 |
| cccgcaattg gcgcgggcaa acaaacgaca cttttgctga gcagggcta cggctttgtt | 1980 |
| cgtgagcatg gcgacgataa agtgctggtc gtctgggcag ggcaacagta a | 2031 |

<210> SEQ ID NO 29
<211> LENGTH: 2394
<212> TYPE: DNA
<213> ORGANISM: Escherichia coli

<400> SEQUENCE: 29

| | |
|---|---|
| atgtcacaac ctatttttaa cgataagcaa tttcaggaag cgctttcacg tcagtggcag | 60 |
| cgttatggct taaattctgc ggctgaaatg actcctcgcc agtggtggct agcagtgagt | 120 |
| gaagcactgg ccgaaatgct gcgtgctcag ccattcgcca agccggtggc gaatcagcga | 180 |
| catgttaact acatctcaat ggagttttg attggtcgcc tgacgggcaa caacctgttg | 240 |
| aatctcggct ggtatcagga tgtacaggat tcgttgaagg cttatgacat caatctgacg | 300 |
| gacctgctgg aagaagagat cgacccggcg ctgggtaacg gtggtctggg acgtctggcg | 360 |
| gcgtgcttcc tcgactcaat ggcaactgtc ggtcagtctg cgacgggtta cggtctgaac | 420 |
| tatcaatatg gtttgttccg ccagtctttt gtcgatggca acaggttga agcgccggat | 480 |
| gactggcatc gcagtaacta cccgtggttc cgccacaacg aagcactgga tgtgcaggta | 540 |
| gggattggcg gtaaagtgac gaaagacgga cgctgggagc cggagtttac cattaccggt | 600 |
| caagcgtggg atctccccgt tgtcggctat cgtaatggcg tggcgcagcc gctgcgtctg | 660 |
| tggcaggcga cgcacgcgca tccgtttgat ctgactaaat ttaacgacgg tgatttcttg | 720 |
| cgtgccgaac agcagggcat caatgcggaa aaactgacca agttctcta tccaaacgac | 780 |
| aaccatactg ccggtaaaaa gctgcgcctg atgcagcaat acttccagtg tgcctgttcg | 840 |
| gtagcggata ttttgcgtcg ccatcatctg gcggggcgta aactgcacga actggcggat | 900 |
| tacgaagtta ttcagctgaa cgataccac ccaactatcg cgattccaga actgctgcgc | 960 |
| gtgctgatcg atgagcacca tgagctgg gatgacgcct gggccattac cagcaaaact | 1020 |
| ttcgcttaca ccaaccatac cctgatgcca gaagcgctgg aacgctggga tgtgaaactg | 1080 |
| gtgaaaggct actgccgcg ccacatgcag attattaacg aaattaatac tcgctttaaa | 1140 |
| acgctggtag agaaaacctg gccgggcgat gaaaaagtgt gggccaaact ggcggtggtg | 1200 |
| cacgacaaac aagtgcatat ggcgaacctg tgtgtggttg gcggtttcgc ggtgaacggt | 1260 |
| gttgcggcgc tgcactcgga tctggtggtg aaagatctgt tcccggaata tcaccagcta | 1320 |
| tggcccgaaca aattccataa cgtcaccaac ggtattaccc cacgtcgctg gatcaaacag | 1380 |

```
tgcaacccgg cactggcggc tctgttggat aaatcactgc aaaaagagtg ggctaacgat      1440
ctcgatcagc tgatcaatct ggaaaaattc gctgatgatg cgaaattccg tcagcaatat      1500
cgcgagatca agcaggcgaa taaagtccgt ctggcggagt tgtgaaagt tcgtaccggt      1560 attgagatca atccacaggc gattttcgat attcagatca aacgtttgca tgagtacaaa      1620
cgccagcacc tgaatctgct gcatattctg gcgttgtaca agaaattccg tgaaaacccg      1680
caggctgatc gcgtaccgcg cgtcttcctc ttcggcgcga aagcggcacc gggctactac      1740
ctggcgaaga atattatctt tgcgatcaac aaagtggctg acgtgatcaa caacgatccg      1800
ctggttggcg ataagttgaa ggtggtgttc ctgccggatt attgcgtttc ggcggcggaa      1860
aaactgatcc cggcggcgga tatctccgaa caaatttcga ctgcaggtaa agaagcttcc      1920
ggtaccggca atatgaaact ggcgctcaat ggtgcgctta ctgtcggtac gctggatggg      1980
gcgaacgttg aaatcgccga aaagtcggt gaagaaaata tctttatttt tggtcatacc      2040
gtggaacaag tgaaggcaat tctggccaaa ggctacgacc cggtgaaatg gcggaagaaa      2100
gataaggtgc tggacgcagt attgaaagag ctggaaagcg gtaaatacag cgacggcgat      2160
aagcatgcct tcgaccagat gctgcacagt atcggcaaac agggcggcga tccgtatctg      2220
gtgatggcgg atttcgcagc ctatgtagag gcacaaaagc aggtggatgt gctgtaccgc      2280
gaccaggagg cctggactcg cgcggcgatc ctcaataccg cccgctgcgg tatgtttagc      2340
tcggatcgct ctattcgcga ttatcaggct cgtatctggc aggcaaaacg ctaa           2394

<210> SEQ ID NO 30
<211> LENGTH: 1815
<212> TYPE: DNA
<213> ORGANISM: Escherichia coli

<400> SEQUENCE: 30
atgttaaatg catggcacct gccggtgccc ccatttgtta aacaaagcaa agatcaactg        60
ctcattacac tgtggctgac gggcgaagac ccaccgcagc gcattatgct gcgtacagaa      120
cacgataacg aagaaatgtc agtaccgatg cataagcagc gcagtcagcc gcagcctggc      180
gtcaccgcat ggcgtgcggc gattgatctc tccagcggac aaccccggcg gcgttacagt      240
ttcaaactgc tgtggcacga tcgccagcgt tggtttacac cgcagggctt cagccgaatg      300
ccgccggcac gactggagca gtttgccgtc gatgtaccgg atatcggccc acaatgggct      360
gcggatcaga ttttttatca gatcttccct gatcgttttg cgcgtagtct tcctcgtgaa      420
gctgaacagg atcatgtcta ttaccatcat gcagccggac aagagatcat cttgcgtgac      480
tgggatgaac cggtcacggc gcaggcgggc ggatcaacgt tctatggcgg cgatctggac      540
gggataagcg aaaaactgcc gtatctgaaa aagcttggcg tgacagcgct gtatctcaat      600
ccggtgttta agctcccag cgtacataaa tacgataccg aggattatcg ccatgtcgat      660
ccgcagtttg gcggtgatgg ggcgttgctg cgtttgcgac acaatacgca gcagctggga      720
atgcggctgg tgctggacgg cgtgtttaac cacagtggcg attcccatgc ctggtttgac      780
aggcataatc gtggcacggg tggtgcttgt cacaaccccg aatcgccctg gcgcgactgg      840
tactcgttta gtgatgatgg cacggcgctc gactggcttg gctatgccag cttgccgaag      900
ctggattatc agtcggaaag tctggtgaat gaaatttatc gcgggaaga cagtattgtc      960 cgccactggc tgaaagcgcc gtggaatatg gacggctggc ggctggatgt ggtgcatatg     1020
ctgggggagg cgggtgggc gcgcaataat atgcagcacg ttgccgggat caccgaagcg     1080
```

```
gcgaaagaaa cccagccgga agcgtatatt gtcggcgaac attttggcga tgcacggcaa   1140
tggttacagg ccgatgtgga agatgccgcc atgaactatc gtggcttcac attcccgttg   1200
tggggatttc ttgccaatac cgatatctct tacgatccgc agcaaattga tgcccaaacc   1260
tgtatggcct ggatggataa ttaccgcgca gggctttctc atcaacaaca attacgtatg   1320
tttaatcagc tcgacagcca cgatactgcg cgatttaaaa cgctgctcgg tcgggatatt   1380
gcgcgcctgc cgctggcggt ggtctggctg ttcacctggc ctggtgtacc gtgcatttat   1440
tacggtgatg aagtaggact ggatggcaaa aacgatccgt tttgccgtaa accgttcccc   1500
tggcaggtgg aaaagcagga tacgcgctta ttcgcgctgt accagcgaat gattgcgctg   1560
cgtaagaaaa gtcaggcgct acgtcatggc ggctgtcagg tgctgtatgc ggaagataac   1620
gtggtggtat ttgtccgcgt gctgaatcag caacgtgtac tggtggcaat caaccgtggc   1680
gaggcctgtg aagtggtgct acccgcgtca ccgtttctca atgccgtgca atggcaatgc   1740
aaagaagggc atgggcaact gactgacggg attctggctt tgcctgccat ttcggctacg   1800
gtatggatga actaa                                                    1815

<210> SEQ ID NO 31
<211> LENGTH: 1488
<212> TYPE: DNA
<213> ORGANISM: Escherichia coli

<400> SEQUENCE: 31
atgcgtaatc ccacgctgtt acaatgtttt cactggtatt acccggaagg cggtaagctc     60
tggcctgaac tggccgagcg cgccgacggt tttaatgata ttggtatcaa tatggtctgg    120
ttgccgcccg cctataaagg cgcatcgggc gggtattcgg tcggctacga ctcctatgat    180
ttatttgatt taggcgagtt tgatcagaaa ggcagcatcc ctactaaata tggcgataaa    240
gcacaactgc tggccgccat tgatgctctg aaacgtaatg acattgcggt gctgttggat    300
gtggtagtca accacaaaat gggcgcggat gaaaaagaag ctattcgcgt gcagcgtgta    360
aatgctgatg accgtacgca aattgacgaa gaaatcattg agtgtgaagg ctggacgcgt    420
tacaccttcc ccgcccgtgc cgggcaatac tcgcagtttta tctgggattt caaatgtttt    480
agcggtatcg accatatcga aaaccctgac gaagatggca tttttaaaat tgttaacgac    540
tacaccggcg aaggctggaa cgatcaggtt gatgatgaat taggtaattt cgattatctg    600
atgggcgaga atatcgattt tcgcaatcat gccgtgacgg aagagattaa atactgggcg    660
cgctgggtga tggaacaaac gcaatgcgac ggttttcgtc ttgatgcggt caaacatatt    720
ccagcctggt tttataaaga gtggatcgaa cacgtacagg aagttgcgcc aaagccgctg    780
tttattgtgg cggagtactg gtcgcatgaa gttgataagc tgcaaacgta tattgatcag    840
gtggaaggca aaaccatgct gtttgatgcg ccgctgcaga tgaaattcca tgaagcatcg    900
cgcatggggc gcgactacga catgacgcag atttttcacgg gtacattagt ggaagccgat    960
cctttccacg ccgtgacgct cgttgccaat cacgacaccc aaccgttgca agccctcgaa   1020
gcgccggtcg aaccgtggtt taaaccgctg gcgtatgcct taattttgtt gcgggaaaat   1080
ggcgttcctt cggtattcta tccggacctc tacggtgcgc attacgaaga tgtcggtggt   1140
gacgggcaaa cctatccgat agatatgcca ataatcgaac agcttgatga gttaattctc   1200
gcccgtcagc gtttcgccca cggtgtacag acgttatttt tcgaccatcc gaactgcatt   1260
gcctttagcc gcagtggcac cgacgaattt cccggctgcg tggtggtcat gtcgaacggg   1320
gatgatggcg aaaaaaccat tcatctggga gagaattacg gcaataaaac ctggcgtgat   1380
```

```
tttctgggga accggcaaga gagagtagtg accgacgaaa acggcgaagc aaccttcttt    1440
tgcaacggcg gcagcgtcag cgtgtgggtt atcgaagagg tgatttaa                 1488
```

<210> SEQ ID NO 32
<211> LENGTH: 36
<212> TYPE: DNA
<213> ORGANISM: artificial sequence
<220> FEATURE:
<223> OTHER INFORMATION: synthetic construct

<400> SEQUENCE: 32

```
ataaaaaacg ctcggttgcc gccgggcgtt ttttat                              36
```

<210> SEQ ID NO 33
<211> LENGTH: 21
<212> TYPE: DNA
<213> ORGANISM: artificial sequence
<220> FEATURE:
<223> OTHER INFORMATION: synthetic construct

<400> SEQUENCE: 33

```
ggatcctgac tgcctgagct t                                              21
```

<210> SEQ ID NO 34
<211> LENGTH: 26
<212> TYPE: PRT
<213> ORGANISM: Bacillus subtilis

<400> SEQUENCE: 34

```
Met Arg Ser Lys Lys Leu Trp Ile Ser Leu Leu Phe Ala Leu Thr Leu
1               5                   10                  15

Ile Phe Thr Met Ala Phe Ser Asn Met Ser
            20                  25
```

<210> SEQ ID NO 35
<211> LENGTH: 1449
<212> TYPE: PRT
<213> ORGANISM: Streptococcus salivarius

<400> SEQUENCE: 35

```
Met Asp Lys Lys Val His Tyr Lys Met His Lys Val Lys Lys Gln Trp
1               5                   10                  15

Val Thr Ile Ala Val Thr Gly Leu Ser Leu Gly Ala Val Ser Ala Val
            20                  25                  30

Ser Leu Gly Thr Asn Asp Gly Val Val Gln Ala Asp Glu His Thr Asp
        35                  40                  45

Ala Thr Val Ala Ile Pro Asp Ile Thr Val Asp Thr Gly Thr Val Ser
    50                  55                  60

Asn Asp Thr Thr Ala Ala Gln Asp Pro Thr Thr Ala Val Ala Ala Thr
65                  70                  75                  80

Asn Asp Val Ala Thr Asp Gln Ala Thr Pro Thr Ala Thr Phe Asp Leu
                85                  90                  95

Thr Thr Asp Thr Thr Asn Thr Val Ala Ala Asn Ala Val Asp Thr Val
                100                 105                 110

Ala Thr Val Gly Thr Asp Arg Ala Ala Thr Thr Asn Asp Thr Thr Ala
            115                 120                 125

Thr Asn Asp Thr Ala Val Asp Thr Asn Asn Asn Thr Thr Asp
        130                 135                 140

Thr Thr Thr Val Thr Asp Arg Ala Ala Thr Thr Glu Arg Arg Ala Thr
```

```
            145                 150                 155                 160
        Gly Ala Arg Arg Gly Pro Thr Gly Arg Arg Ala Thr Pro Val Asn
                        165                 170                 175
        Gly Asn Thr Asn Asn Ala Asn Asn Thr Val Thr Val Val Asn Asn Asp
                        180                 185                 190
        Leu Pro Ala Thr Asn Asn Val Val Thr Asp Gly Pro Ser His Ile Lys
                        195                 200                 205
        Thr Ile Asn Gly Lys Gln Tyr Tyr Val Glu Asp Asp Gly Thr Ile Arg
        210                 215                 220
        Lys Asn Tyr Val Leu Glu Arg Ile Gly Gly Ser Gln Tyr Phe Asn Ala
        225                 230                 235                 240
        Glu Thr Gly Glu Leu Ser Asn Gln Lys Glu Tyr Arg Phe Asp Lys Asn
                        245                 250                 255
        Gly Gly Thr Gly Ser Ser Ala Asp Ser Thr Asn Thr Asn Val Thr Val
                        260                 265                 270
        Asn Gly Asp Lys Asn Ala Phe Tyr Gly Thr Thr Asp Lys Asp Ile Glu
                        275                 280                 285
        Leu Val Asp Gly Tyr Phe Thr Ala Asn Thr Trp Tyr Arg Pro Lys Glu
                        290                 295                 300
        Ile Leu Lys Asp Gly Lys Glu Trp Thr Ala Ser Thr Glu Asn Asp Lys
        305                 310                 315                 320
        Arg Pro Leu Leu Thr Val Trp Trp Pro Ser Lys Ala Ile Gln Ala Ser
                        325                 330                 335
        Tyr Leu Asn Tyr Met Lys Glu Gln Gly Leu Gly Thr Asn Gln Thr Tyr
                        340                 345                 350
        Thr Ser Phe Ser Ser Gln Thr Gln Met Asp Gln Ala Ala Leu Glu Val
                        355                 360                 365
        Gln Lys Arg Ile Glu Glu Arg Ile Ala Arg Glu Gly Asn Thr Asp Trp
                        370                 375                 380
        Leu Arg Thr Thr Ile Lys Asn Phe Val Lys Thr Gln Pro Gly Trp Asn
        385                 390                 395                 400
        Ser Thr Ser Glu Asn Leu Asp Asn Asn Asp His Leu Gln Gly Gly Ala
                        405                 410                 415
        Leu Leu Tyr Asn Asn Asp Ser Arg Thr Ser His Ala Asn Ser Asp Tyr
                        420                 425                 430
        Arg Leu Leu Asn Arg Thr Pro Thr Ser Gln Thr Gly Lys His Asn Pro
                        435                 440                 445
        Lys Tyr Thr Lys Asp Thr Ser Asn Gly Gly Phe Glu Phe Leu Leu Ala
                        450                 455                 460
        Asn Asp Ile Asp Asn Ser Asn Pro Ala Val Gln Ala Glu Gln Leu Asn
        465                 470                 475                 480
        Trp Leu His Tyr Ile Met Asn Ile Gly Thr Ile Thr Gly Gly Ser Glu
                        485                 490                 495
        Asp Glu Asn Phe Asp Gly Val Arg Val Asp Ala Val Asp Asn Val Asn
                        500                 505                 510
        Ala Asp Leu Leu Gln Ile Ala Ser Asp Tyr Phe Lys Ala Lys Tyr Gly
                        515                 520                 525
        Ala Asp Gln Ser Gln Asp Gln Ala Ile Lys His Leu Ser Ile Leu Glu
                        530                 535                 540
        Ala Trp Ser His Asn Asp Ala Tyr Tyr Asn Glu Asp Thr Lys Gly Ala
        545                 550                 555                 560
        Gln Leu Pro Met Asp Asp Pro Met His Leu Ala Leu Val Tyr Ser Leu
                        565                 570                 575
```

```
Leu Arg Pro Ile Gly Asn Arg Ser Gly Val Glu Pro Leu Ile Ser Asn
            580                 585                 590

Ser Leu Asn Asp Arg Ser Glu Ser Gly Lys Asn Ser Lys Arg Met Ala
        595                 600                 605

Asn Tyr Ala Phe Val Arg Ala His Asp Ser Glu Val Gln Ser Ile Ile
    610                 615                 620

Gly Gln Ile Ile Lys Asn Glu Ile Asn Pro Gln Ser Thr Gly Asn Thr
625                 630                 635                 640

Phe Thr Leu Asp Glu Met Lys Lys Ala Phe Glu Ile Tyr Asn Lys Asp
                645                 650                 655

Met Arg Ser Ala Asn Lys Gln Tyr Thr Gln Tyr Asn Ile Pro Ser Ala
            660                 665                 670

Tyr Ala Leu Met Leu Thr His Lys Asp Thr Val Pro Arg Val Tyr Tyr
        675                 680                 685

Gly Asp Met Tyr Thr Asp Asp Gly Gln Tyr Met Ala Gln Lys Ser Pro
    690                 695                 700

Tyr Tyr Asp Ala Ile Glu Thr Leu Leu Lys Gly Arg Ile Arg Tyr Ala
705                 710                 715                 720

Ala Gly Gly Gln Asp Met Lys Val Asn Tyr Ile Gly Tyr Gly Asn Thr
                725                 730                 735

Asn Gly Trp Asp Ala Ala Gly Val Leu Thr Ser Val Arg Tyr Gly Thr
            740                 745                 750

Gly Ala Asn Ser Ala Ser Asp Thr Gly Thr Ala Glu Thr Arg Asn Gln
        755                 760                 765

Gly Met Ala Val Ile Val Ser Asn Gln Pro Ala Leu Arg Leu Thr Ser
    770                 775                 780

Asn Leu Thr Ile Asn Met Gly Ala Ala His Arg Asn Gln Ala Tyr Arg
785                 790                 795                 800

Pro Leu Leu Leu Thr Thr Asn Asp Gly Val Ala Thr Tyr Leu Asn Asp
                805                 810                 815

Ser Asp Ala Asn Gly Ile Val Lys Tyr Thr Asp Gly Asn Gly Asn Leu
            820                 825                 830

Thr Phe Ser Ala Asn Glu Ile Arg Gly Ile Arg Asn Pro Gln Val Asp
        835                 840                 845

Gly Tyr Leu Ala Val Trp Val Pro Val Gly Ala Ser Glu Asn Gln Asp
    850                 855                 860

Val Arg Val Ala Pro Ser Lys Glu Lys Asn Ser Ser Gly Leu Val Tyr
865                 870                 875                 880

Glu Ser Asn Ala Ala Leu Asp Ser Gln Val Ile Tyr Glu Gly Phe Ser
                885                 890                 895

Asn Phe Gln Asp Phe Val Gln Asn Pro Ser Gln Tyr Thr Asn Lys Lys
            900                 905                 910

Ile Ala Glu Asn Ala Asn Leu Phe Lys Ser Trp Gly Ile Thr Ser Phe
        915                 920                 925

Glu Phe Ala Pro Gln Tyr Val Ser Ser Asp Asp Gly Ser Phe Leu Asp
    930                 935                 940

Ser Val Ile Gln Asn Gly Tyr Ala Phe Thr Asp Arg Tyr Asp Ile Gly
945                 950                 955                 960

Met Ser Lys Asp Asn Lys Tyr Gly Ser Leu Ala Asp Leu Lys Ala Ala
                965                 970                 975

Leu Lys Ser Leu His Ala Val Gly Ile Ser Ala Ile Ala Asp Trp Val
            980                 985                 990
```

-continued

Pro Asp Gln Ile Tyr Asn Leu Pro Gly Asp Glu Val Val Thr Ala Thr
            995                 1000                1005

Arg Val Asn Asn Tyr Gly Glu Thr Lys Asp Gly Ala Ile Ile Asp
    1010                1015                1020

His Ser Leu Tyr Ala Ala Lys Thr Arg Thr Phe Gly Asn Asp Tyr
    1025                1030                1035

Gln Gly Lys Tyr Gly Gly Ala Phe Leu Asp Glu Leu Lys Arg Leu
    1040                1045                1050

Tyr Pro Gln Ile Phe Asp Arg Val Gln Ile Ser Thr Gly Lys Arg
    1055                1060                1065

Met Thr Thr Asp Glu Lys Ile Thr Gln Trp Ser Ala Lys Tyr Met
    1070                1075                1080

Asn Gly Thr Asn Ile Leu Asp Arg Gly Ser Glu Tyr Val Leu Lys
    1085                1090                1095

Asn Gly Leu Asn Gly Tyr Tyr Gly Thr Asn Gly Lys Val Ser
    1100                1105                1110

Leu Pro Lys Val Val Gly Ser Asn Gln Ser Thr Asn Gly Asp Asn
    1115                1120                1125

Gln Asn Gly Asp Gly Ser Gly Lys Phe Glu Lys Arg Leu Phe Ser
    1130                1135                1140

Val Arg Tyr Arg Tyr Asn Asn Gly Gln Tyr Ala Lys Asn Ala Phe
    1145                1150                1155

Ile Lys Asp Asn Asp Gly Asn Val Tyr Tyr Phe Asp Asn Ser Gly
    1160                1165                1170

Arg Met Ala Val Gly Glu Lys Thr Ile Asp Gly Lys Gln Tyr Phe
    1175                1180                1185

Phe Leu Ala Asn Gly Val Gln Leu Arg Asp Gly Tyr Arg Gln Asn
    1190                1195                1200

Arg Arg Gly Gln Val Phe Tyr Tyr Asp Gln Asn Gly Val Leu Asn
    1205                1210                1215

Ala Asn Gly Lys Gln Asp Pro Lys Pro Asp Asn Asn Asn Ala
    1220                1225                1230

Ser Gly Arg Asn Gln Phe Val Gln Ile Gly Asn Asn Val Trp Ala
    1235                1240                1245

Tyr Tyr Asp Gly Asn Gly Lys Arg Val Thr Gly His Gln Asn Ile
    1250                1255                1260

Asn Gly Gln Glu Leu Phe Phe Asp Asn Asn Gly Val Gln Val Lys
    1265                1270                1275

Gly Arg Thr Val Asn Glu Asn Gly Ala Ile Arg Tyr Tyr Asp Ala
    1280                1285                1290

Asn Ser Gly Glu Met Ala Arg Asn Arg Phe Ala Glu Ile Glu Pro
    1295                1300                1305

Gly Val Trp Ala Tyr Phe Asn Asn Asp Gly Thr Ala Val Lys Gly
    1310                1315                1320

Ser Gln Asn Ile Asn Gly Gln Asp Leu Tyr Phe Asp Gln Asn Gly
    1325                1330                1335

Arg Gln Val Lys Gly Ala Leu Ala Asn Val Asp Gly Asn Leu Arg
    1340                1345                1350

Tyr Tyr Asp Val Asn Ser Gly Glu Leu Tyr Arg Asn Arg Phe His
    1355                1360                1365

Glu Ile Asp Gly Ser Trp Tyr Tyr Phe Asp Gly Asn Gly Asn Ala
    1370                1375                1380

Val Lys Gly Met Val Asn Ile Asn Gly Gln Asn Leu Leu Phe Asp

```
                1385                1390               1395
Asn Asn Gly Lys Gln Ile Lys Gly His Leu Val Arg Val Asn Gly
        1400                1405               1410
Val Val Arg Tyr Phe Asp Pro Asn Ser Gly Glu Met Ala Val Asn
        1415                1420               1425
Arg Trp Val Glu Val Ser Pro Gly Trp Trp Val Tyr Phe Asp Gly
        1430                1435               1440
Glu Gly Arg Gly Gln Ile
        1445

<210> SEQ ID NO 36
<211> LENGTH: 3744
<212> TYPE: DNA
<213> ORGANISM: Streptococcus salivarius

<400> SEQUENCE: 36
atgccaagcc acattaagac catcaacggc aaacaatact acgtggagga tgacggtacg      60
attcgcaaga attacgtcct ggagcgtatc ggtggcagcc aatactttaa tgcagaaacc     120
ggtgaactgt ctaatcagaa agagtatcgt ttcgacaaaa atggtggtac tggtagcagc     180
gcggacagca cgaacaccaa cgtgactgtg aacggtgaca aaaacgcatt ttacggtacc     240
acggacaaag acattgagct ggtcgacggc tatttcaccg cgaacacctg gtatcgcccg     300
aaagaaatcc tgaaagacgg caaagaatgg accgccagca cggagaacga taaacgcccg     360
ctgctgaccg tctggtggcc tagcaaagca atccaggcgt cttatctgaa ctacatgaaa     420
gagcaaggcc tgggtaccaa ccaaacgtac acgagcttct ccagccaaac ccaaatggat     480
caagcagccc tggaagtgca aaagcgtatt gaagagcgca tcgcacgcga gggcaatacc     540
gactggctgc gcacgaccat caagaacttc gtgaaaaccc aaccgggttg aacagcacc     600
tctgaaaatc tggacaataa tgatcatctg caaggtggcg ccctgctgta caataacgac     660
tcccgcacga gccacgcgaa cagcgactat cgcctgctga tcgtacgcc gaccagccag     720
accggcaaac acaatccgaa atacaccaaa gataccagca tggtggtttt cgaatttctg     780
ctggcgaacg acatcgataa ctctaatccg gcggttcaag cagagcaact gaactggctg     840
cattacatta tgaacatcgg taccatcacg ggcggttctg aggatgaaaa cttcgacggc     900
gttcgtgttg acgctgtgga taatgtgaat gcggatctgc tgcaaatcgc gagcgactat     960
ttcaaagcaa aatacggtgc tgatcaaagc caagatcagg cgatcaaaca cttgagcatc    1020
ctggaagcgt ggtcccataa cgacgcctac tataacgaag ataccaaagg cgcgcagttg    1080
ccgatggatg atccgatgca cctggctctg gtctactcgc tgctgcgtcc gatcggcaat    1140
cgcagcggtg tggaaccgct gatttccaac agcctgaatg accgtagcga gtccggtaag    1200
aacagcaaac gtatggcgaa ctacgcgttc gtacgcgcgc atgatagcga ggtgcaatcg    1260
attattggcc agatcatcaa aaacgagatc aatccgcaaa gcaccggtaa tacgttcacc    1320
ctggatgaga tgaagaaagc gtttgagatt tacaacaagg atatgcgtag cgcgaataag    1380
cagtatacgc agtacaacat cccgagcgcg tatgcgttga tgctgaccca aggatacc     1440
gttccgcgtg tgtattacgg tgatatgtat acgacgacg tcagtacat ggcgcaaaag     1500
agcccatact atgatgcgat cgaaacgctg ctgaaaggtc gcatccgcta tgccgcaggt    1560
ggtcaggaca tgaaggtcaa ctatattggt tacggtaaca ctaacggctg ggatgctgcg    1620
ggcgtgctga ccagcgtacg ttatggcacg ggcgcaaata cgccagcga tacgggtacc    1680
gccgaaacgc gtaatcaagg tatggcagtg attgttagca accaaccggc gctgcgtctg    1740
```

-continued

```
actagcaatt tgaccattaa catgggtgcc gcacaccgta atcaggctta ccgtccgctg    1800
ctgctgacga ccaacgatgg cgtcgcgacc tatttgaacg atagcgatgc gaatggtatc    1860
gttaagtaca ccgacggtaa tggtaatctg accttctccg caaacgagat tcgtggcatc    1920
cgtaacccgc aagttgatgg ctatctggcc gtctgggttc cggtaggtgc gtcggagaat    1980
caggatgttc gtgtggcgcc gagcaaagag aagaacagct ccggtctggt ttacgagagc    2040
aatgctgccc tggatagcca agttatctac gaaggcttca gcaacttcca ggacttcgtt    2100
cagaatccga gccagtatac caacaaaaag attgcagaga atgcaaattt gttcaaatcc    2160
tggggtatta ccagctttga atttgcgccg cagtacgtga gctcggatga tggtagcttc    2220
ctggacagcg ttattcagaa cggttatgcg tttacggacc gctacgacat tggtatgagc    2280
aaagacaaca aatatggttc gctggcggat ttgaaggcag cactgaagag cttgcatgcc    2340
gttggtatta gcgcaatcgc ggattgggtt cctgatcaga tctacaatct gccaggcgac    2400
gaggtcgtca ccgcaacccg cgttaacaac tacggcgaaa ccaaagatgg tgcaatcatt    2460
gatcactctt tgtacgcggc caaaacccgt acttttggta cgactacca gggtaagtat    2520 ggtggtgcgt tcctggacga gctgaaacgt ctgtatccgc agatctttga ccgcgttcag    2580
atttctaccg gtaagcgcat gaccacggac gagaagatca cccaatggtc tgcaaagtat    2640
atgaacggta cgaacatctt ggaccgtggc tctgaatacg ttttgaagaa tggtctgaat    2700
ggttactatg gcaccaatgg tggcaaagtt tcgctgccga agttgtggg tagcaatcaa    2760 agcacgaatg cgacaatca aaacggcgac ggtagcggca gtttgaaaa gcgtctgttc    2820 agcgtgcgtt accgttataa caatggccag tacgcgaaaa atgcctttat caaagataac    2880
gacggcaatg tttactattt cgacaatagc ggtcgtatgg ctgtcggtga aaaacgatt    2940 gacggcaagc agtacttctt cctggctaat ggcgttcagc tgcgtgacgg ctaccgtcaa    3000
aatcgtcgcg gtcaggtgtt ttactacgac cagaatggtg tgctgaacgc aaacggtaaa    3060
caagacccga agcctgacaa caataacaat gcgagcggcc gtaatcaatt cgtccagatc    3120
ggtaacaacg tgtgggcgta ttatgatggc aatggtaaac gtgtcaccgg tcaccagaac    3180
atcaacggtc aggagttgtt tttcgataac aacggtgtcc aggttaaggg tcgtacggtg    3240
aatgagaacg gtgcaattcg ctactatgac gcgaatagcg gtgagatggc acgcaatcgt    3300
ttcgcggaga ttgaaccggg cgtctgggca tactttaaca atgacggcac cgcagtgaag    3360
ggttctcaga atatcaatgg tcaagacctg tacttcgacc agaacggtcg tcaggtcaag    3420
ggtgcgctgg ccaatgttga tggcaacctg cgctattacg acgttaacag cggtgagctg    3480
taccgtaatc gtttccacga aatcgacggc agctggtatt actttgatgg taacggtaat    3540
gcggtgaagg tatggtcaa tatcaacggc caaaatctgt tgtttgacaa taacggcaaa    3600
cagattaagg tcatctggt ccgcgtcaac ggcgtcgtgc gctattttga tccgaactct    3660
ggtgaaatgg cggttaatcg ttgggttgag gtgagcccag ttggtgggt ttactttgac    3720 ggtgaaggtc gtggtcagat ctaa                                          3744
```

<210> SEQ ID NO 37
<211> LENGTH: 1247
<212> TYPE: PRT
<213> ORGANISM: Streptococcus salivarius

<400> SEQUENCE: 37

Met Pro Ser His Ile Lys Thr Ile Asn Gly Lys Gln Tyr Tyr Val Glu
1               5                   10                  15

Asp Asp Gly Thr Ile Arg Lys Asn Tyr Val Leu Glu Arg Ile Gly Gly
            20                  25                  30

Ser Gln Tyr Phe Asn Ala Glu Thr Gly Glu Leu Ser Asn Gln Lys Glu
            35                  40                  45

Tyr Arg Phe Asp Lys Asn Gly Gly Thr Gly Ser Ser Ala Asp Ser Thr
50                  55                  60

Asn Thr Asn Val Thr Val Asn Gly Asp Lys Asn Ala Phe Tyr Gly Thr
65                  70                  75                  80

Thr Asp Lys Asp Ile Glu Leu Val Asp Gly Tyr Phe Thr Ala Asn Thr
                85                  90                  95

Trp Tyr Arg Pro Lys Glu Ile Leu Lys Asp Gly Lys Glu Trp Thr Ala
            100                 105                 110

Ser Thr Glu Asn Asp Lys Arg Pro Leu Leu Thr Val Trp Trp Pro Ser
            115                 120                 125

Lys Ala Ile Gln Ala Ser Tyr Leu Asn Tyr Met Lys Glu Gln Gly Leu
130                 135                 140

Gly Thr Asn Gln Thr Tyr Thr Ser Phe Ser Ser Gln Thr Gln Met Asp
145                 150                 155                 160

Gln Ala Ala Leu Glu Val Gln Lys Arg Ile Glu Glu Arg Ile Ala Arg
                165                 170                 175

Glu Gly Asn Thr Asp Trp Leu Arg Thr Thr Ile Lys Asn Phe Val Lys
            180                 185                 190

Thr Gln Pro Gly Trp Asn Ser Thr Ser Glu Asn Leu Asp Asn Asn Asp
            195                 200                 205

His Leu Gln Gly Gly Ala Leu Leu Tyr Asn Asn Asp Ser Arg Thr Ser
            210                 215                 220

His Ala Asn Ser Asp Tyr Arg Leu Leu Asn Arg Thr Pro Thr Ser Gln
225                 230                 235                 240

Thr Gly Lys His Asn Pro Lys Tyr Thr Lys Asp Thr Ser Asn Gly Gly
                245                 250                 255

Phe Glu Phe Leu Leu Ala Asn Asp Ile Asp Asn Ser Asn Pro Ala Val
            260                 265                 270

Gln Ala Glu Gln Leu Asn Trp Leu His Tyr Ile Met Asn Ile Gly Thr
            275                 280                 285

Ile Thr Gly Gly Ser Glu Asp Glu Asn Phe Asp Gly Val Arg Val Asp
            290                 295                 300

Ala Val Asp Asn Val Asn Ala Asp Leu Leu Gln Ile Ala Ser Asp Tyr
305                 310                 315                 320

Phe Lys Ala Lys Tyr Gly Ala Asp Gln Ser Gln Asp Gln Ala Ile Lys
                325                 330                 335

His Leu Ser Ile Leu Glu Ala Trp Ser His Asn Asp Ala Tyr Tyr Asn
            340                 345                 350

Glu Asp Thr Lys Gly Ala Gln Leu Pro Met Asp Asp Pro Met His Leu
            355                 360                 365

Ala Leu Val Tyr Ser Leu Leu Arg Pro Ile Gly Asn Arg Ser Gly Val
            370                 375                 380

Glu Pro Leu Ile Ser Asn Ser Leu Asn Asp Arg Ser Glu Ser Gly Lys
385                 390                 395                 400

Asn Ser Lys Arg Met Ala Asn Tyr Ala Phe Val Arg Ala His Asp Ser
                405                 410                 415

Glu Val Gln Ser Ile Ile Gly Gln Ile Ile Lys Asn Glu Ile Asn Pro
            420                 425                 430

```
Gln Ser Thr Gly Asn Thr Phe Thr Leu Asp Glu Met Lys Lys Ala Phe
            435                 440                 445

Glu Ile Tyr Asn Lys Asp Met Arg Ser Ala Asn Lys Gln Tyr Thr Gln
    450                 455                 460

Tyr Asn Ile Pro Ser Ala Tyr Ala Leu Met Leu Thr His Lys Asp Thr
465                 470                 475                 480

Val Pro Arg Val Tyr Tyr Gly Asp Met Tyr Thr Asp Asp Gly Gln Tyr
                485                 490                 495

Met Ala Gln Lys Ser Pro Tyr Tyr Asp Ala Ile Glu Thr Leu Leu Lys
            500                 505                 510

Gly Arg Ile Arg Tyr Ala Ala Gly Gly Gln Asp Met Lys Val Asn Tyr
        515                 520                 525

Ile Gly Tyr Gly Asn Thr Asn Gly Trp Asp Ala Ala Gly Val Leu Thr
    530                 535                 540

Ser Val Arg Tyr Gly Thr Gly Ala Asn Ser Ala Ser Asp Thr Gly Thr
545                 550                 555                 560

Ala Glu Thr Arg Asn Gln Gly Met Ala Val Ile Val Ser Asn Gln Pro
                565                 570                 575

Ala Leu Arg Leu Thr Ser Asn Leu Thr Ile Asn Met Gly Ala Ala His
            580                 585                 590

Arg Asn Gln Ala Tyr Arg Pro Leu Leu Leu Thr Thr Asn Asp Gly Val
        595                 600                 605

Ala Thr Tyr Leu Asn Asp Ser Asp Ala Asn Gly Ile Val Lys Tyr Thr
    610                 615                 620

Asp Gly Asn Gly Asn Leu Thr Phe Ser Ala Asn Glu Ile Arg Gly Ile
625                 630                 635                 640

Arg Asn Pro Gln Val Asp Gly Tyr Leu Ala Val Trp Val Pro Val Gly
                645                 650                 655

Ala Ser Glu Asn Gln Asp Val Arg Val Ala Pro Ser Lys Glu Lys Asn
            660                 665                 670

Ser Ser Gly Leu Val Tyr Glu Ser Asn Ala Ala Leu Asp Ser Gln Val
        675                 680                 685

Ile Tyr Glu Gly Phe Ser Asn Phe Gln Asp Phe Val Gln Asn Pro Ser
    690                 695                 700

Gln Tyr Thr Asn Lys Lys Ile Ala Glu Asn Ala Asn Leu Phe Lys Ser
705                 710                 715                 720

Trp Gly Ile Thr Ser Phe Glu Phe Ala Pro Gln Tyr Val Ser Ser Asp
                725                 730                 735

Asp Gly Ser Phe Leu Asp Ser Val Ile Gln Asn Gly Tyr Ala Phe Thr
            740                 745                 750

Asp Arg Tyr Asp Ile Gly Met Ser Lys Asp Asn Lys Tyr Gly Ser Leu
        755                 760                 765

Ala Asp Leu Lys Ala Ala Leu Lys Ser Leu His Ala Val Gly Ile Ser
    770                 775                 780

Ala Ile Ala Asp Trp Val Pro Asp Gln Ile Tyr Asn Leu Pro Gly Asp
785                 790                 795                 800

Glu Val Val Thr Ala Thr Arg Val Asn Asn Tyr Gly Glu Thr Lys Asp
                805                 810                 815

Gly Ala Ile Ile Asp His Ser Leu Tyr Ala Ala Lys Thr Arg Thr Phe
            820                 825                 830

Gly Asn Asp Tyr Gln Gly Lys Tyr Gly Gly Ala Phe Leu Asp Glu Leu
        835                 840                 845

Lys Arg Leu Tyr Pro Gln Ile Phe Asp Arg Val Gln Ile Ser Thr Gly
```

850                 855                 860
Lys Arg Met Thr Thr Asp Glu Lys Ile Thr Gln Trp Ser Ala Lys Tyr
865                 870                 875                 880

Met Asn Gly Thr Asn Ile Leu Asp Arg Gly Ser Glu Tyr Val Leu Lys
                    885                 890                 895

Asn Gly Leu Asn Gly Tyr Tyr Gly Thr Asn Gly Gly Lys Val Ser Leu
                900                 905                 910

Pro Lys Val Val Gly Ser Asn Gln Ser Thr Asn Gly Asp Asn Gln Asn
            915                 920                 925

Gly Asp Gly Ser Gly Lys Phe Glu Lys Arg Leu Phe Ser Val Arg Tyr
        930                 935                 940

Arg Tyr Asn Asn Gly Gln Tyr Ala Lys Asn Ala Phe Ile Lys Asp Asn
945                 950                 955                 960

Asp Gly Asn Val Tyr Tyr Phe Asp Asn Ser Gly Arg Met Ala Val Gly
                    965                 970                 975

Glu Lys Thr Ile Asp Gly Lys Gln Tyr Phe Phe Leu Ala Asn Gly Val
                980                 985                 990

Gln Leu Arg Asp Gly Tyr Arg Gln Asn Arg Arg Gly Gln Val Phe Tyr
            995                 1000                1005

Tyr Asp Gln Asn Gly Val Leu Asn Ala Asn Gly Lys Gln Asp Pro
        1010                1015                1020

Lys Pro Asp Asn Asn Asn Ala Ser Gly Arg Asn Gln Phe Val
    1025                1030                1035

Gln Ile Gly Asn Asn Val Trp Ala Tyr Tyr Asp Gly Asn Gly Lys
    1040                1045                1050

Arg Val Thr Gly His Gln Asn Ile Asn Gly Gln Glu Leu Phe Phe
    1055                1060                1065

Asp Asn Asn Gly Val Gln Val Lys Gly Arg Thr Val Asn Glu Asn
    1070                1075                1080

Gly Ala Ile Arg Tyr Tyr Asp Ala Asn Ser Gly Glu Met Ala Arg
    1085                1090                1095

Asn Arg Phe Ala Glu Ile Glu Pro Gly Val Trp Ala Tyr Phe Asn
    1100                1105                1110

Asn Asp Gly Thr Ala Val Lys Gly Ser Gln Asn Ile Asn Gly Gln
    1115                1120                1125

Asp Leu Tyr Phe Asp Gln Asn Gly Arg Gln Val Lys Gly Ala Leu
    1130                1135                1140

Ala Asn Val Asp Gly Asn Leu Arg Tyr Tyr Asp Val Asn Ser Gly
    1145                1150                1155

Glu Leu Tyr Arg Asn Arg Phe His Glu Ile Asp Gly Ser Trp Tyr
    1160                1165                1170

Tyr Phe Asp Gly Asn Gly Asn Ala Val Lys Gly Met Val Asn Ile
    1175                1180                1185

Asn Gly Gln Asn Leu Leu Phe Asp Asn Asn Gly Lys Gln Ile Lys
    1190                1195                1200

Gly His Leu Val Arg Val Asn Gly Val Val Arg Tyr Phe Asp Pro
    1205                1210                1215

Asn Ser Gly Glu Met Ala Val Asn Arg Trp Val Glu Val Ser Pro
    1220                1225                1230

Gly Trp Trp Val Tyr Phe Asp Gly Glu Gly Arg Gly Gln Ile
    1235                1240                1245

<210> SEQ ID NO 38

<211> LENGTH: 1590
<212> TYPE: PRT
<213> ORGANISM: Streptococcus sobrinus

<400> SEQUENCE: 38

```
Met Glu Lys Asn Val Arg Phe Lys Met His Lys Val Lys Lys Arg Trp
1               5                   10                  15

Val Thr Leu Ser Val Ala Ser Ala Thr Met Leu Ala Ser Ala Leu Gly
            20                  25                  30

Ala Ser Val Ala Ser Ala Asp Thr Asp Thr Ala Ser Asp Ser Asn
            35                  40                  45

Gln Ala Val Val Thr Gly Asp Gln Thr Thr Asn Asn Gln Ala Thr Asp
50                  55                  60

Gln Thr Ser Ile Ala Ala Thr Ala Thr Ser Glu Gln Ser Ala Ser Thr
65                  70                  75                  80

Asp Ala Ala Thr Asp Gln Ala Ser Ala Ala Glu Gln Thr Gln Gly Thr
                85                  90                  95

Thr Ala Ser Thr Asp Thr Ala Ala Gln Thr Thr Asn Ala Asn Glu
            100                 105                 110

Ala Lys Trp Val Pro Thr Glu Asn Glu Asn Gln Gly Phe Thr Asp Glu
            115                 120                 125

Met Leu Ala Glu Ala Lys Asn Val Ala Thr Ala Glu Ser Asp Ser Ile
130                 135                 140

Pro Ser Asp Leu Ala Lys Met Ser Asn Val Lys Gln Val Asp Gly Lys
145                 150                 155                 160

Tyr Tyr Tyr Tyr Asp Gln Asp Gly Asn Val Lys Lys Asn Phe Ala Val
                165                 170                 175

Ser Val Gly Asp Lys Ile Tyr Tyr Phe Asp Glu Thr Gly Ala Tyr Lys
            180                 185                 190

Asp Thr Ser Lys Val Asp Ala Asp Lys Ser Ser Ala Val Ser Gln
            195                 200                 205

Asn Ala Thr Ile Phe Ala Ala Asn Asn Arg Ala Tyr Ser Thr Ser Ala
210                 215                 220

Lys Asn Phe Glu Ala Val Asp Asn Tyr Leu Thr Ala Asp Ser Trp Tyr
225                 230                 235                 240

Arg Pro Lys Ser Ile Leu Lys Asp Gly Lys Thr Trp Thr Glu Ser Gly
                245                 250                 255

Lys Asp Asp Phe Arg Pro Leu Leu Met Ala Trp Trp Pro Asp Thr Glu
            260                 265                 270

Thr Lys Arg Asn Tyr Val Asn Tyr Met Asn Lys Val Val Gly Ile Asp
            275                 280                 285

Lys Thr Tyr Thr Ala Glu Thr Ser Gln Ala Asp Leu Thr Ala Ala Ala
            290                 295                 300

Glu Leu Val Gln Ala Arg Ile Glu Gln Lys Ile Thr Ser Glu Asn Asn
305                 310                 315                 320

Thr Lys Trp Leu Arg Glu Ala Ile Ser Ala Phe Val Lys Thr Gln Pro
                325                 330                 335

Gln Trp Asn Gly Glu Ser Glu Lys Pro Tyr Asp Asp His Leu Gln Asn
            340                 345                 350

Gly Ala Leu Leu Phe Asp Asn Gln Thr Asp Leu Thr Pro Asp Thr Gln
            355                 360                 365

Ser Asn Tyr Arg Leu Leu Asn Arg Thr Pro Thr Asn Gln Thr Gly Ser
370                 375                 380

Leu Asp Ser Arg Phe Thr Tyr Asn Pro Asn Asp Pro Leu Gly Gly Tyr
```

-continued

```
385                 390                 395                 400
Asp Phe Leu Leu Ala Asn Asp Val Asp Asn Ser Asn Pro Val Val Gln
                405                 410                 415
Ala Glu Gln Leu Asn Trp Leu His Tyr Leu Leu Asn Phe Gly Ser Ile
                420                 425                 430
Tyr Ala Asn Asp Ala Asp Ala Asn Phe Asp Ser Ile Arg Val Asp Ala
                435                 440                 445
Val Asp Asn Val Asp Ala Asp Leu Leu Gln Ile Ser Ser Asp Tyr Leu
            450                 455                 460
Lys Ala Ala Tyr Gly Ile Asp Lys Asn Asn Lys Asn Ala Asn His
465                 470                 475                 480
Val Ser Ile Val Glu Ala Trp Ser Asp Asn Asp Thr Pro Tyr Leu His
                485                 490                 495
Asp Asp Gly Asp Asn Leu Met Asn Met Asp Asn Lys Phe Arg Leu Ser
                500                 505                 510
Met Leu Trp Ser Leu Ala Lys Pro Leu Asp Lys Arg Ser Gly Leu Asn
            515                 520                 525
Pro Leu Ile His Asn Ser Leu Val Asp Arg Glu Val Asp Asp Arg Glu
            530                 535                 540
Val Glu Thr Val Pro Ser Tyr Ser Phe Ala Arg Ala His Asp Ser Glu
545                 550                 555                 560
Val Gln Asp Ile Ile Arg Asp Ile Ile Lys Ala Glu Ile Asn Pro Asn
                565                 570                 575
Ser Phe Gly Tyr Ser Phe Thr Gln Glu Glu Ile Glu Gln Ala Phe Lys
            580                 585                 590
Ile Tyr Asn Glu Asp Leu Lys Lys Thr Asp Lys Lys Tyr Thr His Tyr
            595                 600                 605
Asn Val Pro Leu Ser Tyr Thr Leu Leu Leu Thr Asn Lys Gly Ser Ile
            610                 615                 620
Pro Arg Val Tyr Gly Asp Met Phe Thr Asp Asp Gly Gln Tyr Met
625                 630                 635                 640
Ala Asn Lys Thr Val Asn Tyr Asp Ala Ile Glu Ser Leu Leu Lys Ala
                645                 650                 655
Arg Met Lys Tyr Val Ser Gly Gly Gln Ala Met Gln Asn Tyr Gln Ile
                660                 665                 670
Gly Asn Gly Glu Ile Leu Thr Ser Val Arg Tyr Gly Lys Gly Ala Leu
            675                 680                 685
Lys Gln Ser Asp Lys Gly Asp Ala Thr Thr Arg Thr Ser Gly Val Gly
            690                 695                 700
Val Val Met Gly Asn Gln Pro Asn Phe Ser Leu Asp Gly Lys Val Val
705                 710                 715                 720
Ala Leu Asn Met Gly Ala Ala His Ala Asn Gln Glu Tyr Arg Ala Leu
                725                 730                 735
Met Val Ser Thr Lys Asp Gly Val Ala Thr Tyr Ala Thr Asp Ala Asp
                740                 745                 750
Ala Ser Lys Ala Gly Leu Val Lys Arg Thr Asp Glu Asn Gly Tyr Leu
            755                 760                 765
Tyr Phe Leu Asn Asp Asp Leu Lys Gly Val Ala Asn Pro Gln Val Ser
            770                 775                 780
Gly Phe Leu Gln Val Trp Val Pro Val Gly Ala Ala Asp Asp Gln Asp
785                 790                 795                 800
Ile Arg Val Ala Ala Ser Asp Thr Ala Ser Thr Asp Gly Lys Ser Leu
                805                 810                 815
```

```
His Gln Asp Ala Ala Met Asp Ser Arg Val Met Phe Glu Gly Phe Ser
            820                 825                 830

Asn Phe Gln Ser Phe Ala Thr Lys Glu Glu Tyr Thr Asn Val Val
            835                 840                 845

Ile Ala Asn Asn Val Asp Lys Phe Val Ser Trp Gly Ile Thr Asp Phe
850                 855                 860

Glu Met Ala Pro Gln Tyr Val Ser Ser Thr Asp Gly Gln Phe Leu Asp
865                 870                 875                 880

Ser Val Ile Gln Asn Gly Tyr Ala Phe Thr Asp Arg Tyr Asp Leu Gly
                885                 890                 895

Met Ser Lys Ala Asn Lys Tyr Gly Thr Ala Asp Gln Leu Val Lys Ala
                900                 905                 910

Ile Lys Ala Leu His Ala Lys Gly Leu Lys Val Met Ala Asp Trp Val
            915                 920                 925

Pro Asp Gln Met Tyr Thr Phe Pro Lys Gln Glu Val Val Thr Val Thr
            930                 935                 940

Arg Thr Asp Lys Phe Gly Lys Pro Ile Ala Gly Ser Gln Ile Asn His
945                 950                 955                 960

Ser Leu Tyr Val Thr Asp Thr Lys Ser Ser Gly Asp Asp Tyr Gln Ala
                965                 970                 975

Lys Tyr Gly Gly Ala Phe Leu Asp Glu Leu Lys Glu Lys Tyr Pro Glu
                980                 985                 990

Leu Phe Thr Lys Lys Gln Ile Ser Thr Gly Gln Ala Ile Asp Pro Ser
            995                 1000                1005

Val Lys Ile Lys Gln Trp Ser Ala Lys Tyr Phe Asn Gly Ser Asn
        1010                1015                1020

Ile Leu Gly Arg Gly Ala Asp Tyr Val Leu Ser Asp Gln Val Ser
        1025                1030                1035

Asn Lys Tyr Phe Asn Val Ala Ser Asp Thr Leu Phe Leu Pro Ser
        1040                1045                1050

Ser Leu Leu Gly Lys Val Val Glu Ser Gly Ile Arg Tyr Asp Gly
        1055                1060                1065

Lys Gly Tyr Ile Tyr Asn Ser Ser Ala Thr Gly Asp Gln Val Lys
        1070                1075                1080

Ala Ser Phe Ile Thr Glu Ala Gly Asn Leu Tyr Tyr Phe Gly Lys
        1085                1090                1095

Asp Gly Tyr Met Val Thr Gly Ala Gln Thr Ile Asn Gly Ala Asn
        1100                1105                1110

Tyr Phe Phe Leu Glu Asn Gly Thr Ala Leu Arg Asn Thr Ile Tyr
        1115                1120                1125

Thr Asp Ala Gln Gly Asn Ser His Tyr Tyr Ala Asn Asp Gly Lys
        1130                1135                1140

Arg Tyr Glu Asn Gly Tyr Gln Phe Gly Asn Asp Trp Arg Tyr
        1145                1150                1155

Phe Lys Asp Gly Asn Met Ala Val Gly Leu Thr Thr Val Asp Gly
        1160                1165                1170

Asn Val Gln Tyr Phe Asp Lys Asp Gly Val Gln Ala Lys Asp Lys
        1175                1180                1185

Ile Ile Val Thr Arg Asp Gly Lys Val Arg Tyr Phe Asp Gln His
        1190                1195                1200

Asn Gly Asn Ala Ala Thr Asn Thr Phe Ile Ala Asp Lys Thr Gly
        1205                1210                1215
```

His Trp Tyr Tyr Leu Gly Lys Asp Gly Val Ala Val Thr Gly Ala
1220                1225                1230

Gln Thr Val Gly Lys Gln Lys Leu Tyr Phe Glu Ala Asn Gly Gln
1235                1240                1245

Gln Val Lys Gly Asp Phe Val Thr Ser Asp Glu Gly Lys Leu Tyr
1250                1255                1260

Phe Tyr Asp Val Asp Ser Gly Asp Met Trp Thr Asp Thr Phe Ile
1265                1270                1275

Glu Asp Lys Ala Gly Asn Trp Phe Tyr Leu Gly Lys Asp Gly Ala
1280                1285                1290

Ala Val Thr Gly Ala Gln Thr Ile Arg Gly Gln Lys Leu Tyr Phe
1295                1300                1305

Lys Ala Asn Gly Gln Gln Val Lys Gly Asp Ile Val Lys Gly Thr
1310                1315                1320

Asp Gly Lys Ile Arg Tyr Tyr Asp Ala Lys Ser Gly Glu Gln Val
1325                1330                1335

Phe Asn Lys Thr Val Lys Ala Ala Asp Gly Lys Thr Tyr Val Ile
1340                1345                1350

Gly Asn Asp Gly Val Ala Val Asp Pro Ser Val Val Lys Gly Gln
1355                1360                1365

Thr Phe Lys Asp Ala Ser Gly Ala Leu Arg Phe Tyr Asn Leu Lys
1370                1375                1380

Gly Gln Leu Val Thr Gly Ser Gly Trp Tyr Glu Thr Ala Asn His
1385                1390                1395

Asp Trp Val Tyr Ile Gln Ser Gly Lys Ala Leu Thr Gly Glu Gln
1400                1405                1410

Thr Ile Asn Gly Gln His Leu Tyr Phe Lys Glu Asp Gly His Gln
1415                1420                1425

Val Lys Gly Gln Leu Val Thr Gly Thr Asp Gly Lys Val Arg Tyr
1430                1435                1440

Tyr Asp Ala Asn Ser Gly Asp Gln Ala Phe Asn Lys Ser Val Thr
1445                1450                1455

Val Asn Gly Lys Thr Tyr Tyr Phe Gly Asn Asp Gly Thr Ala Gln
1460                1465                1470

Thr Ala Gly Asn Pro Lys Gly Gln Thr Phe Lys Asp Gly Ser Asp
1475                1480                1485

Ile Arg Phe Tyr Ser Met Glu Gly Gln Leu Val Thr Gly Ser Gly
1490                1495                1500

Trp Tyr Glu Asn Ala Gln Gly Gln Trp Leu Tyr Val Lys Asn Gly
1505                1510                1515

Lys Val Leu Thr Gly Leu Gln Thr Val Gly Ser Gln Arg Val Tyr
1520                1525                1530

Phe Asp Glu Asn Gly Ile Gln Ala Lys Gly Lys Ala Val Arg Thr
1535                1540                1545

Ser Asp Gly Lys Ile Arg Tyr Phe Asp Glu Asn Ser Gly Ser Met
1550                1555                1560

Ile Thr Asn Gln Trp Lys Phe Val Tyr Gly Gln Tyr Tyr Tyr Phe
1565                1570                1575

Gly Asn Asp Gly Ala Arg Ile Tyr Arg Gly Trp Asn
1580                1585                1590

<210> SEQ ID NO 39
<211> LENGTH: 4308
<212> TYPE: DNA

<213> ORGANISM: Streptococcus sobrinus

<400> SEQUENCE: 39

| | |
|---|---|
| atggttgacg gcaaatacta ctattatgat caggacggta acgtaaagaa gaatttcgcg | 60 |
| gtgagcgttg gtgacaaaat ctactacttc gatgaaactg gtgcatataa ggataccagc | 120 |
| aaagtggacg ccgacaagag cagcagcgcg gttagccaaa acgcgaccat ctttgcggcg | 180 |
| aataaccgtg cgtacagcac ctctgcaaag aattttgaag cggtggataa ctacctgacc | 240 |
| gcagacagct ggtatcgtcc gaaatccatc ctgaaggacg gcaaaacctg gaccgagagc | 300 |
| ggtaaggatg atttccgtcc actgctgatg gcatggtggc ctgacaccga aactaagcgc | 360 |
| aactacgtga actatatgaa taaagtggtc ggtattgaca agacgtacac tgcggaaacg | 420 |
| tcgcaagcgg atttgaccgc agcggcgag ctggttcaag cgcgtatcga gcagaagatt | 480 |
| accagcgaaa acaacaccaa atggctgcgc gaagcaatct ccgcgttcgt taagacgcag | 540 |
| cctcagtgga acggcgagtc cgaaaagccg tatgacgatc acttgcagaa cggtgcgctg | 600 |
| ctgtttgata ccaaaccga cctgacgcca gacacccaaa gcaattaccg tttgctgaac | 660 |
| cgtaccccga ccaatcagac tggtagcctg gatagccgtt ttacgtataa tccgaatgac | 720 |
| ccgttgggcg gctacgattt cttgctggcg aacgacgttg acaatagcaa tccggtcgtc | 780 |
| caggctgaac agttgaactg gctgcattat ctgctgaact tggctctcat ttacgctaac | 840 |
| gatgccgacg ccaattttga cagcattcgc gttgatgccg tcgataatgt cgatgctgat | 900 |
| ctgctgcaaa tcagcagcga ttacctgaaa gcagcgtatg catcgacaa gaataacaag | 960 |
| aatgcgaaca ccatgttag catcgtcgaa gcgtggagcg acaatgatac cccgtatttg | 1020 |
| cacgacgatg gcgataatct gatgaacatg gacaacaaat ttcgcctgtc catgctgtgg | 1080 |
| agcctggcaa agccgctgga caaacgtagc ggtttgaacc cgctgattca caatagcctg | 1140 |
| gtggaccgcg aggtggacga tcgtgaagtg gaaaccgtgc cgtcctacag ctttgctcgt | 1200 |
| gcacatgata gcgaggtgca ggacatcatc cgtgacatta tcaaggctga gattaaccca | 1260 |
| aatagctttg gttatagctt cactcaagaa gagatcgagc aagcctttaa gatttacaac | 1320 |
| gaggatttga gaaaaacgga caagaaatac acccactaca atgtgccgct gagctacacc | 1380 |
| ctgctgctga ccaacaaggg cagcatcccg cgtgtgtact atggtgatat gttcaccgat | 1440 |
| gatggccaat acatggcaaa caagaccgtc aactacgacg caatcgagag cctgctgaaa | 1500 |
| gcccgtatga aatatgtcag cggtggccaa gcaatgcaga actatcaaat tggtaatggc | 1560 |
| gagattttga ccagcgtgcg ctatggtaaa ggtgccctga gcagagcga taagggtgac | 1620 |
| gcgacgacgc gcactagcgg tgttggcgtg gttatgggta atcagccgaa cttctccctg | 1680 |
| gacggtaaag ttgtggccct gaatatgggt gcggcccatg cgaatcaaga ataccgtgca | 1740 |
| ctgatggtca gcactaaaga cggtgtggca acttacgcaa ccgatgctga cgcatccaaa | 1800 |
| gcgggcctgg tcaagcgtac cgacgagaac ggctacctgt acttcctgaa tgatgatctg | 1860 |
| aagggcgtcg cgaaccctca ggtttccggc ttcttgcaag tgtgggttcc agttggtgcc | 1920 |
| gccgatgacc aggacattcg cgtcgccgcc agcgacacgg cgagcacgga tggtaaaagc | 1980 |
| ctgcatcaag atgcggcgat ggacagccgc gtcatgtttg agggtttcag caattttcaa | 2040 |
| tccttcgcga ccaaagaaga agaatacacg aatgttgtta tcgcgaacaa tgtcgataag | 2100 |
| ttcgttagct ggggtatcac cgattttgaa atggctccgc agtatgttag cagcaccgac | 2160 |
| ggtcagttct tggacagcgt catccagaat ggctatgcgt ttactgatcg ctatgatctg | 2220 |
| ggtatgtcca aggcgaacaa gtatggcacg gcagaccaac tggttaaggc aatcaaagcc | 2280 |

```
ctgcacgcta aaggcctgaa agttatggcg gactgggtcc cggatcaaat gtacaccttt    2340
ccaaaacagg aagttgtgac cgttacccgc accgacaaat tcggtaaacc gatcgccggc    2400
tctcaaatca atcacagctt gtatgtgacc gacaccaaat ccagcggcga cgactaccaa    2460
gcgaagtacg gcggtgcctt cctggatgaa ctgaaagaaa gtacccggga actgttcacg    2520
aaaaagcaaa ttagcacggg ccaagcgatt gatccgagcg tgaaaatcaa gcagtggagc    2580 gcaaatact tcaatggttc gaatatcctg ggtcgcggtg cggactatgt gctgagcgac    2640
caggtcagca ataagtattt caacgtggcg agcgacacct tgttcctgcc gtccagcctg    2700
ctgggcaagt tcgtggagag cggcattcgt tacgacggca agggttacat ctacaacagc    2760
tccgcgaccg gcgatcaggt caaagcgtct tcattacgg aagccggtaa cctgtattac    2820
ttcggcaaag acggttacat ggttactggt gcccagacga ttaatggcgc caactacttc    2880
ttcctggaaa acggtacggc actgcgtaat acgatttaca ccgatgctca aggtaatagc    2940
cactattacg cgaatgatgg caaacgctat gaaaatggct atcaacagtt cggtaacgat    3000
tggcgctact ttaaagatgg taacatggca gtcggcctga ccacggttga tggcaacgtg    3060
caatactttg acaagacgg cgtccaggca aaggataaga ttatcgtcac ccgtgatggc    3120
aaggtccgtt acttcgatca gcacaacggt aacgcggcga ccaacacgtt cattgctgat    3180
aaaactggcc attggtatta cctgggtaaa gatggcgtcg cggtgactgg cgcccagacc    3240
gtcggcaaac aaaaactgta cttcgaggcc aacggtcaac aagttaaagg tgactttgtt    3300
acgtccgatg agggcaaact gtatttctat gacgttgatt ctggtgacat gtggacggac    3360
accttcatcg aggataaggc gggcaactgg ttctatttgg gcaaggatgg tgcggcagtt    3420
acgggtgccc aaacgattcg cggtcagaag ctgtacttca aggccaatgg tcaacaggtc    3480
aagggtgaca ttgttaaggg caccgacggt aaaatccgct actatgatgc aaaatccggt    3540
gaacaggtgt tcaacaaaac ggtgaaagct gcggatggca aaacgtatgt tatcggtaat    3600
gatggtgtcg cggtggaccc tagcgtggtt aaaggtcaaa cctttaagga cgcttcgggc    3660
gctctgcgtt tctacaactt gaagggtcaa ctggtcactg gcagcggctg gtatgaaacc    3720
gcgaaccatg actgggttta cattcagtcc ggcaaggcac tgaccggcga acagaccatt    3780
aacggtcaac acctgtattt caaagaagat ggtcaccaag tcaagggtca gttggtcacg    3840
ggcaccgatg gtaaagtgcg ttactatgac gccaacagcg gtgaccaagc attcaacaag    3900
agcgtcactg tgaatggtaa aacctattac tttggcaacg atggtacggc gcagactgct    3960
ggcaacccga agggtcagac gttcaaggat ggctccgaca tccgtttta ctctatggaa    4020 ggccaactgg tgaccggctc gggttggtac gagaacgcgc aaggccagtg gctgtatgtg    4080
aaaaacggta aggtgctgac tggtctgcaa accgttggca gccagcgtgt ttacttcgac    4140
gagaatggta ttcaggccaa gggcaaagca gtgcgtacca gcgatggcaa aattcgttat    4200
ttcgacgaaa acagcggcag catgatcacg aatcaatgga agttcgtcta tggtcagtat    4260
tactactttg gtaacgacgg tgcacgtatt taccgtggtt ggaactaa                 4308
```

<210> SEQ ID NO 40
<211> LENGTH: 1435
<212> TYPE: PRT
<213> ORGANISM: Streptococcus sobrinus

<400> SEQUENCE: 40

```
Met Val Asp Gly Lys Tyr Tyr Tyr Tyr Asp Gln Asp Gly Asn Val Lys
1               5                   10                  15
```

```
Lys Asn Phe Ala Val Ser Val Gly Asp Lys Ile Tyr Tyr Phe Asp Glu
                20                  25                  30

Thr Gly Ala Tyr Lys Asp Thr Ser Lys Val Asp Ala Asp Lys Ser Ser
            35                  40                  45

Ser Ala Val Ser Gln Asn Ala Thr Ile Phe Ala Ala Asn Asn Arg Ala
 50                  55                  60

Tyr Ser Thr Ser Ala Lys Asn Phe Glu Ala Val Asp Asn Tyr Leu Thr
 65                  70                  75                  80

Ala Asp Ser Trp Tyr Arg Pro Lys Ser Ile Leu Lys Asp Gly Lys Thr
                85                  90                  95

Trp Thr Glu Ser Gly Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
            115                 120                 125

Val Val Gly Ile Asp Lys Thr Tyr Thr Ala Glu Thr Ser Gln Ala Asp
130                 135                 140

Leu Thr Ala Ala Ala Glu Leu Val Gln Ala Arg Ile Glu Gln Lys Ile
145                 150                 155                 160

Thr Ser Glu Asn Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Leu Phe Asp Asn Gln Thr Asp Leu
            195                 200                 205

Thr Pro Asp Thr Gln Ser Asn Tyr Arg Leu Leu Asn Arg Thr Pro Thr
            210                 215                 220

Asn Gln Thr Gly Ser Leu Asp Ser Arg Phe Thr Tyr Asn Pro Asn Asp
225                 230                 235                 240

Pro Leu Gly Gly Tyr Asp Phe Leu Leu Ala Asn Asp Val Asp Asn Ser
                245                 250                 255

Asn Pro Val Val Gln Ala Glu Gln Leu Asn Trp Leu His Tyr Leu Leu
            260                 265                 270

Asn Phe Gly Ser Ile Tyr Ala Asn Asp Ala Asp Ala Asn Phe Asp Ser
            275                 280                 285

Ile Arg Val Asp Ala Val Asp Asn Val Asp Ala Asp Leu Leu Gln Ile
            290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
            340                 345                 350

Lys Phe Arg Leu Ser Met Leu Trp Ser Leu Ala Lys Pro Leu Asp Lys
            355                 360                 365

Arg Ser Gly Leu Asn Pro Leu Ile His Asn Ser Leu Val Asp Arg Glu
            370                 375                 380

Val Asp Asp Arg Glu Val Glu Thr Val Pro Ser Tyr Ser Phe Ala Arg
385                 390                 395                 400

Ala His Asp Ser Glu Val Gln Asp Ile Ile Arg Asp Ile Ile Lys Ala
                405                 410                 415

Glu Ile Asn Pro Asn Ser Phe Gly Tyr Ser Phe Thr Gln Glu Glu Ile
            420                 425                 430
```

-continued

Glu Gln Ala Phe Lys Ile Tyr Asn Glu Asp Leu Lys Lys Thr Asp Lys
                435                 440                 445

Lys Tyr Thr His Tyr Asn Val Pro Leu Ser Tyr Thr Leu Leu Leu Thr
450                 455                 460

Asn Lys Gly Ser Ile Pro Arg Val Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ser Gly Gln Ala Met
                500                 505                 510

Gln Asn Tyr Gln Ile Gly Asn Gly Glu Ile Leu Thr Ser Val Arg Tyr
                515                 520                 525

Gly Lys Gly Ala Leu Lys Gln Ser Asp Lys Gly Asp Ala Thr Thr Arg
530                 535                 540

Thr Ser Gly Val Gly Val Val Met Gly Asn Gln Pro Asn Phe Ser Leu
545                 550                 555                 560

Asp Gly Lys Val Val Ala Leu Asn Met Gly Ala Ala His Ala Asn Gln
                565                 570                 575

Glu Tyr Arg Ala Leu Met Val Ser Thr Lys Asp Gly Val Ala Thr Tyr
                580                 585                 590

Ala Thr Asp Ala Asp Ala Ser Lys Ala Gly Leu Val Lys Arg Thr Asp
                595                 600                 605

Glu Asn Gly Tyr Leu Tyr Phe Leu Asn Asp Asp Leu Lys Gly Val Ala
                610                 615                 620

Asn Pro Gln Val Ser Gly Phe Leu Gln Val Trp Val Pro Val Gly Ala
625                 630                 635                 640

Ala Asp Asp Gln Asp Ile Arg Val Ala Ala Ser Asp Thr Ala Ser Thr
                645                 650                 655

Asp Gly Lys Ser Leu His Gln Asp Ala Ala Met Asp Ser Arg Val Met
                660                 665                 670

Phe Glu Gly Phe Ser Asn Phe Gln Ser Phe Ala Thr Lys Glu Glu Glu
                675                 680                 685

Tyr Thr Asn Val Val Ile Ala Asn Asn Val Asp Lys Phe Val Ser Trp
                690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Asp
                740                 745                 750

Gln Leu Val Lys Ala Ile Lys Ala Leu His Ala Lys Gly Leu Lys Val
                755                 760                 765

Met Ala Asp Trp Val Pro Asp Gln Met Tyr Thr Phe Pro Lys Gln Glu
                770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
                805                 810                 815

Asp Asp Tyr Gln Ala Lys Tyr Gly Gly Ala Phe Leu Asp Glu Leu Lys
                820                 825                 830

Glu Lys Tyr Pro Glu Leu Phe Thr Lys Lys Gln Ile Ser Thr Gly Gln
                835                 840                 845

Ala Ile Asp Pro Ser Val Lys Ile Lys Gln Trp Ser Ala Lys Tyr Phe

```
              850                 855                 860
Asn Gly Ser Asn Ile Leu Gly Arg Gly Ala Asp Tyr Val Leu Ser Asp
865                 870                 875                 880

Gln Val Ser Asn Lys Tyr Phe Asn Val Ala Ser Asp Thr Leu Phe Leu
                885                 890                 895

Pro Ser Ser Leu Leu Gly Lys Val Val Glu Ser Gly Ile Arg Tyr Asp
                900                 905                 910

Gly Lys Gly Tyr Ile Tyr Asn Ser Ser Ala Thr Gly Asp Gln Val Lys
            915                 920                 925

Ala Ser Phe Ile Thr Glu Ala Gly Asn Leu Tyr Tyr Phe Gly Lys Asp
930                 935                 940

Gly Tyr Met Val Thr Gly Ala Gln Thr Ile Asn Gly Ala Asn Tyr Phe
945                 950                 955                 960

Phe Leu Glu Asn Gly Thr Ala Leu Arg Asn Thr Ile Tyr Thr Asp Ala
                965                 970                 975

Gln Gly Asn Ser His Tyr Tyr Ala Asn Asp Gly Lys Arg Tyr Glu Asn
                980                 985                 990

Gly Tyr Gln Gln Phe Gly Asn Asp Trp Arg Tyr Phe Lys Asp Gly Asn
            995                 1000                1005

Met Ala Val Gly Leu Thr Thr Val Asp Gly Asn Val Gln Tyr Phe
        1010                1015                1020

Asp Lys Asp Gly Val Gln Ala Lys Asp Lys Ile Ile Val Thr Arg
        1025                1030                1035

Asp Gly Lys Val Arg Tyr Phe Asp Gln His Asn Gly Asn Ala Ala
        1040                1045                1050

Thr Asn Thr Phe Ile Ala Asp Lys Thr Gly His Trp Tyr Tyr Leu
        1055                1060                1065

Gly Lys Asp Gly Val Ala Val Thr Gly Ala Gln Thr Val Gly Lys
        1070                1075                1080

Gln Lys Leu Tyr Phe Glu Ala Asn Gly Gln Gln Val Lys Gly Asp
        1085                1090                1095

Phe Val Thr Ser Asp Glu Gly Lys Leu Tyr Phe Tyr Asp Val Asp
        1100                1105                1110

Ser Gly Asp Met Trp Thr Asp Thr Phe Ile Glu Asp Lys Ala Gly
        1115                1120                1125

Asn Trp Phe Tyr Leu Gly Lys Asp Gly Ala Ala Val Thr Gly Ala
        1130                1135                1140

Gln Thr Ile Arg Gly Gln Lys Leu Tyr Phe Lys Ala Asn Gly Gln
        1145                1150                1155

Gln Val Lys Gly Asp Ile Val Lys Gly Thr Asp Gly Lys Ile Arg
        1160                1165                1170

Tyr Tyr Asp Ala Lys Ser Gly Glu Gln Val Phe Asn Lys Thr Val
        1175                1180                1185

Lys Ala Ala Asp Gly Lys Thr Tyr Val Ile Gly Asn Asp Gly Val
        1190                1195                1200

Ala Val Asp Pro Ser Val Val Lys Gly Gln Thr Phe Lys Asp Ala
        1205                1210                1215

Ser Gly Ala Leu Arg Phe Tyr Asn Leu Lys Gly Gln Leu Val Thr
        1220                1225                1230

Gly Ser Gly Trp Tyr Glu Thr Ala Asn His Asp Trp Val Tyr Ile
        1235                1240                1245

Gln Ser Gly Lys Ala Leu Thr Gly Glu Gln Thr Ile Asn Gly Gln
        1250                1255                1260
```

```
His Leu Tyr Phe Lys Glu Asp Gly His Gln Val Lys Gly Gln Leu
    1265                1270                1275

Val Thr Gly Thr Asp Gly Lys Val Arg Tyr Tyr Asp Ala Asn Ser
    1280                1285                1290

Gly Asp Gln Ala Phe Asn Lys Ser Val Thr Val Asn Gly Lys Thr
    1295                1300                1305

Tyr Tyr Phe Gly Asn Asp Gly Thr Ala Gln Thr Ala Gly Asn Pro
    1310                1315                1320

Lys Gly Gln Thr Phe Lys Asp Gly Ser Asp Ile Arg Phe Tyr Ser
    1325                1330                1335

Met Glu Gly Gln Leu Val Thr Gly Ser Gly Trp Tyr Glu Asn Ala
    1340                1345                1350

Gln Gly Gln Trp Leu Tyr Val Lys Asn Gly Lys Val Leu Thr Gly
    1355                1360                1365

Leu Gln Thr Val Gly Ser Gln Arg Val Tyr Phe Asp Glu Asn Gly
    1370                1375                1380

Ile Gln Ala Lys Gly Lys Ala Val Arg Thr Ser Asp Gly Lys Ile
    1385                1390                1395

Arg Tyr Phe Asp Glu Asn Ser Gly Ser Met Ile Thr Asn Gln Trp
    1400                1405                1410

Lys Phe Val Tyr Gly Gln Tyr Tyr Phe Gly Asn Asp Gly Ala
    1415                1420                1425

Arg Ile Tyr Arg Gly Trp Asn
    1430                1435

<210> SEQ ID NO 41
<211> LENGTH: 1570
<212> TYPE: PRT
<213> ORGANISM: Streptococcus sp.

<400> SEQUENCE: 41

Met Lys Lys Asn Trp Val Thr Ile Gly Val Thr Ala Leu Ser Met Val
1               5                   10                  15

Thr Val Ala Gly Gly Thr Leu Leu Glu Asp Gln Gln Val Gln Ala Asp
                20                  25                  30

Glu Gln Asn Ala Ala Asn Gln Ser Gly Asp Ser Ser Gln Asp Leu Leu
            35                  40                  45

Arg Glu Ala Ser Ala Thr Thr Asn Asp Thr Ala Thr Thr Val Ala Pro
    50                  55                  60

Thr Ile Ser Ala Asp Ala Asn Thr Ala Ser Val Asn Ile Pro Val Ala
65                  70                  75                  80

Asp Ala Thr Asn Thr Thr Thr Ala Ala Thr Asp Arg Ala Ala Ala Pro
                85                  90                  95

Thr Thr Thr Ala Ala Thr Val Asp Thr Asn Ser Gly Gln Ala Ala Pro
            100                 105                 110

Ser Thr Asn Val Gln Ala Ala Ala Asp Thr Ser Ala Thr Pro Thr
        115                 120                 125

Asp Thr Asn Thr Asn Thr Asn Ala Ser Val Thr Ala Thr Asp Arg Ala
    130                 135                 140

Val Ala Thr Asp Thr Ala Asn Thr Glu Ala Arg Thr Pro Ser Arg Arg
145                 150                 155                 160

Ala Leu Ala Glu Thr Arg Glu Ala Asn Thr Asn Thr Ser Thr Gly Ile
                165                 170                 175

Gln Trp Ile Asn Gly Lys Gln Tyr Tyr Val Asn Ser Asp Gly Ser Val
```

```
                180                 185                 190
Arg Lys Asn Phe Val Phe Glu Gln Asp Gly Lys Ser Tyr Tyr Phe Asp
            195                 200                 205

Ala Glu Thr Gly Ala Leu Ala Thr Lys Ser Gln Asp Glu Phe Ser Thr
            210                 215                 220

Glu Pro Ile Lys Ala Ala Val Asp Phe Ser Ser Gly Asn Gln Leu Tyr
225                 230                 235                 240

Lys Asn Asp Asn Lys Ser Leu Asp Gln Leu Asp Thr Phe Ile Thr Ala
            245                 250                 255

Asp Ala Trp Tyr Arg Pro Lys Ser Ile Leu Lys Asp Gly Lys Thr Trp
            260                 265                 270

Thr Ala Ser Thr Glu Ala Asp Lys Arg Pro Leu Leu Met Val Trp Trp
            275                 280                 285

Pro Asp Lys Ser Thr Gln Val Asn Tyr Leu Asn Tyr Met Gln Asn Gln
            290                 295                 300

Gly Leu Gly Ala Gly Ser Phe Ser Thr Asn Ser Ser Gln Glu Ser Leu
305                 310                 315                 320

Asn Leu Ala Ala Lys Ala Val Gln Thr Lys Ile Glu Glu Arg Ile Ala
            325                 330                 335

Arg Glu Gly Asn Thr Asn Trp Leu Arg Thr Ser Ile Asp Gln Phe Ile
            340                 345                 350

Lys Thr Gln Pro Gly Trp Asn Ser Ser Thr Glu Asn Ser Ser Tyr Asp
            355                 360                 365

His Leu Gln Gly Gly Gln Leu Leu Phe Asn Asn Ser Lys Gly Asp Thr
            370                 375                 380

Gly Asn Arg Thr Ser Tyr Ala Asn Ser Asp Tyr Arg Leu Leu Asn Arg
385                 390                 395                 400

Thr Pro Thr Asn Gln Ser Gly Thr Arg Lys Tyr Phe Lys Asp Asn Ser
            405                 410                 415

Ile Gly Gly Leu Glu Phe Leu Leu Ala Asn Asp Ile Asp Asn Ser Asn
            420                 425                 430

Pro Ala Val Gln Ala Glu Gln Leu Asn Trp Leu His Phe Met Met Asn
            435                 440                 445

Ile Gly Ser Ile Met Ala Asn Asp Pro Thr Ala Asn Phe Asp Gly Leu
            450                 455                 460

Arg Val Asp Ala Leu Asp Asn Val Asp Ala Asp Leu Leu Gln Ile Ala
465                 470                 475                 480

Ser Asp Tyr Phe Lys Ala Val Tyr Gly Val Asp Lys Ser Glu Ala Asn
            485                 490                 495

Ala Ile Lys His Leu Ser Tyr Leu Glu Ala Trp Ser Ala Asn Asp Pro
            500                 505                 510

Tyr Tyr Asn Lys Asp Thr Lys Gly Ala Gln Leu Pro Ile Asp Asn Ala
            515                 520                 525

Leu Arg Asn Ala Leu Thr Asn Leu Leu Met Arg Asp Lys Asn Thr Arg
            530                 535                 540

Met Gln Leu Gly Asp Met Thr Ala Phe Met Asn Ser Ser Leu Asn Pro
545                 550                 555                 560

Arg Gly Ala Asn Asp Lys Asn Gly Glu Arg Met Ala Asn Tyr Ile Phe
            565                 570                 575

Thr Arg Ala His Asp Thr Glu Ala Gln Thr Ile Ile Gln Arg Ile Ile
            580                 585                 590

Arg Asp Arg Ile Asn Pro Asn Leu Phe Gly Tyr Asn Phe Thr Arg Asp
            595                 600                 605
```

Glu Ile Lys Lys Ala Phe Glu Ile Tyr Asn Ala Asp Ile Asn Thr Ala
    610             615             620

His Lys Thr Tyr Ala Ser Tyr Asn Leu Pro Ser Val Tyr Ala Leu Met
625             630             635             640

Leu Thr Asn Lys Asp Ser Val Thr Arg Val Tyr Tyr Gly Asp Leu Tyr
            645             650             655

Arg Glu Asp Gly His Tyr Met Ala Lys Lys Thr Pro Tyr Phe Asp Ala
            660             665             670

Ile Asp Thr Leu Leu Arg Ala Arg Ile Lys Tyr Val Ala Gly Gly Gln
            675             680             685

Asp Met Glu Val Lys Lys Val Gly Asn Asp Gly Leu Leu Thr Ser Val
    690             695             700

Arg Tyr Gly Lys Gly Ala Asn Asn Ser Thr Asp Trp Gly Thr Thr Glu
705             710             715             720

Thr Arg Thr Gln Gly Met Gly Val Ile Leu Thr Asn Asn Tyr Asp Phe
            725             730             735

Arg Leu Gly Ser Asn Glu Thr Val Thr Met Asn Met Gly Arg Ala His
            740             745             750

Arg Asn Gln Leu Tyr Arg Pro Leu Leu Leu Thr Thr Lys Asp Gly Leu
            755             760             765

Ala Thr Tyr Leu Asn Asp Ser Asp Val Pro Ser Asn Leu Leu Lys Arg
    770             775             780

Thr Asp Trp Asn Gly Asn Leu Thr Phe Asn Ala Asn Asp Val Phe Gly
785             790             795             800

Val Glu Asn Val Gln Val Ser Gly Tyr Leu Gly Val Trp Val Pro Val
            805             810             815

Gly Ala Lys Ala Asn Gln Asp Ala Arg Thr Gln Pro Ser Asn Arg Ala
            820             825             830

Asn Ser Asp Gly Gln Val Tyr Lys Ser Ser Ala Ala Leu Asp Ser Gln
            835             840             845

Val Met Tyr Glu Ala Phe Ser Asn Phe Gln Ala Phe Ala Asp Asp Gln
    850             855             860

Pro Glu Leu Tyr Met Asn Arg Val Leu Ala Lys Asn Thr Asp Leu Leu
865             870             875             880

Lys Ala Trp Gly Val Thr Ser Val Gly Leu Pro Pro Gln Tyr Val Ser
            885             890             895

Ser Lys Asp Gly Thr Phe Leu Asp Ser Thr Ile Asp Asn Gly Tyr Ala
            900             905             910

Phe Asp Asp Arg Tyr Asp Met Ala Leu Ser Gln Asn Asn Lys Tyr Gly
            915             920             925

Ser Leu Glu Asp Leu Leu Asn Val Leu Arg Ala Leu His Lys Asp Gly
    930             935             940

Ile Gln Ala Ile Ala Asp Trp Val Pro Asp Gln Ile Tyr Asn Leu Pro
945             950             955             960

Gly Lys Glu Val Val Asn Ala Thr Arg Val Asn Gly Tyr Gly Tyr His
            965             970             975

Gln Gln Gly Tyr Gln Ile Val Asp Gln Ala Tyr Val Ala Asn Thr Arg
            980             985             990

Thr Asp Gly Thr Asp Tyr Gln Gly Arg Tyr Gly Gly Ala Phe Leu Asp
            995             1000            1005

Glu Leu Lys Ala Lys Tyr Pro Ser Ile Phe Asn Arg Val Gln Ile
    1010            1015            1020

-continued

```
Ser Asn Gly Lys Gln Leu Pro Thr Asn Glu Lys Ile Thr Lys Trp
1025                    1030                    1035

Ser Ala Lys Tyr Phe Asn Gly Thr Asn Ile Leu Gly Arg Gly Ile
1040                    1045                    1050

Asn Tyr Val Leu Arg Asp Asp Lys Thr Asn Gln Tyr Phe Asn Thr
1055                    1060                    1065

Ser Ala Asn Gly Gln Leu Leu Pro Thr Pro Leu Arg Asp Thr Gly
1070                    1075                    1080

Ala Ile Thr Ser Thr Gln Val Phe Gln Arg Arg Gly Gln Asp Val
1085                    1090                    1095

Tyr Phe Leu Arg Asp Asn Gln Val Ile Lys Asn Glu Phe Val Gln
1100                    1105                    1110

Asp Gly Asn Gly Asn Trp Tyr Tyr Phe Gly Ala Asp Gly Lys Met
1115                    1120                    1125

Thr Lys Gly Ala Gln Asn Ile Asn Ser Lys Asp Tyr Tyr Phe Phe
1130                    1135                    1140

Asp Asn Gly Val Gln Leu Arg Asn Ala Leu Arg Arg Ala Ser Asn
1145                    1150                    1155

Gly Tyr Thr Tyr Tyr Gly Leu Asp Gly Ala Met Ile Lys Asn
1160                    1165                    1170

Ala Phe Val Asp Phe Asp Lys His Gln Gln Val Arg Ala Phe
1175                    1180                    1185

Thr Thr Gln Gly Thr Met Val Val Gly Asn Leu His Trp Ser Gly
1190                    1195                    1200

His His Phe Tyr Phe Asp Arg Glu Thr Gly Ile Gln Ala Lys Asp
1205                    1210                    1215

Arg Ile Val Arg Thr Asp Asp Gly Lys Leu His Tyr Tyr Val Ala
1220                    1225                    1230

Gln Thr Gly Asp Met Gly Arg Asn Val Phe Ala Thr Asp Ser Arg
1235                    1240                    1245

Thr Gly Lys Arg Tyr Tyr Phe Asp Ala Asp Gly Asn Thr Val Thr
1250                    1255                    1260

Gly Ser Arg Val Ile Asp Gly Lys Thr Tyr Tyr Phe Asn Gln Asp
1265                    1270                    1275

Gly Ser Val Gly Thr Ala Tyr Ser Asn Arg Ala Asp Ser Ile Ile
1280                    1285                    1290

Phe Glu Asn Gly Lys Ala Arg Tyr Ile Thr Pro Ala Gly Glu Ile
1295                    1300                    1305

Gly Arg Ser Ile Phe Val Tyr Asn Pro Ala Thr Lys Ala Trp Asn
1310                    1315                    1320

Tyr Phe Asp Lys Glu Gly Asn Arg Val Thr Gly Arg Gln Tyr Ile
1325                    1330                    1335

Asp Gly Asn Leu Tyr Tyr Phe Lys Glu Asp Gly Ser Gln Val Lys
1340                    1345                    1350

Gly Ala Ile Val Glu Glu Asn Gly Ile Lys Tyr Tyr Tyr Glu Pro
1355                    1360                    1365

Gly Ser Gly Ile Leu Ala Ser Gly Arg Tyr Leu Gln Val Gly Asp
1370                    1375                    1380

Asp Gln Trp Ile Tyr Phe Lys His Asp Gly Ser Leu Ala Ile Gly
1385                    1390                    1395

Gln Val Arg Ala Asp Gly Gly Tyr Leu Lys Tyr Phe Asp Lys Asn
1400                    1405                    1410

Gly Ile Gln Val Lys Gly Gln Thr Ile Val Glu Asp Gly His Thr
```

|   |   |   |   |   |   |   |   |   |   |
|---|---|---|---|---|---|---|---|---|---|
| 1415 | | | | | 1420 | | | | 1425 |
| Tyr | Tyr | Tyr | Asp | Ala | Asp | Ser | Gly | Ala | Leu | Val | Thr | Ser | Ser | Phe |
| | 1430 | | | | | 1435 | | | | | 1440 | | | |

Tyr Tyr Tyr Asp Ala Asp Ser Gly Ala Leu Val Thr Ser Ser Phe
     1430               1435                    1440

Ala Glu Ile Ala Pro Asn Gln Trp Ala Tyr Phe Asn Thr Glu Gly
     1445               1450                    1455

Gln Ala Leu Lys Gly Lys Trp Thr Ile Asn Gly Lys Glu Tyr Tyr
     1460               1465                    1470

Phe Asp Gln Asn Gly Ile Gln Tyr Lys Gly Lys Ala Val Lys Val
     1475               1480                    1485

Gly Ser Arg Tyr Lys Tyr Tyr Asp Glu Asn Asp Gly Gln Pro Val
     1490               1495                    1500

Thr Asn Arg Phe Ala Gln Ile Glu Pro Asn Val Trp Ala Tyr Phe
     1505               1510                    1515

Gly Ala Asp Gly Tyr Ala Val Thr Gly Glu Gln Val Ile Asn Gly
     1520               1525                    1530

Gln His Leu Tyr Phe Asp Gln Ser Gly Arg Gln Val Lys Gly Ala
     1535               1540                    1545

Tyr Val Thr Val Asn Gly Gln Arg Arg Tyr Tyr Asp Ala Asn Thr
     1550               1555                    1560

Gly Glu Tyr Ile Pro Gly Arg
     1565               1570

<210> SEQ ID NO 42
<211> LENGTH: 4182
<212> TYPE: DNA
<213> ORGANISM: Streptococcus sp.

<400> SEQUENCE: 42

| | |
|---|---|
| atgatcaatg gcaaacagta ctatgtaaat tcggacggta gcgtgcgtaa gaatttcgtt | 60 |
| tttgaacagg atggtaagag ctactacttt gacgcggaaa ctggcgcgct ggccactaaa | 120 |
| agccaagatg aatttagcac ggagccgatt aaagcagcag tggacttctc tagcggcaac | 180 |
| cagctgtaca aaaatgacaa caaatcgctg gatcagctgg atacgtttat caccgctgac | 240 |
| gcatggtacc gccctaagtc tattctgaag gatggcaaaa cctggaccgc gtctaccgaa | 300 |
| gctgataagc gtccgttgct gatggtgtgg tggccggaca gtccaccca agttaactac | 360 |
| ctgaactaca tgcagaacca gggtttgggt gcgggtagct tcagcaccaa tagcagccaa | 420 |
| gaatccctga atctggctgc gaaagcagtt cagaccaaga tcgaagaacg catcgcacgt | 480 |
| gagggtaaca ccaattggct gcgtaccagc attgaccaat tcattaagac gcagccaggc | 540 |
| tggaacagca gcactgagaa tagcagctat gatcacttgc agggtggtca actgctgttc | 600 |
| aataacagca aggtgatac gggtaaccgc accagctatg cgaatagcga ctatcgtctg | 660 |
| ctgaaccgta ccccaactaa tcaaagcggc acccgtaagt actttaagga taattccatc | 720 |
| ggtggtctgg aatttctgct ggcaaacgac atcgacaaca gcaaccctgc cgttcaggcg | 780 |
| gagcagctga actggctgca cttcatgatg aacattggtt ctatcatggc gaatgacccg | 840 |
| acggcgaact tgatggtttt gcgtgtggac gcgttggata cgtggatgc ggacctgttg | 900 |
| cagatcgcga gcgattactt caaggcagtc tacggtgttg ataaatccga ggcgaatgcg | 960 |
| atcaagcacc tgagctatct ggaggcgtgg agcgccaatg accgtatta caacaaggat | 1020 |
| accaaaggcg cgcaactgcc gattgacaac gcgctgcgca cgcactgac caacctgttg | 1080 |
| atgcgtgaca gaatacgcg catgcagctg ggtgacatga cggcgtttat gaatagctct | 1140 |
| ctgaacccac gtggtgcgaa tgacaaaaac ggcgagcgta tggcgaatta cattttcacc | 1200 |

```
cgcgcacacg ataccgaggc gcagaccatc attcagcgta ttatccgcga tcgtatcaat    1260
ccgaacctgt ttggctacaa tttcacccgc gatgaaatca aaaaggcgtt tgagatctac    1320
aacgcggaca ttaacacggc gcataagacg tacgcgagct acaatctgcc gtccgtctac    1380
gcactgatgc tgacgaataa ggacagcgtg acccgtgtgt attacggtga cctgtatcgt    1440
gaggacggtc actacatggc caagaaaacg ccttatttcg atgcaatcga taccctgctg    1500
cgtgcgcgca tcaaatacgt ggcgggtggt caagacatgg aggtgaagaa agttggtaat    1560
gacggcttgc tgacgagcgt ccgctatggc aagggtgcga acaatagcac cgactggggc    1620
acgactgaaa cccgtaccca aggtatgggc gttatcctga cgaacaacta tgatttccgc    1680
ctgggcagca acgaaaccgt cacgatgaac atgggccgtg cgcatcgcaa tcagctgtat    1740
cgtccgctgc tgctgacgac caaggatggt ctggccacgt acctgaatga tagcgacgtg    1800
ccttcgaatt tgctgaaacg cacggactgg aatggtaact tgacctttaa tgccaacgat    1860
gtgtttggtg tagagaacgt ccaggtcagc ggttacctgg gtgtttgggt accggttggt    1920
gctaaagcta accaggatgc gcgtacccaa ccgagcaacc gtgcgaacag cgatggtcag    1980
gtctataagt cgtctgcggc attggacagc caggtcatgt atgagcgtt tagcaatttt     2040 caggcatttg cggacgatca accggaactg tacatgaacc gcgttctggc gaagaacacc    2100
gatctgctga agcgtggggg cgttactagc gttggcttgc cgccacaata cgttagcagc    2160
aaagacggca ccttcctgga tagcactatt gataacggct atgcgttcga tgatcgttac    2220
gacatggcgc tgagccagaa caacaaatac ggttctctgg aggacttgct gaacgttctg    2280
cgcgctctgc acaaagacgg tattcaggcg attgcggact gggtcccgga tcaaatctac    2340
aatttgccgg gtaaagaggt tgttaatgcg acgcgtgtta acggttacgg ttaccatcag    2400
cagggctacc agattgttga ccaggcgtac gttgcaaaca cccgtacgga tggtaccgat    2460
tatcagggtc gttacggtgg tgcttttctg gacgaactga aggcgaagta cccgagcatt    2520
ttcaatcgtg tccagattag caacggtaaa cagctgccaa ccaatgagaa aatcacgaaa    2580
tggtccgcga aatacttcaa tggcacgaac atcctgggcc gtggtattaa ctatgtgctg    2640
cgcgacgaca agaccaatca gtatttcaac accagcgcaa acggccaact gctgccgacg    2700
ccactgcgcg acaccggtgc catcaccagc acgcaagttt ccagcgtcg tggccaagac     2760 gtctattttc tgcgtgataa ccaggttatc aaaaacgagt tgtgcaaga tggtaacggt     2820 aattggtact acttcggtgc cgacggtaaa atgacgaagg gtgcacaaaa catcaatagc    2880
aaggattact atttcttcga taatggcgtc cagctgcgta atgcgctgcg tcgcgcgtcc    2940
aatggttaca cctactatta tggcctggac ggtgccatga tcaagaacgc tttcgtcgat    3000
tttgatgata agcaccaaca ggtgcgtgcg tttactacgc agggcacgat ggtggtcggt    3060
aatttgcact ggagcggtca ccacttctat tttgaccgcg aaacgggtat ccaagccaaa    3120
gaccgcattg tgcgtaccga tgatggcaag ctgcactatt atgtcgcaca aaccggcgat    3180
atgggccgca atgtgtttgc gaccgacagc cgcacgggca agcgctatta ctttgatgcg    3240
gacggcaaca ccgttacggg ctcccgtgtc atcgacggca agacctacta cttcaaccag    3300
gacggttcgg tcggtaccgc gtacagcaat cgtgcggata gcattatctt tgagaatggc    3360
aaggctcgct atatcactcc ggctggcgag attggccgtt ccattttgt ctacaacccg     3420 gcgaccaaag cgtggaatta cttcgacaag gaaggtaacc gtgtcaccgg tcgtcagtat    3480
attgacggca atctgtacta ctttaaagag gacggctccc aagtgaaagg tgcgattgtt    3540
```

-continued

```
gaagagaacg gtatcaagta ctactacgaa ccgggcagcg gtatcctggc gagcggtcgt    3600
tatctgcaag tcggtgacga ccaatggatc tacttcaaac acgacggtag cctggcgatc    3660
ggtcaggttc gtgcagacgg tggttacttg aaatactttg ataagaatgg catccaggtc    3720
aagggccaaa ccattgtgga ggatggtcat acctattact acgatgccga ctccggtgct    3780
ctggtgacct ctagcttcgc ggagattgct ccgaaccagt gggcctactt caataccgag    3840
ggccaagccc tgaagggcaa atggaccatc aatggtaaag agtactattt tgatcagaac    3900
ggcattcagt ataaaggcaa ggcagttaag gtcggcagcc gttacaaata ctatgacgag    3960
aatgacggtc aaccggtcac taaccgtttt gcccagattg agccgaacgt ctgggcgtac    4020
tttggtgccg atggctacgc agttactggc gaacaggtga ttaatggcca gcacctgtac    4080
ttcgatcagt cgggtcgtca ggttaaaggt gcgtacgtca ccgtgaatgg tcaacgtcgt    4140
tactacgacg caaacacggg tgaatacatt ccgggtcgtt aa                       4182
```

<210> SEQ ID NO 43
<211> LENGTH: 1393
<212> TYPE: PRT
<213> ORGANISM: Streptococcus sp.

<400> SEQUENCE: 43

```
Met Ile Asn Gly Lys Gln Tyr Tyr Val Asn Ser Asp Gly Ser Val Arg
1               5                   10                  15

Lys Asn Phe Val Phe Glu Gln Asp Gly Lys Ser Tyr Tyr Phe Asp Ala
            20                  25                  30

Glu Thr Gly Ala Leu Ala Thr Lys Ser Gln Asp Glu Phe Ser Thr Glu
        35                  40                  45

Pro Ile Lys Ala Ala Val Asp Phe Ser Ser Gly Asn Gln Leu Tyr Lys
    50                  55                  60

Asn Asp Asn Lys Ser Leu Asp Gln Leu Asp Thr Phe Ile Thr Ala Asp
65                  70                  75                  80

Ala Trp Tyr Arg Pro Lys Ser Ile Leu Lys Asp Gly Lys Thr Trp Thr
                85                  90                  95

Ala Ser Thr Glu Ala Asp Lys Arg Pro Leu Leu Met Val Trp Trp Pro
            100                 105                 110

Asp Lys Ser Thr Gln Val Asn Tyr Leu Asn Tyr Met Gln Asn Gln Gly
        115                 120                 125

Leu Gly Ala Gly Ser Phe Ser Thr Asn Ser Ser Gln Glu Ser Leu Asn
    130                 135                 140

Leu Ala Ala Lys Ala Val Gln Thr Lys Ile Glu Glu Arg Ile Ala Arg
145                 150                 155                 160

Glu Gly Asn Thr Asn Trp Leu Arg Thr Ser Ile Asp Gln Phe Ile Lys
                165                 170                 175

Thr Gln Pro Gly Trp Asn Ser Ser Thr Glu Asn Ser Ser Tyr Asp His
            180                 185                 190

Leu Gln Gly Gly Gln Leu Leu Phe Asn Asn Ser Lys Gly Asp Thr Gly
        195                 200                 205

Asn Arg Thr Ser Tyr Ala Asn Ser Asp Tyr Arg Leu Leu Asn Arg Thr
    210                 215                 220

Pro Thr Asn Gln Ser Gly Thr Arg Lys Tyr Phe Lys Asp Asn Ser Ile
225                 230                 235                 240

Gly Gly Leu Glu Phe Leu Leu Ala Asn Asp Ile Asp Asn Ser Asn Pro
                245                 250                 255

Ala Val Gln Ala Glu Gln Leu Asn Trp Leu His Phe Met Met Asn Ile
```

```
              260                 265                 270
Gly Ser Ile Met Ala Asn Asp Pro Thr Ala Asn Phe Asp Gly Leu Arg
            275                 280                 285

Val Asp Ala Leu Asp Asn Val Asp Ala Asp Leu Leu Gln Ile Ala Ser
290                 295                 300

Asp Tyr Phe Lys Ala Val Tyr Gly Val Asp Lys Ser Glu Ala Asn Ala
305                 310                 315                 320

Ile Lys His Leu Ser Tyr Leu Glu Ala Trp Ser Ala Asn Asp Pro Tyr
            325                 330                 335

Tyr Asn Lys Asp Thr Lys Gly Ala Gln Leu Pro Ile Asp Asn Ala Leu
            340                 345                 350

Arg Asn Ala Leu Thr Asn Leu Leu Met Arg Asp Lys Asn Thr Arg Met
            355                 360                 365

Gln Leu Gly Asp Met Thr Ala Phe Met Asn Ser Ser Leu Asn Pro Arg
            370                 375                 380

Gly Ala Asn Asp Lys Asn Gly Glu Arg Met Ala Asn Tyr Ile Phe Thr
385                 390                 395                 400

Arg Ala His Asp Thr Glu Ala Gln Thr Ile Ile Gln Arg Ile Ile Arg
                405                 410                 415

Asp Arg Ile Asn Pro Asn Leu Phe Gly Tyr Asn Phe Thr Arg Asp Glu
            420                 425                 430

Ile Lys Lys Ala Phe Glu Ile Tyr Asn Ala Asp Ile Asn Thr Ala His
            435                 440                 445

Lys Thr Tyr Ala Ser Tyr Asn Leu Pro Ser Val Tyr Ala Leu Met Leu
450                 455                 460

Thr Asn Lys Asp Ser Val Thr Arg Val Tyr Tyr Gly Asp Leu Tyr Arg
465                 470                 475                 480

Glu Asp Gly His Tyr Met Ala Lys Lys Thr Pro Tyr Phe Asp Ala Ile
                485                 490                 495

Asp Thr Leu Leu Arg Ala Arg Ile Lys Tyr Val Ala Gly Gly Gln Asp
            500                 505                 510

Met Glu Val Lys Lys Val Gly Asn Asp Gly Leu Leu Thr Ser Val Arg
            515                 520                 525

Tyr Gly Lys Gly Ala Asn Asn Ser Thr Asp Trp Gly Thr Thr Glu Thr
            530                 535                 540

Arg Thr Gln Gly Met Gly Val Ile Leu Thr Asn Asn Tyr Asp Phe Arg
545                 550                 555                 560

Leu Gly Ser Asn Glu Thr Val Thr Met Asn Met Gly Arg Ala His Arg
                565                 570                 575

Asn Gln Leu Tyr Arg Pro Leu Leu Leu Thr Lys Asp Gly Leu Ala
            580                 585                 590

Thr Tyr Leu Asn Asp Ser Asp Val Pro Ser Asn Leu Leu Lys Arg Thr
            595                 600                 605

Asp Trp Asn Gly Asn Leu Thr Phe Asn Ala Asn Asp Val Phe Gly Val
            610                 615                 620

Glu Asn Val Gln Val Ser Gly Tyr Leu Gly Val Trp Val Pro Val Gly
625                 630                 635                 640

Ala Lys Ala Asn Gln Asp Ala Arg Thr Gln Pro Ser Asn Arg Ala Asn
                645                 650                 655

Ser Asp Gly Gln Val Tyr Lys Ser Ser Ala Ala Leu Asp Ser Gln Val
            660                 665                 670

Met Tyr Glu Ala Phe Ser Asn Phe Gln Ala Phe Ala Asp Asp Gln Pro
            675                 680                 685
```

```
Glu Leu Tyr Met Asn Arg Val Leu Ala Lys Asn Thr Asp Leu Leu Lys
    690                 695                 700

Ala Trp Gly Val Thr Ser Val Gly Leu Pro Pro Gln Tyr Val Ser Ser
705                 710                 715                 720

Lys Asp Gly Thr Phe Leu Asp Ser Thr Ile Asp Asn Gly Tyr Ala Phe
            725                 730                 735

Asp Asp Arg Tyr Asp Met Ala Leu Ser Gln Asn Asn Lys Tyr Gly Ser
        740                 745                 750

Leu Glu Asp Leu Leu Asn Val Leu Arg Ala Leu His Lys Asp Gly Ile
    755                 760                 765

Gln Ala Ile Ala Asp Trp Val Pro Asp Gln Ile Tyr Asn Leu Pro Gly
770                 775                 780

Lys Glu Val Val Asn Ala Thr Arg Val Asn Gly Tyr Gly Tyr His Gln
785                 790                 795                 800

Gln Gly Tyr Gln Ile Val Asp Gln Ala Tyr Val Ala Asn Thr Arg Thr
            805                 810                 815

Asp Gly Thr Asp Tyr Gln Gly Arg Tyr Gly Gly Ala Phe Leu Asp Glu
        820                 825                 830

Leu Lys Ala Lys Tyr Pro Ser Ile Phe Asn Arg Val Gln Ile Ser Asn
    835                 840                 845

Gly Lys Gln Leu Pro Thr Asn Glu Lys Ile Thr Lys Trp Ser Ala Lys
850                 855                 860

Tyr Phe Asn Gly Thr Asn Ile Leu Gly Arg Gly Ile Asn Tyr Val Leu
865                 870                 875                 880

Arg Asp Asp Lys Thr Asn Gln Tyr Phe Asn Thr Ser Ala Asn Gly Gln
            885                 890                 895

Leu Leu Pro Thr Pro Leu Arg Asp Thr Gly Ala Ile Thr Ser Thr Gln
        900                 905                 910

Val Phe Gln Arg Arg Gly Gln Asp Val Tyr Phe Leu Arg Asp Asn Gln
    915                 920                 925

Val Ile Lys Asn Glu Phe Val Gln Asp Gly Asn Gly Asn Trp Tyr Tyr
930                 935                 940

Phe Gly Ala Asp Gly Lys Met Thr Lys Gly Ala Gln Asn Ile Asn Ser
945                 950                 955                 960

Lys Asp Tyr Tyr Phe Phe Asp Asn Gly Val Gln Leu Arg Asn Ala Leu
            965                 970                 975

Arg Arg Ala Ser Asn Gly Tyr Thr Tyr Tyr Gly Leu Asp Gly Ala
        980                 985                 990

Met Ile Lys Asn Ala Phe Val Asp  Phe Asp Asp Lys His  Gln Gln Val
    995                 1000                1005

Arg Ala  Phe Thr Thr Gln Gly  Thr Met Val Val Gly  Asn Leu His
    1010                1015                1020

Trp Ser  Gly His His Phe Tyr  Phe Asp Arg Glu Thr  Gly Ile Gln
    1025                1030                1035

Ala Lys  Asp Arg Ile Val Arg  Thr Asp Asp Gly Lys  Leu His Tyr
    1040                1045                1050

Tyr Val  Ala Gln Thr Gly Asp  Met Gly Arg Asn Val  Phe Ala Thr
    1055                1060                1065

Asp Ser  Arg Thr Gly Lys Arg  Tyr Tyr Phe Asp Ala  Asp Gly Asn
    1070                1075                1080

Thr Val  Thr Gly Ser Arg Val  Ile Asp Gly Lys Thr  Tyr Tyr Phe
    1085                1090                1095
```

```
Asn Gln Asp Gly Ser Val Gly Thr Ala Tyr Ser Asn Arg Ala Asp
    1100                1105                1110

Ser Ile Ile Phe Glu Asn Gly Lys Ala Arg Tyr Ile Thr Pro Ala
    1115                1120                1125

Gly Glu Ile Gly Arg Ser Ile Phe Val Tyr Asn Pro Ala Thr Lys
    1130                1135                1140

Ala Trp Asn Tyr Phe Asp Lys Glu Gly Asn Arg Val Thr Gly Arg
    1145                1150                1155

Gln Tyr Ile Asp Gly Asn Leu Tyr Tyr Phe Lys Glu Asp Gly Ser
    1160                1165                1170

Gln Val Lys Gly Ala Ile Val Glu Glu Asn Gly Ile Lys Tyr Tyr
    1175                1180                1185

Tyr Glu Pro Gly Ser Gly Ile Leu Ala Ser Gly Arg Tyr Leu Gln
    1190                1195                1200

Val Gly Asp Asp Gln Trp Ile Tyr Phe Lys His Asp Gly Ser Leu
    1205                1210                1215

Ala Ile Gly Gln Val Arg Ala Asp Gly Gly Tyr Leu Lys Tyr Phe
    1220                1225                1230

Asp Lys Asn Gly Ile Gln Val Lys Gly Gln Thr Ile Val Glu Asp
    1235                1240                1245

Gly His Thr Tyr Tyr Tyr Asp Ala Asp Ser Gly Ala Leu Val Thr
    1250                1255                1260

Ser Ser Phe Ala Glu Ile Ala Pro Asn Gln Trp Ala Tyr Phe Asn
    1265                1270                1275

Thr Glu Gly Gln Ala Leu Lys Gly Lys Trp Thr Ile Asn Gly Lys
    1280                1285                1290

Glu Tyr Tyr Phe Asp Gln Asn Gly Ile Gln Tyr Lys Gly Lys Ala
    1295                1300                1305

Val Lys Val Gly Ser Arg Tyr Lys Tyr Tyr Asp Glu Asn Asp Gly
    1310                1315                1320

Gln Pro Val Thr Asn Arg Phe Ala Gln Ile Glu Pro Asn Val Trp
    1325                1330                1335

Ala Tyr Phe Gly Ala Asp Gly Tyr Ala Val Thr Gly Glu Gln Val
    1340                1345                1350

Ile Asn Gly Gln His Leu Tyr Phe Asp Gln Ser Gly Arg Gln Val
    1355                1360                1365

Lys Gly Ala Tyr Val Thr Val Asn Gly Gln Arg Arg Tyr Tyr Asp
    1370                1375                1380

Ala Asn Thr Gly Glu Tyr Ile Pro Gly Arg
    1385                1390

<210> SEQ ID NO 44
<211> LENGTH: 1929
<212> TYPE: DNA
<213> ORGANISM: Aspergillus nidulans

<400> SEQUENCE: 44
atgaagctca gcacatttct ctctgctctg ggagctcttc cccagctgat ctcggctgcc      60
ccgaatgcag tcgctaacaa acccaggcag tcctcggacg accggcttgt ctttgctcac     120
ttcatgattg gaatcgtcag caaccgcaat tccgcagccg actacgacga tgatatgaaa     180
cgtgccaagt ctctcggaat cgatgctttc gcgttgaaca tcggggttga tccctacacc     240
gaccagcaac tcaatctcgc ctatcagtcc gctgccaaca atgacatgaa agtcttcata     300
tcgttcgatt tcaactggta taacaccggc caaggatacc aggttgggca agatcgcc       360
```

-continued

```
caatacgcga acctcccagc gcagcttaag gtcgacggca aagtctttgt ctcctcgttt    420
gcaggggacg gtcttgatat cgcggcgatg cgtcaggccg ccggacagga catctactgg    480
gctccaaact accatccaga gtacggcact aacctggatg gtgtcgatgg cttgctcaat    540
tggatggctt ggcctaatga tggcaacaac aaggcaccgc gtcctggagc ctccgtttcg    600
gtggaagagg gcgatgagat gtatatcaga actggaaagg actacattgc tcctgcttct    660
ccctggttct tcacccattt cggccctgaa gtcccgtaca gcaagaactg gtcttccct     720 ggagatttgt tgtggtatga ccgctggcag caactgttga ccatgggccc acgattcatc    780
gagatcgtca cctggaacga ttacggcgag tcgcactata tcggcccatt gagctcacct    840
cacactgatg atgggcatc caagtgggtg aatgacatgc ccatgatgg atggatggat     900 atgtctaagc cgttcatcgc cgcgtacaag gacggcgcca cctcggttga tgactatatc    960
accgaagacc ttctcgtgta ctggtatcgc ccggctcccc gtgatgtcaa ctgcgatgcc   1020
acagatactt gcatggtccc cgccaacaat gccgtggca attacttcta tggccgcccg    1080
aatggctggg aaacgatgga agacgctgtg ttcgtggtca ccaccctgac tgagcccgcc   1140
actgtgacgg tcaattctgg aggcaatgtc gaggtctttg atgcgcccgc tggagccagc   1200
gctttcaagg tcccgatggg cgtgggctcg caggcgtttt cgctcagtcg taacggacag   1260
gtcatccagt cggatatcag tcttctgccc atcattgatg gctgcgtttg cggactgtac   1320
aatttcaatc cttacgttgg gtctctcccg ccgagtccta ttgactctct cgagcccgca   1380
ggtctctaca gtctcacgca aggccttcat gtacaaacgt gtttgccaac gccttcactc   1440
ggcaagacaa ccccaacacc gcctccaggc tggggagctg ctccaacgac tacaaggacc   1500
tcgtctacaa ccggcacgac cggcacaact acaagaacca gcggacgac cacgcgcacc     1560 acgacgacga gaccaaccac cagtaccagc actagcacaa ccaccaggac aacgacaacc   1620
accagaccaa ccacaaccac ccggacgacg acaaccacaa acccaaccgg cggcaccgga   1680
aatgtctgcg tcgccggcac aggaccgggc aactatgtcg gtctatgcag tttctgctgc   1740
aacttcggtt actgccctcc aggaccatgc acctgtacgg cctatggagc gcccgtgccg   1800
acgccgccga cgacgggtgt ccggggtgtg ccgctgccgt ggctggagaa ctataactcg   1860
tacctggggc tatgcagctt tgcttgtgat cacggatact gtccgccgac tgcctgccag   1920
gttgcttaa                                                            1929
```

<210> SEQ ID NO 45
<211> LENGTH: 642
<212> TYPE: PRT
<213> ORGANISM: Aspergillus nidulans

<400> SEQUENCE: 45

```
Met Lys Leu Ser Thr Phe Leu Ser Ala Leu Gly Ala Leu Pro Gln Leu
1               5                   10                  15

Ile Ser Ala Ala Pro Asn Ala Val Ala Asn Lys Pro Arg Gln Ser Ser
            20                  25                  30

Asp Asp Arg Leu Val Phe Ala His Phe Met Ile Gly Ile Val Ser Asn
        35                  40                  45

Arg Asn Ser Ala Ala Asp Tyr Asp Asp Met Lys Arg Ala Lys Ser
    50                  55                  60

Leu Gly Ile Asp Ala Phe Ala Leu Asn Ile Gly Val Asp Pro Tyr Thr
65                  70                  75                  80

Asp Gln Gln Leu Asn Leu Ala Tyr Gln Ser Ala Ala Asn Asn Asp Met
```

```
            85                  90                  95
Lys Val Phe Ile Ser Phe Asp Phe Asn Trp Tyr Asn Thr Gly Gln Gly
            100                 105                 110

Tyr Gln Val Gly Gln Lys Ile Ala Gln Tyr Ala Asn Leu Pro Ala Gln
            115                 120                 125

Leu Lys Val Asp Gly Lys Val Phe Val Ser Ser Phe Ala Gly Asp Gly
130                 135                 140

Leu Asp Ile Ala Ala Met Arg Gln Ala Ala Gly Gln Asp Ile Tyr Trp
145                 150                 155                 160

Ala Pro Asn Tyr His Pro Glu Tyr Gly Thr Asn Leu Asp Gly Val Asp
                165                 170                 175

Gly Leu Leu Asn Trp Met Ala Trp Pro Asn Asp Gly Asn Asn Lys Ala
            180                 185                 190

Pro Arg Pro Gly Ala Ser Val Ser Val Glu Glu Gly Asp Glu Met Tyr
            195                 200                 205

Ile Arg Thr Gly Lys Asp Tyr Ile Ala Pro Ala Ser Pro Trp Phe Phe
            210                 215                 220

Thr His Phe Gly Pro Glu Val Pro Tyr Ser Lys Asn Trp Val Phe Pro
225                 230                 235                 240

Gly Asp Leu Leu Trp Tyr Asp Arg Trp Gln Gln Leu Leu Thr Met Gly
                245                 250                 255

Pro Arg Phe Ile Glu Ile Val Thr Trp Asn Asp Tyr Gly Glu Ser His
            260                 265                 270

Tyr Ile Gly Pro Leu Ser Ser Pro His Thr Asp Asp Gly Ala Ser Lys
            275                 280                 285

Trp Val Asn Asp Met Pro His Asp Gly Trp Met Asp Met Ser Lys Pro
290                 295                 300

Phe Ile Ala Ala Tyr Lys Asp Gly Ala Thr Ser Val Asp Tyr Ile
305                 310                 315                 320

Thr Glu Asp Leu Leu Val Tyr Trp Tyr Arg Pro Ala Pro Arg Asp Val
                325                 330                 335

Asn Cys Asp Ala Thr Asp Thr Cys Met Val Pro Ala Asn Asn Ala Ser
            340                 345                 350

Gly Asn Tyr Phe Tyr Gly Arg Pro Asn Gly Trp Glu Thr Met Glu Asp
            355                 360                 365

Ala Val Phe Val Val Thr Thr Leu Thr Glu Pro Ala Thr Val Thr Val
370                 375                 380

Asn Ser Gly Gly Asn Val Glu Val Phe Asp Ala Pro Ala Gly Ala Ser
385                 390                 395                 400

Ala Phe Lys Val Pro Met Gly Val Gly Ser Gln Ala Phe Ser Leu Ser
                405                 410                 415

Arg Asn Gly Gln Val Ile Gln Ser Asp Ile Ser Leu Leu Pro Ile Ile
            420                 425                 430

Asp Gly Cys Val Cys Gly Leu Tyr Asn Phe Asn Pro Tyr Val Gly Ser
            435                 440                 445

Leu Pro Pro Ser Pro Ile Asp Ser Leu Glu Pro Ala Gly Leu Tyr Ser
            450                 455                 460

Leu Thr Gln Gly Leu His Val Gln Thr Cys Leu Pro Thr Pro Ser Leu
465                 470                 475                 480

Gly Lys Thr Thr Pro Thr Pro Pro Gly Trp Gly Ala Ala Pro Thr
                485                 490                 495

Thr Thr Arg Thr Ser Ser Thr Thr Gly Thr Thr Gly Thr Thr Thr Arg
            500                 505                 510
```

```
Thr Thr Arg Thr Thr Thr Arg Thr Thr Thr Arg Pro Thr Thr Ser
        515                 520                 525

Thr Ser Thr Ser Thr Thr Thr Arg Thr Thr Thr Thr Thr Arg Pro Thr
    530                 535                 540

Thr Thr Thr Arg Thr Thr Thr Thr Asn Pro Thr Gly Gly Thr Gly
545                 550                 555                 560

Asn Val Cys Val Ala Gly Thr Gly Pro Gly Asn Tyr Val Gly Leu Cys
                565                 570                 575

Ser Phe Cys Cys Asn Phe Gly Tyr Cys Pro Pro Gly Pro Cys Thr Cys
            580                 585                 590

Thr Ala Tyr Gly Ala Pro Val Pro Thr Pro Pro Thr Thr Gly Val Arg
        595                 600                 605

Gly Val Pro Leu Pro Trp Leu Glu Asn Tyr Asn Ser Tyr Leu Gly Leu
    610                 615                 620

Cys Ser Phe Ala Cys Asp His Gly Tyr Cys Pro Pro Thr Ala Cys Gln
625                 630                 635                 640

Val Ala

<210> SEQ ID NO 46
<211> LENGTH: 1908
<212> TYPE: DNA
<213> ORGANISM: Hypocrea tawa

<400> SEQUENCE: 46
atgttgggcg ttttttcgccg cctcgggctc ggctcccttg ccgccgcagc tctgtcttct      60
ctcggcactg ccgctcccgc caatgttgct attcggtctc tcgaggaacg tgcttcttct     120
gccgaccgtc tcgtattctg tcacttcatg attggtattg ttggtgaccg tggcagctcg     180
gcagactatg atgatgatat gcaacgtgcc aaagccgctg gcattgacgc cttcgctctg     240
aatatcggcg ttgacggcta taccgaccag cagcttgggt atgccatga ctctgccgat     300
cgtaatggca tgaaagtctt catttcattc gatttcaatt ggtggagccc cggcaatgca     360
gttggtgttg ccagaagat tgcgcagtat gccaaccgtc cgcccagct atatgtcgat     420
aaccgtccat tcgcctcttc cttcgctggt gacggtctgg atgtaaatgc gttgcgcaat     480
gctgcaggct ccaacgtttta ctttgtgccc aacttccacc ctggtcaatc ttctccctca     540
aacattgacg gcgccctgaa ctggatggcc tgggataatg atgaaacaa caaggcaccc     600
aagcaaggcc agacagtcac ggtggcagac ggcgacaacg cctacaagaa ttggttaggt     660
ggcaagcctt acctagcacc tgtctcacct tggttttttca cccatttcgg ccccgaagtt     720
tcatattcca agaactgggt ttttcccaggt ggtgctctga tctataaccg gtggcaacag     780
gtcttgcagc aaggcttccc catggttgag attgttacat ggaatgacta cggcgagtct     840
cactacgtcg gcccacttaa gtctaagcat ttcgacgatg gcaactccaa atgggtcaat     900
gatatgcccc atgatggatt cctggatctt tcaaagccgt tcattgctgc ttataagaac     960
agggatactg acatctccaa gtatgttcag aatgagcagc ttgtctactg gtaccgccgc    1020
aacttaaagg cactggactg cgacgccacc gacaccacct ctaaccgccc ggctaataat    1080
ggaagcggta attactttat gggacgcccct gatggttggc aaaaccatgga tgatactgtt    1140
tatgttgccg cacttctcaa gactgccggt tctgttacgg tcacgtctgg cggcaccact    1200
caaacgttcc agggcaacgc cggagccaac ctcttccaaa tcccagccag catcggccag    1260
caaaagtttg ctctaactcg taacggtcag accgtcttta gcggaacctc attgatggat    1320
```

-continued

```
atcaccaacg tttgctcttg cggtatctac aacttcaacc catatgtggg taccattcct    1380
gccggcttcg acgaccctct tcaggctgac ggtcttttct ctttgaccat cggattgcat    1440
gtcacgactt gtcaggccaa gccatctctt ggaaccaatc ctcctgtcac ttctggccct    1500
gtgtcctcgc ttccagcttc ctccactacc cgcgcatcct cgcctcctgt ttcttcaact    1560
cgcgtctctt cccccctgt ctcttcccct ccagttactt ctcgcacctc ttcttctcct    1620 cccctccgg ccagcagcac gccgtcatcg ggtcaggttt gcgttgccgg aaccgttgct    1680
gacggcgagt ctggcaacta catcggcctg tgccaattca gctgcaacta cggttactgc    1740
ccaccaggac cgtgcaagtg caccgccttt ggcgctccca tctcgccacc ggcaagcaat    1800
gggcgcaatg gctgccctct accgggcgaa ggagatggtt atctgggcct gtgcagtttc    1860
agttgtaacc ataattactg ccccccaacg gcatgccaat actgctag               1908
```

<210> SEQ ID NO 47
<211> LENGTH: 635
<212> TYPE: PRT
<213> ORGANISM: Hypocrea tawa

<400> SEQUENCE: 47

```
Met Leu Gly Val Phe Arg Arg Leu Gly Leu Gly Ser Leu Ala Ala Ala
1               5                   10                  15

Ala Leu Ser Ser Leu Gly Thr Ala Ala Pro Ala Asn Val Ala Ile Arg
            20                  25                  30

Ser Leu Glu Glu Arg Ala Ser Ala Asp Arg Leu Val Phe Cys His
        35                  40                  45

Phe Met Ile Gly Ile Val Gly Asp Arg Gly Ser Ser Ala Asp Tyr Asp
    50                  55                  60

Asp Asp Met Gln Arg Ala Lys Ala Ala Gly Ile Asp Ala Phe Ala Leu
65                  70                  75                  80

Asn Ile Gly Val Asp Gly Tyr Thr Asp Gln Gln Leu Gly Tyr Ala Tyr
                85                  90                  95

Asp Ser Ala Asp Arg Asn Gly Met Lys Val Phe Ile Ser Phe Asp Phe
            100                 105                 110

Asn Trp Trp Ser Pro Gly Asn Ala Val Gly Val Gly Gln Lys Ile Ala
        115                 120                 125

Gln Tyr Ala Asn Arg Pro Ala Gln Leu Tyr Val Asp Asn Arg Pro Phe
    130                 135                 140

Ala Ser Ser Phe Ala Gly Asp Gly Leu Asp Val Asn Ala Leu Arg Asn
145                 150                 155                 160

Ala Ala Gly Ser Asn Val Tyr Phe Val Pro Asn Phe His Pro Gly Gln
                165                 170                 175

Ser Ser Pro Ser Asn Ile Asp Gly Ala Leu Asn Trp Met Ala Trp Asp
            180                 185                 190

Asn Asp Gly Asn Asn Lys Ala Pro Lys Gln Gly Gln Thr Val Thr Val
        195                 200                 205

Ala Asp Gly Asp Asn Ala Tyr Lys Asn Trp Leu Gly Gly Lys Pro Tyr
    210                 215                 220

Leu Ala Pro Val Ser Pro Trp Phe Phe Thr His Phe Gly Pro Glu Val
225                 230                 235                 240

Ser Tyr Ser Lys Asn Trp Val Phe Pro Gly Gly Ala Leu Ile Tyr Asn
                245                 250                 255

Arg Trp Gln Gln Val Leu Gln Gln Gly Phe Pro Met Val Glu Ile Val
            260                 265                 270
```

```
Thr Trp Asn Asp Tyr Gly Glu Ser His Tyr Val Gly Pro Leu Lys Ser
            275                 280                 285

Lys His Phe Asp Asp Gly Asn Ser Lys Trp Val Asn Asp Met Pro His
        290                 295                 300

Asp Gly Phe Leu Asp Leu Ser Lys Pro Phe Ile Ala Ala Tyr Lys Asn
305                 310                 315                 320

Arg Asp Thr Asp Ile Ser Lys Tyr Val Gln Asn Glu Gln Leu Val Tyr
                325                 330                 335

Trp Tyr Arg Arg Asn Leu Lys Ala Leu Asp Cys Asp Ala Thr Asp Thr
            340                 345                 350

Thr Ser Asn Arg Pro Ala Asn Asn Gly Ser Gly Asn Tyr Phe Met Gly
        355                 360                 365

Arg Pro Asp Gly Trp Gln Thr Met Asp Asp Thr Val Tyr Val Ala Ala
370                 375                 380

Leu Leu Lys Thr Ala Gly Ser Val Thr Val Thr Ser Gly Gly Thr Thr
385                 390                 395                 400

Gln Thr Phe Gln Gly Asn Ala Gly Ala Asn Leu Phe Gln Ile Pro Ala
                405                 410                 415

Ser Ile Gly Gln Gln Lys Phe Ala Leu Thr Arg Asn Gly Gln Thr Val
            420                 425                 430

Phe Ser Gly Thr Ser Leu Met Asp Ile Thr Asn Val Cys Ser Cys Gly
        435                 440                 445

Ile Tyr Asn Phe Asn Pro Tyr Val Gly Thr Ile Pro Ala Gly Phe Asp
            450                 455                 460

Asp Pro Leu Gln Ala Asp Gly Leu Phe Ser Leu Thr Ile Gly Leu His
465                 470                 475                 480

Val Thr Thr Cys Gln Ala Lys Pro Ser Leu Gly Thr Asn Pro Pro Val
                485                 490                 495

Thr Ser Gly Pro Val Ser Ser Leu Pro Ala Ser Ser Thr Thr Arg Ala
            500                 505                 510

Ser Ser Pro Pro Val Ser Ser Thr Arg Val Ser Pro Pro Val Ser
        515                 520                 525

Ser Pro Pro Val Thr Ser Arg Thr Ser Ser Ser Pro Pro Pro Ala
530                 535                 540

Ser Ser Thr Pro Ser Ser Gly Gln Val Cys Val Ala Gly Thr Val Ala
545                 550                 555                 560

Asp Gly Glu Ser Gly Asn Tyr Ile Gly Leu Cys Gln Phe Ser Cys Asn
                565                 570                 575

Tyr Gly Tyr Cys Pro Pro Gly Pro Cys Lys Cys Thr Ala Phe Gly Ala
            580                 585                 590

Pro Ile Ser Pro Pro Ala Ser Asn Gly Arg Asn Gly Cys Pro Leu Pro
        595                 600                 605

Gly Glu Gly Asp Gly Tyr Leu Gly Leu Cys Ser Phe Ser Cys Asn His
            610                 615                 620

Asn Tyr Cys Pro Pro Thr Ala Cys Gln Tyr Cys
625                 630                 635

<210> SEQ ID NO 48
<211> LENGTH: 1884
<212> TYPE: DNA
<213> ORGANISM: Trichoderma konilangbra

<400> SEQUENCE: 48
atgctaggca ttctccgccg tctcgcgctc ggcgccctcg ccgccgcggc cctctctcct    60
```

```
ctcgtcgtcg ccgcgcctgc caatgtcgcc atccgctccc tcgaggaacg ggcgagtagc        120
gcagacaggc tcgtgttctg ccacttcatg attgggatat gcggtgatcg cggctccagc        180
actgattatg acgacgatat gcaaagggcc aaggcagcgg gcatcgacgc gtttgcgttg        240
aacattggcg tcgatggata cacggaccag cagctcaact ttgcgtacga cgccgccgac        300
cgcgccggga tgaaggtgtt catctccttc gacttcaact ggtggagccc cggcaacgca        360
gtaggcgtcg gccagaagat tgcccaatac gcgtcgcggc ccgcacagct ctacgtcgac        420
aaccggccct ttgcgtcgtc gtttgccggc gatggccttg acgtgaatgc gctgcgcaac        480
gccgccggaa gcaacgtata ctttgtgccc aacttccacc ccgggcagtc ctccccgtca        540
accatcgacg gggccctcaa ctggatggcc tgggacaatg acggaaacaa caaggccccc        600
aagcccggcc gcaacgtcac cgtcgccgac ggcgacaact cgtaccgtag ctggctgggc        660
ggcaagccct acctggcccc cgtttcgccc tggttcttca cccacttcgg ccccgaggtt        720
tccttcagca agaactgggt cttcccgggc ggctcgctcc tctacgaccg ctggcaggac        780
gtgctgcrcc agggccccga aatggtcgag atcatcacct ggaacgatta cggtgagagc        840
cactacaccg ggcccctcaa aagtcgccac tatgacgacg gaaactcgaa atggaccaac        900
gacatgccgc acgacggatt cctggacctg tcgaaaccgt ttatagcggc gtacaagaac        960
cgcgacacga acgtggcacg gtacgtccag tccgaccagc tcgtctactg gtacagaagg       1020
acgctcaagg ggctggactg cgacgcgact gacacgacgc caaaccggcc cgcgaacaac       1080
gccagcggca actacttcat gggccggccc gacgggtggc agacgatgga cgacaccgtg       1140
tacgtggtgg cgctrctcac ggccgcggga actgtgacgg tgacgtccgg cggggccacc       1200
cagacgttcc agggcaccrc cggagccaac ctgttcgagg tcccggccaa cctgggccag       1260
cagaagtttg ccctgtcccg caacgggcag accgtcttca gcagcacatc gctgatggat       1320
atcgctaatg tgtgcccgtg cggcctctac aacttcaacc cgtatgtcgg gactgtcccg       1380
cccggttttg acgacccgct gcaggctgat ggccttgcgt cgctgacgat cggactgcac       1440
gtcacgacct gtcaggccag accctccctg gaacgaacc cgcccatcac ttccggcccc       1500
ggctcctcgg tgcccgcttc aaccaccgc tcgacttctc cgcccggttc cacgagccgc        1560
ttctcgtcga ccccggtttc gtcccgctcc atctcttcga cgccaccggt cagcacgccg        1620 cccccctggcc aagtatgtgt ggccggcaca gtcgctgacg gccagtcggg caactatatt       1680
ggcctatgca acttcagctg caacttcggc tactgtcctc ccggcccttg caagtgcacc        1740
gcctttggcg ctcccatcaa cccaccggcg accaatgggc gaaacggatg ccccttgcct        1800
ggagaggatg atagttactt gggcctctgc agcttcagtt gcaaccataa ctactgccct        1860
ccgacggcat gccaatactg ctga                                               1884
```

<210> SEQ ID NO 49
<211> LENGTH: 627
<212> TYPE: PRT
<213> ORGANISM: Trichoderma konilangbra
<220> FEATURE:
<221> NAME/KEY: MISC_FEATURE
<222> LOCATION: (263)..(263)
<223> OTHER INFORMATION: X = R or H
<220> FEATURE:
<221> NAME/KEY: MISC_FEATURE
<222> LOCATION: (407)..(407)
<223> OTHER INFORMATION: X = T or A

<400> SEQUENCE: 49

Met Leu Gly Ile Leu Arg Arg Leu Ala Leu Gly Ala Leu Ala Ala Ala

```
1               5                   10                  15
Ala Leu Ser Pro Leu Val Val Ala Ala Pro Ala Asn Val Ala Ile Arg
            20                  25                  30

Ser Leu Glu Glu Arg Ala Ser Ala Asp Arg Leu Val Phe Cys His
            35                  40                  45

Phe Met Ile Gly Ile Cys Gly Asp Arg Gly Ser Thr Asp Tyr Asp
            50                  55                  60

Asp Asp Met Gln Arg Ala Lys Ala Ala Gly Ile Asp Ala Phe Ala Leu
65                  70                  75                  80

Asn Ile Gly Val Asp Gly Tyr Thr Asp Gln Gln Leu Asn Phe Ala Tyr
                    85                  90                  95

Asp Ala Ala Asp Arg Ala Gly Met Lys Val Phe Ile Ser Phe Asp Phe
                    100                 105                 110

Asn Trp Trp Ser Pro Gly Asn Ala Val Gly Val Gly Gln Lys Ile Ala
                    115                 120                 125

Gln Tyr Ala Ser Arg Pro Ala Gln Leu Tyr Val Asp Asn Arg Pro Phe
            130                 135                 140

Ala Ser Ser Phe Ala Gly Asp Gly Leu Asp Val Asn Ala Leu Arg Asn
145                 150                 155                 160

Ala Ala Gly Ser Asn Val Tyr Phe Val Pro Asn Phe His Pro Gly Gln
                    165                 170                 175

Ser Ser Pro Ser Thr Ile Asp Gly Ala Leu Asn Trp Met Ala Trp Asp
            180                 185                 190

Asn Asp Gly Asn Asn Lys Ala Pro Lys Pro Gly Arg Asn Val Thr Val
            195                 200                 205

Ala Asp Gly Asp Asn Ser Tyr Arg Ser Trp Leu Gly Gly Lys Pro Tyr
210                 215                 220

Leu Ala Pro Val Ser Pro Trp Phe Phe Thr His Phe Gly Pro Glu Val
225                 230                 235                 240

Ser Phe Ser Lys Asn Trp Val Phe Pro Gly Gly Ser Leu Leu Tyr Asp
                    245                 250                 255

Arg Trp Gln Asp Val Leu Xaa Gln Gly Pro Glu Met Val Glu Ile Ile
            260                 265                 270

Thr Trp Asn Asp Tyr Gly Glu Ser His Tyr Thr Gly Pro Leu Lys Ser
            275                 280                 285

Arg His Tyr Asp Asp Gly Asn Ser Lys Trp Thr Asn Asp Met Pro His
            290                 295                 300

Asp Gly Phe Leu Asp Leu Ser Lys Pro Phe Ile Ala Ala Tyr Lys Asn
305                 310                 315                 320

Arg Asp Thr Asn Val Ala Arg Tyr Val Gln Ser Asp Gln Leu Val Tyr
                    325                 330                 335

Trp Tyr Arg Arg Thr Leu Lys Gly Leu Asp Cys Asp Ala Thr Asp Thr
            340                 345                 350

Thr Ser Asn Arg Pro Ala Asn Asn Ala Ser Gly Asn Tyr Phe Met Gly
            355                 360                 365

Arg Pro Asp Gly Trp Gln Thr Met Asp Asp Thr Val Tyr Val Val Ala
            370                 375                 380

Leu Leu Thr Ala Ala Gly Thr Val Thr Val Thr Ser Gly Gly Ala Thr
385                 390                 395                 400

Gln Thr Phe Gln Gly Thr Xaa Gly Ala Asn Leu Phe Glu Val Pro Ala
                    405                 410                 415

Asn Leu Gly Gln Gln Lys Phe Ala Leu Ser Arg Asn Gly Gln Thr Val
            420                 425                 430
```

Phe Ser Ser Thr Ser Leu Met Asp Ile Ala Asn Val Cys Pro Cys Gly
        435                 440                 445

Leu Tyr Asn Phe Asn Pro Tyr Val Gly Thr Val Pro Pro Gly Phe Asp
    450                 455                 460

Asp Pro Leu Gln Ala Asp Gly Leu Ala Ser Leu Thr Ile Gly Leu His
465                 470                 475                 480

Val Thr Thr Cys Gln Ala Arg Pro Ser Leu Gly Thr Asn Pro Pro Ile
            485                 490                 495

Thr Ser Gly Pro Gly Ser Ser Val Pro Ala Ser Thr Thr Arg Ser Thr
        500                 505                 510

Ser Pro Pro Gly Ser Thr Ser Arg Phe Ser Ser Thr Pro Val Ser Ser
        515                 520                 525

Arg Ser Ile Ser Ser Thr Pro Pro Val Ser Thr Pro Pro Gly Gln
        530                 535                 540

Val Cys Val Ala Gly Thr Val Ala Asp Gly Gln Ser Gly Asn Tyr Ile
545                 550                 555                 560

Gly Leu Cys Asn Phe Ser Cys Asn Phe Gly Tyr Cys Pro Pro Gly Pro
                565                 570                 575

Cys Lys Cys Thr Ala Phe Gly Ala Pro Ile Asn Pro Ala Thr Asn
            580                 585                 590

Gly Arg Asn Gly Cys Pro Leu Pro Gly Glu Asp Ser Tyr Leu Gly
        595                 600                 605

Leu Cys Ser Phe Ser Cys Asn His Asn Tyr Cys Pro Pro Thr Ala Cys
    610                 615                 620

Gln Tyr Cys
625

<210> SEQ ID NO 50
<211> LENGTH: 1869
<212> TYPE: DNA
<213> ORGANISM: Trichoderma reesei

<400> SEQUENCE: 50
atgtttggtc ttgtccgccg actcggggtc ggcgcccttg tcgccgcagc cctttcctcc      60
ctcgctgccg ccgcgccagc caacgtcgcc atccgctccc tcgaggaacg ggctagcagc     120
gcagatagac ttgtgttttg ccactttatg attgggatat gtggtgatcg cacctccagt     180
accgattatg atgatgatat gcagcgagcc aaggccgcgg gcattgacgc ctttgcccttt    240 aacattggtg tcgacggata cacgaccag cagctcaact ttgcctacga cgccgctgat      300
cgcgccggga tgaaggtgtt catctccttt gacttcaact ggtggagccc cggcaacgcg     360
gcaggcgtcg gccagaagat tgcccaatat gcgtcgcggc ccgcacagct ctacgtcgac     420
aaccgtccct ttgcatcgtc gtttgccggt gacggccttg acgtgaatac gctgcggaat    480
gcggccggca gcaacgtgta ctttgtgccc aacttccacc ccgggcagtc gtcgccgtcc     540
accatcgacg gggctctgaa ctggatggcc tgggacaacg acggcaacaa caaggccccc    600
aagcccggcc aaaacgtcac agtcgccgac ggcgacaact cctaccgcag ctggctcgcc     660
ggcaagccct acctcgcccc cgtctcgccc tggttcttca cccacttcgg cccagaggta     720
tcgtacagta agaactgggt cttccctggc ggctccctgt ggtacgaccg ctggcaggac     780
gtgctgcgcc agggcttcga gatggtcgaa atcgtcacct ggaacgatta cggtgagagc    840
cactacacgg ggcccctgga aagtcgacac tatgacgacg aaactcgaa atggaccaac     900 gacatgccgc acgacggctt cctggacctg gcgaagccat tcattgccgc gtacaagaac     960

```
cgcgacacgg acgtggcgcc ctacatccag aatgagcagc tgatctactg gtatcggcgg    1020
aatctcaagg ggctggactg cgacgcgacc gacacgacgt cgaaccgccc ggcgaacaac    1080
ggcagcggca actacttcat gggtcggccc gacgggtggc agacgatgga cgacacggtg    1140
tatgtggtgg cgctgctcaa gagcgcgggc acggtgacgg tgacgtcggg cggcgccacg    1200
cagacgttcc agggcaccgc cggcgccaac ctgttcgagg tcccagccaa ccttgggcag    1260
cagaagtttg ccctgtcccg caacgggcag accgtcttca gcagcacgtc gctgatggat    1320
atcaccaatg tgtgcccgtg cggcatctac aacttcaacc cgtatgtcgg gactgtgccc    1380
gctggctttg acgacccgct cgggcccgat ggccttgctt ctttgacaat cggactgcac    1440
gtcacgactt gtcaggccaa gccgtcgctg gggaccaacc cgcccatcac ttccggcccc    1500
ggctcctcgg tgcccgtttc cactccgccc ggttccacga cccgcttctc gtcaacgccg    1560
gtttcatctc gctccagctc gtccacgccg ccggttagca cgccgccgcc tggccaagtc    1620
tgtgtcgccg gtacggtggc tgacggccag tccggcaact atattggcct ctgcaacttc    1680
agctgcaact tcgggtactg tccccccgga ccctgcaagt gcactgccta cggcgctccg    1740
atcaacccac cagcaacgaa tgggcgaaat gggtgcccct tgcctggaga agacgatagt    1800
tatctgggcc tctgcagctt cagctgcaac cacaattact gtccgccaac agcatgccag    1860
tactgctga                                                            1869

<210> SEQ ID NO 51
<211> LENGTH: 622
<212> TYPE: PRT
<213> ORGANISM: Trichoderma reesei

<400> SEQUENCE: 51

Met Phe Gly Leu Val Arg Arg Leu Gly Val Gly Ala Leu Val Ala Ala
1               5                   10                  15

Ala Leu Ser Ser Leu Ala Ala Ala Ala Pro Ala Asn Val Ala Ile Arg
            20                  25                  30

Ser Leu Glu Glu Arg Ala Ser Ser Ala Asp Arg Leu Val Phe Cys His
        35                  40                  45

Phe Met Ile Gly Ile Cys Gly Asp Arg Thr Ser Ser Thr Asp Tyr Asp
    50                  55                  60

Asp Asp Met Gln Arg Ala Lys Ala Ala Gly Ile Asp Ala Phe Ala Leu
65                  70                  75                  80

Asn Ile Gly Val Asp Gly Tyr Thr Asp Gln Gln Leu Asn Phe Ala Tyr
                85                  90                  95

Asp Ala Ala Asp Arg Ala Gly Met Lys Val Phe Ile Ser Phe Asp Phe
            100                 105                 110

Asn Trp Trp Ser Pro Gly Asn Ala Ala Gly Val Gly Gln Lys Ile Ala
        115                 120                 125

Gln Tyr Ala Ser Arg Pro Ala Gln Leu Tyr Val Asp Asn Arg Pro Phe
    130                 135                 140

Ala Ser Ser Phe Ala Gly Asp Gly Leu Asp Val Asn Thr Leu Arg Asn
145                 150                 155                 160

Ala Ala Gly Ser Asn Val Tyr Phe Val Pro Asn Phe His Pro Gly Gln
                165                 170                 175

Ser Ser Pro Ser Thr Ile Asp Gly Ala Leu Asn Trp Met Ala Trp Asp
            180                 185                 190

Asn Asp Gly Asn Asn Lys Ala Pro Lys Pro Gly Gln Asn Val Thr Val
        195                 200                 205
```

```
Ala Asp Gly Asp Asn Ser Tyr Arg Ser Trp Leu Ala Gly Lys Pro Tyr
        210                 215                 220

Leu Ala Pro Val Ser Pro Trp Phe Phe Thr His Phe Gly Pro Glu Val
225                 230                 235                 240

Ser Tyr Ser Lys Asn Trp Val Phe Pro Gly Gly Ser Leu Trp Tyr Asp
                245                 250                 255

Arg Trp Gln Asp Val Leu Arg Gln Gly Phe Glu Met Val Glu Ile Val
            260                 265                 270

Thr Trp Asn Asp Tyr Gly Glu Ser His Tyr Thr Gly Pro Leu Glu Ser
        275                 280                 285

Arg His Tyr Asp Asp Gly Asn Ser Lys Trp Thr Asn Asp Met Pro His
    290                 295                 300

Asp Gly Phe Leu Asp Leu Ala Lys Pro Phe Ile Ala Ala Tyr Lys Asn
305                 310                 315                 320

Arg Asp Thr Asp Val Ala Pro Tyr Ile Gln Asn Glu Gln Leu Ile Tyr
                325                 330                 335

Trp Tyr Arg Arg Asn Leu Lys Gly Leu Asp Cys Asp Ala Thr Asp Thr
            340                 345                 350

Thr Ser Asn Arg Pro Ala Asn Asn Gly Ser Gly Asn Tyr Phe Met Gly
        355                 360                 365

Arg Pro Asp Gly Trp Gln Thr Met Asp Asp Thr Val Tyr Val Val Ala
    370                 375                 380

Leu Leu Lys Ser Ala Gly Thr Val Thr Val Thr Ser Gly Gly Ala Thr
385                 390                 395                 400

Gln Thr Phe Gln Gly Thr Ala Gly Ala Asn Leu Phe Glu Val Pro Ala
                405                 410                 415

Asn Leu Gly Gln Gln Lys Phe Ala Leu Ser Arg Asn Gly Gln Thr Val
            420                 425                 430

Phe Ser Ser Thr Ser Leu Met Asp Ile Thr Asn Val Cys Pro Cys Gly
        435                 440                 445

Ile Tyr Asn Phe Asn Pro Tyr Val Gly Thr Val Pro Ala Gly Phe Asp
    450                 455                 460

Asp Pro Leu Gly Pro Asp Gly Leu Ala Ser Leu Thr Ile Gly Leu His
465                 470                 475                 480

Val Thr Thr Cys Gln Ala Lys Pro Ser Leu Gly Thr Asn Pro Pro Ile
                485                 490                 495

Thr Ser Gly Pro Gly Ser Ser Val Pro Val Ser Thr Pro Pro Gly Ser
            500                 505                 510

Thr Thr Arg Phe Ser Ser Thr Pro Val Ser Ser Arg Ser Ser Ser Ser
        515                 520                 525

Thr Pro Pro Val Ser Thr Pro Pro Gly Gln Val Cys Val Ala Gly
    530                 535                 540

Thr Val Ala Asp Gly Gln Ser Gly Asn Tyr Ile Gly Leu Cys Asn Phe
545                 550                 555                 560

Ser Cys Asn Phe Gly Tyr Cys Pro Pro Gly Pro Cys Lys Cys Thr Ala
                565                 570                 575

Tyr Gly Ala Pro Ile Asn Pro Pro Ala Thr Asn Gly Arg Asn Gly Cys
            580                 585                 590

Pro Leu Pro Gly Glu Asp Asp Ser Tyr Leu Gly Leu Cys Ser Phe Ser
        595                 600                 605

Cys Asn His Asn Tyr Cys Pro Pro Thr Ala Cys Gln Tyr Cys
    610                 615                 620
```

<210> SEQ ID NO 52
<211> LENGTH: 4047
<212> TYPE: DNA
<213> ORGANISM: Streptococcus oralis

<400> SEQUENCE: 52

| | |
|---|---|
| atgatcgacg gcaaaaacta ctacgtacag gatgatggca cggtaaagaa gaatttcgcg | 60 |
| gtagaactga atggtcgtat cctgtatttt gatgcagaaa ccggcgctct ggttgatagc | 120 |
| aacgagtatc agttccaaca gggtacgagc agcctgaaca atgaattttc tcagaagaac | 180 |
| gcattctatg gtacgaccga taaggatatt gagactgtgg atggctacct gaccgcagat | 240 |
| agctggtatc gcccgaaatt catcctgaag gatggcaaga cgtggaccgc gagcacggaa | 300 |
| acggatctgc gtccgctgtt gatggcatgg tggccggaca agcgtaccca aatcaactat | 360 |
| ctgaactaca tgaaccagca gggtctgggt gcgggtgcgt tgagaacaa agtggagcag | 420 |
| gccctgctga cgggtgcaag ccaacaggta caacgcaaga tcgaagagaa gattggtaaa | 480 |
| gagggtgata ccaagtggct gcgcacccctg atgggtgcgt tcgtgaaaac gcaaccaaac | 540 |
| tggaatatca aaaccgagtc tgaaacgacc ggcacgaaaa aggaccatct gcaaggcggt | 600 |
| gcactgctgt atacgaacaa cgagaaatcc ccgcacgcgg acagcaaatt tcgtctgctg | 660 |
| aatcgtaccc cgaccagcca aaccggcacg ccgaagtatt tcatcgacaa gtctaacggt | 720 |
| ggctacgaat ttctgctggc gaacgatttt gacaatagca atcctgcggt acaagctgag | 780 |
| cagctgaatt ggctgcacta catgatgaac tttggcagca ttgttgcgaa tgatccgacc | 840 |
| gcgaatttcg acggcgttcg tgtggatgct gttgataacg tcaatgcgga cttgttgcaa | 900 |
| attgcaagcg attactttaa gagccgttac aaagtcggtg agagcgaaga gaagcgatc | 960 |
| aagcacctgt ccatcctgga agcatggagc gataacgacc cggactacaa caaagatacc | 1020 |
| aagggtgcac agttggcgat tgataacaaa ctgcgcctga gcctgctgta ctctttcatg | 1080 |
| cgtaatctga gcatccgtag cggtgttgaa ccgacgatta ccaatagcct gaatgaccgt | 1140 |
| tccagcgaaa agaagaacgg cgagcgtatg gcaaattaca tcttcgtgcg tgcccacgat | 1200 |
| agcgaggtcc aaacggtgat cgccgacatc attcgcgaaa acatcaatcc gaacaccgac | 1260 |
| ggcctgacgt ttacgatgga cgagctgaag caggcattca agatttacaa cgaggacatg | 1320 |
| cgcaaggcgg acaaaaagta tacccagttt aacattccta ccgcacacgc gctgatgctg | 1380 |
| tctaataagg attctattac ccgcgtgtac tatggtgatc tgtatactga cgatggtcag | 1440 |
| tacatggaga agaaaagccc gtatcacgat gcgattgacg ctctgctgcg tgcacgtatt | 1500 |
| aaatacgtcg cgggtggcca ggatatgaaa gtgacctata tgggcgtgcc gcgtgaagcg | 1560 |
| gataagtgga gctataacgg cattctgacc agcgtgcgct atggcacggg cgctaacgaa | 1620 |
| gccacggatg agggcactgc ggaaacgcgc acgcaaggta tggcagtgat tgcgagcaat | 1680 |
| aatccaaatc tgaaactgaa tgaatgggac aagttgcaag tcaacatggg tgcggcgcat | 1740 |
| aagaatcaat attaccgtcc ggttctgctg accactaagg acggtatcag ccgttatctg | 1800 |
| accgatgaag aagtgcctca gagcctgtgg aaaaagacgg acgcaaacgg tattctgacc | 1860 |
| ttcgacatga atgatattgc tggctacagc aacgtgcaag ttagcggtta cctggccgtc | 1920 |
| tgggtcccgg tcggtgcgaa ggcggatcaa gatgcgcgca cgaccgcatc aagaagaaa | 1980 |
| aatgcgtcgg gtcaggtgta cgaaagcagc gcggctctgg atagccagct gatttacgaa | 2040 |
| ggtttcagca actttcaaga ctttgccact cgcgatgatc agtacacgaa caaggtcatt | 2100 |
| gcgaaaaacg tgaatctgtt caaagaatgg ggtgtgacca gcttcgagct gccgccgcag | 2160 |

| | | |
|---|---|---|
| tacgtgagca gccaagatgg caccttctg dacagcatta tccaaaacgg ctatgcattt | 2220 |
| gaagaccgtt acgatatggc gatgagcaag aataacaagt atggtagcct gaaagacctg | 2280 |
| ttgaacgcgc tgcgcgcact gcacagcgtc aacattcaag caatcgccga ttgggtgccg | 2340 |
| gaccaaattt acaacttgcc gggcaaagag gtggtgaccg caactcgtgt caacaactac | 2400 |
| ggcacctacc gtgagggtgc tgaaatcaaa gaaaagctgt atgtcgccaa tagcaagacc | 2460 |
| aacgaaaccg atttccaagg taaatacggt ggtgcgttcc tggatgagct gaaggcgaag | 2520 |
| tacccggaga ttttcgagcg tgtccaaatc agcaacggcc aaaagatgac taccgatgaa | 2580 |
| aagatcacca atggagcgc gaaatacttt aatggcacca atattctggg tcgtggcgcg | 2640 |
| tactatgtcc tgaaagattg ggccagcaat gattacctga cgaaccgtaa cggcgagatt | 2700 |
| gttttgccga gcaactggt taacaagaat agctataccg gctttgtcag cgacgcgaac | 2760 |
| ggcacgaagt tctattctac ctctggctac caggcgaaga acagcttcat tcaagacgaa | 2820 |
| aacggtaatt ggtattactt tgacaaacgt ggttatctgg ttacgggcgc acacgagatt | 2880 |
| gatggcaagc atgtctactt cctgaaaaac ggtatccaac tgcgtgacag catccgtgag | 2940 |
| gatgagaacg gtaatcaata ctattacgac cagaccggcg cacaagtgct gaaccgttac | 3000 |
| tacacgacgg acggtcagaa ttggcgctat ttcgatgcga aggtgttat ggcacgcggc | 3060 |
| ctggtaaaga ttggtgacgg ccaacagttt ttcgatgaaa acggttacca ggtcaagggc | 3120 |
| aagattgtta gcgcaaaaga cggcaagctg cgctacttg ataaagactc tggcaatgct | 3180 |
| gtcattaatc gttcgcgca gggtgacaat ccgagcgact ggtactattt cggtgtggaa | 3240 |
| tttgctaaac tgacgggttt gcaaaagatc ggccagcaga cgctgtattt tgaccaagac | 3300 |
| ggtaagcaag tcaaaggtaa gatcgtaact ctgtcggaca aaagcattcg ttacttcgat | 3360 |
| gccaacagcg gtgaaatggc ggttggcaag ttcgcggaag gtgcaaagaa tgagtggtat | 3420 |
| tatttcgata aaaccggcaa agcggttact ggttttcaga aaattggtaa gcagaccctg | 3480 |
| tactttgacc aggacggtaa acaggttaaa ggcaaggttg tcacgctggc tgataaaagc | 3540 |
| atccgctact cgacgcaga ctccggcgag atggcggtcg gtaagtttgc agagggtgcg | 3600 |
| aagaacgagt ggtactattt tgatcagact ggcaaggccg tgactggttt gcaaaagatt | 3660 |
| gacaagcaaa ccttgtactt cgaccaggac ggtaaacaag tcaagggtaa gattgtgacg | 3720 |
| ttgagcgaca agtcgatccg ttactttgat gctaatagcg gtgagatggc tactaacaaa | 3780 |
| ttcgtcgagg gctcgcagaa tgaatggtac tacttcgatc aagcgggtaa ggctgttacg | 3840 |
| ggcttgcaac aggtcggtca gcaaactctg tacttcacc aggatggtaa gcaagtgaag | 3900 |
| ggtaaggtcg tggacgtgaa cggtgttct cgttatttcg acgcaaactc cggtgacatg | 3960 |
| gctcgttcta aatggattca actggaagat ggcagctgga tgtatttcga ccgtgacggt | 4020 |
| cgtggccaga ttttggccg taactaa | 4047 |

<210> SEQ ID NO 53
<211> LENGTH: 1348
<212> TYPE: PRT
<213> ORGANISM: Streptococcus oralis

<400> SEQUENCE: 53

Met Ile Asp Gly Lys Asn Tyr Tyr Val Gln Asp Asp Gly Thr Val Lys
1               5                   10                  15

Lys Asn Phe Ala Val Glu Leu Asn Gly Arg Ile Leu Tyr Phe Asp Ala
            20                  25                  30

```
Glu Thr Gly Ala Leu Val Asp Ser Asn Glu Tyr Gln Phe Gln Gln Gly
            35                  40                  45

Thr Ser Ser Leu Asn Asn Glu Phe Ser Gln Lys Asn Ala Phe Tyr Gly
 50                  55                  60

Thr Thr Asp Lys Asp Ile Glu Thr Val Asp Gly Tyr Leu Thr Ala Asp
 65                  70                  75                  80

Ser Trp Tyr Arg Pro Lys Phe Ile Leu Lys Asp Gly Lys Thr Trp Thr
                 85                  90                  95

Ala Ser Thr Glu Thr Asp Leu Arg Pro Leu Leu Met Ala Trp Trp Pro
            100                 105                 110

Asp Lys Arg Thr Gln Ile Asn Tyr Leu Asn Tyr Met Asn Gln Gln Gly
            115                 120                 125

Leu Gly Ala Gly Ala Phe Glu Asn Lys Val Glu Gln Ala Leu Leu Thr
130                 135                 140

Gly Ala Ser Gln Gln Val Gln Arg Lys Ile Glu Glu Lys Ile Gly Lys
145                 150                 155                 160

Glu Gly Asp Thr Lys Trp Leu Arg Thr Leu Met Gly Ala Phe Val Lys
                165                 170                 175

Thr Gln Pro Asn Trp Asn Ile Lys Thr Glu Ser Glu Thr Thr Gly Thr
                180                 185                 190

Lys Lys Asp His Leu Gln Gly Gly Ala Leu Leu Tyr Thr Asn Asn Glu
            195                 200                 205

Lys Ser Pro His Ala Asp Ser Lys Phe Arg Leu Leu Asn Arg Thr Pro
    210                 215                 220

Thr Ser Gln Thr Gly Thr Pro Lys Tyr Phe Ile Asp Lys Ser Asn Gly
225                 230                 235                 240

Gly Tyr Glu Phe Leu Leu Ala Asn Asp Phe Asp Asn Ser Asn Pro Ala
                245                 250                 255

Val Gln Ala Glu Gln Leu Asn Trp Leu His Tyr Met Met Asn Phe Gly
                260                 265                 270

Ser Ile Val Ala Asn Asp Pro Thr Ala Asn Phe Asp Gly Val Arg Val
            275                 280                 285

Asp Ala Val Asp Asn Val Asn Ala Asp Leu Leu Gln Ile Ala Ser Asp
290                 295                 300

Tyr Phe Lys Ser Arg Tyr Lys Val Gly Glu Ser Glu Glu Ala Ile
305                 310                 315                 320

Lys His Leu Ser Ile Leu Glu Ala Trp Ser Asp Asn Asp Pro Asp Tyr
                325                 330                 335

Asn Lys Asp Thr Lys Gly Ala Gln Leu Ala Ile Asp Asn Lys Leu Arg
            340                 345                 350

Leu Ser Leu Leu Tyr Ser Phe Met Arg Asn Leu Ser Ile Arg Ser Gly
            355                 360                 365

Val Glu Pro Thr Ile Thr Asn Ser Leu Asn Asp Arg Ser Ser Glu Lys
            370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Ile Arg Glu Asn Ile Asn
                405                 410                 415

Pro Asn Thr Asp Gly Leu Thr Phe Thr Met Asp Glu Leu Lys Gln Ala
            420                 425                 430

Phe Lys Ile Tyr Asn Glu Asp Met Arg Lys Ala Asp Lys Lys Tyr Thr
            435                 440                 445

Gln Phe Asn Ile Pro Thr Ala His Ala Leu Met Leu Ser Asn Lys Asp
```

```
            450                 455                 460
Ser Ile Thr Arg Val Tyr Tyr Gly Asp Leu Tyr Thr Asp Asp Gly Gln
465                 470                 475                 480

Tyr Met Glu Lys Lys Ser Pro Tyr His Asp Ala Ile Asp Ala Leu Leu
                    485                 490                 495

Arg Ala Arg Ile Lys Tyr Val Ala Gly Gln Asp Met Lys Val Thr
                500                 505                 510

Tyr Met Gly Val Pro Arg Glu Ala Asp Lys Trp Ser Tyr Asn Gly Ile
            515                 520                 525

Leu Thr Ser Val Arg Tyr Gly Thr Gly Ala Asn Glu Ala Thr Asp Glu
        530                 535                 540

Gly Thr Ala Glu Thr Arg Thr Gln Gly Met Ala Val Ile Ala Ser Asn
545                 550                 555                 560

Asn Pro Asn Leu Lys Leu Asn Glu Trp Asp Lys Leu Gln Val Asn Met
                565                 570                 575

Gly Ala Ala His Lys Asn Gln Tyr Tyr Arg Pro Val Leu Leu Thr Thr
                580                 585                 590

Lys Asp Gly Ile Ser Arg Tyr Leu Thr Asp Glu Glu Val Pro Gln Ser
            595                 600                 605

Leu Trp Lys Lys Thr Asp Ala Asn Gly Ile Leu Thr Phe Asp Met Asn
        610                 615                 620

Asp Ile Ala Gly Tyr Ser Asn Val Gln Val Ser Gly Tyr Leu Ala Val
625                 630                 635                 640

Trp Val Pro Val Gly Ala Lys Ala Asp Gln Asp Ala Arg Thr Thr Ala
                645                 650                 655

Ser Lys Lys Lys Asn Ala Ser Gly Gln Val Tyr Glu Ser Ser Ala Ala
                660                 665                 670

Leu Asp Ser Gln Leu Ile Tyr Glu Gly Phe Ser Asn Phe Gln Asp Phe
            675                 680                 685

Ala Thr Arg Asp Asp Gln Tyr Thr Asn Lys Val Ile Ala Lys Asn Val
        690                 695                 700

Asn Leu Phe Lys Glu Trp Gly Val Thr Ser Phe Glu Leu Pro Pro Gln
705                 710                 715                 720

Tyr Val Ser Ser Gln Asp Gly Thr Phe Leu Asp Ser Ile Ile Gln Asn
                725                 730                 735

Gly Tyr Ala Phe Glu Asp Arg Tyr Asp Met Ala Met Ser Lys Asn Asn
                740                 745                 750

Lys Tyr Gly Ser Leu Lys Asp Leu Leu Asn Ala Leu Arg Ala Leu His
            755                 760                 765

Ser Val Asn Ile Gln Ala Ile Ala Asp Trp Val Pro Asp Gln Ile Tyr
        770                 775                 780

Asn Leu Pro Gly Lys Glu Val Val Thr Ala Thr Arg Val Asn Asn Tyr
785                 790                 795                 800

Gly Thr Tyr Arg Glu Gly Ala Glu Ile Lys Glu Lys Leu Tyr Val Ala
                805                 810                 815

Asn Ser Lys Thr Asn Glu Thr Asp Phe Gln Gly Lys Tyr Gly Gly Ala
                820                 825                 830

Phe Leu Asp Glu Leu Lys Ala Lys Tyr Pro Glu Ile Phe Glu Arg Val
            835                 840                 845

Gln Ile Ser Asn Gly Gln Lys Met Thr Thr Asp Glu Lys Ile Thr Lys
        850                 855                 860

Trp Ser Ala Lys Tyr Phe Asn Gly Thr Asn Ile Leu Gly Arg Gly Ala
865                 870                 875                 880
```

-continued

```
Tyr Tyr Val Leu Lys Asp Trp Ala Ser Asn Asp Tyr Leu Thr Asn Arg
            885                 890                 895

Asn Gly Glu Ile Val Leu Pro Lys Gln Leu Val Asn Lys Asn Ser Tyr
            900                 905                 910

Thr Gly Phe Val Ser Asp Ala Asn Gly Thr Lys Phe Tyr Ser Thr Ser
            915                 920                 925

Gly Tyr Gln Ala Lys Asn Ser Phe Ile Gln Asp Glu Asn Gly Asn Trp
    930                 935                 940

Tyr Tyr Phe Asp Lys Arg Gly Tyr Leu Val Thr Gly Ala His Glu Ile
945                 950                 955                 960

Asp Gly Lys His Val Tyr Phe Leu Lys Asn Gly Ile Gln Leu Arg Asp
            965                 970                 975

Ser Ile Arg Glu Asp Glu Asn Gly Asn Gln Tyr Tyr Tyr Asp Gln Thr
            980                 985                 990

Gly Ala Gln Val Leu Asn Arg Tyr Tyr Thr Thr Asp Gly Gln Asn Trp
    995                 1000                1005

Arg Tyr Phe Asp Ala Lys Gly Val Met Ala Arg Gly Leu Val Lys
    1010                1015                1020

Ile Gly Asp Gly Gln Gln Phe Phe Asp Glu Asn Gly Tyr Gln Val
    1025                1030                1035

Lys Gly Lys Ile Val Ser Ala Lys Asp Gly Lys Leu Arg Tyr Phe
    1040                1045                1050

Asp Lys Asp Ser Gly Asn Ala Val Ile Asn Arg Phe Ala Gln Gly
    1055                1060                1065

Asp Asn Pro Ser Asp Trp Tyr Tyr Phe Gly Val Glu Phe Ala Lys
    1070                1075                1080

Leu Thr Gly Leu Gln Lys Ile Gly Gln Gln Thr Leu Tyr Phe Asp
    1085                1090                1095

Gln Asp Gly Lys Gln Val Lys Gly Lys Ile Val Thr Leu Ser Asp
    1100                1105                1110

Lys Ser Ile Arg Tyr Phe Asp Ala Asn Ser Gly Glu Met Ala Val
    1115                1120                1125

Gly Lys Phe Ala Glu Gly Ala Lys Asn Glu Trp Tyr Tyr Phe Asp
    1130                1135                1140

Lys Thr Gly Lys Ala Val Thr Gly Leu Gln Lys Ile Gly Lys Gln
    1145                1150                1155

Thr Leu Tyr Phe Asp Gln Asp Gly Lys Gln Val Lys Gly Lys Val
    1160                1165                1170

Val Thr Leu Ala Asp Lys Ser Ile Arg Tyr Phe Asp Ala Asp Ser
    1175                1180                1185

Gly Glu Met Ala Val Gly Lys Phe Ala Glu Gly Ala Lys Asn Glu
    1190                1195                1200

Trp Tyr Tyr Phe Asp Gln Thr Gly Lys Ala Val Thr Gly Leu Gln
    1205                1210                1215

Lys Ile Asp Lys Gln Thr Leu Tyr Phe Asp Gln Asp Gly Lys Gln
    1220                1225                1230

Val Lys Gly Lys Ile Val Thr Leu Ser Asp Lys Ser Ile Arg Tyr
    1235                1240                1245

Phe Asp Ala Asn Ser Gly Glu Met Ala Thr Asn Lys Phe Val Glu
    1250                1255                1260

Gly Ser Gln Asn Glu Trp Tyr Tyr Phe Asp Gln Ala Gly Lys Ala
    1265                1270                1275
```

```
Val Thr Gly Leu Gln Gln Val Gly Gln Gln Thr Leu Tyr Phe Thr
    1280                1285                1290

Gln Asp Gly Lys Gln Val Lys Gly Lys Val Val Asp Val Asn Gly
    1295                1300                1305

Val Ser Arg Tyr Phe Asp Ala Asn Ser Gly Asp Met Ala Arg Ser
    1310                1315                1320

Lys Trp Ile Gln Leu Glu Asp Gly Ser Trp Met Tyr Phe Asp Arg
    1325                1330                1335

Asp Gly Arg Gly Gln Asn Phe Gly Arg Asn
    1340                1345
```

```
<210> SEQ ID NO 54
<211> LENGTH: 3864
<212> TYPE: DNA
<213> ORGANISM: Streptococcus mutans UA159

<400> SEQUENCE: 54
atgattgacg gcaaatacta ctacatcggc agcgacggtc agccaaagaa gaattttgcg      60
ttgacggtta acaataaagt cctgtatttt gacaagaaca cgggtgcgct gaccgacacc     120
agccaatatc agttcaaaca aggtctgacg aagctgaaca cgactacac ccctcacaat     180
cagattgtca actttgaaaa tactagcctg gaaactattg ataactatgt tactgccgac     240
tcttggtatc gtccgaaaga cattctgaag aacggtaaga cgtggaccgc gtcctctgag     300
agcgatctgc gtccgctgct gatgtcctgg tggcctgata gcagaccca gatcgcatac     360
ctgaactaca tgaaccaaca aggcttgggc actggcgaga actataccgc tgatagctct     420
caagagagcc tgaacctggc ggcacaaacc gttcaagtca aaatcgaaac caagatcagc     480
caaacgcaac agactcagtg gctgcgtgac atcattaact ctttcgttaa gacgcaaccg     540
aactggaata gccaaaccga gtctgacacg agcgctggtg aaaaagatca tttgcagggc     600
ggtgccctgc tgtatagcaa ttcggacaaa accgcatacg caaatagcga ctatcgtctg     660
ctgaaccgta ccccgaccag ccagactggt aagccgaaat acttcgagga caatagcagc     720
ggtggttacg acttcctgtt ggcaaacgat attgataatt ccaatccggt ggtgcaggct     780
gagcagctga attggctgca ttacctgatg aattacggta gcattgtcgc aaatgacccg     840
gaagcgaatt cgatggtgt ccgtgttgac gcggtggata cgtgaacgc agacctgttg     900
cagatcgcaa gcgattatct gaaagcccat atggtgttg ataagagcga agaatgcg     960
atcaaccacc tgagcatcct ggaagcgtgg tctgacaacg acccacagta taacaaagac    1020
accaaaggtg cccagctgcc gatcgacaac aaactgcgtc tgtcgttgct gtacgcactg    1080
acccgtccgc tggagaagga tgcaagcaac aaaaatgaga ttcgtagcgg tctggagccg    1140
gttattacca attccctgaa taatcgttcc gctgagggca agaactctga acgcatggcg    1200
aattacatct tcatccgtgc tcacgattct gaagttcaaa cggtgatcgc aaagatcatc    1260
aaagcgcaga ttaacccgaa acgatggc ctgaccttca ccctggatga gctgaaacag    1320
gcgttcaaaa tctataacga ggatatgcgc caggcgaaga agaagtatac ccagagcaat    1380
atcccgacgg catacgccct gatgctgagc aataaggact ccatcacgcg cctgtattac    1440
ggtgatatgt acagcgatga tggccaatac atggcgacca atcccccgta ctacgatgcg    1500
attgacaccc tgctgaaggc gcgcattaag tatgccgctg gcggtcagga tatgaagatc    1560
acctacgttg agggtgacaa aagccacatg gactgggact atacgggtgt cctgacgagc    1620
gttcgctacg gcacgggcgc aaacgaagcg accgaccagg gcagcgaagc taccaagacg    1680
```

```
caaggtatgg ccgtcatcac ttctaacaac ccgtccctga agctgaatca gaacgacaag   1740
gtcattgtca atatgggcac cgctcacaaa atcaggaat accgtccgtt gctgctgacc    1800
accaaagacg gtctgaccag ctacaccagc gacgccgctg ccaagagcct gtaccgtaaa   1860
acgaacgata agggcgagtt ggtgttcgat gcaagcgaca ttcagggcta tctgaatccg   1920
caagtgagcg gttacctggc tgtttgggtg cctgtgggtg cgagcgacaa ccaggatgtg   1980
cgtgtcgcgg ccagcaataa agccaatgcg accggccaag tctatgaaag cagcagcgca   2040
ctggatagcc aactgattta tgagggtttt tccaactttc aggacttcgt caccaaggat   2100
tctgattaca ccaataaaaa gatcgcgcaa aatgtccagc tgtttaagag ctggggcgtc   2160
accagctttg agatggctcc gcaatacgtc agcagcgagg acggcagctt tttggacagc   2220
attatccaga acggctatgc gttcgaggat cgttacgacc tggcgatgag caaaaacaac   2280
aaatacggct cccagcagga catgatcaac gcggttaagg cgctgcataa gagcggtatc   2340
caagtgatcg cggactgggt cccggatcaa atctacaatt tgcccgggtaa agaggtcgtc   2400 accgcgaccc gtgtgaacga ctacggcgag tatcgcaagg actccgaaat caaaaacacc   2460
ctgtacgccg ccaacaccaa aagcaacggt aaagattatc aagcaaagta cggtggcgcc   2520
tttttgagcg agctggccgc caaatatccg agcatcttta accgcactca gattagcaat   2580
ggcaagaaga tcgacccgtc tgaaaagatc accgcctgga aggccaaata cttcaatggt   2640
acgaacattt gggtcgcgg cgttggttac gtcttgaaag acaatgccag cgacaagtat   2700
tttgagctga agggcaatca gacttatctg ccgaagcaaa tgacgaataa agaagcctcg   2760
actggtttcg ttaatgacgg caatggtatg acctttttaca gcacgagcgg ttatcaagcg   2820
aagaacagct tcgttcagga cgcaaaaggc aactggtact actttgacaa caatggccac   2880
atggtttacg gtctgcaaca tctgaacggc gaggtgcaat acttcctgag caatggcgtg   2940
caactgcgtg aatccttctt ggaaaatgcc gacggcagca aaaactattt cggtcacctg   3000
ggcaaccgtt atagcaatgg ttactacagc ttcgataatg atagcaaatg cgctatttc    3060 gatgcgagcg gtgttatggc agtgggtctg aaaactatta cggtaacac ccagtatttc    3120 gatcaagacg gctaccaagt gaagggtgca tggattaccg gcagcgatgg taagaagcgt   3180
tacttcgacg acggtagcgg caatatggca gttaatcgct ttgctaacga caagaatggc   3240
gattggtatt acctgaatag cgacggtatt gcactggtgg gtgttcagac catcaacggc   3300
aaaacgtatt actttggcca agatggtaaa caaatcaaag gcaaaatcat taccgataat   3360
ggtaaactga atactttct ggcgaacagc ggtgagctgg cgcgtaacat ttttgcgacc    3420
gacagccaga caactggta ttacttcggc tcggatggtg ttgcggttac gggttcgcag    3480
acgattgcgg gtaaaaagtt gtactttgcg tccgacggta acaggtgaa gggtagcttt    3540 gttacttaca atggtaaagt gcactattac catgcggaca gcggcgaact gcaagtcaac   3600
cgtttcgagg cggataaaga cggtaattgg tactatctgg acagcaacgg tgaggcactg   3660
acgggtagcc agcgtatcaa tggtcaacgt gtgttttca cccgcgaggg caaacaggtt    3720
aagggtgatg tcgcgtatga tgaacgcggc ttgctgcgct attacgacaa aaacagcggt   3780
aatatggtgt acaacaaggt ggtcacgctg gcgaacggtc gtcgtattgg tattgaccgc   3840
tggggtattg ctcgctatta ctaa                                          3864
```

<210> SEQ ID NO 55  
<211> LENGTH: 1287  
<212> TYPE: PRT  
<213> ORGANISM: Streptococcus mutans UA159

<400> SEQUENCE: 55

```
Met Ile Asp Gly Lys Tyr Tyr Tyr Ile Gly Ser Asp Gly Gln Pro Lys
1               5                   10                  15

Lys Asn Phe Ala Leu Thr Val Asn Asn Lys Val Leu Tyr Phe Asp Lys
            20                  25                  30

Asn Thr Gly Ala Leu Thr Asp Thr Ser Gln Tyr Gln Phe Lys Gln Gly
        35                  40                  45

Leu Thr Lys Leu Asn Asn Asp Tyr Thr Pro His Asn Gln Ile Val Asn
    50                  55                  60

Phe Glu Asn Thr Ser Leu Glu Thr Ile Asp Asn Tyr Val Thr Ala Asp
65                  70                  75                  80

Ser Trp Tyr Arg Pro Lys Asp Ile Leu Lys Asn Gly Lys Thr Trp Thr
                85                  90                  95

Ala Ser Ser Glu Ser Asp Leu Arg Pro Leu Leu Met Ser Trp Trp Pro
            100                 105                 110

Asp Lys Gln Thr Gln Ile Ala Tyr Leu Asn Tyr Met Asn Gln Gln Gly
        115                 120                 125

Leu Gly Thr Gly Glu Asn Tyr Thr Ala Asp Ser Ser Gln Glu Ser Leu
    130                 135                 140

Asn Leu Ala Ala Gln Thr Val Gln Val Lys Ile Glu Thr Lys Ile Ser
145                 150                 155                 160

Gln Thr Gln Gln Thr Gln Trp Leu Arg Asp Ile Ile Asn Ser Phe Val
                165                 170                 175

Lys Thr Gln Pro Asn Trp Asn Ser Gln Thr Glu Ser Asp Thr Ser Ala
            180                 185                 190

Gly Glu Lys Asp His Leu Gln Gly Gly Ala Leu Leu Tyr Ser Asn Ser
        195                 200                 205

Asp Lys Thr Ala Tyr Ala Asn Ser Asp Tyr Arg Leu Leu Asn Arg Thr
    210                 215                 220

Pro Thr Ser Gln Thr Gly Lys Pro Lys Tyr Phe Glu Asp Asn Ser Ser
225                 230                 235                 240

Gly Gly Tyr Asp Phe Leu Leu Ala Asn Asp Ile Asp Asn Ser Asn Pro
                245                 250                 255

Val Val Gln Ala Glu Gln Leu Asn Trp Leu His Tyr Leu Met Asn Tyr
            260                 265                 270

Gly Ser Ile Val Ala Asn Asp Pro Glu Ala Asn Phe Asp Gly Val Arg
        275                 280                 285

Val Asp Ala Val Asp Asn Val Asn Ala Asp Leu Leu Gln Ile Ala Ser
    290                 295                 300

Asp Tyr Leu Lys Ala His Tyr Gly Val Asp Lys Ser Glu Lys Asn Ala
305                 310                 315                 320

Ile Asn His Leu Ser Ile Leu Glu Ala Trp Ser Asp Asn Asp Pro Gln
                325                 330                 335

Tyr Asn Lys Asp Thr Lys Gly Ala Gln Leu Pro Ile Asp Asn Lys Leu
            340                 345                 350

Arg Leu Ser Leu Leu Tyr Ala Leu Thr Arg Pro Leu Glu Lys Asp Ala
        355                 360                 365

Ser Asn Lys Asn Glu Ile Arg Ser Gly Leu Glu Pro Val Ile Thr Asn
    370                 375                 380

Ser Leu Asn Asn Arg Ser Ala Glu Gly Lys Asn Ser Glu Arg Met Ala
385                 390                 395                 400

Asn Tyr Ile Phe Ile Arg Ala His Asp Ser Glu Val Gln Thr Val Ile
```

```
                405                 410                 415
Ala Lys Ile Ile Lys Ala Gln Ile Asn Pro Lys Thr Asp Gly Leu Thr
                420                 425                 430

Phe Thr Leu Asp Glu Leu Lys Gln Ala Phe Lys Ile Tyr Asn Glu Asp
                435                 440                 445

Met Arg Gln Ala Lys Lys Lys Tyr Thr Gln Ser Asn Ile Pro Thr Ala
450                 455                 460

Tyr Ala Leu Met Leu Ser Asn Lys Asp Ser Ile Thr Arg Leu Tyr Tyr
465                 470                 475                 480

Gly Asp Met Tyr Ser Asp Asp Gly Gln Tyr Met Ala Thr Lys Ser Pro
                485                 490                 495

Tyr Tyr Asp Ala Ile Asp Thr Leu Leu Lys Ala Arg Ile Lys Tyr Ala
                500                 505                 510

Ala Gly Gly Gln Asp Met Lys Ile Thr Tyr Val Glu Gly Asp Lys Ser
                515                 520                 525

His Met Asp Trp Asp Tyr Thr Gly Val Leu Thr Ser Val Arg Tyr Gly
                530                 535                 540

Thr Gly Ala Asn Glu Ala Thr Asp Gln Gly Ser Glu Ala Thr Lys Thr
545                 550                 555                 560

Gln Gly Met Ala Val Ile Thr Ser Asn Asn Pro Ser Leu Lys Leu Asn
                565                 570                 575

Gln Asn Asp Lys Val Ile Val Asn Met Gly Thr Ala His Lys Asn Gln
                580                 585                 590

Glu Tyr Arg Pro Leu Leu Leu Thr Thr Lys Asp Gly Leu Thr Ser Tyr
                595                 600                 605

Thr Ser Asp Ala Ala Ala Lys Ser Leu Tyr Arg Lys Thr Asn Asp Lys
610                 615                 620

Gly Glu Leu Val Phe Asp Ala Ser Asp Ile Gln Gly Tyr Leu Asn Pro
625                 630                 635                 640

Gln Val Ser Gly Tyr Leu Ala Val Trp Val Pro Val Gly Ala Ser Asp
                645                 650                 655

Asn Gln Asp Val Arg Val Ala Ser Asn Lys Ala Asn Ala Thr Gly
                660                 665                 670

Gln Val Tyr Glu Ser Ser Ser Ala Leu Asp Ser Gln Leu Ile Tyr Glu
                675                 680                 685

Gly Phe Ser Asn Phe Gln Asp Phe Val Thr Lys Asp Ser Asp Tyr Thr
                690                 695                 700

Asn Lys Lys Ile Ala Gln Asn Val Gln Leu Phe Lys Ser Trp Gly Val
705                 710                 715                 720

Thr Ser Phe Glu Met Ala Pro Gln Tyr Val Ser Ser Glu Asp Gly Ser
                725                 730                 735

Phe Leu Asp Ser Ile Ile Gln Asn Gly Tyr Ala Phe Glu Asp Arg Tyr
                740                 745                 750

Asp Leu Ala Met Ser Lys Asn Asn Lys Tyr Gly Ser Gln Gln Asp Met
                755                 760                 765

Ile Asn Ala Val Lys Ala Leu His Lys Ser Gly Ile Gln Val Ile Ala
                770                 775                 780

Asp Trp Val Pro Asp Gln Ile Tyr Asn Leu Pro Gly Lys Glu Val Val
785                 790                 795                 800

Thr Ala Thr Arg Val Asn Asp Tyr Gly Glu Tyr Arg Lys Asp Ser Glu
                805                 810                 815

Ile Lys Asn Thr Leu Tyr Ala Ala Asn Thr Lys Ser Asn Gly Lys Asp
                820                 825                 830
```

```
Tyr Gln Ala Lys Tyr Gly Gly Ala Phe Leu Ser Glu Leu Ala Ala Lys
        835                 840                 845

Tyr Pro Ser Ile Phe Asn Arg Thr Gln Ile Ser Asn Gly Lys Lys Ile
850                 855                 860

Asp Pro Ser Glu Lys Ile Thr Ala Trp Lys Ala Lys Tyr Phe Asn Gly
865                 870                 875                 880

Thr Asn Ile Leu Gly Arg Gly Val Gly Tyr Val Leu Lys Asp Asn Ala
            885                 890                 895

Ser Asp Lys Tyr Phe Glu Leu Lys Gly Asn Gln Thr Tyr Leu Pro Lys
            900                 905                 910

Gln Met Thr Asn Lys Glu Ala Ser Thr Gly Phe Val Asn Asp Gly Asn
            915                 920                 925

Gly Met Thr Phe Tyr Ser Thr Ser Gly Tyr Gln Ala Lys Asn Ser Phe
        930                 935                 940

Val Gln Asp Ala Lys Gly Asn Trp Tyr Tyr Phe Asp Asn Asn Gly His
945                 950                 955                 960

Met Val Tyr Gly Leu Gln His Leu Asn Gly Glu Val Gln Tyr Phe Leu
            965                 970                 975

Ser Asn Gly Val Gln Leu Arg Glu Ser Phe Leu Glu Asn Ala Asp Gly
            980                 985                 990

Ser Lys Asn Tyr Phe Gly His Leu Gly Asn Arg Tyr Ser Asn Gly Tyr
            995                 1000                1005

Tyr Ser Phe Asp Asn Asp Ser Lys Trp Arg Tyr Phe Asp Ala Ser
    1010                1015                1020

Gly Val Met Ala Val Gly Leu Lys Thr Ile Asn Gly Asn Thr Gln
    1025                1030                1035

Tyr Phe Asp Gln Asp Gly Tyr Gln Val Lys Gly Ala Trp Ile Thr
    1040                1045                1050

Gly Ser Asp Gly Lys Lys Arg Tyr Phe Asp Asp Gly Ser Gly Asn
    1055                1060                1065

Met Ala Val Asn Arg Phe Ala Asn Asp Lys Asn Gly Asp Trp Tyr
    1070                1075                1080

Tyr Leu Asn Ser Asp Gly Ile Ala Leu Val Gly Val Gln Thr Ile
    1085                1090                1095

Asn Gly Lys Thr Tyr Tyr Phe Gly Gln Asp Gly Lys Gln Ile Lys
    1100                1105                1110

Gly Lys Ile Ile Thr Asp Asn Gly Lys Leu Lys Tyr Phe Leu Ala
    1115                1120                1125

Asn Ser Gly Glu Leu Ala Arg Asn Ile Phe Ala Thr Asp Ser Gln
    1130                1135                1140

Asn Asn Trp Tyr Tyr Phe Gly Ser Asp Gly Val Ala Val Thr Gly
    1145                1150                1155

Ser Gln Thr Ile Ala Gly Lys Lys Leu Tyr Phe Ala Ser Asp Gly
    1160                1165                1170

Lys Gln Val Lys Gly Ser Phe Val Thr Tyr Asn Gly Lys Val His
    1175                1180                1185

Tyr Tyr His Ala Asp Ser Gly Glu Leu Gln Val Asn Arg Phe Glu
    1190                1195                1200

Ala Asp Lys Asp Gly Asn Trp Tyr Tyr Leu Asp Ser Asn Gly Glu
    1205                1210                1215

Ala Leu Thr Gly Ser Gln Arg Ile Asn Gly Gln Arg Val Phe Phe
    1220                1225                1230
```

```
Thr Arg Glu Gly Lys Gln Val Lys Gly Asp Val Ala Tyr Asp Glu
1235                1240                1245

Arg Gly Leu Leu Arg Tyr Tyr Asp Lys Asn Ser Gly Asn Met Val
1250                1255                1260

Tyr Asn Lys Val Val Thr Leu Ala Asn Gly Arg Arg Ile Gly Ile
1265                1270                1275

Asp Arg Trp Gly Ile Ala Arg Tyr Tyr
1280                1285

<210> SEQ ID NO 56
<211> LENGTH: 4068
<212> TYPE: DNA
<213> ORGANISM: Streptococcus gallolyticus ATCC BAA-2069

<400> SEQUENCE: 56
atgatcgacg gcaaatacta ctatattgac gaggacggta acgtaaagaa gaatttcgcg      60
attacggtgg atggtcagtt gctgtacttc gacgctgaaa cgggtgctct gaccagcacg     120
tccacctata gcttctccga gggcctgact aatctggtcg ataacttcag cattaacaac     180
cagtcctacg acagcaccga agagtcgttt gagctgatcg acggttacct gaccgtcaat     240
acttggtacc gtccgaccaa aattctggaa acggtgaaaa cctgggtcga tagcaccgaa     300
acggatttcc gtccgctgct gatggcctgg tggccggatg ttgacaccca aattgactac     360
ttgaactaca tgagcgatta cttcgatctg ggtacgacct atagcgctga cgattcccaa     420
gcgagcctga atctggcagc tgaggcggtt caggtgaaaa ttgaacaaga aattacccgt     480
caagagaaca ccgcctggct gcgcgagatc atctctagct tgttaccacc caggataaa      540 tggaatatca ataccgagaa tgagggcacc gaccatctgc aaggtggtgc cctgctgtac     600
gttaacagcg acttgactcc gtgggcaaac agcgattatc gcctgctgaa ccgcaccccg     660
acgtaccaga cgggtgagac taattacttt aaagcagatc gtactggtgg ctacgaattt     720
ctgctggcaa atgacgtgga taattctaac ccggtcgttc aagccgaaca gttgaaccag     780
ctgtactact tgatgaattg gggctctatt gtattcggtg atgacgacgc caattttgat     840
ggcgtgcgtg ttgacgcggt ggacaatgtg aacgctgacc tgttcagat ttacacgaac      900 ctgttcgaag cggcgtatgg tgttaacgag tctgaggcgc aggccctggc tcacattagc     960
atcctggaag cgtggtctta taacgacccg gactacaacc acgacacgaa tggcgctgcc    1020
ctggcaatcg acaatggtct cgtctgagc tttctgtact ctttgacgcg ccctacggac     1080
gagcgcagcg gtttggagcc actgatcacc tctgagattg gcctgaccga tcgttccgag    1140
gactctgcat acggtgacac catgccgagc tatgttttcg tccgtgcaca tgacagcgag    1200
gttcagacca ttattgcgag cattatcgca gaacagatca cccggaaac cgatggctat     1260 accttcaccc tggacgagct gaaccaggcg tttgagattt acaacgcgga tatgaacagc    1320
gtggataaag agtatacgca ttacaatatc ccggctgcgt atagcctgct gctgaccaac    1380
atggaaagcg tcccgcgtgt ttactacggt gacctgtata cggataacgg tcagtacatg    1440
gcgactaaga gcccgtatta tgaccagatc accaccctgc tgcaagcgcg cattcgttac    1500
gcggcgggtg ccaatctat ggctgttacg tactacaccc ctgcgtcgag catgtctacc     1560
gacaatgcgg atagcgtcct gaatgagact ggtgtgctga cttctgtgcg ttacggctat    1620
ggcatcatga ccgccgacca agaggccacg gacgactccg ttctgacctc tggtattgtt    1680
actattatca gcaacaaccc taatttgcag ctggatgatt ccgaagtgat tgcagtccag    1740
gttggtgtgg cgcacgctgg tcagtattat cgtccgctgt tgtacccgac ggcggatggt    1800
```

```
ctgcaaagct acctgaacga tagcgatacc gacattacta agctggtcga tgataatggt    1860
tatatctact ttacggcaga tgagattaaa ggctacgaaa cggttgacat gaatggctac    1920
ctgagcgttt gggtcccggt tggtgcagac gagaatcagg acatccgtgt cagcgcagac    1980
accagcgcgt acaccgaggg tgaattgatc tatcaagcaa ccgcagcgct ggatagccaa    2040
gtgatctacg agggtttcag caacttccaa gatttcgtta cctctaacag cgagtacact    2100
aacaagctga tcgcggagaa cgtcgatctg tttaccagct ggggcattac gagctttgag    2160
atggcgccac agtatgtgag caccgatgac ggtacttttc tggatagcat cattcaaaac    2220
ggttatgcat ttgacgatcg ctacgacctg gcaatgagcc agaataacaa gtatggtagc    2280
gctgaagatt tgcgtaatgc catcaaggcc ctgcacgctg ctggcattca ggtcattgct    2340
gactgggtgc cggatcaaat ctattcgctg ccaggcgaag aagtcgttac ggcgactcgc    2400
gtgaatgact atggcgaaga accgaaggc gcgtacatta caatacgtt gtatgtggcg    2460
aacagcaaaa gcagcggcga ggactaccag gcacagtatg gtggtgagtt cctggattac    2520
ttgcaagaaa cctacccgga aatgttcgaa gttgcgatga ttagcacggg tgagccgatt    2580
gatccgagca ccaagatcaa gatttggaaa gcagaatact ttaatggtac gaacattctg    2640
ggtaagggcg ctggttacgt gctgagcgat gccgcgactg gcacgtactt taccgtgact    2700
gagaatggca cgtttctgcc gaagcagctg accaccgact ccgccattac gggtttctat    2760
tacgacggta cgggtatgtc ttactttagc acctcgggtt atcgcgctaa agcgagcttc    2820
attgtttaca cggctacta ctactatttt gatgataacg gctacatggt cactggcacg    2880
gtggaaatca acggtaagac ctactatttc ctgccgaatg gtattcagct gcgtgatgcg    2940
atttacgaag acgagaacgg taatcagtac tatttcggtc cgttgggcaa ccagtatttc    3000
aacaactatt acagctttga cgttgaagag gtggtggacg gtgtaacgac tacggtaacg    3060
aagtggcgtc attttgacga gaacggcgtg atggcgcgtg gtttggtcga gattgatggt    3120
gtctaccagt attacgatga aaacggctac caggtcaaag gtgagctgat caccgatgct    3180
gatggtaatt tgcgttattt caaagaagat agcggtgaaa tggttgttag cgattttgtg    3240
aagatcggcg ataacaactg gtactacttt gacgaaaacg gtattgcagt cacgggtgcc    3300
caaaccattg ccggccagaa cttgtatttc gatgacaacg gtgtgcaggc gaaaggtgcc    3360
tttgtcacga acgccgatgg cacgcgcagc tattatgacg cggacagcgg tgagaagatc    3420
gtggcagatt tcttcactac gggcgataat gactggtatt atgcagatga aaatggcaat    3480
ctggtgactg gtagccaaac tatcaatggt caaaacctgt actttgctga ggacggtttg    3540
caggccaagg gtgtgtttgt taccgatacg gctggtaaca ttcactatta tgatgcgaac    3600
tctggcgagt tggcggttaa taccttcgtt ggtgatggcg acgactggta ttactttgat    3660
gagaatggca tcgcagttac cggcgcacaa gtcattaacg gtcaacacct gtatttcgca    3720
gacaacggca tccaagtgaa aggtgaaatc gtcaccgacg caaacggcaa ccgctattac    3780
tacgatgcag attccggcga aatggcagtt aacaccctg tggagattga cggtgtttgg    3840
tactattttg gtgccgatgg tatcgcggtg acgggtgcac aagtaattga tggtcagaat    3900
ttgtacttta acgcagacgg tagccaagtc aagggtgacg ttgtccgtat caacggttg    3960
cgttactact acgacgctaa tagcggcgaa caggtgcgca atcagtgggt cacgctgccg    4020
gatggtactg ttgttttctt taatgcgcgt ggctatactt ggggctaa             4068
```

<210> SEQ ID NO 57

<211> LENGTH: 1355
<212> TYPE: PRT
<213> ORGANISM: Streptococcus gallolyticus ATCC BAA-2069

<400> SEQUENCE: 57

```
Met Ile Asp Gly Lys Tyr Tyr Ile Asp Glu Asp Gly Asn Val Lys
1               5                   10                  15

Lys Asn Phe Ala Ile Thr Val Asp Gly Gln Leu Leu Tyr Phe Asp Ala
                20                  25                  30

Glu Thr Gly Ala Leu Thr Ser Thr Ser Thr Tyr Ser Phe Ser Glu Gly
            35                  40                  45

Leu Thr Asn Leu Val Asp Asn Phe Ser Ile Asn Asn Gln Ser Tyr Asp
        50                  55                  60

Ser Thr Glu Glu Ser Phe Glu Leu Ile Asp Gly Tyr Leu Thr Val Asn
65                  70                  75                  80

Thr Trp Tyr Arg Pro Thr Lys Ile Leu Glu Asn Gly Glu Thr Trp Val
                85                  90                  95

Asp Ser Thr Glu Thr Asp Phe Arg Pro Leu Leu Met Ala Trp Trp Pro
            100                 105                 110

Asp Val Asp Thr Gln Ile Asp Tyr Leu Asn Tyr Met Ser Asp Tyr Phe
        115                 120                 125

Asp Leu Gly Thr Thr Tyr Ser Ala Asp Asp Ser Gln Ala Ser Leu Asn
130                 135                 140

Leu Ala Ala Glu Ala Val Gln Val Lys Ile Glu Gln Glu Ile Thr Arg
145                 150                 155                 160

Gln Glu Asn Thr Ala Trp Leu Arg Glu Ile Ile Ser Ser Phe Val Thr
                165                 170                 175

Thr Gln Asp Lys Trp Asn Ile Asn Thr Glu Asn Glu Gly Thr Asp His
            180                 185                 190

Leu Gln Gly Gly Ala Leu Leu Tyr Val Asn Ser Asp Leu Thr Pro Trp
        195                 200                 205

Ala Asn Ser Asp Tyr Arg Leu Leu Asn Arg Thr Pro Thr Tyr Gln Thr
    210                 215                 220

Gly Glu Thr Asn Tyr Phe Lys Ala Asp Arg Thr Gly Gly Tyr Glu Phe
225                 230                 235                 240

Leu Leu Ala Asn Asp Val Asp Asn Ser Asn Pro Val Val Gln Ala Glu
                245                 250                 255

Gln Leu Asn Gln Leu Tyr Tyr Leu Met Asn Trp Gly Ser Ile Val Phe
            260                 265                 270

Gly Asp Asp Asp Ala Asn Phe Asp Gly Val Arg Val Asp Ala Val Asp
        275                 280                 285

Asn Val Asn Ala Asp Leu Leu Gln Ile Tyr Thr Asn Leu Phe Glu Ala
    290                 295                 300

Ala Tyr Gly Val Asn Glu Ser Glu Ala Gln Ala Leu Ala His Ile Ser
305                 310                 315                 320

Ile Leu Glu Ala Trp Ser Tyr Asn Asp Pro Asp Tyr Asn His Asp Thr
                325                 330                 335

Asn Gly Ala Ala Leu Ala Ile Asp Asn Gly Leu Arg Leu Ser Phe Leu
            340                 345                 350

Tyr Ser Leu Thr Arg Pro Thr Asp Glu Arg Ser Gly Leu Glu Pro Leu
        355                 360                 365

Ile Thr Ser Glu Ile Gly Leu Thr Asp Arg Ser Glu Asp Ser Ala Tyr
    370                 375                 380

Gly Asp Thr Met Pro Ser Tyr Val Phe Val Arg Ala His Asp Ser Glu
```

-continued

```
            385                 390                 395                 400
Val Gln Thr Ile Ile Ala Ser Ile Ile Ala Glu Gln Ile Asn Pro Glu
                    405                 410                 415

Thr Asp Gly Tyr Thr Phe Thr Leu Asp Glu Leu Asn Gln Ala Phe Glu
                    420                 425                 430

Ile Tyr Asn Ala Asp Met Asn Ser Val Asp Lys Glu Tyr Thr His Tyr
                    435                 440                 445

Asn Ile Pro Ala Ala Tyr Ser Leu Leu Leu Thr Asn Met Glu Ser Val
450                 455                 460

Pro Arg Val Tyr Tyr Gly Asp Leu Tyr Thr Asp Asn Gly Gln Tyr Met
465                 470                 475                 480

Ala Thr Lys Ser Pro Tyr Tyr Asp Gln Ile Thr Thr Leu Leu Gln Ala
                    485                 490                 495

Arg Ile Arg Tyr Ala Ala Gly Gly Gln Ser Met Ala Val Thr Tyr Tyr
                    500                 505                 510

Thr Pro Ala Ser Ser Met Ser Thr Asp Asn Ala Asp Ser Val Leu Asn
                    515                 520                 525

Glu Thr Gly Val Leu Thr Ser Val Arg Tyr Gly Tyr Gly Ile Met Thr
                    530                 535                 540

Ala Asp Gln Glu Ala Thr Asp Asp Ser Val Leu Thr Ser Gly Ile Val
545                 550                 555                 560

Thr Ile Ile Ser Asn Asn Pro Asn Leu Gln Leu Asp Asp Ser Glu Val
                    565                 570                 575

Ile Ala Val Gln Val Gly Val Ala His Ala Gly Gln Tyr Tyr Arg Pro
                    580                 585                 590

Leu Leu Tyr Pro Thr Ala Asp Gly Leu Gln Ser Tyr Leu Asn Asp Ser
                    595                 600                 605

Asp Thr Asp Ile Thr Lys Leu Val Asp Asp Asn Gly Tyr Ile Tyr Phe
                    610                 615                 620

Thr Ala Asp Glu Ile Lys Gly Tyr Glu Thr Val Asp Met Asn Gly Tyr
625                 630                 635                 640

Leu Ser Val Trp Val Pro Val Gly Ala Asp Glu Asn Gln Asp Ile Arg
                    645                 650                 655

Val Ser Ala Asp Thr Ser Ala Tyr Thr Glu Gly Glu Leu Ile Tyr Gln
                    660                 665                 670

Ala Thr Ala Ala Leu Asp Ser Gln Val Ile Tyr Glu Gly Phe Ser Asn
                    675                 680                 685

Phe Gln Asp Phe Val Thr Ser Asn Ser Glu Tyr Thr Asn Lys Leu Ile
690                 695                 700

Ala Glu Asn Val Asp Leu Phe Thr Ser Trp Gly Ile Thr Ser Phe Glu
705                 710                 715                 720

Met Ala Pro Gln Tyr Val Ser Thr Asp Gly Thr Phe Leu Asp Ser
                    725                 730                 735

Ile Ile Gln Asn Gly Tyr Ala Phe Asp Asp Arg Tyr Asp Leu Ala Met
                    740                 745                 750

Ser Gln Asn Asn Lys Tyr Gly Ser Ala Glu Asp Leu Arg Asn Ala Ile
                    755                 760                 765

Lys Ala Leu His Ala Ala Gly Ile Gln Val Ile Ala Asp Trp Val Pro
770                 775                 780

Asp Gln Ile Tyr Ser Leu Pro Gly Glu Glu Val Val Thr Ala Thr Arg
785                 790                 795                 800

Val Asn Asp Tyr Gly Glu Glu Thr Glu Gly Ala Tyr Ile Asn Asn Thr
                    805                 810                 815
```

```
Leu Tyr Val Ala Asn Ser Lys Ser Ser Gly Glu Asp Tyr Gln Ala Gln
            820                 825                 830

Tyr Gly Gly Glu Phe Leu Asp Tyr Leu Gln Glu Thr Tyr Pro Glu Met
        835                 840                 845

Phe Glu Val Ala Met Ile Ser Thr Gly Glu Pro Ile Asp Pro Ser Thr
850                 855                 860

Lys Ile Lys Ile Trp Lys Ala Glu Tyr Phe Asn Gly Thr Asn Ile Leu
865                 870                 875                 880

Gly Lys Gly Ala Gly Tyr Val Leu Ser Asp Ala Ala Thr Gly Thr Tyr
                885                 890                 895

Phe Thr Val Thr Glu Asn Gly Thr Phe Leu Pro Lys Gln Leu Thr Thr
            900                 905                 910

Asp Ser Ala Ile Thr Gly Phe Tyr Asp Gly Thr Gly Met Ser Tyr
            915                 920                 925

Phe Ser Thr Ser Gly Tyr Arg Ala Lys Ala Ser Phe Ile Val Tyr Asn
    930                 935                 940

Gly Tyr Tyr Tyr Tyr Phe Asp Asp Asn Gly Tyr Met Val Thr Gly Thr
945                 950                 955                 960

Val Glu Ile Asn Gly Lys Thr Tyr Tyr Phe Leu Pro Asn Gly Ile Gln
                965                 970                 975

Leu Arg Asp Ala Ile Tyr Glu Asp Glu Asn Gly Asn Gln Tyr Tyr Phe
            980                 985                 990

Gly Pro Leu Gly Asn Gln Tyr Phe Asn Asn Tyr Tyr Ser Phe Asp Val
        995                 1000                1005

Glu Glu Val Val Asp Gly Val Thr Thr Thr Val Thr Lys Trp Arg
    1010                1015                1020

His Phe Asp Glu Asn Gly Val Met Ala Arg Gly Leu Val Glu Ile
    1025                1030                1035

Asp Gly Val Tyr Gln Tyr Tyr Asp Glu Asn Gly Tyr Gln Val Lys
    1040                1045                1050

Gly Glu Leu Ile Thr Asp Ala Asp Gly Asn Leu Arg Tyr Phe Lys
    1055                1060                1065

Glu Asp Ser Gly Glu Met Val Val Ser Asp Phe Val Lys Ile Gly
    1070                1075                1080

Asp Asn Asn Trp Tyr Tyr Phe Asp Glu Asn Gly Ile Ala Val Thr
    1085                1090                1095

Gly Ala Gln Thr Ile Ala Gly Gln Asn Leu Tyr Phe Asp Asp Asn
    1100                1105                1110

Gly Val Gln Ala Lys Gly Ala Phe Val Thr Asn Ala Asp Gly Thr
    1115                1120                1125

Arg Ser Tyr Tyr Asp Ala Asp Ser Gly Glu Lys Ile Val Ala Asp
    1130                1135                1140

Phe Phe Thr Thr Gly Asp Asn Asp Trp Tyr Tyr Ala Asp Glu Asn
    1145                1150                1155

Gly Asn Leu Val Thr Gly Ser Gln Thr Ile Asn Gly Gln Asn Leu
    1160                1165                1170

Tyr Phe Ala Glu Asp Gly Leu Gln Ala Lys Gly Val Phe Val Thr
    1175                1180                1185

Asp Thr Ala Gly Asn Ile His Tyr Tyr Asp Ala Asn Ser Gly Glu
    1190                1195                1200

Leu Ala Val Asn Thr Phe Val Gly Asp Gly Asp Trp Tyr Tyr
    1205                1210                1215
```

```
Phe Asp Glu Asn Gly Ile Ala Val Thr Gly Ala Gln Val Ile Asn
    1220                1225                1230

Gly Gln His Leu Tyr Phe Ala Asp Asn Gly Ile Gln Val Lys Gly
        1235                1240                1245

Glu Ile Val Thr Asp Ala Asn Gly Asn Arg Tyr Tyr Tyr Asp Ala
    1250                1255                1260

Asp Ser Gly Glu Met Ala Val Asn Thr Phe Val Glu Ile Asp Gly
    1265                1270                1275

Val Trp Tyr Tyr Phe Gly Ala Asp Gly Ile Ala Val Thr Gly Ala
    1280                1285                1290

Gln Val Ile Asp Gly Gln Asn Leu Tyr Phe Asn Ala Asp Gly Ser
    1295                1300                1305

Gln Val Lys Gly Asp Val Val Arg Ile Asn Gly Leu Arg Tyr Tyr
    1310                1315                1320

Tyr Asp Ala Asn Ser Gly Glu Gln Val Arg Asn Gln Trp Val Thr
    1325                1330                1335

Leu Pro Asp Gly Thr Val Val Phe Phe Asn Ala Arg Gly Tyr Thr
    1340                1345                1350

Trp Gly
    1355

<210> SEQ ID NO 58
<211> LENGTH: 1772
<212> TYPE: PRT
<213> ORGANISM: Lactococcus reuteri

<400> SEQUENCE: 58

Met Glu Ile Lys Lys His Phe Lys Leu Tyr Lys Ser Gly Lys Gln Trp
1               5                   10                  15

Val Thr Ala Ala Val Ala Thr Val Ala Val Ser Thr Ala Leu Leu Tyr
                20                  25                  30

Gly Gly Val Ala His Ala Asp Gln Gln Val Gln Ser Ser Thr Thr Gln
            35                  40                  45

Glu Gln Thr Ser Thr Val Asn Ala Asp Thr Thr Lys Thr Val Asn Leu
        50                  55                  60

Asp Thr Asn Thr Asp Gln Pro Ala Gln Thr Thr Asp Lys Asn Gln Val
65                  70                  75                  80

Ala Asn Asp Thr Thr Thr Asn Gln Ser Lys Thr Asp Ser Thr Ser Thr
                85                  90                  95

Thr Val Lys Asn Pro Thr Phe Ile Pro Val Ser Thr Leu Ser Ser Ser
            100                 105                 110

Asp Asn Glu Lys Gln Ser Gln Asn Tyr Asn Lys Pro Asp Asn Gly Asn
        115                 120                 125

Tyr Gly Asn Val Asp Ala Ala Tyr Phe Asn Asn Gln Leu His Ile
    130                 135                 140

Ser Gly Trp His Ala Thr Asn Ala Ser Gln Gly Thr Asp Ser Arg Gln
145                 150                 155                 160

Val Ile Val Arg Asp Ile Thr Thr Lys Thr Glu Leu Gly Arg Thr Asn
                165                 170                 175

Val Thr Asn Asn Val Leu Arg Pro Asp Val Lys Asn Val His Asn Val
            180                 185                 190

Tyr Asn Ala Asp Asn Ser Gly Phe Asp Val Asn Ile Asn Ile Asp Phe
        195                 200                 205

Ser Lys Met Lys Asp Tyr Arg Asp Ser Ile Glu Ile Val Ser Arg Tyr
    210                 215                 220
```

-continued

```
Ser Gly Asn Gly Lys Ser Val Asp Trp Trp Ser Gln Pro Ile Thr Phe
225                 230                 235                 240

Asp Lys Asn Asn Tyr Ala Tyr Leu Asp Thr Phe Glu Val Lys Asn Gly
            245                 250                 255

Glu Leu His Ala Thr Gly Trp Asn Ala Thr Asn Lys Ala Ile Asn Tyr
        260                 265                 270

Asn His His Phe Val Ile Leu Phe Asp Arg Thr Asn Gly Lys Glu Val
    275                 280                 285

Thr Arg Gln Glu Val Arg Asp Gly Gln Ser Arg Pro Asp Val Ala Lys
290                 295                 300

Val Tyr Pro Gln Val Val Gly Ala Asn Asn Ser Gly Phe Asp Val Thr
305                 310                 315                 320

Phe Asn Ile Gly Asp Leu Asp Tyr Thr His Gln Tyr Gln Ile Leu Ser
                325                 330                 335

Arg Tyr Ser Asn Ala Asp Asn Gly Glu Gly Asp Tyr Val Thr Tyr Trp
            340                 345                 350

Phe Ala Pro Gln Ser Ile Ala Pro Ala Asn Gln Ser Asn Gln Gly Tyr
        355                 360                 365

Leu Asp Ser Phe Asp Ile Ser Lys Asn Gly Glu Val Thr Val Thr Gly
    370                 375                 380

Trp Asn Ala Thr Asp Leu Ser Glu Leu Gln Thr Asn His Tyr Val Ile
385                 390                 395                 400

Leu Phe Asp Gln Thr Ala Gly Gln Gln Val Ala Ser Ala Lys Val Asp
                405                 410                 415

Leu Ile Ser Arg Pro Asp Val Ala Lys Ala Tyr Pro Thr Val Lys Thr
            420                 425                 430

Ala Glu Thr Ser Gly Phe Lys Val Thr Phe Lys Val Ser Asn Leu Gln
        435                 440                 445

Pro Gly His Gln Tyr Ser Val Val Ser Arg Phe Ser Ala Asp Glu Asn
    450                 455                 460

Gly Asn Gly Asn Asp Lys Arg His Thr Asp Tyr Trp Tyr Ser Pro Val
465                 470                 475                 480

Thr Leu Asn Gln Thr Ala Ser Asn Ile Asp Thr Ile Thr Met Thr Ser
                485                 490                 495

Asn Gly Leu His Ile Thr Gly Trp Met Ala Ser Asp Asn Ser Ile Asn
            500                 505                 510

Glu Ala Thr Pro Tyr Ala Ile Ile Leu Asn Asn Gly Arg Glu Val Thr
        515                 520                 525

Arg Gln Lys Leu Thr Leu Ile Ala Arg Pro Asp Val Ala Ala Val Tyr
    530                 535                 540

Pro Ser Leu Tyr Asn Ser Ala Val Ser Gly Phe Asp Thr Thr Ile Lys
545                 550                 555                 560

Leu Thr Asn Ala Gln Tyr Gln Ala Leu Asn Gly Gln Leu Gln Val Leu
                565                 570                 575

Leu Arg Phe Ser Lys Ala Val Asp Gly Asn Pro Asn Gly Thr Asn Thr
            580                 585                 590

Val Thr Asp Gln Phe Ser Lys Asn Tyr Ala Thr Thr Gly Gly Asn Phe
        595                 600                 605

Asp Tyr Val Lys Val Asn Gly Asn Gln Ile Glu Phe Ser Gly Trp His
    610                 615                 620

Ala Thr Asn Gln Ser Asn Asp Lys Asn Ser Gln Trp Ile Ile Val Leu
625                 630                 635                 640
```

-continued

Val Asn Gly Lys Glu Val Lys Arg Gln Leu Val Asn Asp Thr Lys Asp
                    645                 650                 655

Gly Ala Ala Gly Phe Asn Arg Asn Asp Val Tyr Lys Val Asn Pro Ala
            660                 665                 670

Ile Glu Asn Ser Ile Met Ser Gly Phe Gln Gly Ile Ile Thr Leu Pro
        675                 680                 685

Val Thr Val Lys Asp Glu Asn Val Gln Leu Val His Arg Phe Ser Asn
    690                 695                 700

Asp Ala Lys Thr Gly Glu Gly Asn Tyr Val Asp Phe Trp Ser Glu Val
705                 710                 715                 720

Met Ser Val Lys Asp Ser Phe Gln Lys Gly Asn Gly Pro Leu Asn Gln
                725                 730                 735

Phe Gly Leu Gln Thr Ile Asn Gly Gln Gln Tyr Tyr Ile Asp Pro Thr
            740                 745                 750

Thr Gly Gln Pro Arg Lys Asn Phe Leu Leu Gln Asn Gly Asn Asp Trp
        755                 760                 765

Ile Tyr Phe Asp Lys Asp Thr Gly Ala Gly Thr Asn Ala Leu Lys Leu
    770                 775                 780

Gln Phe Asp Lys Gly Thr Ile Ser Ala Asp Glu Gln Tyr Arg Arg Gly
785                 790                 795                 800

Asn Glu Ala Tyr Ser Tyr Asp Asp Lys Ser Ile Glu Asn Val Asn Gly
                805                 810                 815

Tyr Leu Thr Ala Asp Thr Trp Tyr Arg Pro Lys Gln Ile Leu Lys Asp
            820                 825                 830

Gly Thr Thr Trp Thr Asp Ser Lys Glu Thr Asp Met Arg Pro Ile Leu
        835                 840                 845

Met Val Trp Trp Pro Asn Thr Val Thr Gln Ala Tyr Tyr Leu Asn Tyr
    850                 855                 860

Met Lys Gln Tyr Gly Asn Leu Leu Pro Ala Ser Leu Pro Ser Phe Ser
865                 870                 875                 880

Thr Asp Ala Asp Ser Ala Glu Leu Asn His Tyr Ser Glu Leu Val Gln
                885                 890                 895

Gln Asn Ile Glu Lys Arg Ile Ser Glu Thr Gly Ser Thr Asp Trp Leu
            900                 905                 910

Arg Thr Leu Met His Glu Phe Val Thr Lys Asn Ser Met Trp Asn Lys
        915                 920                 925

Asp Ser Glu Asn Val Asp Tyr Gly Gly Leu Gln Leu Gln Gly Gly Phe
    930                 935                 940

Leu Lys Tyr Val Asn Ser Asp Leu Thr Lys Tyr Ala Asn Ser Asp Trp
945                 950                 955                 960

Arg Leu Met Asn Arg Thr Ala Thr Asn Ile Asp Gly Lys Asn Tyr Gly
                965                 970                 975

Gly Ala Glu Phe Leu Leu Ala Asn Asp Ile Asp Asn Ser Asn Pro Val
            980                 985                 990

Val Gln Ala Glu Glu Leu Asn Trp Leu Tyr Tyr Leu Met Asn Phe Gly
        995                 1000                1005

Thr Ile Thr Gly Asn Asn Pro Glu Ala Asn Phe Asp Gly Ile Arg
        1010                1015                1020

Val Asp Ala Val Asp Asn Val Asp Val Asp Leu Leu Ser Ile Ala
        1025                1030                1035

Arg Asp Tyr Phe Asn Ala Ala Tyr Asn Met Glu Gln Ser Asp Ala
        1040                1045                1050

Ser Ala Asn Lys His Ile Asn Ile Leu Glu Asp Trp Gly Trp Asp

-continued

```
            1055                1060                1065
Asp Pro Ala Tyr Val Asn Lys Ile Gly Asn Pro Gln Leu Thr Met
            1070                1075                1080
Asp Asp Arg Leu Arg Asn Ala Ile Met Asp Thr Leu Ser Gly Ala
            1085                1090                1095
Pro Asp Lys Asn Gln Ala Leu Asn Lys Leu Ile Thr Gln Ser Leu
            1100                1105                1110
Val Asn Arg Ala Asn Asp Asn Thr Glu Asn Ala Val Ile Pro Ser
            1115                1120                1125
Tyr Asn Phe Val Arg Ala His Asp Ser Asn Ala Gln Asp Gln Ile
            1130                1135                1140
Arg Gln Ala Ile Gln Ala Ala Thr Gly Lys Pro Tyr Gly Glu Phe
            1145                1150                1155
Asn Leu Asp Asp Glu Lys Lys Gly Met Glu Ala Tyr Ile Asn Asp
            1160                1165                1170
Gln Asn Ser Thr Asn Lys Lys Trp Asn Leu Tyr Asn Met Pro Ser
            1175                1180                1185
Ala Tyr Thr Ile Leu Leu Thr Asn Lys Asp Ser Val Pro Arg Val
            1190                1195                1200
Tyr Tyr Gly Asp Leu Tyr Gln Asp Gly Gly Gln Tyr Met Glu His
            1205                1210                1215
Lys Thr Arg Tyr Phe Asp Thr Ile Thr Asn Leu Leu Lys Thr Arg
            1220                1225                1230
Val Lys Tyr Val Ala Gly Gly Gln Thr Met Ser Val Asp Lys Asn
            1235                1240                1245
Gly Ile Leu Thr Asn Val Arg Phe Gly Lys Gly Ala Met Asn Ala
            1250                1255                1260
Thr Asp Thr Gly Thr Asp Glu Thr Arg Thr Glu Gly Ile Gly Val
            1265                1270                1275
Val Ile Ser Asn Asn Thr Asn Leu Lys Leu Asn Asp Gly Glu Ser
            1280                1285                1290
Val Val Leu His Met Gly Ala Ala His Lys Asn Gln Lys Tyr Arg
            1295                1300                1305
Ala Val Ile Leu Thr Thr Glu Asp Gly Val Lys Asn Tyr Thr Asn
            1310                1315                1320
Asp Thr Asp Ala Pro Val Ala Tyr Thr Asp Ala Asn Gly Asp Leu
            1325                1330                1335
His Phe Thr Asn Thr Asn Leu Asp Gly Gln Gln Tyr Thr Ala Val
            1340                1345                1350
Arg Gly Tyr Ala Asn Pro Asp Val Thr Gly Tyr Leu Ala Val Trp
            1355                1360                1365
Val Pro Ala Gly Ala Ala Asp Asp Gln Asp Ala Arg Thr Ala Pro
            1370                1375                1380
Ser Asp Glu Ala His Thr Thr Lys Thr Ala Tyr Arg Ser Asn Ala
            1385                1390                1395
Ala Leu Asp Ser Asn Val Ile Tyr Glu Gly Phe Ser Asn Phe Ile
            1400                1405                1410
Tyr Trp Pro Thr Thr Glu Ser Glu Arg Thr Asn Val Arg Ile Ala
            1415                1420                1425
Gln Asn Ala Asp Leu Phe Lys Ser Trp Gly Ile Thr Thr Phe Glu
            1430                1435                1440
Leu Ala Pro Gln Tyr Asn Ser Ser Lys Asp Gly Thr Phe Leu Asp
            1445                1450                1455
```

| | | | | | | | | | |
|---|---|---|---|---|---|---|---|---|---|
| Ser | Ile | Ile | Asp | Asn | Gly | Tyr | Ala | Phe | Thr | Asp | Arg | Tyr | Asp | Leu |

Ser Ile Ile Asp Asn Gly Tyr Ala Phe Thr Asp Arg Tyr Asp Leu
    1460            1465               1470

Gly Met Ser Thr Pro Asn Lys Tyr Gly Ser Asp Glu Asp Leu Arg
    1475            1480               1485

Asn Ala Leu Gln Ala Leu His Lys Ala Gly Leu Gln Ala Ile Ala
    1490            1495               1500

Asp Trp Val Pro Asp Gln Ile Tyr Asn Leu Pro Gly Lys Glu Ala
    1505            1510               1515

Val Thr Val Thr Arg Ser Asp Asp His Gly Thr Thr Trp Glu Val
    1520            1525               1530

Ser Pro Ile Lys Asn Val Val Tyr Ile Thr Asn Thr Ile Gly Gly
    1535            1540               1545

Gly Glu Tyr Gln Lys Lys Tyr Gly Gly Glu Phe Leu Asp Thr Leu
    1550            1555               1560

Gln Lys Glu Tyr Pro Gln Leu Phe Ser Gln Val Tyr Pro Val Thr
    1565            1570               1575

Gln Thr Thr Ile Asp Pro Ser Val Lys Ile Lys Glu Trp Ser Ala
    1580            1585               1590

Lys Tyr Phe Asn Gly Thr Asn Ile Leu His Arg Gly Ala Gly Tyr
    1595            1600               1605

Val Leu Arg Ser Asn Asp Gly Lys Tyr Tyr Asn Leu Gly Thr Ser
    1610            1615               1620

Thr Gln Gln Phe Leu Pro Ser Gln Leu Ser Val Gln Asp Asn Glu
    1625            1630               1635

Gly Tyr Gly Phe Val Lys Glu Gly Asn Asn Tyr His Tyr Tyr Asp
    1640            1645               1650

Glu Asn Lys Gln Met Val Lys Asp Ala Phe Ile Gln Asp Ser Val
    1655            1660               1665

Gly Asn Trp Tyr Tyr Phe Asp Lys Asn Gly Asn Met Val Ala Asn
    1670            1675               1680

Gln Ser Pro Val Glu Ile Ser Ser Asn Gly Ala Ser Gly Thr Tyr
    1685            1690               1695

Leu Phe Leu Asn Asn Gly Thr Ser Phe Arg Ser Gly Leu Val Lys
    1700            1705               1710

Thr Asp Ala Gly Thr Tyr Tyr Tyr Asp Gly Asp Gly Arg Met Val
    1715            1720               1725

Arg Asn Gln Thr Val Ser Asp Gly Ala Met Thr Tyr Val Leu Asp
    1730            1735               1740

Glu Asn Gly Lys Leu Val Ser Glu Ser Phe Asp Ser Ser Ala Thr
    1745            1750               1755

Glu Ala His Pro Leu Lys Pro Gly Asp Leu Asn Gly Gln Lys
    1760            1765               1770

<210> SEQ ID NO 59
<211> LENGTH: 5208
<212> TYPE: DNA
<213> ORGANISM: Lactobacillus reuteri

<400> SEQUENCE: 59
atggatcagc aagtacaaag cagcaccacc caggagcaga cgagcacggt taacgcggac      60
acgactaaaa ccgtcaatct ggataccaac actgaccagc cggctcagac gaccgataag     120
aatcaggtcg cgaatgatac caccaccaac caaagcaaga cggacagcac cagcacgacg     180
gttaagaatc cgacgtttat tcctgttagc actttgtcca gctccgataa cgaaaagcag     240

-continued

```
agccagaatt acaataaacc agataacggt aattacggta atgttgatgc ggcctacttc    300
aataacaatc agctgcacat tagcggttgg cacgcaacca acgcgagcca gggtacggat    360
agccgccaag taatcgtacg cgacattacc accaagaccg agctgggtcg tactaatgtg    420
accaacaatg ttctgcgtcc ggacgtgaaa aatgttcaca acgtctacaa cgctgacaac    480
agcggctttg atgtgaatat caatattgat ttcagcaaga tgaaagacta tcgtgacagc    540
atcgagatcg tttctcgtta tagcggcaac ggcaagagcg ttgactggtg gtcgcagccg    600
atcacgtttg acaaaaacaa ttatgcttat ctggacactt tcgaggtgaa gaacggtgaa    660
ctgcatgcaa cgggctggaa tgccaccaac aaggctatca attacaatca ccacttcgtt    720
attctgtttg atcgtacgaa tggcaaagaa gtcacccgcc aagaggtgcg tgatggtcaa    780
agccgtccgg atgtggcgaa ggtatacccg caagtcgttg gcgcgaacaa tagcggtttt    840
gacgttacgt ttaacattgg tgatttggac tacacccatc agtaccagat cctgtctcgt    900
tacagcaacg cagacaacgg tgaaggcgat tatgtgacct attggtttgc gccgcagagc    960
atcgctccgg cgaatcaaag caaccaaggt tacctggaca gcttcgatat ttcgaaaaac   1020
ggtgaggtga ccgtgacggg ttggaatgcg acggatctga gcgagttgca acgaatcac    1080 tacgtgatcc tgtttgatca gacggcgggt caacaggttg catccgctaa ggtcgacctg   1140
atcagccgtc cagacgtcgc gaaggcgtac cctaccgtta aaacggcaga aacctccggt   1200
ttcaaggtca cgtttaaggt tagcaatctg caaccgggcc accaatacag cgtcgttagc   1260
cgctttagcg ccgatgaaaa cggtaatggc aacgacaaac gccacacgga ctactggtac   1320
tctccggtta ccctgaacca aacggctagc aacattgaca ctatcaccat gacttccaac   1380
ggtctgcaca tcaccggctg gatggcgagc gataatagca ttaacgaagc gaccccgtac   1440
gcgattatcc tgaacaacgg tcgcgaggtg acgcgccaga aactgaccct gatcgcgcgt   1500
ccggatgttg cggcagtgta tccgagcctg tacaatagcg cggttagcgg cttcgacacc   1560
accatcaagc tgactaacgc gcaatatcaa gcattgaacg gccagctgca agtgctgctg   1620
cgctttagca aggcggtgga cggtaacccg aatggtacca ataccgtcac ggatcaattt   1680
agcaaaaact acgcaacgac cggtggtaat ttcgattacg tcaaggttaa tggtaaccaa   1740
attgagtttt ctggctggca cgcgacgaat cagagcaatg ataagaacag ccaatggatt   1800
atcgtcttgg ttaacggtaa agaggtcaaa cgccagctgg tcaatgacac gaaagacggc   1860
gcagccggct tcaatcgtaa tgatgtgtat aaagtgaacc cagcgatcga aaatagcatt   1920
atgtctggct tccagggcat tatcacgttg ccggttacgg tgaaagacga aaacgtgcag   1980
ctggtgcacc gcttctccaa tgacgcaaaa acgggtgagg gcaattatgt cgatttctgg   2040
agcgaggtga tgtctgtgaa ggactctttc caaaagggta atggtccgct gaaccagttt   2100
ggcctgcaaa ccatcaacgg ccaacaatac tatattgacc cgacgaccgg ccagccgcgt   2160
aagaatttcc tgctgcaaaa cggcaacgat tggatttact tcgacaaaga cactggcgca   2220
ggcaccaacg cgctgaaatt gcagtttgat aagggcacga ttagcgctga cgaacaatac   2280
cgtcgcggca acgaggcgta ctcctacgat gataagagca ttgaaaatgt caacggttac   2340
ttgacggcgg acacgtggta ccgcccgaag cagatcctga aggatggcac cacttggacc   2400
gattccaaag aaaccgatat gcgtccgatc ttgatggtct ggtggccaaa cacggtgact   2460
caggcgtact atctgaacta catgaaacaa tatggcaatc tgctgccggc gagcctgccg   2520
agctttagca ccgacgccga tagcgcggag ttgaatcatt attccgagct ggtccaacag   2580
```

```
aatatcgaga aacgtattag cgagactggt agcactgatt ggctgcgtac cctgatgcac   2640
gagttcgtga cgaagaatag catgtggaac aaagatagcg agaacgttga ctacggtggc   2700
ctgcaactgc aaggtggttt cctgaagtac gttaacagcg acctgacgaa gtacgcaaac   2760
tctgattggc gtctgatgaa ccgtaccgcg acgaacattg acggtaagaa ttacggtggt   2820
gccgagtttc tgctggcgaa tgacatcgac aactctaacc cggtggtgca ggccgaagaa   2880
ttgaattggc tgtattatct gatgaacttc ggtaccatca ccggtaacaa cccagaagct   2940
aacttcgacg gcatccgtgt cgacgcggtc gataatgtgg atgttgatct gctgagcatt   3000
gcccgtgact actttaatgc agcgtataac atggaacaaa gcgatgctag cgcgaataag   3060
cacatcaata ttctggaaga ttggggctgg gacgatccgg cgtacgtgaa caaaatcggc   3120
aatccacagt tgaccatgga tgaccgcctg cgtaatgcaa ttatggacac cctgagcggt   3180
gcgccggata agaaccaagc gctgaacaag ctgattactc agtctctggt gaatcgcgca   3240
aatgataata ctgaaaacgc ggtgatccct tcctacaact tgtccgcgc tcatgacagc   3300 aatgcccagg accagatccg tcaagcgatc caggcggcaa ccggcaaacc ttatggcgag   3360
ttcaacttgg atgatgagaa aaagggtatg gaggcttaca tcaatgacca aaatagcacc   3420
aataagaaat ggaacctgta caacatgccg agcgcatata ccatcctgct gacgaataag   3480
gactcggtcc cgcgtgtcta ctatggcgac ttgtaccagg atggtggcca gtacatggaa   3540
cacaaaactc gttactttga caccatcacg aatctgctga aacccgcgt caagtatgtc   3600 gcaggcggcc agaccatgtc tgtggataag aatggcattt tgactaatgt ccgtttcggt   3660
aagggtgcga tgaacgcaac tgacacgggt accgatgaaa cccgcaccga aggtatcggc   3720
gttgttatca gcaacaatac gaatttgaaa ctgaatgacg gcgaaagcgt tgtgctgcac   3780
atgggcgctg cccataagaa tcagaagtat cgtgcagtga tcctgaccac ggaggacggt   3840
gtgaagaatt acaccaacga caccgatgcg ccggtcgcat acaccgacgc gaacggcgat   3900
ttgcatttca ccaatactaa cctggacggt cagcaatata ccgccgttcg tggctacgca   3960
aacccggacg ttacgggtta tctggccgtc tgggttcctg ctggtgccgc cgatgaccaa   4020
gacgcacgta ccgctccgag cgacgaggcc cacaccacga aaacggcgta tcgttccaat   4080
gcggcattgg actccaacgt catctacgaa ggcttttcga actttatcta ttggccgacg   4140
accgagagcg agcgcacgaa tgtccgcatc gcgcagaacg cggatctgtt caaatcgtgg   4200
ggtatcacca ccttcgagct ggcgccacag tacaatagca gcaaggacgg tacgtttctg   4260
gattcgatca ttgacaatgg ttacgcgttt accgatcgtt atgacctggg tatgtctacc   4320
ccgaacaagt acggtagcga tgaggatctg cgtaacgccc tgcaagcact gcacaaggcc   4380
ggtctgcaag ccatcgcaga ttgggttccg gaccaaatct acaatctgcc gggcaaagag   4440
gctgtcacgg ttactcgtag cgatgaccac ggcactacct gggaggttag cccgatcaag   4500
aatgtggtgt atatcactaa taccatcggt ggtggcgaat accagaaaaa gtatggtggt   4560
gaatttctgg acaccttgca aaagaatat ccgcagctgt ttagccaagt ttacccggtg   4620
acccaaacga cgattgaccc tagcgttaag attaaagagt ggtccgcgaa gtacttcaat   4680
ggtactaata tcctgcatcg cggtgcgggt tacgtcctgc gtagcaatga tggtaagtat   4740
tacaacctgg gtactagcac ccagcagttc ctgccgagcc agctgagcgt tcaagataat   4800
gagggttacg gtttcgttaa agagggtaac aactatcact attatgacga gaacaaacaa   4860
atggttaagc acgcgtttat ccaggatagc gtcggcaatt ggtactattt tgataagaac   4920
ggcaatatgg ttgcaaaacca agcccggtt gaaatcagca gcaacggtgc gagcggcacc   4980
```

-continued

```
tacttgtttt tgaataatgg taccagcttc cgcagcggcc tggtcaaaac ggatgcaggc     5040
acctattact acgatggtga cggtcgcatg gttcgtaatc aaacggtttc tgacggtgcc     5100
atgacgtacg ttctggacga aaatggtaaa ctggtcagcg aatcttttga tagcagcgcg     5160
accgaggccc atccgctgaa accgggcgat ctgaacggtc aaaagtaa                  5208
```

<210> SEQ ID NO 60
<211> LENGTH: 1735
<212> TYPE: PRT
<213> ORGANISM: Lactobacillus reuteri

<400> SEQUENCE: 60

```
Met Asp Gln Gln Val Gln Ser Ser Thr Thr Gln Glu Gln Thr Ser Thr
1               5                   10                  15

Val Asn Ala Asp Thr Thr Lys Thr Val Asn Leu Asp Thr Asn Thr Asp
            20                  25                  30

Gln Pro Ala Gln Thr Thr Asp Lys Asn Gln Val Ala Asn Asp Thr Thr
        35                  40                  45

Thr Asn Gln Ser Lys Thr Asp Ser Thr Ser Thr Thr Val Lys Asn Pro
    50                  55                  60

Thr Phe Ile Pro Val Ser Thr Leu Ser Ser Ser Asp Asn Glu Lys Gln
65                  70                  75                  80

Ser Gln Asn Tyr Asn Lys Pro Asp Asn Gly Asn Tyr Gly Asn Val Asp
                85                  90                  95

Ala Ala Tyr Phe Asn Asn Asn Gln Leu His Ile Ser Gly Trp His Ala
            100                 105                 110

Thr Asn Ala Ser Gln Gly Thr Asp Ser Arg Gln Val Ile Val Arg Asp
        115                 120                 125

Ile Thr Thr Lys Thr Glu Leu Gly Arg Thr Asn Val Thr Asn Asn Val
    130                 135                 140

Leu Arg Pro Asp Val Lys Asn Val His Asn Val Tyr Asn Ala Asp Asn
145                 150                 155                 160

Ser Gly Phe Asp Val Asn Ile Asn Ile Asp Phe Ser Lys Met Lys Asp
                165                 170                 175

Tyr Arg Asp Ser Ile Glu Ile Val Ser Arg Tyr Ser Gly Asn Gly Lys
            180                 185                 190

Ser Val Asp Trp Trp Ser Gln Pro Ile Thr Phe Asp Lys Asn Asn Tyr
        195                 200                 205

Ala Tyr Leu Asp Thr Phe Glu Val Lys Asn Gly Glu Leu His Ala Thr
    210                 215                 220

Gly Trp Asn Ala Thr Asn Lys Ala Ile Asn Tyr Asn His His Phe Val
225                 230                 235                 240

Ile Leu Phe Asp Arg Thr Asn Gly Lys Glu Val Thr Arg Gln Glu Val
                245                 250                 255

Arg Asp Gly Gln Ser Arg Pro Asp Val Ala Lys Val Tyr Pro Gln Val
            260                 265                 270

Val Gly Ala Asn Asn Ser Gly Phe Asp Val Thr Phe Asn Ile Gly Asp
        275                 280                 285

Leu Asp Tyr Thr His Gln Tyr Gln Ile Leu Ser Arg Tyr Ser Asn Ala
    290                 295                 300

Asp Asn Gly Glu Gly Asp Tyr Val Thr Tyr Trp Phe Ala Pro Gln Ser
305                 310                 315                 320

Ile Ala Pro Ala Asn Gln Ser Asn Gln Gly Tyr Leu Asp Ser Phe Asp
                325                 330                 335
```

-continued

```
Ile Ser Lys Asn Gly Glu Val Thr Val Thr Gly Trp Asn Ala Thr Asp
            340                 345                 350

Leu Ser Glu Leu Gln Thr Asn His Tyr Val Ile Leu Phe Asp Gln Thr
        355                 360                 365

Ala Gly Gln Gln Val Ala Ser Ala Lys Val Asp Leu Ile Ser Arg Pro
    370                 375                 380

Asp Val Ala Lys Ala Tyr Pro Thr Val Lys Thr Ala Glu Thr Ser Gly
385                 390                 395                 400

Phe Lys Val Thr Phe Lys Val Ser Asn Leu Gln Pro Gly His Gln Tyr
                405                 410                 415

Ser Val Val Ser Arg Phe Ser Ala Asp Glu Asn Gly Asn Gly Asn Asp
            420                 425                 430

Lys Arg His Thr Asp Tyr Trp Tyr Ser Pro Val Thr Leu Asn Gln Thr
        435                 440                 445

Ala Ser Asn Ile Asp Thr Ile Thr Met Thr Ser Asn Gly Leu His Ile
    450                 455                 460

Thr Gly Trp Met Ala Ser Asp Asn Ser Ile Asn Glu Ala Thr Pro Tyr
465                 470                 475                 480

Ala Ile Ile Leu Asn Asn Gly Arg Glu Val Thr Arg Gln Lys Leu Thr
                485                 490                 495

Leu Ile Ala Arg Pro Asp Val Ala Ala Val Tyr Pro Ser Leu Tyr Asn
            500                 505                 510

Ser Ala Val Ser Gly Phe Asp Thr Thr Ile Lys Leu Thr Asn Ala Gln
        515                 520                 525

Tyr Gln Ala Leu Asn Gly Leu Gln Val Leu Leu Arg Phe Ser Lys
    530                 535                 540

Ala Val Asp Gly Asn Pro Asn Gly Thr Asn Thr Val Thr Asp Gln Phe
545                 550                 555                 560

Ser Lys Asn Tyr Ala Thr Thr Gly Gly Asn Phe Asp Tyr Val Lys Val
                565                 570                 575

Asn Gly Asn Gln Ile Glu Phe Ser Gly Trp His Ala Thr Asn Gln Ser
            580                 585                 590

Asn Asp Lys Asn Ser Gln Trp Ile Ile Val Leu Val Asn Gly Lys Glu
        595                 600                 605

Val Lys Arg Gln Leu Val Asn Asp Thr Lys Asp Gly Ala Ala Gly Phe
    610                 615                 620

Asn Arg Asn Asp Val Tyr Lys Val Asn Pro Ala Ile Glu Asn Ser Ile
625                 630                 635                 640

Met Ser Gly Phe Gln Gly Ile Ile Thr Leu Pro Val Thr Val Lys Asp
                645                 650                 655

Glu Asn Val Gln Leu Val His Arg Phe Ser Asn Asp Ala Lys Thr Gly
            660                 665                 670

Glu Gly Asn Tyr Val Asp Phe Trp Ser Glu Val Met Ser Val Lys Asp
        675                 680                 685

Ser Phe Gln Lys Gly Asn Gly Pro Leu Asn Gln Phe Gly Leu Gln Thr
    690                 695                 700

Ile Asn Gly Gln Gln Tyr Tyr Ile Asp Pro Thr Thr Gly Gln Pro Arg
705                 710                 715                 720

Lys Asn Phe Leu Leu Gln Asn Gly Asn Asp Trp Ile Tyr Phe Asp Lys
                725                 730                 735

Asp Thr Gly Ala Gly Thr Asn Ala Leu Lys Leu Gln Phe Asp Lys Gly
            740                 745                 750
```

-continued

```
Thr Ile Ser Ala Asp Glu Gln Tyr Arg Arg Gly Asn Glu Ala Tyr Ser
            755                 760                 765

Tyr Asp Asp Lys Ser Ile Glu Asn Val Asn Gly Tyr Leu Thr Ala Asp
        770                 775                 780

Thr Trp Tyr Arg Pro Lys Gln Ile Leu Lys Asp Gly Thr Thr Trp Thr
785                 790                 795                 800

Asp Ser Lys Glu Thr Asp Met Arg Pro Ile Leu Met Val Trp Trp Pro
            805                 810                 815

Asn Thr Val Thr Gln Ala Tyr Tyr Leu Asn Tyr Met Lys Gln Tyr Gly
            820                 825                 830

Asn Leu Leu Pro Ala Ser Leu Pro Ser Phe Ser Thr Asp Ala Asp Ser
            835                 840                 845

Ala Glu Leu Asn His Tyr Ser Glu Leu Val Gln Gln Asn Ile Glu Lys
        850                 855                 860

Arg Ile Ser Glu Thr Gly Ser Thr Asp Trp Leu Arg Thr Leu Met His
865                 870                 875                 880

Glu Phe Val Thr Lys Asn Ser Met Trp Asn Lys Asp Ser Glu Asn Val
            885                 890                 895

Asp Tyr Gly Gly Leu Gln Leu Gln Gly Gly Phe Leu Lys Tyr Val Asn
            900                 905                 910

Ser Asp Leu Thr Lys Tyr Ala Asn Ser Asp Trp Arg Leu Met Asn Arg
        915                 920                 925

Thr Ala Thr Asn Ile Asp Gly Lys Asn Tyr Gly Gly Ala Glu Phe Leu
        930                 935                 940

Leu Ala Asn Asp Ile Asp Asn Ser Asn Pro Val Val Gln Ala Glu Glu
945                 950                 955                 960

Leu Asn Trp Leu Tyr Tyr Leu Met Asn Phe Gly Thr Ile Thr Gly Asn
            965                 970                 975

Asn Pro Glu Ala Asn Phe Asp Gly Ile Arg Val Asp Ala Val Asp Asn
            980                 985                 990

Val Asp Val Asp Leu Leu Ser Ile Ala Arg Asp Tyr Phe Asn Ala Ala
        995                 1000                1005

Tyr Asn Met Glu Gln Ser Asp Ala Ser Ala Asn Lys His Ile Asn
        1010                1015                1020

Ile Leu Glu Asp Trp Gly Trp Asp Asp Pro Ala Tyr Val Asn Lys
        1025                1030                1035

Ile Gly Asn Pro Gln Leu Thr Met Asp Asp Arg Leu Arg Asn Ala
        1040                1045                1050

Ile Met Asp Thr Leu Ser Gly Ala Pro Asp Lys Asn Gln Ala Leu
        1055                1060                1065

Asn Lys Leu Ile Thr Gln Ser Leu Val Asn Arg Ala Asn Asp Asn
        1070                1075                1080

Thr Glu Asn Ala Val Ile Pro Ser Tyr Asn Phe Val Arg Ala His
        1085                1090                1095

Asp Ser Asn Ala Gln Asp Gln Ile Arg Gln Ala Ile Gln Ala Ala
        1100                1105                1110

Thr Gly Lys Pro Tyr Gly Glu Phe Asn Leu Asp Asp Glu Lys Lys
        1115                1120                1125

Gly Met Glu Ala Tyr Ile Asn Asp Gln Asn Ser Thr Asn Lys Lys
        1130                1135                1140

Trp Asn Leu Tyr Asn Met Pro Ser Ala Tyr Thr Ile Leu Leu Thr
        1145                1150                1155

Asn Lys Asp Ser Val Pro Arg Val Tyr Tyr Gly Asp Leu Tyr Gln
```

-continued

```
            1160                1165                1170
Asp Gly Gly Gln Tyr Met Glu His Lys Thr Arg Tyr Phe Asp Thr
            1175                1180                1185
Ile Thr Asn Leu Leu Lys Thr Arg Val Lys Tyr Val Ala Gly Gly
            1190                1195                1200
Gln Thr Met Ser Val Asp Lys Asn Gly Ile Leu Thr Asn Val Arg
            1205                1210                1215
Phe Gly Lys Gly Ala Met Asn Ala Thr Asp Thr Gly Thr Asp Glu
            1220                1225                1230
Thr Arg Thr Glu Gly Ile Gly Val Val Ile Ser Asn Asn Thr Asn
            1235                1240                1245
Leu Lys Leu Asn Asp Gly Glu Ser Val Val Leu His Met Gly Ala
            1250                1255                1260
Ala His Lys Asn Gln Lys Tyr Arg Ala Val Ile Leu Thr Thr Glu
            1265                1270                1275
Asp Gly Val Lys Asn Tyr Thr Asn Asp Thr Asp Ala Pro Val Ala
            1280                1285                1290
Tyr Thr Asp Ala Asn Gly Asp Leu His Phe Thr Asn Thr Asn Leu
            1295                1300                1305
Asp Gly Gln Gln Tyr Thr Ala Val Arg Gly Tyr Ala Asn Pro Asp
            1310                1315                1320
Val Thr Gly Tyr Leu Ala Val Trp Val Pro Ala Gly Ala Ala Asp
            1325                1330                1335
Asp Gln Asp Ala Arg Thr Ala Pro Ser Asp Glu Ala His Thr Thr
            1340                1345                1350
Lys Thr Ala Tyr Arg Ser Asn Ala Ala Leu Asp Ser Asn Val Ile
            1355                1360                1365
Tyr Glu Gly Phe Ser Asn Phe Ile Tyr Trp Pro Thr Thr Glu Ser
            1370                1375                1380
Glu Arg Thr Asn Val Arg Ile Ala Gln Asn Ala Asp Leu Phe Lys
            1385                1390                1395
Ser Trp Gly Ile Thr Thr Phe Glu Leu Ala Pro Gln Tyr Asn Ser
            1400                1405                1410
Ser Lys Asp Gly Thr Phe Leu Asp Ser Ile Ile Asp Asn Gly Tyr
            1415                1420                1425
Ala Phe Thr Asp Arg Tyr Asp Leu Gly Met Ser Thr Pro Asn Lys
            1430                1435                1440
Tyr Gly Ser Asp Glu Asp Leu Arg Asn Ala Leu Gln Ala Leu His
            1445                1450                1455
Lys Ala Gly Leu Gln Ala Ile Ala Asp Trp Val Pro Asp Gln Ile
            1460                1465                1470
Tyr Asn Leu Pro Gly Lys Glu Ala Val Thr Val Thr Arg Ser Asp
            1475                1480                1485
Asp His Gly Thr Thr Trp Glu Val Ser Pro Ile Lys Asn Val Val
            1490                1495                1500
Tyr Ile Thr Asn Thr Ile Gly Gly Gly Glu Tyr Gln Lys Lys Tyr
            1505                1510                1515
Gly Gly Glu Phe Leu Asp Thr Leu Gln Lys Glu Tyr Pro Gln Leu
            1520                1525                1530
Phe Ser Gln Val Tyr Pro Val Thr Gln Thr Thr Ile Asp Pro Ser
            1535                1540                1545
Val Lys Ile Lys Glu Trp Ser Ala Lys Tyr Phe Asn Gly Thr Asn
            1550                1555                1560
```

```
Ile Leu His Arg Gly Ala Gly Tyr Val Leu Arg Ser Asn Asp Gly
    1565                1570                1575

Lys Tyr Tyr Asn Leu Gly Thr Ser Thr Gln Gln Phe Leu Pro Ser
    1580                1585                1590

Gln Leu Ser Val Gln Asp Asn Glu Gly Tyr Gly Phe Val Lys Glu
    1595                1600                1605

Gly Asn Asn Tyr His Tyr Tyr Asp Glu Asn Lys Gln Met Val Lys
    1610                1615                1620

Asp Ala Phe Ile Gln Asp Ser Val Gly Asn Trp Tyr Tyr Phe Asp
    1625                1630                1635

Lys Asn Gly Asn Met Val Ala Asn Gln Ser Pro Val Glu Ile Ser
    1640                1645                1650

Ser Asn Gly Ala Ser Gly Thr Tyr Leu Phe Leu Asn Asn Gly Thr
    1655                1660                1665

Ser Phe Arg Ser Gly Leu Val Lys Thr Asp Ala Gly Thr Tyr Tyr
    1670                1675                1680

Tyr Asp Gly Asp Gly Arg Met Val Arg Asn Gln Thr Val Ser Asp
    1685                1690                1695

Gly Ala Met Thr Tyr Val Leu Asp Glu Asn Gly Lys Leu Val Ser
    1700                1705                1710

Glu Ser Phe Asp Ser Ser Ala Thr Glu Ala His Pro Leu Lys Pro
    1715                1720                1725

Gly Asp Leu Asn Gly Gln Lys
    1730                1735

<210> SEQ ID NO 61
<211> LENGTH: 1574
<212> TYPE: PRT
<213> ORGANISM: Streptococcus gordonii

<400> SEQUENCE: 61

Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Gly Lys
            20                  25                  30

Leu Glu Ser Gly Val Ile Tyr Ala Asp Asp Ala Asn Gln Val Thr Asn
        35                  40                  45

Val Lys Glu Gln Ser Ala Val Gln Ser Lys Asp Ser Glu Gln Thr Thr
    50                  55                  60

Ser Asp Lys Ala Thr Asp Ser Ser Gln Leu Glu Val Lys Glu Gln Ala
65                  70                  75                  80

Ser Ser Ser Lys Glu Thr Tyr Gln Ala Ser Ala Ala Thr Asn Pro Thr
                85                  90                  95

Ala Asn Glu Gln Thr Thr Gln Gln Asp Lys Glu Val Glu Thr Ser Arg
            100                 105                 110

Thr Asp Ser Arg His Glu Leu Thr Gln Lys Thr Ser Asp Asp Ser Ser
        115                 120                 125

Glu Lys Ser Gly Ser Ser Gln Glu Pro Lys Val Ala Asp Gln Ala Glu
    130                 135                 140

Ser Thr Asp Lys Thr Gln Ala Ala Leu Gln Ala Lys Gln Asp Ser Arg
145                 150                 155                 160

Ala Asn Asp Gln Glu Glu Thr Thr Glu Asn Val Ala Lys Ala Thr Val
                165                 170                 175

Ser Asp Lys Ile Ile Ala Thr Pro Lys Lys Glu Arg Leu Pro Glu Pro
```

```
                180               185                190
Ala Gln Arg Lys Glu Ser Ile Thr Glu Lys Met Leu Ala Ala Gln Ala
            195                 200                 205

Gln Ala Ala Pro Val Asn Thr Glu His Asp Asp Val Leu Ala His
            210                 215                 220

Ile Lys Thr Ile Asp Gly Lys Lys Tyr Tyr Val Gln Asp Asp Gly Thr
225                 230                 235                 240

Val Lys Lys Asn Phe Ala Val Glu Leu Asn Gly Lys Ile Leu Tyr Phe
                245                 250                 255

Asp Ala Glu Thr Gly Ala Leu Val Asp Ser Asn Glu Tyr Gln Phe Gln
            260                 265                 270

Gln Gly Thr Ser Ser Leu Asn Asn Glu Phe Thr Gln Lys Asn Ala Phe
            275                 280                 285

Tyr Gly Thr Thr Asp Lys Asp Ile Glu Thr Val Asp Gly Tyr Leu Thr
            290                 295                 300

Ala Asp Ser Trp Tyr Arg Pro Lys Phe Ile Leu Lys Asp Gly Lys Thr
305                 310                 315                 320

Trp Thr Ala Ser Thr Glu Thr Asp Leu Arg Pro Leu Met Ala Trp
                325                 330                 335

Trp Pro Asp Lys Arg Thr Gln Ile Asn Tyr Leu Asn Tyr Met Asn Gln
                340                 345                 350

Glu Asn Leu Gly Ile Gly Ala Phe Glu Ser Lys Thr Glu Gln Val Leu
            355                 360                 365

Leu Thr Asn Ala Val Gln Gln Val Gln Arg Lys Ile Glu Glu Arg Ile
            370                 375                 380

Ser Lys Glu Gly Asp Thr Lys Trp Leu Arg Thr Leu Met Ser Ala Phe
385                 390                 395                 400

Val Lys Thr Gln Pro Asn Trp Asn Ile Lys Thr Glu Ser Glu Thr Thr
                405                 410                 415

Gly Thr Asn Lys Asp His Leu Gln Gly Gly Ala Leu Leu Tyr Thr Asn
                420                 425                 430

Ser Asp Lys Thr Ser His Ala Asn Ser Arg Tyr Arg Leu Leu Asn Arg
                435                 440                 445

Thr Pro Thr Ser Gln Thr Gly Thr Pro Lys Tyr Phe Ile Asp Lys Ser
            450                 455                 460

Asn Gly Gly Tyr Glu Phe Leu Leu Ala Asn Asp Phe Asp Asn Ser Asn
465                 470                 475                 480

Pro Ala Val Gln Ala Glu Gln Leu Asn Trp Leu His Tyr Met Met Asn
                485                 490                 495

Phe Gly Ser Ile Val Ala Asn Asp Pro Thr Ala Asn Phe Asp Gly Val
            500                 505                 510

Arg Val Asp Ala Val Asp Asn Val Asn Ala Asp Leu Leu Gln Ile Ala
            515                 520                 525

Ser Asp Tyr Phe Lys Ser Arg Tyr Lys Val Gly Glu Ser Glu Glu
            530                 535                 540

Ala Leu Lys His Leu Ser Ile Leu Glu Ala Trp Ser Asp Asn Asp Pro
545                 550                 555                 560

Asp Tyr Asn Lys Asp Thr Lys Gly Ala Gln Leu Ala Ile Asp Asn Lys
                565                 570                 575

Leu Arg Leu Ser Leu Leu Tyr Ser Phe Met Arg Lys Leu Ser Ile Arg
                580                 585                 590

Ser Gly Val Glu Pro Thr Ile Thr Asn Ser Leu Asn Asp Arg Ser Thr
            595                 600                 605
```

-continued

Glu Asn Lys Asn Gly Glu Arg Thr Ala Asn Tyr Ile Phe Val Arg Ala
            610                 615                 620

His Asp Ser Glu Val Gln Thr Val Ile Ala Asp Ile Ile Arg Glu Asn
625                 630                 635                 640

Ile Asn Pro Asn Thr Asp Gly Leu Thr Phe Thr Met Asp Glu Leu Lys
                645                 650                 655

Gln Ala Phe Lys Ile Tyr Asn Glu Asp Met Arg Lys Ala Asp Lys Lys
            660                 665                 670

Tyr Thr Gln Phe Asn Ile Pro Thr Ala His Ala Leu Met Leu Ser Asn
        675                 680                 685

Lys Asp Ser Ile Thr Arg Val Tyr Tyr Gly Asp Leu Tyr Thr Asp Asp
690                 695                 700

Gly Gln Tyr Met Glu Lys Lys Ser Pro Tyr His Asp Ala Ile Asp Ala
705                 710                 715                 720

Leu Leu Arg Ala Arg Ile Lys Tyr Val Ala Gly Gln Asp Met Lys
                725                 730                 735

Val Thr Tyr Met Gly Val Pro Arg Glu Ala Asp Lys Trp Ser Tyr Asn
                740                 745                 750

Gly Ile Leu Thr Ser Val Arg Tyr Gly Thr Gly Ala Asn Glu Ala Thr
            755                 760                 765

Asp Glu Gly Thr Ala Glu Thr Arg Thr Gln Gly Met Ala Val Ile Ala
770                 775                 780

Ser Asn Asn Pro Asn Leu Lys Leu Asn Glu Trp Asp Lys Leu Gln Val
785                 790                 795                 800

Asn Met Gly Ala Ala His Lys Asn Gln Tyr Tyr Arg Pro Val Leu Leu
                805                 810                 815

Thr Thr Lys Asp Gly Ile Ser Arg Tyr Leu Thr Asp Glu Val Pro
                820                 825                 830

Gln Ser Leu Trp Lys Lys Thr Asp Ala Asn Gly Ile Leu Thr Phe Asp
            835                 840                 845

Met Asn Asp Ile Ala Gly Tyr Ser Asn Val Gln Val Ser Gly Tyr Leu
850                 855                 860

Ala Val Trp Val Pro Val Gly Ala Lys Glu Asn Gln Asp Ala Arg Val
865                 870                 875                 880

Thr Ala Ser Lys Lys Asn Ala Ser Gly Gln Val Tyr Glu Ser Ser
                885                 890                 895

Pro Ala Leu Asp Ser Gln Leu Ile Tyr Glu Gly Phe Ser Asn Phe Gln
            900                 905                 910

Asp Phe Ala Thr Arg Asp Asp Gln Tyr Thr Asn Lys Val Ile Ala Lys
            915                 920                 925

Asn Val Asn Leu Phe Lys Glu Trp Gly Val Thr Ser Phe Glu Leu Pro
930                 935                 940

Pro Gln Tyr Val Ser Ser Gln Asp Gly Thr Phe Leu Asp Ser Ile Ile
945                 950                 955                 960

Gln Asn Gly Tyr Ala Phe Glu Asp Arg Tyr Asp Met Ala Met Ser Lys
                965                 970                 975

Asn Asn Lys Tyr Gly Ser Leu Asp Leu Leu Asn Ala Leu Arg Ala
            980                 985                 990

Leu His Ser Val Asn Ile Gln Ala Ile Ala Asp Trp Val Pro Asp Gln
        995                 1000                1005

Ile Tyr Asn Leu Pro Gly Lys Glu Val Val Thr Ala Thr Arg Val
        1010                1015                1020

```
Asn Asn Tyr Gly Thr Tyr Arg Glu Gly Ala Glu Ile Lys Glu Lys
    1025                1030                1035

Leu Tyr Val Ala Asn Ser Lys Thr Asn Gly Thr Asp Tyr Gln Gly
    1040                1045                1050

Lys Tyr Gly Gly Ala Phe Leu Asp Glu Leu Lys Ala Lys Tyr Pro
    1055                1060                1065

Glu Ile Phe Glu Arg Val Gln Ile Ser Asn Gly Gln Lys Met Thr
    1070                1075                1080

Thr Asp Glu Lys Ile Thr Lys Trp Ser Ala Lys Tyr Phe Asn Gly
    1085                1090                1095

Thr Asn Ile Leu Gly Arg Gly Ala Tyr Tyr Val Leu Lys Asp Trp
    1100                1105                1110

Gly Ser Lys Glu Tyr Leu Ser Asn Lys Asn Gly Glu Thr Ala Leu
    1115                1120                1125

Pro Lys Gln Leu Val Asn Lys Glu Ala Ser Thr Gly Phe Val Lys
    1130                1135                1140

Asp Thr Asn Gly Phe Lys Phe Tyr Ser Thr Ser Gly Asn Gln Ala
    1145                1150                1155

Lys Asp Thr Phe Ile Gln Asp Glu Asn Gly Asn Trp Tyr Tyr Phe
    1160                1165                1170

Asp Asn Gln Gly Tyr Leu Val Thr Gly Ala Arg Glu Ile Asp Gly
    1175                1180                1185

Lys Gln Leu Tyr Phe Met Lys Asn Gly Val Gln Leu Arg Asp Ala
    1190                1195                1200

Leu Gln Glu Asp Glu Asn Gly Asn Gln Tyr Tyr Tyr Asp Lys Thr
    1205                1210                1215

Gly Ala Lys Val Leu Asn Arg Tyr Tyr Thr Ser Asp Gly Gln Asn
    1220                1225                1230

Trp Arg Tyr Phe Asp Ala Lys Gly Val Met Ala Arg Gly Leu Val
    1235                1240                1245

Lys Ile Gly Asp Gly Gln Gln Tyr Phe Asp Gln Asn Gly Tyr Gln
    1250                1255                1260

Val Lys Gly Lys Val Val Arg Ala Lys Asp Gly Lys Leu Arg Tyr
    1265                1270                1275

Phe Asp Lys Asp Ser Gly Asn Ala Val Ile Asn Arg Phe Ala Gln
    1280                1285                1290

Gly Asp Asn Pro Ser Asp Trp Tyr Tyr Phe Gly Ala Asp Gly Val
    1295                1300                1305

Ala Leu Thr Gly Leu Gln Lys Ile Gly Gln Gln Thr Leu Tyr Phe
    1310                1315                1320

Gly Gln Asp Gly Lys Gln Val Lys Gly Gln Val Val Met Leu Ala
    1325                1330                1335

Asp Lys Ser Ile Arg Tyr Phe Asp Ala Asn Ser Gly Glu Met Ala
    1340                1345                1350

Val Asn Lys Phe Ala Glu Gly Ala Lys Asn Glu Trp Tyr Tyr Phe
    1355                1360                1365

Asp Gln Asp Gly Lys Ala Val Thr Gly Leu Lys Thr Ile Asn Asn
    1370                1375                1380

Gln Val Leu Tyr Phe Asp Gln Asp Gly Lys Gln Val Lys Gly Gln
    1385                1390                1395

Val Val Thr Leu Ala Asp Lys Ser Ile Arg Tyr Phe Asp Ala Asn
    1400                1405                1410

Ser Gly Glu Met Ala Val Asn Lys Phe Ala Glu Gly Ala Lys Asn
```

```
          1415                1420                1425

Glu Trp Tyr Tyr Phe Asp Gln Asp Gly Lys Ala Val Thr Gly Leu
        1430                1435                1440

Gln Thr Ile Asn Lys Gln Val Leu Tyr Phe Gly Gln Asp Gly Lys
        1445                1450                1455

Gln Val Lys Gly Gln Val Val Thr Leu Ala Asp Lys Ser Ile Arg
        1460                1465                1470

Tyr Phe Asp Ala Asn Ser Gly Glu Met Ala Val Asn Lys Phe Ala
        1475                1480                1485

Glu Gly Ala Lys Asn Glu Trp Tyr Tyr Phe Asp Gln Asp Gly Lys
        1490                1495                1500

Ala Val Thr Gly Leu Lys Thr Ile Asn Asn Gln Val Leu Tyr Phe
        1505                1510                1515

Gly Gln Asp Gly Lys Gln Val Lys Gly Gln Val Val Tyr Val Asp
        1520                1525                1530

Gly Ala Glu Arg Tyr Phe Asp Pro Lys Ser Gly Asp Met Val Arg
        1535                1540                1545

Asn Lys Trp Ile Arg Leu Glu Asp Gly Thr Trp Met Tyr Phe Asp
        1550                1555                1560

Arg Asn Gly Arg Gly Arg Arg Phe Gly Arg Asn
        1565                1570

<210> SEQ ID NO 62
<211> LENGTH: 1597
<212> TYPE: PRT
<213> ORGANISM: Streptococcus downei

<400> SEQUENCE: 62

Met Glu Lys Asn Glu Arg Phe Lys Met His Lys Val Lys Lys Arg Trp
1               5                   10                  15

Val Thr Ile Ser Val Ala Ser Ala Thr Met Leu Ala Ser Ala Leu Gly
            20                  25                  30

Ala Ser Val Ala Ser Ala Asp Thr Glu Thr Val Ser Glu Asp Ser Asn
        35                  40                  45

Gln Ala Val Leu Thr Ala Asp Gln Thr Thr Asn Gln Asp Thr Glu
    50                  55                  60

Gln Thr Ser Val Ala Ala Thr Ala Thr Ser Glu Gln Ser Ala Ser Thr
65                  70                  75                  80

Asp Ala Ala Thr Asp Gln Ala Ser Ala Thr Asp Gln Ala Ser Ala Ala
                85                  90                  95

Glu Gln Thr Gln Gly Thr Thr Ala Ser Thr Asp Thr Ala Ala Gln Thr
            100                 105                 110

Thr Thr Asn Ala Asn Glu Ala Lys Trp Val Pro Thr Glu Asn Glu Asn
        115                 120                 125

Gln Val Phe Thr Asp Glu Met Leu Ala Glu Ala Lys Asn Val Ala Thr
    130                 135                 140

Ala Glu Ser Asn Ser Ile Pro Ser Asp Leu Ala Lys Met Ser Asn Val
145                 150                 155                 160

Lys Gln Val Asp Gly Lys Tyr Tyr Tyr Tyr Asp Gln Asp Gly Asn Val
                165                 170                 175

Lys Lys Asn Phe Ala Val Ser Val Gly Glu Lys Ile Tyr Tyr Phe Asp
            180                 185                 190

Glu Thr Gly Ala Tyr Lys Asp Thr Ser Lys Val Glu Ala Asp Lys Ser
        195                 200                 205
```

-continued

Gly Ser Asp Ile Ser Lys Glu Glu Thr Thr Phe Ala Ala Asn Asn Arg
210                 215                 220

Ala Tyr Ser Thr Ser Ala Glu Asn Phe Glu Ala Ile Asp Asn Tyr Leu
225                 230                 235                 240

Thr Ala Asp Ser Trp Tyr Arg Pro Lys Ser Ile Leu Lys Asp Gly Lys
                245                 250                 255

Thr Trp Thr Glu Ser Ser Lys Asp Asp Phe Arg Pro Leu Leu Met Ala
                260                 265                 270

Trp Trp Pro Asp Thr Glu Thr Lys Arg Asn Tyr Val Asn Tyr Met Asn
                275                 280                 285

Lys Val Val Gly Ile Asp Lys Thr Tyr Thr Ala Glu Thr Ser Gln Ala
290                 295                 300

Asp Leu Thr Ala Ala Ala Glu Leu Val Gln Ala Arg Ile Glu Gln Lys
305                 310                 315                 320

Ile Thr Thr Glu Gln Asn Thr Lys Trp Leu Arg Glu Ala Ile Ser Ala
                325                 330                 335

Phe Val Lys Thr Gln Pro Gln Trp Asn Gly Glu Ser Glu Lys Pro Tyr
                340                 345                 350

Asp Asp His Leu Gln Asn Gly Ala Leu Lys Phe Asp Asn Gln Ser Asp
                355                 360                 365

Leu Thr Pro Asp Thr Gln Ser Asn Tyr Arg Leu Leu Asn Arg Thr Pro
370                 375                 380

Thr Asn Gln Thr Gly Ser Leu Asp Ser Arg Phe Thr Tyr Asn Ala Asn
385                 390                 395                 400

Asp Pro Leu Gly Gly Tyr Glu Leu Leu Leu Ala Asn Asp Val Asp Asn
                405                 410                 415

Ser Asn Pro Ile Val Gln Ala Glu Gln Leu Asn Trp Leu His Tyr Leu
                420                 425                 430

Leu Asn Phe Gly Thr Ile Tyr Ala Lys Asp Ala Asp Ala Asn Phe Asp
                435                 440                 445

Ser Ile Arg Val Asp Ala Val Asp Asn Val Asp Ala Asp Leu Leu Gln
450                 455                 460

Ile Ser Ser Asp Tyr Leu Lys Ala Ala Tyr Gly Ile Asp Lys Asn Asn
465                 470                 475                 480

Lys Asn Ala Asn Asn His Val Ser Ile Val Glu Ala Trp Ser Asp Asn
                485                 490                 495

Asp Thr Pro Tyr Leu His Asp Asp Gly Asp Asn Leu Met Asn Met Asp
                500                 505                 510

Asn Lys Phe Arg Leu Ser Met Leu Trp Ser Leu Ala Lys Pro Leu Asp
                515                 520                 525

Lys Arg Ser Gly Leu Asn Pro Leu Ile His Asn Ser Leu Val Asp Arg
530                 535                 540

Glu Val Asp Asp Arg Glu Val Glu Thr Val Pro Ser Tyr Ser Phe Ala
545                 550                 555                 560

Arg Ala His Asp Ser Glu Val Gln Asp Leu Ile Arg Asp Ile Ile Lys
                565                 570                 575

Ala Glu Ile Asn Pro Asn Ala Phe Gly Tyr Ser Phe Thr Gln Asp Glu
                580                 585                 590

Ile Asp Gln Ala Phe Lys Ile Tyr Asn Glu Asp Leu Lys Lys Thr Asp
                595                 600                 605

Lys Lys Tyr Thr His Tyr Asn Val Pro Leu Ser Tyr Thr Leu Leu Leu
610                 615                 620

Thr Asn Lys Gly Ser Ile Pro Arg Val Tyr Tyr Gly Asp Met Phe Thr

```
                625                 630                 635                 640
Asp Asp Gly Gln Tyr Met Ala Asn Lys Thr Val Asn Tyr Asp Ala Ile
                645                 650                 655
Glu Ser Leu Leu Lys Ala Arg Met Lys Tyr Val Ala Gly Gly Gln Ala
                660                 665                 670
Met Gln Asn Tyr Gln Ile Gly Asn Gly Glu Ile Leu Thr Ser Val Arg
                675                 680                 685
Tyr Gly Lys Gly Ala Leu Lys Gln Ser Asp Lys Gly Asp Ala Thr Thr
                690                 695                 700
Arg Thr Ser Gly Val Gly Val Met Gly Asn Gln Pro Asn Phe Ser
705                 710                 715                 720
Leu Asp Gly Lys Val Val Ala Leu Asn Met Gly Ala Ala His Ala Asn
                725                 730                 735
Gln Glu Tyr Arg Ala Leu Met Val Ser Thr Lys Asp Gly Val Ala Thr
                740                 745                 750
Tyr Ala Thr Asp Ala Asp Ala Ser Lys Ala Gly Leu Val Lys Arg Thr
                755                 760                 765
Asp Glu Asn Gly Tyr Leu Tyr Phe Leu Asn Asp Leu Lys Gly Val
                770                 775                 780
Ala Asn Pro Gln Val Ser Gly Phe Leu Gln Val Trp Pro Val Gly
785                 790                 795                 800
Ala Ala Asp Asp Gln Asp Ile Arg Val Ala Ala Ser Asp Thr Ala Ser
                805                 810                 815
Thr Asp Gly Lys Ser Leu His Gln Asp Ala Ala Met Asp Ser Arg Val
                820                 825                 830
Met Phe Glu Gly Phe Ser Asn Phe Gln Ser Phe Ala Thr Lys Glu Glu
                835                 840                 845
Glu Tyr Thr Asn Val Val Ile Ala Asn Asn Val Asp Lys Phe Val Ser
                850                 855                 860
Trp Gly Ile Thr Asp Phe Glu Met Ala Pro Gln Tyr Val Ser Ser Thr
865                 870                 875                 880
Asp Gly Gln Phe Leu Asp Ser Val Ile Gln Asn Gly Tyr Ala Phe Thr
                885                 890                 895
Asp Arg Tyr Asp Leu Gly Met Ser Lys Ala Asn Lys Tyr Gly Thr Ala
                900                 905                 910
Asp Gln Leu Val Lys Ala Ile Lys Ala Leu His Ala Lys Gly Leu Lys
                915                 920                 925
Val Met Ala Asp Trp Val Pro Asp Gln Met Tyr Thr Phe Pro Lys Gln
930                 935                 940
Glu Val Val Thr Val Thr Arg Thr Asp Lys Phe Gly Lys Pro Ile Ala
945                 950                 955                 960
Gly Ser Gln Ile Asn His Ser Leu Tyr Val Thr Asp Thr Lys Ser Ser
                965                 970                 975
Gly Asp Asp Tyr Gln Ala Lys Tyr Gly Gly Ala Phe Leu Asp Glu Leu
                980                 985                 990
Lys Glu Lys Tyr Pro Glu Leu Phe Thr Lys Lys Gln Ile Ser Thr Gly
                995                 1000                1005
Gln Ala Ile Asp Pro Ser Val Lys Ile Lys Gln Trp Ser Ala Lys
                1010                1015                1020
Tyr Phe Asn Gly Ser Asn Ile Leu Gly Arg Gly Ala Asp Tyr Val
                1025                1030                1035
Leu Ser Asp Gln Ala Ser Asn Lys Tyr Leu Asn Val Ser Asp Asp
                1040                1045                1050
```

-continued

```
Lys Leu Phe Leu Pro Lys Thr Leu Leu Gly Gln Val Val Glu Ser
1055                1060                1065

Gly Ile Arg Phe Asp Gly Thr Gly Tyr Val Tyr Asn Ser Ser Thr
1070                1075                1080

Thr Gly Glu Lys Val Thr Asp Ser Phe Ile Thr Glu Ala Gly Asn
1085                1090                1095

Leu Tyr Tyr Phe Gly Gln Asp Gly Tyr Met Val Thr Gly Ala Gln
1100                1105                1110

Asn Ile Lys Gly Ser Asn Tyr Tyr Phe Leu Ala Asn Gly Ala Ala
1115                1120                1125

Leu Arg Asn Thr Val Tyr Thr Asp Ala Gln Gly Gln Asn His Tyr
1130                1135                1140

Tyr Gly Asn Asp Gly Lys Arg Tyr Glu Asn Gly Tyr Gln Gln Phe
1145                1150                1155

Gly Asn Asp Ser Trp Arg Tyr Phe Lys Asn Gly Val Met Ala Leu
1160                1165                1170

Gly Leu Thr Thr Val Asp Gly His Val Gln Tyr Phe Asp Lys Asp
1175                1180                1185

Gly Val Gln Ala Lys Asp Lys Ile Ile Val Thr Arg Asp Gly Lys
1190                1195                1200

Val Arg Tyr Phe Asp Gln His Asn Gly Asn Ala Val Thr Asn Thr
1205                1210                1215

Phe Val Ala Asp Lys Thr Gly His Trp Tyr Tyr Leu Gly Lys Asp
1220                1225                1230

Gly Val Ala Val Thr Gly Ala Gln Thr Val Gly Lys Gln His Leu
1235                1240                1245

Tyr Phe Glu Ala Asn Gly Gln Gln Val Lys Gly Asp Phe Val Thr
1250                1255                1260

Ala Lys Asp Gly Lys Leu Tyr Phe Tyr Asp Val Asp Ser Gly Asp
1265                1270                1275

Met Trp Thr Asn Thr Phe Ile Glu Asp Lys Ala Gly Asn Trp Phe
1280                1285                1290

Tyr Leu Gly Lys Asp Gly Ala Ala Val Thr Gly Ala Gln Thr Ile
1295                1300                1305

Lys Gly Gln Lys Leu Tyr Phe Lys Ala Asn Gly Gln Gln Val Lys
1310                1315                1320

Gly Asp Ile Val Lys Asp Ala Asp Gly Lys Ile Arg Tyr Tyr Asp
1325                1330                1335

Ala Gln Thr Gly Glu Gln Val Phe Asn Lys Ser Val Ser Val Asn
1340                1345                1350

Gly Lys Thr Tyr Tyr Phe Gly Ser Asp Gly Thr Ala Gln Thr Gln
1355                1360                1365

Ala Asn Pro Lys Gly Gln Thr Phe Lys Asp Gly Ser Gly Val Leu
1370                1375                1380

Arg Phe Tyr Asn Leu Glu Gly Gln Tyr Val Ser Gly Ser Gly Trp
1385                1390                1395

Tyr Glu Thr Ala Glu His Glu Trp Val Tyr Val Lys Ser Gly Lys
1400                1405                1410

Val Leu Thr Gly Ala Gln Thr Ile Gly Asn Gln Arg Val Tyr Phe
1415                1420                1425

Lys Asp Asn Gly His Gln Val Lys Gly Gln Leu Val Thr Gly Asn
1430                1435                1440
```

| | | | | | | | | | | |
|---|---|---|---|---|---|---|---|---|---|---|
| Asp | Gly<br>1445 | Lys | Leu | Arg | Tyr<br>1450 | Tyr | Asp | Ala | Asn | Ser<br>1455 | Gly | Asp | Gln | Ala |

Phe Asn Lys Ser Val Thr Val Asn Gly Lys Thr Tyr Tyr Phe Gly
    1460                            1465                          1470

Ser Asp Gly Thr Ala Gln Thr Gln Ala Asn Pro Lys Gly Gln Thr
    1475                            1480                        1485

Phe Lys Asp Gly Ser Gly Val Leu Arg Phe Tyr Asn Leu Glu Gly
    1490                            1495                        1500

Gln Tyr Val Ser Gly Ser Gly Trp Tyr Lys Asn Ala Gln Gly Gln
    1505                          1510                         1515

Trp Leu Tyr Val Lys Asp Gly Lys Val Leu Thr Gly Leu Gln Thr
    1520                          1525                        1530

Val Gly Asn Gln Lys Val Tyr Phe Asp Lys Asn Gly Ile Gln Ala
    1535                          1540                        1545

Lys Gly Lys Ala Val Arg Thr Ser Asp Gly Lys Val Arg Tyr Phe
    1550                          1555                        1560

Asp Glu Asn Ser Gly Ser Met Ile Thr Asn Gln Trp Lys Phe Val
    1565                          1570                        1575

Tyr Gly Gln Tyr Tyr Phe Gly Ser Asp Gly Ala Ala Val Tyr
    1580                          1585                        1590

Arg Gly Trp Asn
    1595

<210> SEQ ID NO 63
<211> LENGTH: 4311
<212> TYPE: DNA
<213> ORGANISM: Streptococcus downei

<400> SEQUENCE: 63

```
atggttgacg gcaaatacta ctactacgat caggacggca acgtaaagaa aaacttcgcg      60
gttagcgtgg gcgagaaaat ctattacttt gacgaaactg gcgcctacaa agacaccagc     120
aaagttgagg cggacaaaag cggcagcgac attagcaagg aagagactac cttcgcggca     180
aacaaccgcg cctacagcac cagcgcggag aatttttgagg cgatcgacaa ttatctgacc     240
gcggactcct ggtatcgtcc taaatccatc ctgaaggatg gcaaaacgtg gacggaaagc     300
agcaaagatg actttcgtcc gctgctgatg gcgtggtggc cggataccga aacgaagcgc     360
aattacgtga actacatgaa caaagttgtt ggcatcgaca agacctatac cgcggaaacc     420
agccaggccg acttgaccgc tgcggcggaa ctggtgcaag cacgcattga gcagaagatc     480
acgaccgaac agaacacgaa atggctgcgt gaggcaatct cggcatttgt taaaacgcaa     540
ccgcagtgga acggtgaaag cgagaagccg tacgacgatc acctgcaaaa cggtgctctg     600
aaatttgata tcagagcga cctgaccccg gatacgcaaa gcaactaccg tctgttgaac     660
cgtaccccga ctaatcagac gggtagcctg acagccgct tcacttataa cgcgaacgac     720
cctttgggcg ttatgagct gctgctggca atgacgtcg ataacagcaa tccgatcgtg     780
caggcggagc agctgaactg gctgcattac ctgctgaatt ttggtacgat ctacgccaaa     840
gatgccgacg ctaacttcga tagcattcgt gtggacgcgg ttgataacgt cgatgcggat     900
ctgctgcaaa ttagcagcga ttacctgaaa gcagcctacg gcattgataa gaataacaaa     960
aacgcgaaca accacgtgag cattgtcgaa gcctggagcg ataatgatac cccgtacctg    1020
catgacgatg gtgacaacct gatgaatatg ataacaaat ttcgcctgtc catgctgtgg    1080
tcgctggcca aaccgctgga caagcgtagc ggtctgaacc cgctgattca taacagcttg    1140
```

```
gtggatcgtg aagttgatga ccgcgaggtt gaaacggttc cgagctattc tttttgcacgt    1200 gcgcatgata gcgaggtcca ggacttgatc cgtgacatca tcaaggcaga gatcaatccg    1260
aacgcattcg gttatagctt tacccaagac gagattgacc aggcctttaa gatttacaat    1320
gaggatctga agaaaacgga taagaaatac acccactata atgtgccgtt gagctacacc    1380
ctgctgctga cgaataaggg tagcatccca cgtgtctact atggtgatat gtttaccgac    1440
gatggtcagt atatggcgaa caaaaccgtc aactatgacg ccattgaatc tctgctgaaa    1500
gcgcgtatga agtatgtcgc tggcggtcaa gcaatgcaga actaccaaat cggtaatggt    1560
gagatcctga ccagcgttcg ttatggtaag ggtgccctga acagagcga caaaggtgat    1620 gcgaccacgc gcaccagcgg tgtcggtgtc gttatgggca atcagccaaa ctttagcttg    1680
gacggcaaag tggtggctct gaacatgggc gcagctcatg cgaatcagga gtatcgtgcg    1740
ctgatggtta gcacgaaaga cggtgttgcc acgtatgcga ccgatgcaga tgcgagcaaa    1800
gccggtctgg tcaaacgtac cgacgaaaac ggctacctgt atttcctgaa tgacgacctg    1860
aagggtgtgg ccaatcctca ggtgagcggt ttcttgcagg tgtgggttcc ggtgggtgcc    1920
gcggatgatc aagatatccg tgttgcagct agcgataccg catccaccga tggcaagagc    1980
ctgcaccaag acgccgcgat ggatagccgt gttatgtttg aaggcttctc taactttcag    2040
tcctttgcca cgaaagaaga ggaatatacc aacgtcgtta cgccaacaa tgtggataag    2100 ttcgttagct ggggtatcac ggatttcgag atggccccac aatatgtttc cagcaccgac    2160
ggtcaattcc tggactctgt cattcagaac ggttatgctt ttacggaccg ttatgacttg    2220
ggcatgtcta aggcaaacaa atacggcacg gccgatcaac tggttaaggc cattaaggcc    2280
ctgcacgcga agggcctgaa ggttatggca gattgggtgc cggatcagat gtataccttc    2340
ccgaaacagg aagtcgtgac cgttacccgt accgacaaat ttggcaaacc gatcgcaggt    2400
tcccaaatca atcatagcct gtatgttacc gataccaagt ccagcggcga tgactatcag    2460
gccaaatatg gtggtgcgtt tctggacgag ctgaaggaga atatccggga gctgttcacg    2520
aagaaacaaa tcagcacggg tcaagctatt gacccgagcg tgaaaatcaa acagtggtct    2580
gctaagtatt tcaatggctc caacatcctg ggtcgcggtg cggactacgt actgtcggat    2640
caggcgagca acaaatacct gaacgtgtct gacgataaac tgttcctgcc gaaaaccttg    2700
ctgggccaag ttgtcgagag cggtatccgc tttgacggca ctggttatgt gtacaactct    2760
agcactacgg gtgaaaaagt taccgattcc ttcattacgg aggcaggtaa tctgtactac    2820
ttcggtcaag acggctatat ggtgaccggc gcacagaaca ttaagggcag caactattac    2880
ttcctggcca atggtgcggc cctgcgtaac accgtttaca ccgatgcgca aggtcagaat    2940
cactattacg gcaacgacgg caagcgttat gagaatggtt accaacagtt cggcaacgat    3000
tcttggcgtt acttcaaaaa tggcgtgatg gcgctgggtc tgactacggt ggatggtcac    3060
gtgcagtatt tcgataaaga tggtgtccag gccaaggata agatcattgt cacccgcgat    3120
ggcaaagtcc gctatttcga ccagcacaac ggtaatgcgg ttactaacac gttcgttgcg    3180
gacaagacgg gtcactggta ctatctgggc aaagacggcg tcgcggttac cggtgcgcag    3240
actgtgggta acagcatttt gtactttgaa gcgaacggtc aacaagtcaa gggtgacttc    3300
gtgacggcta agacggtaa actgtacttc tatgatgtgg acagcggcga catgtggacc    3360
aataccttta tcgaggataa agcgggtaat tggttctacc tgggtaagga cggtgcggcc    3420
gtcaccggtg cacagacgat caaaggccag aaattgtatt tcaaagccaa cggtcagcaa    3480
gttaaaggtg acattgtcaa ggacgcggac ggtaagatcc gttattacga cgctcagacc    3540
```

-continued

```
ggtgaacagg tctttaacaa gtccgttagc gtcaacggta agaccctacta tttcggtagc   3600 gacggcaccg cgcaaaccca ggcgaatccg aaaggccaaa cctttaagga tggtagcggc   3660
gttctgcgtt tctacaattt ggagggccag tatgtctcgg gcagcggctg gtacgaaacg   3720
gccgagcacg agtgggtata tgtgaaatcc ggtaaagttc tgaccggtgc ccagacgatt   3780
ggtaatcaac gtgtttactt caaggacaat ggtcaccagg tgaaaggcca gctggtcacg   3840
ggtaatgacg gtaaattgcg ttactacgac gcgaacagcg tgatcaagc attcaacaaa    3900 tccgtcacgg ttaacggtaa aacctactac tttggcagcg atggtacggc gcagacgcag   3960
gctaatccta agggtcagac cttcaaagat ggtagcggcg tgctgcgttt ttacaacttg   4020
gaaggccaat acgtgtctgg cagcggttgg tacaagaatg cgcagggcca gtggctgtac   4080
gtgaaagatg gcaaggtcct gaccggtctg caaacggtcg gcaatcagaa ggtctacttc   4140
gacaaaaatg gcatccaagc aaagggtaag gccgttcgca cgtccgatgg taaagtgcgc   4200
tactttgatg agaatagcgg tagcatgatt acgaaccaat ggaagttcgt ttacggtcaa   4260
tactattact tcggttctga cggcgcagcg gtttaccgtg gttggaacta a            4311
```

<210> SEQ ID NO 64
<211> LENGTH: 1436
<212> TYPE: PRT
<213> ORGANISM: Streptococcus downei

<400> SEQUENCE: 64

```
Met Val Asp Gly Lys Tyr Tyr Tyr Asp Gln Asp Gly Asn Val Lys
  1               5                  10                  15

Lys Asn Phe Ala Val Ser Val Gly Glu Lys Ile Tyr Tyr Phe Asp Glu
                 20                  25                  30

Thr Gly Ala Tyr Lys Asp Thr Ser Lys Val Glu Ala Asp Lys Ser Gly
             35                  40                  45

Ser Asp Ile Ser Lys Glu Glu Thr Thr Phe Ala Ala Asn Asn Arg Ala
         50                  55                  60

Tyr Ser Thr Ser Ala Glu Asn Phe Glu Ala Ile Asp Asn Tyr Leu Thr
 65                  70                  75                  80

Ala Asp Ser Trp Tyr Arg Pro Lys Ser Ile Leu Lys Asp Gly Lys Thr
                 85                  90                  95

Trp Thr Glu Ser Ser Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Thr Glu Gln Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Gln Ser Asp Leu
        195                 200                 205

Thr Pro Asp Thr Gln Ser Asn Tyr Arg Leu Leu Asn Arg Thr Pro Thr
    210                 215                 220

Asn Gln Thr Gly Ser Leu Asp Ser Arg Phe Thr Tyr Asn Ala Asn Asp
225                 230                 235                 240
```

-continued

Pro Leu Gly Gly Tyr Glu Leu Leu Ala Asn Asp Val Asp Asn Ser
            245                 250                 255

Asn Pro Ile Val Gln Ala Glu Gln Leu Asn Trp Leu His Tyr Leu Leu
        260                 265                 270

Asn Phe Gly Thr Ile Tyr Ala Lys Asp Ala Asp Ala Asn Phe Asp Ser
            275                 280                 285

Ile Arg Val Asp Ala Val Asp Asn Val Asp Ala Asp Leu Leu Gln Ile
        290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
            325                 330                 335

Thr Pro Tyr Leu His Asp Asp Gly Asp Asn Leu Met Asn Met Asp Asn
            340                 345                 350

Lys Phe Arg Leu Ser Met Leu Trp Ser Leu Ala Lys Pro Leu Asp Lys
            355                 360                 365

Arg Ser Gly Leu Asn Pro Leu Ile His Asn Ser Leu Val Asp Arg Glu
        370                 375                 380

Val Asp Asp Arg Glu Val Glu Thr Val Pro Ser Tyr Ser Phe Ala Arg
385                 390                 395                 400

Ala His Asp Ser Glu Val Gln Asp Leu Ile Arg Asp Ile Ile Lys Ala
            405                 410                 415

Glu Ile Asn Pro Asn Ala Phe Gly Tyr Ser Phe Thr Gln Asp Glu Ile
            420                 425                 430

Asp Gln Ala Phe Lys Ile Tyr Asn Glu Asp Leu Lys Lys Thr Asp Lys
            435                 440                 445

Lys Tyr Thr His Tyr Asn Val Pro Leu Ser Tyr Thr Leu Leu Leu Thr
            450                 455                 460

Asn Lys Gly Ser Ile Pro Arg Val Tyr Tyr Gly Asp Met Phe Thr Asp
465                 470                 475                 480

Asp Gly Gln Tyr Met Ala Asn Lys Thr Val Asn Tyr Asp Ala Ile Glu
            485                 490                 495

Ser Leu Leu Lys Ala Arg Met Lys Tyr Val Ala Gly Gly Gln Ala Met
            500                 505                 510

Gln Asn Tyr Gln Ile Gly Asn Gly Glu Ile Leu Thr Ser Val Arg Tyr
            515                 520                 525

Gly Lys Gly Ala Leu Lys Gln Ser Asp Lys Gly Asp Ala Thr Thr Arg
        530                 535                 540

Thr Ser Gly Val Gly Val Val Met Gly Asn Gln Pro Asn Phe Ser Leu
545                 550                 555                 560

Asp Gly Lys Val Val Ala Leu Asn Met Gly Ala Ala His Ala Asn Gln
            565                 570                 575

Glu Tyr Arg Ala Leu Met Val Ser Thr Lys Asp Gly Val Ala Thr Tyr
            580                 585                 590

Ala Thr Asp Ala Asp Ala Ser Lys Ala Gly Leu Val Lys Arg Thr Asp
            595                 600                 605

Glu Asn Gly Tyr Leu Tyr Phe Leu Asn Asp Asp Leu Lys Gly Val Ala
            610                 615                 620

Asn Pro Gln Val Ser Gly Phe Leu Gln Val Trp Val Pro Val Gly Ala
625                 630                 635                 640

Ala Asp Asp Gln Asp Ile Arg Val Ala Ala Ser Asp Thr Ala Ser Thr
            645                 650                 655

```
Asp Gly Lys Ser Leu His Gln Asp Ala Ala Met Asp Ser Arg Val Met
            660                 665                 670

Phe Glu Gly Phe Ser Asn Phe Gln Ser Phe Ala Thr Lys Glu Glu
        675                 680                 685

Tyr Thr Asn Val Val Ile Ala Asn Asn Val Asp Lys Phe Val Ser Trp
    690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Asp
            740                 745                 750

Gln Leu Val Lys Ala Ile Lys Ala Leu His Ala Lys Gly Leu Lys Val
                755                 760                 765

Met Ala Asp Trp Val Pro Asp Gln Met Tyr Thr Phe Pro Lys Gln Glu
            770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Thr Lys Ser Ser Gly
                805                 810                 815

Asp Asp Tyr Gln Ala Lys Tyr Gly Gly Ala Phe Leu Asp Glu Leu Lys
            820                 825                 830

Glu Lys Tyr Pro Glu Leu Phe Thr Lys Lys Gln Ile Ser Thr Gly Gln
                835                 840                 845

Ala Ile Asp Pro Ser Val Lys Ile Lys Gln Trp Ser Ala Lys Tyr Phe
850                 855                 860

Asn Gly Ser Asn Ile Leu Gly Arg Gly Ala Asp Tyr Val Leu Ser Asp
865                 870                 875                 880

Gln Ala Ser Asn Lys Tyr Leu Asn Val Ser Asp Lys Leu Phe Leu
                885                 890                 895

Pro Lys Thr Leu Leu Gly Gln Val Val Glu Ser Gly Ile Arg Phe Asp
                900                 905                 910

Gly Thr Gly Tyr Val Tyr Asn Ser Ser Thr Thr Gly Glu Lys Val Thr
            915                 920                 925

Asp Ser Phe Ile Thr Glu Ala Gly Asn Leu Tyr Tyr Phe Gly Gln Asp
930                 935                 940

Gly Tyr Met Val Thr Gly Ala Gln Asn Ile Lys Gly Ser Asn Tyr Tyr
945                 950                 955                 960

Phe Leu Ala Asn Gly Ala Ala Leu Arg Asn Thr Val Tyr Thr Asp Ala
                965                 970                 975

Gln Gly Gln Asn His Tyr Tyr Gly Asn Asp Gly Lys Arg Tyr Glu Asn
                980                 985                 990

Gly Tyr Gln Gln Phe Gly Asn Asp Ser Trp Arg Tyr Phe Lys Asn Gly
            995                 1000                1005

Val Met Ala Leu Gly Leu Thr Thr Val Asp Gly His Val Gln Tyr
    1010                1015                1020

Phe Asp Lys Asp Gly Val Gln Ala Lys Asp Lys Ile Ile Val Thr
    1025                1030                1035

Arg Asp Gly Lys Val Arg Tyr Phe Asp Gln His Asn Gly Asn Ala
    1040                1045                1050

Val Thr Asn Thr Phe Val Ala Asp Lys Thr Gly His Trp Tyr Tyr
    1055                1060                1065

Leu Gly Lys Asp Gly Val Ala Val Thr Gly Ala Gln Thr Val Gly
```

-continued

```
                1070                1075                1080
Lys Gln His Leu Tyr Phe Glu Ala Asn Gly Gln Gln Val Lys Gly
    1085                1090                1095
Asp Phe Val Thr Ala Lys Asp Gly Lys Leu Tyr Phe Tyr Asp Val
    1100                1105                1110
Asp Ser Gly Asp Met Trp Thr Asn Thr Phe Ile Glu Asp Lys Ala
    1115                1120                1125
Gly Asn Trp Phe Tyr Leu Gly Lys Asp Gly Ala Ala Val Thr Gly
    1130                1135                1140
Ala Gln Thr Ile Lys Gly Gln Lys Leu Tyr Phe Lys Ala Asn Gly
    1145                1150                1155
Gln Gln Val Lys Gly Asp Ile Val Lys Asp Ala Asp Gly Lys Ile
    1160                1165                1170
Arg Tyr Tyr Asp Ala Gln Thr Gly Glu Gln Val Phe Asn Lys Ser
    1175                1180                1185
Val Ser Val Asn Gly Lys Thr Tyr Tyr Phe Gly Ser Asp Gly Thr
    1190                1195                1200
Ala Gln Thr Gln Ala Asn Pro Lys Gly Gln Thr Phe Lys Asp Gly
    1205                1210                1215
Ser Gly Val Leu Arg Phe Tyr Asn Leu Glu Gly Gln Tyr Val Ser
    1220                1225                1230
Gly Ser Gly Trp Tyr Glu Thr Ala Glu His Glu Trp Val Tyr Val
    1235                1240                1245
Lys Ser Gly Lys Val Leu Thr Gly Ala Gln Thr Ile Gly Asn Gln
    1250                1255                1260
Arg Val Tyr Phe Lys Asp Asn Gly His Gln Val Lys Gly Gln Leu
    1265                1270                1275
Val Thr Gly Asn Asp Gly Lys Leu Arg Tyr Tyr Asp Ala Asn Ser
    1280                1285                1290
Gly Asp Gln Ala Phe Asn Lys Ser Val Thr Val Asn Gly Lys Thr
    1295                1300                1305
Tyr Tyr Phe Gly Ser Asp Gly Thr Ala Gln Thr Gln Ala Asn Pro
    1310                1315                1320
Lys Gly Gln Thr Phe Lys Asp Gly Ser Gly Val Leu Arg Phe Tyr
    1325                1330                1335
Asn Leu Glu Gly Gln Tyr Val Ser Gly Ser Gly Trp Tyr Lys Asn
    1340                1345                1350
Ala Gln Gly Gln Trp Leu Tyr Val Lys Asp Gly Lys Val Leu Thr
    1355                1360                1365
Gly Leu Gln Thr Val Gly Asn Gln Lys Val Tyr Phe Asp Lys Asn
    1370                1375                1380
Gly Ile Gln Ala Lys Gly Lys Ala Val Arg Thr Ser Asp Gly Lys
    1385                1390                1395
Val Arg Tyr Phe Asp Glu Asn Ser Gly Ser Met Ile Thr Asn Gln
    1400                1405                1410
Trp Lys Phe Val Tyr Gly Gln Tyr Tyr Phe Gly Ser Asp Gly
    1415                1420                1425
Ala Ala Val Tyr Arg Gly Trp Asn
    1430                1435
```

<210> SEQ ID NO 65
<211> LENGTH: 1597
<212> TYPE: PRT
<213> ORGANISM: Streptococcus dentrirousetti

<400> SEQUENCE: 65

```
Met Glu Lys Asn Glu Arg Phe Lys Met His Lys Val Lys Arg Trp
1               5                   10                  15

Val Thr Ile Ser Val Ala Ser Ala Thr Met Leu Ala Ser Ala Leu Gly
            20                  25                  30

Ala Ser Val Ala Ser Ala Asp Thr Glu Thr Val Ser Glu Asp Ser Asn
        35                  40                  45

Gln Ala Val Leu Thr Ala Asp Gln Thr Thr Asn Gln Asp Thr Glu
    50                  55                  60

Gln Thr Ser Val Ala Ala Thr Ala Thr Ser Glu Gln Ser Ala Ser Thr
65                  70                  75                  80

Asp Ala Ala Thr Asp Gln Ala Ser Ala Thr Asp Gln Ala Ser Ala Ala
                85                  90                  95

Glu Gln Thr Gln Gly Thr Thr Ala Ser Thr Asp Thr Ala Ala Gln Thr
            100                 105                 110

Thr Thr Asn Ala Asn Glu Ala Lys Trp Val Pro Thr Glu Asn Glu Asn
        115                 120                 125

Gln Val Phe Thr Asp Glu Met Leu Ala Glu Ala Lys Asn Val Ala Thr
    130                 135                 140

Ala Glu Ser Asn Ser Ile Pro Ser Asp Leu Ala Lys Met Ser Asn Val
145                 150                 155                 160

Lys Gln Val Asp Gly Lys Tyr Tyr Tyr Asp Gln Asp Gly Asn Val
                165                 170                 175

Lys Lys Asn Phe Ala Val Ser Val Gly Glu Lys Ile Tyr Tyr Phe Asp
            180                 185                 190

Glu Thr Gly Ala Tyr Lys Asp Thr Ser Lys Val Glu Ala Asp Lys Ser
        195                 200                 205

Gly Ser Asp Ile Ser Lys Glu Glu Thr Thr Phe Ala Ala Asn Asn Arg
    210                 215                 220

Ala Tyr Ser Thr Ser Ala Glu Asn Phe Glu Ala Ile Asp Asn Tyr Leu
225                 230                 235                 240

Thr Ala Asp Ser Trp Tyr Arg Pro Lys Ser Ile Leu Lys Asp Gly Lys
                245                 250                 255

Thr Trp Thr Glu Ser Ser Lys Asp Asp Phe Arg Pro Leu Leu Met Ala
            260                 265                 270

Trp Trp Pro Asp Thr Glu Thr Lys Arg Asn Tyr Val Asn Tyr Met Asn
        275                 280                 285

Lys Val Val Gly Ile Asp Lys Thr Tyr Thr Ala Glu Thr Ser Gln Ala
    290                 295                 300

Asp Leu Thr Ala Ala Ala Glu Leu Val Gln Ala Arg Ile Glu Gln Lys
305                 310                 315                 320

Ile Thr Thr Glu Gln Asn Thr Lys Trp Leu Arg Glu Ala Ile Ser Ala
                325                 330                 335

Phe Val Lys Thr Gln Pro Gln Trp Asn Gly Glu Ser Glu Lys Pro Tyr
            340                 345                 350

Asp Asp His Leu Gln Asn Gly Ala Leu Lys Phe Asp Asn Gln Ser Asp
        355                 360                 365

Leu Thr Pro Asp Thr Gln Ser Asn Tyr Arg Leu Leu Asn Arg Thr Pro
    370                 375                 380

Thr Asn Gln Thr Gly Ser Leu Asp Ser Arg Phe Thr Tyr Asn Ala Asn
385                 390                 395                 400

Asp Pro Leu Gly Gly Tyr Glu Leu Leu Leu Ala Asn Asp Val Asp Asn
```

-continued

```
                405                 410                 415
Ser Asn Pro Ile Val Gln Ala Glu Gln Leu Asn Trp Leu His Tyr Leu
            420                 425                 430

Leu Asn Phe Gly Thr Ile Tyr Ala Lys Asp Ala Asp Ala Asn Phe Asp
            435                 440                 445

Ser Ile Arg Val Asp Ala Val Asp Asn Val Asp Ala Asp Leu Leu Gln
450                 455                 460

Ile Ser Ser Asp Tyr Leu Lys Ala Ala Tyr Gly Ile Asp Lys Asn Asn
465                 470                 475                 480

Lys Asn Ala Asn His Val Ser Ile Val Glu Ala Trp Ser Asp Asn
            485                 490                 495

Asp Thr Pro Tyr Leu His Asp Asp Gly Asp Asn Leu Met Asn Met Asp
            500                 505                 510

Asn Lys Phe Arg Leu Ser Met Leu Trp Ser Leu Ala Lys Pro Leu Asp
            515                 520                 525

Lys Arg Ser Gly Leu Asn Pro Leu Ile His Asn Ser Leu Val Asp Arg
530                 535                 540

Glu Val Asp Asp Arg Glu Val Glu Thr Val Pro Ser Tyr Ser Phe Ala
545                 550                 555                 560

Arg Ala His Asp Ser Glu Val Gln Asp Leu Ile Arg Asp Ile Ile Lys
                565                 570                 575

Ala Glu Ile Asn Pro Asn Ala Phe Gly Tyr Ser Phe Thr Gln Asp Glu
            580                 585                 590

Ile Asp Gln Ala Phe Lys Ile Tyr Asn Glu Asp Leu Lys Lys Thr Asp
            595                 600                 605

Lys Lys Tyr Thr His Tyr Asn Val Pro Leu Ser Tyr Thr Leu Leu Leu
610                 615                 620

Thr Asn Lys Gly Ser Ile Pro Arg Val Tyr Tyr Gly Asp Met Phe Thr
625                 630                 635                 640

Asp Asp Gly Gln Tyr Met Ala Asn Lys Thr Val Asn Tyr Asp Ala Ile
                645                 650                 655

Glu Ser Leu Leu Lys Ala Arg Met Lys Tyr Val Ala Gly Gly Gln Ala
            660                 665                 670

Met Gln Asn Tyr Gln Ile Gly Asn Gly Glu Ile Leu Thr Ser Val Arg
            675                 680                 685

Tyr Gly Lys Gly Ala Leu Lys Gln Ser Asp Lys Gly Asp Ala Thr Thr
            690                 695                 700

Arg Thr Ser Gly Val Gly Val Met Gly Asn Gln Pro Asn Phe Ser
705                 710                 715                 720

Leu Asp Gly Lys Val Val Ala Leu Asn Met Gly Ala Ala His Ala Asn
                725                 730                 735

Gln Glu Tyr Arg Ala Leu Met Val Ser Thr Lys Asp Gly Val Ala Thr
            740                 745                 750

Tyr Ala Thr Asp Ala Asp Ala Ser Lys Ala Gly Leu Val Lys Arg Thr
            755                 760                 765

Asp Glu Asn Gly Tyr Leu Tyr Phe Leu Asn Asp Asp Leu Lys Gly Val
            770                 775                 780

Ala Asn Pro Gln Val Ser Gly Phe Leu Gln Val Trp Val Pro Val Gly
785                 790                 795                 800

Ala Ala Asp Asp Gln Asp Ile Arg Val Ala Ala Ser Asp Thr Ala Ser
                805                 810                 815

Thr Asp Gly Lys Ser Leu His Gln Asp Ala Ala Met Asp Ser Arg Val
            820                 825                 830
```

```
Met Phe Glu Gly Phe Ser Asn Phe Gln Ser Phe Ala Thr Lys Glu Glu
        835                 840                 845

Glu Tyr Thr Asn Val Val Ile Ala Asn Asn Val Asp Lys Phe Val Ser
    850                 855                 860

Trp Gly Ile Thr Asp Phe Glu Met Ala Pro Gln Tyr Val Ser Ser Thr
865                 870                 875                 880

Asp Gly Gln Phe Leu Asp Ser Val Ile Gln Asn Gly Tyr Ala Phe Thr
                885                 890                 895

Asp Arg Tyr Asp Leu Gly Met Ser Lys Ala Asn Lys Tyr Gly Thr Ala
                900                 905                 910

Asp Gln Leu Val Lys Ala Ile Lys Ala Leu His Ala Lys Gly Leu Lys
                915                 920                 925

Val Met Ala Asp Trp Val Pro Asp Gln Met Tyr Thr Phe Pro Lys Gln
    930                 935                 940

Glu Val Val Thr Val Thr Arg Thr Asp Lys Phe Gly Lys Pro Ile Ala
945                 950                 955                 960

Gly Ser Gln Ile Asn His Ser Leu Tyr Val Thr Asp Thr Lys Ser Ser
                965                 970                 975

Gly Asp Asp Tyr Gln Ala Lys Tyr Gly Gly Ala Phe Leu Asp Glu Leu
                980                 985                 990

Lys Glu Lys Tyr Pro Glu Leu Phe  Thr Lys Lys Gln Ile  Ser Thr Gly
                995                  1000               1005

Gln Ala  Ile Asp Pro Ser Val  Lys Ile Lys Gln Trp  Ser Ala Lys
    1010                1015                1020

Tyr Phe  Asn Gly Ser Asn Ile  Leu Gly Arg Gly Ala  Asp Tyr Val
    1025                1030                1035

Leu Ser  Asp Gln Ala Ser Asn  Lys Tyr Leu Asn Val  Ser Asp Asp
    1040                1045                1050

Lys Leu  Phe Leu Pro Lys Thr  Leu Leu Gly Gln Val  Val Glu Ser
    1055                1060                1065

Gly Ile  Arg Phe Asp Gly Thr  Gly Tyr Val Tyr Asn  Ser Ser Thr
    1070                1075                1080

Thr Gly  Glu Lys Val Thr Asp  Ser Phe Ile Thr Glu  Ala Gly Asn
    1085                1090                1095

Leu Tyr  Tyr Phe Gly Gln Asp  Gly Tyr Met Val Thr  Gly Ala Gln
    1100                1105                1110

Asn Ile  Lys Gly Ser Asn Tyr  Tyr Phe Leu Ala Asn  Gly Ala Ala
    1115                1120                1125

Leu Arg  Asn Thr Val Tyr Thr  Asp Ala Gln Gly Gln  Asn His Tyr
    1130                1135                1140

Tyr Gly  Asn Asp Gly Lys Arg  Tyr Glu Asn Gly Tyr  Gln Gln Phe
    1145                1150                1155

Gly Asn  Asp Ser Trp Arg Tyr  Phe Lys Asn Gly Val  Met Ala Leu
    1160                1165                1170

Gly Leu  Thr Thr Val Asp Gly  His Val Gln Tyr Phe  Asp Lys Asp
    1175                1180                1185

Gly Val  Gln Ala Lys Asp Lys  Ile Ile Val Thr Arg  Asp Gly Lys
    1190                1195                1200

Val Arg  Tyr Phe Asp Gln His  Asn Gly Asn Ala Val  Thr Asn Thr
    1205                1210                1215

Phe Val  Ala Asp Lys Thr Gly  His Trp Tyr Tyr Leu  Gly Lys Asp
    1220                1225                1230
```

-continued

| | | | | | | | | | | | |
|---|---|---|---|---|---|---|---|---|---|---|---|
| Gly | Val | Ala | Val | Thr | Gly | Ala | Gln | Thr | Val | Gly | Lys | Gln | His | Leu |
| | 1235 | | | | 1240 | | | | | 1245 | | | | |

Gly Val Ala Val Thr Gly Ala Gln Thr Val Gly Lys Gln His Leu
    1235                1240                    1245

Tyr Phe Glu Ala Asn Gly Gln Gln Val Lys Gly Asp Phe Val Thr
    1250                1255                    1260

Ala Lys Asp Gly Lys Leu Tyr Phe Tyr Asp Val Asp Ser Gly Asp
    1265                1270                    1275

Met Trp Thr Asn Thr Phe Ile Glu Asp Lys Ala Gly Asn Trp Phe
    1280                1285                    1290

Tyr Leu Gly Lys Asp Gly Ala Ala Val Thr Gly Ala Gln Thr Ile
    1295                1300                    1305

Lys Gly Gln Lys Leu Tyr Phe Lys Ala Asn Gly Gln Gln Val Lys
    1310                1315                    1320

Gly Asp Ile Val Lys Asp Ala Asp Gly Lys Ile Arg Tyr Tyr Asp
    1325                1330                    1335

Ala Gln Thr Gly Glu Gln Val Phe Asn Lys Ser Val Ser Val Asn
    1340                1345                    1350

Gly Lys Thr Tyr Tyr Phe Gly Ser Asp Gly Thr Ala Gln Thr Gln
    1355                1360                    1365

Ala Asn Pro Lys Gly Gln Thr Phe Lys Asp Gly Ser Gly Val Leu
    1370                1375                    1380

Arg Phe Tyr Asn Leu Glu Gly Gln Tyr Val Ser Gly Ser Gly Trp
    1385                1390                    1395

Tyr Glu Thr Ala Glu His Glu Trp Val Tyr Val Lys Ser Gly Lys
    1400                1405                    1410

Val Leu Thr Gly Ala Gln Thr Ile Gly Asn Gln Arg Val Tyr Phe
    1415                1420                    1425

Lys Asp Asn Gly His Gln Val Lys Gly Gln Leu Val Thr Gly Asn
    1430                1435                    1440

Asp Gly Lys Leu Arg Tyr Tyr Asp Ala Asn Ser Gly Asp Gln Ala
    1445                1450                    1455

Phe Asn Lys Ser Val Thr Val Asn Gly Lys Thr Tyr Tyr Phe Gly
    1460                1465                    1470

Ser Asp Gly Thr Ala Gln Thr Gln Ala Asn Pro Lys Gly Gln Thr
    1475                1480                    1485

Phe Lys Asp Gly Ser Gly Val Leu Arg Phe Tyr Asn Leu Glu Gly
    1490                1495                    1500

Gln Tyr Val Ser Gly Ser Gly Trp Tyr Lys Asn Ala Gln Gly Gln
    1505                1510                    1515

Trp Leu Tyr Val Lys Asp Gly Lys Val Leu Thr Gly Leu Gln Thr
    1520                1525                    1530

Val Gly Asn Gln Lys Val Tyr Phe Asp Lys Asn Gly Ile Gln Ala
    1535                1540                    1545

Lys Gly Lys Ala Val Arg Thr Ser Asp Gly Lys Val Arg Tyr Phe
    1550                1555                    1560

Asp Glu Asn Ser Gly Ser Met Ile Thr Asn Gln Trp Lys Phe Val
    1565                1570                    1575

Tyr Gly Gln Tyr Tyr Tyr Phe Gly Ser Asp Gly Ala Ala Val Tyr
    1580                1585                    1590

Arg Gly Trp Asn
    1595

<210> SEQ ID NO 66
<211> LENGTH: 3972
<212> TYPE: DNA

<213> ORGANISM: Streptococcus dentirousetti

<400> SEQUENCE: 66

```
atggttgacg gcaaatacta ctactacgat gcagacggca acgtaaagaa aaacttcgcg      60
gttagcgttg gcgatgccat tttctatttt gatgaaacgg gtgcctacaa agataccagc     120
aaagttgatg cggataagac cagctctagc gtcaatcaga ccacggaaac gttcgcagcg     180
aataaccgtg cgtatagcac cgcagccgag aactttgaag cgattgataa ctacctgact     240
gcggatagct ggtatcgtcc gaagtctatc ttgaaagatg gtacgacgtg gaccgaaagc     300
accaaggatg attttcgccc gctgctgatg gcgtggtggc cggataccga aaccaaacgt     360
aactacgtga actatatgaa caaggtggtc ggtatcgaca aaacgtacac cgcggaaacg     420
tcccaagctg acctgacggc ggcagccgaa ctggtgcagg cgcgtatcga gcagaaaatc     480
actagcgaaa agaatacgaa gtggctgcgt gaggcgattt ccgcgttcgt taagactcaa     540
ccgcagtgga atggcgagag cgagaaacct tatgatgacc acctgcaaaa tggtgcgctg     600
aagttcgaca atgaaaccag cctgaccccg gatacgcaga gcggctatcg catcctgaac     660
cgtaccccga cgaatcaaac cggtagcctg acccgcgct tcacctttaa tcagaatgac     720
ccgctgggtg gttatgagta tttgctggct aatgatgtcg ataacagcaa cccggtcgtt     780
caggccgaga gcctgaactg gctgcattac ctgctgaatt ttggtagcat ttacgcgaat     840
gatccggagg ccaatttcga cagcatccgt gtggacgcgg tggacaatgt tgacgcagac     900
ctgctgcaaa ttagctcgga ttacctgaaa tcggcgtaca aaattgacaa gaacaacaaa     960
aatgcgaacg accacgttag catcgtcgag gcgtggagcg acaatgatac cccgtacctg    1020
aatgatgatg cgacaatct gatgaacatg gataacaagt tcgtctgag catgctgtgg    1080
agcctggcga agccaaccaa tgtccgtagc ggcttgaatc cgctgatcca acacagcgtg    1140
gttgaccgtg aggtggacga ccgtgaagtt gaggctaccc cgaattacag ctttgcacgc    1200
gcacacgaca gcgaagttca agattttgat cgcgacatca tcaaagctga gatcaaccca    1260
aacagcttcg gttatagctt tacccaagag gaaatcgacc aggccttcaa gatctacaat    1320
gaggattttga gaaaaaccaa taagaagtat acccactaca acgtcccgct gagctacacc    1380
ctgctgctga cgaacaaggg cagcattcca cgcatttact acggtgacat gtttacggat    1440
gacggtcagt atatggccaa caaaaccgtt aactatgacg ccattgagag cctgctgaaa    1500
gcacgtatga agtatgttag cggtggccaa gcgatgcaga attacaacat cggcaacggc    1560
gagattctga ccagcgtccg ttacggtaag ggtgccctga acagagcga caaaggcgat    1620
aagactactc gtaccagcgg tattggcgtt gtgatgggta accagagcaa tttcagcctg    1680
gagggcaagg tggtggccct gaatatgggt gcaacgcata ccaaacagaa gtatcgtgca    1740
ttgatggtgt ctacggaaac cggcgtggcg atttacaata gcgatgaaga agcagaggca    1800
gcaggcctga tcaaaacgac cgatgagaat ggttatttgt actttctgaa tgacgatctg    1860
aagggcgtgg ctaacccgca ggtcagcggc ttcctgcaag tgtgggttcc ggttggtgca    1920
ccggctgacc aggacattcg tgtggcggcg accgatgcgg cttctaccga cggtaagagc    1980
ctgcatcagg acgcagctct ggattctcgc gtcatgtttg aaggtttcag caacttccag    2040
agcttcgcaa ccaaggaaga ggaatacacc aacgttgtta ttgcaaagaa cgtggataag    2100
ttcgtgagct ggggtatcac cgacttcgag atggcaccgc agtacgttag ctctaccgat    2160
ggcacctttc tggatagcgt gattcaaaat ggctatgcct ttacgaccg ttacgacctg    2220
ggtatgagca agcaaacaa gtatggtact gctgaccaac tggtggccgc gattaaagcg    2280
```

-continued

```
ctgcatgcga agggtctgcg tgtgatggcg gattgggtcc cagatcaaat gtacactttc    2340
cctaagaagg aagtggttac cgttacccgt acgacaaat ttggcaatcc agtggcaggc    2400
agccaaatca accacacctt gtacgtcact gatactaagg gtagcggtga cgactaccag    2460
gcgaagtacg gtggcgcatt cctggatgaa ctgaaagaaa agtacccgga gctgtttacc    2520
aagaagcaaa tcagcaccgg tcaggcaatc gacccgagcg tgaaaatcaa gcagtggagc    2580
gcgaagtact tcaacggtag caatatcttg ggtcgcggtg cgaactacgt gctgtccgac    2640
caggcgtcta acaagtactt taacgtggcc gaaggtaaag tctttctgcc agcggcgatg    2700
ctgggtaagg tcgtcgagag cggtatccgt ttcgacggta aaggttatat ctataacagc    2760
agcaccactg gcgaacaagt gaaggacagc ttcattaccg aagcgggtaa cttgtactat    2820
tttggcaaag atggttatat ggtcatgggt gcacagaata tccagggtgc taactactac    2880
ttcttggcga atggtgcggc cctgcgcaat agcatcctga cggatcagga tggcaaaagc    2940
cactattatg caaatgacgg caagcgttat gagaacggct actatcaatt cggtaacgac    3000
tcctggcgct atttttgaaaa cggcgttatg gccgttggtt tgacgcgcgt tgcgggccac    3060
gaccaatact ttgataagga tggtatccaa gcgaagaata agatcattgt tacgcgtgac    3120
ggtaaggtcc gctacttcga cgaacacaac ggcaatgctg ccacgaatac gtttatcagc    3180
gatcaagccg gccattggta ctacctgggt aaagatggtg tcgccgtgac gggtgcgcag    3240
accgttggca agcaacacct gtacttcgag gctaacggcc aacaagtaaa aggcgatttt    3300
gttaccgcca aggacggtaa gttgtatttt ctggacggtg actctggcga catgtggacc    3360
gataccttcg tccaggataa ggctggtcat tggttctatc tgggcaaaga cggtgcggcg    3420
gtaaccggtg cccagaccgt ccgtggtcag aagctgtact tcaaagcgaa tggccagcag    3480
gttaagggtg acattgtgaa aggcgcggat ggtaaaatcc gttactatga tgcaaattcc    3540
ggtgaccagg tttacaatcg cacggtgaaa ggctccgacg gcaagaccta tatcattggt    3600
aatgacggcg tcgcaatcac gcaaaccatc gccaaaggcc agaccatcaa ggatggcagc    3660
gttctgcgct tctatagcat ggagggtcag ctggtgaccg gcagcggctg gtattccaac    3720
gcgaaaggtc aatggttgta tgtcaagaac ggtcaagtcc tgacgggttt gcagacggtg    3780
ggcagccagc gtgtgtactt tgacgcaaat ggtattcaag cgaaaggtaa agcagtgcgt    3840
acctccgatg gcaaactgcg ttacttcgat gcgaacagcg gcagcatgat caccaatcag    3900
tggaaagaag ttaatggtca gtactactat ttcgacaaca acggtgttgc gatctatcgc    3960
ggttggaact aa                                                        3972
```

<210> SEQ ID NO 67
<211> LENGTH: 1323
<212> TYPE: PRT
<213> ORGANISM: Streptococcus dentirousetti

<400> SEQUENCE: 67

```
Met Val Asp Gly Lys Tyr Tyr Tyr Asp Ala Asp Gly Asn Val Lys
1               5                   10                  15

Lys Asn Phe Ala Val Ser Val Gly Asp Ala Ile Phe Tyr Phe Asp Glu
            20                  25                  30

Thr Gly Ala Tyr Lys Asp Thr Ser Lys Val Asp Ala Asp Lys Thr Ser
        35                  40                  45

Ser Ser Val Asn Gln Thr Thr Glu Thr Phe Ala Ala Asn Asn Arg Ala
    50                  55                  60
```

```
Tyr Ser Thr Ala Ala Glu Asn Phe Glu Ala Ile Asp Asn Tyr Leu Thr
 65                  70                  75                  80

Ala Asp Ser Trp Tyr Arg Pro Lys Ser Ile Leu Lys Asp Gly Thr Thr
                 85                  90                  95

Trp Thr Glu Ser Thr Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
            115                 120                 125

Val Val Gly Ile Asp Lys Thr Tyr Thr Ala Glu Thr Ser Gln Ala Asp
130                 135                 140

Leu Thr Ala Ala Glu Leu Val Gln Ala Arg Ile Glu Gln Lys Ile
145                 150                 155                 160

Thr Ser Glu Lys Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Glu Thr Ser Leu
            195                 200                 205

Thr Pro Asp Thr Gln Ser Gly Tyr Arg Ile Leu Asn Arg Thr Pro Thr
210                 215                 220

Asn Gln Thr Gly Ser Leu Asp Pro Arg Phe Thr Phe Asn Gln Asn Asp
225                 230                 235                 240

Pro Leu Gly Gly Tyr Glu Tyr Leu Leu Ala Asn Asp Val Asp Asn Ser
                245                 250                 255

Asn Pro Val Val Gln Ala Glu Ser Leu Asn Trp Leu His Tyr Leu Leu
            260                 265                 270

Asn Phe Gly Ser Ile Tyr Ala Asn Asp Pro Glu Ala Asn Phe Asp Ser
            275                 280                 285

Ile Arg Val Asp Ala Val Asp Asn Val Asp Ala Asp Leu Leu Gln Ile
            290                 295                 300

Ser Ser Asp Tyr Leu Lys Ser Ala Tyr Lys Ile Asp Lys Asn Asn Lys
305                 310                 315                 320

Asn Ala Asn Asp His Val Ser Ile Val Glu Ala Trp Ser Asp Asn Asp
                325                 330                 335

Thr Pro Tyr Leu Asn Asp Asp Gly Asp Asn Leu Met Asn Met Asp Asn
            340                 345                 350

Lys Phe Arg Leu Ser Met Leu Trp Ser Leu Ala Lys Pro Thr Asn Val
            355                 360                 365

Arg Ser Gly Leu Asn Pro Leu Ile His Asn Ser Val Val Asp Arg Glu
370                 375                 380

Val Asp Asp Arg Glu Val Glu Ala Thr Pro Asn Tyr Ser Phe Ala Arg
385                 390                 395                 400

Ala His Asp Ser Glu Val Gln Asp Leu Ile Arg Asp Ile Ile Lys Ala
                405                 410                 415

Glu Ile Asn Pro Asn Ser Phe Gly Tyr Ser Phe Thr Gln Glu Glu Ile
            420                 425                 430

Asp Gln Ala Phe Lys Ile Tyr Asn Glu Asp Leu Lys Lys Thr Asn Lys
            435                 440                 445

Lys Tyr Thr His Tyr Asn Val Pro Leu Ser Tyr Thr Leu Leu Leu Thr
            450                 455                 460

Asn Lys Gly Ser Ile Pro Arg Ile Tyr Tyr Gly Asp Met Phe Thr Asp
465                 470                 475                 480

Asp Gly Gln Tyr Met Ala Asn Lys Thr Val Asn Tyr Asp Ala Ile Glu
```

```
                485               490                495
   Ser Leu Leu Lys Ala Arg Met Lys Tyr Val Ser Gly Gln Ala Met
               500                505                510

Gln Asn Tyr Asn Ile Gly Asn Gly Glu Ile Leu Thr Ser Val Arg Tyr
               515                520                525

Gly Lys Gly Ala Leu Lys Gln Ser Asp Lys Gly Asp Lys Thr Thr Arg
       530                535                540

Thr Ser Gly Ile Gly Val Val Met Gly Asn Gln Ser Asn Phe Ser Leu
   545                550                555                560

Glu Gly Lys Val Val Ala Leu Asn Met Gly Ala Thr His Thr Lys Gln
                   565                570                575

Lys Tyr Arg Ala Leu Met Val Ser Thr Glu Thr Gly Val Ala Ile Tyr
               580                585                590

Asn Ser Asp Glu Glu Ala Glu Ala Ala Gly Leu Ile Lys Thr Thr Asp
                   595                600                605

Glu Asn Gly Tyr Leu Tyr Phe Leu Asn Asp Asp Leu Lys Gly Val Ala
       610                615                620

Asn Pro Gln Val Ser Gly Phe Leu Gln Val Trp Val Pro Val Gly Ala
   625                630                635                640

Pro Ala Asp Gln Asp Ile Arg Val Ala Ala Thr Asp Ala Ala Ser Thr
                       645                650                655

Asp Gly Lys Ser Leu His Gln Asp Ala Ala Leu Asp Ser Arg Val Met
                   660                665                670

Phe Glu Gly Phe Ser Asn Phe Gln Ser Phe Ala Thr Lys Glu Glu Glu
                   675                680                685

Tyr Thr Asn Val Val Ile Ala Lys Asn Val Asp Lys Phe Val Ser Trp
       690                695                700

Gly Ile Thr Asp Phe Glu Met Ala Pro Gln Tyr Val Ser Ser Thr Asp
   705                710                715                720

Gly Thr Phe Leu Asp Ser Val Ile Gln Asn Gly Tyr Ala Phe Thr Asp
                       725                730                735

Arg Tyr Asp Leu Gly Met Ser Lys Ala Asn Lys Tyr Gly Thr Ala Asp
                   740                745                750

Gln Leu Val Ala Ala Ile Lys Ala Leu His Ala Lys Gly Leu Arg Val
           755                760                765

Met Ala Asp Trp Val Pro Asp Gln Met Tyr Thr Phe Pro Lys Lys Glu
       770                775                780

Val Val Thr Val Thr Arg Thr Asp Lys Phe Gly Asn Pro Val Ala Gly
   785                790                795                800

Ser Gln Ile Asn His Thr Leu Tyr Val Thr Asp Thr Lys Gly Ser Gly
                   805                810                815

Asp Asp Tyr Gln Ala Lys Tyr Gly Gly Ala Phe Leu Asp Glu Leu Lys
                   820                825                830

Glu Lys Tyr Pro Glu Leu Phe Thr Lys Gln Ile Ser Thr Gly Gln
                   835                840                845

Ala Ile Asp Pro Ser Val Lys Ile Lys Gln Trp Ser Ala Lys Tyr Phe
       850                855                860

Asn Gly Ser Asn Ile Leu Gly Arg Gly Ala Asn Tyr Val Leu Ser Asp
   865                870                875                880

Gln Ala Ser Asn Lys Tyr Phe Asn Val Ala Glu Gly Lys Val Phe Leu
                   885                890                895

Pro Ala Ala Met Leu Gly Lys Val Val Glu Ser Gly Ile Arg Phe Asp
                   900                905                910
```

```
Gly Lys Gly Tyr Ile Tyr Asn Ser Ser Thr Gly Glu Gln Val Lys
        915                 920                 925

Asp Ser Phe Ile Thr Glu Ala Gly Asn Leu Tyr Tyr Phe Gly Lys Asp
        930                 935                 940

Gly Tyr Met Val Met Gly Ala Gln Asn Ile Gln Gly Ala Asn Tyr Tyr
945                 950                 955                 960

Phe Leu Ala Asn Gly Ala Ala Leu Arg Asn Ser Ile Leu Thr Asp Gln
        965                 970                 975

Asp Gly Lys Ser His Tyr Tyr Ala Asn Asp Gly Lys Arg Tyr Glu Asn
        980                 985                 990

Gly Tyr Tyr Gln Phe Gly Asn Asp Ser Trp Arg Tyr Phe Glu Asn Gly
        995                 1000                1005

Val Met Ala Val Gly Leu Thr Arg Val Ala Gly His Asp Gln Tyr
    1010                1015                1020

Phe Asp Lys Asp Gly Ile Gln Ala Lys Asn Lys Ile Ile Val Thr
    1025                1030                1035

Arg Asp Gly Lys Val Arg Tyr Phe Asp Glu His Asn Gly Asn Ala
    1040                1045                1050

Ala Thr Asn Thr Phe Ile Ser Asp Gln Ala Gly His Trp Tyr Tyr
    1055                1060                1065

Leu Gly Lys Asp Gly Val Ala Val Thr Gly Ala Gln Thr Val Gly
    1070                1075                1080

Lys Gln His Leu Tyr Phe Glu Ala Asn Gly Gln Gln Val Lys Gly
    1085                1090                1095

Asp Phe Val Thr Ala Lys Asp Gly Lys Leu Tyr Phe Leu Asp Gly
    1100                1105                1110

Asp Ser Gly Asp Met Trp Thr Asp Thr Phe Val Gln Asp Lys Ala
    1115                1120                1125

Gly His Trp Phe Tyr Leu Gly Lys Asp Gly Ala Ala Val Thr Gly
    1130                1135                1140

Ala Gln Thr Val Arg Gly Gln Lys Leu Tyr Phe Lys Ala Asn Gly
    1145                1150                1155

Gln Gln Val Lys Gly Asp Ile Val Lys Gly Ala Asp Gly Lys Ile
    1160                1165                1170

Arg Tyr Tyr Asp Ala Asn Ser Gly Asp Gln Val Tyr Asn Arg Thr
    1175                1180                1185

Val Lys Gly Ser Asp Gly Lys Thr Tyr Ile Ile Gly Asn Asp Gly
    1190                1195                1200

Val Ala Ile Thr Gln Thr Ile Ala Lys Gly Gln Thr Ile Lys Asp
    1205                1210                1215

Gly Ser Val Leu Arg Phe Tyr Ser Met Glu Gly Gln Leu Val Thr
    1220                1225                1230

Gly Ser Gly Trp Tyr Ser Asn Ala Lys Gly Gln Trp Leu Tyr Val
    1235                1240                1245

Lys Asn Gly Gln Val Leu Thr Gly Leu Gln Thr Val Gly Ser Gln
    1250                1255                1260

Arg Val Tyr Phe Asp Ala Asn Gly Ile Gln Ala Lys Gly Lys Ala
    1265                1270                1275

Val Arg Thr Ser Asp Gly Lys Leu Arg Tyr Phe Asp Ala Asn Ser
    1280                1285                1290

Gly Ser Met Ile Thr Asn Gln Trp Lys Val Asn Gly Gln Tyr
    1295                1300                1305
```

```
Tyr Tyr Phe Asp Asn Asn Gly Val Ala Ile Tyr Arg Gly Trp Asn
    1310                1315                1320
```

<210> SEQ ID NO 68
<211> LENGTH: 1619
<212> TYPE: PRT
<213> ORGANISM: Lactobacillus reuteri

<400> SEQUENCE: 68

```
Met Glu Leu Lys Lys His Phe Lys Leu Tyr Lys Ser Gly Lys Gln Trp
1               5                   10                  15

Val Thr Ala Ala Val Ala Thr Ile Ala Phe Ser Ala Gly Val Leu Thr
            20                  25                  30

Thr Ser Glu Val Val His Ala Asp Thr Asn Thr Gly Asp Gln Gln Thr
        35                  40                  45

Glu Gln Val Thr Gln Pro Ser Asn Ser Thr Thr Gln Asp Val Lys Pro
    50                  55                  60

Val Ser Thr Asp Ala Ser Ser Asp Thr Lys Ile Val Ser Asp Asn Lys
65                  70                  75                  80

Glu Asn Asn Asn Gln Val Gly Asn Thr Asn Val Ser Gly Gln Asn Ser
                85                  90                  95

Ser Lys Asp Thr Lys Ser Val Leu Thr Gly Thr Asn Ser Val Thr Gln
            100                 105                 110

Asn Tyr Asp His Asn Asp Asn Gly Asn Tyr Gly Tyr Ile Asp Ser Ala
        115                 120                 125

Asn Leu Asn Asn Asn Gln Leu Gln Val Ser Gly Trp Ser Ala Thr Asn
    130                 135                 140

Gln Asn Ile Asn Lys Asp Asn His Phe Ile Ile Ala Tyr Asp Ser Thr
145                 150                 155                 160

Ser Gln Gln Glu Leu Gly Arg Thr Lys Val Glu Thr Pro Val Ala Arg
                165                 170                 175

Pro Asp Val Lys Ala Val His Asn Val Tyr Asn Ala Glu Asn Ser Gly
            180                 185                 190

Phe Asn Val Asn Val Ser Leu Asn Phe Asp Lys Met Asn Asn Tyr Arg
        195                 200                 205

Asp Ala Ile Lys Ile Ile Ser Arg Tyr Ser Gly Val Pro Asp Gly Asn
    210                 215                 220

Ser Asp Tyr Val Asp Phe Val Ser Gln Pro Ile Ile Phe Asp Glu Asn
225                 230                 235                 240

Asn Tyr Ala His Leu Asp Asp Phe Ser Val Gln Asn Gly Lys Leu His
                245                 250                 255

Val Ser Gly Trp Asn Ala Thr Asn Lys Ala Ile Gln Asn Pro Asn His
            260                 265                 270

Phe Leu Ile Leu Phe Asp Arg Thr Ile Asn Arg Glu Val Ala Arg Gln
        275                 280                 285

Lys Val Thr Ala Gly Ile Asn Arg Pro Asp Val Glu Lys Ala Tyr Pro
    290                 295                 300

Gln Val Ile Asn Ala Asn Ile Ser Gly Phe Asp Ala Ala Phe Asp Ile
305                 310                 315                 320

Thr Thr Leu Asn Pro Asn Asp Glu Tyr Gln Ile Leu Ser Arg Tyr Ser
                325                 330                 335

Asn Asp Asp Asn Gly Glu Gly Ser Tyr Val Thr Tyr Trp Phe Lys Pro
            340                 345                 350

Gln Arg Ile Ala Pro Ala Asn Gln Phe Asn Ser Gly His Leu Asp Ser
        355                 360                 365
```

-continued

```
Phe Asn Ile Ser Lys Ala Gly Lys Val Thr Val Ser Gly Trp Gln Ala
    370                 375                 380

Thr Asn Leu Ser Asn Ile Gln Ser Asn Arg Phe Ile Ile Leu Phe Asp
385                 390                 395                 400

Asn Thr Ala Asn His Gln Ile Ala Ser Thr Lys Ile Thr Asn Thr Ala
                405                 410                 415

Arg Pro Asp Val Glu Lys Val Tyr Pro Gln Val Leu Asn Ala Thr Asn
            420                 425                 430

Ser Gly Tyr Asp Val Thr Phe Asp Leu Thr Gln Asp Gln Ile Ala Gln
        435                 440                 445

Leu Leu Pro Asn His Ser Tyr Ser Ile Val Ser Arg Tyr Ser Ala Asp
450                 455                 460

Ala Asn Gly Asn Gly Asn Asp Lys Gln His Thr Asp Phe Trp Ser Thr
465                 470                 475                 480

Pro Ile Thr Leu Asn Lys Thr Ala Ser Tyr Ile Asp Ser Ile Ser Leu
                485                 490                 495

Asn Gly Asn Glu Leu Asn Val Arg Gly Trp Met Ala Ser Asp Ala Ser
            500                 505                 510

Ala Thr Gln Ala Asn Pro Tyr Leu Ile Val Leu Asn Asn Gly Lys Glu
        515                 520                 525

Val Thr Arg Gln Lys Leu Thr Leu Val Ala Arg Pro Asp Val Ala Lys
530                 535                 540

Val Tyr Pro Asp Val Tyr Ser Ser Leu Asp Ser Gly Phe Asn Thr Thr
545                 550                 555                 560

Ile Lys Leu Thr Val Pro Gln Leu Asn Glu Leu Thr Gly Asn Met Gln
                565                 570                 575

Val Leu Leu Arg Tyr Ser Thr Ala Ala Asp Gly Asn Pro Ile Asn Asn
            580                 585                 590

Gly Gly Phe Thr Asp Gln Tyr Ser Lys Asn Tyr Ala Thr Asn Gly Gly
        595                 600                 605

Ser Phe Asp Phe Val Lys Val Asp Asn Asn Gln Val Ala Phe Ser Gly
610                 615                 620

Trp His Val Ser Asp Gln Ala Thr Asp Lys Pro Tyr Gln Trp Ile Ile
625                 630                 635                 640

Val Leu Ala Asn Gly Lys Glu Val Gly Arg Gln Leu Ile Ser Ser Thr
                645                 650                 655

Thr Asn Gly Phe Val Ser Tyr Asn Arg Pro Asp Val Tyr Asn Val Asn
            660                 665                 670

Pro Ala Ile Ser Asn Ser Ser Thr Ser Gly Phe Gln Gly Ile Met Thr
        675                 680                 685

Leu Lys Asp Asn Ile Lys Asn Ala Asn Val Gln Leu Val His Arg Phe
690                 695                 700

Ser Asp Asp Gly Gln Asn Gly Glu Gly Asn Arg Val Asp Tyr Trp Ser
705                 710                 715                 720

Glu Val Met Pro Val Thr Asn Thr Phe Gln Lys Gly Thr Asp Gln Leu
                725                 730                 735

Met Arg Asn Leu Val Ala Lys Pro Asn Lys Asn Gln Leu Lys Ile Tyr
            740                 745                 750

Asn Gly Asn Thr Leu Val Lys Thr Leu Gly Pro Gly Thr Trp Glu Asn
        755                 760                 765

Met Ala Phe Ala Gln Asp Ser Ser Ala Ile Asn Ile Asp Gly Tyr
770                 775                 780
```

```
Leu Ser Tyr Thr Asp Trp Tyr Arg Pro Tyr Gly Thr Ser Gln Asp Gly
785                 790                 795                 800

Lys Thr Trp Tyr Lys Thr Thr Ala Met Asp Trp Arg Pro Leu Leu Met
                805                 810                 815

Tyr Ile Trp Pro Ser Lys Asp Val Gln Ala Gln Phe Ile Lys Tyr Phe
            820                 825                 830

Val Asn Asn Gly Tyr Glu Asn Ala Asn Tyr Gly Leu Thr Lys Asp Thr
        835                 840                 845

Val Ala Asn Ile Asn Lys Asp Thr Asn Thr Thr Val Leu Ala Asn Met
850                 855                 860

Ala Gln Asn Leu Arg Tyr Val Ile Glu Gln Ser Ile Ala Ala Asn Lys
865                 870                 875                 880

Gly Thr Ser Lys Leu Ala Asn Asp Ile Asn Ser Phe Ala Ala Thr Val
                885                 890                 895

Pro Glu Leu Ser Ala Ser Ser Glu Leu Ser Leu Gln Ser Met Pro Asn
            900                 905                 910

Tyr Arg Pro Asp Lys Ser Gly Thr Ile Asp Ser Asp Gln Val Ile Phe
        915                 920                 925

Val Asn Asn Ser Lys Asp Pro Arg Lys Gly Asn Thr Ser Tyr Ala
930                 935                 940

Asp Ser Asn Tyr Arg Leu Met Asn Arg Thr Ile Asn Asn Gln Ala Gly
945                 950                 955                 960

Asn Asn Ser Asp Asn Ser Pro Glu Leu Leu Val Gly Asn Asp Ile
                965                 970                 975

Asp Asn Ser Asn Pro Val Val Gln Ala Glu Asn Leu Asn Trp Glu Tyr
            980                 985                 990

Phe Leu Leu Asn Tyr Gly Lys Leu Met Gly Tyr Asn Pro Asp Gly Asn
        995                 1000                1005

Phe Asp Gly Phe Arg Val Asp Ala Ala Asp Asn Ile Asp Ala Asp
1010                1015                1020

Val Leu Asp Gln Met Gly Gln Leu Met Asn Asp Met Tyr His Thr
1025                1030                1035

Lys Gly Asn Pro Gln Asn Ala Asn Asp His Leu Ser Tyr Asn Glu
1040                1045                1050

Gly Tyr His Ser Gly Ala Ala Gln Met Leu Asn Glu Lys Gly Asn
1055                1060                1065

Pro Gln Leu Tyr Met Asp Ser Gly Glu Phe Tyr Thr Leu Glu Asn
1070                1075                1080

Val Leu Gly Arg Ala Asn Asn Arg Asp Asn Ile Gly Asn Leu Ile
1085                1090                1095

Thr Asn Ser Ile Val Asn Arg Gln Asn Asp Thr Thr Glu Asn Glu
1100                1105                1110

Ala Thr Pro Asn Trp Ser Phe Val Thr Asn His Asp Gln Arg Lys
1115                1120                1125

Asn Leu Ile Asn Arg Leu Ile Ile Lys Asp His Ser Asn Ile Pro
1130                1135                1140

Asp Ile Met Gly Ser Ala Tyr Lys Val Glu Tyr Ala Asn Gln Ala
1145                1150                1155

Trp Gln Glu Phe Tyr Ala Asp Gln Glu Lys Thr Asn Lys Gln Tyr
1160                1165                1170

Ala Gln Tyr Asn Val Pro Ala Gln Tyr Ala Ile Leu Leu Ser Asn
1175                1180                1185

Lys Asp Thr Val Pro Gln Val Tyr Tyr Gly Asp Leu Tyr Asn Glu
```

-continued

```
            1190                1195                1200

Thr Ala Gln Tyr Met Gln Glu Lys Ser Ile Tyr Tyr Asp Ala Ile
    1205                1210                1215

Thr Thr Leu Met Arg Ala Arg Lys Gln Phe Val Ser Gly Gly Gln
    1220                1225                1230

Thr Met Thr Lys Leu Asn Asn Asn Leu Leu Ala Ser Val Arg Tyr
    1235                1240                1245

Gly Lys Gly Val Val Asp Ala Asn Ser Asn Gly Thr Asp Lys Leu
    1250                1255                1260

Ser Arg Thr Ser Gly Met Ala Val Leu Val Gly Asn Asp Ser Asn
    1265                1270                1275

Met Ala Gln Gln Ser Val Ala Ile Asn Met Gly Arg Ala His Ala
    1280                1285                1290

Asn Gln Gln Tyr Arg Asn Leu Ile Asp Thr Thr Glu Asn Gly Leu
    1295                1300                1305

Thr Tyr Asp Ala Asp Asn Ser Glu Asn Pro Ala Ile Leu Thr Thr
    1310                1315                1320

Asp Ser Asn Gly Ile Leu Lys Val Thr Val Lys Gly Tyr Ser Asn
    1325                1330                1335

Pro Tyr Val Ser Gly Tyr Leu Gly Val Trp Val Pro Val Ile Ser
    1340                1345                1350

Gly Asp Gln Asp Val Thr Thr Asn Ala Ser Asp Val Val Ala Asn
    1355                1360                1365

Lys Glu Lys Thr Phe Glu Ser Asn Ala Ala Leu Asp Ser His Met
    1370                1375                1380

Ile Tyr Glu Asp Phe Ser Leu Phe Gln Pro Glu Pro Thr Ser Val
    1385                1390                1395

Glu Asn His Ala Tyr Asn Val Ile Ala Lys Asn Ala Ser Leu Phe
    1400                1405                1410

Ser Asp Leu Gly Ile Thr Asp Phe Trp Met Ala Pro Ala Tyr Thr
    1415                1420                1425

Pro Phe Gly Arg Ser Arg Tyr Asn Glu Gly Tyr Ser Met Thr Asp
    1430                1435                1440

Arg Tyr Asn Leu Gly Thr Thr Ala Asn Pro Thr Lys Tyr Gly Ser
    1445                1450                1455

Gly Glu Glu Leu Ala Asn Thr Ile Ala Ala Leu His Lys Ala Gly
    1460                1465                1470

Leu Lys Val Gln Glu Asp Ile Val Met Asn Gln Met Ile Gly Phe
    1475                1480                1485

Ser Gly Gln Glu Ala Val Thr Val Thr Arg Thr Asn Asn Arg Gly
    1490                1495                1500

Met Gln Ile His Val Asn Gly Gln Thr Tyr Ala Asn Gln Ile Tyr
    1505                1510                1515

Phe Ala Tyr Thr Thr Gly Gly Gly Asn Gly Gln Glu Thr Tyr Gly
    1520                1525                1530

Gly Lys Tyr Leu Ala Glu Leu Gln Lys Asn Tyr Pro Asp Leu Phe
    1535                1540                1545

Thr Thr Lys Ala Ile Ser Thr Gly Val Ala Pro Asp Pro Thr Val
    1550                1555                1560

Arg Ile Asn Lys Trp Ser Ala Lys Tyr Gln Asn Gly Thr Ser Leu
    1565                1570                1575

Gln Asn Ile Gly Ile Gly Leu Ala Val Lys Leu Ala Asn Gly Asp
    1580                1585                1590
```

-continued

Tyr Ala Tyr Leu Asn Ser Gly Asp Asn Lys Ala Phe Asn Thr Leu
1595                1600                1605

Leu Pro Thr Ala Ile Ser Leu Asn Phe Asn Asn
1610                1615

<210> SEQ ID NO 69
<211> LENGTH: 1620
<212> TYPE: PRT
<213> ORGANISM: Lactobacillus reuteri

<400> SEQUENCE: 69

Met Glu Ile Lys Lys His Phe Lys Leu Tyr Lys Ser Gly Lys Gln Trp
1               5                   10                  15

Val Thr Ala Ser Ile Ala Thr Phe Ala Val Ser Thr Gly Leu Val Leu
            20                  25                  30

Gly Gly Gly Val Val His Ala Ala Asp Asn His Pro Thr Thr Thr Ser
        35                  40                  45

Ala Ser Val Thr Asn Thr Val Asn Asn Leu Lys Pro Gln Asn Asp Pro
    50                  55                  60

Glu Gln Gln Asn Asn Thr Gln Glu Ser Asn Thr Val Glu Phe Pro Lys
65                  70                  75                  80

Lys Asp Ser Gln Asp Asn Ala Val Gln Pro Leu Lys Glu Thr Ala Val
                85                  90                  95

Met Pro Asn Ala Thr Asn Lys Asp Gly Ala Lys Ala Ser Ile Thr Asn
            100                 105                 110

Asn Ala His Thr Asp Asn Thr Ile Tyr Gly Asn Ile Asp Pro Thr Thr
        115                 120                 125

Ile Asn Asp Lys Glu Leu His Val Thr Gly Trp Asn Ala Thr Asn Gln
    130                 135                 140

Ala Ile Asn Lys Asn Glu Ser Arg Tyr Val Ile Ala Tyr Asp Asp Thr
145                 150                 155                 160

Thr Asn Ser Glu Leu Gly Arg Thr Lys Ile Thr Asn Gln Ile Ala Arg
                165                 170                 175

Pro Asp Val Glu Lys Val His Lys Asp Ile Tyr Asn Ala Gln Asn Ser
            180                 185                 190

Gly Phe Asn Val Asn Ile Ser Leu Asp Phe Asn Lys Met Asn Asn Tyr
        195                 200                 205

Arg Asp Ala Ile Lys Ile Ile Ser Arg Tyr Ser Gly Val Pro Asn Gly
    210                 215                 220

Asn Ser Asp Tyr Val Asp Phe Val Ser Gln Pro Ile Ile Phe Asp Glu
225                 230                 235                 240

Asn Asn Tyr Ala Tyr Leu Asp Asp Phe Ser Val Gln Asn Gly Arg Leu
                245                 250                 255

His Val Ser Gly Arg Asn Ala Thr Asn Lys Ala Ile Gln Arg Pro Asn
            260                 265                 270

His Phe Leu Ile Leu Phe Asp Arg Thr Val Asn Arg Glu Val Ala Arg
        275                 280                 285

Gln Lys Val Thr Ala Gly Ile Asn Arg Ser Asp Val Glu Lys Val Tyr
    290                 295                 300

Pro Gln Val Val Asn Ala Asn Val Ser Gly Phe Asp Ala Thr Phe Asp
305                 310                 315                 320

Thr Ile Asn Leu Asn Pro Asn His Glu Tyr Gln Ile Leu Ser Arg Tyr
                325                 330                 335

Ser Asn Asn Gly Asp Gly Glu Gly Asp Tyr Val Thr Tyr Trp Phe Asn

-continued

```
            340                 345                 350
Pro Gln Arg Ile Ala Pro Val Asn Gln Phe Asn Asn Gly His Leu Asp
            355                 360                 365
Asn Phe Asp Ile Ser Lys Ala Gly Lys Val Thr Val Ser Gly Trp Gln
            370                 375                 380
Ala Thr Asn Leu Ser Asn Ile Gln Asn Asn Arg Tyr Ile Ile Leu Phe
385                 390                 395                 400
Asp Thr Thr Ala Asn Cys Gln Ile Ala Ser Met Lys Val Thr Gly Val
                    405                 410                 415
Asp Arg Pro Asp Val Ala Lys Val Tyr Pro Gln Ile Leu Asn Ala Asn
            420                 425                 430
Lys Ser Gly Tyr Asn Val Thr Phe Asp Leu Thr Gln Ala Gln Ile Ala
            435                 440                 445
Gln Leu Phe Pro Asn His Ser Tyr Ser Ile Val Ser Arg Tyr Ser Ala
            450                 455                 460
Asp Pro Asn Gly Asn Gly Asn Asp Lys Gln His Thr Asp Phe Trp Ser
465                 470                 475                 480
Ala Pro Ile Val Leu Asn Lys Thr Ala Ser Tyr Ile Asp Asp Ile Ser
                    485                 490                 495
Leu Asn Gly Asp Val Leu Asn Val Lys Gly Trp Met Ala Ser Asp Ala
            500                 505                 510
Ser Ala Thr Gln Ala Asn Pro Tyr Ile Ile Leu Asn Asn Gly Lys
            515                 520                 525
Glu Val Thr Arg Gln Lys Leu Thr Leu Asn Asp Arg Pro Asp Val Ala
            530                 535                 540
Lys Val Tyr Pro Asp Val Tyr Asn Ser Leu Ala Ser Gly Phe Asp Thr
545                 550                 555                 560
Thr Ile Lys Leu Thr Asn Ser Gln Leu Asn Ala Leu Asn Gly Asn Met
                    565                 570                 575
Gln Ile Leu Leu Arg Tyr Ser Ala Ala Ala Asp Gly Asn Pro Ile Asn
            580                 585                 590
Asn Gly Gly Phe Thr Asp Gln Tyr Ser Lys Asn Tyr Ala Thr Asn Gly
            595                 600                 605
Gly Ser Phe Asp Phe Val Lys Val Asp Asn Asn Gln Val Ala Phe Ser
            610                 615                 620
Gly Trp His Val Ser Asp Gln Ala Thr Asp Lys Pro Tyr Gln Trp Ile
625                 630                 635                 640
Ile Val Leu Val Asn Gly Lys Glu Val Gly Arg Gln Leu Ile Ser Ser
                    645                 650                 655
Thr Thr Asn Gly Leu Val Ser Tyr Asn Arg Pro Asp Val Tyr Asn Val
            660                 665                 670
Asn Pro Ala Ile Ser Asn Ser Ser Thr Ser Gly Phe Gln Gly Ile Met
            675                 680                 685
Thr Leu Lys Asp Asn Ile Lys Asn Ala Asn Val Gln Leu Val His Arg
            690                 695                 700
Phe Ser Asp Asp Gly Gln Asn Gly Glu Gly Asn Arg Val Asp Tyr Trp
705                 710                 715                 720
Ser Glu Val Met Pro Val Thr Asn Thr Phe Gln Lys Gly Thr Asp Gln
                    725                 730                 735
Leu Met Arg Asn Leu Val Ala Lys Pro Asn Lys Asn Gln Leu Lys Ile
            740                 745                 750
Tyr Asn Gly Asn Thr Leu Val Lys Thr Leu Gly Pro Gly Thr Trp Glu
            755                 760                 765
```

```
Asn Met Ala Phe Ala Gln Asp Ser Ser Ala Ile Asn Ile Asp Gly
    770                 775                 780

Tyr Leu Ser Tyr Thr Gly Trp Tyr Arg Pro Tyr Gly Thr Ser Gln Asp
785                 790                 795                 800

Gly Lys Thr Trp Tyr Glu Thr Thr Ala Met Asp Trp Arg Pro Leu Leu
                805                 810                 815

Met Tyr Ile Trp Pro Ser Lys Asp Val Gln Ala Gln Phe Ile Lys Tyr
                820                 825                 830

Phe Val Asn Asn Gly Tyr Glu Asn Ala Asn Tyr Gly Leu Thr Glu Ser
            835                 840                 845

Ser Val Ala Ser Phe Ser Lys Asp Thr Asn Ala Asn Leu Leu Asp Val
    850                 855                 860

Thr Ala Gln Asn Leu Arg Tyr Val Ile Glu Gln Ser Ile Ala Ala Asn
865                 870                 875                 880

Lys Gly Thr Ser Lys Leu Ala Asn Asp Ile Asn Ser Phe Ala Ala Thr
                885                 890                 895

Val Pro Glu Leu Ser Ala Ser Ser Glu Leu Ser Leu Gln Ser Met Pro
            900                 905                 910

Asn Tyr Arg Pro Asp Glu Ser Gly Thr Val Ser Asp Gln Val Ile
            915                 920                 925

Phe Val Asn Asn Asn Ser Lys Asp Pro Arg Lys Gly Asn Thr Gly Tyr
    930                 935                 940

Ala Asp Ser Asn Tyr Arg Leu Met Asn Arg Thr Ile Asn Gln Ala
945                 950                 955                 960

Gly Asn Asn Asn Ser Asp Asn Ser Pro Glu Leu Leu Val Gly Asn Asp
                965                 970                 975

Ile Asp Asn Ser Asn Pro Val Val Gln Ala Glu Asn Leu Asn Trp Glu
            980                 985                 990

Tyr Phe Leu Leu Asn Tyr Gly Lys Leu Met Gly Tyr Asn Pro Asp Gly
    995                 1000                1005

Asn Phe Asp Gly Phe Arg Val Asp Ala Ala Asp Asn Ile Asp Ala
    1010                1015                1020

Asp Val Leu Asp Gln Met Gly Gln Leu Met Asn Asp Met Tyr His
    1025                1030                1035

Thr Lys Gly Asn Pro Gln Asn Ala Asn Asp His Leu Ser Tyr Asn
    1040                1045                1050

Glu Gly Tyr His Ser Gly Ala Ala Gln Met Leu Asn Glu Lys Gly
    1055                1060                1065

Asn Pro Gln Leu Tyr Met Asp Ser Gly Glu Phe Tyr Thr Leu Glu
    1070                1075                1080

Asn Val Leu Gly Arg Ala Asn Asn Arg Asp Ser Ile Gly Asn Leu
    1085                1090                1095

Ile Thr Asn Ser Val Val Asn Arg Gln Asn Asp Thr Thr Glu Asn
    1100                1105                1110

Glu Ala Thr Pro Asn Trp Ser Phe Val Thr Asn His Asp Gln Arg
    1115                1120                1125

Lys Asn Leu Ile Asn Arg Leu Ile Ile Lys Gly His Pro Asn Ile
    1130                1135                1140

Pro Asp Ile Met Gly Ser Ala Tyr Lys Ala Glu Tyr Ala Asn Gln
    1145                1150                1155

Ala Trp Gln Glu Phe Tyr Ala Asp Gln Lys Lys Thr Asn Lys Gln
    1160                1165                1170
```

-continued

Tyr Asp Gln Tyr Asn Val Pro Ala Gln Tyr Ala Ile Leu Leu Ser
1175                1180                1185

Asn Lys Asp Thr Val Pro Gln Val Tyr Tyr Gly Asp Leu Tyr Asn
1190                1195                1200

Glu Thr Ala Gln Tyr Met Gln Glu Lys Ser Ile Tyr Tyr Asp Thr
1205                1210                1215

Ile Thr Thr Leu Met Lys Ala Arg Lys Gln Phe Val Ser Gly Gly
1220                1225                1230

Gln Thr Met Thr Lys Leu Asn Asn Asn Leu Leu Ala Ser Val Arg
1235                1240                1245

Tyr Gly Lys Gly Val Ala Asp Ser Asn Ser Asn Gly Thr Asp Lys
1250                1255                1260

Leu Ser Arg Thr Ser Gly Ile Ala Val Leu Val Gly Asn Asp Ser
1265                1270                1275

Asn Met Ala Gln Gln Thr Val Ala Ile Asn Met Gly Arg Ala His
1280                1285                1290

Ala Asn Gln Gln Tyr Arg Asn Leu Ile Asp Thr Thr Glu Asn Gly
1295                1300                1305

Leu Thr Tyr Asp Gly Glu Asn Ser Glu Asn Pro Ala Ile Leu Thr
1310                1315                1320

Thr Asp Ser Asn Gly Ile Leu Lys Val Thr Val Lys Gly Tyr Ser
1325                1330                1335

Asn Pro Tyr Val Ser Gly Tyr Leu Gly Val Trp Val Pro Val Ile
1340                1345                1350

Ser Gly Asp Gln Asp Val Thr Thr Ser Ala Ser Asp Val Val Ala
1355                1360                1365

Asp Lys Glu Lys Thr Phe Glu Ser Asn Ala Ala Leu Asp Ser His
1370                1375                1380

Met Ile Tyr Glu Asp Phe Ser Leu Phe Gln Pro Glu Pro Thr Asn
1385                1390                1395

Val Glu Asn His Ala Tyr Asn Val Ile Ala Lys Asn Ala Asn Leu
1400                1405                1410

Phe Asn Asp Leu Gly Ile Thr Asp Phe Trp Met Ala Pro Ala Tyr
1415                1420                1425

Thr Pro Phe Gly Met Ser Arg Tyr Asn Glu Gly Tyr Ser Met Thr
1430                1435                1440

Asp Arg Tyr Asn Leu Gly Thr Thr Ala Asn Pro Thr Lys Tyr Gly
1445                1450                1455

Ser Gly Glu Glu Leu Ala Asn Thr Ile Ala Ala Leu His Lys Val
1460                1465                1470

Gly Leu Lys Val Gln Glu Asp Ile Val Met Asn Gln Met Ile Gly
1475                1480                1485

Phe Ser Gly Gln Glu Ala Val Thr Val Thr Arg Thr Asn Asn Arg
1490                1495                1500

Gly Met Gln Ile His Val Asn Gly Gln Thr Tyr Ala Asn Gln Ile
1505                1510                1515

Tyr Phe Ala Tyr Thr Thr Gly Gly Gly Asn Gly Gln Glu Thr Tyr
1520                1525                1530

Gly Gly Lys Tyr Leu Ala Glu Leu Gln Lys Asn Tyr Pro Asp Leu
1535                1540                1545

Phe Thr Thr Lys Ala Ile Ser Thr Glu Val Val Pro Asp Pro Thr
1550                1555                1560

Val Arg Ile Asn Lys Trp Ser Ala Lys Tyr Glu Asn Gly Thr Ser

```
                    1565                1570                1575

Leu Gln Asn Ile Gly Ile Gly Leu Ala Val Lys Leu Ala Asn Gly
        1580                1585                1590

Asp Tyr Ala Tyr Leu Asn Ser Gly Asp Asn Lys Ala Phe Asn Thr
        1595                1600                1605

Leu Leu Pro Thr Ala Ile Ser Leu Asn Phe Asn Asn
        1610                1615                1620

<210> SEQ ID NO 70
<211> LENGTH: 1488
<212> TYPE: PRT
<213> ORGANISM: Lactobacillus reuteri

<400> SEQUENCE: 70

Met Asp Ile Lys Lys His Phe Lys Leu Tyr Lys Ser Gly Lys Gln Trp
1               5                   10                  15

Phe Thr Ala Ala Ile Ile Thr Ala Val Ser Ala Gly Leu Ile Leu Asn
                20                  25                  30

Leu Gly Gly Val Ala Ser Ala Asp Ser Ala Thr Asn Ala Asn Asp Asn
            35                  40                  45

Val Ala Val Asn Gln Pro Ala Ala Gln Thr Ser Glu Asn Ile Lys Ser
        50                  55                  60

Val Ser Ser Asn Ala Ser Thr Asn Asp Val Thr Asn Asn Gln Lys Ala
65                  70                  75                  80

Gln Lys Val Gln Ser Pro Lys Ser Ile Asn Pro Lys Ala Asp Asn Ser
                85                  90                  95

Asn Gln Gln Gln Asn Arg Trp Val Lys Asn Ala Gln Gly Gln Met Glu
            100                 105                 110

Tyr Tyr Gln Asn Asn Gln Leu Leu Lys Gly Arg Gln Tyr Val Asn Leu
        115                 120                 125

Pro Thr Ile Pro Asn Thr Asn Val Gln Thr Asp Asn Asn Trp Tyr Leu
    130                 135                 140

Val Asp Asn Gly Ile Ala Gln Ser Gly Val Gln Gln Trp Ala Gly Ser
145                 150                 155                 160

Tyr Tyr Tyr Phe Asn Pro Ser Thr Tyr Leu Arg Val Asp Asn Glu Tyr
                165                 170                 175

Arg Gln Ser Gln Trp Gly Asp Trp Tyr Met Phe Gly Lys Asp Gly Arg
            180                 185                 190

Ala Val Thr Gly Leu Tyr Asp Tyr Asn Gly Asn Thr Tyr Tyr Ala Asn
        195                 200                 205

Pro Thr Thr Tyr Leu Arg Glu Thr Asn Lys Tyr Ile Ser Thr Ser Lys
    210                 215                 220

Gly Asn Met Leu Leu Gly Asn Asp Gly Ala Ala Leu Ser Gly Ile Gln
225                 230                 235                 240

Ser Val Asn Gly Lys Tyr Tyr Phe Asp Pro Val Thr His Leu Gln
                245                 250                 255

Ala Asn Lys Glu Asn Tyr Val Gln Ser Gln Trp Gly Asp Trp Tyr Leu
            260                 265                 270

Ile Gly Asn Asp Gly Gln Val Leu Ser Gly Val Gln Gln Trp Ala Gly
        275                 280                 285

Thr Tyr Tyr Tyr Phe Asp Pro Thr Thr Tyr Leu Arg Val Asp Asn Asp
    290                 295                 300

Tyr Arg Gln Ser Gln Trp Gly Leu Trp Tyr Met Phe Gly His Asp Gly
305                 310                 315                 320
```

-continued

```
Arg Ile Val Thr Lys Val Tyr Pro Trp Ala Gly Tyr Tyr Phe
            325                 330                 335

Asp Pro Thr Thr Tyr Leu Arg Val Asp Asn Ala Tyr Leu Gln Ser Gln
            340                 345                 350

Trp Gly Asp Trp Tyr Leu Phe Gly Asn Asp Gly Arg Ile Gln Ser Gly
            355                 360                 365

Val Gln Arg Trp Ala Gly Thr Tyr Tyr Phe Asp Pro Thr Thr Tyr
370                 375                 380

Leu Arg Val Asp Asn Asp Tyr Val Thr Ser Gln Trp Gly Ser Lys Tyr
385                 390                 395                 400

Met Phe Gly Pro Asp Gly Arg Ile Val Thr Gly Leu Tyr Lys Trp Ser
                405                 410                 415

Lys Asn Asn Gln Leu Tyr Tyr Phe Asp Pro Val Thr Tyr Leu Ala Val
            420                 425                 430

Thr Asn Asn Tyr Ile Lys Ala Asn Asn Gly Asn Trp Tyr Leu Phe Thr
            435                 440                 445

Ala Asp Gly Thr Ala Ala Ser Lys Val Ala Pro Trp Ala Gly Ser Tyr
            450                 455                 460

Tyr Tyr Phe Asp Pro Val Thr His Leu Arg Val Asp Asn Ala Tyr Val
465                 470                 475                 480

Gln Ser Gln Trp Gly Asp Trp Tyr Met Phe Gly Pro Asp Gly Arg Ile
                485                 490                 495

Val Thr Gly Leu Lys Glu Trp Tyr Gly Ser Tyr Tyr Phe Asp Pro
            500                 505                 510

Thr Thr Tyr Leu Lys Val Thr Asn Lys Trp Ile Asp Asn Lys Tyr Phe
            515                 520                 525

Gly Pro Asp Gly Arg Gln Ala Ile Ser Ser Leu Glu Asn Ile Asn Asn
530                 535                 540

Lys Phe Tyr Cys Phe Asp Gly Asn Gly Gln Ile Ile Arg Asn Gln Phe
545                 550                 555                 560

Lys Lys Ile Asp Thr His Thr Tyr Tyr Phe Gly Ser Asp Gly Ala Ala
                565                 570                 575

Leu Val Gly Lys Gln Thr Ile Asp Gly Lys Asn Tyr His Phe Ala Ser
            580                 585                 590

Asn Gly Gln Leu Leu Gly Asn Leu Tyr Gly Lys Ile Val Asp Gly Lys
            595                 600                 605

Phe Asn Ile Tyr Asp Ser Leu Ser Asn Lys Leu Ile Lys Thr Leu Asp
            610                 615                 620

Ser Gly Asp Trp Glu Asn Met Ala Tyr Ser Gln Asp Ser Ser Ser Ile
625                 630                 635                 640

Asn Asn Thr Asp Gly Tyr Leu Ser Tyr Ser Gly Trp Tyr Arg Pro Tyr
                645                 650                 655

Gly Thr Ser Gln Asp Gly Lys Thr Trp Tyr Lys Thr Thr Ala Ser Asp
            660                 665                 670

Trp Arg Pro Leu Leu Met Tyr Thr Trp Pro Ser Lys Asp Val Glu Ala
            675                 680                 685

Lys Phe Ile Lys Tyr Phe Val Asp Asn Gly Tyr Thr Asn Thr Asp Tyr
            690                 695                 700

Gly Leu Thr Lys Asp Asn Val Thr Asn Leu Ser Gln Asp Thr Asp Thr
705                 710                 715                 720

Gln Thr Leu Asn Lys Tyr Ala Arg Asn Leu Arg Phe Val Ile Glu Lys
                725                 730                 735

Ser Ile Ala Ala Asn Lys Ser Thr Gly Pro Leu Ala Asn Asp Ile Asn
```

```
                740             745             750
Lys Phe Met Leu Thr Ile Pro Glu Leu Ser Ala Lys Ser Glu Leu Pro
            755             760             765

Val Glu Tyr Ser Asn Gly Tyr Val Pro Asp Val Ser Gly Ser Ile Asp
            770             775             780

Asn Asn Gln Leu Ile Phe Ile Asn Asn Ser Asp Asn Gln Ala Lys
785             790             795             800

Gly Asn Thr Ser Tyr Ala Asp Ser Asn Tyr Arg Leu Met Asn Arg Thr
            805             810             815

Ile Asn Asn Gln Thr Asn Asn Asp Asn Ser Asp Gln Ser Pro Glu Leu
            820             825             830

Leu Val Gly Asn Asp Ile Asp Asn Ser Asn Pro Ala Val Gln Ala Glu
            835             840             845

Asn Phe Asn Trp Glu Tyr Phe Leu Leu Asn Tyr Gly Lys Leu Met Lys
            850             855             860

Tyr Asn Ala Asp Gly Asn Phe Asp Gly Phe Arg Val Asp Ala Ala Asp
865             870             875             880

Asn Ile Asp Ala Asp Val Leu Asp Gln Leu Gly Gln Leu Val Asn Asp
            885             890             895

Met Tyr His Thr Lys Gly Asn Gln Glu Asn Ala Asn Asn His Leu Val
            900             905             910

Tyr Asn Glu Gly Tyr His Ser Gly Ala Ala Arg Met Leu Asn Asp Lys
            915             920             925

Gly Asn Pro Glu Leu Phe Met Asp Ala Gly Tyr Phe Tyr Thr Leu Glu
            930             935             940

Asn Val Leu Gly Gln Ala Glu Asn Lys Arg Asp Asn Val Asn Asn Leu
945             950             955             960

Ile Thr Asn Ser Val Val Asn Arg Ala Asn Asp Ile Thr Glu Asn Thr
            965             970             975

Ala Thr Pro Asn Trp Ser Phe Val Thr Asn His Asp Gln Arg Lys Asn
            980             985             990

Val Ile Asn Gln Ile Ile Ile Asp Asn His Pro Asn Ile Pro Asp Ile
            995             1000            1005

Met Ala Asn Ser Tyr Lys Ser Thr Tyr Ala Gln Lys Ala Trp Asp
            1010            1015            1020

Glu Phe Tyr Ala Asp Gln Ala Lys Ala Asp Lys Lys Tyr Ala Gln
            1025            1030            1035

Tyr Asn Leu Pro Ala Gln Tyr Ala Leu Leu Leu Ser Asn Lys Asp
            1040            1045            1050

Thr Val Pro Gln Val Tyr Tyr Gly Asp Leu Tyr Lys Glu Thr Asp
            1055            1060            1065

Gln Tyr Met Lys Thr Lys Ser Met Tyr Tyr Asp Ala Ile Thr Thr
            1070            1075            1080

Leu Met Lys Ala Arg Gly Glu Phe Val Asn Gly Gln Thr Met
            1085            1090            1095

Thr Lys Val Asn Asp Asn Leu Ile Thr Ser Val Arg Tyr Gly Lys
            1100            1105            1110

Gly Val Val Asp Val Ser Ser Asn Gly Thr Asp Pro Leu Ser Arg
            1115            1120            1125

Thr Thr Gly Met Ala Val Ile Val Gly Asn Asn Pro Ser Met Ser
            1130            1135            1140

Glu Gln Val Val Ala Ile Asn Met Gly Leu Ala His Ala Asn Glu
            1145            1150            1155
```

Gln Tyr Arg Asn Leu Ile Asp Ser Thr Ala Asp Gly Leu Thr Tyr
1160                1165                1170

Asn Ser Asn Gly Ser Val Asn Pro Ser Val Leu Thr Thr Asp Ser
1175                1180                1185

Lys Gly Ile Leu Arg Val Thr Val Lys Gly Tyr Ser Asn Pro Tyr
1190                1195                1200

Val Ser Gly Tyr Leu Ser Val Trp Val Pro Leu Ile Asn Gly Thr
1205                1210                1215

Gln Asn Ala Arg Thr Ser Ala Gln Glu Val Arg Asn Val Pro Gly
1220                1225                1230

Lys Val Phe Thr Ser Asn Ala Ala Leu Asp Ser His Met Ile Tyr
1235                1240                1245

Glu Asp Phe Ser Leu Phe Gln Pro Glu Pro Thr Thr Val Asn Glu
1250                1255                1260

His Ala Tyr Asn Val Ile Lys Asp Asn Val Ala Leu Phe Asn Gln
1265                1270                1275

Leu Gly Ile Thr Asp Phe Trp Met Ala Pro Ser Tyr Thr Pro Phe
1280                1285                1290

Asn Thr Ser Arg Tyr Asn Glu Gly Tyr Ala Met Thr Asp Arg Tyr
1295                1300                1305

Asn Leu Gly Thr Ala Asp Asn Pro Thr Lys Tyr Gly Asn Gly Glu
1310                1315                1320

Glu Leu Ser Asn Ala Ile Ala Ala Leu His Gln Ala Gly Leu Lys
1325                1330                1335

Val Gln Glu Asp Leu Val Met Asn Gln Met Ile Gly Phe Ser Thr
1340                1345                1350

Gln Glu Ala Val Thr Val Thr Arg Val Asp Arg Asp Ala Lys Gln
1355                1360                1365

Leu Ser Val Asp Gly Gln Thr Phe Ala Asp Gln Ile Tyr Phe Gly
1370                1375                1380

Tyr Thr Arg Gly Gly Gly Gln Gly Gln Gln Asp Tyr Gly Gly Lys
1385                1390                1395

Tyr Leu Ala Glu Leu Lys Gln Lys Tyr Pro Asp Leu Phe Thr Thr
1400                1405                1410

Lys Ala Ala Ser Thr Gly Val Ala Pro Asp Pro Asn Thr Arg Ile
1415                1420                1425

Thr Glu Trp Ser Ala Lys Tyr Glu Asn Gly Thr Ser Leu Gln Asn
1430                1435                1440

Val Gly Ile Gly Leu Ala Val Lys Met Pro Asn Gly Tyr Tyr Ala
1445                1450                1455

Tyr Leu Asn Asp Gly Asn Asn Lys Ala Phe Ala Thr Thr Leu Pro
1460                1465                1470

Asp Ala Ile Ser Ser Ala Asp Tyr Tyr Ala Asn Gln Glu Asn Ile
1475                1480                1485

<210> SEQ ID NO 71
<211> LENGTH: 636
<212> TYPE: PRT
<213> ORGANISM: Neisseria polysaccharea

<400> SEQUENCE: 71

Met Leu Thr Pro Thr Gln Gln Val Gly Leu Ile Leu Gln Tyr Leu Lys
1               5                   10                  15

Thr Arg Ile Leu Asp Ile Tyr Thr Pro Glu Gln Arg Ala Gly Ile Glu

```
            20                  25                  30
Lys Ser Glu Asp Trp Arg Gln Phe Ser Arg Met Asp Thr His Phe
        35                  40                  45
Pro Lys Leu Met Asn Glu Leu Asp Ser Val Tyr Gly Asn Asn Glu Ala
    50                  55                  60
Leu Leu Pro Met Leu Glu Met Leu Leu Ala Gln Ala Trp Gln Ser Tyr
65                  70                  75                  80
Ser Gln Arg Asn Ser Ser Leu Lys Asp Ile Asp Ile Ala Arg Glu Asn
                85                  90                  95
Asn Pro Asp Trp Ile Leu Ser Asn Lys Gln Val Gly Val Cys Tyr
            100                 105                 110
Val Asp Leu Phe Ala Gly Asp Leu Lys Gly Leu Lys Asp Lys Ile Pro
            115                 120                 125
Tyr Phe Gln Glu Leu Gly Leu Thr Tyr Leu His Leu Met Pro Leu Phe
            130                 135                 140
Lys Cys Pro Glu Gly Lys Ser Asp Gly Gly Tyr Ala Val Ser Ser Tyr
145                 150                 155                 160
Arg Asp Val Asn Pro Ala Leu Gly Thr Ile Gly Asp Leu Arg Glu Val
                165                 170                 175
Ile Ala Ala Leu His Glu Ala Gly Ile Ser Ala Val Val Asp Phe Ile
                180                 185                 190
Phe Asn His Thr Ser Asn Glu His Glu Trp Ala Gln Arg Cys Ala Ala
            195                 200                 205
Gly Asp Pro Leu Phe Asp Asn Phe Tyr Ile Phe Pro Asp Arg Arg
            210                 215                 220
Met Pro Asp Gln Tyr Asp Arg Thr Leu Arg Glu Ile Phe Pro Asp Gln
225                 230                 235                 240
His Pro Gly Gly Phe Ser Gln Leu Glu Asp Gly Arg Trp Val Trp Thr
                245                 250                 255
Thr Phe Asn Ser Phe Gln Trp Asp Leu Asn Tyr Ser Asn Pro Trp Val
                260                 265                 270
Phe Arg Ala Met Ala Gly Glu Met Leu Phe Leu Ala Asn Leu Gly Val
            275                 280                 285
Asp Ile Leu Arg Met Asp Ala Val Ala Phe Ile Trp Lys Gln Met Gly
            290                 295                 300
Thr Ser Cys Glu Asn Leu Pro Gln Ala His Ala Leu Ile Arg Ala Phe
305                 310                 315                 320
Asn Ala Val Met Arg Ile Ala Ala Pro Ala Val Phe Phe Lys Ser Glu
                325                 330                 335
Ala Ile Val His Pro Asp Gln Val Val Gln Tyr Ile Gly Gln Asp Glu
                340                 345                 350
Cys Gln Ile Gly Tyr Asn Pro Leu Gln Met Ala Leu Leu Trp Asn Thr
            355                 360                 365
Leu Ala Thr Arg Glu Val Asn Leu Leu His Gln Ala Leu Thr Tyr Arg
            370                 375                 380
His Asn Leu Pro Glu His Thr Ala Trp Val Asn Tyr Val Arg Ser His
385                 390                 395                 400
Asp Asp Ile Gly Trp Thr Phe Ala Asp Glu Ala Ala Tyr Leu Gly
                405                 410                 415
Ile Ser Gly Tyr Asp His Arg Gln Phe Leu Asn Arg Phe Phe Val Asn
                420                 425                 430
Arg Phe Asp Gly Ser Phe Ala Arg Gly Val Pro Phe Gln Tyr Asn Pro
            435                 440                 445
```

-continued

```
Ser Thr Gly Asp Cys Arg Val Ser Gly Thr Ala Ala Ala Leu Val Gly
        450             455             460

Leu Ala Gln Asp Asp Pro His Ala Val Asp Arg Ile Lys Leu Leu Tyr
465             470             475                     480

Ser Ile Ala Leu Ser Thr Gly Gly Leu Pro Leu Ile Tyr Leu Gly Asp
                485             490                     495

Glu Val Gly Thr Leu Asn Asp Asp Trp Ser Gln Asp Ser Asn Lys
            500             505             510

Ser Asp Asp Ser Arg Trp Ala His Arg Pro Arg Tyr Asn Glu Ala Leu
            515             520             525

Tyr Ala Gln Arg Asn Asp Pro Ser Thr Ala Ala Gly Gln Ile Tyr Gln
    530             535             540

Gly Leu Arg His Met Ile Ala Val Arg Gln Ser Asn Pro Arg Phe Asp
545             550             555             560

Gly Gly Arg Leu Val Thr Phe Asn Thr Asn Asn Lys His Ile Ile Gly
                565             570             575

Tyr Ile Arg Asn Asn Ala Leu Leu Ala Phe Gly Asn Phe Ser Glu Tyr
            580             585             590

Pro Gln Thr Val Thr Ala His Thr Leu Gln Ala Met Pro Phe Lys Ala
        595             600             605

His Asp Leu Ile Gly Gly Lys Thr Val Ser Leu Asn Gln Asp Leu Thr
    610             615             620

Leu Gln Pro Tyr Gln Val Met Trp Leu Glu Ile Ala
625             630             635
```